US012454685B2

(12) United States Patent
Doudna et al.

(10) Patent No.: US 12,454,685 B2
(45) Date of Patent: Oct. 28, 2025

(54) VARIANT TYPE V CRISPR/Cas EFFECTOR POLYPEPTIDES AND METHODS OF USE THEREOF

(71) Applicant: The Regents of the University of California, Oakland, CA (US)

(72) Inventors: Jennifer A. Doudna, Berkeley, CA (US); Enbo Ma, Moraga, CA (US); Junjie Liu, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 847 days.

(21) Appl. No.: 17/619,815

(22) PCT Filed: Jul. 6, 2020

(86) PCT No.: PCT/US2020/040927
§ 371 (c)(1),
(2) Date: Dec. 16, 2021

(87) PCT Pub. No.: WO2021/007177
PCT Pub. Date: Jan. 14, 2021

(65) Prior Publication Data

US 2022/0315914 A1 Oct. 6, 2022

Related U.S. Application Data

(60) Provisional application No. 62/881,533, filed on Aug. 1, 2019, provisional application No. 62/871,408, filed on Jul. 8, 2019.

(51) Int. Cl.

| | |
|---|---|
| ***C12N 9/22*** | (2006.01) |
| ***C12N 15/10*** | (2006.01) |
| ***C12N 15/11*** | (2006.01) |
| ***C12N 15/82*** | (2006.01) |
| ***C12N 15/85*** | (2006.01) |

(52) U.S. Cl.
CPC ............ *C12N 15/102* (2013.01); *C12N 15/11* (2013.01); *C12N 15/82* (2013.01); *C12N 15/85* (2013.01); *C12N 2310/20* (2017.05)

(58) Field of Classification Search
CPC ........ C12N 9/22; C12N 15/102; C12N 15/86; C07K 2319/09; C07K 14/005; C12Q 1/701; C12Q 1/686; C12Y 207/07007; C12Y 207/07049
USPC ........................................................ 435/69.1
See application file for complete search history.

(56) References Cited

U.S. PATENT DOCUMENTS

2017/0088833 A1 3/2017 Joung et al.

FOREIGN PATENT DOCUMENTS

WO WO 2016/205613 12/2016

OTHER PUBLICATIONS

Davos et al., (Proteins: Structure, Function and Genetics, 2000, vol. 41: 98-107.*
Wristlock et al., (Quarterly Reviews of Biophysics 2003, vol. 36 (3): 307-340.*
Kwiatkowski et al., (Biochemistry 38:11643-11650, 1999.*
Kisselev L., (Structure, 2002, vol. 10: 8-9.*
Chen, et al.; "CRISPR-Cas12a target binding unleashes indiscriminate single-stranded DNase activity"; Science; vol. 360, pp. 436-439 (Apr. 27, 2018).
Murugan, et al.; "Pervasive off-target and double-stranded DNA nicking by CRISPR-Cas12a"; bioRxiv; 38 pages (Jun. 2, 2019).
Koonin et al. (2017) "Diversity, classification and evolution of CRISPR-Cas systems", Current Opinion in Microbiology, 37: 67-78.

* cited by examiner

*Primary Examiner* — Tekchand Saidha
*Assistant Examiner* — Mohammad Y Meah
(74) *Attorney, Agent, or Firm* — Kyle A. Gurley; Bozicevic, Field & Francis LLP

(57) ABSTRACT

The present disclosure provides variant type V CRISPR/Cas effector polypeptides, nucleic acids encoding the variant polypeptides, and systems comprising the variant polypeptides or nucleic acids encoding same. The present disclosure provides methods for modifying a target nucleic acid, using a variant polypeptide of the present disclosure.

21 Claims, 65 Drawing Sheets

Specification includes a Sequence Listing.

FIG. 1A

*Lachnospiraceae bacterium* Cas12a

MSKLEKFTNCYSLSKTLRFKAIPVGKTQENIDNKRLLVEDEKRAEDYKGVKKLLDRYYLSFINDVLHSIKLKNLNNYISLFRKKTRTEKE
NKELENLEINLRKEIAKAFKGNEGYKSLFKKDIIETILPEFLDDKDEIALVNSFNGFTTAFTGFFDNRENMFSEEAKSTSIAFRCINENLTRYI
SNMDIFEKVDAIFDKHEVQEIKEKILNSDYDVEDFFEGEFFNFVLTQEGIDVYNAIIGGFVTESGEKIKGLNEYINLYNQKTKQKLPKFKPL
YKQVLSDRESLSFYGEGYTSDEEVLEVFRNTLNKNSEIFSSIKKLEKLFKNFDEYSSAGIFVKNGPAISTISKDIFGEWNVIRDKWNAEYDD
IHLKKKAVVTEKYEDDRRKSFKKIGSFSLEQLQEYADADLSVVEKLKEIIIQKVDEIYKVYGSSEKLFDADFVLEKSLKKNDAVVAIMKD
LLDSVKSFENYIKAFFGEGKETNRDESFYGDFVLAYDILLKVDHIYDAIRNYVTQKPYSKDKFKLYFQNPQFMGGWDKDKETDYRATIL
RYGSKYYLAIMDKKYAKCLQKIDKDDVNGNYEKINYKLLPGPNKMLPKVFFSKKWMAYYNPSEDIQKIYKNGTFKKGDMFNLNDCHK
LIDFFKDSISRYPKWSNAYDFNFSETEKYKDIAGFYREVEEQGYKVSFESASKKEVDKLVEEGKLYMFQIYNKDFSDKSHGTPNLHTMYF
KLLFDENNHGQIRLSGGAELFMRRASLKKEELVVHPANSPIANKNPDNPKKTTTLSYDVYKDKRFSEDQYELHIPIAINKCPKNIFKINTE
VRVLLKHDDNPYVIGIDRGERNLLYIVVVDGKGNIVEQYSLNEIINNFNGIRIKTDYHSLLDKKEKERFEARQNWTSIENIKELKAGYISQV
VHKICELVEKYDAVIALEDLNSGFKNSRVKVEKQVYQKFEKMLIDKLNYMVDKKSNPCATGGALKGYQITNKFESFKSMSTQNGFIFYI
PAWLTSKIDPSTGFVNLLKTKYTSIADSKKFISSFDRIMYVPEEDLFEFALDYKNFSRTDADYIKKWKLYSYGNRIRIFRNPKKNNVFDWE
EVCLTSAYKELFNKYGINYQQGDIRALLCEQSDKAFYSSFMALMSLMLQMRNSITGRTDVDFLISPVKNSDGIFYDSRNYEAQENAILPK
NADANGAYNIARKVLWAIGQFKKAEDEKLDKVKIAISNKEWLEYAQTSVKH (SEQ ID NO:1)

FIG. 1B

*Lachnospiraceae bacterium* Cas12a variant (deletion of SGFKNSRVK; SEQ ID NO:60)

MSKLEKFTNCYSLSKTLRFKAIPVGKTQENIDNKRLLVEDEKRAEDYKGVKKLLDRYYLSFINDVLHSIKLKNLNNYISLFRK
KTRTEKENKELENLEINLRKEIAKAFKGNEGYKSLFKKDIIETILPEFLDDKDEIALVNSFNGFTTAFTGFFDNRENMFSEEAKS
TSIAFRCINENLTRYISNMDIFEKVDAIFDKHEVQEIKEKILNSDYDVEDFFEGEFFNFVLTQEGIDVYNAIIGGFVTESGEKIKG
LNEYINLYNQKTKQKLPKFKPLYKQVLSDRESLSFYGEGYTSDEEVLEVFRNTLNKNSEIFSSIKKLEKLFKNFDEYSSAGIFV
KNGPAISTISKDIFGEWNVIRDKWNAEYDDIHLKKKAVVTEKYEDDRRKSFKKIGSFSLEQLQEYADADLSVVEKLKEIIIQK
VDEIYKVYGSSEKLFDADFVLEKSLKKNDAVVAIMKDLLDSVKSFENYIKAFFGEGKETNRDESFYGDFVLAYDILLKVDHI
YDAIRNYVTQKPYSKDKFKLYFQNPQFMGGWDKDKETDYRATILRYGSKYYLAIMDKKYAKCLQKIDKDDVNGNYEKINY
KLLPGPNKMLPKVFFSKKWMAYYNPSEDIQKIYKNGTFKKGDMFNLNDCHKLIDFFKDSISRYPKWSNAYDFNFSETEKYK
DIAGFYREVEEQGYKVSFESASKKEVDKLVEEGKLYMFQIYNKDFSDKSHGTPNLHTMYFKLLFDENNHGQIRLSGGAELF
MRRASLKKEELVVHPANSPIANKNPDNPKKTTTLSYDVYKDKRFSEDQYELHIPIAINKCPKNIFKINTEVRVLLKHDDNPYV
IGIDRGERNLLYIVVVDGKGNIVEQYSLNEIINNFNGIRIKTDYHSLLDKKEKERFEARQNWTSIENIKELKAGYISQVVHKICE
LVEKYDAVIALEDLNVEKQVYQKFEKMLIDKLNYMVDKKSNPCATGGALKGYQITNKFESFKSMSTQNGFIFYIPAWLTSKI
DPSTGFVNLLKTKYTSIADSKKFISSFDRIMYVPEEDLFEFALDYKNFSRTDADYIKKWKLYSYGNRIRIFRNPKKNNVFDWE
EVCLTSAYKELFNKYGINYQQGDIRALLCEQSDKAFYSSFMALMSLMLQMRNSITGRTDVDFLISPVKNSDGIFYDSRNYEA
QENAILPKNADANGAYNIARKVLWAIGQFKKAEDEKLDKVKIAISNKEWLEYAQTSVKH (SEQ ID NO: 2)

FIG. 1C

*Lachnospiraceae bacterium* Cas12a variant (SGFKNSRVK; SEQ ID NO:60 mutated to GGAAGGAAP; SEQ ID NO:76)

MSKLEKFTNCYSLSKTLRFKAIPVGKTQENIDNKRLLVEDEKRAEDYKGVKKLLDRYYLSFINDVLHSIKLKNLNNYISLFRK
KTRTEKENKELENLEINLRKEIAKAFKGNEGYKSLFKKDIIETILPEFLDDKDEIALVNSFNGFTTAFTGFFDNRENMFSEEAKS
TSIAFRCINENLTRYISNMDIFEKVDAIFDKHEVQEIKEKILNSDYDVEDFFEGEFFNFVLTQEGIDVYNAIIGGFVTESGEKIKG
LNEYINLYNQKTKQKLPKFKPLYKQVLSDRESLSFYGEGYTSDEEVLEVFRNTLNKNSEIFSSIKKLEKLFKNFDEYSSAGIFV
KNGPAISTISKDIFGEWNVIRDKWNAEYDDIHLKKKAVVTEKYEDDRRKSFKKIGSFSLEQLQEYADADLSVVEKLKEIIIQK
VDEIYKVYGSSEKLFDADFVLEKSLKKNDAVVAIMKDLLDSVKSFENYIKAFFGEGKETNRDESFYGDFVLAYDILLKVDHI
YDAIRNYVTQKPYSKDKFKLYFQNPQFMGGWDKDKETDYRATILRYGSKYYLAIMDKKYAKCLQKIDKDDVNGNYEKINY
KLLPGPNKMLPKVFFSKKWMAYYNPSEDIQKIYKNGTFKKGDMFNLNDCHKLIDFFKDSISRYPKWSNAYDFNFSETEKYK
DIAGFYREVEEQGYKVSFESASKKEVDKLVEEGKLYMFQIYNKDFSDKSHGTPNLHTMYFKLLFDENNHGQIRLSGGAELF
MRRASLKKEELVVHPANSPIANKNPDNPKKTTTLSYDVYKDKRFSEDQYELHIPIAINKCPKNIFKINTEVRVLLKHDDNPYV
IGIDRGERNLLYIVVVDGKGNIVEQYSLNEIINNFNGIRIKTDYHSLLDKKEKERFEARQNWTSIENIKELKAGYISQVVHKICE
LVEKYDAVIALEDLN<u>GGAAGGAAP</u>VEKQVYQKFEKMLIDKLNYMVDKKSNPCATGGALKGYQITNKFESFKSMSTQNGFI
FYIPAWLTSKIDPSTGFVNLLKTKYTSIADSKKFISSFDRIMYVPEEDLFEFALDYKNFSRTDADYIKKWKLYSYGNRIRIFRNP
KKNNVFDWEEVCLTSAYKELFNKYGINYQQGDIRALLCEQSDKAFYSSFMALMSLMLQMRNSITGRTDVDFLISPVKNSDGI
FYDSRNYEAQENAILPKNADANGAYNIARKVLWAIGQFKKAEDEKLDKVKIAISNKEWLEYAQTSVKH (SEQ ID NO:4)

FIG. 1D

*Lachnospiraceae bacterium* Cas12a variant (SGFKNSRVK; SEQ ID NO:60 mutated to GAP)

MSKLEKFTNCYSLSKTLRFKAIPVGKTQENIDNKRLLVEDEKRAEDYKGVKKLLDRYYLSFINDVLHSIKLKNLNNYISLFRK
KTRTEKENKELENLEINLRKEIAKAFKGNEGYKSLFKKDIIETILPEFLDDKDEIALVNSFNGFTTAFTGFFDNRENMFSEEAKS
TSIAFRCINENLTRYISNMDIFEKVDAIFDKHEVQEIKEKILNSDYDVEDFFEGEFFNFVLTQEGIDVYNAIIGGFVTESGEKIKG
LNEYINLYNQKTKQKLPKFKPLYKQVLSDRESLSFYGEGYTSDEEVLEVFRNTLNKNSEIFSSIKKLEKLFKNFDEYSSAGIFV
KNGPAISTISKDIFGEWNVIRDKWNAEYDDIHLKKKAVVTEKYEDDRRKSFKKIGSFSLEQLQEYADADLSVVEKLKEIIIQK
VDEIYKVYGSSEKLFDADFVLEKSLKKNDAVVAIMKDLLDSVKSFENYIKAFFGEGKETNRDESFYGDFVLAYDILLKVDHI
YDAIRNYVTQKPYSKDKFKLYFQNPQFMGGWDKDKETDYRATILRYGSKYYLAIMDKKYAKCLQKIDKDDVNGNYEKINY
KLLPGPNKMLPKVFFSKKWMAYYNPSEDIQKIYKNGTFKKGDMFNLNDCHKLIDFFKDSISRYPKWSNAYDFNFSETEKYK
DIAGFYREVEEQGYKVSFESASKKEVDKLVEEGKLYMFQIYNKDFSDKSHGTPNLHTMYFKLLFDENNHGQIRLSGGAELF
MRRASLKKEELVVHPANSPIANKNPDNPKKTTTLSYDVYKDKRFSEDQYELHIPIAINKCPKNIFKINTEVRVLLKHDDNPYV
IGIDRGERNLLYIVVVDGKGNIVEQYSLNEIINNFNGIRIKTDYHSLLDKKEKERFEARQNWTSIENIKELKAGYISQVVHKICE
LVEKYDAVIALEDLNGAPVEKQVYQKFEKMLIDKLNYMVDKKSNPCATGGALKGYQITNKFESFKSMSTQNGFIFYIPAWL
TSKIDPSTGFVNLLKTKYTSIADSKKFISSFDRIMYVPEEDLFEFALDYKNFSRTDADYIKKWKLYSYGNRIRIFRNPKKNNVF
DWEEVCLTSAYKELFNKYGINYQQGDIRALLCEQSDKAFYSSFMALMSLMLQMRNSITGRTDVDFLISPVKNSDGIFYDSRN
YEAQENAILPKNADANGAYNIARKVLWAIGQFKKAEDEKLDKVKIAISNKEWLEYAQTSVKH (SEQ ID NO:1)

FIG. 1E

*Lachnospiraceae bacterium* Cas12a variant (SGFKNSRVK; SEQ ID NO:60 mutated to SGFANSRVA; SEQ ID NO:79)

MSKLEKFTNCYSLSKTLRFKAIPVGKTQENIDNKRLLVEDEKRAEDYKGVKKLLDRYYLSFINDVLHSIKLKNLNNYISLFRK
KTRTEKENKELENLEINLRKEIAKAFKGNEGYKSLFKKDIIETILPEFLDDKDEIALVNSFNGFTTAFTGFFDNRENMFSEEAKS
TSIAFRCINENLTRYISNMDIFEKVDAIFDKHEVQEIKEKILNSDYDVEDFFEGEFFNFVLTQEGIDVYNAIIGGFVTESGEKIKG
LNEYINLYNQKTKQKLPKFKPLYKQVLSDRESLSFYGEGYTSDEEVLEVFRNTLNKNSEIFSSIKKLEKLFKNFDEYSSAGIFV
KNGPAISTISKDIFGEWNVIRDKWNAEYDDIHLKKKAVVTEKYEDDRRKSFKKIGSFSLEQLQEYADADLSVVEKLKEIIIQK
VDEIYKVYGSSEKLFDADFVLEKSLKKNDAVVAIMKDLLDSVKSFENYIKAFFGEGKETNRDESFYGDFVLAYDILLKVDHI
YDAIRNYVTQKPYSKDKFKLYFQNPQFMGGWDKDKETDYRATILRYGSKYYLAIMDKKYAKCLQKIDKDDVNGNYEKINY
KLLPGPNKMLPKVFFSKKWMAYYNPSEDIQKIYKNGTFKKGDMFNLNDCHKLIDFFKDSISRYPKWSNAYDFNFSETEKYK
DIAGFYREVEEQGYKVSFESASKKEVDKLVEEGKLYMFQIYNKDFSDKSHGTPNLHTMYFKLLFDENNHGQIRLSGGAELF
MRRASLKKEELVVHPANSPIANKNPDNPKKTTTLSYDVYKDKRFSEDQYELHIPIAINKCPKNIFKINTEVRVLLKHDDNPYV
IGIDRGERNLLYIVVVDGKGNIVEQYSLNEIINNFNGIRIKTDYHSLLDKKEKERFEARQNWTSIENIKELKAGYISQVVHKICE
LVEKYDAVIALEDLNSGFANSRVAVEKQVYQKFEKMLIDKLNYMVDKKSNPCATGGALKGYQITNKFESFKSMSTQNGFIF
YIPAWLTSKIDPSTGFVNLLKTKYTSIADSKKFISSFDRIMYVPEEDLFEFALDYKNFSRTDADYIKKWKLYSYGNRIRIFRNPK
KNNVFDWEEVCLTSAYKELFNKYGINYQQGDIRALLCEQSDKAFYSSFMALMSLMLQMRNSITGRTDVDFLISPVKNSDGIF
YDSRNYEAQENAILPKNADANGAYNIARKVLWAIGQFKKAEDEKLDKVKIAISNKEWLEYAQTSVKH (SEQ ID NO:5)

FIG. 1F

*Lachnospiraceae bacterium* Cas12a variant (SGFKNSRVK; SEQ ID NO:60 mutated to SGAKNSAVA; SEQ ID NO:80)

MSKLEKFTNCYSLSKTLRFKAIPVGKTQENIDNKRLLVEDEKRAEDYKGVKKLLDRYYLSFINDVLHSIKLKNLNNYISLFRK
KTRTEKENKELENLEINLRKEIAKAFKGNEGYKSLFKKDIIETILPEFLDDKDEIALVNSFNGFTTAFTGFFDNRENMFSEEAKS
TSIAFRCINENLTRYISNMDIFEKVDAIFDKHEVQEIKEKILNSDYDVEDFFEGEFFNFVLTQEGIDVYNAIIGGFVTESGEKIKG
LNEYINLYNQKTKQKLPKFKPLYKQVLSDRESLSFYGEGYTSDEEVLEVFRNTLNKNSEIFSSIKKLEKLFKNFDEYSSAGIFV
KNGPAISTISKDIFGEWNVIRDKWNAEYDDIHLKKKAVVTEKYEDDRRKSFKKIGSFSLEQLQEYADADLSVVEKLKEIIIQK
VDEIYKVYGSSEKLFDADFVLEKSLKKNDAVVAIMKDLLDSVKSFENYIKAFFGEGKETNRDESFYGDFVLAYDILLKVDHI
YDAIRNYVTQKPYSKDKFKLYFQNPQFMGGWDKDKETDYRATILRYGSKYYLAIMDKKYAKCLQKIDKDDVNGNYEKINY
KLLPGPNKMLPKVFFSKKWMAYYNPSEDIQKIYKNGTFKKGDMFNLNDCHKLIDFFKDSISRYPKWSNAYDFNFSETEKYK
DIAGFYREVEEQGYKVSFESASKKEVDKLVEEGKLYMFQIYNKDFSDKSHGTPNLHTMYFKLLFDENNHGQIRLSGGAELF
MRRASLKKEELVVHPANSPIANKNPDNPKKTTTLSYDVYKDKRFSEDQYELHIPIAINKCPKNIFKINTEVRVLLKHDDNPYV
IGIDRGERNLLYIVVVDGKGNIVEQYSLNEIINNFNGIRIKTDYHSLLDKKEKERFEARQNWTSIENIKELKAGYISQVVHKICE
LVEKYDAVIALEDLN<u>SGAKNSAVA</u>VEKQVYQKFEKMLIDKLNYMVDKKSNPCATGGALKGYQITNKFESFKSMSTQNGFIF
YIPAWLTSKIDPSTGFVNLLKTKYTSIADSKKFISSFDRIMYVPEEDLFEFALDYKNFSRTDADYIKKWKLYSYGNRIRIFRNPK
KNNVFDWEEVCLTSAYKELFNKYGINYQQGDIRALLCEQSDKAFYSSFMALMSLMLQMRNSITGRTDVDFLISPVKNSDGIF
YDSRNYEAQENAILPKNADANGAYNIARKVLWAIGQFKKAEDEKLDKVKIAISNKEWLEYAQTSVKH (SEQ ID NO:6)

FIG. 2A

Acidaminococcus sp.BV3L6 Cas12a

MTQFEGFTNLYQVSKTLRFELIPQGKTLKHIQEQGFIEEDKARNDHYKELKPIIDRIYKTYADQCLQLVQLDWENLSAAIDSY
RKEKTEETRNALIEEQATYRNAIHDYFIGRTDNLTDAINKRHAEIYKGLFKAELFNGKVLKQLGTVTTTEHENALLRSFDKFT
TYFSGFYENRKNVFSAEDISTAIPHRIVQDNFPKFKENCHIFTRLITAVPSLREHFENVKKAIGIFVSTSIEEVFSFPFYNQLLTQT
QIDLYNQLLGGISREAGTEKIKGLNEVLNLAIQKNDETAHIIASLPHRFIPLFKQILSDRNTLSFILEEFKSDEEVIQSFCKYKTLL
RNENVLETAEALFNELNSIDLTHIFISHKKLETISSALCDHWDTLRNALYERRISELTGKITKSAKEKVQRSLKHEDINLQEIISA
AGKELSEAFKQKTSEILSHAHAALDQPLPTTLKKQEEKEILKSQLDSLLGLYHLLDWFAVDESNEVDPEFSARLTGIKLEMEP
SLSFYNKARNYATKKPYSVEKFKLNFQMPTLASGWDVNKEKNNGAILFVKNGLYYLGIMPKQKGRYKALSFEPTEKTSEGF
DKMYYDYFPDAAKMIPKCSTQLKAVTAHFQTHTTPILLSNNFIEPLEITKEIYDLNNPEKEPKKFQTAYAKKTGDQKGYREAL
CKWIDFTRDFLSKYTKTTSIDLSSLRPSSQYKDLGEYYAELNPLLYHISFQRIAEKEIMDAVETGKLYLFQIYNKDFAKGHHG
KPNLHTLYWTGLFSPENLAKTSIKLNGQAELFYRPKSRMKRMAHRLGEKMLNKKLKDQKTPIPDTLYQELYDYVNHRLSHD
LSDEARALLPNVITKEVSHEIIKDRRFTSDKFFFHVPITLNYQAANSPSKFNQRVNAYLKEHPETPIIGIDRGERNLIYITVIDSTG
KILEQRSLNTIQQFDYQKKLDNREKERVAARQAWSVVGTIKDLKQGYLSQVIHEIVDLMIHYQAVVVLENLNFGFKSKRTG
IAEKAVYQQFEKMLIDKLNCLVLKDYPAEKVGGVLNPYQLTDQFTSFAKMGTQSGFLFYVPAPYTSKIDPLTGFVDPFVWK
TIKNHESRKHFLEGFDFLHYDVKTGDFILHFKMNRNLSFQRGLPGFMPAWDIVFEKNETQFDAKGTPFIAGKRIVPVIENHRF
TGRYRDLYPANELIALLEEKGIVFRDGSNILPKLLENDDSHAIDTMVALIRSVLQMRNSNAATGEDYINSPVRDLNGVCFDSR
FQNPEWPMDADANGAYHIALKGQLLLNHLKESKDLKLQNGISNQDWLAYIQELRN (SEQ ID NO:2)

FIG. 2B

Acidaminococcus sp.BV3L6 Cas12a variant (deletion of FGFKSKRTG; SEQ ID NO:62)

MTQFEGFTNLYQVSKTLRFELIPQGKTLKHIQEQGFIEEDKARNDHYKELKPIIDRIYKTYADQCLQLVQLDWENLSAAIDSY
RKEKTEETRNALIEEQATYRNAIHDYFIGRTDNLTDAINKRHAEIYKGLFKAELFNGKVLKQLGTVTTTEHENALLRSFDKFT
TYFSGFYENRKNVFSAEDISTAIPHRIVQDNFPKFKENCHIFTRLITAVPSLREHFENVKKAIGIFVSTSIEEVFSFPFYNQLLTQT
QIDLYNQLLGGISREAGTEKIKGLNEVLNLAIQKNDETAHIIASLPHRFIPLFKQILSDRNTLSFILEEFKSDEEVIQSFCKYKTLL
RNENVLETAEALFNELNSIDLTHIFISHKKLETISSALCDHWDTLRNALYERRISELTGKITKSAKEKVQRSLKHEDINLQEIISA
AGKELSEAFKQKTSEILSHAHAALDQPLPTTLKKQEEKEILKSQLDSLLGLYHLLDWFAVDESNEVDPEFSARLTGIKLEMEP
SLSFYNKARNYATKKPYSVEKFKLNFQMPTLASGWDVNKEKNNGAILFVKNGLYYLGIMPKQKGRYKALSFEPTEKTSEGF
DKMYYDYFPDAAKMIPKCSTQLKAVTAHFQTHTTPILLSNNFIEPLEITKEIYDLNNPEKEPKKFQTAYAKKTGDQKGYREAL
CKWIDFTRDFLSKYTKTTSIDLSSLRPSSQYKDLGEYYAELNPLLYHISFQRIAEKEIMDAVETGKLYLFQIYNKDFAKGHHG
KPNLHTLYWTGLFSPENLAKTSIKLNGQAELFYRPKSRMKRMAHRLGEKMLNKKLKDQKTPIPDTLYQELYDYVNHRLSHD
LSDEARALLPNVITKEVSHEIIKDRRFTSDKFFFHVPITLNYQAANSPSKFNQRVNAYLKEHPETPIIGIDRGERNLIYITVIDSTG
KILEQRSLNTIQQFDYQKKLDNREKERVAARQAWSVVGTIKDLKQGYLSQVIHEIVDLMIHYQAVVVLENLNIAEKAVYQQ
FEKMLIDKLNCLVLKDYPAEKVGGVLNPYQLTDQFTSFAKMGTQSGFLFYVPAPYTSKIDPLTGFVDPFVWKTIKNHESRKH
FLEGFDFLHYDVKTGDFILHFKMNRNLSFQRGLPGFMPAWDIVFEKNETQFDAKGTPFIAGKRIVPVIENHRFTGRYRDLYPA
NELIALLEEKGIVFRDGSNILPKLLENDDSHAIDTMVALIRSVLQMRNSNAATGEDYINSPVRDLNGVCFDSRFQNPEWPMDA
DANGAYHIALKGQLLLNHLKESKDLKLQNGISNQDWLAYIQELRN (SEQ ID NO:7)

FIG. 2C

Acidaminococcus sp.BV3L6 Cas12a variant (FGFKSKRTG; SEQ ID NO:62 mutated to GGAAGGAAG; SEQ ID NO:77)

MTQFEGFTNLYQVSKTLRFELIPQGKTLKHIQEQGFIEEDKARNDHYKELKPIIDRIYKTYADQCLQLVQLDWENLSAAIDSY
RKEKTEETRNALIEEQATYRNAIHDYFIGRTDNLTDAINKRHAEIYKGLFKAELFNGKVLKQLGTVTTTEHENALLRSFDKFT
TYFSGFYENRKNVFSAEDISTAIPHRIVQDNFPKFKENCHIFTRLITAVPSLREHFENVKKAIGIFVSTSIEEVFSFPFYNQLLTQT
QIDLYNQLLGGISREAGTEKIKGLNEVLNLAIQKNDETAHIIASLPHRFIPLFKQILSDRNTLSFILEEFKSDEEVIQSFCKYKTLL
RNENVLETAEALFNELNSIDLTHIFISHKKLETISSALCDHWDTLRNALYERRISELTGKITKSAKEKVQRSLKHEDINLQEIISA
AGKELSEAFKQKTSEILSHAHAALDQPLPTTLKKQEEKEILKSQLDSLLGLYHLLDWFAVDESNEVDPEFSARLTGIKLEMEP
SLSFYNKARNYATKKPYSVEKFKLNFQMPTLASGWDVNKEKNNGAILFVKNGLYYLGIMPKQKGRYKALSFEPTEKTSEGF
DKMYYDYFPDAAKMIPKCSTQLKAVTAHFQTHTTPILLSNNFIEPLEITKEIYDLNNPEKEPKKFQTAYAKKTGDQKGYREAL
CKWIDFTRDFLSKYTKTTSIDLSSLRPSSQYKDLGEYYAELNPLLYHISFQRIAEKEIMDAVETGKLYLFQIYNKDFAKGHHG
KPNLHTLYWTGLFSPENLAKTSIKLNGQAELFYRPKSRMKRMAHRLGEKMLNKKLKDQKTPIPDTLYQELYDYVNHRLSHD
LSDEARALLPNVITKEVSHEIIKDRRFTSDKFFFHVPITLNYQAANSPSKFNQRVNAYLKEHPETPIIGIDRGERNLIYITVIDSTG
KILEQRSLNTIQQFDYQKKLDNREKERVAARQAWSVVGTIKDLKQGYLSQVIHEIVDLMIHYQAVVVLENLNGGAAGGAA
GIAEKAVYQQFEKMLIDKLNCLVLKDYPAEKVGGVLNPYQLTDQFTSFAKMGTQSGFLFYVPAPYTSKIDPLTGFVDPFVW
KTIKNHESRKHFLEGFDFLHYDVKTGDFILHFKMNRNLSFQRGLPGFMPAWDIVFEKNETQFDAKGTPFIAGKRIVPVIENHR
FTGRYRDLYPANELIALLEEKGIVFRDGSNILPKLLENDDSHAIDTMVALIRSVLQMRNSNAATGEDYINSPVRDLNGVCFDS
RFQNPEWPMDADANGAYHIALKGQLLLNHLKESKDLKLQNGISNQDWLAYIQELRN (SEQ ID NO:8)

FIG. 2D

Acidaminococcus sp.BV3L6 Cas12a variant (FGFKSKRTG; SEQ ID NO:62 mutated to GAA)

MTQFEGFTNLYQVSKTLRFELIPQGKTLKHIQEQGFIEEDKARNDHYKELKPIIDRIYKTYADQCLQLVQLDWENLSAAIDSY
RKEKTEETRNALIEEQATYRNAIHDYFIGRTDNLTDAINKRHAEIYKGLFKAELFNGKVLKQLGTVTTTEHENALLRSFDKFT
TYFSGFYENRKNVFSAEDISTAIPHRIVQDNFPKFKENCHIFTRLITAVPSLREHFENVKKAIGIFVSTSIEEVFSFPFYNQLLTQT
QIDLYNQLLGGISREAGTEKIKGLNEVLNLAIQKNDETAHIIASLPHRFIPLFKQILSDRNTLSFILEEFKSDEEVIQSFCKYKTLL
RNENVLETAEALFNELNSIDLTHIFISHKKLETISSALCDHWDTLRNALYERRISELTGKITKSAKEKVQRSLKHEDINLQEIISA
AGKELSEAFKQKTSEILSHAHAALDQPLPTTLKKQEEKEILKSQLDSLLGLYHLLDWFAVDESNEVDPEFSARLTGIKLEMEP
SLSFYNKARNYATKKPYSVEKFKLNFQMPTLASGWDVNKEKNNGAILFVKNGLYYLGIMPKQKGRYKALSFEPTEKTSEGF
DKMYYDYFPDAAKMIPKCSTQLKAVTAHFQTHTTPILLSNNFIEPLEITKEIYDLNNPEKEPKKFQTAYAKKTGDQKGYREAL
CKWIDFTRDFLSKYTKTTSIDLSSLRPSSQYKDLGEYYAELNPLLYHISFQRIAEKEIMDAVETGKLYLFQIYNKDFAKGHHG
KPNLHTLYWTGLFSPENLAKTSIKLNGQAELFYRPKSRMKRMAHRLGEKMLNKKLKDQKTPIPDTLYQELYDYVNHRLSHD
LSDEARALLPNVITKEVSHEIIKDRRFTSDKFFFHVPITLNYQAANSPSKFNQRVNAYLKEHPETPIIGIDRGERNLIYITVIDSTG
KILEQRSLNTIQQFDYQKKLDNREKERVAARQAWSVVGTIKDLKQGYLSQVIHEIVDLMIHYQAVVVLENLNGAAIAEKAV
YQQFEKMLIDKLNCLVLKDYPAEKVGGVLNPYQLTDQFTSFAKMGTQSGFLFYVPAPYTSKIDPLTGFVDPFVWKTIKNHES
RKHFLEGFDFLHYDVKTGDFILHFKMNRNLSFQRGLPGFMPAWDIVFEKNETQFDAKGTPFIAGKRIVPVIENHRFTGRYRDL
YPANELIALLEEKGIVFRDGSNILPKLLENDDSHAIDTMVALIRSVLQMRNSNAATGEDYINSPVRDLNGVCFDSRFQNPEWP
MDADANGAYHIALKGQLLLNHLKESKDLKLQNGISNQDWLAYIQELRN (SEQ ID NO: 141)

FIG. 2E

*Acidaminococcus* sp.BV3L6 Cas12a variant (FGFKSKRTG; SEQ ID NO:62 mutated to FGFASARTG; SEQ ID NO:82)

MTQFEGFTNLYQVSKTLRFELIPQGKTLKHIQEQGFIEEDKARNDHYKELKPIIDRIYKTYADQCLQLVQLDWENLSAAIDSY
RKEKTEETRNALIEEQATYRNAIHDYFIGRTDNLTDAINKRHAEIYKGLFKAELFNGKVLKQLGTVTTTEHENALLRSFDKFT
TYFSGFYENRKNVFSAEDISTAIPHRIVQDNFPKFKENCHIFTRLITAVPSLREHFENVKKAIGIFVSTSIEEVFSFPFYNQLLTQT
QIDLYNQLLGGISREAGTEKIKGLNEVLNLAIQKNDETAHIIASLPHRFIPLFKQILSDRNTLSFILEEFKSDEEVIQSFCKYKTLL
RNENVLETAEALFNELNSIDLTHIFISHKKLETISSALCDHWDTLRNALYERRISELTGKITKSAKEKVQRSLKHEDINLQEIISA
AGKELSEAFKQKTSEILSHAHAALDQPLPTTLKKQEEKEILKSQLDSLLGLYHLLDWFAVDESNEVDPEFSARLTGIKLEMEP
SLSFYNKARNYATKKPYSVEKFKLNFQMPTLASGWDVNKEKNNGAILFVKNGLYYLGIMPKQKGRYKALSFEPTEKTSEGF
DKMYYDYFPDAAKMIPKCSTQLKAVTAHFQTHTTPILLSNNFIEPLEITKEIYDLNNPEKEPKKFQTAYAKKTGDQKGYREAL
CKWIDFTRDFLSKYTKTTSIDLSSLRPSSQYKDLGEYYAELNPLLYHISFQRIAEKEIMDAVETGKLYLFQIYNKDFAKGHHG
KPNLHTLYWTGLFSPENLAKTSIKLNGQAELFYRPKSRMKRMAHRLGEKMLNKKLKDQKTPIPDTLYQELYDYVNHRLSHD
LSDEARALLPNVITKEVSHEIIKDRRFTSDKFFFHVPITLNYQAANSPSKFNQRVNAYLKEHPETPIIGIDRGERNLIYITVIDSTG
KILEQRSLNTIQQFDYQKKLDNREKERVAARQAWSVVGTIKDLKQGYLSQVIHEIVDLMIHYQAVVVLENLNFGFASARTGI
AEKAVYQQFEKMLIDKLNCLVLKDYPAEKVGGVLNPYQLTDQFTSFAKMGTQSGFLFYVPAPYTSKIDPLTGFVDPFVWKT
IKNHESRKHFLEGFDFLHYDVKTGDFILHFKMNRNLSFQRGLPGFMPAWDIVFEKNETQFDAKGTPFIAGKRIVPVIENHRFT
GRYRDLYPANELIALLEEKGIVFRDGSNILPKLLENDDSHAIDTMVALIRSVLQMRNSNAATGEDYINSPVRDLNGVCFDSRF
QNPEWPMDADANGAYHIALKGQLLLNHLKESKDLKLQNGISNQDWLAYIQELRN (SEQ ID NO:9)

FIG. 2F

*Acidaminococcus* sp.BV3L6 Cas12a variant (FGFKSKRTG; SEQ ID NO:62 mutated to FGFASAATG; SEQ ID NO:83)

MTQFEGFTNLYQVSKTLRFELIPQGKTLKHIQEQGFIEEDKARNDHYKELKPIIDRIYKTYADQCLQLVQLDWENLSAAIDSY
RKEKTEETRNALIEEQATYRNAIHDYFIGRTDNLTDAINKRHAEIYKGLFKAELFNGKVLKQLGTVTTTEHENALLRSFDKFT
TYFSGFYENRKNVFSAEDISTAIPHRIVQDNFPKFKENCHIFTRLITAVPSLREHFENVKKAIGIFVSTSIEEVFSFPFYNQLLTQT
QIDLYNQLLGGISREAGTEKIKGLNEVLNLAIQKNDETAHIIASLPHRFIPLFKQILSDRNTLSFILEEFKSDEEVIQSFCKYKTLL
RNENVLETAEALFNELNSIDLTHIFISHKKLETISSALCDHWDTLRNALYERRISELTGKITKSAKEKVQRSLKHEDINLQEIISA
AGKELSEAFKQKTSEILSHAHAALDQPLPTTLKKQEEKEILKSQLDSLLGLYHLLDWFAVDESNEVDPEFSARLTGIKLEMEP
SLSFYNKARNYATKKPYSVEKFKLNFQMPTLASGWDVNKEKNNGAILFVKNGLYYLGIMPKQKGRYKALSFEPTEKTSEGF
DKMYYDYFPDAAKMIPKCSTQLKAVTAHFQTHTTPILLSNNFIEPLEITKEIYDLNNPEKEPKKFQTAYAKKTGDQKGYREAL
CKWIDFTRDFLSKYTKTTSIDLSSLRPSSQYKDLGEYYAELNPLLYHISFQRIAEKEIMDAVETGKLYLFQIYNKDFAKGHHG
KPNLHTLYWTGLFSPENLAKTSIKLNGQAELFYRPKSRMKRMAHRLGEKMLNKKLKDQKTPIPDTLYQELYDYVNHRLSHD
LSDEARALLPNVITKEVSHEIIKDRRFTSDKFFFHVPITLNYQAANSPSKFNQRVNAYLKEHPETPIIGIDRGERNLIYITVIDSTG
KILEQRSLNTIQQFDYQKKLDNREKERVAARQAWSVVGTIKDLKQGYLSQVIHEIVDLMIHYQAVVVLENLNFGFASAATGI
AEKAVYQQFEKMLIDKLNCLVLKDYPAEKVGGVLNPYQLTDQFTSFAKMGTQSGFLFYVPAPYTSKIDPLTGFVDPFVWKT
IKNHESRKHFLEGFDFLHYDVKTGDFILHFKMNRNLSFQRGLPGFMPAWDIVFEKNETQFDAKGTPFIAGKRIVPVIENHRFT
GRYRDLYPANELIALLEEKGIVFRDGSNILPKLLENDDSHAIDTMVALIRSVLQMRNSNAATGEDYINSPVRDLNGVCFDSRF
QNPEWPMDADANGAYHIALKGQLLLNHLKESKDLKLQNGISNQDWLAYIQELRN (SEQ ID NO:10)

FIG. 3A

*Francisella novicida* U112 Cas12a

MSIYQEFVNKYSLSKTLRFELIPQGKTLENIKARGLILDDEKRAKDYKKAKQIIDKYHQFFIEEILSSVCISEDLLQNYSDVYFK
LKKSDDDNLQKDFKSAKDTIKKQISEYIKDSEKFKNLFNQNLIDAKKGQESDLILWLKQSKDNGIELFKANSDITDIDEALEIIK
SFKGWTTYFKGFHENRKNVYSSNDIPTSIIYRIVDDNLPKFLENKAKYESLKDKAPEAINYEQIKKDLAEELTFDIDYKTSEVN
QRVFSLDEVFEIANFNNYLNQSGITKFNTIIGGKFVNGENTKRKGINEYINLYSQQINDKTLKKYKMSVLFKQILSDTESKSFVI
DKLEDDSDVVTTMQSFYEQIAAFKTVEEKSIKETLSLLFDDLKAQKLDLSKIYFKNDKSLTDLSQQVFDDYSVIGTAVLEYIT
QQIAPKNLDNPSKKEQELIAKKTEKAKYLSLETIKLALEEFNKHRDIDKQCRFEEILANFAAIPMIFDEIAQNKDNLAQISIKYQ
NQGKKDLLQASAEDDVKAIKDLLDQTNNLLHKLKIFHISQSEDKANILDKDEHFYLVFEECYFELANIVPLYNKIRNYITQKP
YSDEKFKLNFENSTLANGWDKNKEPDNTAILFIKDDKYYLGVMNKKNNKIFDDKAIKENKGEGYKKIVYKLLPGANKMLP
KVFFSAKSIKFYNPSEDILRIRNHSTHTKNGSPQKGYEKFEFNIEDCRKFIDFYKQSISKHPEWKDFGFRFSDTQRYNSIDEFYR
EVENQGYKLTFENISESYIDSVVNQGKLYLFQIYNKDFSAYSKGRPNLHTLYWKALFDERNLQDVVYKLNGEAELFYRKQSI
PKKITHPAKEAIANKNKDNPKKESVFEYDLIKDKRFTEDKFFFHCPITINFKSSGANKFNDEINLLLKEKANDVHILSIDRGERH
LAYYTLVDGKGNIIKQDTFNIIGNDRMKTNYHDKLAAIEKDRDSARKDWKKINNIKEMKEGYLSQVVHEIAKLVIEYNAIVV
FEDLNFGFKRGRFKVEKQVYQKLEKMLIEKLNYLVFKDNEFDKTGGVLRAYQLTAPFETFKKMGKQTGIIYYVPAGFTSKI
CPVTGFVNQLYPKYESVSKSQEFFSKFDKICYNLDKGYFEFSFDYKNFGDKAAKGKWTIASFGSRLINFRNSDKNHNWDTRE
VYPTKELEKLLKDYSIEYGHGECIKAAICGESDKKFFAKLTSVLNTILQMRNSKTGTELDYLISPVADVNGNFFDSRQAPKNM
PQDADANGAYHIGLKGLMLLGRIKNNQEGKKLNLVIKNEEYFEFVQNRNN (SEQ ID NO:3)

FIG. 3B

*Francisella novicida* U112 Cas12a variant (deletion of FGFKRGRFK; SEQ ID NO:61)

MSIYQEFVNKYSLSKTLRFELIPQGKTLENIKARGLILDDEKRAKDYKKAKQIIDKYHQFFIEEILSSVCISEDLLQNYSDVYFK
LKKSDDDNLQKDFKSAKDTIKKQISEYIKDSEKFKNLFNQNLIDAKKGQESDLILWLKQSKDNGIELFKANSDITDIDEALEIIK
SFKGWTTYFKGFHENRKNVYSSNDIPTSIIYRIVDDNLPKFLENKAKYESLKDKAPEAINYEQIKKDLAEELTFDIDYKTSEVN
QRVFSLDEVFEIANFNNYLNQSGITKFNTIIGGKFVNGENTKRKGINEYINLYSQQINDKTLKKYKMSVLFKQILSDTESKSFVI
DKLEDDSDVVTTMQSFYEQIAAFKTVEEKSIKETLSLLFDDLKAQKLDLSKIYFKNDKSLTDLSQQVFDDYSVIGTAVLEYIT
QQIAPKNLDNPSKKEQELIAKKTEKAKYLSLETIKLALEEFNKHRDIDKQCRFEEILANFAAIPMIFDEIAQNKDNLAQISIKYQ
NQGKKDLLQASAEDDVKAIKDLLDQTNNLLHKLKIFHISQSEDKANILDKDEHFYLVFEECYFELANIVPLYNKIRNYITQKP
YSDEKFKLNFENSTLANGWDKNKEPDNTAILFIKDDKYYLGVMNKKNNKIFDDKAIKENKGEGYKKIVYKLLPGANKMLP
KVFFSAKSIKFYNPSEDILRIRNHSTHTKNGSPQKGYEKFEFNIEDCRKFIDFYKQSISKHPEWKDFGFRFSDTQRYNSIDEFYR
EVENQGYKLTFENISESYIDSVVNQGKLYLFQIYNKDFSAYSKGRPNLHTLYWKALFDERNLQDVVYKLNGEAELFYRKQSI
PKKITHPAKEAIANKNKDNPKKESVFEYDLIKDKRFTEDKFFFHCPITINFKSSGANKFNDEINLLLKEKANDVHILSIDRGERH
LAYYTLVDGKGNIIKQDTFNIIGNDRMKTNYHDKLAAIEKDRDSARKDWKKINNIKEMKEGYLSQVVHEIAKLVIEYNAIVV
FEDLNVEKQVYQKLEKMLIEKLNYLVFKDNEFDKTGGVLRAYQLTAPFETFKKMGKQTGIIYYVPAGFTSKICPVTGFVNQL
YPKYESVSKSQEFFSKFDKICYNLDKGYFEFSFDYKNFGDKAAKGKWTIASFGSRLINFRNSDKNHNWDTREVYPTKELEKL
LKDYSIEYGHGECIKAAICGESDKKFFAKLTSVLNTILQMRNSKTGTELDYLISPVADVNGNFFDSRQAPKNMPQDADANGA

YHIGLKGLMLLGRIKNNQEGKKLNLVIKNEEYFEFVQNRNN (SEQ ID NO:11)

FIG. 3C

*Francisella novicida* U112 Cas12a variant (FGFKRGRFK; SEQ ID NO:61 mutated to GGAAGGAAG; SEQ ID NO:77)

MSIYQEFVNKYSLSKTLRFELIPQGKTLENIKARGLILDDEKRAKDYKKAKQIIDKYHQFFIEEILSSVCISEDLLQNYSDVYFK
LKKSDDDNLQKDFKSAKDTIKKQISEYIKDSEKFKNLFNQNLIDAKKGQESDLILWLKQSKDNGIELFKANSDITDIDEALEIIK
SFKGWTTYFKGFHENRKNVYSSNDIPTSIIYRIVDDNLPKFLENKAKYESLKDKAPEAINYEQIKKDLAEELTFDIDYKTSEVN
QRVFSLDEVFEIANFNNYLNQSGITKFNTIIGGKFVNGENTKRKGINEYINLYSQQINDKTLKKYKMSVLFKQILSDTESKSFVI
DKLEDDSDVVTTMQSFYEQIAAFKTVEEKSIKETLSLLFDDLKAQKLDLSKIYFKNDKSLTDLSQQVFDDYSVIGTAVLEYIT
QQIAPKNLDNPSKKEQELIAKKTEKAKYLSLETIKLALEEFNKHRDIDKQCRFEEILANFAAIPMIFDEIAQNKDNLAQISIKYQ
NQGKKDLLQASAEDDVKAIKDLLDQTNNLLHKLKIFHISQSEDKANILDKDEHFYLVFEECYFELANIVPLYNKIRNYITQKP
YSDEKFKLNFENSTLANGWDKNKEPDNTAILFIKDDKYYLGVMNKKNNKIFDDKAIKENKGEGYKKIVYKLLPGANKMLP
KVFFSAKSIKFYNPSEDILRIRNHSTHTKNGSPQKGYEKFEFNIEDCRKFIDFYKQSISKHPEWKDFGFRFSDTQRYNSIDEFYR
EVENQGYKLTFENISESYIDSVVNQGKLYLFQIYNKDFSAYSKGRPNLHTLYWKALFDERNLQDVVYKLNGEAELFYRKQSI
PKKITHPAKEAIANKNKDNPKKESVFEYDLIKDKRFTEDKFFFHCPITINFKSSGANKFNDEINLLLKEKANDVHILSIDRGERH
LAYYTLVDGKGNIIKQDTFNIIGNDRMKTNYHDKLAAIEKDRDSARKDWKKINNIKEMKEGYLSQVVHEIAKLVIEYNAIVV
FEDLNGGAAGGAAGVEKQVYQKLEKMLIEKLNYLVFKDNEFDKTGGVLRAYQLTAPFETFKKMGKQTGIIYYVPAGFTSKI
CPVTGFVNQLYPKYESVSKSQEFFSKFDKICYNLDKGYFEFSFDYKNFGDKAAKGKWTIASFGSRLINFRNSDKNHNWDTRE
VYPTKELEKLLKDYSIEYGHGECIKAAICGESDKKFFAKLTSVLNTILQMRNSKTGTELDYLISPVADVNGNFFDSRQAPKNM
PQDADANGAYHIGLKGLMLLGRIKNNQEGKKLNLVIKNEEYFEFVQNRNN (SEQ ID NO:12)

FIG. 3D

*Francisella novicida* U112 Cas12a variant (FGFKRGRFK; SEQ ID NO:61 mutated to GAA)

MSIYQEFVNKYSLSKTLRFELIPQGKTLENIKARGLILDDEKRAKDYKKAKQIIDKYHQFFIEEILSSVCISEDLLQNYSDVYFK
LKKSDDDNLQKDFKSAKDTIKKQISEYIKDSEKFKNLFNQNLIDAKKGQESDLILWLKQSKDNGIELFKANSDITDIDEALEIIK
SFKGWTTYFKGFHENRKNVYSSNDIPTSIIYRIVDDNLPKFLENKAKYESLKDKAPEAINYEQIKKDLAEELTFDIDYKTSEVN
QRVFSLDEVFEIANFNNYLNQSGITKFNTIIGGKFVNGENTKRKGINEYINLYSQQINDKTLKKYKMSVLFKQILSDTESKSFVI
DKLEDDSDVVTTMQSFYEQIAAFKTVEEKSIKETLSLLFDDLKAQKLDLSKIYFKNDKSLTDLSQQVFDDYSVIGTAVLEYIT
QQIAPKNLDNPSKKEQELIAKKTEKAKYLSLETIKLALEEFNKHRDIDKQCRFEEILANFAAIPMIFDEIAQNKDNLAQISIKYQ
NQGKKDLLQASAEDDVKAIKDLLDQTNNLLHKLKIFHISQSEDKANILDKDEHFYLVFEECYFELANIVPLYNKIRNYITQKP
YSDEKFKLNFENSTLANGWDKNKEPDNTAILFIKDDKYYLGVMNKKNNKIFDDKAIKENKGEGYKKIVYKLLPGANKMLP
KVFFSAKSIKFYNPSEDILRIRNHSTHTKNGSPQKGYEKFEFNIEDCRKFIDFYKQSISKHPEWKDFGFRFSDTQRYNSIDEFYR
EVENQGYKLTFENISESYIDSVVNQGKLYLFQIYNKDFSAYSKGRPNLHTLYWKALFDERNLQDVVYKLNGEAELFYRKQSI
PKKITHPAKEAIANKNKDNPKKESVFEYDLIKDKRFTEDKFFFHCPITINFKSSGANKFNDEINLLLKEKANDVHILSIDRGERH
LAYYTLVDGKGNIIKQDTFNIIGNDRMKTNYHDKLAAIEKDRDSARKDWKKINNIKEMKEGYLSQVVHEIAKLVIEYNAIVV
FEDLN<u>GAA</u>VEKQVYQKLEKMLIEKLNYLVFKDNEFDKTGGVLRAYQLTAPFETFKKMGKQTGIIYYVPAGFTSKICPVTGFV
NQLYPKYESVSKSQEFFSKFDKICYNLDKGYFEFSFDYKNFGDKAAKGKWTIASFGSRLINFRNSDKNHNWDTREVYPTKEL
EKLLKDYSIEYGHGECIKAAICGESDKKFFAKLTSVLNTILQMRNSKTGTELDYLISPVADVNGNFFDSRQAPKNMPQDADA

NGAYHIGLKGLMLLGRIKNNQEGKKLNLVIKNEEYFEFVQNRNN (SEQ ID NO:13)

FIG. 3E

*Francisella novicida* U112 Cas12a variant (FGFKRGRFK; SEQ ID NO:61 mutated to FGFARGRFA; SEQ ID NO:84)

MSIYQEFVNKYSLSKTLRFELIPQGKTLENIKARGLILDDEKRAKDYKKAKQIIDKYHQFFIEEILSSVCISEDLLQNYSDVYFK
LKKSDDDNLQKDFKSAKDTIKKQISEYIKDSEKFKNLFNQNLIDAKKGQESDLILWLKQSKDNGIELFKANSDITDIDEALEIIK
SFKGWTTYFKGFHENRKNVYSSNDIPTSIIYRIVDDNLPKFLENKAKYESLKDKAPEAINYEQIKKDLAEELTFDIDYKTSEVN
QRVFSLDEVFEIANFNNYLNQSGITKFNTIIGGKFVNGENTKRKGINEYINLYSQQINDKTLKKYKMSVLFKQILSDTESKSFVI
DKLEDDSDVVTTMQSFYEQIAAFKTVEEKSIKETLSLLFDDLKAQKLDLSKIYFKNDKSLTDLSQQVFDDYSVIGTAVLEYIT
QQIAPKNLDNPSKKEQELIAKKTEKAKYLSLETIKLALEEFNKHRDIDKQCRFEEILANFAAIPMIFDEIAQNKDNLAQISIKYQ
NQGKKDLLQASAEDDVKAIKDLLDQTNNLLHKLKIFHISQSEDKANILDKDEHFYLVFEECYFELANIVPLYNKIRNYITQKP
YSDEKFKLNFENSTLANGWDKNKEPDNTAILFIKDDKYYLGVMNKKNNKIFDDKAIKENKGEGYKKIVYKLLPGANKMLP
KVFFSAKSIKFYNPSEDILRIRNHSTHTKNGSPQKGYEKFEFNIEDCRKFIDFYKQSISKHPEWKDFGFRFSDTQRYNSIDEFYR
EVENQGYKLTFENISESYIDSVVNQGKLYLFQIYNKDFSAYSKGRPNLHTLYWKALFDERNLQDVVYKLNGEAELFYRKQSI
PKKITHPAKEAIANKNKDNPKKESVFEYDLIKDKRFTEDKFFFHCPITINFKSSGANKFNDEINLLLKEKANDVHILSIDRGERH
LAYYTLVDGKGNIIKQDTFNIIGNDRMKTNYHDKLAAIEKDRDSARKDWKKINNIKEMKEGYLSQVVHEIAKLVIEYNAIVV
FEDLN<u>FGFARGRFA</u>VEKQVYQKLEKMLIEKLNYLVFKDNEFDKTGGVLRAYQLTAPFETFKKMGKQTGIIYYVPAGFTSKI
CPVTGFVNQLYPKYESVSKSQEFFSKFDKICYNLDKGYFEFSFDYKNFGDKAAKGKWTIASFGSRLINFRNSDKNHNWDTRE
VYPTKELEKLLKDYSIEYGHGECIKAAICGESDKKFFAKLTSVLNTILQMRNSKTGTELDYLISPVADVNGNFFDSRQAPKNM
PQDADANGAYHIGLKGLMLLGRIKNNQEGKKLNLVIKNEEYFEFVQNRNN (SEQ ID NO:14)

FIG. 3F

*Francisella novicida* U112 Cas12a variant (FGFKRGRFK; SEQ ID NO:61 mutated to FGFKAGAFK; SEQ ID NO:85)

MSIYQEFVNKYSLSKTLRFELIPQGKTLENIKARGLILDDEKRAKDYKKAKQIIDKYHQFFIEEILSSVCISEDLLQNYSDVYFK
LKKSDDDNLQKDFKSAKDTIKKQISEYIKDSEKFKNLFNQNLIDAKKGQESDLILWLKQSKDNGIELFKANSDITDIDEALEIIK
SFKGWTTYFKGFHENRKNVYSSNDIPTSIIYRIVDDNLPKFLENKAKYESLKDKAPEAINYEQIKKDLAEELTFDIDYKTSEVN
QRVFSLDEVFEIANFNNYLNQSGITKFNTIIGGKFVNGENTKRKGINEYINLYSQQINDKTLKKYKMSVLFKQILSDTESKSFVI
DKLEDDSDVVTTMQSFYEQIAAFKTVEEKSIKETLSLLFDDLKAQKLDLSKIYFKNDKSLTDLSQQVFDDYSVIGTAVLEYIT
QQIAPKNLDNPSKKEQELIAKKTEKAKYLSLETIKLALEEFNKHRDIDKQCRFEEILANFAAIPMIFDEIAQNKDNLAQISIKYQ
NQGKKDLLQASAEDDVKAIKDLLDQTNNLLHKLKIFHISQSEDKANILDKDEHFYLVFEECYFELANIVPLYNKIRNYITQKP
YSDEKFKLNFENSTLANGWDKNKEPDNTAILFIKDDKYYLGVMNKKNNKIFDDKAIKENKGEGYKKIVYKLLPGANKMLP
KVFFSAKSIKFYNPSEDILRIRNHSTHTKNGSPQKGYEKFEFNIEDCRKFIDFYKQSISKHPEWKDFGFRFSDTQRYNSIDEFYR
EVENQGYKLTFENISESYIDSVVNQGKLYLFQIYNKDFSAYSKGRPNLHTLYWKALFDERNLQDVVYKLNGEAELFYRKQSI
PKKITHPAKEAIANKNKDNPKKESVFEYDLIKDKRFTEDKFFFHCPITINFKSSGANKFNDEINLLLKEKANDVHILSIDRGERH
LAYYTLVDGKGNIIKQDTFNIIGNDRMKTNYHDKLAAIEKDRDSARKDWKKINNIKEMKEGYLSQVVHEIAKLVIEYNAIVV
FEDLNFGFKAGAFKVEKQVYQKLEKMLIEKLNYLVFKDNEFDKTGGVLRAYQLTAPFETFKKMGKQTGIIYYVPAGFTSKI
CPVTGFVNQLYPKYESVSKSQEFFSKFDKICYNLDKGYFEFSFDYKNFGDKAAKGKWTIASFGSRLINFRNSDKNHNWDTRE
VYPTKELEKLLKDYSIEYGHGECIKAAICGESDKKFFAKLTSVLNTILQMRNSKTGTELDYLISPVADVNGNFFDSRQAPKNM
PQDADANGAYHIGLKGLMLLGRIKNNQEGKKLNLVIKNEEYFEFVQNRNN (SEQ ID NO:15)

FIG. 4A

*Porphyromonas macacae* Cas12a

MKTQHFFEDFTSLYSLSKTIRFELKPIGKTLENIKKNGLIRRDEQRLDDYEKLKKVIDEYHEDFIANILSSFSFSEEILQSYIQNLS
ESEARAKIEKTMRDTLAKAFSEDERYKSIFKKELVKKDIPVWCPAYKSLCKKFDNFTTSLVPFHENRKNLYTSNEITASIPYRI
VHVNLPKFIQNIEALCELQKKMGADLYLEMMENLRNVWPSFVKTPDDLCNLKTYNHLMVQSSISEYNRFVGGYSTEDGTK
HQGINEWINIYRQRNKEMRLPGLVFLHKQILAKVDSSSFISDTLENDDQVFCVLRQFRKLFWNTVSSKEDDAASLKDLFCGLS
GYDPEAIYVSDAHLATISKNIFDRWNYISDAIRRKTEVLMPRKKESVERYAEKISKQIKKRQSYSLAELDDLLAHYSEESLPAG
FSLLSYFTSLGGQKYLVSDGEVILYEEGSNIWDEVLIAFRDLQVILDKDFTEKKLGKDEEAVSVIKKALDSALRLRKFFDLLSG
TGAEIRRDSSFYALYTDRMDKLKGLLKMYDKVRNYLTKKPYSIEKFKLHFDNPSLLSGWDKNKELNNLSVIFRQNGYYYLG
IMTPKGKNLFKTLPKLGAEEMFYEKMEYKQIAEPMLMLPKVFFPKKTKPAFAPDQSVVDIYNKKTFKTGQKGFNKKDLYRL
IDFYKEALTVHEWKLFNFSFSPTEQYRNIGEFFDEVREQAYKVSMVNVPASYIDEAVENGKLYLFQIYNKDFSPYSKGIPNLH
TLYWKALFSEQNQSRVYKLCGGGELFYRKASLHMQDTTVHPKGISIHKKNLNKKGETSLFNYDLVKDKRFTEDKFFFHVPIS
INYKNKKITNVNQMVRDYIAQNDDLQIIGIDRGERNLLYISRIDTRGNLLEQFSLNVIESDKGDLRTDYQKILGDREQERLRRR
QEWKSIESIKDLKDGYMSQVVHKICNMVVEHKAIVVLENLNLSFMKGRKKVEKSVYEKFERMLVDKLNYLVVDKKNLSN
EPGGLYAAYQLTNPLFSFEELHRYPQSGILFFVDPWNTSLTDPSTGFVNLLGRINYTNVGDARKFFDRFNAIRYDGKGNILFD
LDLSRFDVRVETQRKLWTLTTFGSRIAKSKKSGKWMVERIENLSLCFLELFEQFNIGYRVEKDLKKAILSQDRKEFYVRLIYL
FNLMMQIRNSDGEEDYILSPALNEKNLQFDSRLIEAKDLPVDADANGAYNVARKGLMVVQRIKRGDHESIHRIGRAQWLRY
VQEGIVE (SEQ ID NO:16)

FIG. 4B

*Porphyromonas macacae* Cas12a variant (LSFMKGRKK; SEQ ID NO:86 deleted)

MKTQHFFEDFTSLYSLSKTIRFELKPIGKTLENIKKNGLIRRDEQRLDDYEKLKKVIDEYHEDFIANILSSFSFSEEILQSYIQNLS
ESEARAKIEKTMRDTLAKAFSEDERYKSIFKKELVKKDIPVWCPAYKSLCKKFDNFTTSLVPFHENRKNLYTSNEITASIPYRI
VHVNLPKFIQNIEALCELQKKMGADLYLEMMENLRNVWPSFVKTPDDLCNLKTYNHLMVQSSISEYNRFVGGYSTEDGTK
HQGINEWINIYRQRNKEMRLPGLVFLHKQILAKVDSSSFISDTLENDDQVFCVLRQFRKLFWNTVSSKEDDAASLKDLFCGLS
GYDPEAIYVSDAHLATISKNIFDRWNYISDAIRRKTEVLMPRKKESVERYAEKISKQIKKRQSYSLAELDDLLAHYSEESLPAG
FSLLSYFTSLGGQKYLVSDGEVILYEEGSNIWDEVLIAFRDLQVILDKDFTEKKLGKDEEAVSVIKKALDSALRLRKFFDLLSG
TGAEIRRDSSFYALYTDRMDKLKGLLKMYDKVRNYLTKKPYSIEKFKLHFDNPSLLSGWDKNKELNNLSVIFRQNGYYYLG
IMTPKGKNLFKTLPKLGAEEMFYEKMEYKQIAEPMLMLPKVFFPKKTKPAFAPDQSVVDIYNKKTFKTGQKGFNKKDLYRL
IDFYKEALTVHEWKLFNFSFSPTEQYRNIGEFFDEVREQAYKVSMVNVPASYIDEAVENGKLYLFQIYNKDFSPYSKGIPNLH
TLYWKALFSEQNQSRVYKLCGGGELFYRKASLHMQDTTVHPKGISIHKKNLNKKGETSLFNYDLVKDKRFTEDKFFFHVPIS
INYKNKKITNVNQMVRDYIAQNDDLQIIGIDRGERNLLYISRIDTRGNLLEQFSLNVIESDKGDLRTDYQKILGDREQERLRRR
QEWKSIESIKDLKDGYMSQVVHKICNMVVEHKAIVVLENLNVEKSVYEKFERMLVDKLNYLVVDKKNLSNEPGGLYAAYQ
LTNPLFSFEELHRYPQSGILFFVDPWNTSLTDPSTGFVNLLGRINYTNVGDARKFFDRFNAIRYDGKGNILFDLDLSRFDVRVE
TQRKLWTLTTFGSRIAKSKKSGKWMVERIENLSLCFLELFEQFNIGYRVEKDLKKAILSQDRKEFYVRLIYLFNLMMQIRNSD
GEEDYILSPALNEKNLQFDSRLIEAKDLPVDADANGAYNVARKGLMVVQRIKRGDHESIHRIGRAQWLRYVQEGIVE (SEQ
ID NO: 142)

FIG. 5A

*Moraxella bovoculi* 237 Cas12a

MLFQDFTHLYPLSKTVRFELKPIDRTLEHIHAKNFLSQDETMADMHQKVKVILDDYHRDFIADMMGEVKLTKLAEFYDVYL
KFRKNPKDDELQKQLKDLQAVLRKEIVKPIGNGGKYKAGYDRLFGAKLFKDGKELGDLAKFVIAQEGESSPKLAHLAHFEK
FSTYFTGFHDNRKNMYSDEDKHTAIAYRLIHENLPRFIDNLQILTTIKQKHSALYDQIINELTASGLDVSLASHLDGYHKLLTQ
EGITAYNTLLGGISGEAGSPKIQGINELINSHHNQHCHKSERIAKLRPLHKQILSDGMSVSFLPSKFADDSEMCQAVNEFYRHY
ADVFAKVQSLFDGFDDHQKDGIYVEHKNLNELSKQAFGDFALLGRVLDGYYVDVVNPEFNERFAKAKTDNAKAKLTKEK
DKFIKGVHSLASLEQAIEHYTARHDDESVQAGKLGQYFKHGLAGVDNPIQKIHNNHSTIKGFLERERPAGERALPKIKSGKNP
EMTQLRQLKELLDNALNVAHFAKLLTTKTTLDNQDGNFYGEFGVLYDELAKIPTLYNKVRDYLSQKPFSTEKYKLNFGNPT
LLNGWDLNKEKDNFGVILQKDGCYYLALLDKAHKKVFDNAPNTGKSIYQKMIYKYLEVRKQFPKVFFSKEAIAINYHPSKE
LVEIKDKGRQRSDDERLKLYRFILECLKIHPKYDKKFEGAIGDIQLFKKDKKGREVPISEKDLFDKINGIFSSKPKLEMEDFFIG
EFKRYNPSQDLVDQYNIYKKIDSNDNRKKENFYNNHPKFKKDLVRYYYESMCKHEEWEESFEFSKKLQDIGCYVDVNELFT
EIETRRLNYKISFCNINADYIDELVEQGQLYLFQIYNKDFSPKAHGKPNLHTLYFKALFSEDNLADPIYKLNGEAQIFYRKASL
DMNETTIHRAGEVLENKNPDNPKKRQFVYDIIKDKRYTQDKFMLHVPITMNFGVQGMTIKEFNKKVNQSIQQYDEVNVIGID
RGERHLLYLTVINSKGEILEQCSLNDITTASANGTQMTTPYHKILDKREIERLNARVGWGEIETIKELKSGYLSHVVHQISQLM
LKYNAIVVLEDLNFGFKRGRFKVEKQIYQNFENALIKKLNHLVLKDKADDEIGSYKNALQLTNNFTDLKSIGKQTGFLFYVP
AWNTSKIDPETGFVDLLKPRYENIAQSQAFFGKFDKICYNADKDYFEFHIDYAKFTDKAKNSRQIWTICSHGDKRYVYDKTA
NQNKGAAKGINVNDELKSLFARHHINEKQPNLVMDICQNNDKEFHKSLMYLLKTLLALRYSNASSDEDFILSPVANDEGVFF
NSALADDTQPQNADANGAYHIALKGLWLLNELKNSDDLNKVKLAIDNQTWLNFAQNR (SEQ ID NO:17)

FIG. 5B

*Moraxella bovoculi* 237 Cas12a variant (FGFKRGRFK; SEQ ID NO:61 deleted)

MLFQDFTHLYPLSKTVRFELKPIDRTLEHIHAKNFLSQDETMADMHQKVKVILDDYHRDFIADMMGEVKLTKLAEFYDVYL
KFRKNPKDDELQKQLKDLQAVLRKEIVKPIGNGGKYKAGYDRLFGAKLFKDGKELGDLAKFVIAQEGESSPKLAHLAHFEK
FSTYFTGFHDNRKNMYSDEDKHTAIAYRLIHENLPRFIDNLQILTTIKQKHSALYDQIINELTASGLDVSLASHLDGYHKLLTQ
EGITAYNTLLGGISGEAGSPKIQGINELINSHHNQHCHKSERIAKLRPLHKQILSDGMSVSFLPSKFADDSEMCQAVNEFYRHY
ADVFAKVQSLFDGFDDHQKDGIYVEHKNLNELSKQAFGDFALLGRVLDGYYVDVVNPEFNERFAKAKTDNAKAKLTKEK
DKFIKGVHSLASLEQAIEHYTARHDDESVQAGKLGQYFKHGLAGVDNPIQKIHNNHSTIKGFLERERPAGERALPKIKSGKNP
EMTQLRQLKELLDNALNVAHFAKLLTTKTTLDNQDGNFYGEFGVLYDELAKIPTLYNKVRDYLSQKPFSTEKYKLNFGNPT
LLNGWDLNKEKDNFGVILQKDGCYYLALLDKAHKKVFDNAPNTGKSIYQKMIYKYLEVRKQFPKVFFSKEAIAINYHPSKE
LVEIKDKGRQRSDDERLKLYRFILECLKIHPKYDKKFEGAIGDIQLFKKDKKGREVPISEKDLFDKINGIFSSKPKLEMEDFFIG
EFKRYNPSQDLVDQYNIYKKIDSNDNRKKENFYNNHPKFKKDLVRYYYESMCKHEEWEESFEFSKKLQDIGCYVDVNELFT
EIETRRLNYKISFCNINADYIDELVEQGQLYLFQIYNKDFSPKAHGKPNLHTLYFKALFSEDNLADPIYKLNGEAQIFYRKASL
DMNETTIHRAGEVLENKNPDNPKKRQFVYDIIKDKRYTQDKFMLHVPITMNFGVQGMTIKEFNKKVNQSIQQYDEVNVIGID
RGERHLLYLTVINSKGEILEQCSLNDITTASANGTQMTTPYHKILDKREIERLNARVGWGEIETIKELKSGYLSHVVHQISQLM
LKYNAIVVLEDLNVEKQIYQNFENALIKKLNHLVLKDKADDEIGSYKNALQLTNNFTDLKSIGKQTGFLFYVPAWNTSKIDP
ETGFVDLLKPRYENIAQSQAFFGKFDKICYNADKDYFEFHIDYAKFTDKAKNSRQIWTICSHGDKRYVYDKTANQNKGAAK
GINVNDELKSLFARHHINEKQPNLVMDICQNNDKEFHKSLMYLLKTLLALRYSNASSDEDFILSPVANDEGVFFNSALADDT
QPQNADANGAYHIALKGLWLLNELKNSDDLNKVKLAIDNQTWLNFAQNR (SEQ ID NO:18)

FIG. 6A

*Moraxella bovoculi* AAX08_00205 Cas12a

MGIHGVPAALFQDFTHLYPLSKTVRFELKPIGRTLEHIHAKNFLSQDETMADMYQKVKVILDDYHRDFIADMMGEVKLTKL
AEFYDVYLKFRKNPKDDGLQKQLKDLQAVLRKESVKPIGSGGKYKTGYDRLFGAKLFKDGKELGDLAKFVIAQEGESSPKL
AHLAHFEKFSTYFTGFHDNRKNMYSDEDKHTAIAYRLIHENLPRFIDNLQILTTIKQKHSALYDQIINELTASGLDVSLASHLD
GYHKLLTQEGITAYNRIIGEVNGYTNKHNQICHKSERIAKLRPLHKQILSDGMGVSFLPSKFADDSEMCQAVNEFYRHYTDV
FAKVQSLFDGFDDHQKDGIYVEHKNLNELSKQAFGDFALLGRVLDGYYVDVVNPEFNERFAKAKTDNAKAKLTKEKDKFI
KGVHSLASLEQAIEHHTARHDDESVQAGKLGQYFKHGLAGVDNPIQKIHNNHSTIKGFLERERPAGERALPKIKSGKNPEMT
QLRQLKELLDNALNVAHFAKLLTTKTTLDNQDGNFYGEFGVLYDELAKIPTLYNKVRDYLSQKPFSTEKYKLNFGNPTLLN
GWDLNKEKDNFGVILQKDGCYYLALLDKAHKKVFDNAPNTGKNVYQKMVYKLLPGPNKMLPKVFFAKSNLDYYNPSAEL
LDKYAKGTHKKGDNFNLKDCHALIDFFKAGINKHPEWQHFGFKFSPTSSYRDLSDFYREVEPQGYQVKFVDINADYIDELVE
QGKLYLFQIYNKDFSPKAHGKPNLHTLYFKALFSEDNLADPIYKLNGEAQIFYRKASLDMNETTIHRAGEVLENKNPDNPKK
RQFVYDIIKDKRYTQDKFMLHVPITMNFGVQGMTIKEFNKKVNQSIQQYDEVNVIGIDRGERHLLYLTVINSKGEILEQRSLN
DITTASANGTQVTTPYHKILDKREIERLNARVGWGEIETIKELKSGYLSHVVHQINQLMLKYNAIVVLEDLNFGFKRGRFKV
EKQIYQNFENALIKKLNHLVLKDKADDEIGSYKNALQLTNNFTDLKSIGKQTGFLFYVPAWNTSKIDPETGFVDLLKPRYENI
AQSQAFFGKFDKICYNTDKGYFEFHIDYAKFTDKAKNSRQKWAICSHGDKRYVYDKTANQNKGAAKGINVNDELKSLFAR
YHINDKQPNLVMDICQNNDKEFHKSLMCLLKTLLALRYSNASSDEDFILSPVANDEGVFFNSALADDTQPQNADANGAYHI

ALKGLWLLNELKNSDDLNKVKLAIDNQTWLNFAQNR (SEQ ID NO:144)

FIG. 6B

*Moraxella bovoculi* AAX08_00205 Cas12a variant (FGFKRGRFK; SEQ ID NO:61 deleted)

MGIHGVPAALFQDFTHLYPLSKTVRFELKPIGRTLEHIHAKNFLSQDETMADMYQKVKVILDDYHRDFIADMMGEVKLTKL
AEFYDVYLKFRKNPKDDGLQKQLKDLQAVLRKESVKPIGSGGKYKTGYDRLFGAKLFKDGKELGDLAKFVIAQEGESSPKL
AHLAHFEKFSTYFTGFHDNRKNMYSDEDKHTAIAYRLIHENLPRFIDNLQILTTIKQKHSALYDQIINELTASGLDVSLASHLD
GYHKLLTQEGITAYNRIIGEVNGYTNKHNQICHKSERIAKLRPLHKQILSDGMGVSFLPSKFADDSEMCQAVNEFYRHYTDV
FAKVQSLFDGFDDHQKDGIYVEHKNLNELSKQAFGDFALLGRVLDGYYVDVVNPEFNERFAKAKTDNAKAKLTKEKDKFI
KGVHSLASLEQAIEHHTARHDDESVQAGKLGQYFKHGLAGVDNPIQKIHNNHSTIKGFLERERPAGERALPKIKSGKNPEMT
QLRQLKELLDNALNVAHFAKLLTTKTTLDNQDGNFYGEFGVLYDELAKIPTLYNKVRDYLSQKPFSTEKYKLNFGNPTLLN
GWDLNKEKDNFGVILQKDGCYYLALLDKAHKKVFDNAPNTGKNVYQKMVYKLLPGPNKMLPKVFFAKSNLDYYNPSAEL
LDKYAKGTHKKGDNFNLKDCHALIDFFKAGINKHPEWQHFGFKFSPTSSYRDLSDFYREVEPQGYQVKFVDINADYIDELVE
QGKLYLFQIYNKDFSPKAHGKPNLHTLYFKALFSEDNLADPIYKLNGEAQIFYRKASLDMNETTIHRAGEVLENKNPDNPKK
RQFVYDIIKDKRYTQDKFMLHVPITMNFGVQGMTIKEFNKKVNQSIQQYDEVNVIGIDRGERHLLYLTVINSKGEILEQRSLN
DITTASANGTQVTTPYHKILDKREIERLNARVGWGEIETIKELKSGYLSHVVHQINQLMLKYNAIVVLEDLNVEKQIYQNFEN
ALIKKLNHLVLKDKADDEIGSYKNALQLTNNFTDLKSIGKQTGFLFYVPAWNTSKIDPETGFVDLLKPRYENIAQSQAFFGKF
DKICYNTDKGYFEFHIDYAKFTDKAKNSRQKWAICSHGDKRYVYDKTANQNKGAAKGINVNDELKSLFARYHINDKQPNL
VMDICQNNDKEFHKSLMCLLKTLLALRYSNASSDEDFILSPVANDEGVFFNSALADDTQPQNADANGAYHIALKGLWLLNE

LKNSDDLNKVKLAIDNQTWLNFAQNR (SEQ ID NO:19)

FIG. 7A

*Moraxella bovoculi* AAX11_00205 Cas12a

MGIHGVPAALFQDFTHLYPLSKTVRFELKPIGKTLEHIHAKNFLNQDETMADMYQKVKAILDDYHRDFIADMMGEVKLTKL
AEFYDVYLKFRKNPKDDGLQKQLKDLQAVLRKEIVKPIGNGGKYKAGYDRLFGAKLFKDGKELGDLAKFVIAQEGESSPKL
AHLAHFEKFSTYFTGFHDNRKNMYSDEDKHTAIAYRLIHENLPRFIDNLQILATIKQKHSALYDQIINELTASGLDVSLASHLD
GYHKLLTQEGITAYNTLLGGISGEAGSRKIQGINELINSHHNQHCHKSERIAKLRPLHKQILSDGMGVSFLPSKFADDSEVCQA
VNEFYRHYADVFAKVQSLFDGFDDYQKDGIYVEYKNLNELSKQAFGDFALLGRVLDGYYVDVVNPEFNERFAKAKTDNA
KAKLTKEKDKFIKGVHSLASLEQAIEHYTARHDDESVQAGKLGQYFKHGLAGVDNPIQKIHNNHSTIKGFLERERPAGERAL
PKIKSDKSPEIRQLKELLDNALNVAHFAKLLTTKTTLHNQDGNFYGEFGALYDELAKIATLYNKVRDYLSQKPFSTEKYKLN
FGNPTLLNGWDLNKEKDNFGVILQKDGCYYLALLDKAHKKVFDNAPNTGKSVYQKMIYKLLPGPNKMLPKVFFAKSNLDY
YNPSAELLDKYAQGTHKKGDNFNLKDCHALIDFFKAGINKHPEWQHFGFKFSPTSSYQDLSDFYREVEPQGYQVKFVDINA
DYINELVEQGQLYLFQIYNKDFSPKAHGKPNLHTLYFKALFSEDNLVNPIYKLNGEAEIFYRKASLDMNETTIHRAGEVLENK
NPDNPKKRQFVYDIIKDKRYTQDKFMLHVPITMNFGVQGMTIKEFNKKVNQSIQQYDEVNVIGIDRGERHLLYLTVINSKGEI
LEQRSLNDITTASANGTQMTTPYHKILDKREIERLNARVGWGEIETIKELKSGYLSHVVHQISQLMLKYNAIVVLEDLNFGFK
RGRFKVEKQIYQNFENALIKKLNHLVLKDKADDEIGSYKNALQLTNNFTDLKSIGKQTGFLFYVPAWNTSKIDPETGFVDLL
KPRYENIAQSQAFFGKFDKICYNADRGYFEFHIDYAKFNDKAKNSRQIWKICSHGDKRYVYDKTANQNKGATIGVNVNDEL
KSLFTRYHINDKQPNLVMDICQNNDKEFHKSLMYLLKTLLALRYSNASSDEDFILSPVANDEGVFFNSALADDTQPQNADAN

GAYHIALKGLWLLNELKNSDDLNKVKLAIDNQTWLNFAQNR (SEQ ID NO:20)

FIG. 7B

*Moraxella bovoculi* AAX11_00205 Cas12a variant (FGFKRGRFK; SEQ ID NO:61 deleted)

MGIHGVPAALFQDFTHLYPLSKTVRFELKPIGKTLEHIHAKNFLNQDETMADMYQKVKAILDDYHRDFIADMMGEVKLTKL
AEFYDVYLKFRKNPKDDGLQKQLKDLQAVLRKEIVKPIGNGGKYKAGYDRLFGAKLFKDGKELGDLAKFVIAQEGESSPKL
AHLAHFEKFSTYFTGFHDNRKNMYSDEDKHTAIAYRLIHENLPRFIDNLQILATIKQKHSALYDQIINELTASGLDVSLASHLD
GYHKLLTQEGITAYNTLLGGISGEAGSRKIQGINELINSHHNQHCHKSERIAKLRPLHKQILSDGMGVSFLPSKFADDSEVCQA
VNEFYRHYADVFAKVQSLFDGFDDYQKDGIYVEYKNLNELSKQAFGDFALLGRVLDGYYVDVVNPEFNERFAKAKTDNA
KAKLTKEKDKFIKGVHSLASLEQAIEHYTARHDDESVQAGKLGQYFKHGLAGVDNPIQKIHNNHSTIKGFLERERPAGERAL
PKIKSDKSPEIRQLKELLDNALNVAHFAKLLTTKTTLHNQDGNFYGEFGALYDELAKIATLYNKVRDYLSQKPFSTEKYKLN
FGNPTLLNGWDLNKEKDNFGVILQKDGCYYLALLDKAHKKVFDNAPNTGKSVYQKMIYKLLPGPNKMLPKVFFAKSNLDY
YNPSAELLDKYAQGTHKKGDNFNLKDCHALIDFFKAGINKHPEWQHFGFKFSPTSSYQDLSDFYREVEPQGYQVKFVDINA
DYINELVEQGQLYLFQIYNKDFSPKAHGKPNLHTLYFKALFSEDNLVNPIYKLNGEAEIFYRKASLDMNETTIHRAGEVLENK
NPDNPKKRQFVYDIIKDKRYTQDKFMLHVPITMNFGVQGMTIKEFNKKVNQSIQQYDEVNVIGIDRGERHLLYLTVINSKGEI
LEQRSLNDITTASANGTQMTTPYHKILDKREIERLNARVGWGEIETIKELKSGYLSHVVHQISQLMLKYNAIVVLEDLNVEKQ
IYQNFENALIKKLNHLVLKDKADDEIGSYKNALQLTNNFTDLKSIGKQTGFLFYVPAWNTSKIDPETGFVDLLKPRYENIAQS
QAFFGKFDKICYNADRGYFEFHIDYAKFNDKAKNSRQIWKICSHGDKRYVYDKTANQNKGATIGVNVNDELKSLFTRYHIN
DKQPNLVMDICQNNDKEFHKSLMYLLKTLLALRYSNASSDEDFILSPVANDEGVFFNSALADDTQPQNADANGAYHIALKG

LWLLNELKNSDDLNKVKLAIDNQTWLNFAQNR (SEQ ID NO:21)

FIG. 8A

*Thiomicrospira* sp.XS5 Cas12a

MGIHGVPAATKTFDSEFFNLYSLQKTVRFELKPVGETASFVEDFKNEGLKRVVSEDERRAVDYQKVKEIIDDYHRDFIEESLN
YFPEQVSKDALEQAFHLYQKLKAAKVEEREKALKEWEALQKKLREKVVKCFSDSNKARFSRIDKKELIKEDLINWLVAQNR
EDDIPTVETFNNFTTYFTGFHENRKNIYSKDDHATAISFRLIHENLPKFFDNVISFNKLKEGFPELKFDKVKEDLEVDYDLKHA
FEIEYFVNFVTQAGIDQYNYLLGGKTLEDGTKKQGMNEQINLFKQQQTRDKARQIPKLIPLFKQILSERTESQSFIPKQFESDQ
ELFDSLQKLHNNCQDKFTVLQQAILGLAEADLKKVFIKTSDLNALSNTIFGNYSVFSDALNLYKESLKTKKAQEAFEKLPAHS
IHDLIQYLEQFNSSLDAEKQQSTDTVLNYFIKTDELYSRFIKSTSEAFTQVQPLFELEALSSKRRPPESEDEGAKGQEGFEQIKRI
KAYLDTLMEAVHFAKPLYLVKGRKMIEGLDKDQSFYEAFEMAYQELESLIIPIYNKARSYLSRKPFKADKFKINFDNNTLLS
GWDANKETANASILFKKDGLYYLGIMPKGKTFLFDYFVSSEDSEKLKQRRQKTAEEALAQDGESYFEKIRYKLLPGASKML
PKVFFSNKNIGFYNPSDDILRIRNTASHTKNGTPQKGHSKVEFNLNDCHKMIDFFKSSIQKHPEWGSFGFTFSDTSDFEDMSAF
YREVENQGYVISFDKIKETYIQSQVEQGNLYLFQIYNKDFSPYSKGKPNLHTLYWKALFEEANLNNVVAKLNGEAEIFFRRHS
IKASDKVVHPANQAIDNKNPHTEKTQSTFEYDLVKDKRYTQDKFFFHVPISLNFKAQGVSKFNDKVNGFLKGNPDVNIIGID
RGERHLLYFTVVNQKGEILVQESLNTLMSDKGHVNDYQQKLDKKEQERDAARKSWTTVENIKELKEGYLSHVVHKLAHLII
KYNAIVCLEDLN<u>FGFKRGRFK</u>VEKQVYQKFEKALIDKLNYLVFKEKELGEVGHYLTAYQLTAPFESFKKLGKQSGILFYVP
ADYTSKIDPTTGFVNFLDLRYQSVEKAKQLLSDFNAIRFNSVQNYFEFEIDYKKLTPKRKVGTQSKWVICTYGDVRYQNRRN
QKGHWETEEVNVTEKLKALFASDSKTTTVIDYANDDNLIDVILEQDKASFFKELLWLLKLTMTLRHSKIKSEDDFILSPVKNE
QGEFYDSRKAGEVWPKDADANGAYHIALKGLWNLQQINQWEKGKTLNLAIKNQDWFSFIQEKPYQE (SEQ ID NO:22)

FIG. 8B

*Thiomicrospira* sp.XS5 Cas12a variant (FGFKRGRFK; SEQ ID NO: 61 deleted)

MGIHGVPAATKTFDSEFFNLYSLQKTVRFELKPVGETASFVEDFKNEGLKRVVSEDERRAVDYQKVKEIIDDYHRDFIEESLN
YFPEQVSKDALEQAFHLYQKLKAAKVEEREKALKEWEALQKKLREKVVKCFSDSNKARFSRIDKKELIKEDLINWLVAQNR
EDDIPTVETFNNFTTYFTGFHENRKNIYSKDDHATAISFRLIHENLPKFFDNVISFNKLKEGFPELKFDKVKEDLEVDYDLKHA
FEIEYFVNFVTQAGIDQYNYLLGGKTLEDGTKKQGMNEQINLFKQQQTRDKARQIPKLIPLFKQILSERTESQSFIPKQFESDQ
ELFDSLQKLHNNCQDKFTVLQQAILGLAEADLKKVFIKTSDLNALSNTIFGNYSVFSDALNLYKESLKTKKAQEAFEKLPAHS
IHDLIQYLEQFNSSLDAEKQQSTDTVLNYFIKTDELYSRFIKSTSEAFTQVQPLFELEALSSKRRPPESEDEGAKGQEGFEQIKRI
KAYLDTLMEAVHFAKPLYLVKGRKMIEGLDKDQSFYEAFEMAYQELESLIIPIYNKARSYLSRKPFKADKFKINFDNNTLLS
GWDANKETANASILFKKDGLYYLGIMPKGKTFLFDYFVSSEDSEKLKQRRQKTAEEALAQDGESYFEKIRYKLLPGASKML
PKVFFSNKNIGFYNPSDDILRIRNTASHTKNGTPQKGHSKVEFNLNDCHKMIDFFKSSIQKHPEWGSFGFTFSDTSDFEDMSAF
YREVENQGYVISFDKIKETYIQSQVEQGNLYLFQIYNKDFSPYSKGKPNLHTLYWKALFEEANLNNVVAKLNGEAEIFFRRHS
IKASDKVVHPANQAIDNKNPHTEKTQSTFEYDLVKDKRYTQDKFFFHVPISLNFKAQGVSKFNDKVNGFLKGNPDVNIIGID
RGERHLLYFTVVNQKGEILVQESLNTLMSDKGHVNDYQQKLDKKEQERDAARKSWTTVENIKELKEGYLSHVVHKLAHLII
KYNAIVCLEDLNVEKQVYQKFEKALIDKLNYLVFKEKELGEVGHYLTAYQLTAPFESFKKLGKQSGILFYVPADYTSKIDPT
TGFVNFLDLRYQSVEKAKQLLSDFNAIRFNSVQNYFEFEIDYKKLTPKRKVGTQSKWVICTYGDVRYQNRRNQKGHWETEE
VNVTEKLKALFASDSKTTTVIDYANDDNLIDVILEQDKASFFKELLWLLKLTMTLRHSKIKSEDDFILSPVKNEQGEFYDSRK
AGEVWPKDADANGAYHIALKGLWNLQQINQWEKGKTLNLAIKNQDWFSFIQEKPYQE (SEQ ID NO:23)

FIG. 9A

*Butyrivibrio* sp. NC3005 Cas12a

MGIHGVPAAYYQNLTKKYPVSKTIRNELIPIGKTLENIRKNNILESDVKRKQDYEHVKGIMDEYHKQLINEALDNYMLPSLN
QAAEIYLKKHVDVEDREEFKKTQDLLRREVTGRLKEHENYTKIGKKDILDLLEKLPSISEEDYNALESFRNFYTYFTSYNKVR
ENLYSDEEKSSTVAYRLINENLPKFLDNIKSYAFVKAAGVLADCIEEEEQDALFMVETFNMTLTQEGIDMYNYQIGKVNSAIN
LYNQKNHKVEEFKKIPKMKVLYKQILSDREEVFIGEFKDDETLLSSIGAYGNVLMTYLKSEKINIFFDALRESEGKNVYYVKND
LSKTTMSNIVFGSWSAFDELLNQEYDLANENKKKDDKYFEKRQKELKKNKSYTLEQMSNLSKEDISPIENYIERISEDIEKICI
YNGEFEKIVVNEHDSSRKLSKNIKAVKVIKDYLDSIKELEHDIKLINGSGQELEKNLVVYVGQEEALEQLRPVDSLYNLTRNY
LTKKPFSTEKVKLNFNKSTLLNGWDKNKETDNLGILFFKDGKYYLGIMNTTANKAFVNPPAAKTENVFKKVDYKLLPGSNK
MLPKVFFAKSNIGYYNPSTELYSNYKKGTHKKGPSFSIDDCHNLIDFFKESIKKHEDWSKFGFEFSDTADYRDISEFYREVEK
QGYKLTFTDIDESYINDLIEKNELYLFQIYNKDFSEYSKGKLNLHTLYFMMLFDQRNLDNVVYKLNGEAEVFYRPASIAENEL
VIHKAGEGIKNKNPNRAKVKETSTFSYDIVKDKRYSKYKFTLHIPITMNFGVDEVRRFNDVINNALRTDDNVNVIGIDRGERN
LLYVVVINSEGKILEQISLNSIINKEYDIETNYHALLDEREDDRNKARKDWNTIENIKELKTGYLSQVVNVVAKLVLKYNAIIC
LEDLN<u>FGFKRGRQK</u>VEKQVYQKFEKMLIEKLNYLVIDKSREQVSPEKMGGALNALQLTSKFKSFAELGKQSGIIYYVPAYL
TSKIDPTTGFVNLFYIKYENIEKAKQFFDGFDFIRFNKKDDMFEFSFDYKSFTQKACGIRSKWIVYTNGERIIKYPNPEKNNLFD
EKVINVTDEIKGLFKQYRIPYENGEDIKEIIISKAEADFYKRLFRLLHQTLQMRNSTSDGTRDYIISPVKNDRGEFFCSEFSEGT

MPKDADANGAYNIARKGLWVLEQIRQKDEGEKVNLSMTNAEWLKYAQLHLL (SEQ ID NO:24)

FIG. 9B

*Butyrivibrio* sp. NC3005 Cas12a variant (FGFKRGRQK; SEQ ID NO:73 deleted)

MGIHGVPAAYYQNLTKKYPVSKTIRNELIPIGKTLENIRKNNILESDVKRKQDYEHVKGIMDEYHKQLINEALDNYMLPSLN
QAAEIYLKKHVDVEDREEFKKTQDLLRREVTGRLKEHENYTKIGKKDILDLLEKLPSISEEDYNALESFRNFYTYFTSYNKVR
ENLYSDEEKSSTVAYRLINENLPKFLDNIKSYAFVKAAGVLADCIEEEEQDALFMVETFNMTLTQEGIDMYNYQIGKVNSAIN
LYNQKNHKVEEFKKIPKMKVLYKQILSDREEVFIGEFKDDETLLSSIGAYGNVLMTYLKSEKINIFFDALRESEGKNVYVKND
LSKTTMSNIVFGSWSAFDELLNQEYDLANENKKKDDKYFEKRQKELKKNKSYTLEQMSNLSKEDISPIENYIERISEDIEKICI
YNGEFEKIVVNEHDSSRKLSKNIKAVKVIKDYLDSIKELEHDIKLINGSGQELEKNLVVYVGQEEALEQLRPVDSLYNLTRNY
LTKKPFSTEKVKLNFNKSTLLNGWDKNKETDNLGILFFKDGKYYLGIMNTTANKAFVNPPAAKTENVFKKVDYKLLPGSNK
MLPKVFFAKSNIGYYNPSTELYSNYKKGTHKKGPSFSIDDCHNLIDFFKESIKKHEDWSKFGFEFSDTADYRDISEFYREVEK
QGYKLTFTDIDESYINDLIEKNELYLFQIYNKDFSEYSKGKLNLHTLYFMMLFDQRNLDNVVYKLNGEAEVFYRPASIAENEL
VIHKAGEGIKNKNPNRAKVKETSTFSYDIVKDKRYSKYKFTLHIPITMNFGVDEVRRFNDVINNALRTDDNVNVIGIDRGERN
LLYVVVINSEGKILEQISLNSIINKEYDIETNYHALLDEREDDRNKARKDWNTIENIKELKTGYLSQVVNVVAKLVLKYNAIIC
LEDLNVEKQVYQKFEKMLIEKLNYLVIDKSREQVSPEKMGGALNALQLTSKFKSFAELGKQSGIIYYVPAYLTSKIDPTTGFV
NLFYIKYENIEKAKQFFDGFDFIRFNKKDDMFEFSFDYKSFTQKACGIRSKWIVYTNGERIIKYPNPEKNNLFDEKVINVTDEI
KGLFKQYRIPYENGEDIKEIIISKAEADFYKRLFRLLHQTLQMRNSTSDGTRDYIISPVKNDRGEFFCSEFSEGTMPKDADANG

AYNIARKGLWVLEQIRQKDEGEKVNLSMTNAEWLKYAQLHLL (SEQ ID NO:25)

FIG. 10A

*Brumimicrobium aurantiacum* Cas12a

```
   1 MKNQINLFTN KFQLSKTLRF ELKPQGKTLE HINSKGFIKN DEKRADSYKK MKATIDAFHR
  61 DFIDLAMSNV KLTNLIDFEE IYNASNADKK DEKYKTKLSK IQEILRKEIA KGFKGEEVKD
 121 IFSKIDKKDL ITKLLEEWII ENKIEDIHFD PEFKNFTTYF SGFHQNRKNM YTDQEQSTAI
 181 AYRLIHENLP RFIDNINIFQ KINKVPDLEE NLKKLYQEIE EYLGINAINE AFELEYFNET
 241 LSQKGIDIYN LILGGRTAEE GKQKIQGLNE YINLYNQKQD KKNRVPKLKV LYKQILSDRT
 301 RTSFLPDTFE DDEESSASQK VLDSINNFYL ENLIDYLPND KNSTINVLEN LKLLLAELIN
 361 FELDKVYIKN DTSITNISMK IFKNYSVIRE ALNYFYENKI DPNFAHNFNN ANTDKKREKL
 421 EKEKAKITKQ TYLSISFIEE AIHLYINENS NGNQYKNTYK PNCIANYFKD FFIAENKEGS
 481 NKEFDFISKI KARYNTIKGV LNTPFPDNKR LHQEKNNIDN IKHFLDSIME YLHFAKPLVL
 541 SGSFAFEKDE QFYTNFDELY NQLELIIPLY NKVRNYATQK PYSTEKFKLN FENSTLLNGW
 601 DVNKEEANTS ILFIKNGFYY LGIMDKNHNK IFRNTPKSTN TDIYKKVNYK LLPGASKMLP
 661 KVFFGKKNLD YYKPSKDILR IRNHGTHTKG GKPQSGFDKL DFNLNDCHKL IDFFKDSIQK
 721 HPDWSKFKFK FSDTQIYESI DQFYRELEPQ AYSITYTNID SSFIEEQINE GKLYLFQIYN
 781 KDFSKFSNGK PNLHTLYWKA LFDEQNLKDV TYKLNGEAEI FYRKKSIQHD RQIIHKRNQP
 841 IINKNPNNEK KESIFKYNII KDKRYTIDKF QFHVPITLNF KAKGTDYINY DVLDYLKENP
 901 DVKIIGLDRG ERHLIYLTLI DQKGKILEQI SLNEIVNKKH NITTSYHNLL ETKEIERDKA
 961 RKNWGTVETI KELKEGYISQ VVHKISKMMI EHNAIVVMED LNMGFKRGRF KVEKQVYQKL
1021 EKMLIDKLNY LVLKDRQPNE PAGIYNALQL TNKFESFQKL GKQSGFLFYV PAWNTSKIDP
1081 TTGFVNLFHV KYESVRKSQE FFNKFNSIKY NPKEAIFEFD FDYNEFTTRA EGTKTNWTVC
1141 TYGDRIKTFR NPEKLNQWDN KEINITTAFE DFFGRHNITY GNGSDIKSQL ISREEKDFFS
1201 ELIHLFRLTL QMRNSKTNSE IDYLISPVKN ENGFFYDSRH ADKNLPKDAD ANGAYHIAKK
1261 GLQWIKEIQS FEGNEWKKLK LDKTNKGWLK FVQENQ
```

(SEQ ID NO:26)

FIG. 10B

*Brumimicrobium aurantiacum* Cas12a variant (MGFKRGRFK; SEQ ID NO:74 deleted)

```
   1 MKNQINLFTN KFQLSKTLRF ELKPQGKTLE HINSKGFIKN DEKRADSYKK MKATIDAFHR
  61 DFIDLAMSNV KLTNLIDFEE IYNASNADKK DEKYKTKLSK IQEILRKEIA KGFKGEEVKD
 121 IFSKIDKKDL ITKLLEEWII ENKIEDIHFD PEFKNFTTYF SGFHQNRKNM YTDQEQSTAI
 181 AYRLIHENLP RFIDNINIFQ KINKVPDLEE NLKKLYQEIE EYLGINAINE AFELEYFNET
 241 LSQKGIDIYN LILGGRTAEE GKQKIQGLNE YINLYNQKQD KKNRVPKLKV LYKQILSDRT
 301 RTSFLPDTFE DDEESSASQK VLDSINNFYL ENLIDYLPND KNSTINVLEN LKLLLAELIN
 361 FELDKVYIKN DTSITNISMK IFKNYSVIRE ALNYFYENKI DPNFAHNFNN ANTDKKREKL
 421 EKEKAKITKQ TYLSISFIEE AIHLYINENS NGNQYKNTYK PNCIANYFKD FFIAENKEGS
 481 NKEFDFISKI KARYNTIKGV LNTPFPDNKR LHQEKNNIDN IKHFLDSIME YLHFAKPLVL
 541 SGSFAFEKDE QFYTNFDELY NQLELIIPLY NKVRNYATQK PYSTEKFKLN FENSTLLNGW
 601 DVNKEEANTS ILFIKNGFYY LGIMDKNHNK IFRNTPKSTN TDIYKKVNYK LLPGASKMLP
 661 KVFFGKKNLD YYKPSKDILR IRNHGTHTKG GKPQSGFDKL DFNLNDCHKL IDFFKDSIQK
 721 HPDWSKFKFK FSDTQIYESI DQFYRELEPQ AYSITYTNID SSFIEEQINE GKLYLFQIYN
 781 KDFSKFSNGK PNLHTLYWKA LFDEQNLKDV TYKLNGEAEI FYRKKSIQHD RQIIHKRNQP
 841 IINKNPNNEK KESIFKYNII KDKRYTIDKF QFHVPITLNF KAKGTDYINY DVLDYLKENP
 901 DVKIIGLDRG ERHLIYLTLI DQKGKILEQI SLNEIVNKKH NITTSYHNLL ETKEIERDKA
 961 RKNWGTVETI KELKEGYISQ VVHKISKMMI EHNAIVVMED LN VEKQVYQKL
1021 EKMLIDKLNY LVLKDRQPNE PAGIYNALQL TNKFESFQKL GKQSGFLFYV PAWNTSKIDP
1081 TTGFVNLFHV KYESVRKSQE FFNKFNSIKY NPKEAIFEFD FDYNEFTTRA EGTKTNWTVC
1141 TYGDRIKTFR NPEKLNQWDN KEINITTAFE DFFGRHNITY GNGSDIKSQL ISREEKDFFS
1201 ELIHLFRLTL QMRNSKTNSE IDYLISPVKN ENGFFYDSRH ADKNLPKDAD ANGAYHIAKK
1261 GLQWIKEIQS FEGNEWKKLK LDKTNKGWLK FVQENQ
```

(SEQ ID NO:27)

FIG. 11A

*Porphyromonas crevioricanis* Cas12a

```
   1 MDSLKDFTNL YPVSKTLRFE LKPVGKTLEN IEKAGILKED EHRAESYRRV KKIIDTYHKV
  61 FIDSSLENMA KMGIENEIKA MLQSFCELYK KDHRTEGEDK ALDKIRAVLR GLIVGAFTGV
 121 CGRRENTVQN EKYESLFKEK LIKEILPDFV LSTEAESLPF SVEEATRSLK EFDSFTSYFA
 181 GFYENRKNIY STKPQSTAIA YRLIHENLPK FIDNILVFQK IKEPIAKELE HIRADFSAGG
 241 YIKKDERLED IFSLNYYIHV LSQAGIEKYN ALIGKIVTEG DGEMKGLNEH INLYNQQRGR
 301 EDRLPLFRPL YKQILSDREQ LSYLPESFEK DEELLRALKE FYDHIAEDIL GRTQQLMTSI
 361 SEYDLSRIYV RNDSQLTDIS KKMLGDWNAI YMARERAYDH EQAPKRITAK YERDRIKALK
 421 GEESISLANL NSCIAFLDNV RDCRVDTYLS TLGQKEGPHG LSNLVENVFA SYHEAEQLLS
 481 FPYPEENNLI QDKDNVVLIK NLLDNISDLQ RFLKPLWGMG DEPDKDERFY GEYNYIRGAL
 541 DQVIPLYNKV RNYLTRKPYS TRKVKLNFGN SQLLSGWDRN KEKDNSCVIL RKGQNFYLAI
 601 MNNRHKRSFE NKVLPEYKEG EPYFEKMDYK FLPDPNKMLP KVFLSKKGIE IYKPSPKLLE
 661 QYGHGTHKKG DTFSMDDLHE LIDFFKHSIE AHEDWKQFGF KFSDTATYEN VSSFYREVED
 721 QGYKLSFRKV SESYVYSLID QGKLYLFQIY NKDFSPCSKG TPNLHTLYWR MLFDERNLAD
 781 VIYKLDGKAE IFFREKSLKN DHPTHPAGKP IKKKSRQKKG EESLFEYDLV KDRRYTMDKF
 841 QFHVPITMNF KCSAGSKVND MVNAHIREAK DMHVIGIDRG ERNLLYICVI DSRGTILDQI
 901 SLNTINDIDY HDLLESRDKD RQQERRNWQT IEGIKELKQG YLSQAVHRIA ELMVAYKAVV
 961 ALEDLNMGFK RGRQKVESSV YQQFEKQLID KLNYLVDKKK RPEDIGGLLR AYQFTAPFKS
1021 FKEMGKQNGF LFYIPAWNTS NIDPTTGFVN LFHAQYENVD KAKSFFQKFD SISYNPKKDW
1081 FEFAFDYKNF TKKAEGSRSM WILCTHGSRI KNFRNSQKNG QWDSEEFALT EAFKSLFVRY
1141 EIDYTADLKT AIVDEKQKDF FVDLLKLFKL TVQMRNSWKE KDLDYLISPV AGADGRFFDT
1201 REGNKSLPKD ADANGAYNIA LKGLWALRQI RQTSEGGKLK LAISNKEWLQ FVQERSYEKD
```

(SEQ ID NO:28)

FIG. 11B

*Porphyromonas crevioricanis* Cas12a variant (MGFKRGRQK; SEQ ID NO:63 deleted)

```
   1 MDSLKDFTNL YPVSKTLRFE LKPVGKTLEN IEKAGILKED EHRAESYRRV KKIIDTYHKV
  61 FIDSSLENMA KMGIENEIKA MLQSFCELYK KDHRTEGEDK ALDKIRAVLR GLIVGAFTGV
 121 CGRRENTVQN EKYESLFKEK LIKEILPDFV LSTEAESLPF SVEEATRSLK EFDSFTSYFA
 181 GFYENRKNIY STKPQSTAIA YRLIHENLPK FIDNILVFQK IKEPIAKELE HIRADFSAGG
 241 YIKKDERLED IFSLNYYIHV LSQAGIEKYN ALIGKIVTEG DGEMKGLNEH INLYNQQRGR
 301 EDRLPLFRPL YKQILSDREQ LSYLPESFEK DEELLRALKE FYDHIAEDIL GRTQQLMTSI
 361 SEYDLSRIYV RNDSQLTDIS KKMLGDWNAI YMARERAYDH EQAPKRITAK YERDRIKALK
 421 GEESISLANL NSCIAFLDNV RDCRVDTYLS TLGQKEGPHG LSNLVENVFA SYHEAEQLLS
 481 FPYPEENNLI QDKDNVVLIK NLLDNISDLQ RFLKPLWGMG DEPDKDERFY GEYNYIRGAL
 541 DQVIPLYNKV RNYLTRKPYS TRKVKLNFGN SQLLSGWDRN KEKDNSCVIL RKGQNFYLAI
 601 MNNRHKRSFE NKVLPEYKEG EPYFEKMDYK FLPDPNKMLP KVFLSKKGIE IYKPSPKLLE
 661 QYGHGTHKKG DTFSMDDLHE LIDFFKHSIE AHEDWKQFGF KFSDTATYEN VSSFYREVED
 721 QGYKLSFRKV SESYVYSLID QGKLYLFQIY NKDFSPCSKG TPNLHTLYWR MLFDERNLAD
 781 VIYKLDGKAE IFFREKSLKN DHPTHPAGKP IKKKSRQKKG EESLFEYDLV KDRRYTMDKF
 841 QFHVPITMNF KCSAGSKVND MVNAHIREAK DMHVIGIDRG ERNLLYICVI DSRGTILDQI
 901 SLNTINDIDY HDLLESRDKD RQQERRNWQT IEGIKELKQG YLSQAVHRIA ELMVAYKAVV
 961 ALEDLN VESSV YQQFEKQLID KLNYLVDKKK RPEDIGGLLR AYQFTAPFKS
1021 FKEMGKQNGF LFYIPAWNTS NIDPTTGFVN LFHAQYENVD KAKSFFQKFD SISYNPKKDW
1081 FEFAFDYKNF TKKAEGSRSM WILCTHGSRI KNFRNSQKNG QWDSEEFALT EAFKSLFVRY
1141 EIDYTADLKT AIVDEKQKDF FVDLLKLFKL TVQMRNSWKE KDLDYLISPV AGADGRFFDT
1201 REGNKSLPKD ADANGAYNIA LKGLWALRQI RQTSEGGKLK LAISNKEWLQ FVQERSYEKD
```

(SEQ ID NO:29)

FIG. 12A

*Francisella tularensis* Cas12a

1 MSIYQEFVNK YSLSKTLRFE LIPQGKTLEN IKARGLILDD EKRAKDYKKA KQIIDKYHQF
61 FIEEILSSVC ISEDLLQNYS DVYFKLKKSD DDNLQKDFKS AKDTIKKQIS KYINDSEKFK
121 NLFNQNLIDA KKGQESDLIL WLKQSKDNGI ELFKANSDIT DIDEALEIIK SFKGWTTYFK
181 GFHENRKNVY SSNDIPTSII YRIVDDNLPK FLENKAKYES LKDKAPEAIN YEQIKKDLAE
241 ELTFDIDYKT SEVNQRVFSL DEVFEIANFN NYLNQSGITK FNTIIGGKFV NGENTKRKGI
301 NEYINLYSQQ INDKTLKKYK MSVLFKQILS DTESKSFVID KLEDDSDVVT TMQSFYEQIA
361 AFKTVEEKSI KETLSLLFDD LKAQKLDLSK IYFKNDKSLT DLSQQVFDDY SVISTAVLEY
421 ITQQVAPKNL DNPSKKEQEL IAKKTEKAKY LSLETIKLAL EEFNKHRDID KQCRFEEILA
481 NFAAIPMIFD EIAQNKDNLA QISIKYQNQG KKDLLQASAE DDVKAIKDLL DQTNNLLHRL
541 KIFHISQSED KANILDKDEH FYLVFEECYF ELANIVPLYN KIRNYITQKP YSDEKFKLNF
601 ENSTLANGWD KNKEPDNTAI LFIKDDKYYL GVMNKKNNKI FDDKAIKENK GEGYKKIVYK
661 LLPGANKMLP KVFFSAKSIK FYNPSEDILR IRNHSTHTKN GSPQKGYEKF EFNIEDCRKF
721 IDFYKQSISK HPEWKDFGFR FSDTQRYNSI DEFYREVENQ GYKLTFENIS ESYIDSVVNQ
781 GKLYLFQIYN KDFSAYSKGR PNLHTLYWKA LFDERNLQDV VYKLNGEAEL FYRKQSIPKK
841 ITHPAKETIA NKNKDNPKKE SVFEYDLIKD KRFTEDKFFF HCPITINFKS SGANKFNDEI
901 NLLLKEKAND VHILSIDRGE RHLAYYTLVD GKGNIIKQDT FNIIGNDRMK TNYHDKLAAI
961 EKDRDSARKD WKKINNIKEM KEGYLSQVVH EIAKLVIEHN AIVVFEDLNF GFKRGRFKVE
1021 KQVYQKLEKM LIEKLNYLVF KDNEFDKTGG VLRAYQLTAP FETFKKMGKQ TGIIYYVPAG
1081 FTSKICPVTG FVNQLYPKYE SVSKSQEFFS KFDKICYNLD KGYFEFSFDY KNFGDKAAKG
1141 KWTIASFGSR LINFRNSDKN HNWDTREVYP TKELEKLLKD YSIEYGHGEC IKAAICGESD
1201 KKFFAKLTSV LNTILQMRNS KTGTELDYLI SPVADVNGNF FDSRQAPKNM PQDADANGAY
1261 HIGLKGLMLL DRIKNNQEGK KLNLVIKNEE YFEFVQNRNN (SEQ ID NO:30)

FIG. 12B

*Francisella tularensis* Cas12a variant (FGFKRGRFK; SEQ ID NO:61 deleted)

```
   1 MSIYQEFVNK YSLSKTLRFE LIPQGKTLEN IKARGLILDD EKRAKDYKKA KQIIDKYHQF
  61 FIEEILSSVC ISEDLLQNYS DVYFKLKKSD DDNLQKDFKS AKDTIKKQIS KYINDSEKFK
 121 NLFNQNLIDA KKGQESDLIL WLKQSKDNGI ELFKANSDIT DIDEALEIIK SFKGWTTYFK
 181 GFHENRKNVY SSNDIPTSII YRIVDDNLPK FLENKAKYES LKDKAPEAIN YEQIKKDLAE
 241 ELTFDIDYKT SEVNQRVFSL DEVFEIANFN NYLNQSGITK FNTIIGGKFV NGENTKRKGI
 301 NEYINLYSQQ INDKTLKKYK MSVLFKQILS DTESKSFVID KLEDDSDVVT TMQSFYEQIA
 361 AFKTVEEKSI KETLSLLFDD LKAQKLDLSK IYFKNDKSLT DLSQQVFDDY SVISTAVLEY
 421 ITQQVAPKNL DNPSKKEQEL IAKKTEKAKY LSLETIKLAL EEFNKHRDID KQCRFEEILA
 481 NFAAIPMIFD EIAQNKDNLA QISIKYQNQG KKDLLQASAE DDVKAIKDLL DQTNNLLHRL
 541 KIFHISQSED KANILDKDEH FYLVFEECYF ELANIVPLYN KIRNYITQKP YSDEKFKLNF
 601 ENSTLANGWD KNKEPDNTAI LFIKDDKYYL GVMNKKNNKI FDDKAIKENK GEGYKKIVYK
 661 LLPGANKMLP KVFFSAKSIK FYNPSEDILR IRNHSTHTKN GSPQKGYEKF EFNIEDCRKF
 721 IDFYKQSISK HPEWKDFGFR FSDTQRYNSI DEFYREVENQ GYKLTFENIS ESYIDSVVNQ
 781 GKLYLFQIYN KDFSAYSKGR PNLHTLYWKA LFDERNLQDV VYKLNGEAEL FYRKQSIPKK
 841 ITHPAKETIA NKNKDNPKKE SVFEYDLIKD KRFTEDKFFF HCPITINFKS SGANKFNDEI
 901 NLLLKEKAND VHILSIDRGE RHLAYYTLVD GKGNIIKQDT FNIIGNDRMK TNYHDKLAAI
 961 EKDRDSARKD WKKINNIKEM KEGYLSQVVH EIAKLVIEHN AIVVFEDLN VE
1021 KQVYQKLEKM LIEKLNYLVF KDNEFDKTGG VLRAYQLTAP FETFKKMGKQ TGIIYYVPAG
1081 FTSKICPVTG FVNQLYPKYE SVSKSQEFFS KFDKICYNLD KGYFEFSFDY KNFGDKAAKG
1141 KWTIASFGSR LINFRNSDKN HNWDTREVYP TKELEKLLKD YSIEYGHGEC IKAAICGESD
1201 KKFFAKLTSV LNTILQMRNS KTGTELDYLI SPVADVNGNF FDSRQAPKNM PQDADANGAY
1261 HIGLKGLMLL DRIKNNQEGK KLNLVIKNEE YFEFVQNRNN
```

(SEQ ID NO:31)

FIG. 13A

*Eubacterium ventriosum* Cas12a

```
   1 MESNNKIFTE TIGTSSIAKT MRNSLVPTES TKRNIEKNGI IIDDQLRAEK RQQLKEIMDE
  61 YYRAYIDSKL SNVALTRTID WKELFQAIEN NYKQNTTKTK NELEKKQKEK RTEIYKILSD
 121 DEEFKQLFNA KLLTNILPEF IKNQNIDNEE KQEKISTVEL FQRFTSSFTD FFKNRKNVFS
 181 KDEISTSICY RVVQENAWIF YQNLLAFEEI KKTAEQEIKK IEAENRDSIS DYSLKEIFDF
 241 DFYGLLLNQG GIRFYNDVCG KINYHMNLYG QKHNIKSNKF KMKRMHKQIL SIDESTFEVP
 301 TMFENDKEVY QVLNEFLSDL ASKKILERVE KIGENVSEYE INKIYIQSKN FENFSSFMCG
 361 NWQIINDSLK TYYNEKIKSK GKAKVEKVKK AIKAIEYKSL ADINQLVERY NHDELNRKAE
 421 EYISAINEKI KDLYVNEIEF DEKTNLIENE TKSEEIKSKL DSIMEIMHWT KMFIIEEEIE
 481 KDVNFYNEIE EIYDELQPLV TIYNRIRNYV TQKPYSEEKI KLNFGIPTLA NGWSKTKEYD
 541 NNAIIMIRDG KYYLGIFNAK NKPDKKIMEG HQSEENGDYK KMIYRLLPGP NKMLPKVFMS
 601 KTGIAEYKPS QYILECYEQN KHIKSDKNFD IKFCRDLIDF FKTSINRHPE WSKFNFKFSE
 661 TSEYEDISTF YREVEKQGYK IEWTYISEKE IKELDENGQL YLFQIYNKDF SEKSKGKENL
 721 HTMYLKNLFS EENLKNIVLK LNGEAEVFFR KSSIKKPIIH KKGSVLVNKT YNENGERKSI
 781 PEEQYTEIYK YLNSIGTNEL SEKSKKLMEE GKVEYYKANY DIVKDYRYSV DKFFIHLPMT
 841 INFKAAGFSP INNIALKSIA LKEDMHIIGI DRGERNLIYV SVIDTKGNIV EQRNFNIVNG
 901 IDYKEKLKQK ELDRDNARKN WKEIGKIKDL KEGYLSLVVH EIAKLVVKYN AIITMEDLNQ
 961 GFKRGRFKVE RQVYQKFETM LINKLNYLVD KDLAVDQEGG LLRGYQLTYI PESLKVLGRQ
1021 CGYIFYVPAA YTSKIDPTTG FVAIFNYKGM TDKDFVTSFD SIKYDDERGL FAFEFDYENF
1081 VTHKVEMARN KWTVYTYGER IKRKFKNGLW DTAEKVDLTY QMRSILEKYE IEYNKGQDIL
1141 EQIEELDEKA QNGICKEIKY LVKDIVQMRN SLPDNAVEDY DAIISPVINN NGEFFDSTRG
1201 DEDKPLDADA NGAYCIALKG LYEVMQIKKN WNEETEFPRK ELKIRHQDWF DFIQNKRYL
```

(SEQ ID NO:145)

FIG. 13B

*Eubacterium ventriosum* Cas12a variant (QGFKRGRFK; SEQ ID NO:75 deleted)

```
   1 MESNNKIFTE TIGTSSIAKT MRNSLVPTES TKRNIEKNGI IIDDQLRAEK RQQLKEIMDE
  61 YYRAYIDSKL SNVALTRTID WKELFQAIEN NYKQNTTKTK NELEKKQKEK RTEIYKILSD
 121 DEEFKQLFNA KLLTNILPEF IKNQNIDNEE KQEKISTVEL FQRFTSSFTD FFKNRKNVFS
 181 KDEISTSICY RVVQENAWIF YQNLLAFEEI KKTAEQEIKK IEAENRDSIS DYSLKEIFDF
 241 DFYGLLLNQG GIRFYNDVCG KINYHMNLYG QKHNIKSNKF KMKRMHKQIL SIDESTFEVP
 301 TMFENDKEVY QVLNEFLSDL ASKKILERVE KIGENVSEYE INKIYIQSKN FENFSSFMCG
 361 NWQIINDSLK TYYNEKIKSK GKAKVEKVKK AIKAIEYKSL ADINQLVERY NHDELNRKAE
 421 EYISAINEKI KDLYVNEIEF DEKTNLIENE TKSEEIKSKL DSIMEIMHWT KMFIIEEEIE
 481 KDVNFYNEIE EIYDELQPLV TIYNRIRNYV TQKPYSEEKI KLNFGIPTLA NGWSKTKEYDQ
 541 NNAIIMIRDG KYYLGIFNAK NKPDKKIMEG HQSEENGDYK KMIYRLLPGP NKMLPKVFMS
 601 KTGIAEYKPS QYILECYEQN KHIKSDKNFD IKFCRDLIDF FKTSINRHPE WSKFNFKFSE
 661 TSEYEDISTF YREVEKQGYK IEWTYISEKE IKELDENGQL YLFQIYNKDF SEKSKGKENL
 721 HTMYLKNLFS EENLKNIVLK LNGEAEVFFR KSSIKKPIIH KKGSVLVNKT YNENGERKSI
 781 PEEQYTEIYK YLNSIGTNEL SEKSKKLMEE GKVEYYKANY DIVKDYRYSV DKFFIHLPMT
 841 INFKAAGFSP INNIALKSIA LKEDMHIIGI DRGERNLIYV SVIDTKGNIV EQRNFNIVNG
 901 IDYKEKLKQK ELDRDNARKN WKEIGKIKDL KEGYLSLVVH EIAKLVVKYN AIITMEDLN
 961 VE RQVYQKFETM LINKLNYLVD KDLAVDQEGG LLRGYQLTYI PESLKVLGRQ
1021 CGYIFYVPAA YTSKIDPTTG FVAIFNYKGM TDKDFVTSFD SIKYDDERGL FAFEFDYENF
1081 VTHKVEMARN KWTVYTYGER IKRKFKNGLW DTAEKVDLTY QMRSILEKYE IEYNKGQDIL
1141 EQIEELDEKA QNGICKEIKY LVKDIVQMRN SLPDNAVEDY DAIISPVINN NGEFFDSTRG
1201 DEDKPLDADA NGAYCIALKG LYEVMQIKKN WNEETEFPRK ELKIRHQDWF DFIQNKRYL
```

(SEQ ID NO:32)

FIG. 14A

*Alicyclobacillus acidoterrestris*

GenBank WP_021296342

Cas12b

```
   1 MAVKSIKVKL RLDDMPEIRA GLWKLHKEVN AGVRYYTEWL SLLRQENLYR RSPNGDGEQE
  61 CDKTAEECKA ELLERLRARQ VENGHRGPAG SDDELLQLAR QLYELLVPQA IGAKGDAQQI
 121 ARKFLSPLAD KDAVGGLGIA KAGNKPRWVR MREAGEPGWE EEKEKAETRK SADRTADVLR
 181 ALADFGLKPL MRVYTDSEMS SVEWKPLRKG QAVRTWDRDM FQQAIERMMS WESWNQRVGQ
 241 EYAKLVEQKN RFEQKNFVGQ EHLVHLVNQL QQDMKEASPG LESKEQTAHY VTGRALRGSD
 301 KVFEKWGKLA PDAPFDLYDA EIKNVQRRNT RRFGSHDLFA KLAEPEYQAL WREDASFLTR
 361 YAVYNSILRK LNHAKMFATF TLPDATAHPI WTRFDKLGGN LHQYTFLFNE FGERRHAIRF
 421 HKLLKVENGV AREVDDVTVP ISMSEQLDNL LPRDPNEPIA LYFRDYGAEQ HFTGEFGGAK
 481 IQCRRDQLAH MHRRRGARDV YLNVSVRVQS QSEARGERRP PYAAVFRLVG DNHRAFVHFD
 541 KLSDYLAEHP DDGKLGSEGL LSGLRVMSVD LGLRTSASIS VFRVARKDEL KPNSKGRVPF
 601 FFPIKGNDNL VAVHERSQLL KLPGETESKD LRAIREERQR TLRQLRTQLA YLRLLVRCGS
 661 EDVGRRERSW AKLIEQPVDA ANHMTPDWRE AFENELQKLK SLHGICSDKE WMDAVYESVR
 721 RVWRHMGKQV RDWRKDVRSG ERPKIRGYAK DVVGGNSIEQ IEYLERQYKF LKSWSFFGKV
 781 SGQVIRAEKG SRFAITLREH IDHAKEDRLK KLADRIIMEA LGYVYALDER GKGKWVAKYP
 841 PCQLILLEEL SEYQFNNDRP PSENNQLMQW SHRGVFQELI NQAQVHDLLV GTMYAAFSSR
 901 FDARTGAPGI RCRRVPARCT QEHNPEPFPW WLNKFVVEHT LDACPLRADD LIPTGEGEIF
 961 VSPFSAEEGD FHQIHADLNA AQNLQQRLWS DFDISQIRLR CDWGEVDGEL VLIPRLTGKR
1021 TADSYSNKVF YTNTGVTYYE RERGKKRRKV FAQEKLSEEE AELLVEADEA REKSVVLMRD
1081 PSGIINRGNW TRQKEFWSMV NQRIEGYLVK QIRSRVPLQD SACENTGDI
```

(SEQ ID NO:33)

FIG. 14B

*Alicyclobacillus acidoterrestris* Cas12b variant (EYQFNNDRPPSENN; ·············· deleted)

1 MAVKSIKVKL RLDDMPEIRA GLWKLHKEVN AGVRYYTEWL SLLRQENLYR RSPNGDGEQE
61 CDKTAEECKA ELLERLRARQ VENGHRGPAG SDDELLQLAR QLYELLVPQA IGAKGDAQQI
121 ARKFLSPLAD KDAVGGLGIA KAGNKPRWVR MREAGEPGWE EEKEKAETRK SADRTADVLR
181 ALADFGLKPL MRVYTDSEMS SVEWKPLRKG QAVRTWDRDM FQQAIERMMS WESWNQRVGQ
241 EYAKLVEQKN RFEQKNFVGQ EHLVHLVNQL QQDMKEASPG LESKEQTAHY VTGRALRGSD
301 KVFEKWGKLA PDAPFDLYDA EIKNVQRRNT RRFGSHDLFA KLAEPEYQAL WREDASFLTR
361 YAVYNSILRK LNHAKMFATF TLPDATAHPI WTRFDKLGGN LHQYTFLFNE FGERRHAIRF
421 HKLLKVENGV AREVDDVTVP ISMSEQLDNL LPRDPNEPIA LYFRDYGAEQ HFTGEFGGAK
481 IQCRRDQLAH MHRRRGARDV YLNVSVRVQS QSEARGERRP PYAAVFRLVG DNHRAFVHFD
541 KLSDYLAEHP DDGKLGSEGL LSGLRVMSVD LGLRTSASIS VFRVARKDEL KPNSKGRVPF
601 FFPIKGNDNL VAVHERSQLL KLPGETESKD LRAIREERQR TLRQLRTQLA YLRLLVRCGS
661 EDVGRRERSW AKLIEQPVDA ANHMTPDWRE AFENELQKLK SLHGICSDKE WMDAVYESVR
721 RVWRHMGKQV RDWRKDVRSG ERPKIRGYAK DVVGGNSIEQ IEYLERQYKF LKSWSFFGKV
781 SGQVIRAEKG SRFAITLREH IDHAKEDRLK KLADRIIMEA LGYVYALDER GKGKWVAKYP
841 PCQLILLEEL S QLMQW SHRGVFQELI NQAQVHDLLV GTMYAAFSSR
901 FDARTGAPGI RCRRVPARCT QEHNPEPFPW WLNKFVVEHT LDACPLRADD LIPTGEGEIF
961 VSPFSAEEGD FHQIHADLNA AQNLQQRLWS DFDISQIRLR CDWGEVDGEL VLIPRLTGKR
1021 TADSYSNKVF YTNTGVTYYE RERGKKRRKV FAQEKLSEEE AELLVEADEA REKSVVLMRD
1081 PSGIINRGNW TRQKEFWSMV NQRIEGYLVK QIRSRVPLQD SACENTGDI (SEQ ID NO:34)

FIG. 14C

*Alicyclobacillus acidoterrestris* Cas12b variant (EYQFNNDRPPSENN ; SEQ ID NO: 64 mutated to GAAGAAGAAGAAGG; SEQ ID NO:111)

```
   1 MAVKSIKVKL RLDDMPEIRA GLWKLHKEVN AGVRYYTEWL SLLRQENLYR RSPNGDGEQE
  61 CDKTAEECKA ELLERLRARQ VENGHRGPAG SDDELLQLAR QLYELLVPQA IGAKGDAQQI
 121 ARKFLSPLAD KDAVGGLGIA KAGNKPRWVR MREAGEPGWE EEKEKAETRK SADRTADVLR
 181 ALADFGLKPL MRVYTDSEMS SVEWKPLRKG QAVRTWDRDM FQQAIERMMS WESWNQRVGQ
 241 EYAKLVEQKN RFEQKNFVGQ EHLVHLVNQL QQDMKEASPG LESKEQTAHY VTGRALRGSD
 301 KVFEKWGKLA PDAPFDLYDA EIKNVQRRNT RRFGSHDLFA KLAEPEYQAL WREDASFLTR
 361 YAVYNSILRK LNHAKMFATF TLPDATAHPI WTRFDKLGGN LHQYTFLFNE FGERRHAIRF
 421 HKLLKVENGV AREVDDVTVP ISMSEQLDNL LPRDPNEPIA LYFRDYGAEQ HFTGEFGGAK
 481 IQCRRDQLAH MHRRRGARDV YLNVSVRVQS QSEARGERRP PYAAVFRLVG DNHRAFVHFD
 541 KLSDYLAEHP DDGKLGSEGL LSGLRVMSVD LGLRTSASIS VFRVARKDEL KPNSKGRVPF
 601 FFPIKGNDNL VAVHERSQLL KLPGETESKD LRAIREERQR TLRQLRTQLA YLRLLVRCGS
 661 EDVGRRERSW AKLIEQPVDA ANHMTPDWRE AFENELQKLK SLHGICSDKE WMDAVYESVR
 721 RVWRHMGKQV RDWRKDVRSG ERPKIRGYAK DVVGGNSIEQ IEYLERQYKF LKSWSFFGKV
 781 SGQVIRAEKG SRFAITLREH IDHAKEDRLK KLADRIIMEA LGYVYALDER GKGKWVAKYP
 841 PCQLILLEEL SGAAGAAGAA GAAGGQLMQW SHRGVFQELI NQAQVHDLLV GTMYAAFSSR
 901 FDARTGAPGI RCRRVPARCT QEHNPEPFPW WLNKFVVEHT LDACPLRADD LIPTGEGEIF
 961 VSPFSAEEGD FHQIHADLNA AQNLQQRLWS DFDISQIRLR CDWGEVDGEL VLIPRLTGKR
1021 TADSYSNKVF YTNTGVTYYE RERGKKRRKV FAQEKLSEEE AELLVEADEA REKSVVLMRD
1081 PSGIINRGNW TRQKEFWSMV NQRIEGYLVK QIRSRVPLQD SACENTGDI
```

(SEQ ID NO:35)

FIG. 15A

*Alicyclobacillus kakegawensis*
GenBank WP_067936067
Cas12b

```
   1 MAVKSIKVKL RLSECPDILA GMWQLHRATN AGVRYYTEWV SLMRQEILYS RGPDGGQQCY
  61 MTAEDCQREL LRRLRNRQLH NGRQDQPGTD ADLLAISRRL YEILVLQSIG KRGDAQQIAS
 121 SFLSPLVDPN SKGGRGEAKS GRKPAWQKMR DQGDPRWVAA REKYEQRKAV DPSKEILNSL
 181 DALGLRPLFA VFTETYRSGV DWKPLGKSQG VRTWDRDMFQ QALERLMSWE SWNRRVGEEY
 241 ARLFQQKMKF EQEHFAEQSH LVKLARALEA DMRAASQGFE AKRGTAHQIT RRALRGADRV
 301 FEIWKSIPEE ALFSQYDEVI RQVQAEKRRD FGSHDLFAKL AEPKYQPLWR ADETFLTRYA
 361 LYNGVLRDLE KARQFATFTL PDACVNPIWT RFESSQGSNL HKYEFLFDHL GPGRHAVRFQ
 421 RLLVVESEGA KERDSVVVPV APSGQLDKLV LREEEKSSVA LHLHDTARPD GFMAEWAGAK
 481 LQYERSTLAR KARRDKQGMR SWRRQPSMLM SAAQMLEDAK QAGDVYLNIS VRVKSPSEVR
 541 GQRRPPYAAL FRIDDKQRRV TVNYNKLSAY LEEHPDKQIP GAPGLLSGLR VMSVDLGLRT
 601 SASISVFRVA KKEEVEALGD GRPPHYYPIH GTDDLVAVHE RSHLIQMPGE TETKQLRKLR
 661 EERQAVLRPL FAQLALLRLL VRCGAADERI RTRSWQRLTK QGREFTKRLT PSWREALELE
 721 LTRLEAYCGR VPDDEWSRIV DRTVIALWRR MGKQVRDWRK QVKSGAKVKV KGYQLDVVGG
 781 NSLAQIDYLE QQYKFLRRWS FFARASGLVV RADRESHFAV ALRQHIENAK RDRLKKLADR
 841 ILMEALGYVY EASGPREGQW TAQHPPCQLI ILEELSAYRF SDDRPPSENS KLMAWGHRGI
 901 LEELVNQAQV HDVLVGTVYA AFSSRFDART GAPGVRCRRV PARFVGATVD DSLPLWLTEF
 961 LDKHRLDKNL LRPDDVIPTG EGEFLVSPCG EEAARVRQVH ADINAAQNLQ RRLWQNFDIT
1021 ELRLRCDVKM GGEGTVLVPR VNNARAKQLF GKKVLVSQDG VTFFERSQTG GKPHSEKQTD
1081 LTDKELELIA EADEARAKSV VLFRDPSGHI GKGHWIRQRE FWSLVKQRIE SHTAERIRVR
1141 GVGSSLD
```

(SEQ ID NO:36)

FIG. 15B

*Alicyclobacillus kakegawensis* variant Cas12b (AYRFSDDRPPSENS; SEQ ID NO: 67 is deleted)

```
   1 MAVKSIKVKL RLSECPDILA GMWQLHRATN AGVRYYTEWV SLMRQEILYS RGPDGGQQCY
  61 MTAEDCQREL LRRLRNRQLH NGRQDQPGTD ADLLAISRRL YEILVLQSIG KRGDAQQIAS
 121 SFLSPLVDPN SKGGRGEAKS GRKPAWQKMR DQGDPRWVAA REKYEQRKAV DPSKEILNSL
 181 DALGLRPLFA VFTETYRSGV DWKPLGKSQG VRTWDRDMFQ QALERLMSWE SWNRRVGEEY
 241 ARLFQQKMKF EQEHFAEQSH LVKLARALEA DMRAASQGFE AKRGTAHQIT RRALRGADRV
 301 FEIWKSIPEE ALFSQYDEVI RQVQAEKRRD FGSHDLFAKL AEPKYQPLWR ADETFLTRYA
 361 LYNGVLRDLE KARQFATFTL PDACVNPIWT RFESSQGSNL HKYEFLFDHL GPGRHAVRFQ
 421 RLLVVESEGA KERDSVVVPV APSGQLDKLV LREEEKSSVA LHLHDTARPD GFMAEWAGAK
 481 LQYERSTLAR KARRDKQGMR SWRRQPSMLM SAAQMLEDAK QAGDVYLNIS VRVKSPSEVR
 541 GQRRPPYAAL FRIDDKQRRV TVNYNKLSAY LEEHPDKQIP GAPGLLSGLR VMSVDLGLRT
 601 SASISVFRVA KKEEVEALGD GRPPHYYPIH GTDDLVAVHE RSHLIQMPGE TETKQLRKLR
 661 EERQAVLRPL FAQLALLRLL VRCGAADERI RTRSWQRLTK QGREFTKRLT PSWREALELE
 721 LTRLEAYCGR VPDDEWSRIV DRTVIALWRR MGKQVRDWRK QVKSGAKVKV KGYQLDVVGG
 781 NSLAQIDYLE QQYKFLRRWS FFARASGLVV RADRESHFAV ALRQHIENAK RDRLKKLADR
 841 ILMEALGYVY EASGPREGQW TAQHPPCQLI ILEELS KLMAWGHRGI
 901 LEELVNQAQV HDVLVGTVYA AFSSRFDART GAPGVRCRRV PARFVGATVD DSLPLWLTEF
 961 LDKHRLDKNL LRPDDVIPTG EGEFLVSPCG EEAARVRQVH ADINAAQNLQ RRLWQNFDIT
1021 ELRLRCDVKM GGEGTVLVPR VNNARAKQLF GKKVLVSQDG VTFFERSQTG GKPHSEKQTD
1081 LTDKELELIA EADEARAKSV VLFRDPSGHI GKGHWIRQRE FWSLVKQRIE SHTAERIRVR
1141 GVGSSLD
```

(SEQ ID NO:37)

FIG. 15C

*Alicyclobacillus kakegawensis* variant Cas12b (AYRFSDDRPPSENS; SEQ ID NO:67 mutated to GAAGAAGAAGAAGG; SEQ ID NO:111)

```
   1 MAVKSIKVKL RLSECPDILA GMWQLHRATN AGVRYYTEWV SLMRQEILYS RGPDGGQQCY
  61 MTAEDCQREL LRRLRNRQLH NGRQDQPGTD ADLLAISRRL YEILVLQSIG KRGDAQQIAS
 121 SFLSPLVDPN SKGGRGEAKS GRKPAWQKMR DQGDPRWVAA REKYEQRKAV DPSKEILNSL
 181 DALGLRPLFA VFTETYRSGV DWKPLGKSQG VRTWDRDMFQ QALERLMSWE SWNRRVGEEY
 241 ARLFQQKMKF EQEHFAEQSH LVKLARALEA DMRAASQGFE AKRGTAHQIT RRALRGADRV
 301 FEIWKSIPEE ALFSQYDEVI RQVQAEKRRD FGSHDLFAKL AEPKYQPLWR ADETFLTRYA
 361 LYNGVLRDLE KARQFATFTL PDACVNPIWT RFESSQGSNL HKYEFLFDHL GPGRHAVRFQ
 421 RLLVVESEGA KERDSVVVPV APSGQLDKLV LREEEKSSVA LHLHDTARPD GFMAEWAGAK
 481 LQYERSTLAR KARRDKQGMR SWRRQPSMLM SAAQMLEDAK QAGDVYLNIS VRVKSPSEVR
 541 GQRRPPYAAL FRIDDKQRRV TVNYNKLSAY LEEHPDKQIP GAPGLLSGLR VMSVDLGLRT
 601 SASISVFRVA KKEEVEALGD GRPPHYYPIH GTDDLVAVHE RSHLIQMPGE TETKQLRKLR
 661 EERQAVLRPL FAQLALLRLL VRCGAADERI RTRSWQRLTK QGREFTKRLT PSWREALELE
 721 LTRLEAYCGR VPDDEWSRIV DRTVIALWRR MGKQVRDWRK QVKSGAKVKV KGYQLDVVGG
 781 NSLAQIDYLE QQYKFLRRWS FFARASGLVV RADRESHFAV ALRQHIENAK RDRLKKLADR
 841 ILMEALGYVY EASGPREGQW TAQHPPCQLI ILEELSGAAG AAGAAGAAGG KLMAWGHRGI
 901 LEELVNQAQV HDVLVGTVYA AFSSRFDART GAPGVRCRRV PARFVGATVD DSLPLWLTEF
 961 LDKHRLDKNL LRPDDVIPTG EGEFLVSPCG EEAARVRQVH ADINAAQNLQ RRLWQNFDIT
1021 ELRLRCDVKM GGEGTVLVPR VNNARAKQLF GKKVLVSQDG VTFFERSQTG GKPHSEKQTD
1081 LTDKELELIA EADEARAKSV VLFRDPSGHI GKGHWIRQRE FWSLVKQRIE SHTAERIRVR
1141 GVGSSLD
```

(SEQ ID NO:38)

FIG. 16A

*Alicyclobacillus macrosporangiidus*

GenBank SFU30094

Cas12b

```
   1 MAVKSIKVKL MLGHLPEIRE GLWHLHEAVN LGVRYYTEWL ALLRQGNLYR RGKDGAQECY
  61 MTAEQCRQEL LVRLRDRQKR NGHTGDPGTD EELLGVARRL YELLVPQSVG KKGQAQMLAS
 121 GFLSPLADPK SEGGKGTSKS GRKPAWMGMK EAGDSRWVEA KARYEANKAK DPTKQVIASL
 181 EMYGLRPLFD VFTETYKTIR WMPLGKHQGV RAWDRDMFQQ SLERLMSWES WNERVGAEFA
 241 RLVDRRDRFR EKHFTGQEHL VALAQRLEQE MKEASPGFES KSSQAHRITK RALRGADGII
 301 DDWLKLSEGE PVDRFDEILR KRQAQNPRRF GSHDLFLKLA EPVFQPLWRE DPSFLSRWAS
 361 YNEVLNKLED AKQFATFTLP SPCSNPVWAR FENAEGTNIF KYDFLFDHFG KGRHGVRFQR
 421 MIVMRDGVPT EVEGIVVPIA PSRQLDALAP NDAASPIDVF VGDPAAPGAF RGQFGGAKIQ
 481 YRRSALVRKG RREEKAYLCG FRLPSQRRTG TPADDAGEVF LNLSLRVESQ SEQAGRRNPP
 541 YAAVFHISDQ TRRVIVRYGE IERYLAEHPD TGIPGSRGLT SGLRVMSVDL GLRTSAAISV
 601 FRVAHRDELT PDAHGRQPFF FPIHGMDHLV ALHERSHLIR LPGETESKKV RSIREQRLDR
 661 LNRLRSQMAS LRLLVRTGVL DEQKRDRNWE RLQSSMERGG ERMPSDWWDL FQAQVRYLAQ
 721 HRDASGEAWG RMVQAAVRTL WRQLAKQVRD WRKEVRRNAD KVKIRGIARD VPGGHSLAQL
 781 DYLERQYRFL RSWSAFSVQA GQVVRAERDS RFAVALREHI DNGKKDRLKK LADRILMEAL
 841 GYVYVTDGRR AGQWQAVYPP CQLVLLEELS EYRFSNDRPP SENSQLMVWS HRGVLEELIH
 901 QAQVHDVLVG TIPAAFSSRF DARTGAPGIR CRRVPSIPLK DAPSIPIWLS HYLKQTERDA
 961 AALRPGELIP TGDGEFLVTP AGRGASGVRV VHADINAAHN LQRRLWENFD LSDIRVRCDR
1021 REGKDGTVVL IPRLTNQRVK ERYSGVIFTS EDGVSFTVGD AKTRRRSSAS QGEGDDLSDE
1081 EQELLAEADD ARERSVVLFR DPSGFVNGGR WTAQRAFWGM VHNRIETLLA ERFSVSGAAE
1141 KVRG
```

(SEQ ID NO:39)

FIG. 16B

*Alicyclobacillus macrosporangiidus* variant Cas12b (EYRFSNDRPPSENS; SEQ ID NO:65 deleted)

```
   1 MAVKSIKVKL MLGHLPEIRE GLWHLHEAVN LGVRYYTEWL ALLRQGNLYR RGKDGAQECY
  61 MTAEQCRQEL LVRLRDRQKR NGHTGDPGTD EELLGVARRL YELLVPQSVG KKGQAQMLAS
 121 GFLSPLADPK SEGGKGTSKS GRKPAWMGMK EAGDSRWVEA KARYEANKAK DPTKQVIASL
 181 EMYGLRPLFD VFTETYKTIR WMPLGKHQGV RAWDRDMFQQ SLERLMSWES WNERVGAEFA
 241 RLVDRRDRFR EKHFTGQEHL VALAQRLEQE MKEASPGFES KSSQAHRITK RALRGADGII
 301 DDWLKLSEGE PVDRFDEILR KRQAQNPRRF GSHDLFLKLA EPVFQPLWRE DPSFLSRWAS
 361 YNEVLNKLED AKQFATFTLP SPCSNPVWAR FENAEGTNIF KYDFLFDHFG KGRHGVRFQR
 421 MIVMRDGVPT EVEGIVVPIA PSRQLDALAP NDAASPIDVF VGDPAAPGAF RGQFGGAKIQ
 481 YRRSALVRKG RREEKAYLCG FRLPSQRRTG TPADDAGEVF LNLSLRVESQ SEQAGRRNPP
 541 YAAVFHISDQ TRRVIVRYGE IERYLAEHPD TGIPGSRGLT SGLRVMSVDL GLRTSAAISV
 601 FRVAHRDELT PDAHGRQPFF FPIHGMDHLV ALHERSHLIR LPGETESKKV RSIREQRLDR
 661 LNRLRSQMAS LRLLVRTGVL DEQKRDRNWE RLQSSMERGG ERMPSDWWDL FQAQVRYLAQ
 721 HRDASGEAWG RMVQAAVRTL WRQLAKQVRD WRKEVRRNAD KVKIRGIARD VPGGHSLAQL
 781 DYLERQYRFL RSWSAFSVQA GQVVRAERDS RFAVALREHI DNGKKDRLKK LADRILMEAL
 841 GYVYVTDGRR AGQWQAVYPP CQLVLLEELS QLMVWS HRGVLEELIH
 901 QAQVHDVLVG TIPAAFSSRF DARTGAPGIR CRRVPSIPLK DAPSIPIWLS HYLKQTERDA
 961 AALRPGELIP TGDGEFLVTP AGRGASGVRV VHADINAAHN LQRRLWENFD LSDIRVRCDR
1021 REGKDGTVVL IPRLTNQRVK ERYSGVIFTS EDGVSFTVGD AKTRRRSSAS QGEGDDLSDE
1081 EQELLAEADD ARERSVVLFR DPSGFVNGGR WTAQRAFWGM VHNRIETLLA ERFSVSGAAE
1141 KVRG
```

(SEQ ID NO:40)

FIG. 16C

*Alicyclobacillus macrosporangiidus* variant Cas12b (EYRFSNDRPPSENS; SEQ ID NO:65 mutated to GAAGAAGAAGAAGG; SEQ ID NO:111)

```
   1 MAVKSIKVKL MLGHLPEIRE GLWHLHEAVN LGVRYYTEWL ALLRQGNLYR RGKDGAQECY
  61 MTAEQCRQEL LVRLRDRQKR NGHTGDPGTD EELLGVARRL YELLVPQSVG KKGQAQMLAS
 121 GFLSPLADPK SEGGKGTSKS GRKPAWMGMK EAGDSRWVEA KARYEANKAK DPTKQVIASL
 181 EMYGLRPLFD VFTETYKTIR WMPLGKHQGV RAWDRDMFQQ SLERLMSWES WNERVGAEFA
 241 RLVDRRDRFR EKHFTGQEHL VALAQRLEQE MKEASPGFES KSSQAHRITK RALRGADGII
 301 DDWLKLSEGE PVDRFDEILR KRQAQNPRRF GSHDLFLKLA EPVFQPLWRE DPSFLSRWAS
 361 YNEVLNKLED AKQFATFTLP SPCSNPVWAR FENAEGTNIF KYDFLFDHFG KGRHGVRFQR
 421 MIVMRDGVPT EVEGIVVPIA PSRQLDALAP NDAASPIDVF VGDPAAPGAF RGQFGGAKIQ
 481 YRRSALVRKG RREEKAYLCG FRLPSQRRTG TPADDAGEVF LNLSLRVESQ SEQAGRRNPP
 541 YAAVFHISDQ TRRVIVRYGE IERYLAEHPD TGIPGSRGLT SGLRVMSVDL GLRTSAAISV
 601 FRVAHRDELT PDAHGRQPFF FPIHGMDHLV ALHERSHLIR LPGETESKKV RSIREQRLDR
 661 LNRLRSQMAS LRLLVRTGVL DEQKRDRNWE RLQSSMERGG ERMPSDWWDL FQAQVRYLAQ
 721 HRDASGEAWG RMVQAAVRTL WRQLAKQVRD WRKEVRRNAD KVKIRGIARD VPGGHSLAQL
 781 DYLERQYRFL RSWSAFSVQA GQVVRAERDS RFAVALREHI DNGKKDRLKK LADRILMEAL
 841 GYVYVTDGRR AGQWQAVYPP CQLVLLEELS GAAGAAGAAG AAGGQLMVWS HRGVLEELIH
 901 QAQVHDVLVG TIPAAFSSRF DARTGAPGIR CRRVPSIPLK DAPSIPIWLS HYLKQTERDA
 961 AALRPGELIP TGDGEFLVTP AGRGASGVRV VHADINAAHN LQRRLWENFD LSDIRVRCDR
1021 REGKDGTVVL IPRLTNQRVK ERYSGVIFTS EDGVSFTVGD AKTRRRSSAS QGEGDDLSDE
1081 EQELLAEADD ARERSVVLFR DPSGFVNGGR WTAQRAFWGM VHNRIETLLA ERFSVSGAAE
1141 KVRG
```

(SEQ ID NO:41)

FIG. 17A

*Alicyclobacillus hesperidum*
GenBank WP_074693942
Cas12b

```
   1 MTVRSIRVKL AVGSPQYRDV RRGLWKTHEI MNQGVRYYCE WLVLMRQEPI YDEDEHGLTV
  61 VQRTREDIQA ELLSRLRTLQ SAHQHSGDMG TDEELLSLMR QLYEQLVPSS VDKNKSGDAR
 121 MIARNFFNPL TNPNSQGGLG ISNAGRKPKW LLKKLSGDPT WEEDYKKAME QKQESSVSFL
 181 LLELRRFGLH PIFLPYTDTV LEVSWAPKKA RQWVRKWDYD LFQQSIERML SWESWTRRVK
 241 ERFEKLVESE KKFYDENFAT DPEFIKLAET LEGELQASSQ GFVAVDEHAF QIRPRSMRGF
 301 DRVADEWCKL ADDAPIEEYE AAIKRVQARL GRNFGSYVLF AHLAKPEYWS LWRSDPTKIL
 361 RFARLRALQR AVARAKRHAR LTLPDAIHHP IWIRYDAKGK NIYSYRLLIP EKRSKRYYVE
 421 FSSLIMPDGE NRWAEHRNIR VPLAFSRQWE RLHFSIMEDG SLCVQYRDPG VDEPLRAELG
 481 GAKIQFDRRY LIRRSSTLSA GECGPVYLNV SVDVNPAHRP DVQVLQSAKL VSVSRDTNRI
 541 YLRPENLSAY WKSQGDGTLP LRVMSVDLGV RSSAAVVICR LEHRDSVVSS GRRTATIYRI
 601 AGTDEFVAVQ ERAFLLRLPG EGKGTNEDAP LRDVYAQLGT IRQGIQILRS LLRLCDTKTP
 661 DERQEALHGL AQSLEPSGAW KDELHPHLVM LQGVVHDSVD NWKQKVISVH RQMERILGHA
 721 VREWKVARKN AGKPPIRRGA GGLSLRRIRQ LEQERRTLVA WSNHAREPGQ VVRIKRGTQV
 781 AQWLVERVNH LKEDRLKKLA DLLIMTALGY VYDETKPSGH KWDKRYPPCQ IILMEDLSRY
 841 RFQSDRPPSE NSQLMAWSHR RLLEILKLQA DLHKLIVGTV FPAFSSRFDA QSGAPGVRCR
 901 SVKKQDIENA AQGKGWLARE LQRLNWTLEW LQPNDLIPTG DGELFVTPAC CDRQKGIKIV
 961 HADLNAAQNL QRRFWGGHAE SLCRVTCDVV ERDGRRYAVP RISNAFADSF YKVFGQGVFV
1021 STDEEDVYRW MVGEKISSRG RSRGRTSDEE AEAETWIDEA REQQGKVIAL FRDASGQIHG
1081 GDWLVAKVFW GWVERLVTAR LLSRMSEREA AAHKE
```

(SEQ ID NO:42)

FIG. 17B

*Alicyclobacillus hesperidum* variant Cas12b (RYRFQSDRPPSENS; SEQ ID NO:66 deleted)

```
   1 MTVRSIRVKL AVGSPQYRDV RRGLWKTHEI MNQGVRYYCE WLVLMRQEPI YDEDEHGLTV
  61 VQRTREDIQA ELLSRLRTLQ SAHQHSGDMG TDEELLSLMR QLYEQLVPSS VDKNKSGDAR
 121 MIARNFFNPL TNPNSQGGLG ISNAGRKPKW LLKKLSGDPT WEEDYKKAME QKQESSVSFL
 181 LLELRRFGLH PIFLPYTDTV LEVSWAPKKA RQWVRKWDYD LFQQSIERML SWESWTRRVK
 241 ERFEKLVESE KKFYDENFAT DPEFIKLAET LEGELQASSQ GFVAVDEHAF QIRPRSMRGF
 301 DRVADEWCKL ADDAPIEEYE AAIKRVQARL GRNFGSYVLF AHLAKPEYWS LWRSDPTKIL
 361 RFARLRALQR AVARAKRHAR LTLPDAIHHP IWIRYDAKGK NIYSYRLLIP EKRSKRYYVE
 421 FSSLIMPDGE NRWAEHRNIR VPLAFSRQWE RLHFSIMEDG SLCVQYRDPG VDEPLRAELG
 481 GAKIQFDRRY LIRRSSTLSA GECGPVYLNV SVDVNPAHRP DVQVLQSAKL VSVSRDTNRI
 541 YLRPENLSAY WKSQGDGTLP LRVMSVDLGV RSSAAVVICR LEHRDSVVSS GRRTATIYRI
 601 AGTDEFVAVQ ERAFLLRLPG EGKGTNEDAP LRDVYAQLGT IRQGIQILRS LLRLCDTKTP
 661 DERQEALHGL AQSLEPSGAW KDELHPHLVM LQGVVHDSVD NWKQKVISVH RQMERILGHA
 721 VREWKVARKN AGKPPIRRGA GGLSLRRIRQ LEQERRTLVA WSNHAREPGQ VVRIKRGTQV
 781 AQWLVERVNH LKEDRLKKLA DLLIMTALGY VYDETKPSGH KWDKRYPPCQ IILMEDLS
 841 QLMAWSHR RLLEILKLQA DLHKLIVGTV FPAFSSRFDA QSGAPGVRCR
 901 SVKKQDIENA AQGKGWLARE LQRLNWTLEW LQPNDLIPTG DGELFVTPAC CDRQKGIKIV
 961 HADLNAAQNL QRRFWGGHAE SLCRVTCDVV ERDGRRYAVP RISNAFADSF YKVFGQGVFV
1021 STDEEDVYRW MVGEKISSRG RSRGRTSDEE AEAETWIDEA REQQGKVIAL FRDASGQIHG
1081 GDWLVAKVFW GWVERLVTAR LLSRMSEREA AAHKE
```

(SEQ ID NO:43)

FIG. 17C

*Alicyclobacillus hesperidum* variant Cas12b (RYRFQSDRPPSENS; SEQ ID NO:66 mutated to GAAGAAGAAGAAGG; SEQ ID NO:111)

```
   1 MTVRSIRVKL AVGSPQYRDV RRGLWKTHEI MNQGVRYYCE WLVLMRQEPI YDEDEHGLTV
  61 VQRTREDIQA ELLSRLRTLQ SAHQHSGDMG TDEELLSLMR QLYEQLVPSS VDKNKSGDAR
 121 MIARNFFNPL TNPNSQGGLG ISNAGRKPKW LLKKLSGDPT WEEDYKKAME QKQESSVSFL
 181 LLELRRFGLH PIFLPYTDTV LEVSWAPKKA RQWVRKWDYD LFQQSIERML SWESWTRRVK
 241 ERFEKLVESE KKFYDENFAT DPEFIKLAET LEGELQASSQ GFVAVDEHAF QIRPRSMRGF
 301 DRVADEWCKL ADDAPIEEYE AAIKRVQARL GRNFGSYVLF AHLAKPEYWS LWRSDPTKIL
 361 RFARLRALQR AVARAKRHAR LTLPDAIHHP IWIRYDAKGK NIYSYRLLIP EKRSKRYYVE
 421 FSSLIMPDGE NRWAEHRNIR VPLAFSRQWE RLHFSIMEDG SLCVQYRDPG VDEPLRAELG
 481 GAKIQFDRRY LIRRSSTLSA GECGPVYLNV SVDVNPAHRP DVQVLQSAKL VSVSRDTNRI
 541 YLRPENLSAY WKSQGDGTLP LRVMSVDLGV RSSAAVVICR LEHRDSVVSS GRRTATIYRI
 601 AGTDEFVAVQ ERAFLLRLPG EGKGTNEDAP LRDVYAQLGT IRQGIQILRS LLRLCDTKTP
 661 DERQEALHGL AQSLEPSGAW KDELHPHLVM LQGVVHDSVD NWKQKVISVH RQMERILGHA
 721 VREWKVARKN AGKPPIRRGA GGLSLRRIRQ LEQERRTLVA WSNHAREPGQ VVRIKRGTQV
 781 AQWLVERVNH LKEDRLKKLA DLLIMTALGY VYDETKPSGH KWDKRYPPCQ IILMEDLSGA
 841 AGAAGAAGAA GGQLMAWSHR RLLEILKLQA DLHKLIVGTV FPAFSSRFDA QSGAPGVRCR
 901 SVKKQDIENA AQGKGWLARE LQRLNWTLEW LQPNDLIPTG DGELFVTPAC CDRQKGIKIV
 961 HADLNAAQNL QRRFWGGHAE SLCRVTCDVV ERDGRRYAVP RISNAFADSF YKVFGQGVFV
1021 STDEEDVYRW MVGEKISSRG RSRGRTSDEE AEAETWIDEA REQQGKVIAL FRDASGQIHG
1081 GDWLVAKVFW GWVERLVTAR LLSRMSEREA AAHKE
```

(SEQ ID NO: 44)

FIG. 18A

*Sulfobacillus thermotolerans*

GenBank AUW95303

Cas12b

```
   1 MSARNIKVKI DTKGNPELRL GLWKTHQVTN EGVKYYTEWL IKLRQQDIYR QSREDASPRV
  61 IISASDLKAD LLCHARQLQK ERLPRITGSD AEILGTLRQV YELIVPSSVG KSGDSKTLAR
 121 KFLSPLTDPG SAGGRDQSAS GRKPTWMKMK SEGNPRWEET FRKWKDRKDN DPTPLVLNQI
 181 ADYGLLPLIP LFTDVGENIF DPKSKSQFVR TWDRSMFQQA IERLMSWESW NQRVRREWEA
 241 LNQKHSAFYR EQFTADPDAA LYRVAQSLEE EMRKEHQGFA SDAPEAFRIR RVALKGFDRL
 301 LERWQKTLGK NGQSATLLDD IRRVQSDLGD KFGSAPLYQK LLDERWQRLW AVDPTFLQRY
 361 AAFNDLTQRL QRAKRVANLT LPDAVAHPIW SRYEGANASS GNRYHIHLPT KGQPGSVTFD
 421 RILWPDGNGG WYERKRVTVF LRPSHQVDRI HEAPTDSVVD NFPLVVEDQS ARTILRASWG
 481 GAKLEYDRNR LPRQLKKGVP DSIYLSLTLN LDTNKPSGLF HTQQNGRVWI RKDVLMQYYN
 541 ETPGDNVQFK PLYVMSVDLG IRSAAAVSIF SVQLKAGIEE HRLTYPVADC PGLVAVHERS
 601 VLLTMPGERR EQWDRRYEQQ RQGLRELRTD MRGMNDLLRG AYMDGDRREE FLARLSKLEE
 661 TSPELWGPVY RSLNDSKVAS ATEWERLVVY CHRQVEQSLS SRIQNLRSGR SAYRMSGGLS
 721 LDHVQDLERI RGIIASWTNH PRIPGSVVRW QQGRSHTVAL GRHILELKRD RVKKVANYLI
 781 MTTLGYAYDS KRARGEKWVR RYPACHLMVF EDLTRYRFRT DRPRSENRQL MRWTHQELIA
 841 VTGIQAEPHG ISVGTMYAGF SSRFDAVTKA PGVRGATVRQ ILRTRGMVRL KEIAADVGID
 901 INTLRPHDVL PTGDGEYLLS VVRHGESYRL KQVHADINAA HNLQRRLWTQ DEVFRVSCRL
 961 ALNSGRVVAM PPPSYNKRYG KGFFEKGDNG VYIWKTGGKI KISDTLEEDM DIPEDTAELL
1021 RGNSVTLFRD PSGTIAGGNW LEAKEFWGRV NSLVNKGVRD KILGGIPVDN SSAHAE
```

(SEQ ID NO:45)

FIG. 18B

*Sulfobacillus thermotolerans* variant Cas12b (RYRFRTDRPRSENR; SEQ ID NO:109 deleted)

```
   1 MSARNIKVKI DTKGNPELRL GLWKTHQVTN EGVKYYTEWL IKLRQQDIYR QSREDASPRV
  61 IISASDLKAD LLCHARQLQK ERLPRITGSD AEILGTLRQV YELIVPSSVG KSGDSKTLAR
 121 KFLSPLTDPG SAGGRDQSAS GRKPTWMKMK SEGNPRWEET FRKWKDRKDN DPTPLVLNQI
 181 ADYGLLPLIP LFTDVGENIF DPKSKSQFVR TWDRSMFQQA IERLMSWESW NQRVRREWEA
 241 LNQKHSAFYR EQFTADPDAA LYRVAQSLEE EMRKEHQGFA SDAPEAFRIR RVALKGFDRL
 301 LERWQKTLGK NGQSATLLDD IRRVQSDLGD KFGSAPLYQK LLDERWQRLW AVDPTFLQRY
 361 AAFNDLTQRL QRAKRVANLT LPDAVAHPIW SRYEGANASS GNRYHIHLPT KGQPGSVTFD
 421 RILWPDGNGG WYERKRVTVF LRPSHQVDRI HEAPTDSVVD NFPLVVEDQS ARTILRASWG
 481 GAKLEYDRNR LPRQLKKGVP DSIYLSLTLN LDTNKPSGLF HTQQNGRVWI RKDVLMQYYN
 541 ETPGDNVQFK PLYVMSVDLG IRSAAAVSIF SVQLKAGIEE HRLTYPVADC PGLVAVHERS
 601 VLLTMPGERR EQWDRRYEQQ RQGLRELRTD MRGMNDLLRG AYMDGDRREE FLARLSKLEE
 661 TSPELWGPVY RSLNDSKVAS ATEWERLVVY CHRQVEQSLS SRIQNLRSGR SAYRMSGGLS
 721 LDHVQDLERI RGIIASWTNH PRIPGSVVRW QQGRSHTVAL GRHILELKRD RVKKVANYLI
 781 MTTLGYAYDS KRARGEKWVR RYPACHLMVF EDLT QL MRWTHQELIA
 841 VTGIQAEPHG ISVGTMYAGF SSRFDAVTKA PGVRGATVRQ ILRTRGMVRL KEIAADVGID
 901 INTLRPHDVL PTGDGEYLLS VVRHGESYRL KQVHADINAA HNLQRRLWTQ DEVFRVSCRL
 961 ALNSGRVVAM PPPSYNKRYG KGFFEKGDNG VYIWKTGGKI KISDTLEEDM DIPEDTAELL
1021 RGNSVTLFRD PSGTIAGGNW LEAKEFWGRV NSLVNKGVRD KILGGIPVDN SSAHAE
```

(SEQ ID NO:46)

FIG. 18C

*Sulfobacillus thermotolerans* variant Cas12b (RYRFRTDRPRSENR; SEQ ID NO:109 mutated to GAAGAAGAAGAAGG; SEQ ID NO:111)

```
   1 MSARNIKVKI DTKGNPELRL GLWKTHQVTN EGVKYYTEWL IKLRQQDIYR QSREDASPRV
  61 IISASDLKAD LLCHARQLQK ERLPRITGSD AEILGTLRQV YELIVPSSVG KSGDSKTLAR
 121 KFLSPLTDPG SAGGRDQSAS GRKPTWMKMK SEGNPRWEET FRKWKDRKDN DPTPLVLNQI
 181 ADYGLLPLIP LFTDVGENIF DPKSKSQFVR TWDRSMFQQA IERLMSWESW NQRVRREWEA
 241 LNQKHSAFYR EQFTADPDAA LYRVAQSLEE EMRKEHQGFA SDAPEAFRIR RVALKGFDRL
 301 LERWQKTLGK NGQSATLLDD IRRVQSDLGD KFGSAPLYQK LLDERWQRLW AVDPTFLQRY
 361 AAFNDLTQRL QRAKRVANLT LPDAVAHPIW SRYEGANASS GNRYHIHLPT KGQPGSVTFD
 421 RILWPDGNGG WYERKRVTVF LRPSHQVDRI HEAPTDSVVD NFPLVVEDQS ARTILRASWG
 481 GAKLEYDRNR LPRQLKKGVP DSIYLSLTLN LDTNKPSGLF HTQQNGRVWI RKDVLMQYYN
 541 ETPGDNVQFK PLYVMSVDLG IRSAAAVSIF SVQLKAGIEE HRLTYPVADC PGLVAVHERS
 601 VLLTMPGERR EQWDRRYEQQ RQGLRELRTD MRGMNDLLRG AYMDGDRREE FLARLSKLEE
 661 TSPELWGPVY RSLNDSKVAS ATEWERLVVY CHRQVEQSLS SRIQNLRSGR SAYRMSGGLS
 721 LDHVQDLERI RGIIASWTNH PRIPGSVVRW QQGRSHTVAL GRHILELKRD RVKKVANYLI
 781 MTTLGYAYDS KRARGEKWVR RYPACHLMVF EDLTGAAGAA GAAGAAGGQL MRWTHQELIA
 841 VTGIQAEPHG ISVGTMYAGF SSRFDAVTKA PGVRGATVRQ ILRTRGMVRL KEIAADVGID
 901 INTLRPHDVL PTGDGEYLLS VVRHGESYRL KQVHADINAA HNLQRRLWTQ DEVFRVSCRL
 961 ALNSGRVVAM PPPSYNKRYG KGFFEKGDNG VYIWKTGGKI KISDTLEEDM DIPEDTAELL
1021 RGNSVTLFRD PSGTIAGGNW LEAKEFWGRV NSLVNKGVRD KILGGIPVDN SSAHAE
```

(SEQ ID NO:47)

FIG. 19A

*Deltaproteobacteria bacterium* GWA2_43_19
CasX

MEKRINKIRKKLSADNATKPVSRSGPMKTLLVRVMTDDLKKRLEKRRKKPEVMPQVISNNAANNLRMLLDDYTKMKEAIL
QVYWQEFKDDHVGLMCKFAQPASKKIDQNKLKPEMDEKGNLTTAGFACSQCGQPLFVYKLEQVSEKGKAYTNYFGRCNV
AEHEKLILLAQLKPEKDSDEAVTYSLGKFGQRALDFYSIHVTKESTHPVKPLAQIAGNRYASGPVGKALSDACMGTIASFLSK
YQDIIIEHQKVVKGNQKRLESLRELAGKENLEYPSVTLPPQPHTKEGVDAYNEVIARVRMWVNLNLWQKLKLSRDDAKPLL
RLKGFPSFPVVERRENEVDWWNTINEVKKLIDAKRDMGRVFWSGVTAEKRNTILEGYNYLPNENDHKKREGSLENPKKPA
KRQFGDLLLYLEKKYAGDWGKVFDEAWERIDKKIAGLTSHIEREEARNAEDAQSKAVLTDWLRAKASFVLERLKEMDEKE
FYACEIQLQKWYGDLRGNPFAVEAENRVVDISGFSIGSDGHSIQYRNLLAWKYLENGKREFYLLMNYGKKGRIRFTDGTDIK
KSGKWQGLLYGGGKAKVIDLTFDPDDEQLIILPLAFGTRQGREFIWNDLLSLETGLIKLANGRVIEKTIYNKKIGRDEPALFVA
LTFERREVVDPSNIKPVNLIGVDRGENIPAVIALTDPEGCPLPEFKDSSGGPTDILRIGEGYKEKQRAIQAAKEVEQRRAGGYS
RKFASKSRNLADDMVRNSARDLFYHAVTHDAVLVFENLSRGFGRQGKRTFMTERQYTKMEDWLTAKLAYEGLTSKTYL
SKTLAQYTSKTCSNCGFTITTADYDGMLVRLKKTSDGWATTLNNKELKAEGQITYYNRYKRQTVEKELSAELDRLSEESGN
NDISKWTKGRRDEALFLLKKRFSHRPVQEQFVCLDCGHEVHADEQAALNIARSWLFLNSNSTEFKSYKSGKQPFVGAWQAF
YKRRLKEVWKPNA (SEQ ID NO:48)

FIG. 19B

*Deltaproteobacteria bacterium* GWA2_43_19 variant CasX (GRQGKRTFMTERQ; SEQ ID NO:68 deleted)

MEKRINKIRKKLSADNATKPVSRSGPMKTLLVRVMTDDLKKRLEKRRKKPEVMPQVISNNAANNLRMLLDDYTKMKEAIL
QVYWQEFKDDHVGLMCKFAQPASKKIDQNKLKPEMDEKGNLTTAGFACSQCGQPLFVYKLEQVSEKGKAYTNYFGRCNV
AEHEKLILLAQLKPEKDSDEAVTYSLGKFGQRALDFYSIHVTKESTHPVKPLAQIAGNRYASGPVGKALSDACMGTIASFLSK
YQDIIIEHQKVVKGNQKRLESLRELAGKENLEYPSVTLPPQPHTKEGVDAYNEVIARVRMWVNLNLWQKLKLSRDDAKPLL
RLKGFPSFPVVERRENEVDWWNTINEVKKLIDAKRDMGRVFWSGVTAEKRNTILEGYNYLPNENDHKKREGSLENPKKPA
KRQFGDLLLYLEKKYAGDWGKVFDEAWERIDKKIAGLTSHIEREEARNAEDAQSKAVLTDWLRAKASFVLERLKEMDEKE
FYACEIQLQKWYGDLRGNPFAVEAENRVVDISGFSIGSDGHSIQYRNLLAWKYLENGKREFYLLMNYGKKGRIRFTDGTDIK
KSGKWQGLLYGGGKAKVIDLTFDPDDEQLIILPLAFGTRQGREFIWNDLLSLETGLIKLANGRVIEKTIYNKKIGRDEPALFVA
LTFERREVVDPSNIKPVNLIGVDRGENIPAVIALTDPEGCPLPEFKDSSGGPTDILRIGEGYKEKQRAIQAAKEVEQRRAGGYS
RKFASKSRNLADDMVRNSARDLFYHAVTHDAVLVFENLSRGFYTKMEDWLTAKLAYEGLTSKTYLSKTLAQYTSKTCSNC
GFTITTADYDGMLVRLKKTSDGWATTLNNKELKAEGQITYYNRYKRQTVEKELSAELDRLSEESGNNDISKWTKGRRDEAL
FLLKKRFSHRPVQEQFVCLDCGHEVHADEQAALNIARSWLFLNSNSTEFKSYKSGKQPFVGAWQAFYKRRLKEVWKPNA (SEQ ID NO:49)

FIG. 19C

*Deltaproteobacteria bacterium* GWA2_43_19 variant CasX (GRQGKRTFMTERQ; SEQ ID NO:68 mutated to GGAGGAGGAGGAG; SEQ ID NO:143)

MEKRINKIRKKLSADNATKPVSRSGPMKTLLVRVMTDDLKKRLEKRRKKPEVMPQVISNNAANNLRMLLDDYTKMKEAIL
QVYWQEFKDDHVGLMCKFAQPASKKIDQNKLKPEMDEKGNLTTAGFACSQCGQPLFVYKLEQVSEKGKAYTNYFGRCNV
AEHEKLILLAQLKPEKDSDEAVTYSLGKFGQRALDFYSIHVTKESTHPVKPLAQIAGNRYASGPVGKALSDACMGTIASFLSK
YQDIIIEHQKVVKGNQKRLESLRELAGKENLEYPSVTLPPQPHTKEGVDAYNEVIARVRMWVNLNLWQKLKLSRDDAKPLL
RLKGFPSFPVVERRENEVDWWNTINEVKKLIDAKRDMGRVFWSGVTAEKRNTILEGYNYLPNENDHKKREGSLENPKKPA
KRQFGDLLLYLEKKYAGDWGKVFDEAWERIDKKIAGLTSHIEREEARNAEDAQSKAVLTDWLRAKASFVLERLKEMDEKE
FYACEIQLQKWYGDLRGNPFAVEAENRVVDISGFSIGSDGHSIQYRNLLAWKYLENGKREFYLLMNYGKKGRIRFTDGTDIK
KSGKWQGLLYGGGKAKVIDLTFDPDDEQLIILPLAFGTRQGREFIWNDLLSLETGLIKLANGRVIEKTIYNKKIGRDEPALFVA
LTFERREVVDPSNIKPVNLIGVDRGENIPAVIALTDPEGCPLPEFKDSSGGPTDILRIGEGYKEKQRAIQAAKEVEQRRAGGYS
RKFASKSRNLADDMVRNSARDLFYHAVTHDAVLVFENLSRGFGGAGGAGGAGGAGYTKMEDWLTAKLAYEGLTSKTYL
SKTLAQYTSKTCSNCGFTITTADYDGMLVRLKKTSDGWATTLNNKELKAEGQITYYNRYKRQTVEKELSAELDRLSEESGN
NDISKWTKGRRDEALFLLKKRFSHRPVQEQFVCLDCGHEVHADEQAALNIARSWLFLNSNSTEFKSYKSGKQPFVGAWQAF
YKRRLKEVWKPNA (SEQ ID NO:50)

FIG. 20A

*Plantomycetes bacterium*

CasX

```
  1 MQEIKRINKI RRRLVKDSNT KKAGKTGPMK TLLVRVMTPD LRERLENLRK KPENIPQPIS
 61 NTSRANLNKL LTDYTEMKKA ILHVYWEEFQ KDPVGLMSRV AQPAPKNIDQ RKLIPVKDGN
121 ERLTSSGFAC SQCCQPLYVY KLEQVNDKGK PHTNYFGRCN VSEHERLILL SPHKPEANDE
181 LVTYSLGKFG QRALDFYSIH VTRESNHPVK PLEQIGGNSC ASGPVGKALS DACMGAVASF
241 LTKYQDIILE HQKVIKKNEK RLANLKDIAS ANGLAFPKIT LPPQPHTKEG IEAYNNVVAQ
301 IVIWVNLNLW QKLKIGRDEA KPLQRLKGFP SFPLVERQAN EVDWWDMVCN VKKLINEKKE
361 DGKVFWQNLA GYKRQEALLP YLSSEEDRKK GKKFARYQFG DLLLHLEKKH GEDWGKVYDE
421 AWERIDKKVE GLSKHIKLEE ERRSEDAQSK AALTDWLRAK ASFVIEGLKE ADKDEFCRCE
481 LKLQKWYGDL RGKPFAIEAE NSILDISGFS KQYNCAFIWQ KDGVKKLNLY LIINYFKGGK
541 LRFKKIKPEA FEANRFYTVI NKKSGEIVPM EVNFNFDDPN LIILPLAFGK RQGREFIWND
601 LLSLETGSLK LANGRVIEKT LYNRRTRQDE PALFVALTFE RREVLDSSNI KPMNLIGIDR
661 GENIPAVIAL TDPEGCPLSR FKDSLGNPTH ILRIGESYKE KQRTIQAAKE VEQRRAGGYS
721 RKYASKAKNL ADDMVRNTAR DLLYYAVTQD AMLIFENLSR GFGRQGKRTF MAERQYTRME
781 DWLTAKLAYE GLPSKTYLSK TLAQYTSKTC SNCGFTITSA DYDRVLEKLK KTATGWMTTI
841 NGKELKVEGQ ITYYNRYKRQ NVVKDLSVEL DRLSEESVNN DISSWTKGRS GEALSLLKKR
901 FSHRPVQEKF VCLNCGFETH ADEQAALNIA RSWLFLRSQE YKKYQTNKTT GNTDKRAFVE
961 TWQSFYRKKL KEVWKPAV
```

(SEQ ID NO:51)

FIG. 20B

*Plantomycetes bacterium* variant CasX (GRQGKRTFMAERQ; SEQ ID NO:112 deleted)

1 MQEIKRINKI RRRLVKDSNT KKAGKTGPMK TLLVRVMTPD LRERLENLRK KPENIPQPIS
61 NTSRANLNKL LTDYTEMKKA ILHVYWEEFQ KDPVGLMSRV AQPAPKNIDQ RKLIPVKDGN
121 ERLTSSGFAC SQCCQPLYVY KLEQVNDKGK PHTNYFGRCN VSEHERLILL SPHKPEANDE
181 LVTYSLGKFG QRALDFYSIH VTRESNHPVK PLEQIGGNSC ASGPVGKALS DACMGAVASF
241 LTKYQDIILE HQKVIKKNEK RLANLKDIAS ANGLAFPKIT LPPQPHTKEG IEAYNNVVAQ
301 IVIWVNLNLW QKLKIGRDEA KPLQRLKGFP SFPLVERQAN EVDWWDMVCN VKKLINEKKE
361 DGKVFWQNLA GYKRQEALLP YLSSEEDRKK GKKFARYQFG DLLLHLEKKH GEDWGKVYDE
421 AWERIDKKVE GLSKHIKLEE ERRSEDAQSK AALTDWLRAK ASFVIEGLKE ADKDEFCRCE
481 LKLQKWYGDL RGKPFAIEAE NSILDISGFS KQYNCAFIWQ KDGVKKLNLY LIINYFKGGK
541 LRFKKIKPEA FEANRFYTVI NKKSGEIVPM EVNFNFDDPN LIILPLAFGK RQGREFIWND
601 LLSLETGSLK LANGRVIEKT LYNRRTRQDE PALFVALTFE RREVLDSSNI KPMNLIGIDR
661 GENIPAVIAL TDPEGCPLSR FKDSLGNPTH ILRIGESYKE KQRTIQAAKE VEQRRAGGYS
721 RKYASKAKNL ADDMVRNTAR DLLYYAVTQD AMLIFENLSR GFYTRME
781 DWLTAKLAYE GLPSKTYLSK TLAQYTSKTC SNCGFTITSA DYDRVLEKLK KTATGWMTTI
841 NGKELKVEGQ ITYYNRYKRQ NVVKDLSVEL DRLSEESVNN DISSWTKGRS GEALSLLKKR
901 FSHRPVQEKF VCLNCGFETH ADEQAALNIA RSWLFLRSQE YKKYQTNKTT GNTDKRAFVE
961 TWQSFYRKKL KEVWKPAV (SEQ ID NO: 52)

FIG. 20C

*Plantomycetes bacterium* variant CasX (GRQGKRTFMAERQ; SEQ ID NO:112 mutated to GGAGGAGGAGGAG; SEQ ID NO:143)

```
  1 MQEIKRINKI RRRLVKDSNT KKAGKTGPMK TLLVRVMTPD LRERLENLRK KPENIPQPIS
 61 NTSRANLNKL LTDYTEMKKA ILHVYWEEFQ KDPVGLMSRV AQPAPKNIDQ RKLIPVKDGN
121 ERLTSSGFAC SQCCQPLYVY KLEQVNDKGK PHTNYFGRCN VSEHERLILL SPHKPEANDE
181 LVTYSLGKFG QRALDFYSIH VTRESNHPVK PLEQIGGNSC ASGPVGKALS DACMGAVASF
241 LTKYQDIILE HQKVIKKNEK RLANLKDIAS ANGLAFPKIT LPPQPHTKEG IEAYNNVVAQ
301 IVIWVNLNLW QKLKIGRDEA KPLQRLKGFP SFPLVERQAN EVDWWDMVCN VKKLINEKKE
361 DGKVFWQNLA GYKRQEALLP YLSSEEDRKK GKKFARYQFG DLLLHLEKKH GEDWGKVYDE
421 AWERIDKKVE GLSKHIKLEE ERRSEDAQSK AALTDWLRAK ASFVIEGLKE ADKDEFCRCE
481 LKLQKWYGDL RGKPFAIEAE NSILDISGFS KQYNCAFIWQ KDGVKKLNLY LIINYFKGGK
541 LRFKKIKPEA FEANRFYTVI NKKSGEIVPM EVNFNFDDPN LIILPLAFGK RQGREFIWND
601 LLSLETGSLK LANGRVIEKT LYNRRTRQDE PALFVALTFE RREVLDSSNI KPMNLIGIDR
661 GENIPAVIAL TDPEGCPLSR FKDSLGNPTH ILRIGESYKE KQRTIQAAKE VEQRRAGGYS
721 RKYASKAKNL ADDMVRNTAR DLLYYAVTQD AMLIFENLSR GFGGAGGAGG AGGAGYTRME
781 DWLTAKLAYE GLPSKTYLSK TLAQYTSKTC SNCGFTITSA DYDRVLEKLK KTATGWMTTI
841 NGKELKVEGQ ITYYNRYKRQ NVVKDLSVEL DRLSEESVNN DISSWTKGRS GEALSLLKKR
901 FSHRPVQEKF VCLNCGFETH ADEQAALNIA RSWLFLRSQE YKKYQTNKTT GNTDKRAFVE
961 TWQSFYRKKL KEVWKPAV
```

(SEQ ID NO:53)

FIG. 21A crRNA repeat sequences

LbCas12a crRNA:

5′ AAUUUCUACUAAGUGUAGAU [spacer] 3′ (SEQ ID NO:54)

AsCas12a crRNA:

5′ AAUUUCUACUCUUGUAGAU [spacer] 3′ (SEQ ID NO:55)

FnCas12a crRNA:

5′ AAUUUCUACUGUUGUAGAU [spacer] 3′ (SEQ ID NO:56)

PmCas12a crRNA:

5′ AAUUUCUACUAUUGUAGAU [spacer] 3′ (SEQ ID NO:57)

MbCas12a/Mb2Cas12a/Mb3Cas12a crRNA:

5′ AAUUUCUACUGUUUGUAGAU [spacer] 3′ (SEQ ID NO:58)

TsCas12a crRNA

5′ AAUUUCUACUGUUGUAGAU [spacer] 3′ (SEQ ID NO:56)

BsCas12a crRNA

5′ AAUUUCUACUAUUGUAGAU [spacer] 3′ (SEQ ID NO:57)

AacCas12b single guide RNA (sgRNA)

5′

GUCUAGAGGACAGAAUUUUUCAACGGGUGUGCCAAUGGCCACUUUCCAGGUGGCAAAGCC

CGUUGAGCUUCUCAAAUCUGAGAAGUGGCAC [spacer] 3′ (SEQ ID NO: 59)

FIG. 21B

PAMs

LbCas12a PAM: 5′-TTTN-3′

AsCas12a PAM: 5′-TTTN-3′

FnCas12a PAM: 5′-TTN-3′

PmCas12a PAM: 5′-TTN-3′

MbCas12a/Mb2Cas12a/Mb3Cas12a PAM: 5′-TTN-3′

TsCas12a PAM: 5′-TTN-3′

BsCas12a PAM: 5′-TTN-3′

AacCas12b PAM: 5′-TTN-3′

FIG. 22
Cas12a
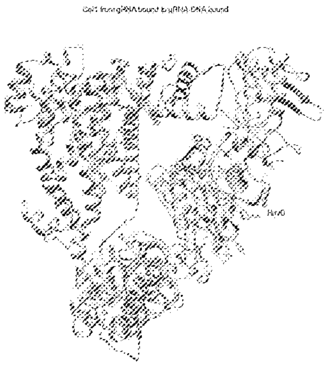
Cas12b
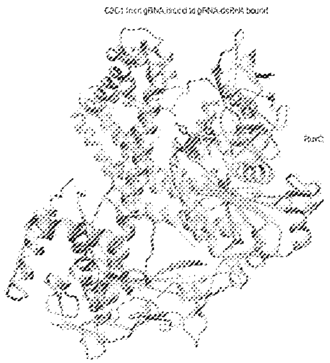
DpbCasX
```
     929      937                      852          865                          776        788
Lb--SCFKNSRVK--SEQ ID NO:60    Aa--EYQFNNDRPPSENN--SEQ ID NO:64    Dpb--CRQGKRTFMTERQ--SEQ ID NO:68
Fn--FCFKRGRFK--SEQ ID NO:61    Am--EYRFSNDRPPSENS--SEQ ID NO:65    Plm--CRQGKRTFMAERQ--SEQ ID NO:68
As--FCFKSKRTG--SEQ ID NO:62    Ah--RYRFQSDRPPSENS--SEQ ID NO:66
Ft--FCFKRGRFK--SEQ ID NO:61    Ak--AYRFSDDRPPSENS--SEQ ID NO:67
Pc--MCFKRGRQK--SEQ ID NO:63
```
LbCas12a
Wild-Type (WT), iL0, IL3, IL9

FIG. 24 cas12a IL mutant Proteins

| | | | | |
|---|---|---|---|---|
| w.t. | EDLN | SGF**K**NS**R**V**K** | V**E**KQ | (SEQ ID NO:69) |
| IL9 | EDLN | GGAAGGAAP | V**E**KQ | (SEQ ID NO:70) |
| IL3 | EDLN | GAP | V**E**KQ | (SEQ ID NO:71) |
| IL0 | EDLN | P | V**E**KQ | (SEQ ID NO:72) |

```
                                SEQUENCE LISTING

<160> NUMBER OF SEQ ID NOS: 145

<210> SEQ ID NO 1
<211> LENGTH: 1228
<212> TYPE: PRT
<213> ORGANISM: Lachnospiraceae bacterium

<400> SEQUENCE: 1

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320
```

```
Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
```

```
        740                 745                 750

Lys Glu Glu Leu Val Val His Pro Ala Asn Ser Pro Ile Ala Asn Lys
    755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Val Asp Gly Lys Gly
        835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
        915                 920                 925

Ser Gly Phe Lys Asn Ser Arg Val Lys Val Glu Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu  Thr Ser Lys Ile Asp  Pro Ser Thr
        995                 1000                1005

Gly Phe  Val Asn Leu Leu Lys  Thr Lys Tyr Thr Ser  Ile Ala Asp
    1010                1015                1020

Ser Lys  Lys Phe Ile Ser Ser  Phe Asp Arg Ile Met  Tyr Val Pro
    1025                1030                1035

Glu Glu  Asp Leu Phe Glu Phe  Ala Leu Asp Tyr Lys  Asn Phe Ser
    1040                1045                1050

Arg Thr  Asp Ala Asp Tyr Ile  Lys Lys Trp Lys Leu  Tyr Ser Tyr
    1055                1060                1065

Gly Asn  Arg Ile Arg Ile Phe  Arg Asn Pro Lys Lys  Asn Asn Val
    1070                1075                1080

Phe Asp  Trp Glu Glu Val Cys  Leu Thr Ser Ala Tyr  Lys Glu Leu
    1085                1090                1095

Phe Asn  Lys Tyr Gly Ile Asn  Tyr Gln Gln Gly Asp  Ile Arg Ala
    1100                1105                1110

Leu Leu  Cys Glu Gln Ser Asp  Lys Ala Phe Tyr Ser  Ser Phe Met
    1115                1120                1125

Ala Leu  Met Ser Leu Met Leu  Gln Met Arg Asn Ser  Ile Thr Gly
    1130                1135                1140

Arg Thr  Asp Val Asp Phe Leu  Ile Ser Pro Val Lys  Asn Ser Asp
    1145                1150                1155
```

Gly Ile Phe Tyr Asp Ser Arg Asn Tyr Glu Ala Gln Glu Asn Ala
1160 1165 1170

Ile Leu Pro Lys Asn Ala Asp Ala Asn Gly Ala Tyr Asn Ile Ala
1175 1180 1185

Arg Lys Val Leu Trp Ala Ile Gly Gln Phe Lys Lys Ala Glu Asp
1190 1195 1200

Glu Lys Leu Asp Lys Val Lys Ile Ala Ile Ser Asn Lys Glu Trp
1205 1210 1215

Leu Glu Tyr Ala Gln Thr Ser Val Lys His
1220 1225

<210> SEQ ID NO 2
<211> LENGTH: 1219
<212> TYPE: PRT
<213> ORGANISM: Lachnospiraceae bacterium

<400> SEQUENCE: 2

Met Ser Lys Leu Glu Lys Phe Thr Asn Cys Tyr Ser Leu Ser Lys Thr
1 5 10 15

Leu Arg Phe Lys Ala Ile Pro Val Gly Lys Thr Gln Glu Asn Ile Asp
20 25 30

Asn Lys Arg Leu Leu Val Glu Asp Glu Lys Arg Ala Glu Asp Tyr Lys
35 40 45

Gly Val Lys Lys Leu Leu Asp Arg Tyr Tyr Leu Ser Phe Ile Asn Asp
50 55 60

Val Leu His Ser Ile Lys Leu Lys Asn Leu Asn Asn Tyr Ile Ser Leu
65 70 75 80

Phe Arg Lys Lys Thr Arg Thr Glu Lys Glu Asn Lys Glu Leu Glu Asn
85 90 95

Leu Glu Ile Asn Leu Arg Lys Glu Ile Ala Lys Ala Phe Lys Gly Asn
100 105 110

Glu Gly Tyr Lys Ser Leu Phe Lys Lys Asp Ile Ile Glu Thr Ile Leu
115 120 125

Pro Glu Phe Leu Asp Asp Lys Asp Glu Ile Ala Leu Val Asn Ser Phe
130 135 140

Asn Gly Phe Thr Thr Ala Phe Thr Gly Phe Phe Asp Asn Arg Glu Asn
145 150 155 160

Met Phe Ser Glu Glu Ala Lys Ser Thr Ser Ile Ala Phe Arg Cys Ile
165 170 175

Asn Glu Asn Leu Thr Arg Tyr Ile Ser Asn Met Asp Ile Phe Glu Lys
180 185 190

Val Asp Ala Ile Phe Asp Lys His Glu Val Gln Glu Ile Lys Glu Lys
195 200 205

Ile Leu Asn Ser Asp Tyr Asp Val Glu Asp Phe Phe Glu Gly Glu Phe
210 215 220

Phe Asn Phe Val Leu Thr Gln Glu Gly Ile Asp Val Tyr Asn Ala Ile
225 230 235 240

Ile Gly Gly Phe Val Thr Glu Ser Gly Glu Lys Ile Lys Gly Leu Asn
245 250 255

Glu Tyr Ile Asn Leu Tyr Asn Gln Lys Thr Lys Gln Lys Leu Pro Lys
260 265 270

Phe Lys Pro Leu Tyr Lys Gln Val Leu Ser Asp Arg Glu Ser Leu Ser
275 280 285

Phe Tyr Gly Glu Gly Tyr Thr Ser Asp Glu Glu Val Leu Glu Val Phe

-continued

```
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720
```

```
Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Val Asp Gly Lys Gly
        835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
        915                 920                 925

Val Glu Lys Gln Val Tyr Gln Lys Phe Glu Lys Met Leu Ile Asp Lys
    930                 935                 940

Leu Asn Tyr Met Val Asp Lys Lys Ser Asn Pro Cys Ala Thr Gly Gly
945                 950                 955                 960

Ala Leu Lys Gly Tyr Gln Ile Thr Asn Lys Phe Glu Ser Phe Lys Ser
                965                 970                 975

Met Ser Thr Gln Asn Gly Phe Ile Phe Tyr Ile Pro Ala Trp Leu Thr
            980                 985                 990

Ser Lys Ile Asp Pro Ser Thr Gly  Phe Val Asn Leu Leu  Lys Thr Lys
        995                 1000                1005

Tyr Thr  Ser Ile Ala Asp Ser  Lys Lys Phe Ile Ser  Ser Phe Asp
    1010                1015                1020

Arg Ile  Met Tyr Val Pro Glu  Glu Asp Leu Phe Glu  Phe Ala Leu
    1025                1030                1035

Asp Tyr  Lys Asn Phe Ser Arg  Thr Asp Ala Asp Tyr  Ile Lys Lys
    1040                1045                1050

Trp Lys  Leu Tyr Ser Tyr Gly  Asn Arg Ile Arg Ile  Phe Arg Asn
    1055                1060                1065

Pro Lys  Lys Asn Asn Val Phe  Asp Trp Glu Glu Val  Cys Leu Thr
    1070                1075                1080

Ser Ala  Tyr Lys Glu Leu Phe  Asn Lys Tyr Gly Ile  Asn Tyr Gln
    1085                1090                1095

Gln Gly  Asp Ile Arg Ala Leu  Leu Cys Glu Gln Ser  Asp Lys Ala
    1100                1105                1110

Phe Tyr  Ser Ser Phe Met Ala  Leu Met Ser Leu Met  Leu Gln Met
    1115                1120                1125
```

Arg Asn Ser Ile Thr Gly Arg Thr Asp Val Asp Phe Leu Ile Ser
1130 1135 1140

Pro Val Lys Asn Ser Asp Gly Ile Phe Tyr Asp Ser Arg Asn Tyr
1145 1150 1155

Glu Ala Gln Glu Asn Ala Ile Leu Pro Lys Asn Ala Asp Ala Asn
1160 1165 1170

Gly Ala Tyr Asn Ile Ala Arg Lys Val Leu Trp Ala Ile Gly Gln
1175 1180 1185

Phe Lys Lys Ala Glu Asp Glu Lys Leu Asp Lys Val Lys Ile Ala
1190 1195 1200

Ile Ser Asn Lys Glu Trp Leu Glu Tyr Ala Gln Thr Ser Val Lys
1205 1210 1215

His

<210> SEQ ID NO 3
<211> LENGTH: 1300
<212> TYPE: PRT
<213> ORGANISM: Francisella novicida

<400> SEQUENCE: 3

Met Ser Ile Tyr Gln Glu Phe Val Asn Lys Tyr Ser Leu Ser Lys Thr
1 5 10 15

Leu Arg Phe Glu Leu Ile Pro Gln Gly Lys Thr Leu Glu Asn Ile Lys
20 25 30

Ala Arg Gly Leu Ile Leu Asp Asp Glu Lys Arg Ala Lys Asp Tyr Lys
35 40 45

Lys Ala Lys Gln Ile Ile Asp Lys Tyr His Gln Phe Phe Ile Glu Glu
50 55 60

Ile Leu Ser Ser Val Cys Ile Ser Glu Asp Leu Leu Gln Asn Tyr Ser
65 70 75 80

Asp Val Tyr Phe Lys Leu Lys Lys Ser Asp Asp Asp Asn Leu Gln Lys
85 90 95

Asp Phe Lys Ser Ala Lys Asp Thr Ile Lys Lys Gln Ile Ser Glu Tyr
100 105 110

Ile Lys Asp Ser Glu Lys Phe Lys Asn Leu Phe Asn Gln Asn Leu Ile
115 120 125

Asp Ala Lys Lys Gly Gln Glu Ser Asp Leu Ile Leu Trp Leu Lys Gln
130 135 140

Ser Lys Asp Asn Gly Ile Glu Leu Phe Lys Ala Asn Ser Asp Ile Thr
145 150 155 160

Asp Ile Asp Glu Ala Leu Glu Ile Ile Lys Ser Phe Lys Gly Trp Thr
165 170 175

Thr Tyr Phe Lys Gly Phe His Glu Asn Arg Lys Asn Val Tyr Ser Ser
180 185 190

Asn Asp Ile Pro Thr Ser Ile Ile Tyr Arg Ile Val Asp Asp Asn Leu
195 200 205

Pro Lys Phe Leu Glu Asn Lys Ala Lys Tyr Glu Ser Leu Lys Asp Lys
210 215 220

Ala Pro Glu Ala Ile Asn Tyr Glu Gln Ile Lys Lys Asp Leu Ala Glu
225 230 235 240

Glu Leu Thr Phe Asp Ile Asp Tyr Lys Thr Ser Glu Val Asn Gln Arg
245 250 255

Val Phe Ser Leu Asp Glu Val Phe Glu Ile Ala Asn Phe Asn Asn Tyr
260 265 270

```
Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
```

-continued

```
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                1005

Asn Phe  Gly Phe Lys Arg Gly  Arg Phe Lys Val Glu  Lys Gln Val
    1010                1015                1020

Tyr Gln  Lys Leu Glu Lys Met  Leu Ile Glu Lys Leu  Asn Tyr Leu
    1025                1030                1035

Val Phe  Lys Asp Asn Glu Phe  Asp Lys Thr Gly Gly  Val Leu Arg
    1040                1045                1050

Ala Tyr  Gln Leu Thr Ala Pro  Phe Glu Thr Phe Lys  Lys Met Gly
    1055                1060                1065

Lys Gln  Thr Gly Ile Ile Tyr  Tyr Val Pro Ala Gly  Phe Thr Ser
    1070                1075                1080

Lys Ile  Cys Pro Val Thr Gly  Phe Val Asn Gln Leu  Tyr Pro Lys
    1085                1090                1095

Tyr Glu  Ser Val Ser Lys Ser  Gln Glu Phe Phe Ser  Lys Phe Asp
    1100                1105                1110
```

```
Lys Ile  Cys Tyr Asn Leu Asp  Lys Gly Tyr Phe Glu  Phe Ser Phe
    1115                 1120                 1125

Asp Tyr  Lys Asn Phe Gly Asp  Lys Ala Ala Lys Gly  Lys Trp Thr
    1130                 1135                 1140

Ile Ala  Ser Phe Gly Ser Arg  Leu Ile Asn Phe Arg  Asn Ser Asp
    1145                 1150                 1155

Lys Asn  His Asn Trp Asp Thr  Arg Glu Val Tyr Pro  Thr Lys Glu
    1160                 1165                 1170

Leu Glu  Lys Leu Leu Lys Asp  Tyr Ser Ile Glu Tyr  Gly His Gly
    1175                 1180                 1185

Glu Cys  Ile Lys Ala Ala Ile  Cys Gly Glu Ser Asp  Lys Lys Phe
    1190                 1195                 1200

Phe Ala  Lys Leu Thr Ser Val  Leu Asn Thr Ile Leu  Gln Met Arg
    1205                 1210                 1215

Asn Ser  Lys Thr Gly Thr Glu  Leu Asp Tyr Leu Ile  Ser Pro Val
    1220                 1225                 1230

Ala Asp  Val Asn Gly Asn Phe  Phe Asp Ser Arg Gln  Ala Pro Lys
    1235                 1240                 1245

Asn Met  Pro Gln Asp Ala Asp  Ala Asn Gly Ala Tyr  His Ile Gly
    1250                 1255                 1260

Leu Lys  Gly Leu Met Leu Leu  Gly Arg Ile Lys Asn  Asn Gln Glu
    1265                 1270                 1275

Gly Lys  Lys Leu Asn Leu Val  Ile Lys Asn Glu Glu  Tyr Phe Glu
    1280                 1285                 1290

Phe Val  Gln Asn Arg Asn Asn
    1295                 1300
```

<210> SEQ ID NO 4
<211> LENGTH: 1211
<212> TYPE: PRT
<213> ORGANISM: Lachnospiraceae bacterium

<400> SEQUENCE: 4

```
Arg Phe Lys Ala Ile Pro Val Gly Lys Thr Gln Glu Asn Ile Asp Asn
1               5                   10                  15

Lys Arg Leu Leu Val Glu Asp Glu Lys Arg Ala Glu Asp Tyr Lys Gly
            20                  25                  30

Val Lys Lys Leu Leu Asp Arg Tyr Tyr Leu Ser Phe Ile Asn Asp Val
        35                  40                  45

Leu His Ser Ile Lys Leu Lys Asn Leu Asn Asn Tyr Ile Ser Leu Phe
    50                  55                  60

Arg Lys Lys Thr Arg Thr Glu Lys Glu Asn Lys Glu Leu Glu Asn Leu
65                  70                  75                  80

Glu Ile Asn Leu Arg Lys Glu Ile Ala Lys Ala Phe Lys Gly Asn Glu
                85                  90                  95

Gly Tyr Lys Ser Leu Phe Lys Lys Asp Ile Ile Glu Thr Ile Leu Pro
            100                 105                 110

Glu Phe Leu Asp Asp Lys Asp Glu Ile Ala Leu Val Asn Ser Phe Asn
        115                 120                 125

Gly Phe Thr Thr Ala Phe Thr Gly Phe Phe Asp Asn Arg Glu Asn Met
    130                 135                 140

Phe Ser Glu Glu Ala Lys Ser Thr Ser Ile Ala Phe Arg Cys Ile Asn
145                 150                 155                 160

Glu Asn Leu Thr Arg Tyr Ile Ser Asn Met Asp Ile Phe Glu Lys Val
```

```
                165                 170                 175

Asp Ala Ile Phe Asp Lys His Glu Val Gln Glu Ile Lys Glu Lys Ile
            180                 185                 190

Leu Asn Ser Asp Tyr Asp Val Glu Asp Phe Phe Glu Gly Glu Phe Phe
        195                 200                 205

Asn Phe Val Leu Thr Gln Glu Gly Ile Asp Val Tyr Asn Ala Ile Ile
    210                 215                 220

Gly Gly Phe Val Thr Glu Ser Gly Glu Lys Ile Lys Gly Leu Asn Glu
225                 230                 235                 240

Tyr Ile Asn Leu Tyr Asn Gln Lys Thr Lys Gln Lys Leu Pro Lys Phe
                245                 250                 255

Lys Pro Leu Tyr Lys Gln Val Leu Ser Asp Arg Glu Ser Leu Ser Phe
            260                 265                 270

Tyr Gly Glu Gly Tyr Thr Ser Asp Glu Glu Val Leu Glu Val Phe Arg
        275                 280                 285

Asn Thr Leu Asn Lys Asn Ser Glu Ile Phe Ser Ser Ile Lys Lys Leu
    290                 295                 300

Glu Lys Leu Phe Lys Asn Phe Asp Glu Tyr Ser Ser Ala Gly Ile Phe
305                 310                 315                 320

Val Lys Asn Gly Pro Ala Ile Ser Thr Ile Ser Lys Asp Ile Phe Gly
                325                 330                 335

Glu Trp Asn Val Ile Arg Asp Lys Trp Asn Ala Glu Tyr Asp Asp Ile
            340                 345                 350

His Leu Lys Lys Lys Ala Val Val Thr Glu Lys Tyr Glu Asp Asp Arg
        355                 360                 365

Arg Lys Ser Phe Lys Lys Ile Gly Ser Phe Ser Leu Glu Gln Leu Gln
    370                 375                 380

Glu Tyr Ala Asp Ala Asp Leu Ser Val Val Glu Lys Leu Lys Glu Ile
385                 390                 395                 400

Ile Ile Gln Lys Val Asp Glu Ile Tyr Lys Val Tyr Gly Ser Ser Glu
                405                 410                 415

Lys Leu Phe Asp Ala Asp Phe Val Leu Glu Lys Ser Leu Lys Lys Asn
            420                 425                 430

Asp Ala Val Val Ala Ile Met Lys Asp Leu Leu Asp Ser Val Lys Ser
        435                 440                 445

Phe Glu Asn Tyr Ile Lys Ala Phe Phe Gly Glu Gly Lys Glu Thr Asn
    450                 455                 460

Arg Asp Glu Ser Phe Tyr Gly Asp Phe Val Leu Ala Tyr Asp Ile Leu
465                 470                 475                 480

Leu Lys Val Asp His Ile Tyr Asp Ala Ile Arg Asn Tyr Val Thr Gln
                485                 490                 495

Lys Pro Tyr Ser Lys Asp Lys Phe Lys Leu Tyr Phe Gln Asn Pro Gln
            500                 505                 510

Phe Met Gly Gly Trp Asp Lys Asp Lys Glu Thr Asp Tyr Arg Ala Thr
        515                 520                 525

Ile Leu Arg Tyr Gly Ser Lys Tyr Tyr Leu Ala Ile Met Asp Lys Lys
    530                 535                 540

Tyr Ala Lys Cys Leu Gln Lys Ile Asp Lys Asp Asp Val Asn Gly Asn
545                 550                 555                 560

Tyr Glu Lys Ile Asn Tyr Lys Leu Leu Pro Gly Pro Asn Lys Met Leu
                565                 570                 575

Pro Lys Val Phe Phe Ser Lys Lys Trp Met Ala Tyr Tyr Asn Pro Ser
            580                 585                 590
```

```
Glu Asp Ile Gln Lys Ile Tyr Lys Asn Gly Thr Phe Lys Lys Gly Asp
        595                 600                 605

Met Phe Asn Leu Asn Asp Cys His Lys Leu Ile Asp Phe Phe Lys Asp
    610                 615                 620

Ser Ile Ser Arg Tyr Pro Lys Trp Ser Asn Ala Tyr Asp Phe Asn Phe
625                 630                 635                 640

Ser Glu Thr Glu Lys Tyr Lys Asp Ile Ala Gly Phe Tyr Arg Glu Val
                645                 650                 655

Glu Glu Gln Gly Tyr Lys Val Ser Phe Glu Ser Ala Ser Lys Lys Glu
            660                 665                 670

Val Asp Lys Leu Val Glu Glu Gly Lys Leu Tyr Met Phe Gln Ile Tyr
        675                 680                 685

Asn Lys Asp Phe Ser Asp Lys Ser His Gly Thr Pro Asn Leu His Thr
    690                 695                 700

Met Tyr Phe Lys Leu Leu Phe Asp Glu Asn Asn His Gly Gln Ile Arg
705                 710                 715                 720

Leu Ser Gly Gly Ala Glu Leu Phe Met Arg Arg Ala Ser Leu Lys Lys
                725                 730                 735

Glu Glu Leu Val Val His Pro Ala Asn Ser Pro Ile Ala Asn Lys Asn
            740                 745                 750

Pro Asp Asn Pro Lys Lys Thr Thr Thr Leu Ser Tyr Asp Val Tyr Lys
        755                 760                 765

Asp Lys Arg Phe Ser Glu Asp Gln Tyr Glu Leu His Ile Pro Ile Ala
    770                 775                 780

Ile Asn Lys Cys Pro Lys Asn Ile Phe Lys Ile Asn Thr Glu Val Arg
785                 790                 795                 800

Val Leu Leu Lys His Asp Asp Asn Pro Tyr Val Ile Gly Ile Asp Arg
                805                 810                 815

Gly Glu Arg Asn Leu Leu Tyr Ile Val Val Val Asp Gly Lys Gly Asn
            820                 825                 830

Ile Val Glu Gln Tyr Ser Leu Asn Glu Ile Ile Asn Asn Phe Asn Gly
        835                 840                 845

Ile Arg Ile Lys Thr Asp Tyr His Ser Leu Leu Asp Lys Lys Glu Lys
    850                 855                 860

Glu Arg Phe Glu Ala Arg Gln Asn Trp Thr Ser Ile Glu Asn Ile Lys
865                 870                 875                 880

Glu Leu Lys Ala Gly Tyr Ile Ser Gln Val Val His Lys Ile Cys Glu
                885                 890                 895

Leu Val Glu Lys Tyr Asp Ala Val Ile Ala Leu Glu Asp Leu Asn Gly
            900                 905                 910

Gly Ala Ala Gly Gly Ala Ala Pro Val Glu Lys Gln Val Tyr Gln Lys
        915                 920                 925

Phe Glu Lys Met Leu Ile Asp Lys Leu Asn Tyr Met Val Asp Lys Lys
    930                 935                 940

Ser Asn Pro Cys Ala Thr Gly Gly Ala Leu Lys Gly Tyr Gln Ile Thr
945                 950                 955                 960

Asn Lys Phe Glu Ser Phe Lys Ser Met Ser Thr Gln Asn Gly Phe Ile
                965                 970                 975

Phe Tyr Ile Pro Ala Trp Leu Thr Ser Lys Ile Asp Pro Ser Thr Gly
            980                 985                 990

Phe Val Asn Leu Leu Lys Thr Lys  Tyr Thr Ser Ile Ala  Asp Ser Lys
        995                 1000                1005
```

Lys Phe Ile Ser Ser Phe Asp Arg Ile Met Tyr Val Pro Glu Glu
    1010                1015                1020

Asp Leu Phe Glu Phe Ala Leu Asp Tyr Lys Asn Phe Ser Arg Thr
    1025                1030                1035

Asp Ala Asp Tyr Ile Lys Lys Trp Lys Leu Tyr Ser Tyr Gly Asn
    1040                1045                1050

Arg Ile Arg Ile Phe Arg Asn Pro Lys Lys Asn Asn Val Phe Asp
    1055                1060                1065

Trp Glu Glu Val Cys Leu Thr Ser Ala Tyr Lys Glu Leu Phe Asn
    1070                1075                1080

Lys Tyr Gly Ile Asn Tyr Gln Gln Gly Asp Ile Arg Ala Leu Leu
    1085                1090                1095

Cys Glu Gln Ser Asp Lys Ala Phe Tyr Ser Ser Phe Met Ala Leu
    1100                1105                1110

Met Ser Leu Met Leu Gln Met Arg Asn Ser Ile Thr Gly Arg Thr
    1115                1120                1125

Asp Val Asp Phe Leu Ile Ser Pro Val Lys Asn Ser Asp Gly Ile
    1130                1135                1140

Phe Tyr Asp Ser Arg Asn Tyr Glu Ala Gln Glu Asn Ala Ile Leu
    1145                1150                1155

Pro Lys Asn Ala Asp Ala Asn Gly Ala Tyr Asn Ile Ala Arg Lys
    1160                1165                1170

Val Leu Trp Ala Ile Gly Gln Phe Lys Lys Ala Glu Asp Glu Lys
    1175                1180                1185

Leu Asp Lys Val Lys Ile Ala Ile Ser Asn Lys Glu Trp Leu Glu
    1190                1195                1200

Tyr Ala Gln Thr Ser Val Lys His
    1205                1210

<210> SEQ ID NO 5
<211> LENGTH: 1228
<212> TYPE: PRT
<213> ORGANISM: Lachnospiraceae bacterium

<400> SEQUENCE: 5

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

-continued

```
Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575
```

```
Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Val Asp Gly Lys Gly
        835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
        915                 920                 925

Ser Gly Phe Ala Asn Ser Arg Val Ala Val Glu Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu  Thr Ser Lys Ile Asp  Pro Ser Thr
```

```
        995                 1000                1005

Gly Phe  Val Asn Leu Leu Lys  Thr Lys Tyr Thr Ser  Ile Ala Asp
    1010                 1015                 1020

Ser Lys  Lys Phe Ile Ser Ser  Phe Asp Arg Ile Met  Tyr Val Pro
    1025                 1030                 1035

Glu Glu  Asp Leu Phe Glu Phe  Ala Leu Asp Tyr Lys  Asn Phe Ser
    1040                 1045                 1050

Arg Thr  Asp Ala Asp Tyr Ile  Lys Lys Trp Lys Leu  Tyr Ser Tyr
    1055                 1060                 1065

Gly Asn  Arg Ile Arg Ile Phe  Arg Asn Pro Lys Lys  Asn Asn Val
    1070                 1075                 1080

Phe Asp  Trp Glu Glu Val Cys  Leu Thr Ser Ala Tyr  Lys Glu Leu
    1085                 1090                 1095

Phe Asn  Lys Tyr Gly Ile Asn  Tyr Gln Gln Gly Asp  Ile Arg Ala
    1100                 1105                 1110

Leu Leu  Cys Glu Gln Ser Asp  Lys Ala Phe Tyr Ser  Ser Phe Met
    1115                 1120                 1125

Ala Leu  Met Ser Leu Met Leu  Gln Met Arg Asn Ser  Ile Thr Gly
    1130                 1135                 1140

Arg Thr  Asp Val Asp Phe Leu  Ile Ser Pro Val Lys  Asn Ser Asp
    1145                 1150                 1155

Gly Ile  Phe Tyr Asp Ser Arg  Asn Tyr Glu Ala Gln  Glu Asn Ala
    1160                 1165                 1170

Ile Leu  Pro Lys Asn Ala Asp  Ala Asn Gly Ala Tyr  Asn Ile Ala
    1175                 1180                 1185

Arg Lys  Val Leu Trp Ala Ile  Gly Gln Phe Lys Lys  Ala Glu Asp
    1190                 1195                 1200

Glu Lys  Leu Asp Lys Val Lys  Ile Ala Ile Ser Asn  Lys Glu Trp
    1205                 1210                 1215

Leu Glu  Tyr Ala Gln Thr Ser  Val Lys His
    1220                 1225


<210> SEQ ID NO 6
<211> LENGTH: 1228
<212> TYPE: PRT
<213> ORGANISM: Lachnospiraceae bacterium

<400> SEQUENCE: 6

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125
```

```
Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
```

```
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Val Asp Gly Lys Gly
        835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
        915                 920                 925

Ser Gly Ala Lys Asn Ser Ala Val Ala Val Glu Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975
```

Thr Asn Lys Phe Glu Ser Phe Lys Ser Met Ser Thr Gln Asn Gly Phe
980 985 990

Ile Phe Tyr Ile Pro Ala Trp Leu Thr Ser Lys Ile Asp Pro Ser Thr
995 1000 1005

Gly Phe Val Asn Leu Leu Lys Thr Lys Tyr Thr Ser Ile Ala Asp
1010 1015 1020

Ser Lys Lys Phe Ile Ser Ser Phe Asp Arg Ile Met Tyr Val Pro
1025 1030 1035

Glu Glu Asp Leu Phe Glu Phe Ala Leu Asp Tyr Lys Asn Phe Ser
1040 1045 1050

Arg Thr Asp Ala Asp Tyr Ile Lys Lys Trp Lys Leu Tyr Ser Tyr
1055 1060 1065

Gly Asn Arg Ile Arg Ile Phe Arg Asn Pro Lys Lys Asn Asn Val
1070 1075 1080

Phe Asp Trp Glu Glu Val Cys Leu Thr Ser Ala Tyr Lys Glu Leu
1085 1090 1095

Phe Asn Lys Tyr Gly Ile Asn Tyr Gln Gln Gly Asp Ile Arg Ala
1100 1105 1110

Leu Leu Cys Glu Gln Ser Asp Lys Ala Phe Tyr Ser Ser Phe Met
1115 1120 1125

Ala Leu Met Ser Leu Met Leu Gln Met Arg Asn Ser Ile Thr Gly
1130 1135 1140

Arg Thr Asp Val Asp Phe Leu Ile Ser Pro Val Lys Asn Ser Asp
1145 1150 1155

Gly Ile Phe Tyr Asp Ser Arg Asn Tyr Glu Ala Gln Glu Asn Ala
1160 1165 1170

Ile Leu Pro Lys Asn Ala Asp Ala Asn Gly Ala Tyr Asn Ile Ala
1175 1180 1185

Arg Lys Val Leu Trp Ala Ile Gly Gln Phe Lys Lys Ala Glu Asp
1190 1195 1200

Glu Lys Leu Asp Lys Val Lys Ile Ala Ile Ser Asn Lys Glu Trp
1205 1210 1215

Leu Glu Tyr Ala Gln Thr Ser Val Lys His
1220 1225

<210> SEQ ID NO 7
<211> LENGTH: 1298
<212> TYPE: PRT
<213> ORGANISM: Acidaminococcus sp.

<400> SEQUENCE: 7

Met Thr Gln Phe Glu Gly Phe Thr Asn Leu Tyr Gln Val Ser Lys Thr
1 5 10 15

Leu Arg Phe Glu Leu Ile Pro Gln Gly Lys Thr Leu Lys His Ile Gln
20 25 30

Glu Gln Gly Phe Ile Glu Glu Asp Lys Ala Arg Asn Asp His Tyr Lys
35 40 45

Glu Leu Lys Pro Ile Ile Asp Arg Ile Tyr Lys Thr Tyr Ala Asp Gln
50 55 60

Cys Leu Gln Leu Val Gln Leu Asp Trp Glu Asn Leu Ser Ala Ala Ile
65 70 75 80

Asp Ser Tyr Arg Lys Glu Lys Thr Glu Glu Thr Arg Asn Ala Leu Ile
85 90 95

Glu Glu Gln Ala Thr Tyr Arg Asn Ala Ile His Asp Tyr Phe Ile Gly

```
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525
```

-continued

```
Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940
```

```
Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Ile Ala Glu Lys  Ala Val Tyr Gln Gln  Phe Glu Lys
        995                 1000                 1005

Met Leu  Ile Asp Lys Leu Asn  Cys Leu Val Leu Lys  Asp Tyr Pro
    1010                 1015                 1020

Ala Glu  Lys Val Gly Gly Val  Leu Asn Pro Tyr Gln  Leu Thr Asp
    1025                 1030                 1035

Gln Phe  Thr Ser Phe Ala Lys  Met Gly Thr Gln Ser  Gly Phe Leu
    1040                 1045                 1050

Phe Tyr  Val Pro Ala Pro Tyr  Thr Ser Lys Ile Asp  Pro Leu Thr
    1055                 1060                 1065

Gly Phe  Val Asp Pro Phe Val  Trp Lys Thr Ile Lys  Asn His Glu
    1070                 1075                 1080

Ser Arg  Lys His Phe Leu Glu  Gly Phe Asp Phe Leu  His Tyr Asp
    1085                 1090                 1095

Val Lys  Thr Gly Asp Phe Ile  Leu His Phe Lys Met  Asn Arg Asn
    1100                 1105                 1110

Leu Ser  Phe Gln Arg Gly Leu  Pro Gly Phe Met Pro  Ala Trp Asp
    1115                 1120                 1125

Ile Val  Phe Glu Lys Asn Glu  Thr Gln Phe Asp Ala  Lys Gly Thr
    1130                 1135                 1140

Pro Phe  Ile Ala Gly Lys Arg  Ile Val Pro Val Ile  Glu Asn His
    1145                 1150                 1155

Arg Phe  Thr Gly Arg Tyr Arg  Asp Leu Tyr Pro Ala  Asn Glu Leu
    1160                 1165                 1170

Ile Ala  Leu Leu Glu Glu Lys  Gly Ile Val Phe Arg  Asp Gly Ser
    1175                 1180                 1185

Asn Ile  Leu Pro Lys Leu Leu  Glu Asn Asp Asp Ser  His Ala Ile
    1190                 1195                 1200

Asp Thr  Met Val Ala Leu Ile  Arg Ser Val Leu Gln  Met Arg Asn
    1205                 1210                 1215

Ser Asn  Ala Ala Thr Gly Glu  Asp Tyr Ile Asn Ser  Pro Val Arg
    1220                 1225                 1230

Asp Leu  Asn Gly Val Cys Phe  Asp Ser Arg Phe Gln  Asn Pro Glu
    1235                 1240                 1245

Trp Pro  Met Asp Ala Asp Ala  Asn Gly Ala Tyr His  Ile Ala Leu
    1250                 1255                 1260

Lys Gly  Gln Leu Leu Leu Asn  His Leu Lys Glu Ser  Lys Asp Leu
    1265                 1270                 1275

Lys Leu  Gln Asn Gly Ile Ser  Asn Gln Asp Trp Leu  Ala Tyr Ile
    1280                 1285                 1290

Gln Glu  Leu Arg Asn
    1295
```

<210> SEQ ID NO 8
<211> LENGTH: 1307
<212> TYPE: PRT
<213> ORGANISM: Acidaminococcus sp.

<400> SEQUENCE: 8

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415
```

-continued

Asp Ile Asn Leu Gln Glu Ile Ile Ser Ala Ala Gly Lys Glu Leu Ser
420 425 430

Glu Ala Phe Lys Gln Lys Thr Ser Glu Ile Leu Ser His Ala His Ala
435 440 445

Ala Leu Asp Gln Pro Leu Pro Thr Thr Leu Lys Lys Gln Glu Glu Lys
450 455 460

Glu Ile Leu Lys Ser Gln Leu Asp Ser Leu Leu Gly Leu Tyr His Leu
465 470 475 480

Leu Asp Trp Phe Ala Val Asp Glu Ser Asn Glu Val Asp Pro Glu Phe
485 490 495

Ser Ala Arg Leu Thr Gly Ile Lys Leu Glu Met Glu Pro Ser Leu Ser
500 505 510

Phe Tyr Asn Lys Ala Arg Asn Tyr Ala Thr Lys Lys Pro Tyr Ser Val
515 520 525

Glu Lys Phe Lys Leu Asn Phe Gln Met Pro Thr Leu Ala Ser Gly Trp
530 535 540

Asp Val Asn Lys Glu Lys Asn Asn Gly Ala Ile Leu Phe Val Lys Asn
545 550 555 560

Gly Leu Tyr Tyr Leu Gly Ile Met Pro Lys Gln Lys Gly Arg Tyr Lys
565 570 575

Ala Leu Ser Phe Glu Pro Thr Glu Lys Thr Ser Glu Gly Phe Asp Lys
580 585 590

Met Tyr Tyr Asp Tyr Phe Pro Asp Ala Ala Lys Met Ile Pro Lys Cys
595 600 605

Ser Thr Gln Leu Lys Ala Val Thr Ala His Phe Gln Thr His Thr Thr
610 615 620

Pro Ile Leu Leu Ser Asn Asn Phe Ile Glu Pro Leu Glu Ile Thr Lys
625 630 635 640

Glu Ile Tyr Asp Leu Asn Asn Pro Glu Lys Glu Pro Lys Lys Phe Gln
645 650 655

Thr Ala Tyr Ala Lys Lys Thr Gly Asp Gln Lys Gly Tyr Arg Glu Ala
660 665 670

Leu Cys Lys Trp Ile Asp Phe Thr Arg Asp Phe Leu Ser Lys Tyr Thr
675 680 685

Lys Thr Thr Ser Ile Asp Leu Ser Ser Leu Arg Pro Ser Ser Gln Tyr
690 695 700

Lys Asp Leu Gly Glu Tyr Tyr Ala Glu Leu Asn Pro Leu Leu Tyr His
705 710 715 720

Ile Ser Phe Gln Arg Ile Ala Glu Lys Glu Ile Met Asp Ala Val Glu
725 730 735

Thr Gly Lys Leu Tyr Leu Phe Gln Ile Tyr Asn Lys Asp Phe Ala Lys
740 745 750

Gly His His Gly Lys Pro Asn Leu His Thr Leu Tyr Trp Thr Gly Leu
755 760 765

Phe Ser Pro Glu Asn Leu Ala Lys Thr Ser Ile Lys Leu Asn Gly Gln
770 775 780

Ala Glu Leu Phe Tyr Arg Pro Lys Ser Arg Met Lys Arg Met Ala His
785 790 795 800

Arg Leu Gly Glu Lys Met Leu Asn Lys Lys Leu Lys Asp Gln Lys Thr
805 810 815

Pro Ile Pro Asp Thr Leu Tyr Gln Glu Leu Tyr Asp Tyr Val Asn His
820 825 830

Arg Leu Ser His Asp Leu Ser Asp Glu Ala Arg Ala Leu Leu Pro Asn

```
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Gly Gly Ala Ala  Gly Gly Ala Ala Gly  Ile Ala Glu
        995                 1000                1005

Lys Ala  Val Tyr Gln Gln Phe  Glu Lys Met Leu Ile  Asp Lys Leu
    1010                1015                1020

Asn Cys  Leu Val Leu Lys Asp  Tyr Pro Ala Glu Lys  Val Gly Gly
    1025                1030                1035

Val Leu  Asn Pro Tyr Gln Leu  Thr Asp Gln Phe Thr  Ser Phe Ala
    1040                1045                1050

Lys Met  Gly Thr Gln Ser Gly  Phe Leu Phe Tyr Val  Pro Ala Pro
    1055                1060                1065

Tyr Thr  Ser Lys Ile Asp Pro  Leu Thr Gly Phe Val  Asp Pro Phe
    1070                1075                1080

Val Trp  Lys Thr Ile Lys Asn  His Glu Ser Arg Lys  His Phe Leu
    1085                1090                1095

Glu Gly  Phe Asp Phe Leu His  Tyr Asp Val Lys Thr  Gly Asp Phe
    1100                1105                1110

Ile Leu  His Phe Lys Met Asn  Arg Asn Leu Ser Phe  Gln Arg Gly
    1115                1120                1125

Leu Pro  Gly Phe Met Pro Ala  Trp Asp Ile Val Phe  Glu Lys Asn
    1130                1135                1140

Glu Thr  Gln Phe Asp Ala Lys  Gly Thr Pro Phe Ile  Ala Gly Lys
    1145                1150                1155

Arg Ile  Val Pro Val Ile Glu  Asn His Arg Phe Thr  Gly Arg Tyr
    1160                1165                1170

Arg Asp  Leu Tyr Pro Ala Asn  Glu Leu Ile Ala Leu  Leu Glu Glu
    1175                1180                1185

Lys Gly  Ile Val Phe Arg Asp  Gly Ser Asn Ile Leu  Pro Lys Leu
    1190                1195                1200

Leu Glu  Asn Asp Asp Ser His  Ala Ile Asp Thr Met  Val Ala Leu
    1205                1210                1215

Ile Arg  Ser Val Leu Gln Met  Arg Asn Ser Asn Ala  Ala Thr Gly
    1220                1225                1230

Glu Asp  Tyr Ile Asn Ser Pro  Val Arg Asp Leu Asn  Gly Val Cys
    1235                1240                1245
```

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn
    1295                1300                1305

<210> SEQ ID NO 9
<211> LENGTH: 1307
<212> TYPE: PRT
<213> ORGANISM: Acidaminococcus sp.

<400> SEQUENCE: 9

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu

```
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735
```

```
Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Ala  Ser Ala Arg Thr Gly  Ile Ala Glu
        995                 1000                1005

Lys Ala  Val Tyr Gln Gln Phe  Glu Lys Met Leu Ile  Asp Lys Leu
    1010                1015                1020

Asn Cys  Leu Val Leu Lys Asp  Tyr Pro Ala Glu Lys  Val Gly Gly
    1025                1030                1035

Val Leu  Asn Pro Tyr Gln Leu  Thr Asp Gln Phe Thr  Ser Phe Ala
    1040                1045                1050

Lys Met  Gly Thr Gln Ser Gly  Phe Leu Phe Tyr Val  Pro Ala Pro
    1055                1060                1065

Tyr Thr  Ser Lys Ile Asp Pro  Leu Thr Gly Phe Val  Asp Pro Phe
    1070                1075                1080

Val Trp  Lys Thr Ile Lys Asn  His Glu Ser Arg Lys  His Phe Leu
    1085                1090                1095

Glu Gly  Phe Asp Phe Leu His  Tyr Asp Val Lys Thr  Gly Asp Phe
    1100                1105                1110

Ile Leu  His Phe Lys Met Asn  Arg Asn Leu Ser Phe  Gln Arg Gly
    1115                1120                1125

Leu Pro  Gly Phe Met Pro Ala  Trp Asp Ile Val Phe  Glu Lys Asn
    1130                1135                1140
```

```
Glu Thr  Gln Phe Asp Ala Lys  Gly Thr Pro Phe Ile  Ala Gly Lys
    1145                 1150                 1155

Arg Ile  Val Pro Val Ile Glu  Asn His Arg Phe Thr  Gly Arg Tyr
    1160                 1165                 1170

Arg Asp  Leu Tyr Pro Ala Asn  Glu Leu Ile Ala Leu  Leu Glu Glu
    1175                 1180                 1185

Lys Gly  Ile Val Phe Arg Asp  Gly Ser Asn Ile Leu  Pro Lys Leu
    1190                 1195                 1200

Leu Glu  Asn Asp Asp Ser His  Ala Ile Asp Thr Met  Val Ala Leu
    1205                 1210                 1215

Ile Arg  Ser Val Leu Gln Met  Arg Asn Ser Asn Ala  Ala Thr Gly
    1220                 1225                 1230

Glu Asp  Tyr Ile Asn Ser Pro  Val Arg Asp Leu Asn  Gly Val Cys
    1235                 1240                 1245

Phe Asp  Ser Arg Phe Gln Asn  Pro Glu Trp Pro Met  Asp Ala Asp
    1250                 1255                 1260

Ala Asn  Gly Ala Tyr His Ile  Ala Leu Lys Gly Gln  Leu Leu Leu
    1265                 1270                 1275

Asn His  Leu Lys Glu Ser Lys  Asp Leu Lys Leu Gln  Asn Gly Ile
    1280                 1285                 1290

Ser Asn  Gln Asp Trp Leu Ala  Tyr Ile Gln Glu Leu  Arg Asn
    1295                 1300                 1305


<210> SEQ ID NO 10
<211> LENGTH: 1307
<212> TYPE: PRT
<213> ORGANISM: Acidaminococcus sp.

<400> SEQUENCE: 10

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205
```

```
Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620
```

```
Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Ala  Ser Ala Ala Thr Gly  Ile Ala Glu
        995                 1000                1005

Lys Ala  Val Tyr Gln Gln Phe  Glu Lys Met Leu Ile  Asp Lys Leu
    1010                1015                1020

Asn Cys  Leu Val Leu Lys Asp  Tyr Pro Ala Glu Lys  Val Gly Gly
    1025                1030                1035

Val Leu  Asn Pro Tyr Gln Leu  Thr Asp Gln Phe Thr  Ser Phe Ala
```

```
    1040                1045                1050

Lys Met  Gly Thr Gln Ser Gly  Phe Leu Phe Tyr Val  Pro Ala Pro
    1055                1060                1065

Tyr Thr  Ser Lys Ile Asp Pro  Leu Thr Gly Phe Val  Asp Pro Phe
    1070                1075                1080

Val Trp  Lys Thr Ile Lys Asn  His Glu Ser Arg Lys  His Phe Leu
    1085                1090                1095

Glu Gly  Phe Asp Phe Leu His  Tyr Asp Val Lys Thr  Gly Asp Phe
    1100                1105                1110

Ile Leu  His Phe Lys Met Asn  Arg Asn Leu Ser Phe  Gln Arg Gly
    1115                1120                1125

Leu Pro  Gly Phe Met Pro Ala  Trp Asp Ile Val Phe  Glu Lys Asn
    1130                1135                1140

Glu Thr  Gln Phe Asp Ala Lys  Gly Thr Pro Phe Ile  Ala Gly Lys
    1145                1150                1155

Arg Ile  Val Pro Val Ile Glu  Asn His Arg Phe Thr  Gly Arg Tyr
    1160                1165                1170

Arg Asp  Leu Tyr Pro Ala Asn  Glu Leu Ile Ala Leu  Leu Glu Glu
    1175                1180                1185

Lys Gly  Ile Val Phe Arg Asp  Gly Ser Asn Ile Leu  Pro Lys Leu
    1190                1195                1200

Leu Glu  Asn Asp Asp Ser His  Ala Ile Asp Thr Met  Val Ala Leu
    1205                1210                1215

Ile Arg  Ser Val Leu Gln Met  Arg Asn Ser Asn Ala  Ala Thr Gly
    1220                1225                1230

Glu Asp  Tyr Ile Asn Ser Pro  Val Arg Asp Leu Asn  Gly Val Cys
    1235                1240                1245

Phe Asp  Ser Arg Phe Gln Asn  Pro Glu Trp Pro Met  Asp Ala Asp
    1250                1255                1260

Ala Asn  Gly Ala Tyr His Ile  Ala Leu Lys Gly Gln  Leu Leu Leu
    1265                1270                1275

Asn His  Leu Lys Glu Ser Lys  Asp Leu Lys Leu Gln  Asn Gly Ile
    1280                1285                1290

Ser Asn  Gln Asp Trp Leu Ala  Tyr Ile Gln Glu Leu  Arg Asn
    1295                1300                1305


<210> SEQ ID NO 11
<211> LENGTH: 1291
<212> TYPE: PRT
<213> ORGANISM: Francisella novicida

<400> SEQUENCE: 11

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95
```

-continued

```
Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
```

```
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940
```

```
Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                1005

Asn Val  Glu Lys Gln Val Tyr  Gln Lys Leu Glu Lys  Met Leu Ile
    1010                1015                1020

Glu Lys  Leu Asn Tyr Leu Val  Phe Lys Asp Asn Glu  Phe Asp Lys
    1025                1030                1035

Thr Gly  Gly Val Leu Arg Ala  Tyr Gln Leu Thr Ala  Pro Phe Glu
    1040                1045                1050

Thr Phe  Lys Lys Met Gly Lys  Gln Thr Gly Ile Ile  Tyr Tyr Val
    1055                1060                1065

Pro Ala  Gly Phe Thr Ser Lys  Ile Cys Pro Val Thr  Gly Phe Val
    1070                1075                1080

Asn Gln  Leu Tyr Pro Lys Tyr  Glu Ser Val Ser Lys  Ser Gln Glu
    1085                1090                1095

Phe Phe  Ser Lys Phe Asp Lys  Ile Cys Tyr Asn Leu  Asp Lys Gly
    1100                1105                1110

Tyr Phe  Glu Phe Ser Phe Asp  Tyr Lys Asn Phe Gly  Asp Lys Ala
    1115                1120                1125

Ala Lys  Gly Lys Trp Thr Ile  Ala Ser Phe Gly Ser  Arg Leu Ile
    1130                1135                1140

Asn Phe  Arg Asn Ser Asp Lys  Asn His Asn Trp Asp  Thr Arg Glu
    1145                1150                1155

Val Tyr  Pro Thr Lys Glu Leu  Glu Lys Leu Leu Lys  Asp Tyr Ser
    1160                1165                1170

Ile Glu  Tyr Gly His Gly Glu  Cys Ile Lys Ala Ala  Ile Cys Gly
    1175                1180                1185

Glu Ser  Asp Lys Lys Phe Phe  Ala Lys Leu Thr Ser  Val Leu Asn
    1190                1195                1200

Thr Ile  Leu Gln Met Arg Asn  Ser Lys Thr Gly Thr  Glu Leu Asp
    1205                1210                1215

Tyr Leu  Ile Ser Pro Val Ala  Asp Val Asn Gly Asn  Phe Phe Asp
    1220                1225                1230

Ser Arg  Gln Ala Pro Lys Asn  Met Pro Gln Asp Ala  Asp Ala Asn
    1235                1240                1245

Gly Ala  Tyr His Ile Gly Leu  Lys Gly Leu Met Leu  Leu Gly Arg
    1250                1255                1260

Ile Lys  Asn Asn Gln Glu Gly  Lys Lys Leu Asn Leu  Val Ile Lys
    1265                1270                1275

Asn Glu  Glu Tyr Phe Glu Phe  Val Gln Asn Arg Asn  Asn
    1280                1285                1290
```

<210> SEQ ID NO 12
<211> LENGTH: 1300
<212> TYPE: PRT
<213> ORGANISM: Francisella novicida

<400> SEQUENCE: 12

```
Met Ser Ile Tyr Gln Glu Phe Val Asn Lys Tyr Ser Leu Ser Lys Thr
```

-continued

```
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430
```

```
Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845
```

```
Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                1005

Asn Gly  Gly Ala Ala Gly Gly  Ala Ala Gly Val Glu  Lys Gln Val
    1010                 1015                 1020

Tyr Gln  Lys Leu Glu Lys Met  Leu Ile Glu Lys Leu  Asn Tyr Leu
    1025                 1030                 1035

Val Phe  Lys Asp Asn Glu Phe  Asp Lys Thr Gly Gly  Val Leu Arg
    1040                 1045                 1050

Ala Tyr  Gln Leu Thr Ala Pro  Phe Glu Thr Phe Lys  Lys Met Gly
    1055                 1060                 1065

Lys Gln  Thr Gly Ile Ile Tyr  Tyr Val Pro Ala Gly  Phe Thr Ser
    1070                 1075                 1080

Lys Ile  Cys Pro Val Thr Gly  Phe Val Asn Gln Leu  Tyr Pro Lys
    1085                 1090                 1095

Tyr Glu  Ser Val Ser Lys Ser  Gln Glu Phe Phe Ser  Lys Phe Asp
    1100                 1105                 1110

Lys Ile  Cys Tyr Asn Leu Asp  Lys Gly Tyr Phe Glu  Phe Ser Phe
    1115                 1120                 1125

Asp Tyr  Lys Asn Phe Gly Asp  Lys Ala Ala Lys Gly  Lys Trp Thr
    1130                 1135                 1140

Ile Ala  Ser Phe Gly Ser Arg  Leu Ile Asn Phe Arg  Asn Ser Asp
    1145                 1150                 1155

Lys Asn  His Asn Trp Asp Thr  Arg Glu Val Tyr Pro  Thr Lys Glu
    1160                 1165                 1170

Leu Glu  Lys Leu Leu Lys Asp  Tyr Ser Ile Glu Tyr  Gly His Gly
    1175                 1180                 1185

Glu Cys  Ile Lys Ala Ala Ile  Cys Gly Glu Ser Asp  Lys Lys Phe
    1190                 1195                 1200

Phe Ala  Lys Leu Thr Ser Val  Leu Asn Thr Ile Leu  Gln Met Arg
    1205                 1210                 1215

Asn Ser  Lys Thr Gly Thr Glu  Leu Asp Tyr Leu Ile  Ser Pro Val
    1220                 1225                 1230

Ala Asp  Val Asn Gly Asn Phe  Phe Asp Ser Arg Gln  Ala Pro Lys
    1235                 1240                 1245

Asn Met  Pro Gln Asp Ala Asp  Ala Asn Gly Ala Tyr  His Ile Gly
```

1250 1255 1260

Leu Lys Gly Leu Met Leu Leu Gly Arg Ile Lys Asn Asn Gln Glu
1265 1270 1275

Gly Lys Lys Leu Asn Leu Val Ile Lys Asn Glu Glu Tyr Phe Glu
1280 1285 1290

Phe Val Gln Asn Arg Asn Asn
1295 1300

<210> SEQ ID NO 13
<211> LENGTH: 1294
<212> TYPE: PRT
<213> ORGANISM: Francisella novicida

<400> SEQUENCE: 13

Met Ser Ile Tyr Gln Glu Phe Val Asn Lys Tyr Ser Leu Ser Lys Thr
1 5 10 15

Leu Arg Phe Glu Leu Ile Pro Gln Gly Lys Thr Leu Glu Asn Ile Lys
20 25 30

Ala Arg Gly Leu Ile Leu Asp Asp Glu Lys Arg Ala Lys Asp Tyr Lys
35 40 45

Lys Ala Lys Gln Ile Ile Asp Lys Tyr His Gln Phe Phe Ile Glu Glu
50 55 60

Ile Leu Ser Ser Val Cys Ile Ser Glu Asp Leu Leu Gln Asn Tyr Ser
65 70 75 80

Asp Val Tyr Phe Lys Leu Lys Lys Ser Asp Asp Asp Asn Leu Gln Lys
85 90 95

Asp Phe Lys Ser Ala Lys Asp Thr Ile Lys Lys Gln Ile Ser Glu Tyr
100 105 110

Ile Lys Asp Ser Glu Lys Phe Lys Asn Leu Phe Asn Gln Asn Leu Ile
115 120 125

Asp Ala Lys Lys Gly Gln Glu Ser Asp Leu Ile Leu Trp Leu Lys Gln
130 135 140

Ser Lys Asp Asn Gly Ile Glu Leu Phe Lys Ala Asn Ser Asp Ile Thr
145 150 155 160

Asp Ile Asp Glu Ala Leu Glu Ile Ile Lys Ser Phe Lys Gly Trp Thr
165 170 175

Thr Tyr Phe Lys Gly Phe His Glu Asn Arg Lys Asn Val Tyr Ser Ser
180 185 190

Asn Asp Ile Pro Thr Ser Ile Ile Tyr Arg Ile Val Asp Asp Asn Leu
195 200 205

Pro Lys Phe Leu Glu Asn Lys Ala Lys Tyr Glu Ser Leu Lys Asp Lys
210 215 220

Ala Pro Glu Ala Ile Asn Tyr Glu Gln Ile Lys Lys Asp Leu Ala Glu
225 230 235 240

Glu Leu Thr Phe Asp Ile Asp Tyr Lys Thr Ser Glu Val Asn Gln Arg
245 250 255

Val Phe Ser Leu Asp Glu Val Phe Glu Ile Ala Asn Phe Asn Asn Tyr
260 265 270

Leu Asn Gln Ser Gly Ile Thr Lys Phe Asn Thr Ile Ile Gly Gly Lys
275 280 285

Phe Val Asn Gly Glu Asn Thr Lys Arg Lys Gly Ile Asn Glu Tyr Ile
290 295 300

Asn Leu Tyr Ser Gln Gln Ile Asn Asp Lys Thr Leu Lys Lys Tyr Lys
305 310 315 320

```
Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
```

```
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                1005

Asn Gly  Ala Ala Val Glu Lys  Gln Val Tyr Gln Lys  Leu Glu Lys
    1010                1015                1020

Met Leu  Ile Glu Lys Leu Asn  Tyr Leu Val Phe Lys  Asp Asn Glu
    1025                1030                1035

Phe Asp  Lys Thr Gly Gly Val  Leu Arg Ala Tyr Gln  Leu Thr Ala
    1040                1045                1050

Pro Phe  Glu Thr Phe Lys Lys  Met Gly Lys Gln Thr  Gly Ile Ile
    1055                1060                1065

Tyr Tyr  Val Pro Ala Gly Phe  Thr Ser Lys Ile Cys  Pro Val Thr
    1070                1075                1080

Gly Phe  Val Asn Gln Leu Tyr  Pro Lys Tyr Glu Ser  Val Ser Lys
    1085                1090                1095

Ser Gln  Glu Phe Phe Ser Lys  Phe Asp Lys Ile Cys  Tyr Asn Leu
    1100                1105                1110

Asp Lys  Gly Tyr Phe Glu Phe  Ser Phe Asp Tyr Lys  Asn Phe Gly
    1115                1120                1125

Asp Lys  Ala Ala Lys Gly Lys  Trp Thr Ile Ala Ser  Phe Gly Ser
    1130                1135                1140

Arg Leu  Ile Asn Phe Arg Asn  Ser Asp Lys Asn His  Asn Trp Asp
    1145                1150                1155
```

```
Thr Arg  Glu Val Tyr Pro Thr  Lys Glu Leu Glu Lys  Leu Leu Lys
    1160                1165                1170

Asp Tyr  Ser Ile Glu Tyr Gly  His Gly Glu Cys Ile  Lys Ala Ala
    1175                1180                1185

Ile Cys  Gly Glu Ser Asp Lys  Lys Phe Phe Ala Lys  Leu Thr Ser
    1190                1195                1200

Val Leu  Asn Thr Ile Leu Gln  Met Arg Asn Ser Lys  Thr Gly Thr
    1205                1210                1215

Glu Leu  Asp Tyr Leu Ile Ser  Pro Val Ala Asp Val  Asn Gly Asn
    1220                1225                1230

Phe Phe  Asp Ser Arg Gln Ala  Pro Lys Asn Met Pro  Gln Asp Ala
    1235                1240                1245

Asp Ala  Asn Gly Ala Tyr His  Ile Gly Leu Lys Gly  Leu Met Leu
    1250                1255                1260

Leu Gly  Arg Ile Lys Asn Asn  Gln Glu Gly Lys Lys  Leu Asn Leu
    1265                1270                1275

Val Ile  Lys Asn Glu Glu Tyr  Phe Glu Phe Val Gln  Asn Arg Asn
    1280                1285                1290

Asn


<210> SEQ ID NO 14
<211> LENGTH: 1300
<212> TYPE: PRT
<213> ORGANISM: Francisella novicida

<400> SEQUENCE: 14

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220
```

```
Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640
```

```
Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                1005

Asn Phe  Gly Phe Ala Arg Gly  Arg Phe Ala Val Glu  Lys Gln Val
    1010                1015                1020

Tyr Gln  Lys Leu Glu Lys Met  Leu Ile Glu Lys Leu  Asn Tyr Leu
    1025                1030                1035

Val Phe  Lys Asp Asn Glu Phe  Asp Lys Thr Gly Gly  Val Leu Arg
    1040                1045                1050

Ala Tyr  Gln Leu Thr Ala Pro  Phe Glu Thr Phe Lys  Lys Met Gly
```

```
    1055                1060                1065

Lys Gln  Thr Gly Ile Ile Tyr  Tyr Val Pro Ala Gly  Phe Thr Ser
    1070                1075                1080

Lys Ile  Cys Pro Val Thr Gly  Phe Val Asn Gln Leu  Tyr Pro Lys
    1085                1090                1095

Tyr Glu  Ser Val Ser Lys Ser  Gln Glu Phe Phe Ser  Lys Phe Asp
    1100                1105                1110

Lys Ile  Cys Tyr Asn Leu Asp  Lys Gly Tyr Phe Glu  Phe Ser Phe
    1115                1120                1125

Asp Tyr  Lys Asn Phe Gly Asp  Lys Ala Ala Lys Gly  Lys Trp Thr
    1130                1135                1140

Ile Ala  Ser Phe Gly Ser Arg  Leu Ile Asn Phe Arg  Asn Ser Asp
    1145                1150                1155

Lys Asn  His Asn Trp Asp Thr  Arg Glu Val Tyr Pro  Thr Lys Glu
    1160                1165                1170

Leu Glu  Lys Leu Leu Lys Asp  Tyr Ser Ile Glu Tyr  Gly His Gly
    1175                1180                1185

Glu Cys  Ile Lys Ala Ala Ile  Cys Gly Glu Ser Asp  Lys Lys Phe
    1190                1195                1200

Phe Ala  Lys Leu Thr Ser Val  Leu Asn Thr Ile Leu  Gln Met Arg
    1205                1210                1215

Asn Ser  Lys Thr Gly Thr Glu  Leu Asp Tyr Leu Ile  Ser Pro Val
    1220                1225                1230

Ala Asp  Val Asn Gly Asn Phe  Phe Asp Ser Arg Gln  Ala Pro Lys
    1235                1240                1245

Asn Met  Pro Gln Asp Ala Asp  Ala Asn Gly Ala Tyr  His Ile Gly
    1250                1255                1260

Leu Lys  Gly Leu Met Leu Leu  Gly Arg Ile Lys Asn  Asn Gln Glu
    1265                1270                1275

Gly Lys  Lys Leu Asn Leu Val  Ile Lys Asn Glu Glu  Tyr Phe Glu
    1280                1285                1290

Phe Val  Gln Asn Arg Asn Asn
    1295                1300


<210> SEQ ID NO 15
<211> LENGTH: 1300
<212> TYPE: PRT
<213> ORGANISM: Francisella novicida

<400> SEQUENCE: 15

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110
```

```
Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
```

```
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960
```

```
Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                1005

Asn Phe  Gly Phe Lys Ala Gly  Ala Phe Lys Val Glu  Lys Gln Val
    1010                1015                1020

Tyr Gln  Lys Leu Glu Lys Met  Leu Ile Glu Lys Leu  Asn Tyr Leu
    1025                1030                1035

Val Phe  Lys Asp Asn Glu Phe  Asp Lys Thr Gly Gly  Val Leu Arg
    1040                1045                1050

Ala Tyr  Gln Leu Thr Ala Pro  Phe Glu Thr Phe Lys  Lys Met Gly
    1055                1060                1065

Lys Gln  Thr Gly Ile Ile Tyr  Tyr Val Pro Ala Gly  Phe Thr Ser
    1070                1075                1080

Lys Ile  Cys Pro Val Thr Gly  Phe Val Asn Gln Leu  Tyr Pro Lys
    1085                1090                1095

Tyr Glu  Ser Val Ser Lys Ser  Gln Glu Phe Phe Ser  Lys Phe Asp
    1100                1105                1110

Lys Ile  Cys Tyr Asn Leu Asp  Lys Gly Tyr Phe Glu  Phe Ser Phe
    1115                1120                1125

Asp Tyr  Lys Asn Phe Gly Asp  Lys Ala Ala Lys Gly  Lys Trp Thr
    1130                1135                1140

Ile Ala  Ser Phe Gly Ser Arg  Leu Ile Asn Phe Arg  Asn Ser Asp
    1145                1150                1155

Lys Asn  His Asn Trp Asp Thr  Arg Glu Val Tyr Pro  Thr Lys Glu
    1160                1165                1170

Leu Glu  Lys Leu Leu Lys Asp  Tyr Ser Ile Glu Tyr  Gly His Gly
    1175                1180                1185

Glu Cys  Ile Lys Ala Ala Ile  Cys Gly Glu Ser Asp  Lys Lys Phe
    1190                1195                1200

Phe Ala  Lys Leu Thr Ser Val  Leu Asn Thr Ile Leu  Gln Met Arg
    1205                1210                1215

Asn Ser  Lys Thr Gly Thr Glu  Leu Asp Tyr Leu Ile  Ser Pro Val
    1220                1225                1230

Ala Asp  Val Asn Gly Asn Phe  Phe Asp Ser Arg Gln  Ala Pro Lys
    1235                1240                1245

Asn Met  Pro Gln Asp Ala Asp  Ala Asn Gly Ala Tyr  His Ile Gly
    1250                1255                1260

Leu Lys  Gly Leu Met Leu Leu  Gly Arg Ile Lys Asn  Asn Gln Glu
    1265                1270                1275

Gly Lys  Lys Leu Asn Leu Val  Ile Lys Asn Glu Glu  Tyr Phe Glu
    1280                1285                1290

Phe Val  Gln Asn Arg Asn Asn
    1295                1300
```

<210> SEQ ID NO 16
<211> LENGTH: 1246
<212> TYPE: PRT
<213> ORGANISM: Porphyromonas macacae

<400> SEQUENCE: 16

```
Met Lys Thr Gln His Phe Phe Glu Asp Phe Thr Ser Leu Tyr Ser Leu
```

```
1               5                   10                  15

Ser Lys Thr Ile Arg Phe Glu Leu Lys Pro Ile Gly Lys Thr Leu Glu
            20                  25                  30

Asn Ile Lys Lys Asn Gly Leu Ile Arg Arg Asp Glu Gln Arg Leu Asp
        35                  40                  45

Asp Tyr Glu Lys Leu Lys Lys Val Ile Asp Glu Tyr His Glu Asp Phe
    50                  55                  60

Ile Ala Asn Ile Leu Ser Ser Phe Ser Phe Ser Glu Glu Ile Leu Gln
65                  70                  75                  80

Ser Tyr Ile Gln Asn Leu Ser Glu Ser Glu Ala Arg Ala Lys Ile Glu
                85                  90                  95

Lys Thr Met Arg Asp Thr Leu Ala Lys Ala Phe Ser Glu Asp Glu Arg
            100                 105                 110

Tyr Lys Ser Ile Phe Lys Lys Glu Leu Val Lys Lys Asp Ile Pro Val
        115                 120                 125

Trp Cys Pro Ala Tyr Lys Ser Leu Cys Lys Lys Phe Asp Asn Phe Thr
    130                 135                 140

Thr Ser Leu Val Pro Phe His Glu Asn Arg Lys Asn Leu Tyr Thr Ser
145                 150                 155                 160

Asn Glu Ile Thr Ala Ser Ile Pro Tyr Arg Ile Val His Val Asn Leu
                165                 170                 175

Pro Lys Phe Ile Gln Asn Ile Glu Ala Leu Cys Glu Leu Gln Lys Lys
            180                 185                 190

Met Gly Ala Asp Leu Tyr Leu Glu Met Met Glu Asn Leu Arg Asn Val
        195                 200                 205

Trp Pro Ser Phe Val Lys Thr Pro Asp Asp Leu Cys Asn Leu Lys Thr
    210                 215                 220

Tyr Asn His Leu Met Val Gln Ser Ser Ile Ser Glu Tyr Asn Arg Phe
225                 230                 235                 240

Val Gly Gly Tyr Ser Thr Glu Asp Gly Thr Lys His Gln Gly Ile Asn
                245                 250                 255

Glu Trp Ile Asn Ile Tyr Arg Gln Arg Asn Lys Glu Met Arg Leu Pro
            260                 265                 270

Gly Leu Val Phe Leu His Lys Gln Ile Leu Ala Lys Val Asp Ser Ser
        275                 280                 285

Ser Phe Ile Ser Asp Thr Leu Glu Asn Asp Asp Gln Val Phe Cys Val
    290                 295                 300

Leu Arg Gln Phe Arg Lys Leu Phe Trp Asn Thr Val Ser Ser Lys Glu
305                 310                 315                 320

Asp Asp Ala Ala Ser Leu Lys Asp Leu Phe Cys Gly Leu Ser Gly Tyr
                325                 330                 335

Asp Pro Glu Ala Ile Tyr Val Ser Asp Ala His Leu Ala Thr Ile Ser
            340                 345                 350

Lys Asn Ile Phe Asp Arg Trp Asn Tyr Ile Ser Asp Ala Ile Arg Arg
        355                 360                 365

Lys Thr Glu Val Leu Met Pro Arg Lys Lys Glu Ser Val Glu Arg Tyr
    370                 375                 380

Ala Glu Lys Ile Ser Lys Gln Ile Lys Lys Arg Gln Ser Tyr Ser Leu
385                 390                 395                 400

Ala Glu Leu Asp Asp Leu Leu Ala His Tyr Ser Glu Glu Ser Leu Pro
                405                 410                 415

Ala Gly Phe Ser Leu Leu Ser Tyr Phe Thr Ser Leu Gly Gly Gln Lys
            420                 425                 430
```

```
Tyr Leu Val Ser Asp Gly Glu Val Ile Leu Tyr Glu Glu Gly Ser Asn
        435                 440                 445

Ile Trp Asp Glu Val Leu Ile Ala Phe Arg Asp Leu Gln Val Ile Leu
    450                 455                 460

Asp Lys Asp Phe Thr Glu Lys Lys Leu Gly Lys Asp Glu Glu Ala Val
465                 470                 475                 480

Ser Val Ile Lys Lys Ala Leu Asp Ser Ala Leu Arg Leu Arg Lys Phe
                485                 490                 495

Phe Asp Leu Leu Ser Gly Thr Gly Ala Glu Ile Arg Arg Asp Ser Ser
            500                 505                 510

Phe Tyr Ala Leu Tyr Thr Asp Arg Met Asp Lys Leu Lys Gly Leu Leu
        515                 520                 525

Lys Met Tyr Asp Lys Val Arg Asn Tyr Leu Thr Lys Lys Pro Tyr Ser
    530                 535                 540

Ile Glu Lys Phe Lys Leu His Phe Asp Asn Pro Ser Leu Leu Ser Gly
545                 550                 555                 560

Trp Asp Lys Asn Lys Glu Leu Asn Asn Leu Ser Val Ile Phe Arg Gln
                565                 570                 575

Asn Gly Tyr Tyr Tyr Leu Gly Ile Met Thr Pro Lys Gly Lys Asn Leu
            580                 585                 590

Phe Lys Thr Leu Pro Lys Leu Gly Ala Glu Glu Met Phe Tyr Glu Lys
        595                 600                 605

Met Glu Tyr Lys Gln Ile Ala Glu Pro Met Leu Met Leu Pro Lys Val
    610                 615                 620

Phe Phe Pro Lys Lys Thr Lys Pro Ala Phe Ala Pro Asp Gln Ser Val
625                 630                 635                 640

Val Asp Ile Tyr Asn Lys Lys Thr Phe Lys Thr Gly Gln Lys Gly Phe
                645                 650                 655

Asn Lys Lys Asp Leu Tyr Arg Leu Ile Asp Phe Tyr Lys Glu Ala Leu
            660                 665                 670

Thr Val His Glu Trp Lys Leu Phe Asn Phe Ser Phe Ser Pro Thr Glu
        675                 680                 685

Gln Tyr Arg Asn Ile Gly Glu Phe Phe Asp Glu Val Arg Glu Gln Ala
    690                 695                 700

Tyr Lys Val Ser Met Val Asn Val Pro Ala Ser Tyr Ile Asp Glu Ala
705                 710                 715                 720

Val Glu Asn Gly Lys Leu Tyr Leu Phe Gln Ile Tyr Asn Lys Asp Phe
                725                 730                 735

Ser Pro Tyr Ser Lys Gly Ile Pro Asn Leu His Thr Leu Tyr Trp Lys
            740                 745                 750

Ala Leu Phe Ser Glu Gln Asn Gln Ser Arg Val Tyr Lys Leu Cys Gly
        755                 760                 765

Gly Gly Glu Leu Phe Tyr Arg Lys Ala Ser Leu His Met Gln Asp Thr
    770                 775                 780

Thr Val His Pro Lys Gly Ile Ser Ile His Lys Lys Asn Leu Asn Lys
785                 790                 795                 800

Lys Gly Glu Thr Ser Leu Phe Asn Tyr Asp Leu Val Lys Asp Lys Arg
                805                 810                 815

Phe Thr Glu Asp Lys Phe Phe Phe His Val Pro Ile Ser Ile Asn Tyr
            820                 825                 830

Lys Asn Lys Lys Ile Thr Asn Val Asn Gln Met Val Arg Asp Tyr Ile
        835                 840                 845
```

```
Ala Gln Asn Asp Asp Leu Gln Ile Ile Gly Ile Asp Arg Gly Glu Arg
    850                 855                 860

Asn Leu Leu Tyr Ile Ser Arg Ile Asp Thr Arg Gly Asn Leu Leu Glu
865                 870                 875                 880

Gln Phe Ser Leu Asn Val Ile Glu Ser Asp Lys Gly Asp Leu Arg Thr
                885                 890                 895

Asp Tyr Gln Lys Ile Leu Gly Asp Arg Glu Gln Glu Arg Leu Arg Arg
            900                 905                 910

Arg Gln Glu Trp Lys Ser Ile Glu Ser Ile Lys Asp Leu Lys Asp Gly
        915                 920                 925

Tyr Met Ser Gln Val Val His Lys Ile Cys Asn Met Val Val Glu His
    930                 935                 940

Lys Ala Ile Val Val Leu Glu Asn Leu Asn Leu Ser Phe Met Lys Gly
945                 950                 955                 960

Arg Lys Lys Val Glu Lys Ser Val Tyr Glu Lys Phe Glu Arg Met Leu
                965                 970                 975

Val Asp Lys Leu Asn Tyr Leu Val Val Asp Lys Lys Asn Leu Ser Asn
            980                 985                 990

Glu Pro Gly Gly Leu Tyr Ala Ala  Tyr Gln Leu Thr Asn  Pro Leu Phe
        995                 1000                1005

Ser Phe  Glu Glu Leu His Arg  Tyr Pro Gln Ser Gly  Ile Leu Phe
    1010                 1015                 1020

Phe Val  Asp Pro Trp Asn Thr  Ser Leu Thr Asp Pro  Ser Thr Gly
    1025                 1030                 1035

Phe Val  Asn Leu Leu Gly Arg  Ile Asn Tyr Thr Asn  Val Gly Asp
    1040                 1045                 1050

Ala Arg  Lys Phe Phe Asp Arg  Phe Asn Ala Ile Arg  Tyr Asp Gly
    1055                 1060                 1065

Lys Gly  Asn Ile Leu Phe Asp  Leu Asp Leu Ser Arg  Phe Asp Val
    1070                 1075                 1080

Arg Val  Glu Thr Gln Arg Lys  Leu Trp Thr Leu Thr  Thr Phe Gly
    1085                 1090                 1095

Ser Arg  Ile Ala Lys Ser Lys  Lys Ser Gly Lys Trp  Met Val Glu
    1100                 1105                 1110

Arg Ile  Glu Asn Leu Ser Leu  Cys Phe Leu Glu Leu  Phe Glu Gln
    1115                 1120                 1125

Phe Asn  Ile Gly Tyr Arg Val  Glu Lys Asp Leu Lys  Lys Ala Ile
    1130                 1135                 1140

Leu Ser  Gln Asp Arg Lys Glu  Phe Tyr Val Arg Leu  Ile Tyr Leu
    1145                 1150                 1155

Phe Asn  Leu Met Met Gln Ile  Arg Asn Ser Asp Gly  Glu Glu Asp
    1160                 1165                 1170

Tyr Ile  Leu Ser Pro Ala Leu  Asn Glu Lys Asn Leu  Gln Phe Asp
    1175                 1180                 1185

Ser Arg  Leu Ile Glu Ala Lys  Asp Leu Pro Val Asp  Ala Asp Ala
    1190                 1195                 1200

Asn Gly  Ala Tyr Asn Val Ala  Arg Lys Gly Leu Met  Val Val Gln
    1205                 1210                 1215

Arg Ile  Lys Arg Gly Asp His  Glu Ser Ile His Arg  Ile Gly Arg
    1220                 1225                 1230

Ala Gln  Trp Leu Arg Tyr Val  Gln Glu Gly Ile Val  Glu
    1235                 1240                 1245
```

<210> SEQ ID NO 17
<211> LENGTH: 1373
<212> TYPE: PRT
<213> ORGANISM: Moraxella bovoculi

<400> SEQUENCE: 17

```
Met Leu Phe Gln Asp Phe Thr His Leu Tyr Pro Leu Ser Lys Thr Val
1               5                   10                  15

Arg Phe Glu Leu Lys Pro Ile Asp Arg Thr Leu Glu His Ile His Ala
            20                  25                  30

Lys Asn Phe Leu Ser Gln Asp Glu Thr Met Ala Asp Met His Gln Lys
        35                  40                  45

Val Lys Val Ile Leu Asp Asp Tyr His Arg Asp Phe Ile Ala Asp Met
    50                  55                  60

Met Gly Glu Val Lys Leu Thr Lys Leu Ala Glu Phe Tyr Asp Val Tyr
65                  70                  75                  80

Leu Lys Phe Arg Lys Asn Pro Lys Asp Asp Glu Leu Gln Lys Gln Leu
                85                  90                  95

Lys Asp Leu Gln Ala Val Leu Arg Lys Glu Ile Val Lys Pro Ile Gly
            100                 105                 110

Asn Gly Gly Lys Tyr Lys Ala Gly Tyr Asp Arg Leu Phe Gly Ala Lys
        115                 120                 125

Leu Phe Lys Asp Gly Lys Glu Leu Gly Asp Leu Ala Lys Phe Val Ile
    130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
            180                 185                 190

His Glu Asn Leu Pro Arg Phe Ile Asp Asn Leu Gln Ile Leu Thr Thr
        195                 200                 205

Ile Lys Gln Lys His Ser Ala Leu Tyr Asp Gln Ile Ile Asn Glu Leu
    210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Thr Leu Leu
                245                 250                 255

Gly Gly Ile Ser Gly Glu Ala Gly Ser Pro Lys Ile Gln Gly Ile Asn
            260                 265                 270

Glu Leu Ile Asn Ser His His Asn Gln His Cys His Lys Ser Glu Arg
        275                 280                 285

Ile Ala Lys Leu Arg Pro Leu His Lys Gln Ile Leu Ser Asp Gly Met
    290                 295                 300

Ser Val Ser Phe Leu Pro Ser Lys Phe Ala Asp Asp Ser Glu Met Cys
305                 310                 315                 320

Gln Ala Val Asn Glu Phe Tyr Arg His Tyr Ala Asp Val Phe Ala Lys
                325                 330                 335

Val Gln Ser Leu Phe Asp Gly Phe Asp Asp His Gln Lys Asp Gly Ile
            340                 345                 350

Tyr Val Glu His Lys Asn Leu Asn Glu Leu Ser Lys Gln Ala Phe Gly
        355                 360                 365

Asp Phe Ala Leu Leu Gly Arg Val Leu Asp Gly Tyr Tyr Val Asp Val
    370                 375                 380
```

```
Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
                405                 410                 415

His Ser Leu Ala Ser Leu Glu Gln Ala Ile Glu His Tyr Thr Ala Arg
            420                 425                 430

His Asp Asp Glu Ser Val Gln Ala Gly Lys Leu Gly Gln Tyr Phe Lys
        435                 440                 445

His Gly Leu Ala Gly Val Asp Asn Pro Ile Gln Lys Ile His Asn Asn
    450                 455                 460

His Ser Thr Ile Lys Gly Phe Leu Glu Arg Glu Arg Pro Ala Gly Glu
465                 470                 475                 480

Arg Ala Leu Pro Lys Ile Lys Ser Gly Lys Asn Pro Glu Met Thr Gln
                485                 490                 495

Leu Arg Gln Leu Lys Glu Leu Leu Asp Asn Ala Leu Asn Val Ala His
            500                 505                 510

Phe Ala Lys Leu Leu Thr Thr Lys Thr Thr Leu Asp Asn Gln Asp Gly
        515                 520                 525

Asn Phe Tyr Gly Glu Phe Gly Val Leu Tyr Asp Glu Leu Ala Lys Ile
    530                 535                 540

Pro Thr Leu Tyr Asn Lys Val Arg Asp Tyr Leu Ser Gln Lys Pro Phe
545                 550                 555                 560

Ser Thr Glu Lys Tyr Lys Leu Asn Phe Gly Asn Pro Thr Leu Leu Asn
                565                 570                 575

Gly Trp Asp Leu Asn Lys Glu Lys Asp Asn Phe Gly Val Ile Leu Gln
            580                 585                 590

Lys Asp Gly Cys Tyr Tyr Leu Ala Leu Leu Asp Lys Ala His Lys Lys
        595                 600                 605

Val Phe Asp Asn Ala Pro Asn Thr Gly Lys Ser Ile Tyr Gln Lys Met
    610                 615                 620

Ile Tyr Lys Tyr Leu Glu Val Arg Lys Gln Phe Pro Lys Val Phe Phe
625                 630                 635                 640

Ser Lys Glu Ala Ile Ala Ile Asn Tyr His Pro Ser Lys Glu Leu Val
                645                 650                 655

Glu Ile Lys Asp Lys Gly Arg Gln Arg Ser Asp Asp Glu Arg Leu Lys
            660                 665                 670

Leu Tyr Arg Phe Ile Leu Glu Cys Leu Lys Ile His Pro Lys Tyr Asp
        675                 680                 685

Lys Lys Phe Glu Gly Ala Ile Gly Asp Ile Gln Leu Phe Lys Lys Asp
    690                 695                 700

Lys Lys Gly Arg Glu Val Pro Ile Ser Glu Lys Asp Leu Phe Asp Lys
705                 710                 715                 720

Ile Asn Gly Ile Phe Ser Ser Lys Pro Lys Leu Glu Met Glu Asp Phe
                725                 730                 735

Phe Ile Gly Glu Phe Lys Arg Tyr Asn Pro Ser Gln Asp Leu Val Asp
            740                 745                 750

Gln Tyr Asn Ile Tyr Lys Lys Ile Asp Ser Asn Asp Asn Arg Lys Lys
        755                 760                 765

Glu Asn Phe Tyr Asn Asn His Pro Lys Phe Lys Lys Asp Leu Val Arg
    770                 775                 780

Tyr Tyr Tyr Glu Ser Met Cys Lys His Glu Glu Trp Glu Glu Ser Phe
785                 790                 795                 800

Glu Phe Ser Lys Lys Leu Gln Asp Ile Gly Cys Tyr Val Asp Val Asn
```

```
                805                 810                 815

Glu Leu Phe Thr Glu Ile Glu Thr Arg Arg Leu Asn Tyr Lys Ile Ser
            820                 825                 830

Phe Cys Asn Ile Asn Ala Asp Tyr Ile Asp Glu Leu Val Glu Gln Gly
        835                 840                 845

Gln Leu Tyr Leu Phe Gln Ile Tyr Asn Lys Asp Phe Ser Pro Lys Ala
    850                 855                 860

His Gly Lys Pro Asn Leu His Thr Leu Tyr Phe Lys Ala Leu Phe Ser
865                 870                 875                 880

Glu Asp Asn Leu Ala Asp Pro Ile Tyr Lys Leu Asn Gly Glu Ala Gln
                885                 890                 895

Ile Phe Tyr Arg Lys Ala Ser Leu Asp Met Asn Glu Thr Thr Ile His
            900                 905                 910

Arg Ala Gly Glu Val Leu Glu Asn Lys Asn Pro Asp Asn Pro Lys Lys
        915                 920                 925

Arg Gln Phe Val Tyr Asp Ile Ile Lys Asp Lys Arg Tyr Thr Gln Asp
    930                 935                 940

Lys Phe Met Leu His Val Pro Ile Thr Met Asn Phe Gly Val Gln Gly
945                 950                 955                 960

Met Thr Ile Lys Glu Phe Asn Lys Lys Val Asn Gln Ser Ile Gln Gln
                965                 970                 975

Tyr Asp Glu Val Asn Val Ile Gly Ile Asp Arg Gly Glu Arg His Leu
            980                 985                 990

Leu Tyr Leu Thr Val Ile Asn Ser  Lys Gly Glu Ile Leu  Glu Gln Cys
        995                 1000                1005

Ser Leu  Asn Asp Ile Thr Thr  Ala Ser Ala Asn Gly  Thr Gln Met
    1010                1015                1020

Thr Thr  Pro Tyr His Lys Ile  Leu Asp Lys Arg Glu  Ile Glu Arg
    1025                1030                1035

Leu Asn  Ala Arg Val Gly Trp  Gly Glu Ile Glu Thr  Ile Lys Glu
    1040                1045                1050

Leu Lys  Ser Gly Tyr Leu Ser  His Val Val His Gln  Ile Ser Gln
    1055                1060                1065

Leu Met  Leu Lys Tyr Asn Ala  Ile Val Val Leu Glu  Asp Leu Asn
    1070                1075                1080

Phe Gly  Phe Lys Arg Gly Arg  Phe Lys Val Glu Lys  Gln Ile Tyr
    1085                1090                1095

Gln Asn  Phe Glu Asn Ala Leu  Ile Lys Lys Leu Asn  His Leu Val
    1100                1105                1110

Leu Lys  Asp Lys Ala Asp Asp  Glu Ile Gly Ser Tyr  Lys Asn Ala
    1115                1120                1125

Leu Gln  Leu Thr Asn Asn Phe  Thr Asp Leu Lys Ser  Ile Gly Lys
    1130                1135                1140

Gln Thr  Gly Phe Leu Phe Tyr  Val Pro Ala Trp Asn  Thr Ser Lys
    1145                1150                1155

Ile Asp  Pro Glu Thr Gly Phe  Val Asp Leu Leu Lys  Pro Arg Tyr
    1160                1165                1170

Glu Asn  Ile Ala Gln Ser Gln  Ala Phe Phe Gly Lys  Phe Asp Lys
    1175                1180                1185

Ile Cys  Tyr Asn Ala Asp Lys  Asp Tyr Phe Glu Phe  His Ile Asp
    1190                1195                1200

Tyr Ala  Lys Phe Thr Asp Lys  Ala Lys Asn Ser Arg  Gln Ile Trp
    1205                1210                1215
```

Thr Ile Cys Ser His Gly Asp Lys Arg Tyr Val Tyr Asp Lys Thr
1220 1225 1230

Ala Asn Gln Asn Lys Gly Ala Ala Lys Gly Ile Asn Val Asn Asp
1235 1240 1245

Glu Leu Lys Ser Leu Phe Ala Arg His His Ile Asn Glu Lys Gln
1250 1255 1260

Pro Asn Leu Val Met Asp Ile Cys Gln Asn Asn Asp Lys Glu Phe
1265 1270 1275

His Lys Ser Leu Met Tyr Leu Leu Lys Thr Leu Leu Ala Leu Arg
1280 1285 1290

Tyr Ser Asn Ala Ser Ser Asp Glu Asp Phe Ile Leu Ser Pro Val
1295 1300 1305

Ala Asn Asp Glu Gly Val Phe Phe Asn Ser Ala Leu Ala Asp Asp
1310 1315 1320

Thr Gln Pro Gln Asn Ala Asp Ala Asn Gly Ala Tyr His Ile Ala
1325 1330 1335

Leu Lys Gly Leu Trp Leu Leu Asn Glu Leu Lys Asn Ser Asp Asp
1340 1345 1350

Leu Asn Lys Val Lys Leu Ala Ile Asp Asn Gln Thr Trp Leu Asn
1355 1360 1365

Phe Ala Gln Asn Arg
1370

<210> SEQ ID NO 18
<211> LENGTH: 1364
<212> TYPE: PRT
<213> ORGANISM: Moraxella bovoculi

<400> SEQUENCE: 18

Met Leu Phe Gln Asp Phe Thr His Leu Tyr Pro Leu Ser Lys Thr Val
1 5 10 15

Arg Phe Glu Leu Lys Pro Ile Asp Arg Thr Leu Glu His Ile His Ala
20 25 30

Lys Asn Phe Leu Ser Gln Asp Glu Thr Met Ala Asp Met His Gln Lys
35 40 45

Val Lys Val Ile Leu Asp Asp Tyr His Arg Asp Phe Ile Ala Asp Met
50 55 60

Met Gly Glu Val Lys Leu Thr Lys Leu Ala Glu Phe Tyr Asp Val Tyr
65 70 75 80

Leu Lys Phe Arg Lys Asn Pro Lys Asp Asp Glu Leu Gln Lys Gln Leu
85 90 95

Lys Asp Leu Gln Ala Val Leu Arg Lys Glu Ile Val Lys Pro Ile Gly
100 105 110

Asn Gly Gly Lys Tyr Lys Ala Gly Tyr Asp Arg Leu Phe Gly Ala Lys
115 120 125

Leu Phe Lys Asp Gly Lys Glu Leu Gly Asp Leu Ala Lys Phe Val Ile
130 135 140

Ala Gln Glu Gly Glu Ser Ser Pro Lys Leu Ala His Leu Ala His Phe
145 150 155 160

Glu Lys Phe Ser Thr Tyr Phe Thr Gly Phe His Asp Asn Arg Lys Asn
165 170 175

Met Tyr Ser Asp Glu Asp Lys His Thr Ala Ile Ala Tyr Arg Leu Ile
180 185 190

His Glu Asn Leu Pro Arg Phe Ile Asp Asn Leu Gln Ile Leu Thr Thr

```
        195                 200                 205

Ile Lys Gln Lys His Ser Ala Leu Tyr Asp Gln Ile Ile Asn Glu Leu
    210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Thr Leu Leu
                245                 250                 255

Gly Gly Ile Ser Gly Glu Ala Gly Ser Pro Lys Ile Gln Gly Ile Asn
            260                 265                 270

Glu Leu Ile Asn Ser His His Asn Gln His Cys His Lys Ser Glu Arg
        275                 280                 285

Ile Ala Lys Leu Arg Pro Leu His Lys Gln Ile Leu Ser Asp Gly Met
    290                 295                 300

Ser Val Ser Phe Leu Pro Ser Lys Phe Ala Asp Asp Ser Glu Met Cys
305                 310                 315                 320

Gln Ala Val Asn Glu Phe Tyr Arg His Tyr Ala Asp Val Phe Ala Lys
                325                 330                 335

Val Gln Ser Leu Phe Asp Gly Phe Asp Asp His Gln Lys Asp Gly Ile
            340                 345                 350

Tyr Val Glu His Lys Asn Leu Asn Glu Leu Ser Lys Gln Ala Phe Gly
        355                 360                 365

Asp Phe Ala Leu Leu Gly Arg Val Leu Asp Gly Tyr Tyr Val Asp Val
    370                 375                 380

Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
                405                 410                 415

His Ser Leu Ala Ser Leu Glu Gln Ala Ile Glu His Tyr Thr Ala Arg
            420                 425                 430

His Asp Asp Glu Ser Val Gln Ala Gly Lys Leu Gly Gln Tyr Phe Lys
        435                 440                 445

His Gly Leu Ala Gly Val Asp Asn Pro Ile Gln Lys Ile His Asn Asn
    450                 455                 460

His Ser Thr Ile Lys Gly Phe Leu Glu Arg Glu Arg Pro Ala Gly Glu
465                 470                 475                 480

Arg Ala Leu Pro Lys Ile Lys Ser Gly Lys Asn Pro Glu Met Thr Gln
                485                 490                 495

Leu Arg Gln Leu Lys Glu Leu Leu Asp Asn Ala Leu Asn Val Ala His
            500                 505                 510

Phe Ala Lys Leu Leu Thr Thr Lys Thr Thr Leu Asp Asn Gln Asp Gly
        515                 520                 525

Asn Phe Tyr Gly Glu Phe Gly Val Leu Tyr Asp Glu Leu Ala Lys Ile
    530                 535                 540

Pro Thr Leu Tyr Asn Lys Val Arg Asp Tyr Leu Ser Gln Lys Pro Phe
545                 550                 555                 560

Ser Thr Glu Lys Tyr Lys Leu Asn Phe Gly Asn Pro Thr Leu Leu Asn
                565                 570                 575

Gly Trp Asp Leu Asn Lys Glu Lys Asp Asn Phe Gly Val Ile Leu Gln
            580                 585                 590

Lys Asp Gly Cys Tyr Tyr Leu Ala Leu Leu Asp Lys Ala His Lys Lys
        595                 600                 605

Val Phe Asp Asn Ala Pro Asn Thr Gly Lys Ser Ile Tyr Gln Lys Met
    610                 615                 620
```

```
Ile Tyr Lys Tyr Leu Glu Val Arg Lys Gln Phe Pro Lys Val Phe Phe
625                 630                 635                 640

Ser Lys Glu Ala Ile Ala Ile Asn Tyr His Pro Ser Lys Glu Leu Val
                645                 650                 655

Glu Ile Lys Asp Lys Gly Arg Gln Arg Ser Asp Asp Glu Arg Leu Lys
            660                 665                 670

Leu Tyr Arg Phe Ile Leu Glu Cys Leu Lys Ile His Pro Lys Tyr Asp
        675                 680                 685

Lys Lys Phe Glu Gly Ala Ile Gly Asp Ile Gln Leu Phe Lys Lys Asp
    690                 695                 700

Lys Lys Gly Arg Glu Val Pro Ile Ser Glu Lys Asp Leu Phe Asp Lys
705                 710                 715                 720

Ile Asn Gly Ile Phe Ser Ser Lys Pro Lys Leu Glu Met Glu Asp Phe
                725                 730                 735

Phe Ile Gly Glu Phe Lys Arg Tyr Asn Pro Ser Gln Asp Leu Val Asp
            740                 745                 750

Gln Tyr Asn Ile Tyr Lys Lys Ile Asp Ser Asn Asp Asn Arg Lys Lys
        755                 760                 765

Glu Asn Phe Tyr Asn Asn His Pro Lys Phe Lys Lys Asp Leu Val Arg
    770                 775                 780

Tyr Tyr Tyr Glu Ser Met Cys Lys His Glu Glu Trp Glu Glu Ser Phe
785                 790                 795                 800

Glu Phe Ser Lys Lys Leu Gln Asp Ile Gly Cys Tyr Val Asp Val Asn
                805                 810                 815

Glu Leu Phe Thr Glu Ile Glu Thr Arg Arg Leu Asn Tyr Lys Ile Ser
            820                 825                 830

Phe Cys Asn Ile Asn Ala Asp Tyr Ile Asp Glu Leu Val Glu Gln Gly
        835                 840                 845

Gln Leu Tyr Leu Phe Gln Ile Tyr Asn Lys Asp Phe Ser Pro Lys Ala
    850                 855                 860

His Gly Lys Pro Asn Leu His Thr Leu Tyr Phe Lys Ala Leu Phe Ser
865                 870                 875                 880

Glu Asp Asn Leu Ala Asp Pro Ile Tyr Lys Leu Asn Gly Glu Ala Gln
                885                 890                 895

Ile Phe Tyr Arg Lys Ala Ser Leu Asp Met Asn Glu Thr Thr Ile His
            900                 905                 910

Arg Ala Gly Glu Val Leu Glu Asn Lys Asn Pro Asp Asn Pro Lys Lys
        915                 920                 925

Arg Gln Phe Val Tyr Asp Ile Ile Lys Asp Lys Arg Tyr Thr Gln Asp
    930                 935                 940

Lys Phe Met Leu His Val Pro Ile Thr Met Asn Phe Gly Val Gln Gly
945                 950                 955                 960

Met Thr Ile Lys Glu Phe Asn Lys Lys Val Asn Gln Ser Ile Gln Gln
                965                 970                 975

Tyr Asp Glu Val Asn Val Ile Gly Ile Asp Arg Gly Glu Arg His Leu
            980                 985                 990

Leu Tyr Leu Thr Val Ile Asn Ser  Lys Gly Glu Ile Leu  Glu Gln Cys
        995                 1000                 1005

Ser Leu  Asn Asp Ile Thr Thr  Ala Ser Ala Asn Gly  Thr Gln Met
    1010                 1015                 1020

Thr Thr  Pro Tyr His Lys Ile  Leu Asp Lys Arg Glu  Ile Glu Arg
    1025                 1030                 1035
```

```
Leu Asn  Ala Arg Val Gly Trp  Gly Glu Ile Glu Thr  Ile Lys Glu
    1040                 1045                 1050

Leu Lys  Ser Gly Tyr Leu Ser  His Val Val His Gln  Ile Ser Gln
    1055                 1060                 1065

Leu Met  Leu Lys Tyr Asn Ala  Ile Val Val Leu Glu  Asp Leu Asn
    1070                 1075                 1080

Val Glu  Lys Gln Ile Tyr Gln  Asn Phe Glu Asn Ala  Leu Ile Lys
    1085                 1090                 1095

Lys Leu  Asn His Leu Val Leu  Lys Asp Lys Ala Asp  Asp Glu Ile
    1100                 1105                 1110

Gly Ser  Tyr Lys Asn Ala Leu  Gln Leu Thr Asn Asn  Phe Thr Asp
    1115                 1120                 1125

Leu Lys  Ser Ile Gly Lys Gln  Thr Gly Phe Leu Phe  Tyr Val Pro
    1130                 1135                 1140

Ala Trp  Asn Thr Ser Lys Ile  Asp Pro Glu Thr Gly  Phe Val Asp
    1145                 1150                 1155

Leu Leu  Lys Pro Arg Tyr Glu  Asn Ile Ala Gln Ser  Gln Ala Phe
    1160                 1165                 1170

Phe Gly  Lys Phe Asp Lys Ile  Cys Tyr Asn Ala Asp  Lys Asp Tyr
    1175                 1180                 1185

Phe Glu  Phe His Ile Asp Tyr  Ala Lys Phe Thr Asp  Lys Ala Lys
    1190                 1195                 1200

Asn Ser  Arg Gln Ile Trp Thr  Ile Cys Ser His Gly  Asp Lys Arg
    1205                 1210                 1215

Tyr Val  Tyr Asp Lys Thr Ala  Asn Gln Asn Lys Gly  Ala Ala Lys
    1220                 1225                 1230

Gly Ile  Asn Val Asn Asp Glu  Leu Lys Ser Leu Phe  Ala Arg His
    1235                 1240                 1245

His Ile  Asn Glu Lys Gln Pro  Asn Leu Val Met Asp  Ile Cys Gln
    1250                 1255                 1260

Asn Asn  Asp Lys Glu Phe His  Lys Ser Leu Met Tyr  Leu Leu Lys
    1265                 1270                 1275

Thr Leu  Leu Ala Leu Arg Tyr  Ser Asn Ala Ser Ser  Asp Glu Asp
    1280                 1285                 1290

Phe Ile  Leu Ser Pro Val Ala  Asn Asp Glu Gly Val  Phe Phe Asn
    1295                 1300                 1305

Ser Ala  Leu Ala Asp Asp Thr  Gln Pro Gln Asn Ala  Asp Ala Asn
    1310                 1315                 1320

Gly Ala  Tyr His Ile Ala Leu  Lys Gly Leu Trp Leu  Leu Asn Glu
    1325                 1330                 1335

Leu Lys  Asn Ser Asp Asp Leu  Asn Lys Val Lys Leu  Ala Ile Asp
    1340                 1345                 1350

Asn Gln  Thr Trp Leu Asn Phe  Ala Gln Asn Arg
    1355                 1360


<210> SEQ ID NO 19
<211> LENGTH: 1250
<212> TYPE: PRT
<213> ORGANISM: Moraxella bovoculi

<400> SEQUENCE: 19

Met Gly Ile His Gly Val Pro Ala Ala Leu Phe Gln Asp Phe Thr His
1               5                   10                  15

Leu Tyr Pro Leu Ser Lys Thr Val Arg Phe Glu Leu Lys Pro Ile Gly
            20                  25                  30
```

```
Arg Thr Leu Glu His Ile His Ala Lys Asn Phe Leu Ser Gln Asp Glu
        35                  40                  45

Thr Met Ala Asp Met Tyr Gln Lys Val Lys Val Ile Leu Asp Asp Tyr
    50                  55                  60

His Arg Asp Phe Ile Ala Asp Met Met Gly Glu Val Lys Leu Thr Lys
65                  70                  75                  80

Leu Ala Glu Phe Tyr Asp Val Tyr Leu Lys Phe Arg Lys Asn Pro Lys
                85                  90                  95

Asp Asp Gly Leu Gln Lys Gln Leu Lys Asp Leu Gln Ala Val Leu Arg
            100                 105                 110

Lys Glu Ser Val Lys Pro Ile Gly Ser Gly Gly Lys Tyr Lys Thr Gly
        115                 120                 125

Tyr Asp Arg Leu Phe Gly Ala Lys Leu Phe Lys Asp Gly Lys Glu Leu
    130                 135                 140

Gly Asp Leu Ala Lys Phe Val Ile Ala Gln Glu Gly Glu Ser Ser Pro
145                 150                 155                 160

Lys Leu Ala His Leu Ala His Phe Glu Lys Phe Ser Thr Tyr Phe Thr
                165                 170                 175

Gly Phe His Asp Asn Arg Lys Asn Met Tyr Ser Asp Glu Asp Lys His
            180                 185                 190

Thr Ala Ile Ala Tyr Arg Leu Ile His Glu Asn Leu Pro Arg Phe Ile
        195                 200                 205

Asp Asn Leu Gln Ile Leu Thr Thr Ile Lys Gln Lys His Ser Ala Leu
    210                 215                 220

Tyr Asp Gln Ile Ile Asn Glu Leu Thr Ala Ser Gly Leu Asp Val Ser
225                 230                 235                 240

Leu Ala Ser His Leu Asp Gly Tyr His Lys Leu Leu Thr Gln Glu Gly
                245                 250                 255

Ile Thr Ala Tyr Asn Arg Ile Ile Gly Glu Val Asn Gly Tyr Thr Asn
            260                 265                 270

Lys His Asn Gln Ile Cys His Lys Ser Glu Arg Ile Ala Lys Leu Arg
        275                 280                 285

Pro Leu His Lys Gln Ile Leu Ser Asp Gly Met Gly Val Ser Phe Leu
    290                 295                 300

Pro Ser Lys Phe Ala Asp Asp Ser Glu Met Cys Gln Ala Val Asn Glu
305                 310                 315                 320

Phe Tyr Arg His Tyr Thr Asp Val Phe Ala Lys Val Gln Ser Leu Phe
                325                 330                 335

Asp Gly Phe Asp Asp His Gln Lys Asp Gly Ile Tyr Val Glu His Lys
            340                 345                 350

Asn Leu Asn Glu Leu Ser Lys Gln Ala Phe Gly Asp Phe Ala Leu Leu
        355                 360                 365

Gly Arg Val Leu Asp Gly Tyr Tyr Val Asp Val Val Asn Pro Glu Phe
    370                 375                 380

Asn Glu Arg Phe Ala Lys Ala Lys Thr Asp Asn Ala Lys Ala Lys Leu
385                 390                 395                 400

Thr Lys Glu Lys Asp Lys Phe Ile Lys Gly Val His Ser Leu Ala Ser
                405                 410                 415

Leu Glu Gln Ala Ile Glu His His Thr Ala Arg His Asp Asp Glu Ser
            420                 425                 430

Val Gln Ala Gly Lys Leu Gly Gln Tyr Phe Lys His Gly Leu Ala Gly
        435                 440                 445
```

```
Val Asp Asn Pro Ile Gln Lys Ile His Asn Asn His Ser Thr Ile Lys
    450                 455                 460

Gly Phe Leu Glu Arg Glu Arg Pro Ala Gly Glu Arg Ala Leu Pro Lys
465                 470                 475                 480

Ile Lys Ser Gly Lys Asn Pro Glu Met Thr Gln Leu Arg Gln Leu Lys
                485                 490                 495

Glu Leu Leu Asp Asn Ala Leu Asn Val Ala His Phe Ala Lys Leu Leu
            500                 505                 510

Thr Thr Lys Thr Thr Leu Asp Asn Gln Asp Gly Asn Phe Tyr Gly Glu
        515                 520                 525

Phe Gly Val Leu Tyr Asp Glu Leu Ala Lys Ile Pro Thr Leu Tyr Asn
    530                 535                 540

Lys Val Arg Asp Tyr Leu Ser Gln Lys Pro Phe Ser Thr Glu Lys Tyr
545                 550                 555                 560

Lys Leu Asn Phe Gly Asn Pro Thr Leu Leu Asn Gly Trp Asp Leu Asn
                565                 570                 575

Lys Glu Lys Asp Asn Phe Gly Val Ile Leu Gln Lys Asp Gly Cys Tyr
            580                 585                 590

Tyr Leu Ala Leu Leu Asp Lys Ala His Lys Lys Val Phe Asp Asn Ala
        595                 600                 605

Pro Asn Thr Gly Lys Asn Val Tyr Gln Lys Met Val Tyr Lys Leu Leu
    610                 615                 620

Pro Gly Pro Asn Lys Met Leu Pro Lys Val Phe Phe Ala Lys Ser Asn
625                 630                 635                 640

Leu Asp Tyr Tyr Asn Pro Ser Ala Glu Leu Leu Asp Lys Tyr Ala Lys
                645                 650                 655

Gly Thr His Lys Lys Gly Asp Asn Phe Asn Leu Lys Asp Cys His Ala
            660                 665                 670

Leu Ile Asp Phe Phe Lys Ala Gly Ile Asn Lys His Pro Glu Trp Gln
        675                 680                 685

His Phe Gly Phe Lys Phe Ser Pro Thr Ser Ser Tyr Arg Asp Leu Ser
    690                 695                 700

Asp Phe Tyr Arg Glu Val Glu Pro Gln Gly Tyr Gln Val Lys Phe Val
705                 710                 715                 720

Asp Ile Asn Ala Asp Tyr Ile Asp Glu Leu Val Glu Gln Gly Lys Leu
                725                 730                 735

Tyr Leu Phe Gln Ile Tyr Asn Lys Asp Phe Ser Pro Lys Ala His Gly
            740                 745                 750

Lys Pro Asn Leu His Thr Leu Tyr Phe Lys Ala Leu Phe Ser Glu Asp
        755                 760                 765

Asn Leu Ala Asp Pro Ile Tyr Lys Leu Asn Gly Glu Ala Gln Ile Phe
    770                 775                 780

Tyr Arg Lys Ala Ser Leu Asp Met Asn Glu Thr Thr Ile His Arg Ala
785                 790                 795                 800

Gly Glu Val Leu Glu Asn Lys Asn Pro Asp Asn Pro Lys Lys Arg Gln
                805                 810                 815

Phe Val Tyr Asp Ile Ile Lys Asp Lys Arg Tyr Thr Gln Asp Lys Phe
            820                 825                 830

Met Leu His Val Pro Ile Thr Met Asn Phe Gly Val Gln Gly Met Thr
        835                 840                 845

Ile Lys Glu Phe Asn Lys Lys Val Asn Gln Ser Ile Gln Gln Tyr Asp
    850                 855                 860

Glu Val Asn Val Ile Gly Ile Asp Arg Gly Glu Arg His Leu Leu Tyr
```

```
865                 870                 875                 880

Leu Thr Val Ile Asn Ser Lys Gly Glu Ile Leu Glu Gln Arg Ser Leu
                885                 890                 895

Asn Asp Ile Thr Thr Ala Ser Ala Asn Gly Thr Gln Val Thr Thr Pro
            900                 905                 910

Tyr His Lys Ile Leu Asp Lys Arg Glu Ile Glu Arg Leu Asn Ala Arg
        915                 920                 925

Val Gly Trp Gly Glu Ile Glu Thr Ile Lys Glu Leu Lys Ser Gly Tyr
    930                 935                 940

Leu Ser His Val Val His Gln Ile Asn Gln Leu Met Leu Lys Tyr Asn
945                 950                 955                 960

Ala Ile Val Val Leu Glu Asp Leu Asn Val Glu Lys Gln Ile Tyr Gln
                965                 970                 975

Asn Phe Glu Asn Ala Leu Ile Lys Lys Leu Asn His Leu Val Leu Lys
            980                 985                 990

Asp Lys Ala Asp Asp Glu Ile Gly  Ser Tyr Lys Asn Ala  Leu Gln Leu
        995                 1000                1005

Thr Asn  Asn Phe Thr Asp Leu  Lys Ser Ile Gly Lys  Gln Thr Gly
    1010                1015                1020

Phe Leu  Phe Tyr Val Pro Ala  Trp Asn Thr Ser Lys  Ile Asp Pro
    1025                1030                1035

Glu Thr  Gly Phe Val Asp Leu  Leu Lys Pro Arg Tyr  Glu Asn Ile
    1040                1045                1050

Ala Gln  Ser Gln Ala Phe Phe  Gly Lys Phe Asp Lys  Ile Cys Tyr
    1055                1060                1065

Asn Thr  Asp Lys Gly Tyr Phe  Glu Phe His Ile Asp  Tyr Ala Lys
    1070                1075                1080

Phe Thr  Asp Lys Ala Lys Asn  Ser Arg Gln Lys Trp  Ala Ile Cys
    1085                1090                1095

Ser His  Gly Asp Lys Arg Tyr  Val Tyr Asp Lys Thr  Ala Asn Gln
    1100                1105                1110

Asn Lys  Gly Ala Ala Lys Gly  Ile Asn Val Asn Asp  Glu Leu Lys
    1115                1120                1125

Ser Leu  Phe Ala Arg Tyr His  Ile Asn Asp Lys Gln  Pro Asn Leu
    1130                1135                1140

Val Met  Asp Ile Cys Gln Asn  Asn Asp Lys Glu Phe  His Lys Ser
    1145                1150                1155

Leu Met  Cys Leu Leu Lys Thr  Leu Leu Ala Leu Arg  Tyr Ser Asn
    1160                1165                1170

Ala Ser  Ser Asp Glu Asp Phe  Ile Leu Ser Pro Val  Ala Asn Asp
    1175                1180                1185

Glu Gly  Val Phe Phe Asn Ser  Ala Leu Ala Asp Asp  Thr Gln Pro
    1190                1195                1200

Gln Asn  Ala Asp Ala Asn Gly  Ala Tyr His Ile Ala  Leu Lys Gly
    1205                1210                1215

Leu Trp  Leu Leu Asn Glu Leu  Lys Asn Ser Asp Asp  Leu Asn Lys
    1220                1225                1230

Val Lys  Leu Ala Ile Asp Asn  Gln Thr Trp Leu Asn  Phe Ala Gln
    1235                1240                1245

Asn Arg
    1250
```

<210> SEQ ID NO 20

<211> LENGTH: 1269
<212> TYPE: PRT
<213> ORGANISM: Moraxella bovoculi

<400> SEQUENCE: 20

Met Gly Ile His Gly Val Pro Ala Ala Leu Phe Gln Asp Phe Thr His
1               5                   10                  15

Leu Tyr Pro Leu Ser Lys Thr Val Arg Phe Glu Leu Lys Pro Ile Gly
            20                  25                  30

Lys Thr Leu Glu His Ile His Ala Lys Asn Phe Leu Asn Gln Asp Glu
        35                  40                  45

Thr Met Ala Asp Met Tyr Gln Lys Val Lys Ala Ile Leu Asp Asp Tyr
    50                  55                  60

His Arg Asp Phe Ile Ala Asp Met Met Gly Glu Val Lys Leu Thr Lys
65                  70                  75                  80

Leu Ala Glu Phe Tyr Asp Val Tyr Leu Lys Phe Arg Lys Asn Pro Lys
                85                  90                  95

Asp Asp Gly Leu Gln Lys Gln Leu Lys Asp Leu Gln Ala Val Leu Arg
            100                 105                 110

Lys Glu Ile Val Lys Pro Ile Gly Asn Gly Gly Lys Tyr Lys Ala Gly
        115                 120                 125

Tyr Asp Arg Leu Phe Gly Ala Lys Leu Phe Lys Asp Gly Lys Glu Leu
    130                 135                 140

Gly Asp Leu Ala Lys Phe Val Ile Ala Gln Glu Gly Glu Ser Ser Pro
145                 150                 155                 160

Lys Leu Ala His Leu Ala His Phe Glu Lys Phe Ser Thr Tyr Phe Thr
                165                 170                 175

Gly Phe His Asp Asn Arg Lys Asn Met Tyr Ser Asp Glu Asp Lys His
            180                 185                 190

Thr Ala Ile Ala Tyr Arg Leu Ile His Glu Asn Leu Pro Arg Phe Ile
        195                 200                 205

Asp Asn Leu Gln Ile Leu Ala Thr Ile Lys Gln Lys His Ser Ala Leu
    210                 215                 220

Tyr Asp Gln Ile Ile Asn Glu Leu Thr Ala Ser Gly Leu Asp Val Ser
225                 230                 235                 240

Leu Ala Ser His Leu Asp Gly Tyr His Lys Leu Leu Thr Gln Glu Gly
                245                 250                 255

Ile Thr Ala Tyr Asn Thr Leu Leu Gly Gly Ile Ser Gly Glu Ala Gly
            260                 265                 270

Ser Arg Lys Ile Gln Gly Ile Asn Glu Leu Ile Asn Ser His His Asn
        275                 280                 285

Gln His Cys His Lys Ser Glu Arg Ile Ala Lys Leu Arg Pro Leu His
    290                 295                 300

Lys Gln Ile Leu Ser Asp Gly Met Gly Val Ser Phe Leu Pro Ser Lys
305                 310                 315                 320

Phe Ala Asp Asp Ser Glu Val Cys Gln Ala Val Asn Glu Phe Tyr Arg
                325                 330                 335

His Tyr Ala Asp Val Phe Ala Lys Val Gln Ser Leu Phe Asp Gly Phe
            340                 345                 350

Asp Asp Tyr Gln Lys Asp Gly Ile Tyr Val Glu Tyr Lys Asn Leu Asn
        355                 360                 365

Glu Leu Ser Lys Gln Ala Phe Gly Asp Phe Ala Leu Leu Gly Arg Val
    370                 375                 380

Leu Asp Gly Tyr Tyr Val Asp Val Val Asn Pro Glu Phe Asn Glu Arg

```
385                 390                 395                 400

Phe Ala Lys Ala Lys Thr Asp Asn Ala Lys Ala Lys Leu Thr Lys Glu
                405                 410                 415

Lys Asp Lys Phe Ile Lys Gly Val His Ser Leu Ala Ser Leu Glu Gln
            420                 425                 430

Ala Ile Glu His Tyr Thr Ala Arg His Asp Asp Glu Ser Val Gln Ala
        435                 440                 445

Gly Lys Leu Gly Gln Tyr Phe Lys His Gly Leu Ala Gly Val Asp Asn
    450                 455                 460

Pro Ile Gln Lys Ile His Asn Asn His Ser Thr Ile Lys Gly Phe Leu
465                 470                 475                 480

Glu Arg Glu Arg Pro Ala Gly Glu Arg Ala Leu Pro Lys Ile Lys Ser
                485                 490                 495

Asp Lys Ser Pro Glu Ile Arg Gln Leu Lys Glu Leu Leu Asp Asn Ala
            500                 505                 510

Leu Asn Val Ala His Phe Ala Lys Leu Leu Thr Thr Lys Thr Thr Leu
        515                 520                 525

His Asn Gln Asp Gly Asn Phe Tyr Gly Glu Phe Gly Ala Leu Tyr Asp
    530                 535                 540

Glu Leu Ala Lys Ile Ala Thr Leu Tyr Asn Lys Val Arg Asp Tyr Leu
545                 550                 555                 560

Ser Gln Lys Pro Phe Ser Thr Glu Lys Tyr Lys Leu Asn Phe Gly Asn
                565                 570                 575

Pro Thr Leu Leu Asn Gly Trp Asp Leu Asn Lys Glu Lys Asp Asn Phe
            580                 585                 590

Gly Val Ile Leu Gln Lys Asp Gly Cys Tyr Tyr Leu Ala Leu Leu Asp
        595                 600                 605

Lys Ala His Lys Lys Val Phe Asp Asn Ala Pro Asn Thr Gly Lys Ser
    610                 615                 620

Val Tyr Gln Lys Met Ile Tyr Lys Leu Leu Pro Gly Pro Asn Lys Met
625                 630                 635                 640

Leu Pro Lys Val Phe Phe Ala Lys Ser Asn Leu Asp Tyr Tyr Asn Pro
                645                 650                 655

Ser Ala Glu Leu Leu Asp Lys Tyr Ala Gln Gly Thr His Lys Lys Gly
            660                 665                 670

Asp Asn Phe Asn Leu Lys Asp Cys His Ala Leu Ile Asp Phe Phe Lys
        675                 680                 685

Ala Gly Ile Asn Lys His Pro Glu Trp Gln His Phe Gly Phe Lys Phe
    690                 695                 700

Ser Pro Thr Ser Ser Tyr Gln Asp Leu Ser Asp Phe Tyr Arg Glu Val
705                 710                 715                 720

Glu Pro Gln Gly Tyr Gln Val Lys Phe Val Asp Ile Asn Ala Asp Tyr
                725                 730                 735

Ile Asn Glu Leu Val Glu Gln Gly Gln Leu Tyr Leu Phe Gln Ile Tyr
            740                 745                 750

Asn Lys Asp Phe Ser Pro Lys Ala His Gly Lys Pro Asn Leu His Thr
        755                 760                 765

Leu Tyr Phe Lys Ala Leu Phe Ser Glu Asp Asn Leu Val Asn Pro Ile
    770                 775                 780

Tyr Lys Leu Asn Gly Glu Ala Glu Ile Phe Tyr Arg Lys Ala Ser Leu
785                 790                 795                 800

Asp Met Asn Glu Thr Thr Ile His Arg Ala Gly Glu Val Leu Glu Asn
                805                 810                 815
```

```
Lys Asn Pro Asp Asn Pro Lys Lys Arg Gln Phe Val Tyr Asp Ile Ile
            820                 825                 830

Lys Asp Lys Arg Tyr Thr Gln Asp Lys Phe Met Leu His Val Pro Ile
        835                 840                 845

Thr Met Asn Phe Gly Val Gln Gly Met Thr Ile Lys Glu Phe Asn Lys
    850                 855                 860

Lys Val Asn Gln Ser Ile Gln Gln Tyr Asp Glu Val Asn Val Ile Gly
865                 870                 875                 880

Ile Asp Arg Gly Glu Arg His Leu Leu Tyr Leu Thr Val Ile Asn Ser
                885                 890                 895

Lys Gly Glu Ile Leu Glu Gln Arg Ser Leu Asn Asp Ile Thr Thr Ala
            900                 905                 910

Ser Ala Asn Gly Thr Gln Met Thr Thr Pro Tyr His Lys Ile Leu Asp
        915                 920                 925

Lys Arg Glu Ile Glu Arg Leu Asn Ala Arg Val Gly Trp Gly Glu Ile
    930                 935                 940

Glu Thr Ile Lys Glu Leu Lys Ser Gly Tyr Leu Ser His Val Val His
945                 950                 955                 960

Gln Ile Ser Gln Leu Met Leu Lys Tyr Asn Ala Ile Val Val Leu Glu
                965                 970                 975

Asp Leu Asn Phe Gly Phe Lys Arg Gly Arg Phe Lys Val Glu Lys Gln
            980                 985                 990

Ile Tyr Gln Asn Phe Glu Asn Ala  Leu Ile Lys Lys Leu  Asn His Leu
        995                 1000                1005

Val Leu  Lys Asp Lys Ala Asp  Asp Glu Ile Gly Ser  Tyr Lys Asn
    1010                 1015                1020

Ala Leu  Gln Leu Thr Asn Asn  Phe Thr Asp Leu Lys  Ser Ile Gly
    1025                 1030                1035

Lys Gln  Thr Gly Phe Leu Phe  Tyr Val Pro Ala Trp  Asn Thr Ser
    1040                 1045                1050

Lys Ile  Asp Pro Glu Thr Gly  Phe Val Asp Leu Leu  Lys Pro Arg
    1055                 1060                1065

Tyr Glu  Asn Ile Ala Gln Ser  Gln Ala Phe Phe Gly  Lys Phe Asp
    1070                 1075                1080

Lys Ile  Cys Tyr Asn Ala Asp  Arg Gly Tyr Phe Glu  Phe His Ile
    1085                 1090                1095

Asp Tyr  Ala Lys Phe Asn Asp  Lys Ala Lys Asn Ser  Arg Gln Ile
    1100                 1105                1110

Trp Lys  Ile Cys Ser His Gly  Asp Lys Arg Tyr Val  Tyr Asp Lys
    1115                 1120                1125

Thr Ala  Asn Gln Asn Lys Gly  Ala Thr Ile Gly Val  Asn Val Asn
    1130                 1135                1140

Asp Glu  Leu Lys Ser Leu Phe  Thr Arg Tyr His Ile  Asn Asp Lys
    1145                 1150                1155

Gln Pro  Asn Leu Val Met Asp  Ile Cys Gln Asn Asn  Asp Lys Glu
    1160                 1165                1170

Phe His  Lys Ser Leu Met Tyr  Leu Leu Lys Thr Leu  Leu Ala Leu
    1175                 1180                1185

Arg Tyr  Ser Asn Ala Ser Ser  Asp Glu Asp Phe Ile  Leu Ser Pro
    1190                 1195                1200

Val Ala  Asn Asp Glu Gly Val  Phe Phe Asn Ser Ala  Leu Ala Asp
    1205                 1210                1215
```

Asp Thr Gln Pro Gln Asn Ala Asp Ala Asn Gly Ala Tyr His Ile
    1220                1225                1230

Ala Leu Lys Gly Leu Trp Leu Leu Asn Glu Leu Lys Asn Ser Asp
    1235                1240                1245

Asp Leu Asn Lys Val Lys Leu Ala Ile Asp Asn Gln Thr Trp Leu
    1250                1255                1260

Asn Phe Ala Gln Asn Arg
    1265

<210> SEQ ID NO 21
<211> LENGTH: 1260
<212> TYPE: PRT
<213> ORGANISM: Moraxella bovoculi

<400> SEQUENCE: 21

Met Gly Ile His Gly Val Pro Ala Ala Leu Phe Gln Asp Phe Thr His
1               5                   10                  15

Leu Tyr Pro Leu Ser Lys Thr Val Arg Phe Glu Leu Lys Pro Ile Gly
            20                  25                  30

Lys Thr Leu Glu His Ile His Ala Lys Asn Phe Leu Asn Gln Asp Glu
        35                  40                  45

Thr Met Ala Asp Met Tyr Gln Lys Val Lys Ala Ile Leu Asp Asp Tyr
    50                  55                  60

His Arg Asp Phe Ile Ala Asp Met Met Gly Glu Val Lys Leu Thr Lys
65                  70                  75                  80

Leu Ala Glu Phe Tyr Asp Val Tyr Leu Lys Phe Arg Lys Asn Pro Lys
                85                  90                  95

Asp Asp Gly Leu Gln Lys Gln Leu Lys Asp Leu Gln Ala Val Leu Arg
            100                 105                 110

Lys Glu Ile Val Lys Pro Ile Gly Asn Gly Gly Lys Tyr Lys Ala Gly
        115                 120                 125

Tyr Asp Arg Leu Phe Gly Ala Lys Leu Phe Lys Asp Gly Lys Glu Leu
    130                 135                 140

Gly Asp Leu Ala Lys Phe Val Ile Ala Gln Glu Gly Glu Ser Ser Pro
145                 150                 155                 160

Lys Leu Ala His Leu Ala His Phe Glu Lys Phe Ser Thr Tyr Phe Thr
                165                 170                 175

Gly Phe His Asp Asn Arg Lys Asn Met Tyr Ser Asp Glu Asp Lys His
            180                 185                 190

Thr Ala Ile Ala Tyr Arg Leu Ile His Glu Asn Leu Pro Arg Phe Ile
        195                 200                 205

Asp Asn Leu Gln Ile Leu Ala Thr Ile Lys Gln Lys His Ser Ala Leu
    210                 215                 220

Tyr Asp Gln Ile Ile Asn Glu Leu Thr Ala Ser Gly Leu Asp Val Ser
225                 230                 235                 240

Leu Ala Ser His Leu Asp Gly Tyr His Lys Leu Leu Thr Gln Glu Gly
                245                 250                 255

Ile Thr Ala Tyr Asn Thr Leu Leu Gly Gly Ile Ser Gly Glu Ala Gly
            260                 265                 270

Ser Arg Lys Ile Gln Gly Ile Asn Glu Leu Ile Asn Ser His His Asn
        275                 280                 285

Gln His Cys His Lys Ser Glu Arg Ile Ala Lys Leu Arg Pro Leu His
    290                 295                 300

Lys Gln Ile Leu Ser Asp Gly Met Gly Val Ser Phe Leu Pro Ser Lys
305                 310                 315                 320

```
Phe Ala Asp Asp Ser Glu Val Cys Gln Ala Val Asn Glu Phe Tyr Arg
                325                 330                 335

His Tyr Ala Asp Val Phe Ala Lys Val Gln Ser Leu Phe Asp Gly Phe
            340                 345                 350

Asp Asp Tyr Gln Lys Asp Gly Ile Tyr Val Glu Tyr Lys Asn Leu Asn
        355                 360                 365

Glu Leu Ser Lys Gln Ala Phe Gly Asp Phe Ala Leu Leu Gly Arg Val
    370                 375                 380

Leu Asp Gly Tyr Tyr Val Asp Val Val Asn Pro Glu Phe Asn Glu Arg
385                 390                 395                 400

Phe Ala Lys Ala Lys Thr Asp Asn Ala Lys Ala Lys Leu Thr Lys Glu
                405                 410                 415

Lys Asp Lys Phe Ile Lys Gly Val His Ser Leu Ala Ser Leu Glu Gln
            420                 425                 430

Ala Ile Glu His Tyr Thr Ala Arg His Asp Asp Glu Ser Val Gln Ala
        435                 440                 445

Gly Lys Leu Gly Gln Tyr Phe Lys His Gly Leu Ala Gly Val Asp Asn
    450                 455                 460

Pro Ile Gln Lys Ile His Asn Asn His Ser Thr Ile Lys Gly Phe Leu
465                 470                 475                 480

Glu Arg Glu Arg Pro Ala Gly Glu Arg Ala Leu Pro Lys Ile Lys Ser
                485                 490                 495

Asp Lys Ser Pro Glu Ile Arg Gln Leu Lys Glu Leu Leu Asp Asn Ala
            500                 505                 510

Leu Asn Val Ala His Phe Ala Lys Leu Leu Thr Thr Lys Thr Thr Leu
        515                 520                 525

His Asn Gln Asp Gly Asn Phe Tyr Gly Glu Phe Gly Ala Leu Tyr Asp
    530                 535                 540

Glu Leu Ala Lys Ile Ala Thr Leu Tyr Asn Lys Val Arg Asp Tyr Leu
545                 550                 555                 560

Ser Gln Lys Pro Phe Ser Thr Glu Lys Tyr Lys Leu Asn Phe Gly Asn
                565                 570                 575

Pro Thr Leu Leu Asn Gly Trp Asp Leu Asn Lys Glu Lys Asp Asn Phe
            580                 585                 590

Gly Val Ile Leu Gln Lys Asp Gly Cys Tyr Tyr Leu Ala Leu Leu Asp
        595                 600                 605

Lys Ala His Lys Lys Val Phe Asp Asn Ala Pro Asn Thr Gly Lys Ser
    610                 615                 620

Val Tyr Gln Lys Met Ile Tyr Lys Leu Leu Pro Gly Pro Asn Lys Met
625                 630                 635                 640

Leu Pro Lys Val Phe Phe Ala Lys Ser Asn Leu Asp Tyr Tyr Asn Pro
                645                 650                 655

Ser Ala Glu Leu Leu Asp Lys Tyr Ala Gln Gly Thr His Lys Lys Gly
            660                 665                 670

Asp Asn Phe Asn Leu Lys Asp Cys His Ala Leu Ile Asp Phe Phe Lys
        675                 680                 685

Ala Gly Ile Asn Lys His Pro Glu Trp Gln His Phe Gly Phe Lys Phe
    690                 695                 700

Ser Pro Thr Ser Ser Tyr Gln Asp Leu Ser Asp Phe Tyr Arg Glu Val
705                 710                 715                 720

Glu Pro Gln Gly Tyr Gln Val Lys Phe Val Asp Ile Asn Ala Asp Tyr
                725                 730                 735
```

```
Ile Asn Glu Leu Val Glu Gln Gly Gln Leu Tyr Leu Phe Gln Ile Tyr
            740                 745                 750

Asn Lys Asp Phe Ser Pro Lys Ala His Gly Lys Pro Asn Leu His Thr
        755                 760                 765

Leu Tyr Phe Lys Ala Leu Phe Ser Glu Asp Asn Leu Val Asn Pro Ile
    770                 775                 780

Tyr Lys Leu Asn Gly Glu Ala Glu Ile Phe Tyr Arg Lys Ala Ser Leu
785                 790                 795                 800

Asp Met Asn Glu Thr Thr Ile His Arg Ala Gly Glu Val Leu Glu Asn
                805                 810                 815

Lys Asn Pro Asp Asn Pro Lys Lys Arg Gln Phe Val Tyr Asp Ile Ile
            820                 825                 830

Lys Asp Lys Arg Tyr Thr Gln Asp Lys Phe Met Leu His Val Pro Ile
        835                 840                 845

Thr Met Asn Phe Gly Val Gln Gly Met Thr Ile Lys Glu Phe Asn Lys
    850                 855                 860

Lys Val Asn Gln Ser Ile Gln Gln Tyr Asp Glu Val Asn Val Ile Gly
865                 870                 875                 880

Ile Asp Arg Gly Glu Arg His Leu Leu Tyr Leu Thr Val Ile Asn Ser
                885                 890                 895

Lys Gly Glu Ile Leu Glu Gln Arg Ser Leu Asn Asp Ile Thr Thr Ala
            900                 905                 910

Ser Ala Asn Gly Thr Gln Met Thr Thr Pro Tyr His Lys Ile Leu Asp
        915                 920                 925

Lys Arg Glu Ile Glu Arg Leu Asn Ala Arg Val Gly Trp Gly Glu Ile
    930                 935                 940

Glu Thr Ile Lys Glu Leu Lys Ser Gly Tyr Leu Ser His Val Val His
945                 950                 955                 960

Gln Ile Ser Gln Leu Met Leu Lys Tyr Asn Ala Ile Val Val Leu Glu
                965                 970                 975

Asp Leu Asn Val Glu Lys Gln Ile Tyr Gln Asn Phe Glu Asn Ala Leu
            980                 985                 990

Ile Lys Lys Leu Asn His Leu Val  Leu Lys Asp Lys Ala  Asp Asp Glu
        995                 1000                 1005

Ile Gly  Ser Tyr Lys Asn Ala  Leu Gln Leu Thr Asn  Asn Phe Thr
    1010                 1015                 1020

Asp Leu  Lys Ser Ile Gly Lys  Gln Thr Gly Phe Leu  Phe Tyr Val
    1025                 1030                 1035

Pro Ala  Trp Asn Thr Ser Lys  Ile Asp Pro Glu Thr  Gly Phe Val
    1040                 1045                 1050

Asp Leu  Leu Lys Pro Arg Tyr  Glu Asn Ile Ala Gln  Ser Gln Ala
    1055                 1060                 1065

Phe Phe  Gly Lys Phe Asp Lys  Ile Cys Tyr Asn Ala  Asp Arg Gly
    1070                 1075                 1080

Tyr Phe  Glu Phe His Ile Asp  Tyr Ala Lys Phe Asn  Asp Lys Ala
    1085                 1090                 1095

Lys Asn  Ser Arg Gln Ile Trp  Lys Ile Cys Ser His  Gly Asp Lys
    1100                 1105                 1110

Arg Tyr  Val Tyr Asp Lys Thr  Ala Asn Gln Asn Lys  Gly Ala Thr
    1115                 1120                 1125

Ile Gly  Val Asn Val Asn Asp  Glu Leu Lys Ser Leu  Phe Thr Arg
    1130                 1135                 1140

Tyr His  Ile Asn Asp Lys Gln  Pro Asn Leu Val Met  Asp Ile Cys
```

```
    1145                1150                1155

Gln Asn  Asn Asp Lys Glu Phe  His Lys Ser Leu Met  Tyr Leu Leu
    1160                1165                1170

Lys Thr  Leu Leu Ala Leu Arg  Tyr Ser Asn Ala Ser  Ser Asp Glu
    1175                1180                1185

Asp Phe  Ile Leu Ser Pro Val  Ala Asn Asp Glu Gly  Val Phe Phe
    1190                1195                1200

Asn Ser  Ala Leu Ala Asp Asp  Thr Gln Pro Gln Asn  Ala Asp Ala
    1205                1210                1215

Asn Gly  Ala Tyr His Ile Ala  Leu Lys Gly Leu Trp  Leu Leu Asn
    1220                1225                1230

Glu Leu  Lys Asn Ser Asp Asp  Leu Asn Lys Val Lys  Leu Ala Ile
    1235                1240                1245

Asp Asn  Gln Thr Trp Leu Asn  Phe Ala Gln Asn Arg
    1250                1255                1260


<210> SEQ ID NO 22
<211> LENGTH: 1306
<212> TYPE: PRT
<213> ORGANISM: Thiomicrospira sp.

<400> SEQUENCE: 22

Met Gly Ile His Gly Val Pro Ala Ala Thr Lys Thr Phe Asp Ser Glu
1               5                   10                  15

Phe Phe Asn Leu Tyr Ser Leu Gln Lys Thr Val Arg Phe Glu Leu Lys
            20                  25                  30

Pro Val Gly Glu Thr Ala Ser Phe Val Glu Asp Phe Lys Asn Glu Gly
        35                  40                  45

Leu Lys Arg Val Val Ser Glu Asp Glu Arg Arg Ala Val Asp Tyr Gln
    50                  55                  60

Lys Val Lys Glu Ile Ile Asp Asp Tyr His Arg Asp Phe Ile Glu Glu
65                  70                  75                  80

Ser Leu Asn Tyr Phe Pro Glu Gln Val Ser Lys Asp Ala Leu Glu Gln
                85                  90                  95

Ala Phe His Leu Tyr Gln Lys Leu Lys Ala Ala Lys Val Glu Glu Arg
            100                 105                 110

Glu Lys Ala Leu Lys Glu Trp Glu Ala Leu Gln Lys Lys Leu Arg Glu
        115                 120                 125

Lys Val Val Lys Cys Phe Ser Asp Ser Asn Lys Ala Arg Phe Ser Arg
    130                 135                 140

Ile Asp Lys Lys Glu Leu Ile Lys Glu Asp Leu Ile Asn Trp Leu Val
145                 150                 155                 160

Ala Gln Asn Arg Glu Asp Asp Ile Pro Thr Val Glu Thr Phe Asn Asn
                165                 170                 175

Phe Thr Thr Tyr Phe Thr Gly Phe His Glu Asn Arg Lys Asn Ile Tyr
            180                 185                 190

Ser Lys Asp Asp His Ala Thr Ala Ile Ser Phe Arg Leu Ile His Glu
        195                 200                 205

Asn Leu Pro Lys Phe Phe Asp Asn Val Ile Ser Phe Asn Lys Leu Lys
    210                 215                 220

Glu Gly Phe Pro Glu Leu Lys Phe Asp Lys Val Lys Glu Asp Leu Glu
225                 230                 235                 240

Val Asp Tyr Asp Leu Lys His Ala Phe Glu Ile Glu Tyr Phe Val Asn
                245                 250                 255
```

```
Phe Val Thr Gln Ala Gly Ile Asp Gln Tyr Asn Tyr Leu Leu Gly Gly
            260                 265                 270

Lys Thr Leu Glu Asp Gly Thr Lys Lys Gln Gly Met Asn Glu Gln Ile
        275                 280                 285

Asn Leu Phe Lys Gln Gln Gln Thr Arg Asp Lys Ala Arg Gln Ile Pro
    290                 295                 300

Lys Leu Ile Pro Leu Phe Lys Gln Ile Leu Ser Glu Arg Thr Glu Ser
305                 310                 315                 320

Gln Ser Phe Ile Pro Lys Gln Phe Glu Ser Asp Gln Glu Leu Phe Asp
                325                 330                 335

Ser Leu Gln Lys Leu His Asn Asn Cys Gln Asp Lys Phe Thr Val Leu
            340                 345                 350

Gln Gln Ala Ile Leu Gly Leu Ala Glu Ala Asp Leu Lys Lys Val Phe
        355                 360                 365

Ile Lys Thr Ser Asp Leu Asn Ala Leu Ser Asn Thr Ile Phe Gly Asn
    370                 375                 380

Tyr Ser Val Phe Ser Asp Ala Leu Asn Leu Tyr Lys Glu Ser Leu Lys
385                 390                 395                 400

Thr Lys Lys Ala Gln Glu Ala Phe Glu Lys Leu Pro Ala His Ser Ile
                405                 410                 415

His Asp Leu Ile Gln Tyr Leu Glu Gln Phe Asn Ser Ser Leu Asp Ala
            420                 425                 430

Glu Lys Gln Gln Ser Thr Asp Thr Val Leu Asn Tyr Phe Ile Lys Thr
        435                 440                 445

Asp Glu Leu Tyr Ser Arg Phe Ile Lys Ser Thr Ser Glu Ala Phe Thr
    450                 455                 460

Gln Val Gln Pro Leu Phe Glu Leu Glu Ala Leu Ser Ser Lys Arg Arg
465                 470                 475                 480

Pro Pro Glu Ser Glu Asp Glu Gly Ala Lys Gly Gln Glu Gly Phe Glu
                485                 490                 495

Gln Ile Lys Arg Ile Lys Ala Tyr Leu Asp Thr Leu Met Glu Ala Val
            500                 505                 510

His Phe Ala Lys Pro Leu Tyr Leu Val Lys Gly Arg Lys Met Ile Glu
        515                 520                 525

Gly Leu Asp Lys Asp Gln Ser Phe Tyr Glu Ala Phe Glu Met Ala Tyr
    530                 535                 540

Gln Glu Leu Glu Ser Leu Ile Ile Pro Ile Tyr Asn Lys Ala Arg Ser
545                 550                 555                 560

Tyr Leu Ser Arg Lys Pro Phe Lys Ala Asp Lys Phe Lys Ile Asn Phe
                565                 570                 575

Asp Asn Asn Thr Leu Leu Ser Gly Trp Asp Ala Asn Lys Glu Thr Ala
            580                 585                 590

Asn Ala Ser Ile Leu Phe Lys Lys Asp Gly Leu Tyr Tyr Leu Gly Ile
        595                 600                 605

Met Pro Lys Gly Lys Thr Phe Leu Phe Asp Tyr Phe Val Ser Ser Glu
    610                 615                 620

Asp Ser Glu Lys Leu Lys Gln Arg Arg Gln Lys Thr Ala Glu Glu Ala
625                 630                 635                 640

Leu Ala Gln Asp Gly Glu Ser Tyr Phe Glu Lys Ile Arg Tyr Lys Leu
                645                 650                 655

Leu Pro Gly Ala Ser Lys Met Leu Pro Lys Val Phe Phe Ser Asn Lys
            660                 665                 670

Asn Ile Gly Phe Tyr Asn Pro Ser Asp Asp Ile Leu Arg Ile Arg Asn
```

```
        675                 680                 685

Thr Ala Ser His Thr Lys Asn Gly Thr Pro Gln Lys Gly His Ser Lys
    690                 695                 700

Val Glu Phe Asn Leu Asn Asp Cys His Lys Met Ile Asp Phe Phe Lys
705                 710                 715                 720

Ser Ser Ile Gln Lys His Pro Glu Trp Gly Ser Phe Gly Phe Thr Phe
                725                 730                 735

Ser Asp Thr Ser Asp Phe Glu Asp Met Ser Ala Phe Tyr Arg Glu Val
            740                 745                 750

Glu Asn Gln Gly Tyr Val Ile Ser Phe Asp Lys Ile Lys Glu Thr Tyr
        755                 760                 765

Ile Gln Ser Gln Val Glu Gln Gly Asn Leu Tyr Leu Phe Gln Ile Tyr
    770                 775                 780

Asn Lys Asp Phe Ser Pro Tyr Ser Lys Gly Lys Pro Asn Leu His Thr
785                 790                 795                 800

Leu Tyr Trp Lys Ala Leu Phe Glu Glu Ala Asn Leu Asn Asn Val Val
                805                 810                 815

Ala Lys Leu Asn Gly Glu Ala Glu Ile Phe Phe Arg Arg His Ser Ile
            820                 825                 830

Lys Ala Ser Asp Lys Val Val His Pro Ala Asn Gln Ala Ile Asp Asn
        835                 840                 845

Lys Asn Pro His Thr Glu Lys Thr Gln Ser Thr Phe Glu Tyr Asp Leu
    850                 855                 860

Val Lys Asp Lys Arg Tyr Thr Gln Asp Lys Phe Phe Phe His Val Pro
865                 870                 875                 880

Ile Ser Leu Asn Phe Lys Ala Gln Gly Val Ser Lys Phe Asn Asp Lys
                885                 890                 895

Val Asn Gly Phe Leu Lys Gly Asn Pro Asp Val Asn Ile Ile Gly Ile
            900                 905                 910

Asp Arg Gly Glu Arg His Leu Leu Tyr Phe Thr Val Val Asn Gln Lys
        915                 920                 925

Gly Glu Ile Leu Val Gln Glu Ser Leu Asn Thr Leu Met Ser Asp Lys
    930                 935                 940

Gly His Val Asn Asp Tyr Gln Gln Lys Leu Asp Lys Lys Glu Gln Glu
945                 950                 955                 960

Arg Asp Ala Ala Arg Lys Ser Trp Thr Thr Val Glu Asn Ile Lys Glu
                965                 970                 975

Leu Lys Glu Gly Tyr Leu Ser His Val Val His Lys Leu Ala His Leu
            980                 985                 990

Ile Ile Lys Tyr Asn Ala Ile Val  Cys Leu Glu Asp Leu  Asn Phe Gly
        995                 1000                1005

Phe Lys  Arg Gly Arg Phe Lys  Val Glu Lys Gln Val  Tyr Gln Lys
    1010                1015                1020

Phe Glu  Lys Ala Leu Ile Asp  Lys Leu Asn Tyr Leu  Val Phe Lys
    1025                1030                1035

Glu Lys  Glu Leu Gly Glu Val  Gly His Tyr Leu Thr  Ala Tyr Gln
    1040                1045                1050

Leu Thr  Ala Pro Phe Glu Ser  Phe Lys Lys Leu Gly  Lys Gln Ser
    1055                1060                1065

Gly Ile  Leu Phe Tyr Val Pro  Ala Asp Tyr Thr Ser  Lys Ile Asp
    1070                1075                1080

Pro Thr  Thr Gly Phe Val Asn  Phe Leu Asp Leu Arg  Tyr Gln Ser
    1085                1090                1095
```

```
Val Glu  Lys Ala Lys Gln Leu  Leu Ser Asp Phe Asn  Ala Ile Arg
    1100                 1105                 1110

Phe Asn  Ser Val Gln Asn Tyr  Phe Glu Phe Glu Ile  Asp Tyr Lys
    1115                 1120                 1125

Lys Leu  Thr Pro Lys Arg Lys  Val Gly Thr Gln Ser  Lys Trp Val
    1130                 1135                 1140

Ile Cys  Thr Tyr Gly Asp Val  Arg Tyr Gln Asn Arg  Arg Asn Gln
    1145                 1150                 1155

Lys Gly  His Trp Glu Thr Glu  Glu Val Asn Val Thr  Glu Lys Leu
    1160                 1165                 1170

Lys Ala  Leu Phe Ala Ser Asp  Ser Lys Thr Thr Thr  Val Ile Asp
    1175                 1180                 1185

Tyr Ala  Asn Asp Asp Asn Leu  Ile Asp Val Ile Leu  Glu Gln Asp
    1190                 1195                 1200

Lys Ala  Ser Phe Phe Lys Glu  Leu Leu Trp Leu Leu  Lys Leu Thr
    1205                 1210                 1215

Met Thr  Leu Arg His Ser Lys  Ile Lys Ser Glu Asp  Asp Phe Ile
    1220                 1225                 1230

Leu Ser  Pro Val Lys Asn Glu  Gln Gly Glu Phe Tyr  Asp Ser Arg
    1235                 1240                 1245

Lys Ala  Gly Glu Val Trp Pro  Lys Asp Ala Asp Ala  Asn Gly Ala
    1250                 1255                 1260

Tyr His  Ile Ala Leu Lys Gly  Leu Trp Asn Leu Gln  Gln Ile Asn
    1265                 1270                 1275

Gln Trp  Glu Lys Gly Lys Thr  Leu Asn Leu Ala Ile  Lys Asn Gln
    1280                 1285                 1290

Asp Trp  Phe Ser Phe Ile Gln  Glu Lys Pro Tyr Gln  Glu
    1295                 1300                 1305
```

<210> SEQ ID NO 23
<211> LENGTH: 1297
<212> TYPE: PRT
<213> ORGANISM: Thiomicrospira sp.

<400> SEQUENCE: 23

```
Met Gly Ile His Gly Val Pro Ala Ala Thr Lys Thr Phe Asp Ser Glu
1               5                   10                  15

Phe Phe Asn Leu Tyr Ser Leu Gln Lys Thr Val Arg Phe Glu Leu Lys
            20                  25                  30

Pro Val Gly Glu Thr Ala Ser Phe Val Glu Asp Phe Lys Asn Glu Gly
        35                  40                  45

Leu Lys Arg Val Val Ser Glu Asp Glu Arg Arg Ala Val Asp Tyr Gln
    50                  55                  60

Lys Val Lys Glu Ile Ile Asp Asp Tyr His Arg Asp Phe Ile Glu Glu
65                  70                  75                  80

Ser Leu Asn Tyr Phe Pro Glu Gln Val Ser Lys Asp Ala Leu Glu Gln
                85                  90                  95

Ala Phe His Leu Tyr Gln Lys Leu Lys Ala Ala Lys Val Glu Glu Arg
            100                 105                 110

Glu Lys Ala Leu Lys Glu Trp Glu Ala Leu Gln Lys Lys Leu Arg Glu
        115                 120                 125

Lys Val Val Lys Cys Phe Ser Asp Ser Asn Lys Ala Arg Phe Ser Arg
    130                 135                 140

Ile Asp Lys Lys Glu Leu Ile Lys Glu Asp Leu Ile Asn Trp Leu Val
```

```
145                 150                 155                 160

Ala Gln Asn Arg Glu Asp Asp Ile Pro Thr Val Glu Thr Phe Asn Asn
                165                 170                 175

Phe Thr Thr Tyr Phe Thr Gly Phe His Glu Asn Arg Lys Asn Ile Tyr
            180                 185                 190

Ser Lys Asp Asp His Ala Thr Ala Ile Ser Phe Arg Leu Ile His Glu
        195                 200                 205

Asn Leu Pro Lys Phe Phe Asp Asn Val Ile Ser Phe Asn Lys Leu Lys
    210                 215                 220

Glu Gly Phe Pro Glu Leu Lys Phe Asp Lys Val Lys Glu Asp Leu Glu
225                 230                 235                 240

Val Asp Tyr Asp Leu Lys His Ala Phe Glu Ile Glu Tyr Phe Val Asn
                245                 250                 255

Phe Val Thr Gln Ala Gly Ile Asp Gln Tyr Asn Tyr Leu Leu Gly Gly
            260                 265                 270

Lys Thr Leu Glu Asp Gly Thr Lys Lys Gln Gly Met Asn Glu Gln Ile
        275                 280                 285

Asn Leu Phe Lys Gln Gln Gln Thr Arg Asp Lys Ala Arg Gln Ile Pro
    290                 295                 300

Lys Leu Ile Pro Leu Phe Lys Gln Ile Leu Ser Glu Arg Thr Glu Ser
305                 310                 315                 320

Gln Ser Phe Ile Pro Lys Gln Phe Glu Ser Asp Gln Glu Leu Phe Asp
                325                 330                 335

Ser Leu Gln Lys Leu His Asn Asn Cys Gln Asp Lys Phe Thr Val Leu
            340                 345                 350

Gln Gln Ala Ile Leu Gly Leu Ala Glu Ala Asp Leu Lys Lys Val Phe
        355                 360                 365

Ile Lys Thr Ser Asp Leu Asn Ala Leu Ser Asn Thr Ile Phe Gly Asn
    370                 375                 380

Tyr Ser Val Phe Ser Asp Ala Leu Asn Leu Tyr Lys Glu Ser Leu Lys
385                 390                 395                 400

Thr Lys Lys Ala Gln Glu Ala Phe Glu Lys Leu Pro Ala His Ser Ile
                405                 410                 415

His Asp Leu Ile Gln Tyr Leu Glu Gln Phe Asn Ser Ser Leu Asp Ala
            420                 425                 430

Glu Lys Gln Gln Ser Thr Asp Thr Val Leu Asn Tyr Phe Ile Lys Thr
        435                 440                 445

Asp Glu Leu Tyr Ser Arg Phe Ile Lys Ser Thr Ser Glu Ala Phe Thr
    450                 455                 460

Gln Val Gln Pro Leu Phe Glu Leu Glu Ala Leu Ser Ser Lys Arg Arg
465                 470                 475                 480

Pro Pro Glu Ser Glu Asp Glu Gly Ala Lys Gly Gln Glu Gly Phe Glu
                485                 490                 495

Gln Ile Lys Arg Ile Lys Ala Tyr Leu Asp Thr Leu Met Glu Ala Val
            500                 505                 510

His Phe Ala Lys Pro Leu Tyr Leu Val Lys Gly Arg Lys Met Ile Glu
        515                 520                 525

Gly Leu Asp Lys Asp Gln Ser Phe Tyr Glu Ala Phe Glu Met Ala Tyr
    530                 535                 540

Gln Glu Leu Glu Ser Leu Ile Ile Pro Ile Tyr Asn Lys Ala Arg Ser
545                 550                 555                 560

Tyr Leu Ser Arg Lys Pro Phe Lys Ala Asp Lys Phe Lys Ile Asn Phe
                565                 570                 575
```

```
Asp Asn Asn Thr Leu Leu Ser Gly Trp Asp Ala Asn Lys Glu Thr Ala
            580                 585                 590

Asn Ala Ser Ile Leu Phe Lys Lys Asp Gly Leu Tyr Tyr Leu Gly Ile
        595                 600                 605

Met Pro Lys Gly Lys Thr Phe Leu Phe Asp Tyr Phe Val Ser Ser Glu
    610                 615                 620

Asp Ser Glu Lys Leu Lys Gln Arg Arg Gln Lys Thr Ala Glu Glu Ala
625                 630                 635                 640

Leu Ala Gln Asp Gly Glu Ser Tyr Phe Glu Lys Ile Arg Tyr Lys Leu
                645                 650                 655

Leu Pro Gly Ala Ser Lys Met Leu Pro Lys Val Phe Phe Ser Asn Lys
            660                 665                 670

Asn Ile Gly Phe Tyr Asn Pro Ser Asp Asp Ile Leu Arg Ile Arg Asn
        675                 680                 685

Thr Ala Ser His Thr Lys Asn Gly Thr Pro Gln Lys Gly His Ser Lys
    690                 695                 700

Val Glu Phe Asn Leu Asn Asp Cys His Lys Met Ile Asp Phe Phe Lys
705                 710                 715                 720

Ser Ser Ile Gln Lys His Pro Glu Trp Gly Ser Phe Gly Phe Thr Phe
                725                 730                 735

Ser Asp Thr Ser Asp Phe Glu Asp Met Ser Ala Phe Tyr Arg Glu Val
            740                 745                 750

Glu Asn Gln Gly Tyr Val Ile Ser Phe Asp Lys Ile Lys Glu Thr Tyr
        755                 760                 765

Ile Gln Ser Gln Val Glu Gln Gly Asn Leu Tyr Leu Phe Gln Ile Tyr
    770                 775                 780

Asn Lys Asp Phe Ser Pro Tyr Ser Lys Gly Lys Pro Asn Leu His Thr
785                 790                 795                 800

Leu Tyr Trp Lys Ala Leu Phe Glu Glu Ala Asn Leu Asn Asn Val Val
                805                 810                 815

Ala Lys Leu Asn Gly Glu Ala Glu Ile Phe Phe Arg Arg His Ser Ile
            820                 825                 830

Lys Ala Ser Asp Lys Val Val His Pro Ala Asn Gln Ala Ile Asp Asn
        835                 840                 845

Lys Asn Pro His Thr Glu Lys Thr Gln Ser Thr Phe Glu Tyr Asp Leu
    850                 855                 860

Val Lys Asp Lys Arg Tyr Thr Gln Asp Lys Phe Phe Phe His Val Pro
865                 870                 875                 880

Ile Ser Leu Asn Phe Lys Ala Gln Gly Val Ser Lys Phe Asn Asp Lys
                885                 890                 895

Val Asn Gly Phe Leu Lys Gly Asn Pro Asp Val Asn Ile Ile Gly Ile
            900                 905                 910

Asp Arg Gly Glu Arg His Leu Leu Tyr Phe Thr Val Val Asn Gln Lys
        915                 920                 925

Gly Glu Ile Leu Val Gln Glu Ser Leu Asn Thr Leu Met Ser Asp Lys
    930                 935                 940

Gly His Val Asn Asp Tyr Gln Gln Lys Leu Asp Lys Lys Glu Gln Glu
945                 950                 955                 960

Arg Asp Ala Ala Arg Lys Ser Trp Thr Thr Val Glu Asn Ile Lys Glu
                965                 970                 975

Leu Lys Glu Gly Tyr Leu Ser His Val Val His Lys Leu Ala His Leu
            980                 985                 990
```

Ile Ile Lys Tyr Asn Ala Ile Val Cys Leu Glu Asp Leu Asn Val Glu
995 1000 1005

Lys Gln Val Tyr Gln Lys Phe Glu Lys Ala Leu Ile Asp Lys Leu
1010 1015 1020

Asn Tyr Leu Val Phe Lys Glu Lys Glu Leu Gly Glu Val Gly His
1025 1030 1035

Tyr Leu Thr Ala Tyr Gln Leu Thr Ala Pro Phe Glu Ser Phe Lys
1040 1045 1050

Lys Leu Gly Lys Gln Ser Gly Ile Leu Phe Tyr Val Pro Ala Asp
1055 1060 1065

Tyr Thr Ser Lys Ile Asp Pro Thr Thr Gly Phe Val Asn Phe Leu
1070 1075 1080

Asp Leu Arg Tyr Gln Ser Val Glu Lys Ala Lys Gln Leu Leu Ser
1085 1090 1095

Asp Phe Asn Ala Ile Arg Phe Asn Ser Val Gln Asn Tyr Phe Glu
1100 1105 1110

Phe Glu Ile Asp Tyr Lys Lys Leu Thr Pro Lys Arg Lys Val Gly
1115 1120 1125

Thr Gln Ser Lys Trp Val Ile Cys Thr Tyr Gly Asp Val Arg Tyr
1130 1135 1140

Gln Asn Arg Arg Asn Gln Lys Gly His Trp Glu Thr Glu Glu Val
1145 1150 1155

Asn Val Thr Glu Lys Leu Lys Ala Leu Phe Ala Ser Asp Ser Lys
1160 1165 1170

Thr Thr Thr Val Ile Asp Tyr Ala Asn Asp Asp Asn Leu Ile Asp
1175 1180 1185

Val Ile Leu Glu Gln Asp Lys Ala Ser Phe Phe Lys Glu Leu Leu
1190 1195 1200

Trp Leu Leu Lys Leu Thr Met Thr Leu Arg His Ser Lys Ile Lys
1205 1210 1215

Ser Glu Asp Asp Phe Ile Leu Ser Pro Val Lys Asn Glu Gln Gly
1220 1225 1230

Glu Phe Tyr Asp Ser Arg Lys Ala Gly Glu Val Trp Pro Lys Asp
1235 1240 1245

Ala Asp Ala Asn Gly Ala Tyr His Ile Ala Leu Lys Gly Leu Trp
1250 1255 1260

Asn Leu Gln Gln Ile Asn Gln Trp Glu Lys Gly Lys Thr Leu Asn
1265 1270 1275

Leu Ala Ile Lys Asn Gln Asp Trp Phe Ser Phe Ile Gln Glu Lys
1280 1285 1290

Pro Tyr Gln Glu
1295

<210> SEQ ID NO 24
<211> LENGTH: 1214
<212> TYPE: PRT
<213> ORGANISM: Butyrivibrio sp.

<400> SEQUENCE: 24

Met Gly Ile His Gly Val Pro Ala Ala Tyr Tyr Gln Asn Leu Thr Lys
1 5 10 15

Lys Tyr Pro Val Ser Lys Thr Ile Arg Asn Glu Leu Ile Pro Ile Gly
20 25 30

Lys Thr Leu Glu Asn Ile Arg Lys Asn Asn Ile Leu Glu Ser Asp Val
35 40 45

```
Lys Arg Lys Gln Asp Tyr Glu His Val Lys Gly Ile Met Asp Glu Tyr
    50                  55                  60

His Lys Gln Leu Ile Asn Glu Ala Leu Asp Asn Tyr Met Leu Pro Ser
65                  70                  75                  80

Leu Asn Gln Ala Ala Glu Ile Tyr Leu Lys Lys His Val Asp Val Glu
                85                  90                  95

Asp Arg Glu Glu Phe Lys Lys Thr Gln Asp Leu Leu Arg Arg Glu Val
            100                 105                 110

Thr Gly Arg Leu Lys Glu His Glu Asn Tyr Thr Lys Ile Gly Lys Lys
        115                 120                 125

Asp Ile Leu Asp Leu Leu Glu Lys Leu Pro Ser Ile Ser Glu Glu Asp
    130                 135                 140

Tyr Asn Ala Leu Glu Ser Phe Arg Asn Phe Tyr Thr Tyr Phe Thr Ser
145                 150                 155                 160

Tyr Asn Lys Val Arg Glu Asn Leu Tyr Ser Asp Glu Glu Lys Ser Ser
                165                 170                 175

Thr Val Ala Tyr Arg Leu Ile Asn Glu Asn Leu Pro Lys Phe Leu Asp
            180                 185                 190

Asn Ile Lys Ser Tyr Ala Phe Val Lys Ala Ala Gly Val Leu Ala Asp
        195                 200                 205

Cys Ile Glu Glu Glu Glu Gln Asp Ala Leu Phe Met Val Glu Thr Phe
    210                 215                 220

Asn Met Thr Leu Thr Gln Glu Gly Ile Asp Met Tyr Asn Tyr Gln Ile
225                 230                 235                 240

Gly Lys Val Asn Ser Ala Ile Asn Leu Tyr Asn Gln Lys Asn His Lys
                245                 250                 255

Val Glu Glu Phe Lys Lys Ile Pro Lys Met Lys Val Leu Tyr Lys Gln
            260                 265                 270

Ile Leu Ser Asp Arg Glu Glu Val Phe Ile Gly Glu Phe Lys Asp Asp
        275                 280                 285

Glu Thr Leu Leu Ser Ser Ile Gly Ala Tyr Gly Asn Val Leu Met Thr
    290                 295                 300

Tyr Leu Lys Ser Glu Lys Ile Asn Ile Phe Phe Asp Ala Leu Arg Glu
305                 310                 315                 320

Ser Glu Gly Lys Asn Val Tyr Val Lys Asn Asp Leu Ser Lys Thr Thr
                325                 330                 335

Met Ser Asn Ile Val Phe Gly Ser Trp Ser Ala Phe Asp Glu Leu Leu
            340                 345                 350

Asn Gln Glu Tyr Asp Leu Ala Asn Glu Asn Lys Lys Lys Asp Asp Lys
        355                 360                 365

Tyr Phe Glu Lys Arg Gln Lys Glu Leu Lys Lys Asn Lys Ser Tyr Thr
    370                 375                 380

Leu Glu Gln Met Ser Asn Leu Ser Lys Glu Asp Ile Ser Pro Ile Glu
385                 390                 395                 400

Asn Tyr Ile Glu Arg Ile Ser Glu Asp Ile Glu Lys Ile Cys Ile Tyr
                405                 410                 415

Asn Gly Glu Phe Glu Lys Ile Val Val Asn Glu His Asp Ser Ser Arg
            420                 425                 430

Lys Leu Ser Lys Asn Ile Lys Ala Val Lys Val Ile Lys Asp Tyr Leu
        435                 440                 445

Asp Ser Ile Lys Glu Leu Glu His Asp Ile Lys Leu Ile Asn Gly Ser
    450                 455                 460
```

```
Gly Gln Glu Leu Glu Lys Asn Leu Val Val Tyr Val Gly Gln Glu Glu
465                 470                 475                 480

Ala Leu Glu Gln Leu Arg Pro Val Asp Ser Leu Tyr Asn Leu Thr Arg
                485                 490                 495

Asn Tyr Leu Thr Lys Lys Pro Phe Ser Thr Glu Lys Val Lys Leu Asn
            500                 505                 510

Phe Asn Lys Ser Thr Leu Leu Asn Gly Trp Asp Lys Asn Lys Glu Thr
        515                 520                 525

Asp Asn Leu Gly Ile Leu Phe Phe Lys Asp Gly Lys Tyr Tyr Leu Gly
    530                 535                 540

Ile Met Asn Thr Thr Ala Asn Lys Ala Phe Val Asn Pro Pro Ala Ala
545                 550                 555                 560

Lys Thr Glu Asn Val Phe Lys Lys Val Asp Tyr Lys Leu Leu Pro Gly
                565                 570                 575

Ser Asn Lys Met Leu Pro Lys Val Phe Phe Ala Lys Ser Asn Ile Gly
            580                 585                 590

Tyr Tyr Asn Pro Ser Thr Glu Leu Tyr Ser Asn Tyr Lys Lys Gly Thr
        595                 600                 605

His Lys Lys Gly Pro Ser Phe Ser Ile Asp Asp Cys His Asn Leu Ile
    610                 615                 620

Asp Phe Phe Lys Glu Ser Ile Lys Lys His Glu Asp Trp Ser Lys Phe
625                 630                 635                 640

Gly Phe Glu Phe Ser Asp Thr Ala Asp Tyr Arg Asp Ile Ser Glu Phe
                645                 650                 655

Tyr Arg Glu Val Glu Lys Gln Gly Tyr Lys Leu Thr Phe Thr Asp Ile
            660                 665                 670

Asp Glu Ser Tyr Ile Asn Asp Leu Ile Glu Lys Asn Glu Leu Tyr Leu
        675                 680                 685

Phe Gln Ile Tyr Asn Lys Asp Phe Ser Glu Tyr Ser Lys Gly Lys Leu
    690                 695                 700

Asn Leu His Thr Leu Tyr Phe Met Met Leu Phe Asp Gln Arg Asn Leu
705                 710                 715                 720

Asp Asn Val Val Tyr Lys Leu Asn Gly Glu Ala Glu Val Phe Tyr Arg
                725                 730                 735

Pro Ala Ser Ile Ala Glu Asn Glu Leu Val Ile His Lys Ala Gly Glu
            740                 745                 750

Gly Ile Lys Asn Lys Asn Pro Asn Arg Ala Lys Val Lys Glu Thr Ser
        755                 760                 765

Thr Phe Ser Tyr Asp Ile Val Lys Asp Lys Arg Tyr Ser Lys Tyr Lys
    770                 775                 780

Phe Thr Leu His Ile Pro Ile Thr Met Asn Phe Gly Val Asp Glu Val
785                 790                 795                 800

Arg Arg Phe Asn Asp Val Ile Asn Asn Ala Leu Arg Thr Asp Asp Asn
                805                 810                 815

Val Asn Val Ile Gly Ile Asp Arg Gly Glu Arg Asn Leu Leu Tyr Val
            820                 825                 830

Val Val Ile Asn Ser Glu Gly Lys Ile Leu Glu Gln Ile Ser Leu Asn
        835                 840                 845

Ser Ile Ile Asn Lys Glu Tyr Asp Ile Glu Thr Asn Tyr His Ala Leu
    850                 855                 860

Leu Asp Glu Arg Glu Asp Asp Arg Asn Lys Ala Arg Lys Asp Trp Asn
865                 870                 875                 880

Thr Ile Glu Asn Ile Lys Glu Leu Lys Thr Gly Tyr Leu Ser Gln Val
```

```
                885                 890                 895

Val Asn Val Val Ala Lys Leu Val Leu Lys Tyr Asn Ala Ile Ile Cys
            900                 905                 910

Leu Glu Asp Leu Asn Phe Gly Phe Lys Arg Gly Arg Gln Lys Val Glu
        915                 920                 925

Lys Gln Val Tyr Gln Lys Phe Glu Lys Met Leu Ile Glu Lys Leu Asn
    930                 935                 940

Tyr Leu Val Ile Asp Lys Ser Arg Glu Gln Val Ser Pro Glu Lys Met
945                 950                 955                 960

Gly Gly Ala Leu Asn Ala Leu Gln Leu Thr Ser Lys Phe Lys Ser Phe
                965                 970                 975

Ala Glu Leu Gly Lys Gln Ser Gly Ile Ile Tyr Tyr Val Pro Ala Tyr
            980                 985                 990

Leu Thr Ser Lys Ile Asp Pro Thr  Thr Gly Phe Val Asn  Leu Phe Tyr
        995                 1000                1005

Ile Lys  Tyr Glu Asn Ile Glu  Lys Ala Lys Gln Phe  Phe Asp Gly
    1010                1015                1020

Phe Asp  Phe Ile Arg Phe Asn  Lys Lys Asp Asp Met  Phe Glu Phe
    1025                1030                1035

Ser Phe  Asp Tyr Lys Ser Phe  Thr Gln Lys Ala Cys  Gly Ile Arg
    1040                1045                1050

Ser Lys  Trp Ile Val Tyr Thr  Asn Gly Glu Arg Ile  Ile Lys Tyr
    1055                1060                1065

Pro Asn  Pro Glu Lys Asn Asn  Leu Phe Asp Glu Lys  Val Ile Asn
    1070                1075                1080

Val Thr  Asp Glu Ile Lys Gly  Leu Phe Lys Gln Tyr  Arg Ile Pro
    1085                1090                1095

Tyr Glu  Asn Gly Glu Asp Ile  Lys Glu Ile Ile Ile  Ser Lys Ala
    1100                1105                1110

Glu Ala  Asp Phe Tyr Lys Arg  Leu Phe Arg Leu Leu  His Gln Thr
    1115                1120                1125

Leu Gln  Met Arg Asn Ser Thr  Ser Asp Gly Thr Arg  Asp Tyr Ile
    1130                1135                1140

Ile Ser  Pro Val Lys Asn Asp  Arg Gly Glu Phe Phe  Cys Ser Glu
    1145                1150                1155

Phe Ser  Glu Gly Thr Met Pro  Lys Asp Ala Asp Ala  Asn Gly Ala
    1160                1165                1170

Tyr Asn  Ile Ala Arg Lys Gly  Leu Trp Val Leu Glu  Gln Ile Arg
    1175                1180                1185

Gln Lys  Asp Glu Gly Glu Lys  Val Asn Leu Ser Met  Thr Asn Ala
    1190                1195                1200

Glu Trp  Leu Lys Tyr Ala Gln  Leu His Leu Leu
    1205                1210


<210> SEQ ID NO 25
<211> LENGTH: 1205
<212> TYPE: PRT
<213> ORGANISM: Butyrivibrio sp.

<400> SEQUENCE: 25

Met Gly Ile His Gly Val Pro Ala Ala Tyr Tyr Gln Asn Leu Thr Lys
1               5                   10                  15

Lys Tyr Pro Val Ser Lys Thr Ile Arg Asn Glu Leu Ile Pro Ile Gly
            20                  25                  30
```

-continued

```
Lys Thr Leu Glu Asn Ile Arg Lys Asn Asn Ile Leu Glu Ser Asp Val
        35                  40                  45

Lys Arg Lys Gln Asp Tyr Glu His Val Lys Gly Ile Met Asp Glu Tyr
    50                  55                  60

His Lys Gln Leu Ile Asn Glu Ala Leu Asp Asn Tyr Met Leu Pro Ser
65                  70                  75                  80

Leu Asn Gln Ala Ala Glu Ile Tyr Leu Lys Lys His Val Asp Val Glu
                85                  90                  95

Asp Arg Glu Glu Phe Lys Lys Thr Gln Asp Leu Leu Arg Arg Glu Val
            100                 105                 110

Thr Gly Arg Leu Lys Glu His Glu Asn Tyr Thr Lys Ile Gly Lys Lys
        115                 120                 125

Asp Ile Leu Asp Leu Leu Glu Lys Leu Pro Ser Ile Ser Glu Glu Asp
    130                 135                 140

Tyr Asn Ala Leu Glu Ser Phe Arg Asn Phe Tyr Thr Tyr Phe Thr Ser
145                 150                 155                 160

Tyr Asn Lys Val Arg Glu Asn Leu Tyr Ser Asp Glu Glu Lys Ser Ser
                165                 170                 175

Thr Val Ala Tyr Arg Leu Ile Asn Glu Asn Leu Pro Lys Phe Leu Asp
            180                 185                 190

Asn Ile Lys Ser Tyr Ala Phe Val Lys Ala Ala Gly Val Leu Ala Asp
        195                 200                 205

Cys Ile Glu Glu Glu Glu Gln Asp Ala Leu Phe Met Val Glu Thr Phe
    210                 215                 220

Asn Met Thr Leu Thr Gln Glu Gly Ile Asp Met Tyr Asn Tyr Gln Ile
225                 230                 235                 240

Gly Lys Val Asn Ser Ala Ile Asn Leu Tyr Asn Gln Lys Asn His Lys
                245                 250                 255

Val Glu Glu Phe Lys Lys Ile Pro Lys Met Lys Val Leu Tyr Lys Gln
            260                 265                 270

Ile Leu Ser Asp Arg Glu Glu Val Phe Ile Gly Glu Phe Lys Asp Asp
        275                 280                 285

Glu Thr Leu Leu Ser Ser Ile Gly Ala Tyr Gly Asn Val Leu Met Thr
    290                 295                 300

Tyr Leu Lys Ser Glu Lys Ile Asn Ile Phe Phe Asp Ala Leu Arg Glu
305                 310                 315                 320

Ser Glu Gly Lys Asn Val Tyr Val Lys Asn Asp Leu Ser Lys Thr Thr
                325                 330                 335

Met Ser Asn Ile Val Phe Gly Ser Trp Ser Ala Phe Asp Glu Leu Leu
            340                 345                 350

Asn Gln Glu Tyr Asp Leu Ala Asn Glu Asn Lys Lys Lys Asp Asp Lys
        355                 360                 365

Tyr Phe Glu Lys Arg Gln Lys Glu Leu Lys Lys Asn Lys Ser Tyr Thr
    370                 375                 380

Leu Glu Gln Met Ser Asn Leu Ser Lys Glu Asp Ile Ser Pro Ile Glu
385                 390                 395                 400

Asn Tyr Ile Glu Arg Ile Ser Glu Asp Ile Glu Lys Ile Cys Ile Tyr
                405                 410                 415

Asn Gly Glu Phe Glu Lys Ile Val Val Asn Glu His Asp Ser Ser Arg
            420                 425                 430

Lys Leu Ser Lys Asn Ile Lys Ala Val Lys Val Ile Lys Asp Tyr Leu
        435                 440                 445

Asp Ser Ile Lys Glu Leu Glu His Asp Ile Lys Leu Ile Asn Gly Ser
```

-continued

```
    450                 455                 460

Gly Gln Glu Leu Glu Lys Asn Leu Val Val Tyr Val Gly Gln Glu Glu
465                 470                 475                 480

Ala Leu Glu Gln Leu Arg Pro Val Asp Ser Leu Tyr Asn Leu Thr Arg
                485                 490                 495

Asn Tyr Leu Thr Lys Lys Pro Phe Ser Thr Glu Lys Val Lys Leu Asn
            500                 505                 510

Phe Asn Lys Ser Thr Leu Leu Asn Gly Trp Asp Lys Asn Lys Glu Thr
        515                 520                 525

Asp Asn Leu Gly Ile Leu Phe Phe Lys Asp Gly Lys Tyr Tyr Leu Gly
    530                 535                 540

Ile Met Asn Thr Thr Ala Asn Lys Ala Phe Val Asn Pro Pro Ala Ala
545                 550                 555                 560

Lys Thr Glu Asn Val Phe Lys Lys Val Asp Tyr Lys Leu Leu Pro Gly
                565                 570                 575

Ser Asn Lys Met Leu Pro Lys Val Phe Phe Ala Lys Ser Asn Ile Gly
            580                 585                 590

Tyr Tyr Asn Pro Ser Thr Glu Leu Tyr Ser Asn Tyr Lys Lys Gly Thr
        595                 600                 605

His Lys Lys Gly Pro Ser Phe Ser Ile Asp Asp Cys His Asn Leu Ile
    610                 615                 620

Asp Phe Phe Lys Glu Ser Ile Lys Lys His Glu Asp Trp Ser Lys Phe
625                 630                 635                 640

Gly Phe Glu Phe Ser Asp Thr Ala Asp Tyr Arg Asp Ile Ser Glu Phe
                645                 650                 655

Tyr Arg Glu Val Glu Lys Gln Gly Tyr Lys Leu Thr Phe Thr Asp Ile
            660                 665                 670

Asp Glu Ser Tyr Ile Asn Asp Leu Ile Glu Lys Asn Glu Leu Tyr Leu
        675                 680                 685

Phe Gln Ile Tyr Asn Lys Asp Phe Ser Glu Tyr Ser Lys Gly Lys Leu
    690                 695                 700

Asn Leu His Thr Leu Tyr Phe Met Met Leu Phe Asp Gln Arg Asn Leu
705                 710                 715                 720

Asp Asn Val Val Tyr Lys Leu Asn Gly Glu Ala Glu Val Phe Tyr Arg
                725                 730                 735

Pro Ala Ser Ile Ala Glu Asn Glu Leu Val Ile His Lys Ala Gly Glu
            740                 745                 750

Gly Ile Lys Asn Lys Asn Pro Asn Arg Ala Lys Val Lys Glu Thr Ser
        755                 760                 765

Thr Phe Ser Tyr Asp Ile Val Lys Asp Lys Arg Tyr Ser Lys Tyr Lys
    770                 775                 780

Phe Thr Leu His Ile Pro Ile Thr Met Asn Phe Gly Val Asp Glu Val
785                 790                 795                 800

Arg Arg Phe Asn Asp Val Ile Asn Asn Ala Leu Arg Thr Asp Asp Asn
                805                 810                 815

Val Asn Val Ile Gly Ile Asp Arg Gly Glu Arg Asn Leu Leu Tyr Val
            820                 825                 830

Val Val Ile Asn Ser Glu Gly Lys Ile Leu Glu Gln Ile Ser Leu Asn
        835                 840                 845

Ser Ile Ile Asn Lys Glu Tyr Asp Ile Glu Thr Asn Tyr His Ala Leu
    850                 855                 860

Leu Asp Glu Arg Glu Asp Asp Arg Asn Lys Ala Arg Lys Asp Trp Asn
865                 870                 875                 880
```

```
Thr Ile Glu Asn Ile Lys Glu Leu Lys Thr Gly Tyr Leu Ser Gln Val
                885                 890                 895

Val Asn Val Val Ala Lys Leu Val Leu Lys Tyr Asn Ala Ile Ile Cys
            900                 905                 910

Leu Glu Asp Leu Asn Val Glu Lys Gln Val Tyr Gln Lys Phe Glu Lys
        915                 920                 925

Met Leu Ile Glu Lys Leu Asn Tyr Leu Val Ile Asp Lys Ser Arg Glu
    930                 935                 940

Gln Val Ser Pro Glu Lys Met Gly Gly Ala Leu Asn Ala Leu Gln Leu
945                 950                 955                 960

Thr Ser Lys Phe Lys Ser Phe Ala Glu Leu Gly Lys Gln Ser Gly Ile
                965                 970                 975

Ile Tyr Tyr Val Pro Ala Tyr Leu Thr Ser Lys Ile Asp Pro Thr Thr
            980                 985                 990

Gly Phe Val Asn Leu Phe Tyr Ile  Lys Tyr Glu Asn Ile  Glu Lys Ala
        995                 1000                1005

Lys Gln  Phe Phe Asp Gly Phe  Asp Phe Ile Arg Phe  Asn Lys Lys
    1010                1015                1020

Asp Asp  Met Phe Glu Phe Ser  Phe Asp Tyr Lys Ser  Phe Thr Gln
    1025                1030                1035

Lys Ala  Cys Gly Ile Arg Ser  Lys Trp Ile Val Tyr  Thr Asn Gly
    1040                1045                1050

Glu Arg  Ile Ile Lys Tyr Pro  Asn Pro Glu Lys Asn  Asn Leu Phe
    1055                1060                1065

Asp Glu  Lys Val Ile Asn Val  Thr Asp Glu Ile Lys  Gly Leu Phe
    1070                1075                1080

Lys Gln  Tyr Arg Ile Pro Tyr  Glu Asn Gly Glu Asp  Ile Lys Glu
    1085                1090                1095

Ile Ile  Ile Ser Lys Ala Glu  Ala Asp Phe Tyr Lys  Arg Leu Phe
    1100                1105                1110

Arg Leu  Leu His Gln Thr Leu  Gln Met Arg Asn Ser  Thr Ser Asp
    1115                1120                1125

Gly Thr  Arg Asp Tyr Ile Ile  Ser Pro Val Lys Asn  Asp Arg Gly
    1130                1135                1140

Glu Phe  Phe Cys Ser Glu Phe  Ser Glu Gly Thr Met  Pro Lys Asp
    1145                1150                1155

Ala Asp  Ala Asn Gly Ala Tyr  Asn Ile Ala Arg Lys  Gly Leu Trp
    1160                1165                1170

Val Leu  Glu Gln Ile Arg Gln  Lys Asp Glu Gly Glu  Lys Val Asn
    1175                1180                1185

Leu Ser  Met Thr Asn Ala Glu  Trp Leu Lys Tyr Ala  Gln Leu His
    1190                1195                1200

Leu Leu
    1205
```

<210> SEQ ID NO 26
<211> LENGTH: 1296
<212> TYPE: PRT
<213> ORGANISM: Brumimicrobium aurantiacum

<400> SEQUENCE: 26

```
Met Lys Asn Gln Ile Asn Leu Phe Thr Asn Lys Phe Gln Leu Ser Lys
1               5                   10                  15

Thr Leu Arg Phe Glu Leu Lys Pro Gln Gly Lys Thr Leu Glu His Ile
```

```
            20                  25                  30

Asn Ser Lys Gly Phe Ile Lys Asn Asp Glu Lys Arg Ala Asp Ser Tyr
        35                  40                  45

Lys Lys Met Lys Ala Thr Ile Asp Ala Phe His Arg Asp Phe Ile Asp
    50                  55                  60

Leu Ala Met Ser Asn Val Lys Leu Thr Asn Leu Ile Asp Phe Glu Glu
65                  70                  75                  80

Ile Tyr Asn Ala Ser Asn Ala Asp Lys Lys Asp Glu Lys Tyr Lys Thr
                85                  90                  95

Lys Leu Ser Lys Ile Gln Glu Ile Leu Arg Lys Glu Ile Ala Lys Gly
            100                 105                 110

Phe Lys Gly Glu Glu Val Lys Asp Ile Phe Ser Lys Ile Asp Lys Lys
        115                 120                 125

Asp Leu Ile Thr Lys Leu Leu Glu Glu Trp Ile Ile Glu Asn Lys Ile
    130                 135                 140

Glu Asp Ile His Phe Asp Pro Glu Phe Lys Asn Phe Thr Thr Tyr Phe
145                 150                 155                 160

Ser Gly Phe His Gln Asn Arg Lys Asn Met Tyr Thr Asp Gln Glu Gln
                165                 170                 175

Ser Thr Ala Ile Ala Tyr Arg Leu Ile His Glu Asn Leu Pro Arg Phe
            180                 185                 190

Ile Asp Asn Ile Asn Ile Phe Gln Lys Ile Asn Lys Val Pro Asp Leu
        195                 200                 205

Glu Glu Asn Leu Lys Lys Leu Tyr Gln Glu Ile Glu Glu Tyr Leu Gly
    210                 215                 220

Ile Asn Ala Ile Asn Glu Ala Phe Glu Leu Glu Tyr Phe Asn Glu Thr
225                 230                 235                 240

Leu Ser Gln Lys Gly Ile Asp Ile Tyr Asn Leu Ile Leu Gly Gly Arg
                245                 250                 255

Thr Ala Glu Glu Gly Lys Gln Lys Ile Gln Gly Leu Asn Glu Tyr Ile
            260                 265                 270

Asn Leu Tyr Asn Gln Lys Gln Asp Lys Lys Asn Arg Val Pro Lys Leu
        275                 280                 285

Lys Val Leu Tyr Lys Gln Ile Leu Ser Asp Arg Thr Arg Thr Ser Phe
    290                 295                 300

Leu Pro Asp Thr Phe Glu Asp Asp Glu Glu Ser Ser Ala Ser Gln Lys
305                 310                 315                 320

Val Leu Asp Ser Ile Asn Asn Phe Tyr Leu Glu Asn Leu Ile Asp Tyr
                325                 330                 335

Leu Pro Asn Asp Lys Asn Ser Thr Ile Asn Val Leu Glu Asn Leu Lys
            340                 345                 350

Leu Leu Leu Ala Glu Leu Ile Asn Phe Glu Leu Asp Lys Val Tyr Ile
        355                 360                 365

Lys Asn Asp Thr Ser Ile Thr Asn Ile Ser Met Lys Ile Phe Lys Asn
    370                 375                 380

Tyr Ser Val Ile Arg Glu Ala Leu Asn Tyr Phe Tyr Glu Asn Lys Ile
385                 390                 395                 400

Asp Pro Asn Phe Ala His Asn Phe Asn Asn Ala Asn Thr Asp Lys Lys
                405                 410                 415

Arg Glu Lys Leu Glu Lys Glu Lys Ala Lys Ile Thr Lys Gln Thr Tyr
            420                 425                 430

Leu Ser Ile Ser Phe Ile Glu Glu Ala Ile His Leu Tyr Ile Asn Glu
        435                 440                 445
```

```
Asn Ser Asn Gly Asn Gln Tyr Lys Asn Thr Tyr Lys Pro Asn Cys Ile
    450                 455                 460

Ala Asn Tyr Phe Lys Asp Phe Phe Ile Ala Glu Asn Lys Glu Gly Ser
465                 470                 475                 480

Asn Lys Glu Phe Asp Phe Ile Ser Lys Ile Lys Ala Arg Tyr Asn Thr
                485                 490                 495

Ile Lys Gly Val Leu Asn Thr Pro Phe Pro Asp Asn Lys Arg Leu His
            500                 505                 510

Gln Glu Lys Asn Asn Ile Asp Asn Ile Lys His Phe Leu Asp Ser Ile
        515                 520                 525

Met Glu Tyr Leu His Phe Ala Lys Pro Leu Val Leu Ser Gly Ser Phe
    530                 535                 540

Ala Phe Glu Lys Asp Glu Gln Phe Tyr Thr Asn Phe Asp Glu Leu Tyr
545                 550                 555                 560

Asn Gln Leu Glu Leu Ile Ile Pro Leu Tyr Asn Lys Val Arg Asn Tyr
                565                 570                 575

Ala Thr Gln Lys Pro Tyr Ser Thr Glu Lys Phe Lys Leu Asn Phe Glu
            580                 585                 590

Asn Ser Thr Leu Leu Asn Gly Trp Asp Val Asn Lys Glu Glu Ala Asn
        595                 600                 605

Thr Ser Ile Leu Phe Ile Lys Asn Gly Phe Tyr Tyr Leu Gly Ile Met
    610                 615                 620

Asp Lys Asn His Asn Lys Ile Phe Arg Asn Thr Pro Lys Ser Thr Asn
625                 630                 635                 640

Thr Asp Ile Tyr Lys Lys Val Asn Tyr Lys Leu Leu Pro Gly Ala Ser
                645                 650                 655

Lys Met Leu Pro Lys Val Phe Phe Gly Lys Lys Asn Leu Asp Tyr Tyr
            660                 665                 670

Lys Pro Ser Lys Asp Ile Leu Arg Ile Arg Asn His Gly Thr His Thr
        675                 680                 685

Lys Gly Gly Lys Pro Gln Ser Gly Phe Asp Lys Leu Asp Phe Asn Leu
    690                 695                 700

Asn Asp Cys His Lys Leu Ile Asp Phe Phe Lys Asp Ser Ile Gln Lys
705                 710                 715                 720

His Pro Asp Trp Ser Lys Phe Lys Phe Lys Phe Ser Asp Thr Gln Ile
                725                 730                 735

Tyr Glu Ser Ile Asp Gln Phe Tyr Arg Glu Leu Glu Pro Gln Ala Tyr
            740                 745                 750

Ser Ile Thr Tyr Thr Asn Ile Asp Ser Ser Phe Ile Glu Glu Gln Ile
        755                 760                 765

Asn Glu Gly Lys Leu Tyr Leu Phe Gln Ile Tyr Asn Lys Asp Phe Ser
    770                 775                 780

Lys Phe Ser Asn Gly Lys Pro Asn Leu His Thr Leu Tyr Trp Lys Ala
785                 790                 795                 800

Leu Phe Asp Glu Gln Asn Leu Lys Asp Val Thr Tyr Lys Leu Asn Gly
                805                 810                 815

Glu Ala Glu Ile Phe Tyr Arg Lys Lys Ser Ile Gln His Asp Arg Gln
            820                 825                 830

Ile Ile His Lys Arg Asn Gln Pro Ile Ile Asn Lys Asn Pro Asn Asn
        835                 840                 845

Glu Lys Lys Glu Ser Ile Phe Lys Tyr Asn Ile Ile Lys Asp Lys Arg
    850                 855                 860
```

```
Tyr Thr Ile Asp Lys Phe Gln Phe His Val Pro Ile Thr Leu Asn Phe
865                 870                 875                 880

Lys Ala Lys Gly Thr Asp Tyr Ile Asn Tyr Asp Val Leu Asp Tyr Leu
                885                 890                 895

Lys Glu Asn Pro Asp Val Lys Ile Ile Gly Leu Asp Arg Gly Glu Arg
            900                 905                 910

His Leu Ile Tyr Leu Thr Leu Ile Asp Gln Lys Gly Lys Ile Leu Glu
        915                 920                 925

Gln Ile Ser Leu Asn Glu Ile Val Asn Lys Lys His Asn Ile Thr Thr
    930                 935                 940

Ser Tyr His Asn Leu Leu Glu Thr Lys Glu Ile Glu Arg Asp Lys Ala
945                 950                 955                 960

Arg Lys Asn Trp Gly Thr Val Glu Thr Ile Lys Glu Leu Lys Glu Gly
                965                 970                 975

Tyr Ile Ser Gln Val Val His Lys Ile Ser Lys Met Met Ile Glu His
            980                 985                 990

Asn Ala Ile Val Val Met Glu Asp  Leu Asn Met Gly Phe  Lys Arg Gly
        995                 1000                1005

Arg Phe  Lys Val Glu Lys Gln  Val Tyr Gln Lys Leu  Glu Lys Met
    1010                1015                1020

Leu Ile  Asp Lys Leu Asn Tyr  Leu Val Leu Lys Asp  Arg Gln Pro
    1025                1030                1035

Asn Glu  Pro Ala Gly Ile Tyr  Asn Ala Leu Gln Leu  Thr Asn Lys
    1040                1045                1050

Phe Glu  Ser Phe Gln Lys Leu  Gly Lys Gln Ser Gly  Phe Leu Phe
    1055                1060                1065

Tyr Val  Pro Ala Trp Asn Thr  Ser Lys Ile Asp Pro  Thr Thr Gly
    1070                1075                1080

Phe Val  Asn Leu Phe His Val  Lys Tyr Glu Ser Val  Arg Lys Ser
    1085                1090                1095

Gln Glu  Phe Phe Asn Lys Phe  Asn Ser Ile Lys Tyr  Asn Pro Lys
    1100                1105                1110

Glu Ala  Ile Phe Glu Phe Asp  Phe Asp Tyr Asn Glu  Phe Thr Thr
    1115                1120                1125

Arg Ala  Glu Gly Thr Lys Thr  Asn Trp Thr Val Cys  Thr Tyr Gly
    1130                1135                1140

Asp Arg  Ile Lys Thr Phe Arg  Asn Pro Glu Lys Leu  Asn Gln Trp
    1145                1150                1155

Asp Asn  Lys Glu Ile Asn Ile  Thr Thr Ala Phe Glu  Asp Phe Phe
    1160                1165                1170

Gly Arg  His Asn Ile Thr Tyr  Gly Asn Gly Ser Asp  Ile Lys Ser
    1175                1180                1185

Gln Leu  Ile Ser Arg Glu Glu  Lys Asp Phe Phe Ser  Glu Leu Ile
    1190                1195                1200

His Leu  Phe Arg Leu Thr Leu  Gln Met Arg Asn Ser  Lys Thr Asn
    1205                1210                1215

Ser Glu  Ile Asp Tyr Leu Ile  Ser Pro Val Lys Asn  Glu Asn Gly
    1220                1225                1230

Phe Phe  Tyr Asp Ser Arg His  Ala Asp Lys Asn Leu  Pro Lys Asp
    1235                1240                1245

Ala Asp  Ala Asn Gly Ala Tyr  His Ile Ala Lys Lys  Gly Leu Gln
    1250                1255                1260

Trp Ile  Lys Glu Ile Gln Ser  Phe Glu Gly Asn Glu  Trp Lys Lys
```

```
    1265                1270                1275

Leu Lys  Leu Asp Lys Thr Asn  Lys Gly Trp Leu Lys  Phe Val Gln
    1280                1285                1290

Glu Asn  Gln
    1295


<210> SEQ ID NO 27
<211> LENGTH: 1287
<212> TYPE: PRT
<213> ORGANISM: Brumimicrobium aurantiacum

<400> SEQUENCE: 27

Met Lys Asn Gln Ile Asn Leu Phe Thr Asn Lys Phe Gln Leu Ser Lys
1               5                   10                  15

Thr Leu Arg Phe Glu Leu Lys Pro Gln Gly Lys Thr Leu Glu His Ile
            20                  25                  30

Asn Ser Lys Gly Phe Ile Lys Asn Asp Glu Lys Arg Ala Asp Ser Tyr
        35                  40                  45

Lys Lys Met Lys Ala Thr Ile Asp Ala Phe His Arg Asp Phe Ile Asp
    50                  55                  60

Leu Ala Met Ser Asn Val Lys Leu Thr Asn Leu Ile Asp Phe Glu Glu
65                  70                  75                  80

Ile Tyr Asn Ala Ser Asn Ala Asp Lys Lys Asp Glu Lys Tyr Lys Thr
                85                  90                  95

Lys Leu Ser Lys Ile Gln Glu Ile Leu Arg Lys Glu Ile Ala Lys Gly
            100                 105                 110

Phe Lys Gly Glu Glu Val Lys Asp Ile Phe Ser Lys Ile Asp Lys Lys
        115                 120                 125

Asp Leu Ile Thr Lys Leu Leu Glu Glu Trp Ile Ile Glu Asn Lys Ile
    130                 135                 140

Glu Asp Ile His Phe Asp Pro Glu Phe Lys Asn Phe Thr Thr Tyr Phe
145                 150                 155                 160

Ser Gly Phe His Gln Asn Arg Lys Asn Met Tyr Thr Asp Gln Glu Gln
                165                 170                 175

Ser Thr Ala Ile Ala Tyr Arg Leu Ile His Glu Asn Leu Pro Arg Phe
            180                 185                 190

Ile Asp Asn Ile Asn Ile Phe Gln Lys Ile Asn Lys Val Pro Asp Leu
        195                 200                 205

Glu Glu Asn Leu Lys Lys Leu Tyr Gln Glu Ile Glu Glu Tyr Leu Gly
    210                 215                 220

Ile Asn Ala Ile Asn Glu Ala Phe Glu Leu Glu Tyr Phe Asn Glu Thr
225                 230                 235                 240

Leu Ser Gln Lys Gly Ile Asp Ile Tyr Asn Leu Ile Leu Gly Gly Arg
                245                 250                 255

Thr Ala Glu Glu Gly Lys Gln Lys Ile Gln Gly Leu Asn Glu Tyr Ile
            260                 265                 270

Asn Leu Tyr Asn Gln Lys Gln Asp Lys Lys Asn Arg Val Pro Lys Leu
        275                 280                 285

Lys Val Leu Tyr Lys Gln Ile Leu Ser Asp Arg Thr Arg Thr Ser Phe
    290                 295                 300

Leu Pro Asp Thr Phe Glu Asp Asp Glu Glu Ser Ser Ala Ser Gln Lys
305                 310                 315                 320

Val Leu Asp Ser Ile Asn Asn Phe Tyr Leu Glu Asn Leu Ile Asp Tyr
                325                 330                 335
```

```
Leu Pro Asn Asp Lys Asn Ser Thr Ile Asn Val Leu Glu Asn Leu Lys
            340                 345                 350

Leu Leu Leu Ala Glu Leu Ile Asn Phe Glu Leu Asp Lys Val Tyr Ile
        355                 360                 365

Lys Asn Asp Thr Ser Ile Thr Asn Ile Ser Met Lys Ile Phe Lys Asn
    370                 375                 380

Tyr Ser Val Ile Arg Glu Ala Leu Asn Tyr Phe Tyr Glu Asn Lys Ile
385                 390                 395                 400

Asp Pro Asn Phe Ala His Asn Phe Asn Asn Ala Asn Thr Asp Lys Lys
                405                 410                 415

Arg Glu Lys Leu Glu Lys Glu Lys Ala Lys Ile Thr Lys Gln Thr Tyr
            420                 425                 430

Leu Ser Ile Ser Phe Ile Glu Glu Ala Ile His Leu Tyr Ile Asn Glu
        435                 440                 445

Asn Ser Asn Gly Asn Gln Tyr Lys Asn Thr Tyr Lys Pro Asn Cys Ile
    450                 455                 460

Ala Asn Tyr Phe Lys Asp Phe Phe Ile Ala Glu Asn Lys Glu Gly Ser
465                 470                 475                 480

Asn Lys Glu Phe Asp Phe Ile Ser Lys Ile Lys Ala Arg Tyr Asn Thr
                485                 490                 495

Ile Lys Gly Val Leu Asn Thr Pro Phe Pro Asp Asn Lys Arg Leu His
            500                 505                 510

Gln Glu Lys Asn Asn Ile Asp Asn Ile Lys His Phe Leu Asp Ser Ile
        515                 520                 525

Met Glu Tyr Leu His Phe Ala Lys Pro Leu Val Leu Ser Gly Ser Phe
    530                 535                 540

Ala Phe Glu Lys Asp Glu Gln Phe Tyr Thr Asn Phe Asp Glu Leu Tyr
545                 550                 555                 560

Asn Gln Leu Glu Leu Ile Ile Pro Leu Tyr Asn Lys Val Arg Asn Tyr
                565                 570                 575

Ala Thr Gln Lys Pro Tyr Ser Thr Glu Lys Phe Lys Leu Asn Phe Glu
            580                 585                 590

Asn Ser Thr Leu Leu Asn Gly Trp Asp Val Asn Lys Glu Glu Ala Asn
        595                 600                 605

Thr Ser Ile Leu Phe Ile Lys Asn Gly Phe Tyr Tyr Leu Gly Ile Met
    610                 615                 620

Asp Lys Asn His Asn Lys Ile Phe Arg Asn Thr Pro Lys Ser Thr Asn
625                 630                 635                 640

Thr Asp Ile Tyr Lys Lys Val Asn Tyr Lys Leu Leu Pro Gly Ala Ser
                645                 650                 655

Lys Met Leu Pro Lys Val Phe Phe Gly Lys Lys Asn Leu Asp Tyr Tyr
            660                 665                 670

Lys Pro Ser Lys Asp Ile Leu Arg Ile Arg Asn His Gly Thr His Thr
        675                 680                 685

Lys Gly Gly Lys Pro Gln Ser Gly Phe Asp Lys Leu Asp Phe Asn Leu
    690                 695                 700

Asn Asp Cys His Lys Leu Ile Asp Phe Phe Lys Asp Ser Ile Gln Lys
705                 710                 715                 720

His Pro Asp Trp Ser Lys Phe Lys Phe Lys Phe Ser Asp Thr Gln Ile
                725                 730                 735

Tyr Glu Ser Ile Asp Gln Phe Tyr Arg Glu Leu Glu Pro Gln Ala Tyr
            740                 745                 750

Ser Ile Thr Tyr Thr Asn Ile Asp Ser Ser Phe Ile Glu Glu Gln Ile
```

```
        755                 760                 765

Asn Glu Gly Lys Leu Tyr Leu Phe Gln Ile Tyr Asn Lys Asp Phe Ser
    770                 775                 780

Lys Phe Ser Asn Gly Lys Pro Asn Leu His Thr Leu Tyr Trp Lys Ala
785                 790                 795                 800

Leu Phe Asp Glu Gln Asn Leu Lys Asp Val Thr Tyr Lys Leu Asn Gly
                805                 810                 815

Glu Ala Glu Ile Phe Tyr Arg Lys Lys Ser Ile Gln His Asp Arg Gln
            820                 825                 830

Ile Ile His Lys Arg Asn Gln Pro Ile Ile Asn Lys Asn Pro Asn Asn
        835                 840                 845

Glu Lys Lys Glu Ser Ile Phe Lys Tyr Asn Ile Ile Lys Asp Lys Arg
    850                 855                 860

Tyr Thr Ile Asp Lys Phe Gln Phe His Val Pro Ile Thr Leu Asn Phe
865                 870                 875                 880

Lys Ala Lys Gly Thr Asp Tyr Ile Asn Tyr Asp Val Leu Asp Tyr Leu
                885                 890                 895

Lys Glu Asn Pro Asp Val Lys Ile Ile Gly Leu Asp Arg Gly Glu Arg
            900                 905                 910

His Leu Ile Tyr Leu Thr Leu Ile Asp Gln Lys Gly Lys Ile Leu Glu
        915                 920                 925

Gln Ile Ser Leu Asn Glu Ile Val Asn Lys Lys His Asn Ile Thr Thr
    930                 935                 940

Ser Tyr His Asn Leu Leu Glu Thr Lys Glu Ile Glu Arg Asp Lys Ala
945                 950                 955                 960

Arg Lys Asn Trp Gly Thr Val Glu Thr Ile Lys Glu Leu Lys Glu Gly
                965                 970                 975

Tyr Ile Ser Gln Val Val His Lys Ile Ser Lys Met Met Ile Glu His
            980                 985                 990

Asn Ala Ile Val Val Met Glu Asp  Leu Asn Val Glu Lys  Gln Val Tyr
        995                 1000                1005

Gln Lys  Leu Glu Lys Met Leu  Ile Asp Lys Leu Asn  Tyr Leu Val
    1010                1015                1020

Leu Lys  Asp Arg Gln Pro Asn  Glu Pro Ala Gly Ile  Tyr Asn Ala
    1025                1030                1035

Leu Gln  Leu Thr Asn Lys Phe  Glu Ser Phe Gln Lys  Leu Gly Lys
    1040                1045                1050

Gln Ser  Gly Phe Leu Phe Tyr  Val Pro Ala Trp Asn  Thr Ser Lys
    1055                1060                1065

Ile Asp  Pro Thr Thr Gly Phe  Val Asn Leu Phe His  Val Lys Tyr
    1070                1075                1080

Glu Ser  Val Arg Lys Ser Gln  Glu Phe Phe Asn Lys  Phe Asn Ser
    1085                1090                1095

Ile Lys  Tyr Asn Pro Lys Glu  Ala Ile Phe Glu Phe  Asp Phe Asp
    1100                1105                1110

Tyr Asn  Glu Phe Thr Thr Arg  Ala Glu Gly Thr Lys  Thr Asn Trp
    1115                1120                1125

Thr Val  Cys Thr Tyr Gly Asp  Arg Ile Lys Thr Phe  Arg Asn Pro
    1130                1135                1140

Glu Lys  Leu Asn Gln Trp Asp  Asn Lys Glu Ile Asn  Ile Thr Thr
    1145                1150                1155

Ala Phe  Glu Asp Phe Phe Gly  Arg His Asn Ile Thr  Tyr Gly Asn
    1160                1165                1170
```

```
Gly Ser  Asp Ile Lys Ser Gln  Leu Ile Ser Arg Glu  Glu Lys Asp
    1175                1180                1185

Phe Phe  Ser Glu Leu Ile His  Leu Phe Arg Leu Thr  Leu Gln Met
    1190                1195                1200

Arg Asn  Ser Lys Thr Asn Ser  Glu Ile Asp Tyr Leu  Ile Ser Pro
    1205                1210                1215

Val Lys  Asn Glu Asn Gly Phe  Phe Tyr Asp Ser Arg  His Ala Asp
    1220                1225                1230

Lys Asn  Leu Pro Lys Asp Ala  Asp Ala Asn Gly Ala  Tyr His Ile
    1235                1240                1245

Ala Lys  Lys Gly Leu Gln Trp  Ile Lys Glu Ile Gln  Ser Phe Glu
    1250                1255                1260

Gly Asn  Glu Trp Lys Lys Leu  Lys Leu Asp Lys Thr  Asn Lys Gly
    1265                1270                1275

Trp Leu  Lys Phe Val Gln Glu  Asn Gln
    1280                1285
```

```
<210> SEQ ID NO 28
<211> LENGTH: 1260
<212> TYPE: PRT
<213> ORGANISM: Porphyromonas crevioricanis

<400> SEQUENCE: 28

Met Asp Ser Leu Lys Asp Phe Thr Asn Leu Tyr Pro Val Ser Lys Thr
1               5                   10                  15

Leu Arg Phe Glu Leu Lys Pro Val Gly Lys Thr Leu Glu Asn Ile Glu
            20                  25                  30

Lys Ala Gly Ile Leu Lys Glu Asp Glu His Arg Ala Glu Ser Tyr Arg
        35                  40                  45

Arg Val Lys Lys Ile Ile Asp Thr Tyr His Lys Val Phe Ile Asp Ser
    50                  55                  60

Ser Leu Glu Asn Met Ala Lys Met Gly Ile Glu Asn Glu Ile Lys Ala
65                  70                  75                  80

Met Leu Gln Ser Phe Cys Glu Leu Tyr Lys Lys Asp His Arg Thr Glu
                85                  90                  95

Gly Glu Asp Lys Ala Leu Asp Lys Ile Arg Ala Val Leu Arg Gly Leu
            100                 105                 110

Ile Val Gly Ala Phe Thr Gly Val Cys Gly Arg Arg Glu Asn Thr Val
        115                 120                 125

Gln Asn Glu Lys Tyr Glu Ser Leu Phe Lys Glu Lys Leu Ile Lys Glu
    130                 135                 140

Ile Leu Pro Asp Phe Val Leu Ser Thr Glu Ala Glu Ser Leu Pro Phe
145                 150                 155                 160

Ser Val Glu Glu Ala Thr Arg Ser Leu Lys Glu Phe Asp Ser Phe Thr
                165                 170                 175

Ser Tyr Phe Ala Gly Phe Tyr Glu Asn Arg Lys Asn Ile Tyr Ser Thr
            180                 185                 190

Lys Pro Gln Ser Thr Ala Ile Ala Tyr Arg Leu Ile His Glu Asn Leu
        195                 200                 205

Pro Lys Phe Ile Asp Asn Ile Leu Val Phe Gln Lys Ile Lys Glu Pro
    210                 215                 220

Ile Ala Lys Glu Leu Glu His Ile Arg Ala Asp Phe Ser Ala Gly Gly
225                 230                 235                 240

Tyr Ile Lys Lys Asp Glu Arg Leu Glu Asp Ile Phe Ser Leu Asn Tyr
```

```
                245                 250                 255

Tyr Ile His Val Leu Ser Gln Ala Gly Ile Glu Lys Tyr Asn Ala Leu
            260                 265                 270

Ile Gly Lys Ile Val Thr Glu Gly Asp Gly Glu Met Lys Gly Leu Asn
        275                 280                 285

Glu His Ile Asn Leu Tyr Asn Gln Gln Arg Gly Arg Glu Asp Arg Leu
    290                 295                 300

Pro Leu Phe Arg Pro Leu Tyr Lys Gln Ile Leu Ser Asp Arg Glu Gln
305                 310                 315                 320

Leu Ser Tyr Leu Pro Glu Ser Phe Glu Lys Asp Glu Glu Leu Leu Arg
                325                 330                 335

Ala Leu Lys Glu Phe Tyr Asp His Ile Ala Glu Asp Ile Leu Gly Arg
            340                 345                 350

Thr Gln Gln Leu Met Thr Ser Ile Ser Glu Tyr Asp Leu Ser Arg Ile
        355                 360                 365

Tyr Val Arg Asn Asp Ser Gln Leu Thr Asp Ile Ser Lys Lys Met Leu
    370                 375                 380

Gly Asp Trp Asn Ala Ile Tyr Met Ala Arg Glu Arg Ala Tyr Asp His
385                 390                 395                 400

Glu Gln Ala Pro Lys Arg Ile Thr Ala Lys Tyr Glu Arg Asp Arg Ile
                405                 410                 415

Lys Ala Leu Lys Gly Glu Glu Ser Ile Ser Leu Ala Asn Leu Asn Ser
            420                 425                 430

Cys Ile Ala Phe Leu Asp Asn Val Arg Asp Cys Arg Val Asp Thr Tyr
        435                 440                 445

Leu Ser Thr Leu Gly Gln Lys Glu Gly Pro His Gly Leu Ser Asn Leu
    450                 455                 460

Val Glu Asn Val Phe Ala Ser Tyr His Glu Ala Glu Gln Leu Leu Ser
465                 470                 475                 480

Phe Pro Tyr Pro Glu Glu Asn Asn Leu Ile Gln Asp Lys Asp Asn Val
                485                 490                 495

Val Leu Ile Lys Asn Leu Leu Asp Asn Ile Ser Asp Leu Gln Arg Phe
            500                 505                 510

Leu Lys Pro Leu Trp Gly Met Gly Asp Glu Pro Asp Lys Asp Glu Arg
        515                 520                 525

Phe Tyr Gly Glu Tyr Asn Tyr Ile Arg Gly Ala Leu Asp Gln Val Ile
    530                 535                 540

Pro Leu Tyr Asn Lys Val Arg Asn Tyr Leu Thr Arg Lys Pro Tyr Ser
545                 550                 555                 560

Thr Arg Lys Val Lys Leu Asn Phe Gly Asn Ser Gln Leu Leu Ser Gly
                565                 570                 575

Trp Asp Arg Asn Lys Glu Lys Asp Asn Ser Cys Val Ile Leu Arg Lys
            580                 585                 590

Gly Gln Asn Phe Tyr Leu Ala Ile Met Asn Asn Arg His Lys Arg Ser
        595                 600                 605

Phe Glu Asn Lys Val Leu Pro Glu Tyr Lys Glu Gly Glu Pro Tyr Phe
    610                 615                 620

Glu Lys Met Asp Tyr Lys Phe Leu Pro Asp Pro Asn Lys Met Leu Pro
625                 630                 635                 640

Lys Val Phe Leu Ser Lys Lys Gly Ile Glu Ile Tyr Lys Pro Ser Pro
                645                 650                 655

Lys Leu Leu Glu Gln Tyr Gly His Gly Thr His Lys Lys Gly Asp Thr
            660                 665                 670
```

```
Phe Ser Met Asp Asp Leu His Glu Leu Ile Asp Phe Phe Lys His Ser
        675                 680                 685

Ile Glu Ala His Glu Asp Trp Lys Gln Phe Gly Phe Lys Phe Ser Asp
    690                 695                 700

Thr Ala Thr Tyr Glu Asn Val Ser Ser Phe Tyr Arg Glu Val Glu Asp
705                 710                 715                 720

Gln Gly Tyr Lys Leu Ser Phe Arg Lys Val Ser Glu Ser Tyr Val Tyr
                725                 730                 735

Ser Leu Ile Asp Gln Gly Lys Leu Tyr Leu Phe Gln Ile Tyr Asn Lys
            740                 745                 750

Asp Phe Ser Pro Cys Ser Lys Gly Thr Pro Asn Leu His Thr Leu Tyr
        755                 760                 765

Trp Arg Met Leu Phe Asp Glu Arg Asn Leu Ala Asp Val Ile Tyr Lys
    770                 775                 780

Leu Asp Gly Lys Ala Glu Ile Phe Phe Arg Glu Lys Ser Leu Lys Asn
785                 790                 795                 800

Asp His Pro Thr His Pro Ala Gly Lys Pro Ile Lys Lys Lys Ser Arg
                805                 810                 815

Gln Lys Lys Gly Glu Glu Ser Leu Phe Glu Tyr Asp Leu Val Lys Asp
            820                 825                 830

Arg Arg Tyr Thr Met Asp Lys Phe Gln Phe His Val Pro Ile Thr Met
        835                 840                 845

Asn Phe Lys Cys Ser Ala Gly Ser Lys Val Asn Asp Met Val Asn Ala
    850                 855                 860

His Ile Arg Glu Ala Lys Asp Met His Val Ile Gly Ile Asp Arg Gly
865                 870                 875                 880

Glu Arg Asn Leu Leu Tyr Ile Cys Val Ile Asp Ser Arg Gly Thr Ile
                885                 890                 895

Leu Asp Gln Ile Ser Leu Asn Thr Ile Asn Asp Ile Asp Tyr His Asp
            900                 905                 910

Leu Leu Glu Ser Arg Asp Lys Asp Arg Gln Gln Glu Arg Arg Asn Trp
        915                 920                 925

Gln Thr Ile Glu Gly Ile Lys Glu Leu Lys Gln Gly Tyr Leu Ser Gln
    930                 935                 940

Ala Val His Arg Ile Ala Glu Leu Met Val Ala Tyr Lys Ala Val Val
945                 950                 955                 960

Ala Leu Glu Asp Leu Asn Met Gly Phe Lys Arg Gly Arg Gln Lys Val
                965                 970                 975

Glu Ser Ser Val Tyr Gln Gln Phe Glu Lys Gln Leu Ile Asp Lys Leu
            980                 985                 990

Asn Tyr Leu Val Asp Lys Lys Lys  Arg Pro Glu Asp Ile  Gly Gly Leu
        995                 1000                 1005

Leu Arg  Ala Tyr Gln Phe Thr  Ala Pro Phe Lys Ser  Phe Lys Glu
    1010                 1015                 1020

Met Gly  Lys Gln Asn Gly Phe  Leu Phe Tyr Ile Pro  Ala Trp Asn
    1025                 1030                 1035

Thr Ser  Asn Ile Asp Pro Thr  Thr Gly Phe Val Asn  Leu Phe His
    1040                 1045                 1050

Ala Gln  Tyr Glu Asn Val Asp  Lys Ala Lys Ser Phe  Phe Gln Lys
    1055                 1060                 1065

Phe Asp  Ser Ile Ser Tyr Asn  Pro Lys Lys Asp Trp  Phe Glu Phe
    1070                 1075                 1080
```

```
Ala Phe  Asp Tyr Lys Asn Phe  Thr Lys Lys Ala Glu  Gly Ser Arg
    1085                 1090                 1095

Ser Met  Trp Ile Leu Cys Thr  His Gly Ser Arg Ile  Lys Asn Phe
    1100                 1105                 1110

Arg Asn  Ser Gln Lys Asn Gly  Gln Trp Asp Ser Glu  Glu Phe Ala
    1115                 1120                 1125

Leu Thr  Glu Ala Phe Lys Ser  Leu Phe Val Arg Tyr  Glu Ile Asp
    1130                 1135                 1140

Tyr Thr  Ala Asp Leu Lys Thr  Ala Ile Val Asp Glu  Lys Gln Lys
    1145                 1150                 1155

Asp Phe  Phe Val Asp Leu Leu  Lys Leu Phe Lys Leu  Thr Val Gln
    1160                 1165                 1170

Met Arg  Asn Ser Trp Lys Glu  Lys Asp Leu Asp Tyr  Leu Ile Ser
    1175                 1180                 1185

Pro Val  Ala Gly Ala Asp Gly  Arg Phe Phe Asp Thr  Arg Glu Gly
    1190                 1195                 1200

Asn Lys  Ser Leu Pro Lys Asp  Ala Asp Ala Asn Gly  Ala Tyr Asn
    1205                 1210                 1215

Ile Ala  Leu Lys Gly Leu Trp  Ala Leu Arg Gln Ile  Arg Gln Thr
    1220                 1225                 1230

Ser Glu  Gly Gly Lys Leu Lys  Leu Ala Ile Ser Asn  Lys Glu Trp
    1235                 1240                 1245

Leu Gln  Phe Val Gln Glu Arg  Ser Tyr Glu Lys Asp
    1250                 1255                 1260


<210> SEQ ID NO 29
<211> LENGTH: 1251
<212> TYPE: PRT
<213> ORGANISM: Porphyromonas crevioricanis

<400> SEQUENCE: 29

Met Asp Ser Leu Lys Asp Phe Thr Asn Leu Tyr Pro Val Ser Lys Thr
1               5                   10                  15

Leu Arg Phe Glu Leu Lys Pro Val Gly Lys Thr Leu Glu Asn Ile Glu
            20                  25                  30

Lys Ala Gly Ile Leu Lys Glu Asp Glu His Arg Ala Glu Ser Tyr Arg
        35                  40                  45

Arg Val Lys Lys Ile Ile Asp Thr Tyr His Lys Val Phe Ile Asp Ser
    50                  55                  60

Ser Leu Glu Asn Met Ala Lys Met Gly Ile Glu Asn Glu Ile Lys Ala
65                  70                  75                  80

Met Leu Gln Ser Phe Cys Glu Leu Tyr Lys Lys Asp His Arg Thr Glu
                85                  90                  95

Gly Glu Asp Lys Ala Leu Asp Lys Ile Arg Ala Val Leu Arg Gly Leu
            100                 105                 110

Ile Val Gly Ala Phe Thr Gly Val Cys Gly Arg Arg Glu Asn Thr Val
        115                 120                 125

Gln Asn Glu Lys Tyr Glu Ser Leu Phe Lys Glu Lys Leu Ile Lys Glu
    130                 135                 140

Ile Leu Pro Asp Phe Val Leu Ser Thr Glu Ala Glu Ser Leu Pro Phe
145                 150                 155                 160

Ser Val Glu Glu Ala Thr Arg Ser Leu Lys Glu Phe Asp Ser Phe Thr
                165                 170                 175

Ser Tyr Phe Ala Gly Phe Tyr Glu Asn Arg Lys Asn Ile Tyr Ser Thr
            180                 185                 190
```

```
Lys Pro Gln Ser Thr Ala Ile Ala Tyr Arg Leu Ile His Glu Asn Leu
        195                 200                 205

Pro Lys Phe Ile Asp Asn Ile Leu Val Phe Gln Lys Ile Lys Glu Pro
    210                 215                 220

Ile Ala Lys Glu Leu Glu His Ile Arg Ala Asp Phe Ser Ala Gly Gly
225                 230                 235                 240

Tyr Ile Lys Lys Asp Glu Arg Leu Glu Asp Ile Phe Ser Leu Asn Tyr
                245                 250                 255

Tyr Ile His Val Leu Ser Gln Ala Gly Ile Glu Lys Tyr Asn Ala Leu
            260                 265                 270

Ile Gly Lys Ile Val Thr Glu Gly Asp Gly Glu Met Lys Gly Leu Asn
        275                 280                 285

Glu His Ile Asn Leu Tyr Asn Gln Gln Arg Gly Arg Glu Asp Arg Leu
    290                 295                 300

Pro Leu Phe Arg Pro Leu Tyr Lys Gln Ile Leu Ser Asp Arg Glu Gln
305                 310                 315                 320

Leu Ser Tyr Leu Pro Glu Ser Phe Glu Lys Asp Glu Glu Leu Leu Arg
                325                 330                 335

Ala Leu Lys Glu Phe Tyr Asp His Ile Ala Glu Asp Ile Leu Gly Arg
            340                 345                 350

Thr Gln Gln Leu Met Thr Ser Ile Ser Glu Tyr Asp Leu Ser Arg Ile
        355                 360                 365

Tyr Val Arg Asn Asp Ser Gln Leu Thr Asp Ile Ser Lys Lys Met Leu
    370                 375                 380

Gly Asp Trp Asn Ala Ile Tyr Met Ala Arg Glu Arg Ala Tyr Asp His
385                 390                 395                 400

Glu Gln Ala Pro Lys Arg Ile Thr Ala Lys Tyr Glu Arg Asp Arg Ile
                405                 410                 415

Lys Ala Leu Lys Gly Glu Glu Ser Ile Ser Leu Ala Asn Leu Asn Ser
            420                 425                 430

Cys Ile Ala Phe Leu Asp Asn Val Arg Asp Cys Arg Val Asp Thr Tyr
        435                 440                 445

Leu Ser Thr Leu Gly Gln Lys Glu Gly Pro His Gly Leu Ser Asn Leu
    450                 455                 460

Val Glu Asn Val Phe Ala Ser Tyr His Glu Ala Glu Gln Leu Leu Ser
465                 470                 475                 480

Phe Pro Tyr Pro Glu Glu Asn Asn Leu Ile Gln Asp Lys Asp Asn Val
                485                 490                 495

Val Leu Ile Lys Asn Leu Leu Asp Asn Ile Ser Asp Leu Gln Arg Phe
            500                 505                 510

Leu Lys Pro Leu Trp Gly Met Gly Asp Glu Pro Asp Lys Asp Glu Arg
        515                 520                 525

Phe Tyr Gly Glu Tyr Asn Tyr Ile Arg Gly Ala Leu Asp Gln Val Ile
    530                 535                 540

Pro Leu Tyr Asn Lys Val Arg Asn Tyr Leu Thr Arg Lys Pro Tyr Ser
545                 550                 555                 560

Thr Arg Lys Val Lys Leu Asn Phe Gly Asn Ser Gln Leu Leu Ser Gly
                565                 570                 575

Trp Asp Arg Asn Lys Glu Lys Asp Asn Ser Cys Val Ile Leu Arg Lys
            580                 585                 590

Gly Gln Asn Phe Tyr Leu Ala Ile Met Asn Asn Arg His Lys Arg Ser
        595                 600                 605
```

```
Phe Glu Asn Lys Val Leu Pro Glu Tyr Lys Glu Gly Glu Pro Tyr Phe
    610                 615                 620

Glu Lys Met Asp Tyr Lys Phe Leu Pro Asp Pro Asn Lys Met Leu Pro
625                 630                 635                 640

Lys Val Phe Leu Ser Lys Lys Gly Ile Glu Ile Tyr Lys Pro Ser Pro
                645                 650                 655

Lys Leu Leu Glu Gln Tyr Gly His Gly Thr His Lys Lys Gly Asp Thr
            660                 665                 670

Phe Ser Met Asp Asp Leu His Glu Leu Ile Asp Phe Phe Lys His Ser
        675                 680                 685

Ile Glu Ala His Glu Asp Trp Lys Gln Phe Gly Phe Lys Phe Ser Asp
    690                 695                 700

Thr Ala Thr Tyr Glu Asn Val Ser Ser Phe Tyr Arg Glu Val Glu Asp
705                 710                 715                 720

Gln Gly Tyr Lys Leu Ser Phe Arg Lys Val Ser Glu Ser Tyr Val Tyr
                725                 730                 735

Ser Leu Ile Asp Gln Gly Lys Leu Tyr Leu Phe Gln Ile Tyr Asn Lys
            740                 745                 750

Asp Phe Ser Pro Cys Ser Lys Gly Thr Pro Asn Leu His Thr Leu Tyr
        755                 760                 765

Trp Arg Met Leu Phe Asp Glu Arg Asn Leu Ala Asp Val Ile Tyr Lys
    770                 775                 780

Leu Asp Gly Lys Ala Glu Ile Phe Phe Arg Glu Lys Ser Leu Lys Asn
785                 790                 795                 800

Asp His Pro Thr His Pro Ala Gly Lys Pro Ile Lys Lys Lys Ser Arg
                805                 810                 815

Gln Lys Lys Gly Glu Glu Ser Leu Phe Glu Tyr Asp Leu Val Lys Asp
            820                 825                 830

Arg Arg Tyr Thr Met Asp Lys Phe Gln Phe His Val Pro Ile Thr Met
        835                 840                 845

Asn Phe Lys Cys Ser Ala Gly Ser Lys Val Asn Asp Met Val Asn Ala
    850                 855                 860

His Ile Arg Glu Ala Lys Asp Met His Val Ile Gly Ile Asp Arg Gly
865                 870                 875                 880

Glu Arg Asn Leu Leu Tyr Ile Cys Val Ile Asp Ser Arg Gly Thr Ile
                885                 890                 895

Leu Asp Gln Ile Ser Leu Asn Thr Ile Asn Asp Ile Asp Tyr His Asp
            900                 905                 910

Leu Leu Glu Ser Arg Asp Lys Asp Arg Gln Gln Glu Arg Arg Asn Trp
        915                 920                 925

Gln Thr Ile Glu Gly Ile Lys Glu Leu Lys Gln Gly Tyr Leu Ser Gln
    930                 935                 940

Ala Val His Arg Ile Ala Glu Leu Met Val Ala Tyr Lys Ala Val Val
945                 950                 955                 960

Ala Leu Glu Asp Leu Asn Val Glu Ser Ser Val Tyr Gln Gln Phe Glu
                965                 970                 975

Lys Gln Leu Ile Asp Lys Leu Asn Tyr Leu Val Asp Lys Lys Lys Arg
            980                 985                 990

Pro Glu Asp Ile Gly Gly Leu Leu  Arg Ala Tyr Gln Phe  Thr Ala Pro
        995                 1000                1005

Phe Lys  Ser Phe Lys Glu Met  Gly Lys Gln Asn Gly  Phe Leu Phe
    1010                1015                1020

Tyr Ile  Pro Ala Trp Asn Thr  Ser Asn Ile Asp Pro  Thr Thr Gly
```

1025 1030 1035

Phe Val Asn Leu Phe His Ala Gln Tyr Glu Asn Val Asp Lys Ala
1040 1045 1050

Lys Ser Phe Phe Gln Lys Phe Asp Ser Ile Ser Tyr Asn Pro Lys
1055 1060 1065

Lys Asp Trp Phe Glu Phe Ala Phe Asp Tyr Lys Asn Phe Thr Lys
1070 1075 1080

Lys Ala Glu Gly Ser Arg Ser Met Trp Ile Leu Cys Thr His Gly
1085 1090 1095

Ser Arg Ile Lys Asn Phe Arg Asn Ser Gln Lys Asn Gly Gln Trp
1100 1105 1110

Asp Ser Glu Glu Phe Ala Leu Thr Glu Ala Phe Lys Ser Leu Phe
1115 1120 1125

Val Arg Tyr Glu Ile Asp Tyr Thr Ala Asp Leu Lys Thr Ala Ile
1130 1135 1140

Val Asp Glu Lys Gln Lys Asp Phe Phe Val Asp Leu Leu Lys Leu
1145 1150 1155

Phe Lys Leu Thr Val Gln Met Arg Asn Ser Trp Lys Glu Lys Asp
1160 1165 1170

Leu Asp Tyr Leu Ile Ser Pro Val Ala Gly Ala Asp Gly Arg Phe
1175 1180 1185

Phe Asp Thr Arg Glu Gly Asn Lys Ser Leu Pro Lys Asp Ala Asp
1190 1195 1200

Ala Asn Gly Ala Tyr Asn Ile Ala Leu Lys Gly Leu Trp Ala Leu
1205 1210 1215

Arg Gln Ile Arg Gln Thr Ser Glu Gly Gly Lys Leu Lys Leu Ala
1220 1225 1230

Ile Ser Asn Lys Glu Trp Leu Gln Phe Val Gln Glu Arg Ser Tyr
1235 1240 1245

Glu Lys Asp
1250

<210> SEQ ID NO 30
<211> LENGTH: 1300
<212> TYPE: PRT
<213> ORGANISM: Francisella tularensis

<400> SEQUENCE: 30

Met Ser Ile Tyr Gln Glu Phe Val Asn Lys Tyr Ser Leu Ser Lys Thr
1 5 10 15

Leu Arg Phe Glu Leu Ile Pro Gln Gly Lys Thr Leu Glu Asn Ile Lys
20 25 30

Ala Arg Gly Leu Ile Leu Asp Asp Glu Lys Arg Ala Lys Asp Tyr Lys
35 40 45

Lys Ala Lys Gln Ile Ile Asp Lys Tyr His Gln Phe Phe Ile Glu Glu
50 55 60

Ile Leu Ser Ser Val Cys Ile Ser Glu Asp Leu Leu Gln Asn Tyr Ser
65 70 75 80

Asp Val Tyr Phe Lys Leu Lys Lys Ser Asp Asp Asp Asn Leu Gln Lys
85 90 95

Asp Phe Lys Ser Ala Lys Asp Thr Ile Lys Lys Gln Ile Ser Lys Tyr
100 105 110

Ile Asn Asp Ser Glu Lys Phe Lys Asn Leu Phe Asn Gln Asn Leu Ile
115 120 125

```
Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Ser Thr Ala
                405                 410                 415

Val Leu Glu Tyr Ile Thr Gln Gln Val Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Arg Leu Lys Ile Phe His
    530                 535                 540

Ile Ser Gln Ser Glu Asp Lys Ala Asn Ile Leu Asp Lys Asp Glu His
```

```
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Thr
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975
```

Ile Lys Glu Met Lys Glu Gly Tyr Leu Ser Gln Val Val His Glu Ile
980 985 990

Ala Lys Leu Val Ile Glu His Asn Ala Ile Val Val Phe Glu Asp Leu
995 1000 1005

Asn Phe Gly Phe Lys Arg Gly Arg Phe Lys Val Glu Lys Gln Val
1010 1015 1020

Tyr Gln Lys Leu Glu Lys Met Leu Ile Glu Lys Leu Asn Tyr Leu
1025 1030 1035

Val Phe Lys Asp Asn Glu Phe Asp Lys Thr Gly Gly Val Leu Arg
1040 1045 1050

Ala Tyr Gln Leu Thr Ala Pro Phe Glu Thr Phe Lys Lys Met Gly
1055 1060 1065

Lys Gln Thr Gly Ile Ile Tyr Tyr Val Pro Ala Gly Phe Thr Ser
1070 1075 1080

Lys Ile Cys Pro Val Thr Gly Phe Val Asn Gln Leu Tyr Pro Lys
1085 1090 1095

Tyr Glu Ser Val Ser Lys Ser Gln Glu Phe Phe Ser Lys Phe Asp
1100 1105 1110

Lys Ile Cys Tyr Asn Leu Asp Lys Gly Tyr Phe Glu Phe Ser Phe
1115 1120 1125

Asp Tyr Lys Asn Phe Gly Asp Lys Ala Ala Lys Gly Lys Trp Thr
1130 1135 1140

Ile Ala Ser Phe Gly Ser Arg Leu Ile Asn Phe Arg Asn Ser Asp
1145 1150 1155

Lys Asn His Asn Trp Asp Thr Arg Glu Val Tyr Pro Thr Lys Glu
1160 1165 1170

Leu Glu Lys Leu Leu Lys Asp Tyr Ser Ile Glu Tyr Gly His Gly
1175 1180 1185

Glu Cys Ile Lys Ala Ala Ile Cys Gly Glu Ser Asp Lys Lys Phe
1190 1195 1200

Phe Ala Lys Leu Thr Ser Val Leu Asn Thr Ile Leu Gln Met Arg
1205 1210 1215

Asn Ser Lys Thr Gly Thr Glu Leu Asp Tyr Leu Ile Ser Pro Val
1220 1225 1230

Ala Asp Val Asn Gly Asn Phe Phe Asp Ser Arg Gln Ala Pro Lys
1235 1240 1245

Asn Met Pro Gln Asp Ala Asp Ala Asn Gly Ala Tyr His Ile Gly
1250 1255 1260

Leu Lys Gly Leu Met Leu Leu Asp Arg Ile Lys Asn Asn Gln Glu
1265 1270 1275

Gly Lys Lys Leu Asn Leu Val Ile Lys Asn Glu Glu Tyr Phe Glu
1280 1285 1290

Phe Val Gln Asn Arg Asn Asn
1295 1300

<210> SEQ ID NO 31
<211> LENGTH: 1291
<212> TYPE: PRT
<213> ORGANISM: Francisella tularensis

<400> SEQUENCE: 31

Met Ser Ile Tyr Gln Glu Phe Val Asn Lys Tyr Ser Leu Ser Lys Thr
1 5 10 15

Leu Arg Phe Glu Leu Ile Pro Gln Gly Lys Thr Leu Glu Asn Ile Lys

-continued

```
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Lys Tyr
            100                 105                 110

Ile Asn Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Ser Thr Ala
                405                 410                 415

Val Leu Glu Tyr Ile Thr Gln Gln Val Ala Pro Lys Asn Leu Asp Asn
            420                 425                 430

Pro Ser Lys Lys Glu Gln Glu Leu Ile Ala Lys Lys Thr Glu Lys Ala
        435                 440                 445
```

```
Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Arg Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Thr
        835                 840                 845

Ile Ala Asn Lys Asn Lys Asp Asn Pro Lys Lys Glu Ser Val Phe Glu
    850                 855                 860
```

-continued

```
Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu His Asn  Ala Ile Val Val Phe  Glu Asp Leu
        995                 1000                1005

Asn Val  Glu Lys Gln Val Tyr  Gln Lys Leu Glu Lys  Met Leu Ile
    1010                1015                1020

Glu Lys  Leu Asn Tyr Leu Val  Phe Lys Asp Asn Glu  Phe Asp Lys
    1025                1030                1035

Thr Gly  Gly Val Leu Arg Ala  Tyr Gln Leu Thr Ala  Pro Phe Glu
    1040                1045                1050

Thr Phe  Lys Lys Met Gly Lys  Gln Thr Gly Ile Ile  Tyr Tyr Val
    1055                1060                1065

Pro Ala  Gly Phe Thr Ser Lys  Ile Cys Pro Val Thr  Gly Phe Val
    1070                1075                1080

Asn Gln  Leu Tyr Pro Lys Tyr  Glu Ser Val Ser Lys  Ser Gln Glu
    1085                1090                1095

Phe Phe  Ser Lys Phe Asp Lys  Ile Cys Tyr Asn Leu  Asp Lys Gly
    1100                1105                1110

Tyr Phe  Glu Phe Ser Phe Asp  Tyr Lys Asn Phe Gly  Asp Lys Ala
    1115                1120                1125

Ala Lys  Gly Lys Trp Thr Ile  Ala Ser Phe Gly Ser  Arg Leu Ile
    1130                1135                1140

Asn Phe  Arg Asn Ser Asp Lys  Asn His Asn Trp Asp  Thr Arg Glu
    1145                1150                1155

Val Tyr  Pro Thr Lys Glu Leu  Glu Lys Leu Leu Lys  Asp Tyr Ser
    1160                1165                1170

Ile Glu  Tyr Gly His Gly Glu  Cys Ile Lys Ala Ala  Ile Cys Gly
    1175                1180                1185

Glu Ser  Asp Lys Lys Phe Phe  Ala Lys Leu Thr Ser  Val Leu Asn
    1190                1195                1200

Thr Ile  Leu Gln Met Arg Asn  Ser Lys Thr Gly Thr  Glu Leu Asp
    1205                1210                1215

Tyr Leu  Ile Ser Pro Val Ala  Asp Val Asn Gly Asn  Phe Phe Asp
    1220                1225                1230

Ser Arg  Gln Ala Pro Lys Asn  Met Pro Gln Asp Ala  Asp Ala Asn
    1235                1240                1245

Gly Ala  Tyr His Ile Gly Leu  Lys Gly Leu Met Leu  Leu Asp Arg
    1250                1255                1260

Ile Lys  Asn Asn Gln Glu Gly  Lys Lys Leu Asn Leu  Val Ile Lys
```

```
    1265                1270                1275

Asn Glu  Glu Tyr Phe Glu Phe  Val Gln Asn Arg Asn  Asn
    1280                1285                1290


<210> SEQ ID NO 32
<211> LENGTH: 1251
<212> TYPE: PRT
<213> ORGANISM: Eubacterium ventriosum

<400> SEQUENCE: 32

Met Glu Ser Asn Asn Lys Ile Phe Thr Glu Thr Ile Gly Thr Ser Ser
1               5                   10                  15

Ile Ala Lys Thr Met Arg Asn Ser Leu Val Pro Thr Glu Ser Thr Lys
            20                  25                  30

Arg Asn Ile Glu Lys Asn Gly Ile Ile Ile Asp Asp Gln Leu Arg Ala
        35                  40                  45

Glu Lys Arg Gln Gln Leu Lys Glu Ile Met Asp Glu Tyr Tyr Arg Ala
    50                  55                  60

Tyr Ile Asp Ser Lys Leu Ser Asn Val Ala Leu Thr Arg Thr Ile Asp
65                  70                  75                  80

Trp Lys Glu Leu Phe Gln Ala Ile Glu Asn Asn Tyr Lys Gln Asn Thr
                85                  90                  95

Thr Lys Thr Lys Asn Glu Leu Glu Lys Lys Gln Lys Glu Lys Arg Thr
            100                 105                 110

Glu Ile Tyr Lys Ile Leu Ser Asp Asp Glu Glu Phe Lys Gln Leu Phe
        115                 120                 125

Asn Ala Lys Leu Leu Thr Asn Ile Leu Pro Glu Phe Ile Lys Asn Gln
    130                 135                 140

Asn Ile Asp Asn Glu Glu Lys Gln Glu Lys Ile Ser Thr Val Glu Leu
145                 150                 155                 160

Phe Gln Arg Phe Thr Ser Ser Phe Thr Asp Phe Phe Lys Asn Arg Lys
                165                 170                 175

Asn Val Phe Ser Lys Asp Glu Ile Ser Thr Ser Ile Cys Tyr Arg Val
            180                 185                 190

Val Gln Glu Asn Ala Trp Ile Phe Tyr Gln Asn Leu Leu Ala Phe Glu
        195                 200                 205

Glu Ile Lys Lys Thr Ala Glu Gln Glu Ile Lys Lys Ile Glu Ala Glu
    210                 215                 220

Asn Arg Asp Ser Ile Ser Asp Tyr Ser Leu Lys Glu Ile Phe Asp Phe
225                 230                 235                 240

Asp Phe Tyr Gly Leu Leu Leu Asn Gln Gly Gly Ile Arg Phe Tyr Asn
                245                 250                 255

Asp Val Cys Gly Lys Ile Asn Tyr His Met Asn Leu Tyr Gly Gln Lys
            260                 265                 270

His Asn Ile Lys Ser Asn Lys Phe Lys Met Lys Arg Met His Lys Gln
        275                 280                 285

Ile Leu Ser Ile Asp Glu Ser Thr Phe Glu Val Pro Thr Met Phe Glu
    290                 295                 300

Asn Asp Lys Glu Val Tyr Gln Val Leu Asn Glu Phe Leu Ser Asp Leu
305                 310                 315                 320

Ala Ser Lys Lys Ile Leu Glu Arg Val Glu Lys Ile Gly Glu Asn Val
                325                 330                 335

Ser Glu Tyr Glu Ile Asn Lys Ile Tyr Ile Gln Ser Lys Asn Phe Glu
            340                 345                 350
```

```
Asn Phe Ser Ser Phe Met Cys Gly Asn Trp Gln Ile Ile Asn Asp Ser
        355                 360                 365

Leu Lys Thr Tyr Tyr Asn Glu Lys Ile Lys Ser Lys Gly Lys Ala Lys
    370                 375                 380

Val Glu Lys Val Lys Lys Ala Ile Lys Ala Ile Glu Tyr Lys Ser Leu
385                 390                 395                 400

Ala Asp Ile Asn Gln Leu Val Glu Arg Tyr Asn His Asp Glu Leu Asn
                405                 410                 415

Arg Lys Ala Glu Glu Tyr Ile Ser Ala Ile Asn Glu Lys Ile Lys Asp
            420                 425                 430

Leu Tyr Val Asn Glu Ile Glu Phe Asp Glu Lys Thr Asn Leu Ile Glu
        435                 440                 445

Asn Glu Thr Lys Ser Glu Glu Ile Lys Ser Lys Leu Asp Ser Ile Met
    450                 455                 460

Glu Ile Met His Trp Thr Lys Met Phe Ile Ile Glu Glu Glu Ile Glu
465                 470                 475                 480

Lys Asp Val Asn Phe Tyr Asn Glu Ile Glu Glu Ile Tyr Asp Glu Leu
                485                 490                 495

Gln Pro Leu Val Thr Ile Tyr Asn Arg Ile Arg Asn Tyr Val Thr Gln
            500                 505                 510

Lys Pro Tyr Ser Glu Glu Lys Ile Lys Leu Asn Phe Gly Ile Pro Thr
        515                 520                 525

Leu Ala Asn Gly Trp Ser Lys Thr Lys Glu Tyr Asp Gln Asn Asn Ala
    530                 535                 540

Ile Ile Met Ile Arg Asp Gly Lys Tyr Tyr Leu Gly Ile Phe Asn Ala
545                 550                 555                 560

Lys Asn Lys Pro Asp Lys Lys Ile Met Glu Gly His Gln Ser Glu Glu
                565                 570                 575

Asn Gly Asp Tyr Lys Lys Met Ile Tyr Arg Leu Leu Pro Gly Pro Asn
            580                 585                 590

Lys Met Leu Pro Lys Val Phe Met Ser Lys Thr Gly Ile Ala Glu Tyr
        595                 600                 605

Lys Pro Ser Gln Tyr Ile Leu Glu Cys Tyr Glu Gln Asn Lys His Ile
    610                 615                 620

Lys Ser Asp Lys Asn Phe Asp Ile Lys Phe Cys Arg Asp Leu Ile Asp
625                 630                 635                 640

Phe Phe Lys Thr Ser Ile Asn Arg His Pro Glu Trp Ser Lys Phe Asn
                645                 650                 655

Phe Lys Phe Ser Glu Thr Ser Glu Tyr Glu Asp Ile Ser Thr Phe Tyr
            660                 665                 670

Arg Glu Val Glu Lys Gln Gly Tyr Lys Ile Glu Trp Thr Tyr Ile Ser
        675                 680                 685

Glu Lys Glu Ile Lys Glu Leu Asp Glu Asn Gly Gln Leu Tyr Leu Phe
    690                 695                 700

Gln Ile Tyr Asn Lys Asp Phe Ser Glu Lys Ser Lys Gly Lys Glu Asn
705                 710                 715                 720

Leu His Thr Met Tyr Leu Lys Asn Leu Phe Ser Glu Glu Asn Leu Lys
                725                 730                 735

Asn Ile Val Leu Lys Leu Asn Gly Glu Ala Glu Val Phe Phe Arg Lys
            740                 745                 750

Ser Ser Ile Lys Lys Pro Ile Ile His Lys Lys Gly Ser Val Leu Val
        755                 760                 765

Asn Lys Thr Tyr Asn Glu Asn Gly Glu Arg Lys Ser Ile Pro Glu Glu
```

```
    770                 775                 780

Gln Tyr Thr Glu Ile Tyr Lys Tyr Leu Asn Ser Ile Gly Thr Asn Glu
785                 790                 795                 800

Leu Ser Glu Lys Ser Lys Lys Leu Met Glu Glu Gly Lys Val Glu Tyr
                805                 810                 815

Tyr Lys Ala Asn Tyr Asp Ile Val Lys Asp Tyr Arg Tyr Ser Val Asp
            820                 825                 830

Lys Phe Phe Ile His Leu Pro Met Thr Ile Asn Phe Lys Ala Ala Gly
        835                 840                 845

Phe Ser Pro Ile Asn Asn Ile Ala Leu Lys Ser Ile Ala Leu Lys Glu
    850                 855                 860

Asp Met His Ile Ile Gly Ile Asp Arg Gly Glu Arg Asn Leu Ile Tyr
865                 870                 875                 880

Val Ser Val Ile Asp Thr Lys Gly Asn Ile Val Glu Gln Arg Asn Phe
                885                 890                 895

Asn Ile Val Asn Gly Ile Asp Tyr Lys Glu Lys Leu Lys Gln Lys Glu
            900                 905                 910

Leu Asp Arg Asp Asn Ala Arg Lys Asn Trp Lys Glu Ile Gly Lys Ile
        915                 920                 925

Lys Asp Leu Lys Glu Gly Tyr Leu Ser Leu Val Val His Glu Ile Ala
    930                 935                 940

Lys Leu Val Val Lys Tyr Asn Ala Ile Ile Thr Met Glu Asp Leu Asn
945                 950                 955                 960

Val Glu Arg Gln Val Tyr Gln Lys Phe Glu Thr Met Leu Ile Asn Lys
                965                 970                 975

Leu Asn Tyr Leu Val Asp Lys Asp Leu Ala Val Asp Gln Glu Gly Gly
            980                 985                 990

Leu Leu Arg Gly Tyr Gln Leu Thr  Tyr Ile Pro Glu Ser  Leu Lys Val
        995                 1000                1005

Leu Gly  Arg Gln Cys Gly Tyr  Ile Phe Tyr Val Pro  Ala Ala Tyr
    1010                1015                1020

Thr Ser  Lys Ile Asp Pro Thr  Thr Gly Phe Val Ala  Ile Phe Asn
    1025                1030                1035

Tyr Lys  Gly Met Thr Asp Lys  Asp Phe Val Thr Ser  Phe Asp Ser
    1040                1045                1050

Ile Lys  Tyr Asp Asp Glu Arg  Gly Leu Phe Ala Phe  Glu Phe Asp
    1055                1060                1065

Tyr Glu  Asn Phe Val Thr His  Lys Val Glu Met Ala  Arg Asn Lys
    1070                1075                1080

Trp Thr  Val Tyr Thr Tyr Gly  Glu Arg Ile Lys Arg  Lys Phe Lys
    1085                1090                1095

Asn Gly  Leu Trp Asp Thr Ala  Glu Lys Val Asp Leu  Thr Tyr Gln
    1100                1105                1110

Met Arg  Ser Ile Leu Glu Lys  Tyr Glu Ile Glu Tyr  Asn Lys Gly
    1115                1120                1125

Gln Asp  Ile Leu Glu Gln Ile  Glu Glu Leu Asp Glu  Lys Ala Gln
    1130                1135                1140

Asn Gly  Ile Cys Lys Glu Ile  Lys Tyr Leu Val Lys  Asp Ile Val
    1145                1150                1155

Gln Met  Arg Asn Ser Leu Pro  Asp Asn Ala Val Glu  Asp Tyr Asp
    1160                1165                1170

Ala Ile  Ile Ser Pro Val Ile  Asn Asn Asn Gly Glu  Phe Phe Asp
    1175                1180                1185
```

Ser Thr Arg Gly Asp Glu Asp Lys Pro Leu Asp Ala Asp Ala Asn
1190 1195 1200

Gly Ala Tyr Cys Ile Ala Leu Lys Gly Leu Tyr Glu Val Met Gln
1205 1210 1215

Ile Lys Lys Asn Trp Asn Glu Glu Thr Glu Phe Pro Arg Lys Glu
1220 1225 1230

Leu Lys Ile Arg His Gln Asp Trp Phe Asp Phe Ile Gln Asn Lys
1235 1240 1245

Arg Tyr Leu
1250

<210> SEQ ID NO 33
<211> LENGTH: 1129
<212> TYPE: PRT
<213> ORGANISM: Alicyclobacillus acidoterrestris

<400> SEQUENCE: 33

Met Ala Val Lys Ser Ile Lys Val Lys Leu Arg Leu Asp Asp Met Pro
1 5 10 15

Glu Ile Arg Ala Gly Leu Trp Lys Leu His Lys Glu Val Asn Ala Gly
20 25 30

Val Arg Tyr Tyr Thr Glu Trp Leu Ser Leu Leu Arg Gln Glu Asn Leu
35 40 45

Tyr Arg Arg Ser Pro Asn Gly Asp Gly Glu Gln Glu Cys Asp Lys Thr
50 55 60

Ala Glu Glu Cys Lys Ala Glu Leu Leu Glu Arg Leu Arg Ala Arg Gln
65 70 75 80

Val Glu Asn Gly His Arg Gly Pro Ala Gly Ser Asp Asp Glu Leu Leu
85 90 95

Gln Leu Ala Arg Gln Leu Tyr Glu Leu Leu Val Pro Gln Ala Ile Gly
100 105 110

Ala Lys Gly Asp Ala Gln Gln Ile Ala Arg Lys Phe Leu Ser Pro Leu
115 120 125

Ala Asp Lys Asp Ala Val Gly Gly Leu Gly Ile Ala Lys Ala Gly Asn
130 135 140

Lys Pro Arg Trp Val Arg Met Arg Glu Ala Gly Glu Pro Gly Trp Glu
145 150 155 160

Glu Glu Lys Glu Lys Ala Glu Thr Arg Lys Ser Ala Asp Arg Thr Ala
165 170 175

Asp Val Leu Arg Ala Leu Ala Asp Phe Gly Leu Lys Pro Leu Met Arg
180 185 190

Val Tyr Thr Asp Ser Glu Met Ser Ser Val Glu Trp Lys Pro Leu Arg
195 200 205

Lys Gly Gln Ala Val Arg Thr Trp Asp Arg Asp Met Phe Gln Gln Ala
210 215 220

Ile Glu Arg Met Met Ser Trp Glu Ser Trp Asn Gln Arg Val Gly Gln
225 230 235 240

Glu Tyr Ala Lys Leu Val Glu Gln Lys Asn Arg Phe Glu Gln Lys Asn
245 250 255

Phe Val Gly Gln Glu His Leu Val His Leu Val Asn Gln Leu Gln Gln
260 265 270

Asp Met Lys Glu Ala Ser Pro Gly Leu Glu Ser Lys Glu Gln Thr Ala
275 280 285

His Tyr Val Thr Gly Arg Ala Leu Arg Gly Ser Asp Lys Val Phe Glu

```
    290                 295                 300

Lys Trp Gly Lys Leu Ala Pro Asp Ala Pro Phe Asp Leu Tyr Asp Ala
305                 310                 315                 320

Glu Ile Lys Asn Val Gln Arg Arg Asn Thr Arg Arg Phe Gly Ser His
                325                 330                 335

Asp Leu Phe Ala Lys Leu Ala Glu Pro Glu Tyr Gln Ala Leu Trp Arg
            340                 345                 350

Glu Asp Ala Ser Phe Leu Thr Arg Tyr Ala Val Tyr Asn Ser Ile Leu
        355                 360                 365

Arg Lys Leu Asn His Ala Lys Met Phe Ala Thr Phe Thr Leu Pro Asp
    370                 375                 380

Ala Thr Ala His Pro Ile Trp Thr Arg Phe Asp Lys Leu Gly Gly Asn
385                 390                 395                 400

Leu His Gln Tyr Thr Phe Leu Phe Asn Glu Phe Gly Glu Arg Arg His
                405                 410                 415

Ala Ile Arg Phe His Lys Leu Leu Lys Val Glu Asn Gly Val Ala Arg
            420                 425                 430

Glu Val Asp Asp Val Thr Val Pro Ile Ser Met Ser Glu Gln Leu Asp
        435                 440                 445

Asn Leu Leu Pro Arg Asp Pro Asn Glu Pro Ile Ala Leu Tyr Phe Arg
    450                 455                 460

Asp Tyr Gly Ala Glu Gln His Phe Thr Gly Glu Phe Gly Gly Ala Lys
465                 470                 475                 480

Ile Gln Cys Arg Arg Asp Gln Leu Ala His Met His Arg Arg Arg Gly
                485                 490                 495

Ala Arg Asp Val Tyr Leu Asn Val Ser Val Arg Val Gln Ser Gln Ser
            500                 505                 510

Glu Ala Arg Gly Glu Arg Arg Pro Pro Tyr Ala Ala Val Phe Arg Leu
        515                 520                 525

Val Gly Asp Asn His Arg Ala Phe Val His Phe Asp Lys Leu Ser Asp
    530                 535                 540

Tyr Leu Ala Glu His Pro Asp Asp Gly Lys Leu Gly Ser Glu Gly Leu
545                 550                 555                 560

Leu Ser Gly Leu Arg Val Met Ser Val Asp Leu Gly Leu Arg Thr Ser
                565                 570                 575

Ala Ser Ile Ser Val Phe Arg Val Ala Arg Lys Asp Glu Leu Lys Pro
            580                 585                 590

Asn Ser Lys Gly Arg Val Pro Phe Phe Phe Pro Ile Lys Gly Asn Asp
        595                 600                 605

Asn Leu Val Ala Val His Glu Arg Ser Gln Leu Leu Lys Leu Pro Gly
    610                 615                 620

Glu Thr Glu Ser Lys Asp Leu Arg Ala Ile Arg Glu Glu Arg Gln Arg
625                 630                 635                 640

Thr Leu Arg Gln Leu Arg Thr Gln Leu Ala Tyr Leu Arg Leu Leu Val
                645                 650                 655

Arg Cys Gly Ser Glu Asp Val Gly Arg Arg Glu Arg Ser Trp Ala Lys
            660                 665                 670

Leu Ile Glu Gln Pro Val Asp Ala Ala Asn His Met Thr Pro Asp Trp
        675                 680                 685

Arg Glu Ala Phe Glu Asn Glu Leu Gln Lys Leu Lys Ser Leu His Gly
    690                 695                 700

Ile Cys Ser Asp Lys Glu Trp Met Asp Ala Val Tyr Glu Ser Val Arg
705                 710                 715                 720
```

```
Arg Val Trp Arg His Met Gly Lys Gln Val Arg Asp Trp Arg Lys Asp
                725                 730                 735

Val Arg Ser Gly Glu Arg Pro Lys Ile Arg Gly Tyr Ala Lys Asp Val
            740                 745                 750

Val Gly Gly Asn Ser Ile Glu Gln Ile Glu Tyr Leu Glu Arg Gln Tyr
        755                 760                 765

Lys Phe Leu Lys Ser Trp Ser Phe Phe Gly Lys Val Ser Gly Gln Val
    770                 775                 780

Ile Arg Ala Glu Lys Gly Ser Arg Phe Ala Ile Thr Leu Arg Glu His
785                 790                 795                 800

Ile Asp His Ala Lys Glu Asp Arg Leu Lys Lys Leu Ala Asp Arg Ile
                805                 810                 815

Ile Met Glu Ala Leu Gly Tyr Val Tyr Ala Leu Asp Glu Arg Gly Lys
            820                 825                 830

Gly Lys Trp Val Ala Lys Tyr Pro Pro Cys Gln Leu Ile Leu Leu Glu
        835                 840                 845

Glu Leu Ser Glu Tyr Gln Phe Asn Asn Asp Arg Pro Pro Ser Glu Asn
    850                 855                 860

Asn Gln Leu Met Gln Trp Ser His Arg Gly Val Phe Gln Glu Leu Ile
865                 870                 875                 880

Asn Gln Ala Gln Val His Asp Leu Leu Val Gly Thr Met Tyr Ala Ala
                885                 890                 895

Phe Ser Ser Arg Phe Asp Ala Arg Thr Gly Ala Pro Gly Ile Arg Cys
            900                 905                 910

Arg Arg Val Pro Ala Arg Cys Thr Gln Glu His Asn Pro Glu Pro Phe
        915                 920                 925

Pro Trp Trp Leu Asn Lys Phe Val Val Glu His Thr Leu Asp Ala Cys
    930                 935                 940

Pro Leu Arg Ala Asp Asp Leu Ile Pro Thr Gly Glu Gly Glu Ile Phe
945                 950                 955                 960

Val Ser Pro Phe Ser Ala Glu Glu Gly Asp Phe His Gln Ile His Ala
                965                 970                 975

Asp Leu Asn Ala Ala Gln Asn Leu Gln Gln Arg Leu Trp Ser Asp Phe
            980                 985                 990

Asp Ile Ser Gln Ile Arg Leu Arg  Cys Asp Trp Gly Glu  Val Asp Gly
        995                 1000                1005

Glu Leu  Val Leu Ile Pro Arg  Leu Thr Gly Lys Arg  Thr Ala Asp
    1010                1015                1020

Ser Tyr  Ser Asn Lys Val Phe  Tyr Thr Asn Thr Gly  Val Thr Tyr
    1025                1030                1035

Tyr Glu  Arg Glu Arg Gly Lys  Lys Arg Arg Lys Val  Phe Ala Gln
    1040                1045                1050

Glu Lys  Leu Ser Glu Glu Glu  Ala Glu Leu Leu Val  Glu Ala Asp
    1055                1060                1065

Glu Ala  Arg Glu Lys Ser Val  Val Leu Met Arg Asp  Pro Ser Gly
    1070                1075                1080

Ile Ile  Asn Arg Gly Asn Trp  Thr Arg Gln Lys Glu  Phe Trp Ser
    1085                1090                1095

Met Val  Asn Gln Arg Ile Glu  Gly Tyr Leu Val Lys  Gln Ile Arg
    1100                1105                1110

Ser Arg  Val Pro Leu Gln Asp  Ser Ala Cys Glu Asn  Thr Gly Asp
    1115                1120                1125
```

Ile

<210> SEQ ID NO 34
<211> LENGTH: 1115
<212> TYPE: PRT
<213> ORGANISM: Alicyclobacillus acidoterrestris

<400> SEQUENCE: 34

Met Ala Val Lys Ser Ile Lys Val Lys Leu Arg Leu Asp Asp Met Pro
1 5 10 15

Glu Ile Arg Ala Gly Leu Trp Lys Leu His Lys Glu Val Asn Ala Gly
20 25 30

Val Arg Tyr Tyr Thr Glu Trp Leu Ser Leu Leu Arg Gln Glu Asn Leu
35 40 45

Tyr Arg Arg Ser Pro Asn Gly Asp Gly Glu Gln Glu Cys Asp Lys Thr
50 55 60

Ala Glu Glu Cys Lys Ala Glu Leu Leu Glu Arg Leu Arg Ala Arg Gln
65 70 75 80

Val Glu Asn Gly His Arg Gly Pro Ala Gly Ser Asp Asp Glu Leu Leu
85 90 95

Gln Leu Ala Arg Gln Leu Tyr Glu Leu Leu Val Pro Gln Ala Ile Gly
100 105 110

Ala Lys Gly Asp Ala Gln Gln Ile Ala Arg Lys Phe Leu Ser Pro Leu
115 120 125

Ala Asp Lys Asp Ala Val Gly Gly Leu Gly Ile Ala Lys Ala Gly Asn
130 135 140

Lys Pro Arg Trp Val Arg Met Arg Glu Ala Gly Glu Pro Gly Trp Glu
145 150 155 160

Glu Glu Lys Glu Lys Ala Glu Thr Arg Lys Ser Ala Asp Arg Thr Ala
165 170 175

Asp Val Leu Arg Ala Leu Ala Asp Phe Gly Leu Lys Pro Leu Met Arg
180 185 190

Val Tyr Thr Asp Ser Glu Met Ser Ser Val Glu Trp Lys Pro Leu Arg
195 200 205

Lys Gly Gln Ala Val Arg Thr Trp Asp Arg Asp Met Phe Gln Gln Ala
210 215 220

Ile Glu Arg Met Met Ser Trp Glu Ser Trp Asn Gln Arg Val Gly Gln
225 230 235 240

Glu Tyr Ala Lys Leu Val Glu Gln Lys Asn Arg Phe Glu Gln Lys Asn
245 250 255

Phe Val Gly Gln Glu His Leu Val His Leu Val Asn Gln Leu Gln Gln
260 265 270

Asp Met Lys Glu Ala Ser Pro Gly Leu Glu Ser Lys Glu Gln Thr Ala
275 280 285

His Tyr Val Thr Gly Arg Ala Leu Arg Gly Ser Asp Lys Val Phe Glu
290 295 300

Lys Trp Gly Lys Leu Ala Pro Asp Ala Pro Phe Asp Leu Tyr Asp Ala
305 310 315 320

Glu Ile Lys Asn Val Gln Arg Arg Asn Thr Arg Arg Phe Gly Ser His
325 330 335

Asp Leu Phe Ala Lys Leu Ala Glu Pro Glu Tyr Gln Ala Leu Trp Arg
340 345 350

Glu Asp Ala Ser Phe Leu Thr Arg Tyr Ala Val Tyr Asn Ser Ile Leu
355 360 365

```
Arg Lys Leu Asn His Ala Lys Met Phe Ala Thr Phe Thr Leu Pro Asp
    370                 375                 380

Ala Thr Ala His Pro Ile Trp Thr Arg Phe Asp Lys Leu Gly Gly Asn
385                 390                 395                 400

Leu His Gln Tyr Thr Phe Leu Phe Asn Glu Phe Gly Glu Arg Arg His
                405                 410                 415

Ala Ile Arg Phe His Lys Leu Leu Lys Val Glu Asn Gly Val Ala Arg
            420                 425                 430

Glu Val Asp Asp Val Thr Val Pro Ile Ser Met Ser Glu Gln Leu Asp
        435                 440                 445

Asn Leu Leu Pro Arg Asp Pro Asn Glu Pro Ile Ala Leu Tyr Phe Arg
    450                 455                 460

Asp Tyr Gly Ala Glu Gln His Phe Thr Gly Glu Phe Gly Gly Ala Lys
465                 470                 475                 480

Ile Gln Cys Arg Arg Asp Gln Leu Ala His Met His Arg Arg Arg Gly
                485                 490                 495

Ala Arg Asp Val Tyr Leu Asn Val Ser Val Arg Val Gln Ser Gln Ser
            500                 505                 510

Glu Ala Arg Gly Glu Arg Arg Pro Pro Tyr Ala Ala Val Phe Arg Leu
        515                 520                 525

Val Gly Asp Asn His Arg Ala Phe Val His Phe Asp Lys Leu Ser Asp
    530                 535                 540

Tyr Leu Ala Glu His Pro Asp Asp Gly Lys Leu Gly Ser Glu Gly Leu
545                 550                 555                 560

Leu Ser Gly Leu Arg Val Met Ser Val Asp Leu Gly Leu Arg Thr Ser
                565                 570                 575

Ala Ser Ile Ser Val Phe Arg Val Ala Arg Lys Asp Glu Leu Lys Pro
            580                 585                 590

Asn Ser Lys Gly Arg Val Pro Phe Phe Phe Pro Ile Lys Gly Asn Asp
        595                 600                 605

Asn Leu Val Ala Val His Glu Arg Ser Gln Leu Leu Lys Leu Pro Gly
    610                 615                 620

Glu Thr Glu Ser Lys Asp Leu Arg Ala Ile Arg Glu Glu Arg Gln Arg
625                 630                 635                 640

Thr Leu Arg Gln Leu Arg Thr Gln Leu Ala Tyr Leu Arg Leu Leu Val
                645                 650                 655

Arg Cys Gly Ser Glu Asp Val Gly Arg Arg Glu Arg Ser Trp Ala Lys
            660                 665                 670

Leu Ile Glu Gln Pro Val Asp Ala Ala Asn His Met Thr Pro Asp Trp
        675                 680                 685

Arg Glu Ala Phe Glu Asn Glu Leu Gln Lys Leu Lys Ser Leu His Gly
    690                 695                 700

Ile Cys Ser Asp Lys Glu Trp Met Asp Ala Val Tyr Glu Ser Val Arg
705                 710                 715                 720

Arg Val Trp Arg His Met Gly Lys Gln Val Arg Asp Trp Arg Lys Asp
                725                 730                 735

Val Arg Ser Gly Glu Arg Pro Lys Ile Arg Gly Tyr Ala Lys Asp Val
            740                 745                 750

Val Gly Gly Asn Ser Ile Glu Gln Ile Glu Tyr Leu Glu Arg Gln Tyr
        755                 760                 765

Lys Phe Leu Lys Ser Trp Ser Phe Phe Gly Lys Val Ser Gly Gln Val
    770                 775                 780

Ile Arg Ala Glu Lys Gly Ser Arg Phe Ala Ile Thr Leu Arg Glu His
```

785 790 795 800

Ile Asp His Ala Lys Glu Asp Arg Leu Lys Lys Leu Ala Asp Arg Ile
805 810 815

Ile Met Glu Ala Leu Gly Tyr Val Tyr Ala Leu Asp Glu Arg Gly Lys
820 825 830

Gly Lys Trp Val Ala Lys Tyr Pro Pro Cys Gln Leu Ile Leu Leu Glu
835 840 845

Glu Leu Ser Gln Leu Met Gln Trp Ser His Arg Gly Val Phe Gln Glu
850 855 860

Leu Ile Asn Gln Ala Gln Val His Asp Leu Leu Val Gly Thr Met Tyr
865 870 875 880

Ala Ala Phe Ser Ser Arg Phe Asp Ala Arg Thr Gly Ala Pro Gly Ile
885 890 895

Arg Cys Arg Arg Val Pro Ala Arg Cys Thr Gln Glu His Asn Pro Glu
900 905 910

Pro Phe Pro Trp Trp Leu Asn Lys Phe Val Val Glu His Thr Leu Asp
915 920 925

Ala Cys Pro Leu Arg Ala Asp Asp Leu Ile Pro Thr Gly Glu Gly Glu
930 935 940

Ile Phe Val Ser Pro Phe Ser Ala Glu Glu Gly Asp Phe His Gln Ile
945 950 955 960

His Ala Asp Leu Asn Ala Ala Gln Asn Leu Gln Gln Arg Leu Trp Ser
965 970 975

Asp Phe Asp Ile Ser Gln Ile Arg Leu Arg Cys Asp Trp Gly Glu Val
980 985 990

Asp Gly Glu Leu Val Leu Ile Pro Arg Leu Thr Gly Lys Arg Thr Ala
995 1000 1005

Asp Ser Tyr Ser Asn Lys Val Phe Tyr Thr Asn Thr Gly Val Thr
1010 1015 1020

Tyr Tyr Glu Arg Glu Arg Gly Lys Lys Arg Arg Lys Val Phe Ala
1025 1030 1035

Gln Glu Lys Leu Ser Glu Glu Glu Ala Glu Leu Leu Val Glu Ala
1040 1045 1050

Asp Glu Ala Arg Glu Lys Ser Val Val Leu Met Arg Asp Pro Ser
1055 1060 1065

Gly Ile Ile Asn Arg Gly Asn Trp Thr Arg Gln Lys Glu Phe Trp
1070 1075 1080

Ser Met Val Asn Gln Arg Ile Glu Gly Tyr Leu Val Lys Gln Ile
1085 1090 1095

Arg Ser Arg Val Pro Leu Gln Asp Ser Ala Cys Glu Asn Thr Gly
1100 1105 1110

Asp Ile
1115

<210> SEQ ID NO 35
<211> LENGTH: 1129
<212> TYPE: PRT
<213> ORGANISM: Alicyclobacillus acidoterrestris

<400> SEQUENCE: 35

Met Ala Val Lys Ser Ile Lys Val Lys Leu Arg Leu Asp Asp Met Pro
1 5 10 15

Glu Ile Arg Ala Gly Leu Trp Lys Leu His Lys Glu Val Asn Ala Gly
20 25 30

```
Val Arg Tyr Tyr Thr Glu Trp Leu Ser Leu Leu Arg Gln Glu Asn Leu
        35                  40                  45

Tyr Arg Arg Ser Pro Asn Gly Asp Gly Glu Gln Glu Cys Asp Lys Thr
    50                  55                  60

Ala Glu Glu Cys Lys Ala Glu Leu Leu Glu Arg Leu Arg Ala Arg Gln
65                  70                  75                  80

Val Glu Asn Gly His Arg Gly Pro Ala Gly Ser Asp Asp Glu Leu Leu
                85                  90                  95

Gln Leu Ala Arg Gln Leu Tyr Glu Leu Leu Val Pro Gln Ala Ile Gly
            100                 105                 110

Ala Lys Gly Asp Ala Gln Gln Ile Ala Arg Lys Phe Leu Ser Pro Leu
        115                 120                 125

Ala Asp Lys Asp Ala Val Gly Gly Leu Gly Ile Ala Lys Ala Gly Asn
    130                 135                 140

Lys Pro Arg Trp Val Arg Met Arg Glu Ala Gly Glu Pro Gly Trp Glu
145                 150                 155                 160

Glu Glu Lys Glu Lys Ala Glu Thr Arg Lys Ser Ala Asp Arg Thr Ala
                165                 170                 175

Asp Val Leu Arg Ala Leu Ala Asp Phe Gly Leu Lys Pro Leu Met Arg
            180                 185                 190

Val Tyr Thr Asp Ser Glu Met Ser Ser Val Glu Trp Lys Pro Leu Arg
        195                 200                 205

Lys Gly Gln Ala Val Arg Thr Trp Asp Arg Asp Met Phe Gln Gln Ala
    210                 215                 220

Ile Glu Arg Met Met Ser Trp Glu Ser Trp Asn Gln Arg Val Gly Gln
225                 230                 235                 240

Glu Tyr Ala Lys Leu Val Glu Gln Lys Asn Arg Phe Glu Gln Lys Asn
                245                 250                 255

Phe Val Gly Gln Glu His Leu Val His Leu Val Asn Gln Leu Gln Gln
            260                 265                 270

Asp Met Lys Glu Ala Ser Pro Gly Leu Glu Ser Lys Glu Gln Thr Ala
        275                 280                 285

His Tyr Val Thr Gly Arg Ala Leu Arg Gly Ser Asp Lys Val Phe Glu
    290                 295                 300

Lys Trp Gly Lys Leu Ala Pro Asp Ala Pro Phe Asp Leu Tyr Asp Ala
305                 310                 315                 320

Glu Ile Lys Asn Val Gln Arg Arg Asn Thr Arg Arg Phe Gly Ser His
                325                 330                 335

Asp Leu Phe Ala Lys Leu Ala Glu Pro Glu Tyr Gln Ala Leu Trp Arg
            340                 345                 350

Glu Asp Ala Ser Phe Leu Thr Arg Tyr Ala Val Tyr Asn Ser Ile Leu
        355                 360                 365

Arg Lys Leu Asn His Ala Lys Met Phe Ala Thr Phe Thr Leu Pro Asp
    370                 375                 380

Ala Thr Ala His Pro Ile Trp Thr Arg Phe Asp Lys Leu Gly Gly Asn
385                 390                 395                 400

Leu His Gln Tyr Thr Phe Leu Phe Asn Glu Phe Gly Glu Arg Arg His
                405                 410                 415

Ala Ile Arg Phe His Lys Leu Leu Lys Val Glu Asn Gly Val Ala Arg
            420                 425                 430

Glu Val Asp Asp Val Thr Val Pro Ile Ser Met Ser Glu Gln Leu Asp
        435                 440                 445

Asn Leu Leu Pro Arg Asp Pro Asn Glu Pro Ile Ala Leu Tyr Phe Arg
```

```
    450                 455                 460

Asp Tyr Gly Ala Glu Gln His Phe Thr Gly Glu Phe Gly Gly Ala Lys
465                 470                 475                 480

Ile Gln Cys Arg Arg Asp Gln Leu Ala His Met His Arg Arg Arg Gly
                485                 490                 495

Ala Arg Asp Val Tyr Leu Asn Val Ser Val Arg Val Gln Ser Gln Ser
            500                 505                 510

Glu Ala Arg Gly Glu Arg Arg Pro Pro Tyr Ala Ala Val Phe Arg Leu
        515                 520                 525

Val Gly Asp Asn His Arg Ala Phe Val His Phe Asp Lys Leu Ser Asp
    530                 535                 540

Tyr Leu Ala Glu His Pro Asp Asp Gly Lys Leu Gly Ser Glu Gly Leu
545                 550                 555                 560

Leu Ser Gly Leu Arg Val Met Ser Val Asp Leu Gly Leu Arg Thr Ser
                565                 570                 575

Ala Ser Ile Ser Val Phe Arg Val Ala Arg Lys Asp Glu Leu Lys Pro
            580                 585                 590

Asn Ser Lys Gly Arg Val Pro Phe Phe Phe Pro Ile Lys Gly Asn Asp
        595                 600                 605

Asn Leu Val Ala Val His Glu Arg Ser Gln Leu Leu Lys Leu Pro Gly
    610                 615                 620

Glu Thr Glu Ser Lys Asp Leu Arg Ala Ile Arg Glu Glu Arg Gln Arg
625                 630                 635                 640

Thr Leu Arg Gln Leu Arg Thr Gln Leu Ala Tyr Leu Arg Leu Leu Val
                645                 650                 655

Arg Cys Gly Ser Glu Asp Val Gly Arg Arg Glu Arg Ser Trp Ala Lys
            660                 665                 670

Leu Ile Glu Gln Pro Val Asp Ala Ala Asn His Met Thr Pro Asp Trp
        675                 680                 685

Arg Glu Ala Phe Glu Asn Glu Leu Gln Lys Leu Lys Ser Leu His Gly
    690                 695                 700

Ile Cys Ser Asp Lys Glu Trp Met Asp Ala Val Tyr Glu Ser Val Arg
705                 710                 715                 720

Arg Val Trp Arg His Met Gly Lys Gln Val Arg Asp Trp Arg Lys Asp
                725                 730                 735

Val Arg Ser Gly Glu Arg Pro Lys Ile Arg Gly Tyr Ala Lys Asp Val
            740                 745                 750

Val Gly Gly Asn Ser Ile Glu Gln Ile Glu Tyr Leu Glu Arg Gln Tyr
        755                 760                 765

Lys Phe Leu Lys Ser Trp Ser Phe Phe Gly Lys Val Ser Gly Gln Val
    770                 775                 780

Ile Arg Ala Glu Lys Gly Ser Arg Phe Ala Ile Thr Leu Arg Glu His
785                 790                 795                 800

Ile Asp His Ala Lys Glu Asp Arg Leu Lys Lys Leu Ala Asp Arg Ile
                805                 810                 815

Ile Met Glu Ala Leu Gly Tyr Val Tyr Ala Leu Asp Glu Arg Gly Lys
            820                 825                 830

Gly Lys Trp Val Ala Lys Tyr Pro Pro Cys Gln Leu Ile Leu Leu Glu
        835                 840                 845

Glu Leu Ser Gly Ala Ala Gly Ala Ala Gly Ala Ala Gly Ala Ala Gly
    850                 855                 860

Gly Gln Leu Met Gln Trp Ser His Arg Gly Val Phe Gln Glu Leu Ile
865                 870                 875                 880
```

Asn Gln Ala Gln Val His Asp Leu Leu Val Gly Thr Met Tyr Ala Ala
885 890 895

Phe Ser Ser Arg Phe Asp Ala Arg Thr Gly Ala Pro Gly Ile Arg Cys
900 905 910

Arg Arg Val Pro Ala Arg Cys Thr Gln Glu His Asn Pro Glu Pro Phe
915 920 925

Pro Trp Trp Leu Asn Lys Phe Val Val Glu His Thr Leu Asp Ala Cys
930 935 940

Pro Leu Arg Ala Asp Asp Leu Ile Pro Thr Gly Glu Gly Glu Ile Phe
945 950 955 960

Val Ser Pro Phe Ser Ala Glu Glu Gly Asp Phe His Gln Ile His Ala
965 970 975

Asp Leu Asn Ala Ala Gln Asn Leu Gln Gln Arg Leu Trp Ser Asp Phe
980 985 990

Asp Ile Ser Gln Ile Arg Leu Arg Cys Asp Trp Gly Glu Val Asp Gly
995 1000 1005

Glu Leu Val Leu Ile Pro Arg Leu Thr Gly Lys Arg Thr Ala Asp
1010 1015 1020

Ser Tyr Ser Asn Lys Val Phe Tyr Thr Asn Thr Gly Val Thr Tyr
1025 1030 1035

Tyr Glu Arg Glu Arg Gly Lys Lys Arg Arg Lys Val Phe Ala Gln
1040 1045 1050

Glu Lys Leu Ser Glu Glu Glu Ala Glu Leu Leu Val Glu Ala Asp
1055 1060 1065

Glu Ala Arg Glu Lys Ser Val Val Leu Met Arg Asp Pro Ser Gly
1070 1075 1080

Ile Ile Asn Arg Gly Asn Trp Thr Arg Gln Lys Glu Phe Trp Ser
1085 1090 1095

Met Val Asn Gln Arg Ile Glu Gly Tyr Leu Val Lys Gln Ile Arg
1100 1105 1110

Ser Arg Val Pro Leu Gln Asp Ser Ala Cys Glu Asn Thr Gly Asp
1115 1120 1125

Ile

<210> SEQ ID NO 36
<211> LENGTH: 1147
<212> TYPE: PRT
<213> ORGANISM: Alicyclobacillus kakegawensis

<400> SEQUENCE: 36

Met Ala Val Lys Ser Ile Lys Val Lys Leu Arg Leu Ser Glu Cys Pro
1 5 10 15

Asp Ile Leu Ala Gly Met Trp Gln Leu His Arg Ala Thr Asn Ala Gly
20 25 30

Val Arg Tyr Tyr Thr Glu Trp Val Ser Leu Met Arg Gln Glu Ile Leu
35 40 45

Tyr Ser Arg Gly Pro Asp Gly Gly Gln Gln Cys Tyr Met Thr Ala Glu
50 55 60

Asp Cys Gln Arg Glu Leu Leu Arg Arg Leu Arg Asn Arg Gln Leu His
65 70 75 80

Asn Gly Arg Gln Asp Gln Pro Gly Thr Asp Ala Asp Leu Leu Ala Ile
85 90 95

Ser Arg Arg Leu Tyr Glu Ile Leu Val Leu Gln Ser Ile Gly Lys Arg
100 105 110

```
Gly Asp Ala Gln Gln Ile Ala Ser Ser Phe Leu Ser Pro Leu Val Asp
        115                 120                 125

Pro Asn Ser Lys Gly Gly Arg Gly Glu Ala Lys Ser Gly Arg Lys Pro
    130                 135                 140

Ala Trp Gln Lys Met Arg Asp Gln Gly Asp Pro Arg Trp Val Ala Ala
145                 150                 155                 160

Arg Glu Lys Tyr Glu Gln Arg Lys Ala Val Asp Pro Ser Lys Glu Ile
                165                 170                 175

Leu Asn Ser Leu Asp Ala Leu Gly Leu Arg Pro Leu Phe Ala Val Phe
            180                 185                 190

Thr Glu Thr Tyr Arg Ser Gly Val Asp Trp Lys Pro Leu Gly Lys Ser
        195                 200                 205

Gln Gly Val Arg Thr Trp Asp Arg Asp Met Phe Gln Gln Ala Leu Glu
    210                 215                 220

Arg Leu Met Ser Trp Glu Ser Trp Asn Arg Arg Val Gly Glu Glu Tyr
225                 230                 235                 240

Ala Arg Leu Phe Gln Gln Lys Met Lys Phe Glu Gln Glu His Phe Ala
                245                 250                 255

Glu Gln Ser His Leu Val Lys Leu Ala Arg Ala Leu Glu Ala Asp Met
            260                 265                 270

Arg Ala Ala Ser Gln Gly Phe Glu Ala Lys Arg Gly Thr Ala His Gln
        275                 280                 285

Ile Thr Arg Arg Ala Leu Arg Gly Ala Asp Arg Val Phe Glu Ile Trp
    290                 295                 300

Lys Ser Ile Pro Glu Glu Ala Leu Phe Ser Gln Tyr Asp Glu Val Ile
305                 310                 315                 320

Arg Gln Val Gln Ala Glu Lys Arg Arg Asp Phe Gly Ser His Asp Leu
                325                 330                 335

Phe Ala Lys Leu Ala Glu Pro Lys Tyr Gln Pro Leu Trp Arg Ala Asp
            340                 345                 350

Glu Thr Phe Leu Thr Arg Tyr Ala Leu Tyr Asn Gly Val Leu Arg Asp
        355                 360                 365

Leu Glu Lys Ala Arg Gln Phe Ala Thr Phe Thr Leu Pro Asp Ala Cys
    370                 375                 380

Val Asn Pro Ile Trp Thr Arg Phe Glu Ser Ser Gln Gly Ser Asn Leu
385                 390                 395                 400

His Lys Tyr Glu Phe Leu Phe Asp His Leu Gly Pro Gly Arg His Ala
                405                 410                 415

Val Arg Phe Gln Arg Leu Leu Val Val Glu Ser Glu Gly Ala Lys Glu
            420                 425                 430

Arg Asp Ser Val Val Val Pro Val Ala Pro Ser Gly Gln Leu Asp Lys
        435                 440                 445

Leu Val Leu Arg Glu Glu Glu Lys Ser Ser Val Ala Leu His Leu His
    450                 455                 460

Asp Thr Ala Arg Pro Asp Gly Phe Met Ala Glu Trp Ala Gly Ala Lys
465                 470                 475                 480

Leu Gln Tyr Glu Arg Ser Thr Leu Ala Arg Lys Ala Arg Arg Asp Lys
                485                 490                 495

Gln Gly Met Arg Ser Trp Arg Arg Gln Pro Ser Met Leu Met Ser Ala
            500                 505                 510

Ala Gln Met Leu Glu Asp Ala Lys Gln Ala Gly Asp Val Tyr Leu Asn
        515                 520                 525
```

```
Ile Ser Val Arg Val Lys Ser Pro Ser Glu Val Arg Gly Gln Arg Arg
    530                 535                 540

Pro Pro Tyr Ala Ala Leu Phe Arg Ile Asp Asp Lys Gln Arg Arg Val
545                 550                 555                 560

Thr Val Asn Tyr Asn Lys Leu Ser Ala Tyr Leu Glu Glu His Pro Asp
                565                 570                 575

Lys Gln Ile Pro Gly Ala Pro Gly Leu Leu Ser Gly Leu Arg Val Met
            580                 585                 590

Ser Val Asp Leu Gly Leu Arg Thr Ser Ala Ser Ile Ser Val Phe Arg
        595                 600                 605

Val Ala Lys Lys Glu Glu Val Glu Ala Leu Gly Asp Gly Arg Pro Pro
    610                 615                 620

His Tyr Tyr Pro Ile His Gly Thr Asp Asp Leu Val Ala Val His Glu
625                 630                 635                 640

Arg Ser His Leu Ile Gln Met Pro Gly Glu Thr Glu Thr Lys Gln Leu
                645                 650                 655

Arg Lys Leu Arg Glu Glu Arg Gln Ala Val Leu Arg Pro Leu Phe Ala
            660                 665                 670

Gln Leu Ala Leu Leu Arg Leu Leu Val Arg Cys Gly Ala Ala Asp Glu
        675                 680                 685

Arg Ile Arg Thr Arg Ser Trp Gln Arg Leu Thr Lys Gln Gly Arg Glu
    690                 695                 700

Phe Thr Lys Arg Leu Thr Pro Ser Trp Arg Glu Ala Leu Glu Leu Glu
705                 710                 715                 720

Leu Thr Arg Leu Glu Ala Tyr Cys Gly Arg Val Pro Asp Asp Glu Trp
                725                 730                 735

Ser Arg Ile Val Asp Arg Thr Val Ile Ala Leu Trp Arg Arg Met Gly
            740                 745                 750

Lys Gln Val Arg Asp Trp Arg Lys Gln Val Lys Ser Gly Ala Lys Val
        755                 760                 765

Lys Val Lys Gly Tyr Gln Leu Asp Val Val Gly Gly Asn Ser Leu Ala
    770                 775                 780

Gln Ile Asp Tyr Leu Glu Gln Gln Tyr Lys Phe Leu Arg Arg Trp Ser
785                 790                 795                 800

Phe Phe Ala Arg Ala Ser Gly Leu Val Val Arg Ala Asp Arg Glu Ser
                805                 810                 815

His Phe Ala Val Ala Leu Arg Gln His Ile Glu Asn Ala Lys Arg Asp
            820                 825                 830

Arg Leu Lys Lys Leu Ala Asp Arg Ile Leu Met Glu Ala Leu Gly Tyr
        835                 840                 845

Val Tyr Glu Ala Ser Gly Pro Arg Glu Gly Gln Trp Thr Ala Gln His
    850                 855                 860

Pro Pro Cys Gln Leu Ile Ile Leu Glu Glu Leu Ser Ala Tyr Arg Phe
865                 870                 875                 880

Ser Asp Asp Arg Pro Pro Ser Glu Asn Ser Lys Leu Met Ala Trp Gly
                885                 890                 895

His Arg Gly Ile Leu Glu Glu Leu Val Asn Gln Ala Gln Val His Asp
            900                 905                 910

Val Leu Val Gly Thr Val Tyr Ala Ala Phe Ser Ser Arg Phe Asp Ala
        915                 920                 925

Arg Thr Gly Ala Pro Gly Val Arg Cys Arg Arg Val Pro Ala Arg Phe
    930                 935                 940

Val Gly Ala Thr Val Asp Asp Ser Leu Pro Leu Trp Leu Thr Glu Phe
```

945 950 955 960

Leu Asp Lys His Arg Leu Asp Lys Asn Leu Leu Arg Pro Asp Asp Val
965 970 975

Ile Pro Thr Gly Glu Gly Glu Phe Leu Val Ser Pro Cys Gly Glu Glu
980 985 990

Ala Ala Arg Val Arg Gln Val His Ala Asp Ile Asn Ala Ala Gln Asn
995 1000 1005

Leu Gln Arg Arg Leu Trp Gln Asn Phe Asp Ile Thr Glu Leu Arg
1010 1015 1020

Leu Arg Cys Asp Val Lys Met Gly Gly Glu Gly Thr Val Leu Val
1025 1030 1035

Pro Arg Val Asn Asn Ala Arg Ala Lys Gln Leu Phe Gly Lys Lys
1040 1045 1050

Val Leu Val Ser Gln Asp Gly Val Thr Phe Phe Glu Arg Ser Gln
1055 1060 1065

Thr Gly Gly Lys Pro His Ser Glu Lys Gln Thr Asp Leu Thr Asp
1070 1075 1080

Lys Glu Leu Glu Leu Ile Ala Glu Ala Asp Glu Ala Arg Ala Lys
1085 1090 1095

Ser Val Val Leu Phe Arg Asp Pro Ser Gly His Ile Gly Lys Gly
1100 1105 1110

His Trp Ile Arg Gln Arg Glu Phe Trp Ser Leu Val Lys Gln Arg
1115 1120 1125

Ile Glu Ser His Thr Ala Glu Arg Ile Arg Val Arg Gly Val Gly
1130 1135 1140

Ser Ser Leu Asp
1145

<210> SEQ ID NO 37
<211> LENGTH: 1133
<212> TYPE: PRT
<213> ORGANISM: Alicyclobacillus kakegawensis

<400> SEQUENCE: 37

Met Ala Val Lys Ser Ile Lys Val Lys Leu Arg Leu Ser Glu Cys Pro
1 5 10 15

Asp Ile Leu Ala Gly Met Trp Gln Leu His Arg Ala Thr Asn Ala Gly
20 25 30

Val Arg Tyr Tyr Thr Glu Trp Val Ser Leu Met Arg Gln Glu Ile Leu
35 40 45

Tyr Ser Arg Gly Pro Asp Gly Gly Gln Gln Cys Tyr Met Thr Ala Glu
50 55 60

Asp Cys Gln Arg Glu Leu Leu Arg Arg Leu Arg Asn Arg Gln Leu His
65 70 75 80

Asn Gly Arg Gln Asp Gln Pro Gly Thr Asp Ala Asp Leu Leu Ala Ile
85 90 95

Ser Arg Arg Leu Tyr Glu Ile Leu Val Leu Gln Ser Ile Gly Lys Arg
100 105 110

Gly Asp Ala Gln Gln Ile Ala Ser Ser Phe Leu Ser Pro Leu Val Asp
115 120 125

Pro Asn Ser Lys Gly Gly Arg Gly Glu Ala Lys Ser Gly Arg Lys Pro
130 135 140

Ala Trp Gln Lys Met Arg Asp Gln Gly Asp Pro Arg Trp Val Ala Ala
145 150 155 160

```
Arg Glu Lys Tyr Glu Gln Arg Lys Ala Val Asp Pro Ser Lys Glu Ile
                165                 170                 175

Leu Asn Ser Leu Asp Ala Leu Gly Leu Arg Pro Leu Phe Ala Val Phe
            180                 185                 190

Thr Glu Thr Tyr Arg Ser Gly Val Asp Trp Lys Pro Leu Gly Lys Ser
        195                 200                 205

Gln Gly Val Arg Thr Trp Asp Arg Asp Met Phe Gln Gln Ala Leu Glu
    210                 215                 220

Arg Leu Met Ser Trp Glu Ser Trp Asn Arg Arg Val Gly Glu Glu Tyr
225                 230                 235                 240

Ala Arg Leu Phe Gln Gln Lys Met Lys Phe Glu Gln Glu His Phe Ala
                245                 250                 255

Glu Gln Ser His Leu Val Lys Leu Ala Arg Ala Leu Glu Ala Asp Met
            260                 265                 270

Arg Ala Ala Ser Gln Gly Phe Glu Ala Lys Arg Gly Thr Ala His Gln
        275                 280                 285

Ile Thr Arg Arg Ala Leu Arg Gly Ala Asp Arg Val Phe Glu Ile Trp
    290                 295                 300

Lys Ser Ile Pro Glu Glu Ala Leu Phe Ser Gln Tyr Asp Glu Val Ile
305                 310                 315                 320

Arg Gln Val Gln Ala Glu Lys Arg Arg Asp Phe Gly Ser His Asp Leu
                325                 330                 335

Phe Ala Lys Leu Ala Glu Pro Lys Tyr Gln Pro Leu Trp Arg Ala Asp
            340                 345                 350

Glu Thr Phe Leu Thr Arg Tyr Ala Leu Tyr Asn Gly Val Leu Arg Asp
        355                 360                 365

Leu Glu Lys Ala Arg Gln Phe Ala Thr Phe Thr Leu Pro Asp Ala Cys
    370                 375                 380

Val Asn Pro Ile Trp Thr Arg Phe Glu Ser Ser Gln Gly Ser Asn Leu
385                 390                 395                 400

His Lys Tyr Glu Phe Leu Phe Asp His Leu Gly Pro Gly Arg His Ala
                405                 410                 415

Val Arg Phe Gln Arg Leu Leu Val Val Glu Ser Glu Gly Ala Lys Glu
            420                 425                 430

Arg Asp Ser Val Val Val Pro Val Ala Pro Ser Gly Gln Leu Asp Lys
        435                 440                 445

Leu Val Leu Arg Glu Glu Glu Lys Ser Ser Val Ala Leu His Leu His
    450                 455                 460

Asp Thr Ala Arg Pro Asp Gly Phe Met Ala Glu Trp Ala Gly Ala Lys
465                 470                 475                 480

Leu Gln Tyr Glu Arg Ser Thr Leu Ala Arg Lys Ala Arg Arg Asp Lys
                485                 490                 495

Gln Gly Met Arg Ser Trp Arg Arg Gln Pro Ser Met Leu Met Ser Ala
            500                 505                 510

Ala Gln Met Leu Glu Asp Ala Lys Gln Ala Gly Asp Val Tyr Leu Asn
        515                 520                 525

Ile Ser Val Arg Val Lys Ser Pro Ser Glu Val Arg Gly Gln Arg Arg
    530                 535                 540

Pro Pro Tyr Ala Ala Leu Phe Arg Ile Asp Asp Lys Gln Arg Arg Val
545                 550                 555                 560

Thr Val Asn Tyr Asn Lys Leu Ser Ala Tyr Leu Glu Glu His Pro Asp
                565                 570                 575

Lys Gln Ile Pro Gly Ala Pro Gly Leu Leu Ser Gly Leu Arg Val Met
```

```
            580                 585                 590

Ser Val Asp Leu Gly Leu Arg Thr Ser Ala Ser Ile Ser Val Phe Arg
        595                 600                 605

Val Ala Lys Lys Glu Glu Val Glu Ala Leu Gly Asp Gly Arg Pro Pro
    610                 615                 620

His Tyr Tyr Pro Ile His Gly Thr Asp Asp Leu Val Ala Val His Glu
625                 630                 635                 640

Arg Ser His Leu Ile Gln Met Pro Gly Glu Thr Glu Thr Lys Gln Leu
                645                 650                 655

Arg Lys Leu Arg Glu Glu Arg Gln Ala Val Leu Arg Pro Leu Phe Ala
            660                 665                 670

Gln Leu Ala Leu Leu Arg Leu Leu Val Arg Cys Gly Ala Ala Asp Glu
        675                 680                 685

Arg Ile Arg Thr Arg Ser Trp Gln Arg Leu Thr Lys Gln Gly Arg Glu
    690                 695                 700

Phe Thr Lys Arg Leu Thr Pro Ser Trp Arg Glu Ala Leu Glu Leu Glu
705                 710                 715                 720

Leu Thr Arg Leu Glu Ala Tyr Cys Gly Arg Val Pro Asp Asp Glu Trp
                725                 730                 735

Ser Arg Ile Val Asp Arg Thr Val Ile Ala Leu Trp Arg Arg Met Gly
            740                 745                 750

Lys Gln Val Arg Asp Trp Arg Lys Gln Val Lys Ser Gly Ala Lys Val
        755                 760                 765

Lys Val Lys Gly Tyr Gln Leu Asp Val Val Gly Gly Asn Ser Leu Ala
    770                 775                 780

Gln Ile Asp Tyr Leu Glu Gln Gln Tyr Lys Phe Leu Arg Arg Trp Ser
785                 790                 795                 800

Phe Phe Ala Arg Ala Ser Gly Leu Val Val Arg Ala Asp Arg Glu Ser
                805                 810                 815

His Phe Ala Val Ala Leu Arg Gln His Ile Glu Asn Ala Lys Arg Asp
            820                 825                 830

Arg Leu Lys Lys Leu Ala Asp Arg Ile Leu Met Glu Ala Leu Gly Tyr
        835                 840                 845

Val Tyr Glu Ala Ser Gly Pro Arg Glu Gly Gln Trp Thr Ala Gln His
    850                 855                 860

Pro Pro Cys Gln Leu Ile Ile Leu Glu Glu Leu Ser Lys Leu Met Ala
865                 870                 875                 880

Trp Gly His Arg Gly Ile Leu Glu Glu Leu Val Asn Gln Ala Gln Val
                885                 890                 895

His Asp Val Leu Val Gly Thr Val Tyr Ala Ala Phe Ser Ser Arg Phe
            900                 905                 910

Asp Ala Arg Thr Gly Ala Pro Gly Val Arg Cys Arg Arg Val Pro Ala
        915                 920                 925

Arg Phe Val Gly Ala Thr Val Asp Asp Ser Leu Pro Leu Trp Leu Thr
    930                 935                 940

Glu Phe Leu Asp Lys His Arg Leu Asp Lys Asn Leu Leu Arg Pro Asp
945                 950                 955                 960

Asp Val Ile Pro Thr Gly Glu Gly Glu Phe Leu Val Ser Pro Cys Gly
                965                 970                 975

Glu Glu Ala Ala Arg Val Arg Gln Val His Ala Asp Ile Asn Ala Ala
            980                 985                 990

Gln Asn Leu Gln Arg Arg Leu Trp  Gln Asn Phe Asp Ile  Thr Glu Leu
        995                 1000                1005
```

```
Arg Leu  Arg Cys Asp Val Lys  Met Gly Gly Glu Gly  Thr Val Leu
    1010                 1015                 1020

Val Pro  Arg Val Asn Asn Ala  Arg Ala Lys Gln Leu  Phe Gly Lys
    1025                 1030                 1035

Lys Val  Leu Val Ser Gln Asp  Gly Val Thr Phe Phe  Glu Arg Ser
    1040                 1045                 1050

Gln Thr  Gly Gly Lys Pro His  Ser Glu Lys Gln Thr  Asp Leu Thr
    1055                 1060                 1065

Asp Lys  Glu Leu Glu Leu Ile  Ala Glu Ala Asp Glu  Ala Arg Ala
    1070                 1075                 1080

Lys Ser  Val Val Leu Phe Arg  Asp Pro Ser Gly His  Ile Gly Lys
    1085                 1090                 1095

Gly His  Trp Ile Arg Gln Arg  Glu Phe Trp Ser Leu  Val Lys Gln
    1100                 1105                 1110

Arg Ile  Glu Ser His Thr Ala  Glu Arg Ile Arg Val  Arg Gly Val
    1115                 1120                 1125

Gly Ser  Ser Leu Asp
    1130


<210> SEQ ID NO 38
<211> LENGTH: 1147
<212> TYPE: PRT
<213> ORGANISM: Alicyclobacillus kakegawensis

<400> SEQUENCE: 38

Met Ala Val Lys Ser Ile Lys Val Lys Leu Arg Leu Ser Glu Cys Pro
1               5                   10                  15

Asp Ile Leu Ala Gly Met Trp Gln Leu His Arg Ala Thr Asn Ala Gly
            20                  25                  30

Val Arg Tyr Tyr Thr Glu Trp Val Ser Leu Met Arg Gln Glu Ile Leu
        35                  40                  45

Tyr Ser Arg Gly Pro Asp Gly Gly Gln Gln Cys Tyr Met Thr Ala Glu
    50                  55                  60

Asp Cys Gln Arg Glu Leu Leu Arg Arg Leu Arg Asn Arg Gln Leu His
65                  70                  75                  80

Asn Gly Arg Gln Asp Gln Pro Gly Thr Asp Ala Asp Leu Leu Ala Ile
                85                  90                  95

Ser Arg Arg Leu Tyr Glu Ile Leu Val Leu Gln Ser Ile Gly Lys Arg
            100                 105                 110

Gly Asp Ala Gln Gln Ile Ala Ser Ser Phe Leu Ser Pro Leu Val Asp
        115                 120                 125

Pro Asn Ser Lys Gly Gly Arg Gly Glu Ala Lys Ser Gly Arg Lys Pro
    130                 135                 140

Ala Trp Gln Lys Met Arg Asp Gln Gly Asp Pro Arg Trp Val Ala Ala
145                 150                 155                 160

Arg Glu Lys Tyr Glu Gln Arg Lys Ala Val Asp Pro Ser Lys Glu Ile
                165                 170                 175

Leu Asn Ser Leu Asp Ala Leu Gly Leu Arg Pro Leu Phe Ala Val Phe
            180                 185                 190

Thr Glu Thr Tyr Arg Ser Gly Val Asp Trp Lys Pro Leu Gly Lys Ser
        195                 200                 205

Gln Gly Val Arg Thr Trp Asp Arg Asp Met Phe Gln Gln Ala Leu Glu
    210                 215                 220

Arg Leu Met Ser Trp Glu Ser Trp Asn Arg Arg Val Gly Glu Glu Tyr
```

```
225                 230                 235                 240

Ala Arg Leu Phe Gln Gln Lys Met Lys Phe Glu Gln Glu His Phe Ala
                245                 250                 255

Glu Gln Ser His Leu Val Lys Leu Ala Arg Ala Leu Glu Ala Asp Met
            260                 265                 270

Arg Ala Ala Ser Gln Gly Phe Glu Ala Lys Arg Gly Thr Ala His Gln
        275                 280                 285

Ile Thr Arg Arg Ala Leu Arg Gly Ala Asp Arg Val Phe Glu Ile Trp
    290                 295                 300

Lys Ser Ile Pro Glu Glu Ala Leu Phe Ser Gln Tyr Asp Glu Val Ile
305                 310                 315                 320

Arg Gln Val Gln Ala Glu Lys Arg Arg Asp Phe Gly Ser His Asp Leu
                325                 330                 335

Phe Ala Lys Leu Ala Glu Pro Lys Tyr Gln Pro Leu Trp Arg Ala Asp
            340                 345                 350

Glu Thr Phe Leu Thr Arg Tyr Ala Leu Tyr Asn Gly Val Leu Arg Asp
        355                 360                 365

Leu Glu Lys Ala Arg Gln Phe Ala Thr Phe Thr Leu Pro Asp Ala Cys
    370                 375                 380

Val Asn Pro Ile Trp Thr Arg Phe Glu Ser Ser Gln Gly Ser Asn Leu
385                 390                 395                 400

His Lys Tyr Glu Phe Leu Phe Asp His Leu Gly Pro Gly Arg His Ala
                405                 410                 415

Val Arg Phe Gln Arg Leu Leu Val Val Glu Ser Glu Gly Ala Lys Glu
            420                 425                 430

Arg Asp Ser Val Val Val Pro Val Ala Pro Ser Gly Gln Leu Asp Lys
        435                 440                 445

Leu Val Leu Arg Glu Glu Glu Lys Ser Ser Val Ala Leu His Leu His
    450                 455                 460

Asp Thr Ala Arg Pro Asp Gly Phe Met Ala Glu Trp Ala Gly Ala Lys
465                 470                 475                 480

Leu Gln Tyr Glu Arg Ser Thr Leu Ala Arg Lys Ala Arg Arg Asp Lys
                485                 490                 495

Gln Gly Met Arg Ser Trp Arg Arg Gln Pro Ser Met Leu Met Ser Ala
            500                 505                 510

Ala Gln Met Leu Glu Asp Ala Lys Gln Ala Gly Asp Val Tyr Leu Asn
        515                 520                 525

Ile Ser Val Arg Val Lys Ser Pro Ser Glu Val Arg Gly Gln Arg Arg
    530                 535                 540

Pro Pro Tyr Ala Ala Leu Phe Arg Ile Asp Asp Lys Gln Arg Arg Val
545                 550                 555                 560

Thr Val Asn Tyr Asn Lys Leu Ser Ala Tyr Leu Glu Glu His Pro Asp
                565                 570                 575

Lys Gln Ile Pro Gly Ala Pro Gly Leu Leu Ser Gly Leu Arg Val Met
            580                 585                 590

Ser Val Asp Leu Gly Leu Arg Thr Ser Ala Ser Ile Ser Val Phe Arg
        595                 600                 605

Val Ala Lys Lys Glu Glu Val Glu Ala Leu Gly Asp Gly Arg Pro Pro
    610                 615                 620

His Tyr Tyr Pro Ile His Gly Thr Asp Asp Leu Val Ala Val His Glu
625                 630                 635                 640

Arg Ser His Leu Ile Gln Met Pro Gly Glu Thr Glu Thr Lys Gln Leu
                645                 650                 655
```

```
Arg Lys Leu Arg Glu Glu Arg Gln Ala Val Leu Arg Pro Leu Phe Ala
            660                 665                 670

Gln Leu Ala Leu Leu Arg Leu Leu Val Arg Cys Gly Ala Ala Asp Glu
        675                 680                 685

Arg Ile Arg Thr Arg Ser Trp Gln Arg Leu Thr Lys Gln Gly Arg Glu
    690                 695                 700

Phe Thr Lys Arg Leu Thr Pro Ser Trp Arg Glu Ala Leu Glu Leu Glu
705                 710                 715                 720

Leu Thr Arg Leu Glu Ala Tyr Cys Gly Arg Val Pro Asp Asp Glu Trp
                725                 730                 735

Ser Arg Ile Val Asp Arg Thr Val Ile Ala Leu Trp Arg Arg Met Gly
            740                 745                 750

Lys Gln Val Arg Asp Trp Arg Lys Gln Val Lys Ser Gly Ala Lys Val
        755                 760                 765

Lys Val Lys Gly Tyr Gln Leu Asp Val Val Gly Gly Asn Ser Leu Ala
    770                 775                 780

Gln Ile Asp Tyr Leu Glu Gln Gln Tyr Lys Phe Leu Arg Arg Trp Ser
785                 790                 795                 800

Phe Phe Ala Arg Ala Ser Gly Leu Val Val Arg Ala Asp Arg Glu Ser
                805                 810                 815

His Phe Ala Val Ala Leu Arg Gln His Ile Glu Asn Ala Lys Arg Asp
            820                 825                 830

Arg Leu Lys Lys Leu Ala Asp Arg Ile Leu Met Glu Ala Leu Gly Tyr
        835                 840                 845

Val Tyr Glu Ala Ser Gly Pro Arg Glu Gly Gln Trp Thr Ala Gln His
    850                 855                 860

Pro Pro Cys Gln Leu Ile Ile Leu Glu Glu Leu Ser Gly Ala Ala Gly
865                 870                 875                 880

Ala Ala Gly Ala Ala Gly Ala Ala Gly Gly Lys Leu Met Ala Trp Gly
                885                 890                 895

His Arg Gly Ile Leu Glu Glu Leu Val Asn Gln Ala Gln Val His Asp
            900                 905                 910

Val Leu Val Gly Thr Val Tyr Ala Ala Phe Ser Ser Arg Phe Asp Ala
        915                 920                 925

Arg Thr Gly Ala Pro Gly Val Arg Cys Arg Arg Val Pro Ala Arg Phe
    930                 935                 940

Val Gly Ala Thr Val Asp Asp Ser Leu Pro Leu Trp Leu Thr Glu Phe
945                 950                 955                 960

Leu Asp Lys His Arg Leu Asp Lys Asn Leu Leu Arg Pro Asp Asp Val
                965                 970                 975

Ile Pro Thr Gly Glu Gly Glu Phe Leu Val Ser Pro Cys Gly Glu Glu
            980                 985                 990

Ala Ala Arg Val Arg Gln Val His  Ala Asp Ile Asn Ala  Ala Gln Asn
        995                 1000                1005

Leu Gln  Arg Arg Leu Trp Gln  Asn Phe Asp Ile Thr  Glu Leu Arg
    1010                1015                1020

Leu Arg  Cys Asp Val Lys Met  Gly Gly Glu Gly Thr  Val Leu Val
    1025                1030                1035

Pro Arg  Val Asn Asn Ala Arg  Ala Lys Gln Leu Phe  Gly Lys Lys
    1040                1045                1050

Val Leu  Val Ser Gln Asp Gly  Val Thr Phe Phe Glu  Arg Ser Gln
    1055                1060                1065
```

```
Thr Gly  Gly Lys Pro His Ser  Glu Lys Gln Thr Asp  Leu Thr Asp
    1070                1075                1080

Lys Glu  Leu Glu Leu Ile Ala  Glu Ala Asp Glu Ala  Arg Ala Lys
    1085                1090                1095

Ser Val  Val Leu Phe Arg Asp  Pro Ser Gly His Ile  Gly Lys Gly
    1100                1105                1110

His Trp  Ile Arg Gln Arg Glu  Phe Trp Ser Leu Val  Lys Gln Arg
    1115                1120                1125

Ile Glu  Ser His Thr Ala Glu  Arg Ile Arg Val Arg  Gly Val Gly
    1130                1135                1140

Ser Ser  Leu Asp
    1145


<210> SEQ ID NO 39
<211> LENGTH: 1144
<212> TYPE: PRT
<213> ORGANISM: Alicyclobacillus macrosporangiidus

<400> SEQUENCE: 39

Met Ala Val Lys Ser Ile Lys Val Lys Leu Met Leu Gly His Leu Pro
1               5                   10                  15

Glu Ile Arg Glu Gly Leu Trp His Leu His Glu Ala Val Asn Leu Gly
            20                  25                  30

Val Arg Tyr Tyr Thr Glu Trp Leu Ala Leu Leu Arg Gln Gly Asn Leu
        35                  40                  45

Tyr Arg Arg Gly Lys Asp Gly Ala Gln Glu Cys Tyr Met Thr Ala Glu
    50                  55                  60

Gln Cys Arg Gln Glu Leu Leu Val Arg Leu Arg Asp Arg Gln Lys Arg
65                  70                  75                  80

Asn Gly His Thr Gly Asp Pro Gly Thr Asp Glu Glu Leu Leu Gly Val
                85                  90                  95

Ala Arg Arg Leu Tyr Glu Leu Leu Val Pro Gln Ser Val Gly Lys Lys
            100                 105                 110

Gly Gln Ala Gln Met Leu Ala Ser Gly Phe Leu Ser Pro Leu Ala Asp
        115                 120                 125

Pro Lys Ser Glu Gly Gly Lys Gly Thr Ser Lys Ser Gly Arg Lys Pro
    130                 135                 140

Ala Trp Met Gly Met Lys Glu Ala Gly Asp Ser Arg Trp Val Glu Ala
145                 150                 155                 160

Lys Ala Arg Tyr Glu Ala Asn Lys Ala Lys Asp Pro Thr Lys Gln Val
                165                 170                 175

Ile Ala Ser Leu Glu Met Tyr Gly Leu Arg Pro Leu Phe Asp Val Phe
            180                 185                 190

Thr Glu Thr Tyr Lys Thr Ile Arg Trp Met Pro Leu Gly Lys His Gln
        195                 200                 205

Gly Val Arg Ala Trp Asp Arg Asp Met Phe Gln Gln Ser Leu Glu Arg
    210                 215                 220

Leu Met Ser Trp Glu Ser Trp Asn Glu Arg Val Gly Ala Glu Phe Ala
225                 230                 235                 240

Arg Leu Val Asp Arg Arg Asp Arg Phe Arg Glu Lys His Phe Thr Gly
                245                 250                 255

Gln Glu His Leu Val Ala Leu Ala Gln Arg Leu Glu Gln Glu Met Lys
            260                 265                 270

Glu Ala Ser Pro Gly Phe Glu Ser Lys Ser Ser Gln Ala His Arg Ile
        275                 280                 285
```

```
Thr Lys Arg Ala Leu Arg Gly Ala Asp Gly Ile Ile Asp Asp Trp Leu
    290                 295                 300

Lys Leu Ser Glu Gly Glu Pro Val Asp Arg Phe Asp Glu Ile Leu Arg
305                 310                 315                 320

Lys Arg Gln Ala Gln Asn Pro Arg Arg Phe Gly Ser His Asp Leu Phe
                325                 330                 335

Leu Lys Leu Ala Glu Pro Val Phe Gln Pro Leu Trp Arg Glu Asp Pro
            340                 345                 350

Ser Phe Leu Ser Arg Trp Ala Ser Tyr Asn Glu Val Leu Asn Lys Leu
        355                 360                 365

Glu Asp Ala Lys Gln Phe Ala Thr Phe Thr Leu Pro Ser Pro Cys Ser
    370                 375                 380

Asn Pro Val Trp Ala Arg Phe Glu Asn Ala Glu Gly Thr Asn Ile Phe
385                 390                 395                 400

Lys Tyr Asp Phe Leu Phe Asp His Phe Gly Lys Gly Arg His Gly Val
                405                 410                 415

Arg Phe Gln Arg Met Ile Val Met Arg Asp Gly Val Pro Thr Glu Val
            420                 425                 430

Glu Gly Ile Val Val Pro Ile Ala Pro Ser Arg Gln Leu Asp Ala Leu
        435                 440                 445

Ala Pro Asn Asp Ala Ala Ser Pro Ile Asp Val Phe Val Gly Asp Pro
    450                 455                 460

Ala Ala Pro Gly Ala Phe Arg Gly Gln Phe Gly Gly Ala Lys Ile Gln
465                 470                 475                 480

Tyr Arg Arg Ser Ala Leu Val Arg Lys Gly Arg Arg Glu Glu Lys Ala
                485                 490                 495

Tyr Leu Cys Gly Phe Arg Leu Pro Ser Gln Arg Arg Thr Gly Thr Pro
            500                 505                 510

Ala Asp Asp Ala Gly Glu Val Phe Leu Asn Leu Ser Leu Arg Val Glu
        515                 520                 525

Ser Gln Ser Glu Gln Ala Gly Arg Arg Asn Pro Pro Tyr Ala Ala Val
    530                 535                 540

Phe His Ile Ser Asp Gln Thr Arg Arg Val Ile Val Arg Tyr Gly Glu
545                 550                 555                 560

Ile Glu Arg Tyr Leu Ala Glu His Pro Asp Thr Gly Ile Pro Gly Ser
                565                 570                 575

Arg Gly Leu Thr Ser Gly Leu Arg Val Met Ser Val Asp Leu Gly Leu
            580                 585                 590

Arg Thr Ser Ala Ala Ile Ser Val Phe Arg Val Ala His Arg Asp Glu
        595                 600                 605

Leu Thr Pro Asp Ala His Gly Arg Gln Pro Phe Phe Phe Pro Ile His
    610                 615                 620

Gly Met Asp His Leu Val Ala Leu His Glu Arg Ser His Leu Ile Arg
625                 630                 635                 640

Leu Pro Gly Glu Thr Glu Ser Lys Lys Val Arg Ser Ile Arg Glu Gln
                645                 650                 655

Arg Leu Asp Arg Leu Asn Arg Leu Arg Ser Gln Met Ala Ser Leu Arg
            660                 665                 670

Leu Leu Val Arg Thr Gly Val Leu Asp Glu Gln Lys Arg Asp Arg Asn
        675                 680                 685

Trp Glu Arg Leu Gln Ser Ser Met Glu Arg Gly Gly Glu Arg Met Pro
    690                 695                 700
```

```
Ser Asp Trp Trp Asp Leu Phe Gln Ala Gln Val Arg Tyr Leu Ala Gln
705                 710                 715                 720

His Arg Asp Ala Ser Gly Glu Ala Trp Gly Arg Met Val Gln Ala Ala
                725                 730                 735

Val Arg Thr Leu Trp Arg Gln Leu Ala Lys Gln Val Arg Asp Trp Arg
            740                 745                 750

Lys Glu Val Arg Arg Asn Ala Asp Lys Val Lys Ile Arg Gly Ile Ala
        755                 760                 765

Arg Asp Val Pro Gly Gly His Ser Leu Ala Gln Leu Asp Tyr Leu Glu
    770                 775                 780

Arg Gln Tyr Arg Phe Leu Arg Ser Trp Ser Ala Phe Ser Val Gln Ala
785                 790                 795                 800

Gly Gln Val Val Arg Ala Glu Arg Asp Ser Arg Phe Ala Val Ala Leu
                805                 810                 815

Arg Glu His Ile Asp Asn Gly Lys Lys Asp Arg Leu Lys Lys Leu Ala
            820                 825                 830

Asp Arg Ile Leu Met Glu Ala Leu Gly Tyr Val Tyr Val Thr Asp Gly
        835                 840                 845

Arg Arg Ala Gly Gln Trp Gln Ala Val Tyr Pro Pro Cys Gln Leu Val
    850                 855                 860

Leu Leu Glu Glu Leu Ser Glu Tyr Arg Phe Ser Asn Asp Arg Pro Pro
865                 870                 875                 880

Ser Glu Asn Ser Gln Leu Met Val Trp Ser His Arg Gly Val Leu Glu
                885                 890                 895

Glu Leu Ile His Gln Ala Gln Val His Asp Val Leu Val Gly Thr Ile
            900                 905                 910

Pro Ala Ala Phe Ser Ser Arg Phe Asp Ala Arg Thr Gly Ala Pro Gly
        915                 920                 925

Ile Arg Cys Arg Arg Val Pro Ser Ile Pro Leu Lys Asp Ala Pro Ser
    930                 935                 940

Ile Pro Ile Trp Leu Ser His Tyr Leu Lys Gln Thr Glu Arg Asp Ala
945                 950                 955                 960

Ala Ala Leu Arg Pro Gly Glu Leu Ile Pro Thr Gly Asp Gly Glu Phe
                965                 970                 975

Leu Val Thr Pro Ala Gly Arg Gly Ala Ser Gly Val Arg Val Val His
            980                 985                 990

Ala Asp Ile Asn Ala Ala His Asn  Leu Gln Arg Arg Leu  Trp Glu Asn
        995                 1000                1005

Phe Asp  Leu Ser Asp Ile Arg  Val Arg Cys Asp Arg  Arg Glu Gly
    1010                1015                1020

Lys Asp  Gly Thr Val Val Leu  Ile Pro Arg Leu Thr  Asn Gln Arg
    1025                1030                1035

Val Lys  Glu Arg Tyr Ser Gly  Val Ile Phe Thr Ser  Glu Asp Gly
    1040                1045                1050

Val Ser  Phe Thr Val Gly Asp  Ala Lys Thr Arg Arg  Arg Ser Ser
    1055                1060                1065

Ala Ser  Gln Gly Glu Gly Asp  Asp Leu Ser Asp Glu  Glu Gln Glu
    1070                1075                1080

Leu Leu  Ala Glu Ala Asp Asp  Ala Arg Glu Arg Ser  Val Val Leu
    1085                1090                1095

Phe Arg  Asp Pro Ser Gly Phe  Val Asn Gly Gly Arg  Trp Thr Ala
    1100                1105                1110

Gln Arg  Ala Phe Trp Gly Met  Val His Asn Arg Ile  Glu Thr Leu
```

1115 1120 1125

Leu Ala Glu Arg Phe Ser Val Ser Gly Ala Ala Glu Lys Val Arg
1130 1135 1140

Gly

<210> SEQ ID NO 40
<211> LENGTH: 1130
<212> TYPE: PRT
<213> ORGANISM: Alicyclobacillus macrosporangiidus

<400> SEQUENCE: 40

Met Ala Val Lys Ser Ile Lys Val Lys Leu Met Leu Gly His Leu Pro
1 5 10 15

Glu Ile Arg Glu Gly Leu Trp His Leu His Glu Ala Val Asn Leu Gly
20 25 30

Val Arg Tyr Tyr Thr Glu Trp Leu Ala Leu Leu Arg Gln Gly Asn Leu
35 40 45

Tyr Arg Arg Gly Lys Asp Gly Ala Gln Glu Cys Tyr Met Thr Ala Glu
50 55 60

Gln Cys Arg Gln Glu Leu Leu Val Arg Leu Arg Asp Arg Gln Lys Arg
65 70 75 80

Asn Gly His Thr Gly Asp Pro Gly Thr Asp Glu Glu Leu Leu Gly Val
85 90 95

Ala Arg Arg Leu Tyr Glu Leu Leu Val Pro Gln Ser Val Gly Lys Lys
100 105 110

Gly Gln Ala Gln Met Leu Ala Ser Gly Phe Leu Ser Pro Leu Ala Asp
115 120 125

Pro Lys Ser Glu Gly Gly Lys Gly Thr Ser Lys Ser Gly Arg Lys Pro
130 135 140

Ala Trp Met Gly Met Lys Glu Ala Gly Asp Ser Arg Trp Val Glu Ala
145 150 155 160

Lys Ala Arg Tyr Glu Ala Asn Lys Ala Lys Asp Pro Thr Lys Gln Val
165 170 175

Ile Ala Ser Leu Glu Met Tyr Gly Leu Arg Pro Leu Phe Asp Val Phe
180 185 190

Thr Glu Thr Tyr Lys Thr Ile Arg Trp Met Pro Leu Gly Lys His Gln
195 200 205

Gly Val Arg Ala Trp Asp Arg Asp Met Phe Gln Gln Ser Leu Glu Arg
210 215 220

Leu Met Ser Trp Glu Ser Trp Asn Glu Arg Val Gly Ala Glu Phe Ala
225 230 235 240

Arg Leu Val Asp Arg Arg Asp Arg Phe Arg Glu Lys His Phe Thr Gly
245 250 255

Gln Glu His Leu Val Ala Leu Ala Gln Arg Leu Glu Gln Glu Met Lys
260 265 270

Glu Ala Ser Pro Gly Phe Glu Ser Lys Ser Ser Gln Ala His Arg Ile
275 280 285

Thr Lys Arg Ala Leu Arg Gly Ala Asp Gly Ile Ile Asp Asp Trp Leu
290 295 300

Lys Leu Ser Glu Gly Glu Pro Val Asp Arg Phe Asp Glu Ile Leu Arg
305 310 315 320

Lys Arg Gln Ala Gln Asn Pro Arg Arg Phe Gly Ser His Asp Leu Phe
325 330 335

Leu Lys Leu Ala Glu Pro Val Phe Gln Pro Leu Trp Arg Glu Asp Pro

```
            340                 345                 350

Ser Phe Leu Ser Arg Trp Ala Ser Tyr Asn Glu Val Leu Asn Lys Leu
        355                 360                 365

Glu Asp Ala Lys Gln Phe Ala Thr Phe Thr Leu Pro Ser Pro Cys Ser
    370                 375                 380

Asn Pro Val Trp Ala Arg Phe Glu Asn Ala Glu Gly Thr Asn Ile Phe
385                 390                 395                 400

Lys Tyr Asp Phe Leu Phe Asp His Phe Gly Lys Gly Arg His Gly Val
                405                 410                 415

Arg Phe Gln Arg Met Ile Val Met Arg Asp Gly Val Pro Thr Glu Val
            420                 425                 430

Glu Gly Ile Val Val Pro Ile Ala Pro Ser Arg Gln Leu Asp Ala Leu
        435                 440                 445

Ala Pro Asn Asp Ala Ala Ser Pro Ile Asp Val Phe Val Gly Asp Pro
    450                 455                 460

Ala Ala Pro Gly Ala Phe Arg Gly Gln Phe Gly Gly Ala Lys Ile Gln
465                 470                 475                 480

Tyr Arg Arg Ser Ala Leu Val Arg Lys Gly Arg Arg Glu Glu Lys Ala
                485                 490                 495

Tyr Leu Cys Gly Phe Arg Leu Pro Ser Gln Arg Arg Thr Gly Thr Pro
            500                 505                 510

Ala Asp Asp Ala Gly Glu Val Phe Leu Asn Leu Ser Leu Arg Val Glu
        515                 520                 525

Ser Gln Ser Glu Gln Ala Gly Arg Arg Asn Pro Pro Tyr Ala Ala Val
    530                 535                 540

Phe His Ile Ser Asp Gln Thr Arg Arg Val Ile Val Arg Tyr Gly Glu
545                 550                 555                 560

Ile Glu Arg Tyr Leu Ala Glu His Pro Asp Thr Gly Ile Pro Gly Ser
                565                 570                 575

Arg Gly Leu Thr Ser Gly Leu Arg Val Met Ser Val Asp Leu Gly Leu
            580                 585                 590

Arg Thr Ser Ala Ala Ile Ser Val Phe Arg Val Ala His Arg Asp Glu
        595                 600                 605

Leu Thr Pro Asp Ala His Gly Arg Gln Pro Phe Phe Phe Pro Ile His
    610                 615                 620

Gly Met Asp His Leu Val Ala Leu His Glu Arg Ser His Leu Ile Arg
625                 630                 635                 640

Leu Pro Gly Glu Thr Glu Ser Lys Lys Val Arg Ser Ile Arg Glu Gln
                645                 650                 655

Arg Leu Asp Arg Leu Asn Arg Leu Arg Ser Gln Met Ala Ser Leu Arg
            660                 665                 670

Leu Leu Val Arg Thr Gly Val Leu Asp Glu Gln Lys Arg Asp Arg Asn
        675                 680                 685

Trp Glu Arg Leu Gln Ser Ser Met Glu Arg Gly Gly Glu Arg Met Pro
    690                 695                 700

Ser Asp Trp Trp Asp Leu Phe Gln Ala Gln Val Arg Tyr Leu Ala Gln
705                 710                 715                 720

His Arg Asp Ala Ser Gly Glu Ala Trp Gly Arg Met Val Gln Ala Ala
                725                 730                 735

Val Arg Thr Leu Trp Arg Gln Leu Ala Lys Gln Val Arg Asp Trp Arg
            740                 745                 750

Lys Glu Val Arg Arg Asn Ala Asp Lys Val Lys Ile Arg Gly Ile Ala
        755                 760                 765
```

```
Arg Asp Val Pro Gly Gly His Ser Leu Ala Gln Leu Asp Tyr Leu Glu
    770                 775                 780

Arg Gln Tyr Arg Phe Leu Arg Ser Trp Ser Ala Phe Ser Val Gln Ala
785                 790                 795                 800

Gly Gln Val Val Arg Ala Glu Arg Asp Ser Arg Phe Ala Val Ala Leu
                805                 810                 815

Arg Glu His Ile Asp Asn Gly Lys Lys Asp Arg Leu Lys Lys Leu Ala
            820                 825                 830

Asp Arg Ile Leu Met Glu Ala Leu Gly Tyr Val Tyr Val Thr Asp Gly
        835                 840                 845

Arg Arg Ala Gly Gln Trp Gln Ala Val Tyr Pro Pro Cys Gln Leu Val
    850                 855                 860

Leu Leu Glu Glu Leu Ser Gln Leu Met Val Trp Ser His Arg Gly Val
865                 870                 875                 880

Leu Glu Glu Leu Ile His Gln Ala Gln Val His Asp Val Leu Val Gly
                885                 890                 895

Thr Ile Pro Ala Ala Phe Ser Ser Arg Phe Asp Ala Arg Thr Gly Ala
            900                 905                 910

Pro Gly Ile Arg Cys Arg Arg Val Pro Ser Ile Pro Leu Lys Asp Ala
        915                 920                 925

Pro Ser Ile Pro Ile Trp Leu Ser His Tyr Leu Lys Gln Thr Glu Arg
    930                 935                 940

Asp Ala Ala Ala Leu Arg Pro Gly Glu Leu Ile Pro Thr Gly Asp Gly
945                 950                 955                 960

Glu Phe Leu Val Thr Pro Ala Gly Arg Gly Ala Ser Gly Val Arg Val
                965                 970                 975

Val His Ala Asp Ile Asn Ala Ala His Asn Leu Gln Arg Arg Leu Trp
            980                 985                 990

Glu Asn Phe Asp Leu Ser Asp Ile  Arg Val Arg Cys Asp  Arg Arg Glu
        995                 1000                 1005

Gly Lys  Asp Gly Thr Val Val  Leu Ile Pro Arg Leu  Thr Asn Gln
    1010                 1015                 1020

Arg Val  Lys Glu Arg Tyr Ser  Gly Val Ile Phe Thr  Ser Glu Asp
    1025                 1030                 1035

Gly Val  Ser Phe Thr Val Gly  Asp Ala Lys Thr Arg  Arg Arg Ser
    1040                 1045                 1050

Ser Ala  Ser Gln Gly Glu Gly  Asp Asp Leu Ser Asp  Glu Glu Gln
    1055                 1060                 1065

Glu Leu  Leu Ala Glu Ala Asp  Asp Ala Arg Glu Arg  Ser Val Val
    1070                 1075                 1080

Leu Phe  Arg Asp Pro Ser Gly  Phe Val Asn Gly Gly  Arg Trp Thr
    1085                 1090                 1095

Ala Gln  Arg Ala Phe Trp Gly  Met Val His Asn Arg  Ile Glu Thr
    1100                 1105                 1110

Leu Leu  Ala Glu Arg Phe Ser  Val Ser Gly Ala Ala  Glu Lys Val
    1115                 1120                 1125

Arg Gly
    1130
```

<210> SEQ ID NO 41
<211> LENGTH: 1144
<212> TYPE: PRT
<213> ORGANISM: Alicyclobacillus macrosporangiidus

<400> SEQUENCE: 41

```
Met Ala Val Lys Ser Ile Lys Val Lys Leu Met Leu Gly His Leu Pro
1               5                   10                  15

Glu Ile Arg Glu Gly Leu Trp His Leu His Glu Ala Val Asn Leu Gly
            20                  25                  30

Val Arg Tyr Tyr Thr Glu Trp Leu Ala Leu Leu Arg Gln Gly Asn Leu
        35                  40                  45

Tyr Arg Arg Gly Lys Asp Gly Ala Gln Glu Cys Tyr Met Thr Ala Glu
    50                  55                  60

Gln Cys Arg Gln Glu Leu Leu Val Arg Leu Arg Asp Arg Gln Lys Arg
65                  70                  75                  80

Asn Gly His Thr Gly Asp Pro Gly Thr Asp Glu Glu Leu Leu Gly Val
                85                  90                  95

Ala Arg Arg Leu Tyr Glu Leu Leu Val Pro Gln Ser Val Gly Lys Lys
            100                 105                 110

Gly Gln Ala Gln Met Leu Ala Ser Gly Phe Leu Ser Pro Leu Ala Asp
        115                 120                 125

Pro Lys Ser Glu Gly Gly Lys Gly Thr Ser Lys Ser Gly Arg Lys Pro
    130                 135                 140

Ala Trp Met Gly Met Lys Glu Ala Gly Asp Ser Arg Trp Val Glu Ala
145                 150                 155                 160

Lys Ala Arg Tyr Glu Ala Asn Lys Ala Lys Asp Pro Thr Lys Gln Val
                165                 170                 175

Ile Ala Ser Leu Glu Met Tyr Gly Leu Arg Pro Leu Phe Asp Val Phe
            180                 185                 190

Thr Glu Thr Tyr Lys Thr Ile Arg Trp Met Pro Leu Gly Lys His Gln
        195                 200                 205

Gly Val Arg Ala Trp Asp Arg Asp Met Phe Gln Gln Ser Leu Glu Arg
    210                 215                 220

Leu Met Ser Trp Glu Ser Trp Asn Glu Arg Val Gly Ala Glu Phe Ala
225                 230                 235                 240

Arg Leu Val Asp Arg Arg Asp Arg Phe Arg Glu Lys His Phe Thr Gly
                245                 250                 255

Gln Glu His Leu Val Ala Leu Ala Gln Arg Leu Glu Gln Glu Met Lys
            260                 265                 270

Glu Ala Ser Pro Gly Phe Glu Ser Lys Ser Ser Gln Ala His Arg Ile
        275                 280                 285

Thr Lys Arg Ala Leu Arg Gly Ala Asp Gly Ile Ile Asp Asp Trp Leu
    290                 295                 300

Lys Leu Ser Glu Gly Glu Pro Val Asp Arg Phe Asp Glu Ile Leu Arg
305                 310                 315                 320

Lys Arg Gln Ala Gln Asn Pro Arg Arg Phe Gly Ser His Asp Leu Phe
                325                 330                 335

Leu Lys Leu Ala Glu Pro Val Phe Gln Pro Leu Trp Arg Glu Asp Pro
            340                 345                 350

Ser Phe Leu Ser Arg Trp Ala Ser Tyr Asn Glu Val Leu Asn Lys Leu
        355                 360                 365

Glu Asp Ala Lys Gln Phe Ala Thr Phe Thr Leu Pro Ser Pro Cys Ser
    370                 375                 380

Asn Pro Val Trp Ala Arg Phe Glu Asn Ala Glu Gly Thr Asn Ile Phe
385                 390                 395                 400

Lys Tyr Asp Phe Leu Phe Asp His Phe Gly Lys Gly Arg His Gly Val
                405                 410                 415
```

```
Arg Phe Gln Arg Met Ile Val Met Arg Asp Gly Val Pro Thr Glu Val
            420                 425                 430

Glu Gly Ile Val Val Pro Ile Ala Pro Ser Arg Gln Leu Asp Ala Leu
        435                 440                 445

Ala Pro Asn Asp Ala Ala Ser Pro Ile Asp Val Phe Val Gly Asp Pro
    450                 455                 460

Ala Ala Pro Gly Ala Phe Arg Gly Gln Phe Gly Gly Ala Lys Ile Gln
465                 470                 475                 480

Tyr Arg Arg Ser Ala Leu Val Arg Lys Gly Arg Arg Glu Glu Lys Ala
                485                 490                 495

Tyr Leu Cys Gly Phe Arg Leu Pro Ser Gln Arg Arg Thr Gly Thr Pro
            500                 505                 510

Ala Asp Asp Ala Gly Glu Val Phe Leu Asn Leu Ser Leu Arg Val Glu
        515                 520                 525

Ser Gln Ser Glu Gln Ala Gly Arg Arg Asn Pro Pro Tyr Ala Ala Val
    530                 535                 540

Phe His Ile Ser Asp Gln Thr Arg Arg Val Ile Val Arg Tyr Gly Glu
545                 550                 555                 560

Ile Glu Arg Tyr Leu Ala Glu His Pro Asp Thr Gly Ile Pro Gly Ser
                565                 570                 575

Arg Gly Leu Thr Ser Gly Leu Arg Val Met Ser Val Asp Leu Gly Leu
            580                 585                 590

Arg Thr Ser Ala Ala Ile Ser Val Phe Arg Val Ala His Arg Asp Glu
        595                 600                 605

Leu Thr Pro Asp Ala His Gly Arg Gln Pro Phe Phe Phe Pro Ile His
    610                 615                 620

Gly Met Asp His Leu Val Ala Leu His Glu Arg Ser His Leu Ile Arg
625                 630                 635                 640

Leu Pro Gly Glu Thr Glu Ser Lys Lys Val Arg Ser Ile Arg Glu Gln
                645                 650                 655

Arg Leu Asp Arg Leu Asn Arg Leu Arg Ser Gln Met Ala Ser Leu Arg
            660                 665                 670

Leu Leu Val Arg Thr Gly Val Leu Asp Glu Gln Lys Arg Asp Arg Asn
        675                 680                 685

Trp Glu Arg Leu Gln Ser Ser Met Glu Arg Gly Gly Glu Arg Met Pro
    690                 695                 700

Ser Asp Trp Trp Asp Leu Phe Gln Ala Gln Val Arg Tyr Leu Ala Gln
705                 710                 715                 720

His Arg Asp Ala Ser Gly Glu Ala Trp Gly Arg Met Val Gln Ala Ala
                725                 730                 735

Val Arg Thr Leu Trp Arg Gln Leu Ala Lys Gln Val Arg Asp Trp Arg
            740                 745                 750

Lys Glu Val Arg Arg Asn Ala Asp Lys Val Lys Ile Arg Gly Ile Ala
        755                 760                 765

Arg Asp Val Pro Gly Gly His Ser Leu Ala Gln Leu Asp Tyr Leu Glu
    770                 775                 780

Arg Gln Tyr Arg Phe Leu Arg Ser Trp Ser Ala Phe Ser Val Gln Ala
785                 790                 795                 800

Gly Gln Val Val Arg Ala Glu Arg Asp Ser Arg Phe Ala Val Ala Leu
                805                 810                 815

Arg Glu His Ile Asp Asn Gly Lys Lys Asp Arg Leu Lys Lys Leu Ala
            820                 825                 830
```

Asp Arg Ile Leu Met Glu Ala Leu Gly Tyr Val Tyr Val Thr Asp Gly
835 840 845

Arg Arg Ala Gly Gln Trp Gln Ala Val Tyr Pro Pro Cys Gln Leu Val
850 855 860

Leu Leu Glu Glu Leu Ser Gly Ala Ala Gly Ala Ala Gly Ala Ala Gly
865 870 875 880

Ala Ala Gly Gly Gln Leu Met Val Trp Ser His Arg Gly Val Leu Glu
885 890 895

Glu Leu Ile His Gln Ala Gln Val His Asp Val Leu Val Gly Thr Ile
900 905 910

Pro Ala Ala Phe Ser Ser Arg Phe Asp Ala Arg Thr Gly Ala Pro Gly
915 920 925

Ile Arg Cys Arg Arg Val Pro Ser Ile Pro Leu Lys Asp Ala Pro Ser
930 935 940

Ile Pro Ile Trp Leu Ser His Tyr Leu Lys Gln Thr Glu Arg Asp Ala
945 950 955 960

Ala Ala Leu Arg Pro Gly Glu Leu Ile Pro Thr Gly Asp Gly Glu Phe
965 970 975

Leu Val Thr Pro Ala Gly Arg Gly Ala Ser Gly Val Arg Val Val His
980 985 990

Ala Asp Ile Asn Ala Ala His Asn Leu Gln Arg Arg Leu Trp Glu Asn
995 1000 1005

Phe Asp Leu Ser Asp Ile Arg Val Arg Cys Asp Arg Arg Glu Gly
1010 1015 1020

Lys Asp Gly Thr Val Val Leu Ile Pro Arg Leu Thr Asn Gln Arg
1025 1030 1035

Val Lys Glu Arg Tyr Ser Gly Val Ile Phe Thr Ser Glu Asp Gly
1040 1045 1050

Val Ser Phe Thr Val Gly Asp Ala Lys Thr Arg Arg Arg Ser Ser
1055 1060 1065

Ala Ser Gln Gly Glu Gly Asp Asp Leu Ser Asp Glu Glu Gln Glu
1070 1075 1080

Leu Leu Ala Glu Ala Asp Asp Ala Arg Glu Arg Ser Val Val Leu
1085 1090 1095

Phe Arg Asp Pro Ser Gly Phe Val Asn Gly Gly Arg Trp Thr Ala
1100 1105 1110

Gln Arg Ala Phe Trp Gly Met Val His Asn Arg Ile Glu Thr Leu
1115 1120 1125

Leu Ala Glu Arg Phe Ser Val Ser Gly Ala Ala Glu Lys Val Arg
1130 1135 1140

Gly

<210> SEQ ID NO 42
<211> LENGTH: 1115
<212> TYPE: PRT
<213> ORGANISM: Alicyclobacillus hesperidum

<400> SEQUENCE: 42

Met Thr Val Arg Ser Ile Arg Val Lys Leu Ala Val Gly Ser Pro Gln
1 5 10 15

Tyr Arg Asp Val Arg Arg Gly Leu Trp Lys Thr His Glu Ile Met Asn
20 25 30

Gln Gly Val Arg Tyr Tyr Cys Glu Trp Leu Val Leu Met Arg Gln Glu
35 40 45

```
Pro Ile Tyr Asp Glu Asp Glu His Gly Leu Thr Val Val Gln Arg Thr
    50                  55                  60

Arg Glu Asp Ile Gln Ala Glu Leu Leu Ser Arg Leu Arg Thr Leu Gln
65                  70                  75                  80

Ser Ala His Gln His Ser Gly Asp Met Gly Thr Asp Glu Glu Leu Leu
                85                  90                  95

Ser Leu Met Arg Gln Leu Tyr Glu Gln Leu Val Pro Ser Ser Val Asp
            100                 105                 110

Lys Asn Lys Ser Gly Asp Ala Arg Met Ile Ala Arg Asn Phe Phe Asn
        115                 120                 125

Pro Leu Thr Asn Pro Asn Ser Gln Gly Gly Leu Gly Ile Ser Asn Ala
    130                 135                 140

Gly Arg Lys Pro Lys Trp Leu Leu Lys Lys Leu Ser Gly Asp Pro Thr
145                 150                 155                 160

Trp Glu Glu Asp Tyr Lys Lys Ala Met Glu Gln Lys Gln Glu Ser Ser
                165                 170                 175

Val Ser Phe Leu Leu Leu Glu Leu Arg Arg Phe Gly Leu His Pro Ile
            180                 185                 190

Phe Leu Pro Tyr Thr Asp Thr Val Leu Glu Val Ser Trp Ala Pro Lys
        195                 200                 205

Lys Ala Arg Gln Trp Val Arg Lys Trp Asp Tyr Asp Leu Phe Gln Gln
    210                 215                 220

Ser Ile Glu Arg Met Leu Ser Trp Glu Ser Trp Thr Arg Arg Val Lys
225                 230                 235                 240

Glu Arg Phe Glu Lys Leu Val Glu Ser Glu Lys Lys Phe Tyr Asp Glu
                245                 250                 255

Asn Phe Ala Thr Asp Pro Glu Phe Ile Lys Leu Ala Glu Thr Leu Glu
            260                 265                 270

Gly Glu Leu Gln Ala Ser Ser Gln Gly Phe Val Ala Val Asp Glu His
        275                 280                 285

Ala Phe Gln Ile Arg Pro Arg Ser Met Arg Gly Phe Asp Arg Val Ala
    290                 295                 300

Asp Glu Trp Cys Lys Leu Ala Asp Asp Ala Pro Ile Glu Glu Tyr Glu
305                 310                 315                 320

Ala Ala Ile Lys Arg Val Gln Ala Arg Leu Gly Arg Asn Phe Gly Ser
                325                 330                 335

Tyr Val Leu Phe Ala His Leu Ala Lys Pro Glu Tyr Trp Ser Leu Trp
            340                 345                 350

Arg Ser Asp Pro Thr Lys Ile Leu Arg Phe Ala Arg Leu Arg Ala Leu
        355                 360                 365

Gln Arg Ala Val Ala Arg Ala Lys Arg His Ala Arg Leu Thr Leu Pro
    370                 375                 380

Asp Ala Ile His His Pro Ile Trp Ile Arg Tyr Asp Ala Lys Gly Lys
385                 390                 395                 400

Asn Ile Tyr Ser Tyr Arg Leu Leu Ile Pro Glu Lys Arg Ser Lys Arg
                405                 410                 415

Tyr Tyr Val Glu Phe Ser Ser Leu Ile Met Pro Asp Gly Glu Asn Arg
            420                 425                 430

Trp Ala Glu His Arg Asn Ile Arg Val Pro Leu Ala Phe Ser Arg Gln
        435                 440                 445

Trp Glu Arg Leu His Phe Ser Ile Met Glu Asp Gly Ser Leu Cys Val
    450                 455                 460

Gln Tyr Arg Asp Pro Gly Val Asp Glu Pro Leu Arg Ala Glu Leu Gly
```

```
465                 470                 475                 480

Gly Ala Lys Ile Gln Phe Asp Arg Arg Tyr Leu Ile Arg Arg Ser Ser
                485                 490                 495

Thr Leu Ser Ala Gly Glu Cys Gly Pro Val Tyr Leu Asn Val Ser Val
            500                 505                 510

Asp Val Asn Pro Ala His Arg Pro Asp Val Gln Val Leu Gln Ser Ala
        515                 520                 525

Lys Leu Val Ser Val Ser Arg Asp Thr Asn Arg Ile Tyr Leu Arg Pro
    530                 535                 540

Glu Asn Leu Ser Ala Tyr Trp Lys Ser Gln Gly Asp Gly Thr Leu Pro
545                 550                 555                 560

Leu Arg Val Met Ser Val Asp Leu Gly Val Arg Ser Ser Ala Ala Val
                565                 570                 575

Val Ile Cys Arg Leu Glu His Arg Asp Ser Val Val Ser Ser Gly Arg
            580                 585                 590

Arg Thr Ala Thr Ile Tyr Arg Ile Ala Gly Thr Asp Glu Phe Val Ala
        595                 600                 605

Val Gln Glu Arg Ala Phe Leu Leu Arg Leu Pro Gly Glu Gly Lys Gly
    610                 615                 620

Thr Asn Glu Asp Ala Pro Leu Arg Asp Val Tyr Ala Gln Leu Gly Thr
625                 630                 635                 640

Ile Arg Gln Gly Ile Gln Ile Leu Arg Ser Leu Leu Arg Leu Cys Asp
                645                 650                 655

Thr Lys Thr Pro Asp Glu Arg Gln Glu Ala Leu His Gly Leu Ala Gln
            660                 665                 670

Ser Leu Glu Pro Ser Gly Ala Trp Lys Asp Glu Leu His Pro His Leu
        675                 680                 685

Val Met Leu Gln Gly Val Val His Asp Ser Val Asp Asn Trp Lys Gln
    690                 695                 700

Lys Val Ile Ser Val His Arg Gln Met Glu Arg Ile Leu Gly His Ala
705                 710                 715                 720

Val Arg Glu Trp Lys Val Ala Arg Lys Asn Ala Gly Lys Pro Pro Ile
                725                 730                 735

Arg Arg Gly Ala Gly Gly Leu Ser Leu Arg Arg Ile Arg Gln Leu Glu
            740                 745                 750

Gln Glu Arg Arg Thr Leu Val Ala Trp Ser Asn His Ala Arg Glu Pro
        755                 760                 765

Gly Gln Val Val Arg Ile Lys Arg Gly Thr Gln Val Ala Gln Trp Leu
    770                 775                 780

Val Glu Arg Val Asn His Leu Lys Glu Asp Arg Leu Lys Lys Leu Ala
785                 790                 795                 800

Asp Leu Leu Ile Met Thr Ala Leu Gly Tyr Val Tyr Asp Glu Thr Lys
                805                 810                 815

Pro Ser Gly His Lys Trp Asp Lys Arg Tyr Pro Pro Cys Gln Ile Ile
            820                 825                 830

Leu Met Glu Asp Leu Ser Arg Tyr Arg Phe Gln Ser Asp Arg Pro Pro
        835                 840                 845

Ser Glu Asn Ser Gln Leu Met Ala Trp Ser His Arg Arg Leu Leu Glu
    850                 855                 860

Ile Leu Lys Leu Gln Ala Asp Leu His Lys Leu Ile Val Gly Thr Val
865                 870                 875                 880

Phe Pro Ala Phe Ser Ser Arg Phe Asp Ala Gln Ser Gly Ala Pro Gly
                885                 890                 895
```

```
Val Arg Cys Arg Ser Val Lys Lys Gln Asp Ile Glu Asn Ala Ala Gln
            900                 905                 910

Gly Lys Gly Trp Leu Ala Arg Glu Leu Gln Arg Leu Asn Trp Thr Leu
        915                 920                 925

Glu Trp Leu Gln Pro Asn Asp Leu Ile Pro Thr Gly Asp Gly Glu Leu
    930                 935                 940

Phe Val Thr Pro Ala Cys Cys Asp Arg Gln Lys Gly Ile Lys Ile Val
945                 950                 955                 960

His Ala Asp Leu Asn Ala Ala Gln Asn Leu Gln Arg Arg Phe Trp Gly
                965                 970                 975

Gly His Ala Glu Ser Leu Cys Arg Val Thr Cys Asp Val Val Glu Arg
            980                 985                 990

Asp Gly Arg Arg Tyr Ala Val Pro  Arg Ile Ser Asn Ala  Phe Ala Asp
        995                 1000                1005

Ser Phe  Tyr Lys Val Phe Gly  Gln Gly Val Phe Val  Ser Thr Asp
    1010                1015                1020

Glu Glu  Asp Val Tyr Arg Trp  Met Val Gly Glu Lys  Ile Ser Ser
    1025                1030                1035

Arg Gly  Arg Ser Arg Gly Arg  Thr Ser Asp Glu Glu  Ala Glu Ala
    1040                1045                1050

Glu Thr  Trp Ile Asp Glu Ala  Arg Glu Gln Gln Gly  Lys Val Ile
    1055                1060                1065

Ala Leu  Phe Arg Asp Ala Ser  Gly Gln Ile His Gly  Gly Asp Trp
    1070                1075                1080

Leu Val  Ala Lys Val Phe Trp  Gly Trp Val Glu Arg  Leu Val Thr
    1085                1090                1095

Ala Arg  Leu Leu Ser Arg Met  Ser Glu Arg Glu Ala  Ala Ala His
    1100                1105                1110

Lys Glu
    1115


<210> SEQ ID NO 43
<211> LENGTH: 1101
<212> TYPE: PRT
<213> ORGANISM: Alicyclobacillus hesperidum

<400> SEQUENCE: 43

Met Thr Val Arg Ser Ile Arg Val Lys Leu Ala Val Gly Ser Pro Gln
1               5                   10                  15

Tyr Arg Asp Val Arg Arg Gly Leu Trp Lys Thr His Glu Ile Met Asn
            20                  25                  30

Gln Gly Val Arg Tyr Tyr Cys Glu Trp Leu Val Leu Met Arg Gln Glu
        35                  40                  45

Pro Ile Tyr Asp Glu Asp Glu His Gly Leu Thr Val Val Gln Arg Thr
    50                  55                  60

Arg Glu Asp Ile Gln Ala Glu Leu Leu Ser Arg Leu Arg Thr Leu Gln
65                  70                  75                  80

Ser Ala His Gln His Ser Gly Asp Met Gly Thr Asp Glu Glu Leu Leu
                85                  90                  95

Ser Leu Met Arg Gln Leu Tyr Glu Gln Leu Val Pro Ser Ser Val Asp
            100                 105                 110

Lys Asn Lys Ser Gly Asp Ala Arg Met Ile Ala Arg Asn Phe Phe Asn
        115                 120                 125

Pro Leu Thr Asn Pro Asn Ser Gln Gly Gly Leu Gly Ile Ser Asn Ala
```

```
    130                 135                 140

Gly Arg Lys Pro Lys Trp Leu Leu Lys Lys Leu Ser Gly Asp Pro Thr
145                 150                 155                 160

Trp Glu Glu Asp Tyr Lys Lys Ala Met Glu Gln Lys Gln Glu Ser Ser
                165                 170                 175

Val Ser Phe Leu Leu Leu Glu Leu Arg Arg Phe Gly Leu His Pro Ile
            180                 185                 190

Phe Leu Pro Tyr Thr Asp Thr Val Leu Glu Val Ser Trp Ala Pro Lys
        195                 200                 205

Lys Ala Arg Gln Trp Val Arg Lys Trp Asp Tyr Asp Leu Phe Gln Gln
    210                 215                 220

Ser Ile Glu Arg Met Leu Ser Trp Glu Ser Trp Thr Arg Arg Val Lys
225                 230                 235                 240

Glu Arg Phe Glu Lys Leu Val Glu Ser Glu Lys Lys Phe Tyr Asp Glu
                245                 250                 255

Asn Phe Ala Thr Asp Pro Glu Phe Ile Lys Leu Ala Glu Thr Leu Glu
            260                 265                 270

Gly Glu Leu Gln Ala Ser Ser Gln Gly Phe Val Ala Val Asp Glu His
        275                 280                 285

Ala Phe Gln Ile Arg Pro Arg Ser Met Arg Gly Phe Asp Arg Val Ala
    290                 295                 300

Asp Glu Trp Cys Lys Leu Ala Asp Asp Ala Pro Ile Glu Glu Tyr Glu
305                 310                 315                 320

Ala Ala Ile Lys Arg Val Gln Ala Arg Leu Gly Arg Asn Phe Gly Ser
                325                 330                 335

Tyr Val Leu Phe Ala His Leu Ala Lys Pro Glu Tyr Trp Ser Leu Trp
            340                 345                 350

Arg Ser Asp Pro Thr Lys Ile Leu Arg Phe Ala Arg Leu Arg Ala Leu
        355                 360                 365

Gln Arg Ala Val Ala Arg Ala Lys Arg His Ala Arg Leu Thr Leu Pro
    370                 375                 380

Asp Ala Ile His His Pro Ile Trp Ile Arg Tyr Asp Ala Lys Gly Lys
385                 390                 395                 400

Asn Ile Tyr Ser Tyr Arg Leu Leu Ile Pro Glu Lys Arg Ser Lys Arg
                405                 410                 415

Tyr Tyr Val Glu Phe Ser Ser Leu Ile Met Pro Asp Gly Glu Asn Arg
            420                 425                 430

Trp Ala Glu His Arg Asn Ile Arg Val Pro Leu Ala Phe Ser Arg Gln
        435                 440                 445

Trp Glu Arg Leu His Phe Ser Ile Met Glu Asp Gly Ser Leu Cys Val
    450                 455                 460

Gln Tyr Arg Asp Pro Gly Val Asp Glu Pro Leu Arg Ala Glu Leu Gly
465                 470                 475                 480

Gly Ala Lys Ile Gln Phe Asp Arg Arg Tyr Leu Ile Arg Arg Ser Ser
                485                 490                 495

Thr Leu Ser Ala Gly Glu Cys Gly Pro Val Tyr Leu Asn Val Ser Val
            500                 505                 510

Asp Val Asn Pro Ala His Arg Pro Asp Val Gln Val Leu Gln Ser Ala
        515                 520                 525

Lys Leu Val Ser Val Ser Arg Asp Thr Asn Arg Ile Tyr Leu Arg Pro
    530                 535                 540

Glu Asn Leu Ser Ala Tyr Trp Lys Ser Gln Gly Asp Gly Thr Leu Pro
545                 550                 555                 560
```

```
Leu Arg Val Met Ser Val Asp Leu Gly Val Arg Ser Ser Ala Ala Val
                565                 570                 575

Val Ile Cys Arg Leu Glu His Arg Asp Ser Val Val Ser Ser Gly Arg
            580                 585                 590

Arg Thr Ala Thr Ile Tyr Arg Ile Ala Gly Thr Asp Glu Phe Val Ala
        595                 600                 605

Val Gln Glu Arg Ala Phe Leu Leu Arg Leu Pro Gly Glu Gly Lys Gly
    610                 615                 620

Thr Asn Glu Asp Ala Pro Leu Arg Asp Val Tyr Ala Gln Leu Gly Thr
625                 630                 635                 640

Ile Arg Gln Gly Ile Gln Ile Leu Arg Ser Leu Leu Arg Leu Cys Asp
                645                 650                 655

Thr Lys Thr Pro Asp Glu Arg Gln Glu Ala Leu His Gly Leu Ala Gln
            660                 665                 670

Ser Leu Glu Pro Ser Gly Ala Trp Lys Asp Glu Leu His Pro His Leu
        675                 680                 685

Val Met Leu Gln Gly Val Val His Asp Ser Val Asp Asn Trp Lys Gln
    690                 695                 700

Lys Val Ile Ser Val His Arg Gln Met Glu Arg Ile Leu Gly His Ala
705                 710                 715                 720

Val Arg Glu Trp Lys Val Ala Arg Lys Asn Ala Gly Lys Pro Pro Ile
                725                 730                 735

Arg Arg Gly Ala Gly Gly Leu Ser Leu Arg Arg Ile Arg Gln Leu Glu
            740                 745                 750

Gln Glu Arg Arg Thr Leu Val Ala Trp Ser Asn His Ala Arg Glu Pro
        755                 760                 765

Gly Gln Val Val Arg Ile Lys Arg Gly Thr Gln Val Ala Gln Trp Leu
    770                 775                 780

Val Glu Arg Val Asn His Leu Lys Glu Asp Arg Leu Lys Lys Leu Ala
785                 790                 795                 800

Asp Leu Leu Ile Met Thr Ala Leu Gly Tyr Val Tyr Asp Glu Thr Lys
                805                 810                 815

Pro Ser Gly His Lys Trp Asp Lys Arg Tyr Pro Pro Cys Gln Ile Ile
            820                 825                 830

Leu Met Glu Asp Leu Ser Gln Leu Met Ala Trp Ser His Arg Arg Leu
        835                 840                 845

Leu Glu Ile Leu Lys Leu Gln Ala Asp Leu His Lys Leu Ile Val Gly
    850                 855                 860

Thr Val Phe Pro Ala Phe Ser Ser Arg Phe Asp Ala Gln Ser Gly Ala
865                 870                 875                 880

Pro Gly Val Arg Cys Arg Ser Val Lys Lys Gln Asp Ile Glu Asn Ala
                885                 890                 895

Ala Gln Gly Lys Gly Trp Leu Ala Arg Glu Leu Gln Arg Leu Asn Trp
            900                 905                 910

Thr Leu Glu Trp Leu Gln Pro Asn Asp Leu Ile Pro Thr Gly Asp Gly
        915                 920                 925

Glu Leu Phe Val Thr Pro Ala Cys Cys Asp Arg Gln Lys Gly Ile Lys
    930                 935                 940

Ile Val His Ala Asp Leu Asn Ala Ala Gln Asn Leu Gln Arg Arg Phe
945                 950                 955                 960

Trp Gly Gly His Ala Glu Ser Leu Cys Arg Val Thr Cys Asp Val Val
                965                 970                 975
```

Glu Arg Asp Gly Arg Arg Tyr Ala Val Pro Arg Ile Ser Asn Ala Phe
980 985 990

Ala Asp Ser Phe Tyr Lys Val Phe Gly Gln Gly Val Phe Val Ser Thr
995 1000 1005

Asp Glu Glu Asp Val Tyr Arg Trp Met Val Gly Glu Lys Ile Ser
1010 1015 1020

Ser Arg Gly Arg Ser Arg Gly Arg Thr Ser Asp Glu Glu Ala Glu
1025 1030 1035

Ala Glu Thr Trp Ile Asp Glu Ala Arg Glu Gln Gln Gly Lys Val
1040 1045 1050

Ile Ala Leu Phe Arg Asp Ala Ser Gly Gln Ile His Gly Gly Asp
1055 1060 1065

Trp Leu Val Ala Lys Val Phe Trp Gly Trp Val Glu Arg Leu Val
1070 1075 1080

Thr Ala Arg Leu Leu Ser Arg Met Ser Glu Arg Glu Ala Ala Ala
1085 1090 1095

His Lys Glu
1100

<210> SEQ ID NO 44
<211> LENGTH: 1115
<212> TYPE: PRT
<213> ORGANISM: Alicyclobacillus hesperidum

<400> SEQUENCE: 44

Met Thr Val Arg Ser Ile Arg Val Lys Leu Ala Val Gly Ser Pro Gln
1 5 10 15

Tyr Arg Asp Val Arg Arg Gly Leu Trp Lys Thr His Glu Ile Met Asn
20 25 30

Gln Gly Val Arg Tyr Tyr Cys Glu Trp Leu Val Leu Met Arg Gln Glu
35 40 45

Pro Ile Tyr Asp Glu Asp Glu His Gly Leu Thr Val Val Gln Arg Thr
50 55 60

Arg Glu Asp Ile Gln Ala Glu Leu Leu Ser Arg Leu Arg Thr Leu Gln
65 70 75 80

Ser Ala His Gln His Ser Gly Asp Met Gly Thr Asp Glu Glu Leu Leu
85 90 95

Ser Leu Met Arg Gln Leu Tyr Glu Gln Leu Val Pro Ser Ser Val Asp
100 105 110

Lys Asn Lys Ser Gly Asp Ala Arg Met Ile Ala Arg Asn Phe Phe Asn
115 120 125

Pro Leu Thr Asn Pro Asn Ser Gln Gly Gly Leu Gly Ile Ser Asn Ala
130 135 140

Gly Arg Lys Pro Lys Trp Leu Leu Lys Lys Leu Ser Gly Asp Pro Thr
145 150 155 160

Trp Glu Glu Asp Tyr Lys Lys Ala Met Glu Gln Lys Gln Glu Ser Ser
165 170 175

Val Ser Phe Leu Leu Leu Glu Leu Arg Arg Phe Gly Leu His Pro Ile
180 185 190

Phe Leu Pro Tyr Thr Asp Thr Val Leu Glu Val Ser Trp Ala Pro Lys
195 200 205

Lys Ala Arg Gln Trp Val Arg Lys Trp Asp Tyr Asp Leu Phe Gln Gln
210 215 220

Ser Ile Glu Arg Met Leu Ser Trp Glu Ser Trp Thr Arg Arg Val Lys
225 230 235 240

```
Glu Arg Phe Glu Lys Leu Val Glu Ser Glu Lys Lys Phe Tyr Asp Glu
                245                 250                 255

Asn Phe Ala Thr Asp Pro Glu Phe Ile Lys Leu Ala Glu Thr Leu Glu
            260                 265                 270

Gly Glu Leu Gln Ala Ser Ser Gln Gly Phe Val Ala Val Asp Glu His
        275                 280                 285

Ala Phe Gln Ile Arg Pro Arg Ser Met Arg Gly Phe Asp Arg Val Ala
    290                 295                 300

Asp Glu Trp Cys Lys Leu Ala Asp Asp Ala Pro Ile Glu Glu Tyr Glu
305                 310                 315                 320

Ala Ala Ile Lys Arg Val Gln Ala Arg Leu Gly Arg Asn Phe Gly Ser
                325                 330                 335

Tyr Val Leu Phe Ala His Leu Ala Lys Pro Glu Tyr Trp Ser Leu Trp
            340                 345                 350

Arg Ser Asp Pro Thr Lys Ile Leu Arg Phe Ala Arg Leu Arg Ala Leu
        355                 360                 365

Gln Arg Ala Val Ala Arg Ala Lys Arg His Ala Arg Leu Thr Leu Pro
    370                 375                 380

Asp Ala Ile His His Pro Ile Trp Ile Arg Tyr Asp Ala Lys Gly Lys
385                 390                 395                 400

Asn Ile Tyr Ser Tyr Arg Leu Leu Ile Pro Glu Lys Arg Ser Lys Arg
                405                 410                 415

Tyr Tyr Val Glu Phe Ser Ser Leu Ile Met Pro Asp Gly Glu Asn Arg
            420                 425                 430

Trp Ala Glu His Arg Asn Ile Arg Val Pro Leu Ala Phe Ser Arg Gln
        435                 440                 445

Trp Glu Arg Leu His Phe Ser Ile Met Glu Asp Gly Ser Leu Cys Val
    450                 455                 460

Gln Tyr Arg Asp Pro Gly Val Asp Glu Pro Leu Arg Ala Glu Leu Gly
465                 470                 475                 480

Gly Ala Lys Ile Gln Phe Asp Arg Arg Tyr Leu Ile Arg Arg Ser Ser
                485                 490                 495

Thr Leu Ser Ala Gly Glu Cys Gly Pro Val Tyr Leu Asn Val Ser Val
            500                 505                 510

Asp Val Asn Pro Ala His Arg Pro Asp Val Gln Val Leu Gln Ser Ala
        515                 520                 525

Lys Leu Val Ser Val Ser Arg Asp Thr Asn Arg Ile Tyr Leu Arg Pro
    530                 535                 540

Glu Asn Leu Ser Ala Tyr Trp Lys Ser Gln Gly Asp Gly Thr Leu Pro
545                 550                 555                 560

Leu Arg Val Met Ser Val Asp Leu Gly Val Arg Ser Ser Ala Ala Val
                565                 570                 575

Val Ile Cys Arg Leu Glu His Arg Asp Ser Val Val Ser Ser Gly Arg
            580                 585                 590

Arg Thr Ala Thr Ile Tyr Arg Ile Ala Gly Thr Asp Glu Phe Val Ala
        595                 600                 605

Val Gln Glu Arg Ala Phe Leu Leu Arg Leu Pro Gly Glu Gly Lys Gly
    610                 615                 620

Thr Asn Glu Asp Ala Pro Leu Arg Asp Val Tyr Ala Gln Leu Gly Thr
625                 630                 635                 640

Ile Arg Gln Gly Ile Gln Ile Leu Arg Ser Leu Leu Arg Leu Cys Asp
                645                 650                 655
```

```
Thr Lys Thr Pro Asp Glu Arg Gln Glu Ala Leu His Gly Leu Ala Gln
            660                 665                 670

Ser Leu Glu Pro Ser Gly Ala Trp Lys Asp Glu Leu His Pro His Leu
        675                 680                 685

Val Met Leu Gln Gly Val Val His Asp Ser Val Asp Asn Trp Lys Gln
    690                 695                 700

Lys Val Ile Ser Val His Arg Gln Met Glu Arg Ile Leu Gly His Ala
705                 710                 715                 720

Val Arg Glu Trp Lys Val Ala Arg Lys Asn Ala Gly Lys Pro Pro Ile
                725                 730                 735

Arg Arg Gly Ala Gly Gly Leu Ser Leu Arg Arg Ile Arg Gln Leu Glu
            740                 745                 750

Gln Glu Arg Arg Thr Leu Val Ala Trp Ser Asn His Ala Arg Glu Pro
        755                 760                 765

Gly Gln Val Val Arg Ile Lys Arg Gly Thr Gln Val Ala Gln Trp Leu
    770                 775                 780

Val Glu Arg Val Asn His Leu Lys Glu Asp Arg Leu Lys Lys Leu Ala
785                 790                 795                 800

Asp Leu Leu Ile Met Thr Ala Leu Gly Tyr Val Tyr Asp Glu Thr Lys
                805                 810                 815

Pro Ser Gly His Lys Trp Asp Lys Arg Tyr Pro Pro Cys Gln Ile Ile
            820                 825                 830

Leu Met Glu Asp Leu Ser Gly Ala Ala Gly Ala Ala Gly Ala Ala Gly
        835                 840                 845

Ala Ala Gly Gly Gln Leu Met Ala Trp Ser His Arg Arg Leu Leu Glu
    850                 855                 860

Ile Leu Lys Leu Gln Ala Asp Leu His Lys Leu Ile Val Gly Thr Val
865                 870                 875                 880

Phe Pro Ala Phe Ser Ser Arg Phe Asp Ala Gln Ser Gly Ala Pro Gly
                885                 890                 895

Val Arg Cys Arg Ser Val Lys Lys Gln Asp Ile Glu Asn Ala Ala Gln
            900                 905                 910

Gly Lys Gly Trp Leu Ala Arg Glu Leu Gln Arg Leu Asn Trp Thr Leu
        915                 920                 925

Glu Trp Leu Gln Pro Asn Asp Leu Ile Pro Thr Gly Asp Gly Glu Leu
    930                 935                 940

Phe Val Thr Pro Ala Cys Cys Asp Arg Gln Lys Gly Ile Lys Ile Val
945                 950                 955                 960

His Ala Asp Leu Asn Ala Ala Gln Asn Leu Gln Arg Arg Phe Trp Gly
                965                 970                 975

Gly His Ala Glu Ser Leu Cys Arg Val Thr Cys Asp Val Val Glu Arg
            980                 985                 990

Asp Gly Arg Arg Tyr Ala Val Pro  Arg Ile Ser Asn Ala  Phe Ala Asp
        995                 1000                1005

Ser Phe  Tyr Lys Val Phe Gly  Gln Gly Val Phe Val  Ser Thr Asp
    1010                1015                1020

Glu Glu  Asp Val Tyr Arg Trp  Met Val Gly Glu Lys  Ile Ser Ser
    1025                1030                1035

Arg Gly  Arg Ser Arg Gly Arg  Thr Ser Asp Glu Glu  Ala Glu Ala
    1040                1045                1050

Glu Thr  Trp Ile Asp Glu Ala  Arg Glu Gln Gln Gly  Lys Val Ile
    1055                1060                1065

Ala Leu  Phe Arg Asp Ala Ser  Gly Gln Ile His Gly  Gly Asp Trp
```

```
    1070                1075                1080

Leu Val  Ala Lys Val Phe Trp  Gly Trp Val Glu Arg  Leu Val Thr
    1085                1090                1095

Ala Arg  Leu Leu Ser Arg Met  Ser Glu Arg Glu Ala  Ala Ala His
    1100                1105                1110

Lys Glu
    1115


<210> SEQ ID NO 45
<211> LENGTH: 1076
<212> TYPE: PRT
<213> ORGANISM: Sulfobacillus thermotolerans

<400> SEQUENCE: 45

Met Ser Ala Arg Asn Ile Lys Val Lys Ile Asp Thr Lys Gly Asn Pro
1               5                   10                  15

Glu Leu Arg Leu Gly Leu Trp Lys Thr His Gln Val Thr Asn Glu Gly
            20                  25                  30

Val Lys Tyr Tyr Thr Glu Trp Leu Ile Lys Leu Arg Gln Gln Asp Ile
        35                  40                  45

Tyr Arg Gln Ser Arg Glu Asp Ala Ser Pro Arg Val Ile Ile Ser Ala
    50                  55                  60

Ser Asp Leu Lys Ala Asp Leu Leu Cys His Ala Arg Gln Leu Gln Lys
65                  70                  75                  80

Glu Arg Leu Pro Arg Ile Thr Gly Ser Asp Ala Glu Ile Leu Gly Thr
                85                  90                  95

Leu Arg Gln Val Tyr Glu Leu Ile Val Pro Ser Ser Val Gly Lys Ser
            100                 105                 110

Gly Asp Ser Lys Thr Leu Ala Arg Lys Phe Leu Ser Pro Leu Thr Asp
        115                 120                 125

Pro Gly Ser Ala Gly Gly Arg Asp Gln Ser Ala Ser Gly Arg Lys Pro
    130                 135                 140

Thr Trp Met Lys Met Lys Ser Glu Gly Asn Pro Arg Trp Glu Glu Thr
145                 150                 155                 160

Phe Arg Lys Trp Lys Asp Arg Lys Asp Asn Asp Pro Thr Pro Leu Val
                165                 170                 175

Leu Asn Gln Ile Ala Asp Tyr Gly Leu Leu Pro Leu Ile Pro Leu Phe
            180                 185                 190

Thr Asp Val Gly Glu Asn Ile Phe Asp Pro Lys Ser Lys Ser Gln Phe
        195                 200                 205

Val Arg Thr Trp Asp Arg Ser Met Phe Gln Gln Ala Ile Glu Arg Leu
    210                 215                 220

Met Ser Trp Glu Ser Trp Asn Gln Arg Val Arg Arg Glu Trp Glu Ala
225                 230                 235                 240

Leu Asn Gln Lys His Ser Ala Phe Tyr Arg Glu Gln Phe Thr Ala Asp
                245                 250                 255

Pro Asp Ala Ala Leu Tyr Arg Val Ala Gln Ser Leu Glu Glu Glu Met
            260                 265                 270

Arg Lys Glu His Gln Gly Phe Ala Ser Asp Ala Pro Glu Ala Phe Arg
        275                 280                 285

Ile Arg Arg Val Ala Leu Lys Gly Phe Asp Arg Leu Leu Glu Arg Trp
    290                 295                 300

Gln Lys Thr Leu Gly Lys Asn Gly Gln Ser Ala Thr Leu Leu Asp Asp
305                 310                 315                 320
```

-continued

```
Ile Arg Arg Val Gln Ser Asp Leu Gly Asp Lys Phe Gly Ser Ala Pro
                325                 330                 335

Leu Tyr Gln Lys Leu Leu Asp Glu Arg Trp Gln Arg Leu Trp Ala Val
            340                 345                 350

Asp Pro Thr Phe Leu Gln Arg Tyr Ala Ala Phe Asn Asp Leu Thr Gln
        355                 360                 365

Arg Leu Gln Arg Ala Lys Arg Val Ala Asn Leu Thr Leu Pro Asp Ala
    370                 375                 380

Val Ala His Pro Ile Trp Ser Arg Tyr Glu Gly Ala Asn Ala Ser Ser
385                 390                 395                 400

Gly Asn Arg Tyr His Ile His Leu Pro Thr Lys Gly Gln Pro Gly Ser
                405                 410                 415

Val Thr Phe Asp Arg Ile Leu Trp Pro Asp Gly Asn Gly Gly Trp Tyr
            420                 425                 430

Glu Arg Lys Arg Val Thr Val Phe Leu Arg Pro Ser His Gln Val Asp
        435                 440                 445

Arg Ile His Glu Ala Pro Thr Asp Ser Val Val Asp Asn Phe Pro Leu
    450                 455                 460

Val Val Glu Asp Gln Ser Ala Arg Thr Ile Leu Arg Ala Ser Trp Gly
465                 470                 475                 480

Gly Ala Lys Leu Glu Tyr Asp Arg Asn Arg Leu Pro Arg Gln Leu Lys
                485                 490                 495

Lys Gly Val Pro Asp Ser Ile Tyr Leu Ser Leu Thr Leu Asn Leu Asp
            500                 505                 510

Thr Asn Lys Pro Ser Gly Leu Phe His Thr Gln Gln Asn Gly Arg Val
        515                 520                 525

Trp Ile Arg Lys Asp Val Leu Met Gln Tyr Tyr Asn Glu Thr Pro Gly
    530                 535                 540

Asp Asn Val Gln Phe Lys Pro Leu Tyr Val Met Ser Val Asp Leu Gly
545                 550                 555                 560

Ile Arg Ser Ala Ala Ala Val Ser Ile Phe Ser Val Gln Leu Lys Ala
                565                 570                 575

Gly Ile Glu Glu His Arg Leu Thr Tyr Pro Val Ala Asp Cys Pro Gly
            580                 585                 590

Leu Val Ala Val His Glu Arg Ser Val Leu Leu Thr Met Pro Gly Glu
        595                 600                 605

Arg Arg Glu Gln Trp Asp Arg Arg Tyr Glu Gln Gln Arg Gln Gly Leu
    610                 615                 620

Arg Glu Leu Arg Thr Asp Met Arg Gly Met Asn Asp Leu Leu Arg Gly
625                 630                 635                 640

Ala Tyr Met Asp Gly Asp Arg Arg Glu Glu Phe Leu Ala Arg Leu Ser
                645                 650                 655

Lys Leu Glu Glu Thr Ser Pro Glu Leu Trp Gly Pro Val Tyr Arg Ser
            660                 665                 670

Leu Asn Asp Ser Lys Val Ala Ser Ala Thr Glu Trp Glu Arg Leu Val
        675                 680                 685

Val Tyr Cys His Arg Gln Val Glu Gln Ser Leu Ser Ser Arg Ile Gln
    690                 695                 700

Asn Leu Arg Ser Gly Arg Ser Ala Tyr Arg Met Ser Gly Gly Leu Ser
705                 710                 715                 720

Leu Asp His Val Gln Asp Leu Glu Arg Ile Arg Gly Ile Ile Ala Ser
                725                 730                 735

Trp Thr Asn His Pro Arg Ile Pro Gly Ser Val Val Arg Trp Gln Gln
```

```
            740                 745                 750

Gly Arg Ser His Thr Val Ala Leu Gly Arg His Ile Leu Glu Leu Lys
        755                 760                 765

Arg Asp Arg Val Lys Lys Val Ala Asn Tyr Leu Ile Met Thr Thr Leu
    770                 775                 780

Gly Tyr Ala Tyr Asp Ser Lys Arg Ala Arg Gly Glu Lys Trp Val Arg
785                 790                 795                 800

Arg Tyr Pro Ala Cys His Leu Met Val Phe Glu Asp Leu Thr Arg Tyr
                805                 810                 815

Arg Phe Arg Thr Asp Arg Pro Arg Ser Glu Asn Arg Gln Leu Met Arg
            820                 825                 830

Trp Thr His Gln Glu Leu Ile Ala Val Thr Gly Ile Gln Ala Glu Pro
        835                 840                 845

His Gly Ile Ser Val Gly Thr Met Tyr Ala Gly Phe Ser Ser Arg Phe
    850                 855                 860

Asp Ala Val Thr Lys Ala Pro Gly Val Arg Gly Ala Thr Val Arg Gln
865                 870                 875                 880

Ile Leu Arg Thr Arg Gly Met Val Arg Leu Lys Glu Ile Ala Ala Asp
                885                 890                 895

Val Gly Ile Asp Ile Asn Thr Leu Arg Pro His Asp Val Leu Pro Thr
            900                 905                 910

Gly Asp Gly Glu Tyr Leu Leu Ser Val Val Arg His Gly Glu Ser Tyr
        915                 920                 925

Arg Leu Lys Gln Val His Ala Asp Ile Asn Ala Ala His Asn Leu Gln
    930                 935                 940

Arg Arg Leu Trp Thr Gln Asp Glu Val Phe Arg Val Ser Cys Arg Leu
945                 950                 955                 960

Ala Leu Asn Ser Gly Arg Val Val Ala Met Pro Pro Pro Ser Tyr Asn
                965                 970                 975

Lys Arg Tyr Gly Lys Gly Phe Phe Glu Lys Gly Asp Asn Gly Val Tyr
            980                 985                 990

Ile Trp Lys Thr Gly Gly Lys Ile  Lys Ile Ser Asp Thr  Leu Glu Glu
        995                 1000                1005

Asp Met  Asp Ile Pro Glu Asp  Thr Ala Glu Leu Leu  Arg Gly Asn
    1010                1015                1020

Ser Val  Thr Leu Phe Arg Asp  Pro Ser Gly Thr Ile  Ala Gly Gly
    1025                1030                1035

Asn Trp  Leu Glu Ala Lys Glu  Phe Trp Gly Arg Val  Asn Ser Leu
    1040                1045                1050

Val Asn  Lys Gly Val Arg Asp  Lys Ile Leu Gly Gly  Ile Pro Val
    1055                1060                1065

Asp Asn  Ser Ser Ala His Ala  Glu
    1070                1075


<210> SEQ ID NO 46
<211> LENGTH: 1062
<212> TYPE: PRT
<213> ORGANISM: Sulfobacillus thermotolerans

<400> SEQUENCE: 46

Met Ser Ala Arg Asn Ile Lys Val Lys Ile Asp Thr Lys Gly Asn Pro
1               5                   10                  15

Glu Leu Arg Leu Gly Leu Trp Lys Thr His Gln Val Thr Asn Glu Gly
            20                  25                  30
```

```
Val Lys Tyr Tyr Thr Glu Trp Leu Ile Lys Leu Arg Gln Gln Asp Ile
        35                  40                  45

Tyr Arg Gln Ser Arg Glu Asp Ala Ser Pro Arg Val Ile Ile Ser Ala
    50                  55                  60

Ser Asp Leu Lys Ala Asp Leu Leu Cys His Ala Arg Gln Leu Gln Lys
65                  70                  75                  80

Glu Arg Leu Pro Arg Ile Thr Gly Ser Asp Ala Glu Ile Leu Gly Thr
                85                  90                  95

Leu Arg Gln Val Tyr Glu Leu Ile Val Pro Ser Ser Val Gly Lys Ser
            100                 105                 110

Gly Asp Ser Lys Thr Leu Ala Arg Lys Phe Leu Ser Pro Leu Thr Asp
        115                 120                 125

Pro Gly Ser Ala Gly Gly Arg Asp Gln Ser Ala Ser Gly Arg Lys Pro
    130                 135                 140

Thr Trp Met Lys Met Lys Ser Glu Gly Asn Pro Arg Trp Glu Glu Thr
145                 150                 155                 160

Phe Arg Lys Trp Lys Asp Arg Lys Asp Asn Asp Pro Thr Pro Leu Val
                165                 170                 175

Leu Asn Gln Ile Ala Asp Tyr Gly Leu Leu Pro Leu Ile Pro Leu Phe
            180                 185                 190

Thr Asp Val Gly Glu Asn Ile Phe Asp Pro Lys Ser Lys Ser Gln Phe
        195                 200                 205

Val Arg Thr Trp Asp Arg Ser Met Phe Gln Gln Ala Ile Glu Arg Leu
    210                 215                 220

Met Ser Trp Glu Ser Trp Asn Gln Arg Val Arg Arg Glu Trp Glu Ala
225                 230                 235                 240

Leu Asn Gln Lys His Ser Ala Phe Tyr Arg Glu Gln Phe Thr Ala Asp
                245                 250                 255

Pro Asp Ala Ala Leu Tyr Arg Val Ala Gln Ser Leu Glu Glu Glu Met
            260                 265                 270

Arg Lys Glu His Gln Gly Phe Ala Ser Asp Ala Pro Glu Ala Phe Arg
        275                 280                 285

Ile Arg Arg Val Ala Leu Lys Gly Phe Asp Arg Leu Leu Glu Arg Trp
    290                 295                 300

Gln Lys Thr Leu Gly Lys Asn Gly Gln Ser Ala Thr Leu Leu Asp Asp
305                 310                 315                 320

Ile Arg Arg Val Gln Ser Asp Leu Gly Asp Lys Phe Gly Ser Ala Pro
                325                 330                 335

Leu Tyr Gln Lys Leu Leu Asp Glu Arg Trp Gln Arg Leu Trp Ala Val
            340                 345                 350

Asp Pro Thr Phe Leu Gln Arg Tyr Ala Ala Phe Asn Asp Leu Thr Gln
        355                 360                 365

Arg Leu Gln Arg Ala Lys Arg Val Ala Asn Leu Thr Leu Pro Asp Ala
    370                 375                 380

Val Ala His Pro Ile Trp Ser Arg Tyr Glu Gly Ala Asn Ala Ser Ser
385                 390                 395                 400

Gly Asn Arg Tyr His Ile His Leu Pro Thr Lys Gly Gln Pro Gly Ser
                405                 410                 415

Val Thr Phe Asp Arg Ile Leu Trp Pro Asp Gly Asn Gly Gly Trp Tyr
            420                 425                 430

Glu Arg Lys Arg Val Thr Val Phe Leu Arg Pro Ser His Gln Val Asp
        435                 440                 445

Arg Ile His Glu Ala Pro Thr Asp Ser Val Val Asp Asn Phe Pro Leu
```

```
    450                 455                 460

Val Val Glu Asp Gln Ser Ala Arg Thr Ile Leu Arg Ala Ser Trp Gly
465                 470                 475                 480

Gly Ala Lys Leu Glu Tyr Asp Arg Asn Arg Leu Pro Arg Gln Leu Lys
                485                 490                 495

Lys Gly Val Pro Asp Ser Ile Tyr Leu Ser Leu Thr Leu Asn Leu Asp
            500                 505                 510

Thr Asn Lys Pro Ser Gly Leu Phe His Thr Gln Gln Asn Gly Arg Val
        515                 520                 525

Trp Ile Arg Lys Asp Val Leu Met Gln Tyr Tyr Asn Glu Thr Pro Gly
    530                 535                 540

Asp Asn Val Gln Phe Lys Pro Leu Tyr Val Met Ser Val Asp Leu Gly
545                 550                 555                 560

Ile Arg Ser Ala Ala Ala Val Ser Ile Phe Ser Val Gln Leu Lys Ala
                565                 570                 575

Gly Ile Glu Glu His Arg Leu Thr Tyr Pro Val Ala Asp Cys Pro Gly
            580                 585                 590

Leu Val Ala Val His Glu Arg Ser Val Leu Leu Thr Met Pro Gly Glu
        595                 600                 605

Arg Arg Glu Gln Trp Asp Arg Arg Tyr Glu Gln Gln Arg Gln Gly Leu
    610                 615                 620

Arg Glu Leu Arg Thr Asp Met Arg Gly Met Asn Asp Leu Leu Arg Gly
625                 630                 635                 640

Ala Tyr Met Asp Gly Asp Arg Arg Glu Glu Phe Leu Ala Arg Leu Ser
                645                 650                 655

Lys Leu Glu Glu Thr Ser Pro Glu Leu Trp Gly Pro Val Tyr Arg Ser
            660                 665                 670

Leu Asn Asp Ser Lys Val Ala Ser Ala Thr Glu Trp Glu Arg Leu Val
        675                 680                 685

Val Tyr Cys His Arg Gln Val Glu Gln Ser Leu Ser Ser Arg Ile Gln
    690                 695                 700

Asn Leu Arg Ser Gly Arg Ser Ala Tyr Arg Met Ser Gly Gly Leu Ser
705                 710                 715                 720

Leu Asp His Val Gln Asp Leu Glu Arg Ile Arg Gly Ile Ile Ala Ser
                725                 730                 735

Trp Thr Asn His Pro Arg Ile Pro Gly Ser Val Val Arg Trp Gln Gln
            740                 745                 750

Gly Arg Ser His Thr Val Ala Leu Gly Arg His Ile Leu Glu Leu Lys
        755                 760                 765

Arg Asp Arg Val Lys Lys Val Ala Asn Tyr Leu Ile Met Thr Thr Leu
    770                 775                 780

Gly Tyr Ala Tyr Asp Ser Lys Arg Ala Arg Gly Glu Lys Trp Val Arg
785                 790                 795                 800

Arg Tyr Pro Ala Cys His Leu Met Val Phe Glu Asp Leu Thr Gln Leu
                805                 810                 815

Met Arg Trp Thr His Gln Glu Leu Ile Ala Val Thr Gly Ile Gln Ala
            820                 825                 830

Glu Pro His Gly Ile Ser Val Gly Thr Met Tyr Ala Gly Phe Ser Ser
        835                 840                 845

Arg Phe Asp Ala Val Thr Lys Ala Pro Gly Val Arg Gly Ala Thr Val
    850                 855                 860

Arg Gln Ile Leu Arg Thr Arg Gly Met Val Arg Leu Lys Glu Ile Ala
865                 870                 875                 880
```

Ala Asp Val Gly Ile Asp Ile Asn Thr Leu Arg Pro His Asp Val Leu
885 890 895

Pro Thr Gly Asp Gly Glu Tyr Leu Leu Ser Val Val Arg His Gly Glu
900 905 910

Ser Tyr Arg Leu Lys Gln Val His Ala Asp Ile Asn Ala Ala His Asn
915 920 925

Leu Gln Arg Arg Leu Trp Thr Gln Asp Glu Val Phe Arg Val Ser Cys
930 935 940

Arg Leu Ala Leu Asn Ser Gly Arg Val Val Ala Met Pro Pro Pro Ser
945 950 955 960

Tyr Asn Lys Arg Tyr Gly Lys Gly Phe Phe Glu Lys Gly Asp Asn Gly
965 970 975

Val Tyr Ile Trp Lys Thr Gly Gly Lys Ile Lys Ile Ser Asp Thr Leu
980 985 990

Glu Glu Asp Met Asp Ile Pro Glu Asp Thr Ala Glu Leu Leu Arg Gly
995 1000 1005

Asn Ser Val Thr Leu Phe Arg Asp Pro Ser Gly Thr Ile Ala Gly
1010 1015 1020

Gly Asn Trp Leu Glu Ala Lys Glu Phe Trp Gly Arg Val Asn Ser
1025 1030 1035

Leu Val Asn Lys Gly Val Arg Asp Lys Ile Leu Gly Gly Ile Pro
1040 1045 1050

Val Asp Asn Ser Ser Ala His Ala Glu
1055 1060

<210> SEQ ID NO 47
<211> LENGTH: 1076
<212> TYPE: PRT
<213> ORGANISM: Sulfobacillus thermotolerans

<400> SEQUENCE: 47

Met Ser Ala Arg Asn Ile Lys Val Lys Ile Asp Thr Lys Gly Asn Pro
1 5 10 15

Glu Leu Arg Leu Gly Leu Trp Lys Thr His Gln Val Thr Asn Glu Gly
20 25 30

Val Lys Tyr Tyr Thr Glu Trp Leu Ile Lys Leu Arg Gln Gln Asp Ile
35 40 45

Tyr Arg Gln Ser Arg Glu Asp Ala Ser Pro Arg Val Ile Ile Ser Ala
50 55 60

Ser Asp Leu Lys Ala Asp Leu Leu Cys His Ala Arg Gln Leu Gln Lys
65 70 75 80

Glu Arg Leu Pro Arg Ile Thr Gly Ser Asp Ala Glu Ile Leu Gly Thr
85 90 95

Leu Arg Gln Val Tyr Glu Leu Ile Val Pro Ser Ser Val Gly Lys Ser
100 105 110

Gly Asp Ser Lys Thr Leu Ala Arg Lys Phe Leu Ser Pro Leu Thr Asp
115 120 125

Pro Gly Ser Ala Gly Gly Arg Asp Gln Ser Ala Ser Gly Arg Lys Pro
130 135 140

Thr Trp Met Lys Met Lys Ser Glu Gly Asn Pro Arg Trp Glu Glu Thr
145 150 155 160

Phe Arg Lys Trp Lys Asp Arg Lys Asp Asn Asp Pro Thr Pro Leu Val
165 170 175

Leu Asn Gln Ile Ala Asp Tyr Gly Leu Leu Pro Leu Ile Pro Leu Phe

```
            180                 185                 190

Thr Asp Val Gly Glu Asn Ile Phe Asp Pro Lys Ser Lys Ser Gln Phe
        195                 200                 205

Val Arg Thr Trp Asp Arg Ser Met Phe Gln Gln Ala Ile Glu Arg Leu
    210                 215                 220

Met Ser Trp Glu Ser Trp Asn Gln Arg Val Arg Arg Glu Trp Glu Ala
225                 230                 235                 240

Leu Asn Gln Lys His Ser Ala Phe Tyr Arg Glu Gln Phe Thr Ala Asp
                245                 250                 255

Pro Asp Ala Ala Leu Tyr Arg Val Ala Gln Ser Leu Glu Glu Glu Met
            260                 265                 270

Arg Lys Glu His Gln Gly Phe Ala Ser Asp Ala Pro Glu Ala Phe Arg
        275                 280                 285

Ile Arg Arg Val Ala Leu Lys Gly Phe Asp Arg Leu Leu Glu Arg Trp
    290                 295                 300

Gln Lys Thr Leu Gly Lys Asn Gly Gln Ser Ala Thr Leu Leu Asp Asp
305                 310                 315                 320

Ile Arg Arg Val Gln Ser Asp Leu Gly Asp Lys Phe Gly Ser Ala Pro
                325                 330                 335

Leu Tyr Gln Lys Leu Leu Asp Glu Arg Trp Gln Arg Leu Trp Ala Val
            340                 345                 350

Asp Pro Thr Phe Leu Gln Arg Tyr Ala Ala Phe Asn Asp Leu Thr Gln
        355                 360                 365

Arg Leu Gln Arg Ala Lys Arg Val Ala Asn Leu Thr Leu Pro Asp Ala
    370                 375                 380

Val Ala His Pro Ile Trp Ser Arg Tyr Glu Gly Ala Asn Ala Ser Ser
385                 390                 395                 400

Gly Asn Arg Tyr His Ile His Leu Pro Thr Lys Gly Gln Pro Gly Ser
                405                 410                 415

Val Thr Phe Asp Arg Ile Leu Trp Pro Asp Gly Asn Gly Gly Trp Tyr
            420                 425                 430

Glu Arg Lys Arg Val Thr Val Phe Leu Arg Pro Ser His Gln Val Asp
        435                 440                 445

Arg Ile His Glu Ala Pro Thr Asp Ser Val Val Asp Asn Phe Pro Leu
    450                 455                 460

Val Val Glu Asp Gln Ser Ala Arg Thr Ile Leu Arg Ala Ser Trp Gly
465                 470                 475                 480

Gly Ala Lys Leu Glu Tyr Asp Arg Asn Arg Leu Pro Arg Gln Leu Lys
                485                 490                 495

Lys Gly Val Pro Asp Ser Ile Tyr Leu Ser Leu Thr Leu Asn Leu Asp
            500                 505                 510

Thr Asn Lys Pro Ser Gly Leu Phe His Thr Gln Gln Asn Gly Arg Val
        515                 520                 525

Trp Ile Arg Lys Asp Val Leu Met Gln Tyr Tyr Asn Glu Thr Pro Gly
    530                 535                 540

Asp Asn Val Gln Phe Lys Pro Leu Tyr Val Met Ser Val Asp Leu Gly
545                 550                 555                 560

Ile Arg Ser Ala Ala Ala Val Ser Ile Phe Ser Val Gln Leu Lys Ala
                565                 570                 575

Gly Ile Glu Glu His Arg Leu Thr Tyr Pro Val Ala Asp Cys Pro Gly
            580                 585                 590

Leu Val Ala Val His Glu Arg Ser Val Leu Leu Thr Met Pro Gly Glu
        595                 600                 605
```

```
Arg Arg Glu Gln Trp Asp Arg Arg Tyr Glu Gln Gln Arg Gln Gly Leu
    610                 615                 620

Arg Glu Leu Arg Thr Asp Met Arg Gly Met Asn Asp Leu Leu Arg Gly
625                 630                 635                 640

Ala Tyr Met Asp Gly Asp Arg Arg Glu Glu Phe Leu Ala Arg Leu Ser
                645                 650                 655

Lys Leu Glu Glu Thr Ser Pro Glu Leu Trp Gly Pro Val Tyr Arg Ser
            660                 665                 670

Leu Asn Asp Ser Lys Val Ala Ser Ala Thr Glu Trp Glu Arg Leu Val
        675                 680                 685

Val Tyr Cys His Arg Gln Val Glu Gln Ser Leu Ser Ser Arg Ile Gln
    690                 695                 700

Asn Leu Arg Ser Gly Arg Ser Ala Tyr Arg Met Ser Gly Gly Leu Ser
705                 710                 715                 720

Leu Asp His Val Gln Asp Leu Glu Arg Ile Arg Gly Ile Ile Ala Ser
                725                 730                 735

Trp Thr Asn His Pro Arg Ile Pro Gly Ser Val Val Arg Trp Gln Gln
            740                 745                 750

Gly Arg Ser His Thr Val Ala Leu Gly Arg His Ile Leu Glu Leu Lys
        755                 760                 765

Arg Asp Arg Val Lys Lys Val Ala Asn Tyr Leu Ile Met Thr Thr Leu
    770                 775                 780

Gly Tyr Ala Tyr Asp Ser Lys Arg Ala Arg Gly Glu Lys Trp Val Arg
785                 790                 795                 800

Arg Tyr Pro Ala Cys His Leu Met Val Phe Glu Asp Leu Thr Gly Ala
                805                 810                 815

Ala Gly Ala Ala Gly Ala Ala Gly Ala Ala Gly Gly Gln Leu Met Arg
            820                 825                 830

Trp Thr His Gln Glu Leu Ile Ala Val Thr Gly Ile Gln Ala Glu Pro
        835                 840                 845

His Gly Ile Ser Val Gly Thr Met Tyr Ala Gly Phe Ser Ser Arg Phe
    850                 855                 860

Asp Ala Val Thr Lys Ala Pro Gly Val Arg Gly Ala Thr Val Arg Gln
865                 870                 875                 880

Ile Leu Arg Thr Arg Gly Met Val Arg Leu Lys Glu Ile Ala Ala Asp
                885                 890                 895

Val Gly Ile Asp Ile Asn Thr Leu Arg Pro His Asp Val Leu Pro Thr
            900                 905                 910

Gly Asp Gly Glu Tyr Leu Leu Ser Val Val Arg His Gly Glu Ser Tyr
        915                 920                 925

Arg Leu Lys Gln Val His Ala Asp Ile Asn Ala Ala His Asn Leu Gln
    930                 935                 940

Arg Arg Leu Trp Thr Gln Asp Glu Val Phe Arg Val Ser Cys Arg Leu
945                 950                 955                 960

Ala Leu Asn Ser Gly Arg Val Val Ala Met Pro Pro Pro Ser Tyr Asn
                965                 970                 975

Lys Arg Tyr Gly Lys Gly Phe Phe Glu Lys Gly Asp Asn Gly Val Tyr
            980                 985                 990

Ile Trp Lys Thr Gly Gly Lys Ile  Lys Ile Ser Asp Thr  Leu Glu Glu
        995                 1000                1005

Asp Met  Asp Ile Pro Glu Asp  Thr Ala Glu Leu Leu  Arg Gly Asn
    1010                1015                1020
```

```
Ser Val  Thr Leu Phe Arg Asp  Pro Ser Gly Thr Ile  Ala Gly Gly
    1025                1030                1035

Asn Trp  Leu Glu Ala Lys Glu  Phe Trp Gly Arg Val  Asn Ser Leu
    1040                1045                1050

Val Asn  Lys Gly Val Arg Asp  Lys Ile Leu Gly Gly  Ile Pro Val
    1055                1060                1065

Asp Asn  Ser Ser Ala His Ala  Glu
    1070                1075


<210> SEQ ID NO 48
<211> LENGTH: 986
<212> TYPE: PRT
<213> ORGANISM: Deltaproteobacteria bacterium

<400> SEQUENCE: 48

Met Glu Lys Arg Ile Asn Lys Ile Arg Lys Lys Leu Ser Ala Asp Asn
1               5                   10                  15

Ala Thr Lys Pro Val Ser Arg Ser Gly Pro Met Lys Thr Leu Leu Val
            20                  25                  30

Arg Val Met Thr Asp Asp Leu Lys Lys Arg Leu Glu Lys Arg Arg Lys
        35                  40                  45

Lys Pro Glu Val Met Pro Gln Val Ile Ser Asn Asn Ala Ala Asn Asn
    50                  55                  60

Leu Arg Met Leu Leu Asp Asp Tyr Thr Lys Met Lys Glu Ala Ile Leu
65                  70                  75                  80

Gln Val Tyr Trp Gln Glu Phe Lys Asp Asp His Val Gly Leu Met Cys
                85                  90                  95

Lys Phe Ala Gln Pro Ala Ser Lys Lys Ile Asp Gln Asn Lys Leu Lys
            100                 105                 110

Pro Glu Met Asp Glu Lys Gly Asn Leu Thr Thr Ala Gly Phe Ala Cys
        115                 120                 125

Ser Gln Cys Gly Gln Pro Leu Phe Val Tyr Lys Leu Glu Gln Val Ser
    130                 135                 140

Glu Lys Gly Lys Ala Tyr Thr Asn Tyr Phe Gly Arg Cys Asn Val Ala
145                 150                 155                 160

Glu His Glu Lys Leu Ile Leu Leu Ala Gln Leu Lys Pro Glu Lys Asp
                165                 170                 175

Ser Asp Glu Ala Val Thr Tyr Ser Leu Gly Lys Phe Gly Gln Arg Ala
            180                 185                 190

Leu Asp Phe Tyr Ser Ile His Val Thr Lys Glu Ser Thr His Pro Val
        195                 200                 205

Lys Pro Leu Ala Gln Ile Ala Gly Asn Arg Tyr Ala Ser Gly Pro Val
    210                 215                 220

Gly Lys Ala Leu Ser Asp Ala Cys Met Gly Thr Ile Ala Ser Phe Leu
225                 230                 235                 240

Ser Lys Tyr Gln Asp Ile Ile Ile Glu His Gln Lys Val Val Lys Gly
                245                 250                 255

Asn Gln Lys Arg Leu Glu Ser Leu Arg Glu Leu Ala Gly Lys Glu Asn
            260                 265                 270

Leu Glu Tyr Pro Ser Val Thr Leu Pro Pro Gln Pro His Thr Lys Glu
        275                 280                 285

Gly Val Asp Ala Tyr Asn Glu Val Ile Ala Arg Val Arg Met Trp Val
    290                 295                 300

Asn Leu Asn Leu Trp Gln Lys Leu Lys Leu Ser Arg Asp Asp Ala Lys
305                 310                 315                 320
```

```
Pro Leu Leu Arg Leu Lys Gly Phe Pro Ser Phe Pro Val Val Glu Arg
                325                 330                 335

Arg Glu Asn Glu Val Asp Trp Trp Asn Thr Ile Asn Glu Val Lys Lys
            340                 345                 350

Leu Ile Asp Ala Lys Arg Asp Met Gly Arg Val Phe Trp Ser Gly Val
        355                 360                 365

Thr Ala Glu Lys Arg Asn Thr Ile Leu Glu Gly Tyr Asn Tyr Leu Pro
    370                 375                 380

Asn Glu Asn Asp His Lys Lys Arg Glu Gly Ser Leu Glu Asn Pro Lys
385                 390                 395                 400

Lys Pro Ala Lys Arg Gln Phe Gly Asp Leu Leu Leu Tyr Leu Glu Lys
                405                 410                 415

Lys Tyr Ala Gly Asp Trp Gly Lys Val Phe Asp Glu Ala Trp Glu Arg
            420                 425                 430

Ile Asp Lys Lys Ile Ala Gly Leu Thr Ser His Ile Glu Arg Glu Glu
        435                 440                 445

Ala Arg Asn Ala Glu Asp Ala Gln Ser Lys Ala Val Leu Thr Asp Trp
    450                 455                 460

Leu Arg Ala Lys Ala Ser Phe Val Leu Glu Arg Leu Lys Glu Met Asp
465                 470                 475                 480

Glu Lys Glu Phe Tyr Ala Cys Glu Ile Gln Leu Gln Lys Trp Tyr Gly
                485                 490                 495

Asp Leu Arg Gly Asn Pro Phe Ala Val Glu Ala Glu Asn Arg Val Val
            500                 505                 510

Asp Ile Ser Gly Phe Ser Ile Gly Ser Asp Gly His Ser Ile Gln Tyr
        515                 520                 525

Arg Asn Leu Leu Ala Trp Lys Tyr Leu Glu Asn Gly Lys Arg Glu Phe
    530                 535                 540

Tyr Leu Leu Met Asn Tyr Gly Lys Lys Gly Arg Ile Arg Phe Thr Asp
545                 550                 555                 560

Gly Thr Asp Ile Lys Lys Ser Gly Lys Trp Gln Gly Leu Leu Tyr Gly
                565                 570                 575

Gly Gly Lys Ala Lys Val Ile Asp Leu Thr Phe Asp Pro Asp Asp Glu
            580                 585                 590

Gln Leu Ile Ile Leu Pro Leu Ala Phe Gly Thr Arg Gln Gly Arg Glu
        595                 600                 605

Phe Ile Trp Asn Asp Leu Leu Ser Leu Glu Thr Gly Leu Ile Lys Leu
    610                 615                 620

Ala Asn Gly Arg Val Ile Glu Lys Thr Ile Tyr Asn Lys Lys Ile Gly
625                 630                 635                 640

Arg Asp Glu Pro Ala Leu Phe Val Ala Leu Thr Phe Glu Arg Arg Glu
                645                 650                 655

Val Val Asp Pro Ser Asn Ile Lys Pro Val Asn Leu Ile Gly Val Asp
            660                 665                 670

Arg Gly Glu Asn Ile Pro Ala Val Ile Ala Leu Thr Asp Pro Glu Gly
        675                 680                 685

Cys Pro Leu Pro Glu Phe Lys Asp Ser Ser Gly Gly Pro Thr Asp Ile
    690                 695                 700

Leu Arg Ile Gly Glu Gly Tyr Lys Glu Lys Gln Arg Ala Ile Gln Ala
705                 710                 715                 720

Ala Lys Glu Val Glu Gln Arg Arg Ala Gly Gly Tyr Ser Arg Lys Phe
                725                 730                 735
```

```
Ala Ser Lys Ser Arg Asn Leu Ala Asp Asp Met Val Arg Asn Ser Ala
            740                 745                 750

Arg Asp Leu Phe Tyr His Ala Val Thr His Asp Ala Val Leu Val Phe
        755                 760                 765

Glu Asn Leu Ser Arg Gly Phe Gly Arg Gln Gly Lys Arg Thr Phe Met
    770                 775                 780

Thr Glu Arg Gln Tyr Thr Lys Met Glu Asp Trp Leu Thr Ala Lys Leu
785                 790                 795                 800

Ala Tyr Glu Gly Leu Thr Ser Lys Thr Tyr Leu Ser Lys Thr Leu Ala
                805                 810                 815

Gln Tyr Thr Ser Lys Thr Cys Ser Asn Cys Gly Phe Thr Ile Thr Thr
            820                 825                 830

Ala Asp Tyr Asp Gly Met Leu Val Arg Leu Lys Lys Thr Ser Asp Gly
        835                 840                 845

Trp Ala Thr Thr Leu Asn Asn Lys Glu Leu Lys Ala Glu Gly Gln Ile
    850                 855                 860

Thr Tyr Tyr Asn Arg Tyr Lys Arg Gln Thr Val Glu Lys Glu Leu Ser
865                 870                 875                 880

Ala Glu Leu Asp Arg Leu Ser Glu Glu Ser Gly Asn Asn Asp Ile Ser
                885                 890                 895

Lys Trp Thr Lys Gly Arg Arg Asp Glu Ala Leu Phe Leu Leu Lys Lys
            900                 905                 910

Arg Phe Ser His Arg Pro Val Gln Glu Gln Phe Val Cys Leu Asp Cys
        915                 920                 925

Gly His Glu Val His Ala Asp Glu Gln Ala Ala Leu Asn Ile Ala Arg
    930                 935                 940

Ser Trp Leu Phe Leu Asn Ser Asn Ser Thr Glu Phe Lys Ser Tyr Lys
945                 950                 955                 960

Ser Gly Lys Gln Pro Phe Val Gly Ala Trp Gln Ala Phe Tyr Lys Arg
                965                 970                 975

Arg Leu Lys Glu Val Trp Lys Pro Asn Ala
            980                 985


<210> SEQ ID NO 49
<211> LENGTH: 973
<212> TYPE: PRT
<213> ORGANISM: Deltaproteobacteria bacterium

<400> SEQUENCE: 49

Met Glu Lys Arg Ile Asn Lys Ile Arg Lys Lys Leu Ser Ala Asp Asn
1               5                   10                  15

Ala Thr Lys Pro Val Ser Arg Ser Gly Pro Met Lys Thr Leu Leu Val
            20                  25                  30

Arg Val Met Thr Asp Asp Leu Lys Lys Arg Leu Glu Lys Arg Arg Lys
        35                  40                  45

Lys Pro Glu Val Met Pro Gln Val Ile Ser Asn Asn Ala Ala Asn Asn
    50                  55                  60

Leu Arg Met Leu Leu Asp Asp Tyr Thr Lys Met Lys Glu Ala Ile Leu
65                  70                  75                  80

Gln Val Tyr Trp Gln Glu Phe Lys Asp Asp His Val Gly Leu Met Cys
                85                  90                  95

Lys Phe Ala Gln Pro Ala Ser Lys Lys Ile Asp Gln Asn Lys Leu Lys
            100                 105                 110

Pro Glu Met Asp Glu Lys Gly Asn Leu Thr Thr Ala Gly Phe Ala Cys
        115                 120                 125
```

```
Ser Gln Cys Gly Gln Pro Leu Phe Val Tyr Lys Leu Glu Gln Val Ser
    130                 135                 140

Glu Lys Gly Lys Ala Tyr Thr Asn Tyr Phe Gly Arg Cys Asn Val Ala
145                 150                 155                 160

Glu His Glu Lys Leu Ile Leu Leu Ala Gln Leu Lys Pro Glu Lys Asp
                165                 170                 175

Ser Asp Glu Ala Val Thr Tyr Ser Leu Gly Lys Phe Gly Gln Arg Ala
            180                 185                 190

Leu Asp Phe Tyr Ser Ile His Val Thr Lys Glu Ser Thr His Pro Val
        195                 200                 205

Lys Pro Leu Ala Gln Ile Ala Gly Asn Arg Tyr Ala Ser Gly Pro Val
    210                 215                 220

Gly Lys Ala Leu Ser Asp Ala Cys Met Gly Thr Ile Ala Ser Phe Leu
225                 230                 235                 240

Ser Lys Tyr Gln Asp Ile Ile Ile Glu His Gln Lys Val Val Lys Gly
                245                 250                 255

Asn Gln Lys Arg Leu Glu Ser Leu Arg Glu Leu Ala Gly Lys Glu Asn
            260                 265                 270

Leu Glu Tyr Pro Ser Val Thr Leu Pro Pro Gln Pro His Thr Lys Glu
        275                 280                 285

Gly Val Asp Ala Tyr Asn Glu Val Ile Ala Arg Val Arg Met Trp Val
    290                 295                 300

Asn Leu Asn Leu Trp Gln Lys Leu Lys Leu Ser Arg Asp Asp Ala Lys
305                 310                 315                 320

Pro Leu Leu Arg Leu Lys Gly Phe Pro Ser Phe Pro Val Val Glu Arg
                325                 330                 335

Arg Glu Asn Glu Val Asp Trp Trp Asn Thr Ile Asn Glu Val Lys Lys
            340                 345                 350

Leu Ile Asp Ala Lys Arg Asp Met Gly Arg Val Phe Trp Ser Gly Val
        355                 360                 365

Thr Ala Glu Lys Arg Asn Thr Ile Leu Glu Gly Tyr Asn Tyr Leu Pro
    370                 375                 380

Asn Glu Asn Asp His Lys Lys Arg Glu Gly Ser Leu Glu Asn Pro Lys
385                 390                 395                 400

Lys Pro Ala Lys Arg Gln Phe Gly Asp Leu Leu Leu Tyr Leu Glu Lys
                405                 410                 415

Lys Tyr Ala Gly Asp Trp Gly Lys Val Phe Asp Glu Ala Trp Glu Arg
            420                 425                 430

Ile Asp Lys Lys Ile Ala Gly Leu Thr Ser His Ile Glu Arg Glu Glu
        435                 440                 445

Ala Arg Asn Ala Glu Asp Ala Gln Ser Lys Ala Val Leu Thr Asp Trp
    450                 455                 460

Leu Arg Ala Lys Ala Ser Phe Val Leu Glu Arg Leu Lys Glu Met Asp
465                 470                 475                 480

Glu Lys Glu Phe Tyr Ala Cys Glu Ile Gln Leu Gln Lys Trp Tyr Gly
                485                 490                 495

Asp Leu Arg Gly Asn Pro Phe Ala Val Glu Ala Glu Asn Arg Val Val
            500                 505                 510

Asp Ile Ser Gly Phe Ser Ile Gly Ser Asp Gly His Ser Ile Gln Tyr
        515                 520                 525

Arg Asn Leu Leu Ala Trp Lys Tyr Leu Glu Asn Gly Lys Arg Glu Phe
    530                 535                 540
```

```
Tyr Leu Leu Met Asn Tyr Gly Lys Lys Gly Arg Ile Arg Phe Thr Asp
545                 550                 555                 560

Gly Thr Asp Ile Lys Lys Ser Gly Lys Trp Gln Gly Leu Leu Tyr Gly
                565                 570                 575

Gly Gly Lys Ala Lys Val Ile Asp Leu Thr Phe Asp Pro Asp Asp Glu
            580                 585                 590

Gln Leu Ile Ile Leu Pro Leu Ala Phe Gly Thr Arg Gln Gly Arg Glu
        595                 600                 605

Phe Ile Trp Asn Asp Leu Leu Ser Leu Glu Thr Gly Leu Ile Lys Leu
    610                 615                 620

Ala Asn Gly Arg Val Ile Glu Lys Thr Ile Tyr Asn Lys Lys Ile Gly
625                 630                 635                 640

Arg Asp Glu Pro Ala Leu Phe Val Ala Leu Thr Phe Glu Arg Arg Glu
                645                 650                 655

Val Val Asp Pro Ser Asn Ile Lys Pro Val Asn Leu Ile Gly Val Asp
            660                 665                 670

Arg Gly Glu Asn Ile Pro Ala Val Ile Ala Leu Thr Asp Pro Glu Gly
        675                 680                 685

Cys Pro Leu Pro Glu Phe Lys Asp Ser Ser Gly Gly Pro Thr Asp Ile
    690                 695                 700

Leu Arg Ile Gly Glu Gly Tyr Lys Glu Lys Gln Arg Ala Ile Gln Ala
705                 710                 715                 720

Ala Lys Glu Val Glu Gln Arg Arg Ala Gly Gly Tyr Ser Arg Lys Phe
                725                 730                 735

Ala Ser Lys Ser Arg Asn Leu Ala Asp Asp Met Val Arg Asn Ser Ala
            740                 745                 750

Arg Asp Leu Phe Tyr His Ala Val Thr His Asp Ala Val Leu Val Phe
        755                 760                 765

Glu Asn Leu Ser Arg Gly Phe Tyr Thr Lys Met Glu Asp Trp Leu Thr
    770                 775                 780

Ala Lys Leu Ala Tyr Glu Gly Leu Thr Ser Lys Thr Tyr Leu Ser Lys
785                 790                 795                 800

Thr Leu Ala Gln Tyr Thr Ser Lys Thr Cys Ser Asn Cys Gly Phe Thr
                805                 810                 815

Ile Thr Thr Ala Asp Tyr Asp Gly Met Leu Val Arg Leu Lys Lys Thr
            820                 825                 830

Ser Asp Gly Trp Ala Thr Thr Leu Asn Asn Lys Glu Leu Lys Ala Glu
        835                 840                 845

Gly Gln Ile Thr Tyr Tyr Asn Arg Tyr Lys Arg Gln Thr Val Glu Lys
    850                 855                 860

Glu Leu Ser Ala Glu Leu Asp Arg Leu Ser Glu Glu Ser Gly Asn Asn
865                 870                 875                 880

Asp Ile Ser Lys Trp Thr Lys Gly Arg Arg Asp Glu Ala Leu Phe Leu
                885                 890                 895

Leu Lys Lys Arg Phe Ser His Arg Pro Val Gln Glu Gln Phe Val Cys
            900                 905                 910

Leu Asp Cys Gly His Glu Val His Ala Asp Glu Gln Ala Ala Leu Asn
        915                 920                 925

Ile Ala Arg Ser Trp Leu Phe Leu Asn Ser Asn Ser Thr Glu Phe Lys
    930                 935                 940

Ser Tyr Lys Ser Gly Lys Gln Pro Phe Val Gly Ala Trp Gln Ala Phe
945                 950                 955                 960

Tyr Lys Arg Arg Leu Lys Glu Val Trp Lys Pro Asn Ala
```

965 970

<210> SEQ ID NO 50
<211> LENGTH: 986
<212> TYPE: PRT
<213> ORGANISM: Deltaproteobacteria bacterium

<400> SEQUENCE: 50

```
Met Glu Lys Arg Ile Asn Lys Ile Arg Lys Lys Leu Ser Ala Asp Asn
1               5                   10                  15

Ala Thr Lys Pro Val Ser Arg Ser Gly Pro Met Lys Thr Leu Leu Val
            20                  25                  30

Arg Val Met Thr Asp Asp Leu Lys Lys Arg Leu Glu Lys Arg Arg Lys
        35                  40                  45

Lys Pro Glu Val Met Pro Gln Val Ile Ser Asn Asn Ala Ala Asn Asn
    50                  55                  60

Leu Arg Met Leu Leu Asp Asp Tyr Thr Lys Met Lys Glu Ala Ile Leu
65                  70                  75                  80

Gln Val Tyr Trp Gln Glu Phe Lys Asp Asp His Val Gly Leu Met Cys
                85                  90                  95

Lys Phe Ala Gln Pro Ala Ser Lys Lys Ile Asp Gln Asn Lys Leu Lys
            100                 105                 110

Pro Glu Met Asp Glu Lys Gly Asn Leu Thr Thr Ala Gly Phe Ala Cys
        115                 120                 125

Ser Gln Cys Gly Gln Pro Leu Phe Val Tyr Lys Leu Glu Gln Val Ser
    130                 135                 140

Glu Lys Gly Lys Ala Tyr Thr Asn Tyr Phe Gly Arg Cys Asn Val Ala
145                 150                 155                 160

Glu His Glu Lys Leu Ile Leu Leu Ala Gln Leu Lys Pro Glu Lys Asp
                165                 170                 175

Ser Asp Glu Ala Val Thr Tyr Ser Leu Gly Lys Phe Gly Gln Arg Ala
            180                 185                 190

Leu Asp Phe Tyr Ser Ile His Val Thr Lys Glu Ser Thr His Pro Val
        195                 200                 205

Lys Pro Leu Ala Gln Ile Ala Gly Asn Arg Tyr Ala Ser Gly Pro Val
    210                 215                 220

Gly Lys Ala Leu Ser Asp Ala Cys Met Gly Thr Ile Ala Ser Phe Leu
225                 230                 235                 240

Ser Lys Tyr Gln Asp Ile Ile Ile Glu His Gln Lys Val Val Lys Gly
                245                 250                 255

Asn Gln Lys Arg Leu Glu Ser Leu Arg Glu Leu Ala Gly Lys Glu Asn
            260                 265                 270

Leu Glu Tyr Pro Ser Val Thr Leu Pro Pro Gln Pro His Thr Lys Glu
        275                 280                 285

Gly Val Asp Ala Tyr Asn Glu Val Ile Ala Arg Val Arg Met Trp Val
    290                 295                 300

Asn Leu Asn Leu Trp Gln Lys Leu Lys Leu Ser Arg Asp Asp Ala Lys
305                 310                 315                 320

Pro Leu Leu Arg Leu Lys Gly Phe Pro Ser Phe Pro Val Val Glu Arg
                325                 330                 335

Arg Glu Asn Glu Val Asp Trp Trp Asn Thr Ile Asn Glu Val Lys Lys
            340                 345                 350

Leu Ile Asp Ala Lys Arg Asp Met Gly Arg Val Phe Trp Ser Gly Val
        355                 360                 365
```

```
Thr Ala Glu Lys Arg Asn Thr Ile Leu Glu Gly Tyr Asn Tyr Leu Pro
    370                 375                 380

Asn Glu Asn Asp His Lys Lys Arg Glu Gly Ser Leu Glu Asn Pro Lys
385                 390                 395                 400

Lys Pro Ala Lys Arg Gln Phe Gly Asp Leu Leu Leu Tyr Leu Glu Lys
                405                 410                 415

Lys Tyr Ala Gly Asp Trp Gly Lys Val Phe Asp Glu Ala Trp Glu Arg
            420                 425                 430

Ile Asp Lys Lys Ile Ala Gly Leu Thr Ser His Ile Glu Arg Glu Glu
        435                 440                 445

Ala Arg Asn Ala Glu Asp Ala Gln Ser Lys Ala Val Leu Thr Asp Trp
    450                 455                 460

Leu Arg Ala Lys Ala Ser Phe Val Leu Glu Arg Leu Lys Glu Met Asp
465                 470                 475                 480

Glu Lys Glu Phe Tyr Ala Cys Glu Ile Gln Leu Gln Lys Trp Tyr Gly
                485                 490                 495

Asp Leu Arg Gly Asn Pro Phe Ala Val Glu Ala Glu Asn Arg Val Val
            500                 505                 510

Asp Ile Ser Gly Phe Ser Ile Gly Ser Asp Gly His Ser Ile Gln Tyr
        515                 520                 525

Arg Asn Leu Leu Ala Trp Lys Tyr Leu Glu Asn Gly Lys Arg Glu Phe
    530                 535                 540

Tyr Leu Leu Met Asn Tyr Gly Lys Lys Gly Arg Ile Arg Phe Thr Asp
545                 550                 555                 560

Gly Thr Asp Ile Lys Lys Ser Gly Lys Trp Gln Gly Leu Leu Tyr Gly
                565                 570                 575

Gly Gly Lys Ala Lys Val Ile Asp Leu Thr Phe Asp Pro Asp Asp Glu
            580                 585                 590

Gln Leu Ile Ile Leu Pro Leu Ala Phe Gly Thr Arg Gln Gly Arg Glu
        595                 600                 605

Phe Ile Trp Asn Asp Leu Leu Ser Leu Glu Thr Gly Leu Ile Lys Leu
    610                 615                 620

Ala Asn Gly Arg Val Ile Glu Lys Thr Ile Tyr Asn Lys Lys Ile Gly
625                 630                 635                 640

Arg Asp Glu Pro Ala Leu Phe Val Ala Leu Thr Phe Glu Arg Arg Glu
                645                 650                 655

Val Val Asp Pro Ser Asn Ile Lys Pro Val Asn Leu Ile Gly Val Asp
            660                 665                 670

Arg Gly Glu Asn Ile Pro Ala Val Ile Ala Leu Thr Asp Pro Glu Gly
        675                 680                 685

Cys Pro Leu Pro Glu Phe Lys Asp Ser Ser Gly Gly Pro Thr Asp Ile
    690                 695                 700

Leu Arg Ile Gly Glu Gly Tyr Lys Glu Lys Gln Arg Ala Ile Gln Ala
705                 710                 715                 720

Ala Lys Glu Val Glu Gln Arg Arg Ala Gly Gly Tyr Ser Arg Lys Phe
                725                 730                 735

Ala Ser Lys Ser Arg Asn Leu Ala Asp Asp Met Val Arg Asn Ser Ala
            740                 745                 750

Arg Asp Leu Phe Tyr His Ala Val Thr His Asp Ala Val Leu Val Phe
        755                 760                 765

Glu Asn Leu Ser Arg Gly Phe Gly Gly Ala Gly Gly Ala Gly Gly Ala
    770                 775                 780

Gly Gly Ala Gly Tyr Thr Lys Met Glu Asp Trp Leu Thr Ala Lys Leu
```

```
785                 790                 795                 800

Ala Tyr Glu Gly Leu Thr Ser Lys Thr Tyr Leu Ser Lys Thr Leu Ala
                805                 810                 815

Gln Tyr Thr Ser Lys Thr Cys Ser Asn Cys Gly Phe Thr Ile Thr Thr
            820                 825                 830

Ala Asp Tyr Asp Gly Met Leu Val Arg Leu Lys Lys Thr Ser Asp Gly
        835                 840                 845

Trp Ala Thr Thr Leu Asn Asn Lys Glu Leu Lys Ala Glu Gly Gln Ile
    850                 855                 860

Thr Tyr Tyr Asn Arg Tyr Lys Arg Gln Thr Val Glu Lys Glu Leu Ser
865                 870                 875                 880

Ala Glu Leu Asp Arg Leu Ser Glu Glu Ser Gly Asn Asn Asp Ile Ser
                885                 890                 895

Lys Trp Thr Lys Gly Arg Arg Asp Glu Ala Leu Phe Leu Leu Lys Lys
            900                 905                 910

Arg Phe Ser His Arg Pro Val Gln Glu Gln Phe Val Cys Leu Asp Cys
        915                 920                 925

Gly His Glu Val His Ala Asp Glu Gln Ala Ala Leu Asn Ile Ala Arg
    930                 935                 940

Ser Trp Leu Phe Leu Asn Ser Asn Ser Thr Glu Phe Lys Ser Tyr Lys
945                 950                 955                 960

Ser Gly Lys Gln Pro Phe Val Gly Ala Trp Gln Ala Phe Tyr Lys Arg
                965                 970                 975

Arg Leu Lys Glu Val Trp Lys Pro Asn Ala
            980                 985


<210> SEQ ID NO 51
<211> LENGTH: 978
<212> TYPE: PRT
<213> ORGANISM: Plantomycetes bacterium

<400> SEQUENCE: 51

Met Gln Glu Ile Lys Arg Ile Asn Lys Ile Arg Arg Arg Leu Val Lys
1               5                   10                  15

Asp Ser Asn Thr Lys Lys Ala Gly Lys Thr Gly Pro Met Lys Thr Leu
            20                  25                  30

Leu Val Arg Val Met Thr Pro Asp Leu Arg Glu Arg Leu Glu Asn Leu
        35                  40                  45

Arg Lys Lys Pro Glu Asn Ile Pro Gln Pro Ile Ser Asn Thr Ser Arg
    50                  55                  60

Ala Asn Leu Asn Lys Leu Leu Thr Asp Tyr Thr Glu Met Lys Lys Ala
65                  70                  75                  80

Ile Leu His Val Tyr Trp Glu Glu Phe Gln Lys Asp Pro Val Gly Leu
                85                  90                  95

Met Ser Arg Val Ala Gln Pro Ala Pro Lys Asn Ile Asp Gln Arg Lys
            100                 105                 110

Leu Ile Pro Val Lys Asp Gly Asn Glu Arg Leu Thr Ser Ser Gly Phe
        115                 120                 125

Ala Cys Ser Gln Cys Cys Gln Pro Leu Tyr Val Tyr Lys Leu Glu Gln
    130                 135                 140

Val Asn Asp Lys Gly Lys Pro His Thr Asn Tyr Phe Gly Arg Cys Asn
145                 150                 155                 160

Val Ser Glu His Glu Arg Leu Ile Leu Leu Ser Pro His Lys Pro Glu
                165                 170                 175
```

```
Ala Asn Asp Glu Leu Val Thr Tyr Ser Leu Gly Lys Phe Gly Gln Arg
            180                 185                 190

Ala Leu Asp Phe Tyr Ser Ile His Val Thr Arg Glu Ser Asn His Pro
        195                 200                 205

Val Lys Pro Leu Glu Gln Ile Gly Gly Asn Ser Cys Ala Ser Gly Pro
    210                 215                 220

Val Gly Lys Ala Leu Ser Asp Ala Cys Met Gly Ala Val Ala Ser Phe
225                 230                 235                 240

Leu Thr Lys Tyr Gln Asp Ile Ile Leu Glu His Gln Lys Val Ile Lys
                245                 250                 255

Lys Asn Glu Lys Arg Leu Ala Asn Leu Lys Asp Ile Ala Ser Ala Asn
            260                 265                 270

Gly Leu Ala Phe Pro Lys Ile Thr Leu Pro Pro Gln Pro His Thr Lys
        275                 280                 285

Glu Gly Ile Glu Ala Tyr Asn Asn Val Val Ala Gln Ile Val Ile Trp
    290                 295                 300

Val Asn Leu Asn Leu Trp Gln Lys Leu Lys Ile Gly Arg Asp Glu Ala
305                 310                 315                 320

Lys Pro Leu Gln Arg Leu Lys Gly Phe Pro Ser Phe Pro Leu Val Glu
                325                 330                 335

Arg Gln Ala Asn Glu Val Asp Trp Trp Asp Met Val Cys Asn Val Lys
            340                 345                 350

Lys Leu Ile Asn Glu Lys Lys Glu Asp Gly Lys Val Phe Trp Gln Asn
        355                 360                 365

Leu Ala Gly Tyr Lys Arg Gln Glu Ala Leu Leu Pro Tyr Leu Ser Ser
    370                 375                 380

Glu Glu Asp Arg Lys Lys Gly Lys Lys Phe Ala Arg Tyr Gln Phe Gly
385                 390                 395                 400

Asp Leu Leu Leu His Leu Glu Lys Lys His Gly Glu Asp Trp Gly Lys
                405                 410                 415

Val Tyr Asp Glu Ala Trp Glu Arg Ile Asp Lys Lys Val Glu Gly Leu
            420                 425                 430

Ser Lys His Ile Lys Leu Glu Glu Glu Arg Arg Ser Glu Asp Ala Gln
        435                 440                 445

Ser Lys Ala Ala Leu Thr Asp Trp Leu Arg Ala Lys Ala Ser Phe Val
    450                 455                 460

Ile Glu Gly Leu Lys Glu Ala Asp Lys Asp Glu Phe Cys Arg Cys Glu
465                 470                 475                 480

Leu Lys Leu Gln Lys Trp Tyr Gly Asp Leu Arg Gly Lys Pro Phe Ala
                485                 490                 495

Ile Glu Ala Glu Asn Ser Ile Leu Asp Ile Ser Gly Phe Ser Lys Gln
            500                 505                 510

Tyr Asn Cys Ala Phe Ile Trp Gln Lys Asp Gly Val Lys Lys Leu Asn
        515                 520                 525

Leu Tyr Leu Ile Ile Asn Tyr Phe Lys Gly Gly Lys Leu Arg Phe Lys
    530                 535                 540

Lys Ile Lys Pro Glu Ala Phe Glu Ala Asn Arg Phe Tyr Thr Val Ile
545                 550                 555                 560

Asn Lys Lys Ser Gly Glu Ile Val Pro Met Glu Val Asn Phe Asn Phe
                565                 570                 575

Asp Asp Pro Asn Leu Ile Ile Leu Pro Leu Ala Phe Gly Lys Arg Gln
            580                 585                 590

Gly Arg Glu Phe Ile Trp Asn Asp Leu Leu Ser Leu Glu Thr Gly Ser
```

```
        595                 600                 605

Leu Lys Leu Ala Asn Gly Arg Val Ile Glu Lys Thr Leu Tyr Asn Arg
    610                 615                 620

Arg Thr Arg Gln Asp Glu Pro Ala Leu Phe Val Ala Leu Thr Phe Glu
625                 630                 635                 640

Arg Arg Glu Val Leu Asp Ser Ser Asn Ile Lys Pro Met Asn Leu Ile
                645                 650                 655

Gly Ile Asp Arg Gly Glu Asn Ile Pro Ala Val Ile Ala Leu Thr Asp
            660                 665                 670

Pro Glu Gly Cys Pro Leu Ser Arg Phe Lys Asp Ser Leu Gly Asn Pro
        675                 680                 685

Thr His Ile Leu Arg Ile Gly Glu Ser Tyr Lys Glu Lys Gln Arg Thr
    690                 695                 700

Ile Gln Ala Ala Lys Glu Val Glu Gln Arg Arg Ala Gly Gly Tyr Ser
705                 710                 715                 720

Arg Lys Tyr Ala Ser Lys Ala Lys Asn Leu Ala Asp Asp Met Val Arg
                725                 730                 735

Asn Thr Ala Arg Asp Leu Leu Tyr Tyr Ala Val Thr Gln Asp Ala Met
            740                 745                 750

Leu Ile Phe Glu Asn Leu Ser Arg Gly Phe Gly Arg Gln Gly Lys Arg
        755                 760                 765

Thr Phe Met Ala Glu Arg Gln Tyr Thr Arg Met Glu Asp Trp Leu Thr
    770                 775                 780

Ala Lys Leu Ala Tyr Glu Gly Leu Pro Ser Lys Thr Tyr Leu Ser Lys
785                 790                 795                 800

Thr Leu Ala Gln Tyr Thr Ser Lys Thr Cys Ser Asn Cys Gly Phe Thr
                805                 810                 815

Ile Thr Ser Ala Asp Tyr Asp Arg Val Leu Glu Lys Leu Lys Lys Thr
            820                 825                 830

Ala Thr Gly Trp Met Thr Thr Ile Asn Gly Lys Glu Leu Lys Val Glu
        835                 840                 845

Gly Gln Ile Thr Tyr Tyr Asn Arg Tyr Lys Arg Gln Asn Val Val Lys
    850                 855                 860

Asp Leu Ser Val Glu Leu Asp Arg Leu Ser Glu Glu Ser Val Asn Asn
865                 870                 875                 880

Asp Ile Ser Ser Trp Thr Lys Gly Arg Ser Gly Glu Ala Leu Ser Leu
                885                 890                 895

Leu Lys Lys Arg Phe Ser His Arg Pro Val Gln Glu Lys Phe Val Cys
            900                 905                 910

Leu Asn Cys Gly Phe Glu Thr His Ala Asp Glu Gln Ala Ala Leu Asn
        915                 920                 925

Ile Ala Arg Ser Trp Leu Phe Leu Arg Ser Gln Glu Tyr Lys Lys Tyr
    930                 935                 940

Gln Thr Asn Lys Thr Thr Gly Asn Thr Asp Lys Arg Ala Phe Val Glu
945                 950                 955                 960

Thr Trp Gln Ser Phe Tyr Arg Lys Lys Leu Lys Glu Val Trp Lys Pro
                965                 970                 975

Ala Val
```

<210> SEQ ID NO 52
<211> LENGTH: 965
<212> TYPE: PRT
<213> ORGANISM: Plantomycetes bacterium

<400> SEQUENCE: 52

Met Gln Glu Ile Lys Arg Ile Asn Lys Ile Arg Arg Arg Leu Val Lys
1               5                   10                  15

Asp Ser Asn Thr Lys Lys Ala Gly Lys Thr Gly Pro Met Lys Thr Leu
            20                  25                  30

Leu Val Arg Val Met Thr Pro Asp Leu Arg Glu Arg Leu Glu Asn Leu
        35                  40                  45

Arg Lys Lys Pro Glu Asn Ile Pro Gln Pro Ile Ser Asn Thr Ser Arg
    50                  55                  60

Ala Asn Leu Asn Lys Leu Leu Thr Asp Tyr Thr Glu Met Lys Lys Ala
65                  70                  75                  80

Ile Leu His Val Tyr Trp Glu Glu Phe Gln Lys Asp Pro Val Gly Leu
                85                  90                  95

Met Ser Arg Val Ala Gln Pro Ala Pro Lys Asn Ile Asp Gln Arg Lys
            100                 105                 110

Leu Ile Pro Val Lys Asp Gly Asn Glu Arg Leu Thr Ser Ser Gly Phe
        115                 120                 125

Ala Cys Ser Gln Cys Cys Gln Pro Leu Tyr Val Tyr Lys Leu Glu Gln
    130                 135                 140

Val Asn Asp Lys Gly Lys Pro His Thr Asn Tyr Phe Gly Arg Cys Asn
145                 150                 155                 160

Val Ser Glu His Glu Arg Leu Ile Leu Leu Ser Pro His Lys Pro Glu
                165                 170                 175

Ala Asn Asp Glu Leu Val Thr Tyr Ser Leu Gly Lys Phe Gly Gln Arg
            180                 185                 190

Ala Leu Asp Phe Tyr Ser Ile His Val Thr Arg Glu Ser Asn His Pro
        195                 200                 205

Val Lys Pro Leu Glu Gln Ile Gly Gly Asn Ser Cys Ala Ser Gly Pro
    210                 215                 220

Val Gly Lys Ala Leu Ser Asp Ala Cys Met Gly Ala Val Ala Ser Phe
225                 230                 235                 240

Leu Thr Lys Tyr Gln Asp Ile Ile Leu Glu His Gln Lys Val Ile Lys
                245                 250                 255

Lys Asn Glu Lys Arg Leu Ala Asn Leu Lys Asp Ile Ala Ser Ala Asn
            260                 265                 270

Gly Leu Ala Phe Pro Lys Ile Thr Leu Pro Pro Gln Pro His Thr Lys
        275                 280                 285

Glu Gly Ile Glu Ala Tyr Asn Asn Val Val Ala Gln Ile Val Ile Trp
    290                 295                 300

Val Asn Leu Asn Leu Trp Gln Lys Leu Lys Ile Gly Arg Asp Glu Ala
305                 310                 315                 320

Lys Pro Leu Gln Arg Leu Lys Gly Phe Pro Ser Phe Pro Leu Val Glu
                325                 330                 335

Arg Gln Ala Asn Glu Val Asp Trp Trp Asp Met Val Cys Asn Val Lys
            340                 345                 350

Lys Leu Ile Asn Glu Lys Lys Glu Asp Gly Lys Val Phe Trp Gln Asn
        355                 360                 365

Leu Ala Gly Tyr Lys Arg Gln Glu Ala Leu Leu Pro Tyr Leu Ser Ser
    370                 375                 380

Glu Glu Asp Arg Lys Lys Gly Lys Lys Phe Ala Arg Tyr Gln Phe Gly
385                 390                 395                 400

Asp Leu Leu Leu His Leu Glu Lys Lys His Gly Glu Asp Trp Gly Lys
                405                 410                 415

```
Val Tyr Asp Glu Ala Trp Glu Arg Ile Asp Lys Lys Val Glu Gly Leu
            420                 425                 430

Ser Lys His Ile Lys Leu Glu Glu Glu Arg Arg Ser Glu Asp Ala Gln
        435                 440                 445

Ser Lys Ala Ala Leu Thr Asp Trp Leu Arg Ala Lys Ala Ser Phe Val
    450                 455                 460

Ile Glu Gly Leu Lys Glu Ala Asp Lys Asp Glu Phe Cys Arg Cys Glu
465                 470                 475                 480

Leu Lys Leu Gln Lys Trp Tyr Gly Asp Leu Arg Gly Lys Pro Phe Ala
                485                 490                 495

Ile Glu Ala Glu Asn Ser Ile Leu Asp Ile Ser Gly Phe Ser Lys Gln
            500                 505                 510

Tyr Asn Cys Ala Phe Ile Trp Gln Lys Asp Gly Val Lys Lys Leu Asn
        515                 520                 525

Leu Tyr Leu Ile Ile Asn Tyr Phe Lys Gly Gly Lys Leu Arg Phe Lys
    530                 535                 540

Lys Ile Lys Pro Glu Ala Phe Glu Ala Asn Arg Phe Tyr Thr Val Ile
545                 550                 555                 560

Asn Lys Lys Ser Gly Glu Ile Val Pro Met Glu Val Asn Phe Asn Phe
                565                 570                 575

Asp Asp Pro Asn Leu Ile Ile Leu Pro Leu Ala Phe Gly Lys Arg Gln
            580                 585                 590

Gly Arg Glu Phe Ile Trp Asn Asp Leu Leu Ser Leu Glu Thr Gly Ser
        595                 600                 605

Leu Lys Leu Ala Asn Gly Arg Val Ile Glu Lys Thr Leu Tyr Asn Arg
    610                 615                 620

Arg Thr Arg Gln Asp Glu Pro Ala Leu Phe Val Ala Leu Thr Phe Glu
625                 630                 635                 640

Arg Arg Glu Val Leu Asp Ser Ser Asn Ile Lys Pro Met Asn Leu Ile
                645                 650                 655

Gly Ile Asp Arg Gly Glu Asn Ile Pro Ala Val Ile Ala Leu Thr Asp
            660                 665                 670

Pro Glu Gly Cys Pro Leu Ser Arg Phe Lys Asp Ser Leu Gly Asn Pro
        675                 680                 685

Thr His Ile Leu Arg Ile Gly Glu Ser Tyr Lys Glu Lys Gln Arg Thr
    690                 695                 700

Ile Gln Ala Ala Lys Glu Val Glu Gln Arg Arg Ala Gly Gly Tyr Ser
705                 710                 715                 720

Arg Lys Tyr Ala Ser Lys Ala Lys Asn Leu Ala Asp Asp Met Val Arg
                725                 730                 735

Asn Thr Ala Arg Asp Leu Leu Tyr Tyr Ala Val Thr Gln Asp Ala Met
            740                 745                 750

Leu Ile Phe Glu Asn Leu Ser Arg Gly Phe Tyr Thr Arg Met Glu Asp
        755                 760                 765

Trp Leu Thr Ala Lys Leu Ala Tyr Glu Gly Leu Pro Ser Lys Thr Tyr
    770                 775                 780

Leu Ser Lys Thr Leu Ala Gln Tyr Thr Ser Lys Thr Cys Ser Asn Cys
785                 790                 795                 800

Gly Phe Thr Ile Thr Ser Ala Asp Tyr Asp Arg Val Leu Glu Lys Leu
                805                 810                 815

Lys Lys Thr Ala Thr Gly Trp Met Thr Thr Ile Asn Gly Lys Glu Leu
            820                 825                 830
```

Lys Val Glu Gly Gln Ile Thr Tyr Tyr Asn Arg Tyr Lys Arg Gln Asn
        835                 840                 845

Val Val Lys Asp Leu Ser Val Glu Leu Asp Arg Leu Ser Glu Glu Ser
    850                 855                 860

Val Asn Asn Asp Ile Ser Ser Trp Thr Lys Gly Arg Ser Gly Glu Ala
865                 870                 875                 880

Leu Ser Leu Leu Lys Lys Arg Phe Ser His Arg Pro Val Gln Glu Lys
                885                 890                 895

Phe Val Cys Leu Asn Cys Gly Phe Glu Thr His Ala Asp Glu Gln Ala
            900                 905                 910

Ala Leu Asn Ile Ala Arg Ser Trp Leu Phe Leu Arg Ser Gln Glu Tyr
        915                 920                 925

Lys Lys Tyr Gln Thr Asn Lys Thr Thr Gly Asn Thr Asp Lys Arg Ala
    930                 935                 940

Phe Val Glu Thr Trp Gln Ser Phe Tyr Arg Lys Lys Leu Lys Glu Val
945                 950                 955                 960

Trp Lys Pro Ala Val
                965

<210> SEQ ID NO 53
<211> LENGTH: 978
<212> TYPE: PRT
<213> ORGANISM: Plantomycetes bacterium

<400> SEQUENCE: 53

Met Gln Glu Ile Lys Arg Ile Asn Lys Ile Arg Arg Arg Leu Val Lys
1               5                   10                  15

Asp Ser Asn Thr Lys Lys Ala Gly Lys Thr Gly Pro Met Lys Thr Leu
            20                  25                  30

Leu Val Arg Val Met Thr Pro Asp Leu Arg Glu Arg Leu Glu Asn Leu
        35                  40                  45

Arg Lys Lys Pro Glu Asn Ile Pro Gln Pro Ile Ser Asn Thr Ser Arg
    50                  55                  60

Ala Asn Leu Asn Lys Leu Leu Thr Asp Tyr Thr Glu Met Lys Lys Ala
65                  70                  75                  80

Ile Leu His Val Tyr Trp Glu Glu Phe Gln Lys Asp Pro Val Gly Leu
                85                  90                  95

Met Ser Arg Val Ala Gln Pro Ala Pro Lys Asn Ile Asp Gln Arg Lys
            100                 105                 110

Leu Ile Pro Val Lys Asp Gly Asn Glu Arg Leu Thr Ser Ser Gly Phe
        115                 120                 125

Ala Cys Ser Gln Cys Cys Gln Pro Leu Tyr Val Tyr Lys Leu Glu Gln
    130                 135                 140

Val Asn Asp Lys Gly Lys Pro His Thr Asn Tyr Phe Gly Arg Cys Asn
145                 150                 155                 160

Val Ser Glu His Glu Arg Leu Ile Leu Leu Ser Pro His Lys Pro Glu
                165                 170                 175

Ala Asn Asp Glu Leu Val Thr Tyr Ser Leu Gly Lys Phe Gly Gln Arg
            180                 185                 190

Ala Leu Asp Phe Tyr Ser Ile His Val Thr Arg Glu Ser Asn His Pro
        195                 200                 205

Val Lys Pro Leu Glu Gln Ile Gly Gly Asn Ser Cys Ala Ser Gly Pro
    210                 215                 220

Val Gly Lys Ala Leu Ser Asp Ala Cys Met Gly Ala Val Ala Ser Phe
225                 230                 235                 240

```
Leu Thr Lys Tyr Gln Asp Ile Ile Leu Glu His Gln Lys Val Ile Lys
                245                 250                 255

Lys Asn Glu Lys Arg Leu Ala Asn Leu Lys Asp Ile Ala Ser Ala Asn
            260                 265                 270

Gly Leu Ala Phe Pro Lys Ile Thr Leu Pro Pro Gln Pro His Thr Lys
        275                 280                 285

Glu Gly Ile Glu Ala Tyr Asn Asn Val Val Ala Gln Ile Val Ile Trp
    290                 295                 300

Val Asn Leu Asn Leu Trp Gln Lys Leu Lys Ile Gly Arg Asp Glu Ala
305                 310                 315                 320

Lys Pro Leu Gln Arg Leu Lys Gly Phe Pro Ser Phe Pro Leu Val Glu
                325                 330                 335

Arg Gln Ala Asn Glu Val Asp Trp Trp Asp Met Val Cys Asn Val Lys
            340                 345                 350

Lys Leu Ile Asn Glu Lys Lys Glu Asp Gly Lys Val Phe Trp Gln Asn
        355                 360                 365

Leu Ala Gly Tyr Lys Arg Gln Glu Ala Leu Leu Pro Tyr Leu Ser Ser
    370                 375                 380

Glu Glu Asp Arg Lys Lys Gly Lys Lys Phe Ala Arg Tyr Gln Phe Gly
385                 390                 395                 400

Asp Leu Leu Leu His Leu Glu Lys Lys His Gly Glu Asp Trp Gly Lys
                405                 410                 415

Val Tyr Asp Glu Ala Trp Glu Arg Ile Asp Lys Lys Val Glu Gly Leu
            420                 425                 430

Ser Lys His Ile Lys Leu Glu Glu Glu Arg Arg Ser Glu Asp Ala Gln
        435                 440                 445

Ser Lys Ala Ala Leu Thr Asp Trp Leu Arg Ala Lys Ala Ser Phe Val
    450                 455                 460

Ile Glu Gly Leu Lys Glu Ala Asp Lys Asp Glu Phe Cys Arg Cys Glu
465                 470                 475                 480

Leu Lys Leu Gln Lys Trp Tyr Gly Asp Leu Arg Gly Lys Pro Phe Ala
                485                 490                 495

Ile Glu Ala Glu Asn Ser Ile Leu Asp Ile Ser Gly Phe Ser Lys Gln
            500                 505                 510

Tyr Asn Cys Ala Phe Ile Trp Gln Lys Asp Gly Val Lys Lys Leu Asn
        515                 520                 525

Leu Tyr Leu Ile Ile Asn Tyr Phe Lys Gly Gly Lys Leu Arg Phe Lys
    530                 535                 540

Lys Ile Lys Pro Glu Ala Phe Glu Ala Asn Arg Phe Tyr Thr Val Ile
545                 550                 555                 560

Asn Lys Lys Ser Gly Glu Ile Val Pro Met Glu Val Asn Phe Asn Phe
                565                 570                 575

Asp Asp Pro Asn Leu Ile Ile Leu Pro Leu Ala Phe Gly Lys Arg Gln
            580                 585                 590

Gly Arg Glu Phe Ile Trp Asn Asp Leu Leu Ser Leu Glu Thr Gly Ser
        595                 600                 605

Leu Lys Leu Ala Asn Gly Arg Val Ile Glu Lys Thr Leu Tyr Asn Arg
    610                 615                 620

Arg Thr Arg Gln Asp Glu Pro Ala Leu Phe Val Ala Leu Thr Phe Glu
625                 630                 635                 640

Arg Arg Glu Val Leu Asp Ser Ser Asn Ile Lys Pro Met Asn Leu Ile
                645                 650                 655
```

```
Gly Ile Asp Arg Gly Glu Asn Ile Pro Ala Val Ile Ala Leu Thr Asp
            660                 665                 670

Pro Glu Gly Cys Pro Leu Ser Arg Phe Lys Asp Ser Leu Gly Asn Pro
        675                 680                 685

Thr His Ile Leu Arg Ile Gly Glu Ser Tyr Lys Glu Lys Gln Arg Thr
    690                 695                 700

Ile Gln Ala Ala Lys Glu Val Glu Gln Arg Arg Ala Gly Gly Tyr Ser
705                 710                 715                 720

Arg Lys Tyr Ala Ser Lys Ala Lys Asn Leu Ala Asp Asp Met Val Arg
                725                 730                 735

Asn Thr Ala Arg Asp Leu Leu Tyr Tyr Ala Val Thr Gln Asp Ala Met
            740                 745                 750

Leu Ile Phe Glu Asn Leu Ser Arg Gly Phe Gly Gly Ala Gly Gly Ala
        755                 760                 765

Gly Gly Ala Gly Gly Ala Gly Tyr Thr Arg Met Glu Asp Trp Leu Thr
    770                 775                 780

Ala Lys Leu Ala Tyr Glu Gly Leu Pro Ser Lys Thr Tyr Leu Ser Lys
785                 790                 795                 800

Thr Leu Ala Gln Tyr Thr Ser Lys Thr Cys Ser Asn Cys Gly Phe Thr
                805                 810                 815

Ile Thr Ser Ala Asp Tyr Asp Arg Val Leu Glu Lys Leu Lys Lys Thr
            820                 825                 830

Ala Thr Gly Trp Met Thr Thr Ile Asn Gly Lys Glu Leu Lys Val Glu
        835                 840                 845

Gly Gln Ile Thr Tyr Tyr Asn Arg Tyr Lys Arg Gln Asn Val Val Lys
    850                 855                 860

Asp Leu Ser Val Glu Leu Asp Arg Leu Ser Glu Glu Ser Val Asn Asn
865                 870                 875                 880

Asp Ile Ser Ser Trp Thr Lys Gly Arg Ser Gly Glu Ala Leu Ser Leu
                885                 890                 895

Leu Lys Lys Arg Phe Ser His Arg Pro Val Gln Glu Lys Phe Val Cys
            900                 905                 910

Leu Asn Cys Gly Phe Glu Thr His Ala Asp Glu Gln Ala Ala Leu Asn
        915                 920                 925

Ile Ala Arg Ser Trp Leu Phe Leu Arg Ser Gln Glu Tyr Lys Lys Tyr
    930                 935                 940

Gln Thr Asn Lys Thr Thr Gly Asn Thr Asp Lys Arg Ala Phe Val Glu
945                 950                 955                 960

Thr Trp Gln Ser Phe Tyr Arg Lys Lys Leu Lys Glu Val Trp Lys Pro
                965                 970                 975

Ala Val
```

<210> SEQ ID NO 54
<211> LENGTH: 20
<212> TYPE: RNA
<213> ORGANISM: Artificial sequence
<220> FEATURE:
<223> OTHER INFORMATION: synthetic sequence

<400> SEQUENCE: 54
aauuucuacu aaguguagau 20

<210> SEQ ID NO 55
<211> LENGTH: 19
<212> TYPE: RNA
<213> ORGANISM: Artificial sequence
<220> FEATURE:
<223> OTHER INFORMATION: synthetic sequence

<400> SEQUENCE: 55
aauuucuacu cuuguagau 19

<210> SEQ ID NO 56
<211> LENGTH: 19
<212> TYPE: RNA
<213> ORGANISM: Artificial sequence
<220> FEATURE:
<223> OTHER INFORMATION: synthetic sequence

<400> SEQUENCE: 56
aauuucuacu guuguagau 19

<210> SEQ ID NO 57
<211> LENGTH: 19
<212> TYPE: RNA
<213> ORGANISM: Artificial sequence
<220> FEATURE:
<223> OTHER INFORMATION: synthetic sequence

<400> SEQUENCE: 57
aauuucuacu auuguagau 19

<210> SEQ ID NO 58
<211> LENGTH: 20
<212> TYPE: RNA
<213> ORGANISM: Artificial sequence
<220> FEATURE:
<223> OTHER INFORMATION: synthetic sequence

<400> SEQUENCE: 58
aauuucuacu guuuguagau 20

<210> SEQ ID NO 59
<211> LENGTH: 91
<212> TYPE: RNA
<213> ORGANISM: Artificial sequence
<220> FEATURE:
<223> OTHER INFORMATION: synthetic sequence

<400> SEQUENCE: 59
gucuagagga cagaauuuuu caacgggugu gccaauggcc acuuuccagg uggcaaagcc 60
cguugagcuu cucaaaucug agaaguggca c 91

<210> SEQ ID NO 60
<211> LENGTH: 9
<212> TYPE: PRT
<213> ORGANISM: Artificial sequence
<220> FEATURE:
<223> OTHER INFORMATION: synthetic sequence

<400> SEQUENCE: 60

Ser Gly Phe Lys Asn Ser Arg Val Lys
1               5

<210> SEQ ID NO 61
<211> LENGTH: 9
<212> TYPE: PRT
<213> ORGANISM: Artificial sequence
<220> FEATURE:
<223> OTHER INFORMATION: synthetic sequence

<400> SEQUENCE: 61

Phe Gly Phe Lys Arg Gly Arg Phe Lys
1 5

<210> SEQ ID NO 62
<211> LENGTH: 9
<212> TYPE: PRT
<213> ORGANISM: Artificial sequence
<220> FEATURE:
<223> OTHER INFORMATION: synthetic sequence

<400> SEQUENCE: 62

Phe Gly Phe Lys Ser Lys Arg Thr Gly
1 5

<210> SEQ ID NO 63
<211> LENGTH: 9
<212> TYPE: PRT
<213> ORGANISM: Artificial sequence
<220> FEATURE:
<223> OTHER INFORMATION: synthetic sequence

<400> SEQUENCE: 63

Met Gly Phe Lys Arg Gly Arg Gln Lys
1 5

<210> SEQ ID NO 64
<211> LENGTH: 14
<212> TYPE: PRT
<213> ORGANISM: Artificial sequence
<220> FEATURE:
<223> OTHER INFORMATION: synthetic sequence

<400> SEQUENCE: 64

Glu Tyr Gln Phe Asn Asn Asp Arg Pro Pro Ser Glu Asn Asn
1 5 10

<210> SEQ ID NO 65
<211> LENGTH: 14
<212> TYPE: PRT
<213> ORGANISM: Artificial sequence
<220> FEATURE:
<223> OTHER INFORMATION: synthetic sequence

<400> SEQUENCE: 65

Glu Tyr Arg Phe Ser Asn Asp Arg Pro Pro Ser Glu Asn Ser
1 5 10

<210> SEQ ID NO 66
<211> LENGTH: 14
<212> TYPE: PRT
<213> ORGANISM: Artificial sequence
<220> FEATURE:
<223> OTHER INFORMATION: synthetic sequence

<400> SEQUENCE: 66

Arg Tyr Arg Phe Gln Ser Asp Arg Pro Pro Ser Glu Asn Ser
1 5 10

<210> SEQ ID NO 67
<211> LENGTH: 14
<212> TYPE: PRT
<213> ORGANISM: Artificial sequence
<220> FEATURE:
<223> OTHER INFORMATION: synthetic sequence

<400> SEQUENCE: 67

```
Ala Tyr Arg Phe Ser Asp Asp Arg Pro Pro Ser Glu Asn Ser
1               5                   10


<210> SEQ ID NO 68
<211> LENGTH: 13
<212> TYPE: PRT
<213> ORGANISM: Artificial sequence
<220> FEATURE:
<223> OTHER INFORMATION: synthetic sequence

<400> SEQUENCE: 68

Gly Arg Gln Gly Lys Arg Thr Phe Met Thr Glu Arg Gln
1               5                   10


<210> SEQ ID NO 69
<211> LENGTH: 17
<212> TYPE: PRT
<213> ORGANISM: Artificial sequence
<220> FEATURE:
<223> OTHER INFORMATION: synthetic sequence

<400> SEQUENCE: 69

Glu Asp Leu Asn Ser Gly Phe Lys Asn Ser Arg Val Lys Val Glu Lys
1               5                   10                  15

Gln


<210> SEQ ID NO 70
<211> LENGTH: 17
<212> TYPE: PRT
<213> ORGANISM: Artificial sequence
<220> FEATURE:
<223> OTHER INFORMATION: synthetic sequence

<400> SEQUENCE: 70

Glu Asp Leu Asn Gly Gly Ala Ala Gly Gly Ala Ala Pro Val Glu Lys
1               5                   10                  15

Gln


<210> SEQ ID NO 71
<211> LENGTH: 11
<212> TYPE: PRT
<213> ORGANISM: Artificial sequence
<220> FEATURE:
<223> OTHER INFORMATION: synthetic sequence

<400> SEQUENCE: 71

Glu Asp Leu Asn Gly Ala Pro Val Glu Lys Gln
1               5                   10


<210> SEQ ID NO 72
<211> LENGTH: 9
<212> TYPE: PRT
<213> ORGANISM: Artificial sequence
<220> FEATURE:
<223> OTHER INFORMATION: synthetic sequence

<400> SEQUENCE: 72

Glu Asp Leu Asn Pro Val Glu Lys Gln
1               5


<210> SEQ ID NO 73
<211> LENGTH: 9
<212> TYPE: PRT
<213> ORGANISM: Artificial sequence
<220> FEATURE:
<223> OTHER INFORMATION: synthetic sequence
```

<400> SEQUENCE: 73

Phe Gly Phe Lys Arg Gly Arg Gln Lys
1 5

<210> SEQ ID NO 74
<211> LENGTH: 9
<212> TYPE: PRT
<213> ORGANISM: Artificial sequence
<220> FEATURE:
<223> OTHER INFORMATION: synthetic sequence

<400> SEQUENCE: 74

Met Gly Phe Lys Arg Gly Arg Phe Lys
1 5

<210> SEQ ID NO 75
<211> LENGTH: 9
<212> TYPE: PRT
<213> ORGANISM: Artificial sequence
<220> FEATURE:
<223> OTHER INFORMATION: synthetic sequence

<400> SEQUENCE: 75

Gln Gly Phe Lys Arg Gly Arg Phe Lys
1 5

<210> SEQ ID NO 76
<211> LENGTH: 9
<212> TYPE: PRT
<213> ORGANISM: Artificial sequence
<220> FEATURE:
<223> OTHER INFORMATION: synthetic sequence

<400> SEQUENCE: 76

Gly Gly Ala Ala Gly Gly Ala Ala Pro
1 5

<210> SEQ ID NO 77
<211> LENGTH: 9
<212> TYPE: PRT
<213> ORGANISM: Artificial sequence
<220> FEATURE:
<223> OTHER INFORMATION: synthetic sequence

<400> SEQUENCE: 77

Gly Gly Ala Ala Gly Gly Ala Ala Gly
1 5

<210> SEQ ID NO 78
<211> LENGTH: 9
<212> TYPE: PRT
<213> ORGANISM: Artificial sequence
<220> FEATURE:
<223> OTHER INFORMATION: synthetic sequence

<400> SEQUENCE: 78

Gly Gly Ala Ala Gly Gly Ala Ala Ala
1 5

<210> SEQ ID NO 79
<211> LENGTH: 9
<212> TYPE: PRT
<213> ORGANISM: Artificial sequence
<220> FEATURE:
<223> OTHER INFORMATION: synthetic sequence

<400> SEQUENCE: 79

Ser Gly Phe Ala Asn Ser Arg Val Ala
1 5

<210> SEQ ID NO 80
<211> LENGTH: 9
<212> TYPE: PRT
<213> ORGANISM: Artificial sequence
<220> FEATURE:
<223> OTHER INFORMATION: synthetic sequence

<400> SEQUENCE: 80

Ser Gly Ala Lys Asn Ser Ala Val Ala
1 5

<210> SEQ ID NO 81
<211> LENGTH: 9
<212> TYPE: PRT
<213> ORGANISM: Artificial sequence
<220> FEATURE:
<223> OTHER INFORMATION: synthetic sequence

<400> SEQUENCE: 81

Gly Gly Ala Ala Gly Gly Gly Ala Gly
1 5

<210> SEQ ID NO 82
<211> LENGTH: 9
<212> TYPE: PRT
<213> ORGANISM: Artificial sequence
<220> FEATURE:
<223> OTHER INFORMATION: synthetic sequence

<400> SEQUENCE: 82

Phe Gly Phe Ala Ser Ala Arg Thr Gly
1 5

<210> SEQ ID NO 83
<211> LENGTH: 9
<212> TYPE: PRT
<213> ORGANISM: Artificial sequence
<220> FEATURE:
<223> OTHER INFORMATION: synthetic sequence

<400> SEQUENCE: 83

Phe Gly Phe Ala Ser Ala Ala Thr Gly
1 5

<210> SEQ ID NO 84
<211> LENGTH: 9
<212> TYPE: PRT
<213> ORGANISM: Artificial sequence
<220> FEATURE:
<223> OTHER INFORMATION: synthetic sequence

<400> SEQUENCE: 84

Phe Gly Phe Ala Arg Gly Arg Phe Ala
1 5

<210> SEQ ID NO 85
<211> LENGTH: 9
<212> TYPE: PRT
<213> ORGANISM: Artificial sequence
<220> FEATURE:
<223> OTHER INFORMATION: synthetic sequence

<400> SEQUENCE: 85

Phe Gly Phe Lys Ala Gly Ala Phe Lys
1 5

<210> SEQ ID NO 86
<211> LENGTH: 9
<212> TYPE: PRT
<213> ORGANISM: Artificial sequence
<220> FEATURE:
<223> OTHER INFORMATION: synthetic sequence

<400> SEQUENCE: 86

Leu Ser Phe Met Lys Gly Arg Lys Lys
1 5

<210> SEQ ID NO 87
<211> LENGTH: 9
<212> TYPE: PRT
<213> ORGANISM: Artificial sequence
<220> FEATURE:
<223> OTHER INFORMATION: synthetic sequence

<400> SEQUENCE: 87

Leu Ser Phe Met Lys Gly Arg Ala Ala
1 5

<210> SEQ ID NO 88
<211> LENGTH: 9
<212> TYPE: PRT
<213> ORGANISM: Artificial sequence
<220> FEATURE:
<223> OTHER INFORMATION: synthetic sequence

<400> SEQUENCE: 88

Leu Ser Phe Met Ala Gly Arg Ala Ala
1 5

<210> SEQ ID NO 89
<211> LENGTH: 9
<212> TYPE: PRT
<213> ORGANISM: Artificial sequence
<220> FEATURE:
<223> OTHER INFORMATION: synthetic sequence

<400> SEQUENCE: 89

Leu Ser Phe Met Ala Gly Ala Lys Lys
1 5

<210> SEQ ID NO 90
<211> LENGTH: 9
<212> TYPE: PRT
<213> ORGANISM: Artificial sequence
<220> FEATURE:
<223> OTHER INFORMATION: synthetic sequence

<400> SEQUENCE: 90

Phe Gly Phe Ala Ala Gly Ala Phe Ala
1 5

<210> SEQ ID NO 91
<211> LENGTH: 9
<212> TYPE: PRT
<213> ORGANISM: Artificial sequence
<220> FEATURE:
<223> OTHER INFORMATION: synthetic sequence

<400> SEQUENCE: 91

Phe Gly Phe Ala Arg Gly Ala Phe Lys
1 5

<210> SEQ ID NO 92
<211> LENGTH: 9
<212> TYPE: PRT
<213> ORGANISM: Artificial sequence
<220> FEATURE:
<223> OTHER INFORMATION: synthetic sequence

<400> SEQUENCE: 92

Phe Gly Phe Lys Ala Gly Arg Phe Ala
1 5

<210> SEQ ID NO 93
<211> LENGTH: 9
<212> TYPE: PRT
<213> ORGANISM: Artificial sequence
<220> FEATURE:
<223> OTHER INFORMATION: synthetic sequence

<400> SEQUENCE: 93

Phe Gly Phe Ala Arg Gly Arg Gln Ala
1 5

<210> SEQ ID NO 94
<211> LENGTH: 9
<212> TYPE: PRT
<213> ORGANISM: Artificial sequence
<220> FEATURE:
<223> OTHER INFORMATION: synthetic sequence

<400> SEQUENCE: 94

Phe Gly Phe Lys Ala Gly Ala Gln Lys
1 5

<210> SEQ ID NO 95
<211> LENGTH: 9
<212> TYPE: PRT
<213> ORGANISM: Artificial sequence
<220> FEATURE:
<223> OTHER INFORMATION: synthetic sequence

<400> SEQUENCE: 95

Phe Gly Phe Ala Arg Gly Ala Gln Lys
1 5

<210> SEQ ID NO 96
<211> LENGTH: 9
<212> TYPE: PRT
<213> ORGANISM: Artificial sequence
<220> FEATURE:
<223> OTHER INFORMATION: synthetic sequence

<400> SEQUENCE: 96

Phe Gly Phe Lys Ala Gly Arg Gln Ala
1 5

<210> SEQ ID NO 97
<211> LENGTH: 9
<212> TYPE: PRT
<213> ORGANISM: Artificial sequence
<220> FEATURE:
<223> OTHER INFORMATION: synthetic sequence

<400> SEQUENCE: 97

Met Gly Phe Ala Arg Gly Arg Phe Ala 1 5

<210> SEQ ID NO 98
<211> LENGTH: 9
<212> TYPE: PRT
<213> ORGANISM: Artificial sequence
<220> FEATURE:
<223> OTHER INFORMATION: synthetic sequence

<400> SEQUENCE: 98

Met Gly Phe Lys Ala Gly Ala Phe Lys
1 5

<210> SEQ ID NO 99
<211> LENGTH: 9
<212> TYPE: PRT
<213> ORGANISM: Artificial sequence
<220> FEATURE:
<223> OTHER INFORMATION: synthetic sequence

<400> SEQUENCE: 99

Met Gly Phe Ala Ala Gly Arg Phe Lys
1 5

<210> SEQ ID NO 100
<211> LENGTH: 9
<212> TYPE: PRT
<213> ORGANISM: Artificial sequence
<220> FEATURE:
<223> OTHER INFORMATION: synthetic sequence

<400> SEQUENCE: 100

Met Gly Phe Lys Arg Gly Ala Phe Ala
1 5

<210> SEQ ID NO 101
<211> LENGTH: 9
<212> TYPE: PRT
<213> ORGANISM: Artificial sequence
<220> FEATURE:
<223> OTHER INFORMATION: synthetic sequence

<400> SEQUENCE: 101

Met Gly Phe Ala Arg Gly Arg Gln Ala
1 5

<210> SEQ ID NO 102
<211> LENGTH: 9
<212> TYPE: PRT
<213> ORGANISM: Artificial sequence
<220> FEATURE:
<223> OTHER INFORMATION: synthetic sequence

<400> SEQUENCE: 102

Met Gly Phe Lys Ala Gly Ala Gln Lys
1 5

<210> SEQ ID NO 103
<211> LENGTH: 9
<212> TYPE: PRT
<213> ORGANISM: Artificial sequence
<220> FEATURE:
<223> OTHER INFORMATION: synthetic sequence

<400> SEQUENCE: 103

Met Gly Phe Ala Arg Gly Ala Gln Lys
1 5

<210> SEQ ID NO 104
<211> LENGTH: 9
<212> TYPE: PRT
<213> ORGANISM: Artificial sequence
<220> FEATURE:
<223> OTHER INFORMATION: synthetic sequence

<400> SEQUENCE: 104

Met Gly Phe Lys Ala Gly Arg Gln Ala
1 5

<210> SEQ ID NO 105
<211> LENGTH: 9
<212> TYPE: PRT
<213> ORGANISM: Artificial sequence
<220> FEATURE:
<223> OTHER INFORMATION: synthetic sequence

<400> SEQUENCE: 105

Gln Gly Phe Ala Arg Gly Arg Phe Ala
1 5

<210> SEQ ID NO 106
<211> LENGTH: 9
<212> TYPE: PRT
<213> ORGANISM: Artificial sequence
<220> FEATURE:
<223> OTHER INFORMATION: synthetic sequence

<400> SEQUENCE: 106

Gln Gly Phe Lys Ala Gly Ala Phe Lys
1 5

<210> SEQ ID NO 107
<211> LENGTH: 9
<212> TYPE: PRT
<213> ORGANISM: Artificial sequence
<220> FEATURE:
<223> OTHER INFORMATION: synthetic sequence

<400> SEQUENCE: 107

Gln Gly Phe Ala Arg Gly Ala Phe Lys
1 5

<210> SEQ ID NO 108
<211> LENGTH: 9
<212> TYPE: PRT
<213> ORGANISM: Artificial sequence
<220> FEATURE:
<223> OTHER INFORMATION: synthetic sequence

<400> SEQUENCE: 108

Gln Gly Phe Lys Ala Gly Arg Phe Ala
1 5

<210> SEQ ID NO 109
<211> LENGTH: 14
<212> TYPE: PRT
<213> ORGANISM: Artificial sequence
<220> FEATURE:
<223> OTHER INFORMATION: synthetic sequence

<400> SEQUENCE: 109

Arg Tyr Arg Phe Arg Thr Asp Arg Pro Arg Ser Glu Asn Arg
1 5 10

<210> SEQ ID NO 110
<211> LENGTH: 13
<212> TYPE: PRT
<213> ORGANISM: Artificial sequence
<220> FEATURE:
<223> OTHER INFORMATION: synthetic sequence

<400> SEQUENCE: 110

Glu Tyr Gln Phe Asn Asn Asp Arg Pro Pro Ser Glu Asn
1 5 10

<210> SEQ ID NO 111
<211> LENGTH: 14
<212> TYPE: PRT
<213> ORGANISM: Artificial sequence
<220> FEATURE:
<223> OTHER INFORMATION: synthetic sequence

<400> SEQUENCE: 111

Gly Ala Ala Gly Ala Ala Gly Ala Ala Gly Ala Ala Gly Gly
1 5 10

<210> SEQ ID NO 112
<211> LENGTH: 13
<212> TYPE: PRT
<213> ORGANISM: Artificial sequence
<220> FEATURE:
<223> OTHER INFORMATION: synthetic sequence

<400> SEQUENCE: 112

Gly Arg Gln Gly Lys Arg Thr Phe Met Ala Glu Arg Gln
1 5 10

<210> SEQ ID NO 113
<211> LENGTH: 7
<212> TYPE: PRT
<213> ORGANISM: Artificial sequence
<220> FEATURE:
<223> OTHER INFORMATION: synthetic sequence

<400> SEQUENCE: 113

Pro Lys Lys Lys Arg Lys Val
1 5

<210> SEQ ID NO 114
<211> LENGTH: 16
<212> TYPE: PRT
<213> ORGANISM: Artificial sequence
<220> FEATURE:
<223> OTHER INFORMATION: synthetic sequence

<400> SEQUENCE: 114

Lys Arg Pro Ala Ala Thr Lys Lys Ala Gly Gln Ala Lys Lys Lys Lys
1 5 10 15

<210> SEQ ID NO 115
<211> LENGTH: 9
<212> TYPE: PRT
<213> ORGANISM: Artificial sequence
<220> FEATURE:
<223> OTHER INFORMATION: synthetic sequence

<400> SEQUENCE: 115

Pro Ala Ala Lys Arg Val Lys Leu Asp
1 5

<210> SEQ ID NO 116
<211> LENGTH: 11
<212> TYPE: PRT
<213> ORGANISM: Artificial sequence
<220> FEATURE:
<223> OTHER INFORMATION: synthetic sequence

<400> SEQUENCE: 116

Arg Gln Arg Arg Asn Glu Leu Lys Arg Ser Pro
1               5                   10

<210> SEQ ID NO 117
<211> LENGTH: 38
<212> TYPE: PRT
<213> ORGANISM: Artificial sequence
<220> FEATURE:
<223> OTHER INFORMATION: synthetic sequence

<400> SEQUENCE: 117

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 118
<211> LENGTH: 42
<212> TYPE: PRT
<213> ORGANISM: Artificial sequence
<220> FEATURE:
<223> OTHER INFORMATION: synthetic sequence

<400> SEQUENCE: 118

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 119
<211> LENGTH: 8
<212> TYPE: PRT
<213> ORGANISM: Artificial sequence
<220> FEATURE:
<223> OTHER INFORMATION: synthetic sequence

<400> SEQUENCE: 119

Val Ser Arg Lys Arg Pro Arg Pro
1               5

<210> SEQ ID NO 120
<211> LENGTH: 8
<212> TYPE: PRT
<213> ORGANISM: Artificial sequence
<220> FEATURE:
<223> OTHER INFORMATION: synthetic sequence

<400> SEQUENCE: 120

Pro Pro Lys Lys Ala Arg Glu Asp
1               5

<210> SEQ ID NO 121
<211> LENGTH: 8

<212> TYPE: PRT
<213> ORGANISM: Artificial sequence
<220> FEATURE:
<223> OTHER INFORMATION: synthetic sequence

<400> SEQUENCE: 121

Pro Gln Pro Lys Lys Lys Pro Leu
1               5

<210> SEQ ID NO 122
<211> LENGTH: 12
<212> TYPE: PRT
<213> ORGANISM: Artificial sequence
<220> FEATURE:
<223> OTHER INFORMATION: synthetic sequence

<400> SEQUENCE: 122

Ser Ala Leu Ile Lys Lys Lys Lys Lys Met Ala Pro
1               5                   10

<210> SEQ ID NO 123
<211> LENGTH: 5
<212> TYPE: PRT
<213> ORGANISM: Artificial sequence
<220> FEATURE:
<223> OTHER INFORMATION: synthetic sequence

<400> SEQUENCE: 123

Asp Arg Leu Arg Arg
1               5

<210> SEQ ID NO 124
<211> LENGTH: 7
<212> TYPE: PRT
<213> ORGANISM: Artificial sequence
<220> FEATURE:
<223> OTHER INFORMATION: synthetic sequence

<400> SEQUENCE: 124

Pro Lys Gln Lys Lys Arg Lys
1               5

<210> SEQ ID NO 125
<211> LENGTH: 10
<212> TYPE: PRT
<213> ORGANISM: Artificial sequence
<220> FEATURE:
<223> OTHER INFORMATION: synthetic sequence

<400> SEQUENCE: 125

Arg Lys Leu Lys Lys Lys Ile Lys Lys Leu
1               5                   10

<210> SEQ ID NO 126
<211> LENGTH: 10
<212> TYPE: PRT
<213> ORGANISM: Artificial sequence
<220> FEATURE:
<223> OTHER INFORMATION: synthetic sequence

<400> SEQUENCE: 126

Arg Glu Lys Lys Lys Phe Leu Lys Arg Arg
1               5                   10

<210> SEQ ID NO 127
<211> LENGTH: 20
<212> TYPE: PRT

<213> ORGANISM: Artificial sequence
<220> FEATURE:
<223> OTHER INFORMATION: synthetic sequence

<400> SEQUENCE: 127

Lys Arg Lys Gly Asp Glu Val Asp Gly Val Asp Glu Val Ala Lys Lys
1               5                   10                  15

Lys Ser Lys Lys
            20

<210> SEQ ID NO 128
<211> LENGTH: 17
<212> TYPE: PRT
<213> ORGANISM: Artificial sequence
<220> FEATURE:
<223> OTHER INFORMATION: synthetic sequence

<400> SEQUENCE: 128

Arg Lys Cys Leu Gln Ala Gly Met Asn Leu Glu Ala Arg Lys Thr Lys
1               5                   10                  15

Lys

<210> SEQ ID NO 129
<211> LENGTH: 20
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (4)..(4)
<223> OTHER INFORMATION: The amino acid at position 4 is selected from
      Lys, His, and Arg
<220> FEATURE:
<221> NAME/KEY: MISC_FEATURE
<222> LOCATION: (8)..(8)
<223> OTHER INFORMATION: The amino acid at position 8 is selected from
      Lys, His, and Arg
<220> FEATURE:
<221> NAME/KEY: MISC_FEATURE
<222> LOCATION: (11)..(11)
<223> OTHER INFORMATION: The amino acid at position 11 is selected from
      Lys, His, and Arg
<220> FEATURE:
<221> NAME/KEY: MISC_FEATURE
<222> LOCATION: (15)..(15)
<223> OTHER INFORMATION: The amino acid at position 15 is selected from
      Lys, His, and Arg
<220> FEATURE:
<221> NAME/KEY: MISC_FEATURE
<222> LOCATION: (19)..(19)
<223> OTHER INFORMATION: The amino acid at position 19 is selected from
      Lys, His, and Arg

<400> SEQUENCE: 129

Gly Leu Phe Xaa Ala Leu Leu Xaa Leu Leu Xaa Ser Leu Trp Xaa Leu
1               5                   10                  15

Leu Leu Xaa Ala
            20

<210> SEQ ID NO 130
<211> LENGTH: 20
<212> TYPE: PRT
<213> ORGANISM: Artificial sequence
<220> FEATURE:
<223> OTHER INFORMATION: synthetic sequence

<400> SEQUENCE: 130

Gly Leu Phe His Ala Leu Leu His Leu Leu His Ser Leu Trp His Leu

```
1               5                   10                  15

Leu Leu His Ala
            20


<210> SEQ ID NO 131
<211> LENGTH: 11
<212> TYPE: PRT
<213> ORGANISM: Artificial sequence
<220> FEATURE:
<223> OTHER INFORMATION: synthetic sequence

<400> SEQUENCE: 131

Tyr Gly Arg Lys Lys Arg Arg Gln Arg Arg Arg
1               5                   10


<210> SEQ ID NO 132
<211> LENGTH: 12
<212> TYPE: PRT
<213> ORGANISM: Artificial sequence
<220> FEATURE:
<223> OTHER INFORMATION: synthetic sequence

<400> SEQUENCE: 132

Arg Arg Gln Arg Arg Thr Ser Lys Leu Met Lys Arg
1               5                   10


<210> SEQ ID NO 133
<211> LENGTH: 27
<212> TYPE: PRT
<213> ORGANISM: Artificial sequence
<220> FEATURE:
<223> OTHER INFORMATION: synthetic sequence

<400> SEQUENCE: 133

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25


<210> SEQ ID NO 134
<211> LENGTH: 33
<212> TYPE: PRT
<213> ORGANISM: Artificial sequence
<220> FEATURE:
<223> OTHER INFORMATION: synthetic sequence

<400> SEQUENCE: 134

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala


<210> SEQ ID NO 135
<211> LENGTH: 16
<212> TYPE: PRT
<213> ORGANISM: Artificial sequence
<220> FEATURE:
<223> OTHER INFORMATION: synthetic sequence

<400> SEQUENCE: 135

Arg Gln Ile Lys Ile Trp Phe Gln Asn Arg Arg Met Lys Trp Lys Lys
1               5                   10                  15
```

```
<210> SEQ ID NO 136
<211> LENGTH: 9
<212> TYPE: PRT
<213> ORGANISM: Artificial sequence
<220> FEATURE:
<223> OTHER INFORMATION: synthetic sequence

<400> SEQUENCE: 136

Arg Lys Lys Arg Arg Gln Arg Arg Arg
1               5


<210> SEQ ID NO 137
<211> LENGTH: 8
<212> TYPE: PRT
<213> ORGANISM: Artificial sequence
<220> FEATURE:
<223> OTHER INFORMATION: synthetic sequence

<400> SEQUENCE: 137

Arg Lys Lys Arg Arg Gln Arg Arg
1               5


<210> SEQ ID NO 138
<211> LENGTH: 11
<212> TYPE: PRT
<213> ORGANISM: Artificial sequence
<220> FEATURE:
<223> OTHER INFORMATION: synthetic sequence

<400> SEQUENCE: 138

Tyr Ala Arg Ala Ala Ala Arg Gln Ala Arg Ala
1               5                   10


<210> SEQ ID NO 139
<211> LENGTH: 11
<212> TYPE: PRT
<213> ORGANISM: Artificial sequence
<220> FEATURE:
<223> OTHER INFORMATION: synthetic sequence

<400> SEQUENCE: 139

Thr His Arg Leu Pro Arg Arg Arg Arg Arg Arg
1               5                   10


<210> SEQ ID NO 140
<211> LENGTH: 11
<212> TYPE: PRT
<213> ORGANISM: Artificial sequence
<220> FEATURE:
<223> OTHER INFORMATION: synthetic sequence

<400> SEQUENCE: 140

Gly Gly Arg Arg Ala Arg Arg Arg Arg Arg Arg
1               5                   10


<210> SEQ ID NO 141
<211> LENGTH: 1301
<212> TYPE: PRT
<213> ORGANISM: Acidaminococcus sp.

<400> SEQUENCE: 141

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
```

```
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460
```

Glu Ile Leu Lys Ser Gln Leu Asp Ser Leu Leu Gly Leu Tyr His Leu
465 470 475 480

Leu Asp Trp Phe Ala Val Asp Glu Ser Asn Glu Val Asp Pro Glu Phe
485 490 495

Ser Ala Arg Leu Thr Gly Ile Lys Leu Glu Met Glu Pro Ser Leu Ser
500 505 510

Phe Tyr Asn Lys Ala Arg Asn Tyr Ala Thr Lys Lys Pro Tyr Ser Val
515 520 525

Glu Lys Phe Lys Leu Asn Phe Gln Met Pro Thr Leu Ala Ser Gly Trp
530 535 540

Asp Val Asn Lys Glu Lys Asn Asn Gly Ala Ile Leu Phe Val Lys Asn
545 550 555 560

Gly Leu Tyr Tyr Leu Gly Ile Met Pro Lys Gln Lys Gly Arg Tyr Lys
565 570 575

Ala Leu Ser Phe Glu Pro Thr Glu Lys Thr Ser Glu Gly Phe Asp Lys
580 585 590

Met Tyr Tyr Asp Tyr Phe Pro Asp Ala Ala Lys Met Ile Pro Lys Cys
595 600 605

Ser Thr Gln Leu Lys Ala Val Thr Ala His Phe Gln Thr His Thr Thr
610 615 620

Pro Ile Leu Leu Ser Asn Asn Phe Ile Glu Pro Leu Glu Ile Thr Lys
625 630 635 640

Glu Ile Tyr Asp Leu Asn Asn Pro Glu Lys Glu Pro Lys Lys Phe Gln
645 650 655

Thr Ala Tyr Ala Lys Lys Thr Gly Asp Gln Lys Gly Tyr Arg Glu Ala
660 665 670

Leu Cys Lys Trp Ile Asp Phe Thr Arg Asp Phe Leu Ser Lys Tyr Thr
675 680 685

Lys Thr Thr Ser Ile Asp Leu Ser Ser Leu Arg Pro Ser Ser Gln Tyr
690 695 700

Lys Asp Leu Gly Glu Tyr Tyr Ala Glu Leu Asn Pro Leu Leu Tyr His
705 710 715 720

Ile Ser Phe Gln Arg Ile Ala Glu Lys Glu Ile Met Asp Ala Val Glu
725 730 735

Thr Gly Lys Leu Tyr Leu Phe Gln Ile Tyr Asn Lys Asp Phe Ala Lys
740 745 750

Gly His His Gly Lys Pro Asn Leu His Thr Leu Tyr Trp Thr Gly Leu
755 760 765

Phe Ser Pro Glu Asn Leu Ala Lys Thr Ser Ile Lys Leu Asn Gly Gln
770 775 780

Ala Glu Leu Phe Tyr Arg Pro Lys Ser Arg Met Lys Arg Met Ala His
785 790 795 800

Arg Leu Gly Glu Lys Met Leu Asn Lys Lys Leu Lys Asp Gln Lys Thr
805 810 815

Pro Ile Pro Asp Thr Leu Tyr Gln Glu Leu Tyr Asp Tyr Val Asn His
820 825 830

Arg Leu Ser His Asp Leu Ser Asp Glu Ala Arg Ala Leu Leu Pro Asn
835 840 845

Val Ile Thr Lys Glu Val Ser His Glu Ile Ile Lys Asp Arg Arg Phe
850 855 860

Thr Ser Asp Lys Phe Phe Phe His Val Pro Ile Thr Leu Asn Tyr Gln
865 870 875 880

```
Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Gly Ala Ala Ile  Ala Glu Lys Ala Val  Tyr Gln Gln
        995                 1000                1005

Phe Glu  Lys Met Leu Ile Asp  Lys Leu Asn Cys Leu  Val Leu Lys
    1010                 1015                1020

Asp Tyr  Pro Ala Glu Lys Val  Gly Gly Val Leu Asn  Pro Tyr Gln
    1025                 1030                1035

Leu Thr  Asp Gln Phe Thr Ser  Phe Ala Lys Met Gly  Thr Gln Ser
    1040                 1045                1050

Gly Phe  Leu Phe Tyr Val Pro  Ala Pro Tyr Thr Ser  Lys Ile Asp
    1055                 1060                1065

Pro Leu  Thr Gly Phe Val Asp  Pro Phe Val Trp Lys  Thr Ile Lys
    1070                 1075                1080

Asn His  Glu Ser Arg Lys His  Phe Leu Glu Gly Phe  Asp Phe Leu
    1085                 1090                1095

His Tyr  Asp Val Lys Thr Gly  Asp Phe Ile Leu His  Phe Lys Met
    1100                 1105                1110

Asn Arg  Asn Leu Ser Phe Gln  Arg Gly Leu Pro Gly  Phe Met Pro
    1115                 1120                1125

Ala Trp  Asp Ile Val Phe Glu  Lys Asn Glu Thr Gln  Phe Asp Ala
    1130                 1135                1140

Lys Gly  Thr Pro Phe Ile Ala  Gly Lys Arg Ile Val  Pro Val Ile
    1145                 1150                1155

Glu Asn  His Arg Phe Thr Gly  Arg Tyr Arg Asp Leu  Tyr Pro Ala
    1160                 1165                1170

Asn Glu  Leu Ile Ala Leu Leu  Glu Glu Lys Gly Ile  Val Phe Arg
    1175                 1180                1185

Asp Gly  Ser Asn Ile Leu Pro  Lys Leu Leu Glu Asn  Asp Asp Ser
    1190                 1195                1200

His Ala  Ile Asp Thr Met Val  Ala Leu Ile Arg Ser  Val Leu Gln
    1205                 1210                1215

Met Arg  Asn Ser Asn Ala Ala  Thr Gly Glu Asp Tyr  Ile Asn Ser
    1220                 1225                1230

Pro Val  Arg Asp Leu Asn Gly  Val Cys Phe Asp Ser  Arg Phe Gln
    1235                 1240                1245

Asn Pro  Glu Trp Pro Met Asp  Ala Asp Ala Asn Gly  Ala Tyr His
    1250                 1255                1260

Ile Ala  Leu Lys Gly Gln Leu  Leu Leu Asn His Leu  Lys Glu Ser
    1265                 1270                1275

Lys Asp  Leu Lys Leu Gln Asn  Gly Ile Ser Asn Gln  Asp Trp Leu
```

1280 1285 1290

Ala Tyr Ile Gln Glu Leu Arg Asn
1295 1300

<210> SEQ ID NO 142
<211> LENGTH: 1237
<212> TYPE: PRT
<213> ORGANISM: Porphyromonas macacae

<400> SEQUENCE: 142

Met Lys Thr Gln His Phe Phe Glu Asp Phe Thr Ser Leu Tyr Ser Leu
1 5 10 15

Ser Lys Thr Ile Arg Phe Glu Leu Lys Pro Ile Gly Lys Thr Leu Glu
20 25 30

Asn Ile Lys Lys Asn Gly Leu Ile Arg Arg Asp Glu Gln Arg Leu Asp
35 40 45

Asp Tyr Glu Lys Leu Lys Lys Val Ile Asp Glu Tyr His Glu Asp Phe
50 55 60

Ile Ala Asn Ile Leu Ser Ser Phe Ser Phe Ser Glu Glu Ile Leu Gln
65 70 75 80

Ser Tyr Ile Gln Asn Leu Ser Glu Ser Glu Ala Arg Ala Lys Ile Glu
85 90 95

Lys Thr Met Arg Asp Thr Leu Ala Lys Ala Phe Ser Glu Asp Glu Arg
100 105 110

Tyr Lys Ser Ile Phe Lys Lys Glu Leu Val Lys Lys Asp Ile Pro Val
115 120 125

Trp Cys Pro Ala Tyr Lys Ser Leu Cys Lys Lys Phe Asp Asn Phe Thr
130 135 140

Thr Ser Leu Val Pro Phe His Glu Asn Arg Lys Asn Leu Tyr Thr Ser
145 150 155 160

Asn Glu Ile Thr Ala Ser Ile Pro Tyr Arg Ile Val His Val Asn Leu
165 170 175

Pro Lys Phe Ile Gln Asn Ile Glu Ala Leu Cys Glu Leu Gln Lys Lys
180 185 190

Met Gly Ala Asp Leu Tyr Leu Glu Met Met Glu Asn Leu Arg Asn Val
195 200 205

Trp Pro Ser Phe Val Lys Thr Pro Asp Asp Leu Cys Asn Leu Lys Thr
210 215 220

Tyr Asn His Leu Met Val Gln Ser Ser Ile Ser Glu Tyr Asn Arg Phe
225 230 235 240

Val Gly Gly Tyr Ser Thr Glu Asp Gly Thr Lys His Gln Gly Ile Asn
245 250 255

Glu Trp Ile Asn Ile Tyr Arg Gln Arg Asn Lys Glu Met Arg Leu Pro
260 265 270

Gly Leu Val Phe Leu His Lys Gln Ile Leu Ala Lys Val Asp Ser Ser
275 280 285

Ser Phe Ile Ser Asp Thr Leu Glu Asn Asp Asp Gln Val Phe Cys Val
290 295 300

Leu Arg Gln Phe Arg Lys Leu Phe Trp Asn Thr Val Ser Ser Lys Glu
305 310 315 320

Asp Asp Ala Ala Ser Leu Lys Asp Leu Phe Cys Gly Leu Ser Gly Tyr
325 330 335

Asp Pro Glu Ala Ile Tyr Val Ser Asp Ala His Leu Ala Thr Ile Ser
340 345 350

```
Lys Asn Ile Phe Asp Arg Trp Asn Tyr Ile Ser Asp Ala Ile Arg Arg
        355                 360                 365

Lys Thr Glu Val Leu Met Pro Arg Lys Lys Glu Ser Val Glu Arg Tyr
    370                 375                 380

Ala Glu Lys Ile Ser Lys Gln Ile Lys Lys Arg Gln Ser Tyr Ser Leu
385                 390                 395                 400

Ala Glu Leu Asp Asp Leu Leu Ala His Tyr Ser Glu Glu Ser Leu Pro
                405                 410                 415

Ala Gly Phe Ser Leu Leu Ser Tyr Phe Thr Ser Leu Gly Gly Gln Lys
            420                 425                 430

Tyr Leu Val Ser Asp Gly Glu Val Ile Leu Tyr Glu Glu Gly Ser Asn
        435                 440                 445

Ile Trp Asp Glu Val Leu Ile Ala Phe Arg Asp Leu Gln Val Ile Leu
    450                 455                 460

Asp Lys Asp Phe Thr Glu Lys Lys Leu Gly Lys Asp Glu Glu Ala Val
465                 470                 475                 480

Ser Val Ile Lys Lys Ala Leu Asp Ser Ala Leu Arg Leu Arg Lys Phe
                485                 490                 495

Phe Asp Leu Leu Ser Gly Thr Gly Ala Glu Ile Arg Arg Asp Ser Ser
            500                 505                 510

Phe Tyr Ala Leu Tyr Thr Asp Arg Met Asp Lys Leu Lys Gly Leu Leu
        515                 520                 525

Lys Met Tyr Asp Lys Val Arg Asn Tyr Leu Thr Lys Lys Pro Tyr Ser
    530                 535                 540

Ile Glu Lys Phe Lys Leu His Phe Asp Asn Pro Ser Leu Leu Ser Gly
545                 550                 555                 560

Trp Asp Lys Asn Lys Glu Leu Asn Asn Leu Ser Val Ile Phe Arg Gln
                565                 570                 575

Asn Gly Tyr Tyr Tyr Leu Gly Ile Met Thr Pro Lys Gly Lys Asn Leu
            580                 585                 590

Phe Lys Thr Leu Pro Lys Leu Gly Ala Glu Glu Met Phe Tyr Glu Lys
        595                 600                 605

Met Glu Tyr Lys Gln Ile Ala Glu Pro Met Leu Met Leu Pro Lys Val
    610                 615                 620

Phe Phe Pro Lys Lys Thr Lys Pro Ala Phe Ala Pro Asp Gln Ser Val
625                 630                 635                 640

Val Asp Ile Tyr Asn Lys Lys Thr Phe Lys Thr Gly Gln Lys Gly Phe
                645                 650                 655

Asn Lys Lys Asp Leu Tyr Arg Leu Ile Asp Phe Tyr Lys Glu Ala Leu
            660                 665                 670

Thr Val His Glu Trp Lys Leu Phe Asn Phe Ser Phe Ser Pro Thr Glu
        675                 680                 685

Gln Tyr Arg Asn Ile Gly Glu Phe Phe Asp Glu Val Arg Glu Gln Ala
    690                 695                 700

Tyr Lys Val Ser Met Val Asn Val Pro Ala Ser Tyr Ile Asp Glu Ala
705                 710                 715                 720

Val Glu Asn Gly Lys Leu Tyr Leu Phe Gln Ile Tyr Asn Lys Asp Phe
                725                 730                 735

Ser Pro Tyr Ser Lys Gly Ile Pro Asn Leu His Thr Leu Tyr Trp Lys
            740                 745                 750

Ala Leu Phe Ser Glu Gln Asn Gln Ser Arg Val Tyr Lys Leu Cys Gly
        755                 760                 765

Gly Gly Glu Leu Phe Tyr Arg Lys Ala Ser Leu His Met Gln Asp Thr
```

```
    770                 775                 780

Thr Val His Pro Lys Gly Ile Ser Ile His Lys Lys Asn Leu Asn Lys
785                 790                 795                 800

Lys Gly Glu Thr Ser Leu Phe Asn Tyr Asp Leu Val Lys Asp Lys Arg
                805                 810                 815

Phe Thr Glu Asp Lys Phe Phe Phe His Val Pro Ile Ser Ile Asn Tyr
            820                 825                 830

Lys Asn Lys Lys Ile Thr Asn Val Asn Gln Met Val Arg Asp Tyr Ile
        835                 840                 845

Ala Gln Asn Asp Asp Leu Gln Ile Ile Gly Ile Asp Arg Gly Glu Arg
    850                 855                 860

Asn Leu Leu Tyr Ile Ser Arg Ile Asp Thr Arg Gly Asn Leu Leu Glu
865                 870                 875                 880

Gln Phe Ser Leu Asn Val Ile Glu Ser Asp Lys Gly Asp Leu Arg Thr
                885                 890                 895

Asp Tyr Gln Lys Ile Leu Gly Asp Arg Glu Gln Glu Arg Leu Arg Arg
            900                 905                 910

Arg Gln Glu Trp Lys Ser Ile Glu Ser Ile Lys Asp Leu Lys Asp Gly
        915                 920                 925

Tyr Met Ser Gln Val Val His Lys Ile Cys Asn Met Val Val Glu His
    930                 935                 940

Lys Ala Ile Val Val Leu Glu Asn Leu Asn Val Glu Lys Ser Val Tyr
945                 950                 955                 960

Glu Lys Phe Glu Arg Met Leu Val Asp Lys Leu Asn Tyr Leu Val Val
                965                 970                 975

Asp Lys Lys Asn Leu Ser Asn Glu Pro Gly Gly Leu Tyr Ala Ala Tyr
            980                 985                 990

Gln Leu Thr Asn Pro Leu Phe Ser  Phe Glu Glu Leu His  Arg Tyr Pro
        995                 1000                1005

Gln Ser  Gly Ile Leu Phe Phe  Val Asp Pro Trp Asn  Thr Ser Leu
    1010                1015                1020

Thr Asp  Pro Ser Thr Gly Phe  Val Asn Leu Leu Gly  Arg Ile Asn
    1025                1030                1035

Tyr Thr  Asn Val Gly Asp Ala  Arg Lys Phe Phe Asp  Arg Phe Asn
    1040                1045                1050

Ala Ile  Arg Tyr Asp Gly Lys  Gly Asn Ile Leu Phe  Asp Leu Asp
    1055                1060                1065

Leu Ser  Arg Phe Asp Val Arg  Val Glu Thr Gln Arg  Lys Leu Trp
    1070                1075                1080

Thr Leu  Thr Thr Phe Gly Ser  Arg Ile Ala Lys Ser  Lys Lys Ser
    1085                1090                1095

Gly Lys  Trp Met Val Glu Arg  Ile Glu Asn Leu Ser  Leu Cys Phe
    1100                1105                1110

Leu Glu  Leu Phe Glu Gln Phe  Asn Ile Gly Tyr Arg  Val Glu Lys
    1115                1120                1125

Asp Leu  Lys Lys Ala Ile Leu  Ser Gln Asp Arg Lys  Glu Phe Tyr
    1130                1135                1140

Val Arg  Leu Ile Tyr Leu Phe  Asn Leu Met Met Gln  Ile Arg Asn
    1145                1150                1155

Ser Asp  Gly Glu Glu Asp Tyr  Ile Leu Ser Pro Ala  Leu Asn Glu
    1160                1165                1170

Lys Asn  Leu Gln Phe Asp Ser  Arg Leu Ile Glu Ala  Lys Asp Leu
    1175                1180                1185
```

```
Pro Val  Asp Ala Asp Ala Asn  Gly Ala Tyr Asn Val  Ala Arg Lys
    1190                 1195                 1200

Gly Leu  Met Val Val Gln Arg  Ile Lys Arg Gly Asp  His Glu Ser
    1205                 1210                 1215

Ile His  Arg Ile Gly Arg Ala  Gln Trp Leu Arg Tyr  Val Gln Glu
    1220                 1225                 1230

Gly Ile  Val Glu
    1235


<210> SEQ ID NO 143
<211> LENGTH: 13
<212> TYPE: PRT
<213> ORGANISM: Artificial sequence
<220> FEATURE:
<223> OTHER INFORMATION: synthetic sequence

<400> SEQUENCE: 143

Gly Gly Ala Gly Gly Ala Gly Gly Ala Gly Gly Ala Gly
1               5                   10


<210> SEQ ID NO 144
<211> LENGTH: 1259
<212> TYPE: PRT
<213> ORGANISM: Moraxella bovoculi

<400> SEQUENCE: 144

Met Gly Ile His Gly Val Pro Ala Ala Leu Phe Gln Asp Phe Thr His
1               5                   10                  15

Leu Tyr Pro Leu Ser Lys Thr Val Arg Phe Glu Leu Lys Pro Ile Gly
            20                  25                  30

Arg Thr Leu Glu His Ile His Ala Lys Asn Phe Leu Ser Gln Asp Glu
        35                  40                  45

Thr Met Ala Asp Met Tyr Gln Lys Val Lys Val Ile Leu Asp Asp Tyr
    50                  55                  60

His Arg Asp Phe Ile Ala Asp Met Met Gly Glu Val Lys Leu Thr Lys
65                  70                  75                  80

Leu Ala Glu Phe Tyr Asp Val Tyr Leu Lys Phe Arg Lys Asn Pro Lys
                85                  90                  95

Asp Asp Gly Leu Gln Lys Gln Leu Lys Asp Leu Gln Ala Val Leu Arg
            100                 105                 110

Lys Glu Ser Val Lys Pro Ile Gly Ser Gly Gly Lys Tyr Lys Thr Gly
        115                 120                 125

Tyr Asp Arg Leu Phe Gly Ala Lys Leu Phe Lys Asp Gly Lys Glu Leu
    130                 135                 140

Gly Asp Leu Ala Lys Phe Val Ile Ala Gln Glu Gly Glu Ser Ser Pro
145                 150                 155                 160

Lys Leu Ala His Leu Ala His Phe Glu Lys Phe Ser Thr Tyr Phe Thr
                165                 170                 175

Gly Phe His Asp Asn Arg Lys Asn Met Tyr Ser Asp Glu Asp Lys His
            180                 185                 190

Thr Ala Ile Ala Tyr Arg Leu Ile His Glu Asn Leu Pro Arg Phe Ile
        195                 200                 205

Asp Asn Leu Gln Ile Leu Thr Thr Ile Lys Gln Lys His Ser Ala Leu
    210                 215                 220

Tyr Asp Gln Ile Ile Asn Glu Leu Thr Ala Ser Gly Leu Asp Val Ser
225                 230                 235                 240
```

```
Leu Ala Ser His Leu Asp Gly Tyr His Lys Leu Leu Thr Gln Glu Gly
                245                 250                 255

Ile Thr Ala Tyr Asn Arg Ile Ile Gly Glu Val Asn Gly Tyr Thr Asn
            260                 265                 270

Lys His Asn Gln Ile Cys His Lys Ser Glu Arg Ile Ala Lys Leu Arg
        275                 280                 285

Pro Leu His Lys Gln Ile Leu Ser Asp Gly Met Gly Val Ser Phe Leu
    290                 295                 300

Pro Ser Lys Phe Ala Asp Asp Ser Glu Met Cys Gln Ala Val Asn Glu
305                 310                 315                 320

Phe Tyr Arg His Tyr Thr Asp Val Phe Ala Lys Val Gln Ser Leu Phe
                325                 330                 335

Asp Gly Phe Asp Asp His Gln Lys Asp Gly Ile Tyr Val Glu His Lys
            340                 345                 350

Asn Leu Asn Glu Leu Ser Lys Gln Ala Phe Gly Asp Phe Ala Leu Leu
        355                 360                 365

Gly Arg Val Leu Asp Gly Tyr Tyr Val Asp Val Val Asn Pro Glu Phe
    370                 375                 380

Asn Glu Arg Phe Ala Lys Ala Lys Thr Asp Asn Ala Lys Ala Lys Leu
385                 390                 395                 400

Thr Lys Glu Lys Asp Lys Phe Ile Lys Gly Val His Ser Leu Ala Ser
                405                 410                 415

Leu Glu Gln Ala Ile Glu His His Thr Ala Arg His Asp Asp Glu Ser
            420                 425                 430

Val Gln Ala Gly Lys Leu Gly Gln Tyr Phe Lys His Gly Leu Ala Gly
        435                 440                 445

Val Asp Asn Pro Ile Gln Lys Ile His Asn Asn His Ser Thr Ile Lys
    450                 455                 460

Gly Phe Leu Glu Arg Glu Arg Pro Ala Gly Glu Arg Ala Leu Pro Lys
465                 470                 475                 480

Ile Lys Ser Gly Lys Asn Pro Glu Met Thr Gln Leu Arg Gln Leu Lys
                485                 490                 495

Glu Leu Leu Asp Asn Ala Leu Asn Val Ala His Phe Ala Lys Leu Leu
            500                 505                 510

Thr Thr Lys Thr Thr Leu Asp Asn Gln Asp Gly Asn Phe Tyr Gly Glu
        515                 520                 525

Phe Gly Val Leu Tyr Asp Glu Leu Ala Lys Ile Pro Thr Leu Tyr Asn
    530                 535                 540

Lys Val Arg Asp Tyr Leu Ser Gln Lys Pro Phe Ser Thr Glu Lys Tyr
545                 550                 555                 560

Lys Leu Asn Phe Gly Asn Pro Thr Leu Leu Asn Gly Trp Asp Leu Asn
                565                 570                 575

Lys Glu Lys Asp Asn Phe Gly Val Ile Leu Gln Lys Asp Gly Cys Tyr
            580                 585                 590

Tyr Leu Ala Leu Leu Asp Lys Ala His Lys Lys Val Phe Asp Asn Ala
        595                 600                 605

Pro Asn Thr Gly Lys Asn Val Tyr Gln Lys Met Val Tyr Lys Leu Leu
    610                 615                 620

Pro Gly Pro Asn Lys Met Leu Pro Lys Val Phe Phe Ala Lys Ser Asn
625                 630                 635                 640

Leu Asp Tyr Tyr Asn Pro Ser Ala Glu Leu Leu Asp Lys Tyr Ala Lys
                645                 650                 655

Gly Thr His Lys Lys Gly Asp Asn Phe Asn Leu Lys Asp Cys His Ala
```

```
            660                 665                 670

Leu Ile Asp Phe Phe Lys Ala Gly Ile Asn Lys His Pro Glu Trp Gln
        675                 680                 685

His Phe Gly Phe Lys Phe Ser Pro Thr Ser Ser Tyr Arg Asp Leu Ser
    690                 695                 700

Asp Phe Tyr Arg Glu Val Glu Pro Gln Gly Tyr Gln Val Lys Phe Val
705                 710                 715                 720

Asp Ile Asn Ala Asp Tyr Ile Asp Glu Leu Val Glu Gln Gly Lys Leu
                725                 730                 735

Tyr Leu Phe Gln Ile Tyr Asn Lys Asp Phe Ser Pro Lys Ala His Gly
            740                 745                 750

Lys Pro Asn Leu His Thr Leu Tyr Phe Lys Ala Leu Phe Ser Glu Asp
        755                 760                 765

Asn Leu Ala Asp Pro Ile Tyr Lys Leu Asn Gly Glu Ala Gln Ile Phe
    770                 775                 780

Tyr Arg Lys Ala Ser Leu Asp Met Asn Glu Thr Thr Ile His Arg Ala
785                 790                 795                 800

Gly Glu Val Leu Glu Asn Lys Asn Pro Asp Asn Pro Lys Lys Arg Gln
                805                 810                 815

Phe Val Tyr Asp Ile Ile Lys Asp Lys Arg Tyr Thr Gln Asp Lys Phe
            820                 825                 830

Met Leu His Val Pro Ile Thr Met Asn Phe Gly Val Gln Gly Met Thr
        835                 840                 845

Ile Lys Glu Phe Asn Lys Lys Val Asn Gln Ser Ile Gln Gln Tyr Asp
    850                 855                 860

Glu Val Asn Val Ile Gly Ile Asp Arg Gly Glu Arg His Leu Leu Tyr
865                 870                 875                 880

Leu Thr Val Ile Asn Ser Lys Gly Glu Ile Leu Glu Gln Arg Ser Leu
                885                 890                 895

Asn Asp Ile Thr Thr Ala Ser Ala Asn Gly Thr Gln Val Thr Thr Pro
            900                 905                 910

Tyr His Lys Ile Leu Asp Lys Arg Glu Ile Glu Arg Leu Asn Ala Arg
        915                 920                 925

Val Gly Trp Gly Glu Ile Glu Thr Ile Lys Glu Leu Lys Ser Gly Tyr
    930                 935                 940

Leu Ser His Val Val His Gln Ile Asn Gln Leu Met Leu Lys Tyr Asn
945                 950                 955                 960

Ala Ile Val Val Leu Glu Asp Leu Asn Phe Gly Phe Lys Arg Gly Arg
                965                 970                 975

Phe Lys Val Glu Lys Gln Ile Tyr Gln Asn Phe Glu Asn Ala Leu Ile
            980                 985                 990

Lys Lys Leu Asn His Leu Val Leu  Lys Asp Lys Ala Asp  Asp Glu Ile
        995                 1000                1005

Gly Ser  Tyr Lys Asn Ala Leu  Gln Leu Thr Asn Asn  Phe Thr Asp
    1010                1015                1020

Leu Lys  Ser Ile Gly Lys Gln  Thr Gly Phe Leu Phe  Tyr Val Pro
    1025                1030                1035

Ala Trp  Asn Thr Ser Lys Ile  Asp Pro Glu Thr Gly  Phe Val Asp
    1040                1045                1050

Leu Leu  Lys Pro Arg Tyr Glu  Asn Ile Ala Gln Ser  Gln Ala Phe
    1055                1060                1065

Phe Gly  Lys Phe Asp Lys Ile  Cys Tyr Asn Thr Asp  Lys Gly Tyr
    1070                1075                1080
```

```
Phe Glu  Phe His Ile Asp Tyr  Ala Lys Phe Thr Asp  Lys Ala Lys
    1085                 1090                 1095

Asn Ser  Arg Gln Lys Trp Ala  Ile Cys Ser His Gly  Asp Lys Arg
    1100                 1105                 1110

Tyr Val  Tyr Asp Lys Thr Ala  Asn Gln Asn Lys Gly  Ala Ala Lys
    1115                 1120                 1125

Gly Ile  Asn Val Asn Asp Glu  Leu Lys Ser Leu Phe  Ala Arg Tyr
    1130                 1135                 1140

His Ile  Asn Asp Lys Gln Pro  Asn Leu Val Met Asp  Ile Cys Gln
    1145                 1150                 1155

Asn Asn  Asp Lys Glu Phe His  Lys Ser Leu Met Cys  Leu Leu Lys
    1160                 1165                 1170

Thr Leu  Leu Ala Leu Arg Tyr  Ser Asn Ala Ser Ser  Asp Glu Asp
    1175                 1180                 1185

Phe Ile  Leu Ser Pro Val Ala  Asn Asp Glu Gly Val  Phe Phe Asn
    1190                 1195                 1200

Ser Ala  Leu Ala Asp Asp Thr  Gln Pro Gln Asn Ala  Asp Ala Asn
    1205                 1210                 1215

Gly Ala  Tyr His Ile Ala Leu  Lys Gly Leu Trp Leu  Leu Asn Glu
    1220                 1225                 1230

Leu Lys  Asn Ser Asp Asp Leu  Asn Lys Val Lys Leu  Ala Ile Asp
    1235                 1240                 1245

Asn Gln  Thr Trp Leu Asn Phe  Ala Gln Asn Arg
    1250                 1255
```

<210> SEQ ID NO 145
<211> LENGTH: 1259
<212> TYPE: PRT
<213> ORGANISM: Eubacterium ventriosum

<400> SEQUENCE: 145

```
Met Glu Ser Asn Asn Lys Ile Phe Thr Glu Thr Ile Gly Thr Ser Ser
1               5                   10                  15

Ile Ala Lys Thr Met Arg Asn Ser Leu Val Pro Thr Glu Ser Thr Lys
            20                  25                  30

Arg Asn Ile Glu Lys Asn Gly Ile Ile Ile Asp Asp Gln Leu Arg Ala
        35                  40                  45

Glu Lys Arg Gln Gln Leu Lys Glu Ile Met Asp Glu Tyr Tyr Arg Ala
    50                  55                  60

Tyr Ile Asp Ser Lys Leu Ser Asn Val Ala Leu Thr Arg Thr Ile Asp
65                  70                  75                  80

Trp Lys Glu Leu Phe Gln Ala Ile Glu Asn Asn Tyr Lys Gln Asn Thr
                85                  90                  95

Thr Lys Thr Lys Asn Glu Leu Glu Lys Lys Gln Lys Glu Lys Arg Thr
            100                 105                 110

Glu Ile Tyr Lys Ile Leu Ser Asp Asp Glu Glu Phe Lys Gln Leu Phe
        115                 120                 125

Asn Ala Lys Leu Leu Thr Asn Ile Leu Pro Glu Phe Ile Lys Asn Gln
    130                 135                 140

Asn Ile Asp Asn Glu Glu Lys Gln Glu Lys Ile Ser Thr Val Glu Leu
145                 150                 155                 160

Phe Gln Arg Phe Thr Ser Ser Phe Thr Asp Phe Phe Lys Asn Arg Lys
                165                 170                 175

Asn Val Phe Ser Lys Asp Glu Ile Ser Thr Ser Ile Cys Tyr Arg Val
```

```
            180                 185                 190

Val Gln Glu Asn Ala Trp Ile Phe Tyr Gln Asn Leu Leu Ala Phe Glu
        195                 200                 205

Glu Ile Lys Lys Thr Ala Glu Gln Glu Ile Lys Lys Ile Glu Ala Glu
    210                 215                 220

Asn Arg Asp Ser Ile Ser Asp Tyr Ser Leu Lys Glu Ile Phe Asp Phe
225                 230                 235                 240

Asp Phe Tyr Gly Leu Leu Leu Asn Gln Gly Gly Ile Arg Phe Tyr Asn
                245                 250                 255

Asp Val Cys Gly Lys Ile Asn Tyr His Met Asn Leu Tyr Gly Gln Lys
            260                 265                 270

His Asn Ile Lys Ser Asn Lys Phe Lys Met Lys Arg Met His Lys Gln
        275                 280                 285

Ile Leu Ser Ile Asp Glu Ser Thr Phe Glu Val Pro Thr Met Phe Glu
    290                 295                 300

Asn Asp Lys Glu Val Tyr Gln Val Leu Asn Glu Phe Leu Ser Asp Leu
305                 310                 315                 320

Ala Ser Lys Lys Ile Leu Glu Arg Val Glu Lys Ile Gly Glu Asn Val
                325                 330                 335

Ser Glu Tyr Glu Ile Asn Lys Ile Tyr Ile Gln Ser Lys Asn Phe Glu
            340                 345                 350

Asn Phe Ser Ser Phe Met Cys Gly Asn Trp Gln Ile Ile Asn Asp Ser
        355                 360                 365

Leu Lys Thr Tyr Tyr Asn Glu Lys Ile Lys Ser Lys Gly Lys Ala Lys
    370                 375                 380

Val Glu Lys Val Lys Lys Ala Ile Lys Ala Ile Glu Tyr Lys Ser Leu
385                 390                 395                 400

Ala Asp Ile Asn Gln Leu Val Glu Arg Tyr Asn His Asp Glu Leu Asn
                405                 410                 415

Arg Lys Ala Glu Glu Tyr Ile Ser Ala Ile Asn Glu Lys Ile Lys Asp
            420                 425                 430

Leu Tyr Val Asn Glu Ile Glu Phe Asp Glu Lys Thr Asn Leu Ile Glu
        435                 440                 445

Asn Glu Thr Lys Ser Glu Glu Ile Lys Ser Lys Leu Asp Ser Ile Met
    450                 455                 460

Glu Ile Met His Trp Thr Lys Met Phe Ile Ile Glu Glu Glu Ile Glu
465                 470                 475                 480

Lys Asp Val Asn Phe Tyr Asn Glu Ile Glu Glu Ile Tyr Asp Glu Leu
                485                 490                 495

Gln Pro Leu Val Thr Ile Tyr Asn Arg Ile Arg Asn Tyr Val Thr Gln
            500                 505                 510

Lys Pro Tyr Ser Glu Glu Lys Ile Lys Leu Asn Phe Gly Ile Pro Thr
        515                 520                 525

Leu Ala Asn Gly Trp Ser Lys Thr Lys Glu Tyr Asp Asn Asn Ala Ile
    530                 535                 540

Ile Met Ile Arg Asp Gly Lys Tyr Tyr Leu Gly Ile Phe Asn Ala Lys
545                 550                 555                 560

Asn Lys Pro Asp Lys Lys Ile Met Glu Gly His Gln Ser Glu Glu Asn
                565                 570                 575

Gly Asp Tyr Lys Lys Met Ile Tyr Arg Leu Leu Pro Gly Pro Asn Lys
            580                 585                 590

Met Leu Pro Lys Val Phe Met Ser Lys Thr Gly Ile Ala Glu Tyr Lys
        595                 600                 605
```

```
Pro Ser Gln Tyr Ile Leu Glu Cys Tyr Glu Gln Asn Lys His Ile Lys
    610                 615                 620

Ser Asp Lys Asn Phe Asp Ile Lys Phe Cys Arg Asp Leu Ile Asp Phe
625                 630                 635                 640

Phe Lys Thr Ser Ile Asn Arg His Pro Glu Trp Ser Lys Phe Asn Phe
                645                 650                 655

Lys Phe Ser Glu Thr Ser Glu Tyr Glu Asp Ile Ser Thr Phe Tyr Arg
            660                 665                 670

Glu Val Glu Lys Gln Gly Tyr Lys Ile Glu Trp Thr Tyr Ile Ser Glu
        675                 680                 685

Lys Glu Ile Lys Glu Leu Asp Glu Asn Gly Gln Leu Tyr Leu Phe Gln
    690                 695                 700

Ile Tyr Asn Lys Asp Phe Ser Glu Lys Ser Lys Gly Lys Glu Asn Leu
705                 710                 715                 720

His Thr Met Tyr Leu Lys Asn Leu Phe Ser Glu Glu Asn Leu Lys Asn
                725                 730                 735

Ile Val Leu Lys Leu Asn Gly Glu Ala Glu Val Phe Phe Arg Lys Ser
            740                 745                 750

Ser Ile Lys Lys Pro Ile Ile His Lys Lys Gly Ser Val Leu Val Asn
        755                 760                 765

Lys Thr Tyr Asn Glu Asn Gly Glu Arg Lys Ser Ile Pro Glu Glu Gln
    770                 775                 780

Tyr Thr Glu Ile Tyr Lys Tyr Leu Asn Ser Ile Gly Thr Asn Glu Leu
785                 790                 795                 800

Ser Glu Lys Ser Lys Lys Leu Met Glu Glu Gly Lys Val Glu Tyr Tyr
                805                 810                 815

Lys Ala Asn Tyr Asp Ile Val Lys Asp Tyr Arg Tyr Ser Val Asp Lys
            820                 825                 830

Phe Phe Ile His Leu Pro Met Thr Ile Asn Phe Lys Ala Ala Gly Phe
        835                 840                 845

Ser Pro Ile Asn Asn Ile Ala Leu Lys Ser Ile Ala Leu Lys Glu Asp
    850                 855                 860

Met His Ile Ile Gly Ile Asp Arg Gly Glu Arg Asn Leu Ile Tyr Val
865                 870                 875                 880

Ser Val Ile Asp Thr Lys Gly Asn Ile Val Glu Gln Arg Asn Phe Asn
                885                 890                 895

Ile Val Asn Gly Ile Asp Tyr Lys Glu Lys Leu Lys Gln Lys Glu Leu
            900                 905                 910

Asp Arg Asp Asn Ala Arg Lys Asn Trp Lys Glu Ile Gly Lys Ile Lys
        915                 920                 925

Asp Leu Lys Glu Gly Tyr Leu Ser Leu Val Val His Glu Ile Ala Lys
    930                 935                 940

Leu Val Val Lys Tyr Asn Ala Ile Ile Thr Met Glu Asp Leu Asn Gln
945                 950                 955                 960

Gly Phe Lys Arg Gly Arg Phe Lys Val Glu Arg Gln Val Tyr Gln Lys
                965                 970                 975

Phe Glu Thr Met Leu Ile Asn Lys Leu Asn Tyr Leu Val Asp Lys Asp
            980                 985                 990

Leu Ala Val Asp Gln Glu Gly Gly  Leu Leu Arg Gly Tyr  Gln Leu Thr
        995                 1000                1005

Tyr Ile  Pro Glu Ser Leu Lys  Val Leu Gly Arg Gln  Cys Gly Tyr
    1010                1015                1020
```

-continued

```
Ile Phe  Tyr Val Pro Ala Ala  Tyr Thr Ser Lys Ile  Asp Pro Thr
    1025                 1030                 1035

Thr Gly  Phe Val Ala Ile Phe  Asn Tyr Lys Gly Met  Thr Asp Lys
    1040                 1045                 1050

Asp Phe  Val Thr Ser Phe Asp  Ser Ile Lys Tyr Asp  Asp Glu Arg
    1055                 1060                 1065

Gly Leu  Phe Ala Phe Glu Phe  Asp Tyr Glu Asn Phe  Val Thr His
    1070                 1075                 1080

Lys Val  Glu Met Ala Arg Asn  Lys Trp Thr Val Tyr  Thr Tyr Gly
    1085                 1090                 1095

Glu Arg  Ile Lys Arg Lys Phe  Lys Asn Gly Leu Trp  Asp Thr Ala
    1100                 1105                 1110

Glu Lys  Val Asp Leu Thr Tyr  Gln Met Arg Ser Ile  Leu Glu Lys
    1115                 1120                 1125

Tyr Glu  Ile Glu Tyr Asn Lys  Gly Gln Asp Ile Leu  Glu Gln Ile
    1130                 1135                 1140

Glu Glu  Leu Asp Glu Lys Ala  Gln Asn Gly Ile Cys  Lys Glu Ile
    1145                 1150                 1155

Lys Tyr  Leu Val Lys Asp Ile  Val Gln Met Arg Asn  Ser Leu Pro
    1160                 1165                 1170

Asp Asn  Ala Val Glu Asp Tyr  Asp Ala Ile Ile Ser  Pro Val Ile
    1175                 1180                 1185

Asn Asn  Asn Gly Glu Phe Phe  Asp Ser Thr Arg Gly  Asp Glu Asp
    1190                 1195                 1200

Lys Pro  Leu Asp Ala Asp Ala  Asn Gly Ala Tyr Cys  Ile Ala Leu
    1205                 1210                 1215

Lys Gly  Leu Tyr Glu Val Met  Gln Ile Lys Lys Asn  Trp Asn Glu
    1220                 1225                 1230

Glu Thr  Glu Phe Pro Arg Lys  Glu Leu Lys Ile Arg  His Gln Asp
    1235                 1240                 1245

Trp Phe  Asp Phe Ile Gln Asn  Lys Arg Tyr Leu
    1250                 1255
```

VARIANT TYPE V CRISPR/Cas EFFECTOR POLYPEPTIDES AND METHODS OF USE THEREOF

CROSS-REFERENCE

This application is national phase filing under 35 U.S.C. § 371 of PCT Application No. PCT/US2020/040927, filed Jul. 6, 2020, which claims the benefit of U.S. Provisional Patent Application No. 62/871,408, filed Jul. 8, 2019, and U.S. Provisional Patent Application No. 62/881,533, filed Aug. 1, 2019, which applications are incorporated herein by reference in their entirety.

STATEMENT REGARDING FEDERALLY SPONSORED RESEARCH

This invention was made with government support under 1244557 awarded by the National Science Foundation. The government has certain rights in the invention

INTRODUCTION

Bacterial adaptive immune systems employ CRISPRs (clustered regularly interspaced short palindromic repeats) and CRISPR-associated (Cas) proteins for RNA-guided nucleic acid cleavage. The CRISPR-Cas systems thereby confer adaptive immunity in bacteria and archaea via RNA-guided nucleic acid interference. To provide anti-viral immunity, processed CRISPR array transcripts (crRNAs) assemble with Cas protein-containing surveillance complexes that recognize nucleic acids bearing sequence complementarity to the virus derived segment of the crRNAs, known as the spacer. Class 2 CRISPR-Cas are streamlined versions in which a single Cas protein bound to RNA is responsible for binding to and cleavage of a targeted sequence. The programmable nature of these minimal systems has facilitated their use as a versatile technology for genome editing.

SUMMARY

The present disclosure provides variant type V CRISPR/Cas effector polypeptides, nucleic acids encoding the variant polypeptides, and systems comprising the variant polypeptides or nucleic acids encoding same. The present disclosure provides methods for modifying a target nucleic acid, using a variant polypeptide of the present disclosure.

BRIEF DESCRIPTION OF THE DRAWINGS

FIG. 1A-1F provide amino acid sequences of wild-type *Lachnospiraceae bacterium* Cas12a (Lb Cas12a) (FIG. 1A) and examples of variants (FIG. 1B-1F).

FIG. 2A-2F provide amino acid sequences of wild-type *Acidaminococcus* sp.BV3L6 Cas12a (FIG. 2A) and examples of variants (FIG. 2B-2F).

FIG. 3A-3F provide amino acid sequences of wild-type *Francisella novicida* U112 Cas12a (Fn Cas12a) (FIG. 3A) and examples of variants (FIG. 3B-3F).

FIG. 4A-4B provide amino acid sequences of wild-type *Porphyromonas macacae* Cas12a (FIG. 4A) and an example of a variant (FIG. 4B).

FIG. 5A-5B provide amino acid sequences of wild-type *Moraxella bovoculi* 237 Cas12a (FIG. 5A) and an example of a variant (FIG. 5B).

FIG. 6A-6B provide amino acid sequences of wild-type *Moraxella bovoculi* AAX08_00205 Cas12a (FIG. 6A) and an example of a variant (FIG. 6B).

FIG. 7A-7B provide amino acid sequences of wild-type *Moraxella bovoculi* AAX11_00205 Cas12a (FIG. 7A) and an example of a variant (FIG. 7B).

FIG. 8A-8B provide amino acid sequences of wild-type *Thiomicrospira* sp.XS5 Cas12a (FIG. 8A) and an example of a variant (FIG. 8B).

FIG. 9A-9B provide amino acid sequences of wild-type *Butyrivibrio* sp. NC3005 Cas12a (FIG. 9A) and an example of a variant (FIG. 9B).

FIG. 10A-10B provide amino acid sequences of wild-type *Brumimicrobium aurantiacum* Cas12a (FIG. 10A) and an example of a variant (FIG. 10B).

FIG. 11A-11B provide amino acid sequences of wild-type *Porphyromonas crevioricanis* Cas12a (FIG. 11A) and an example of a variant (FIG. 11B).

FIG. 12A-12B provide amino acid sequences of wild-type *Francisella tularensis* Cas12a (Ft Cas12a) (FIG. 12A) and an example of a variant (FIG. 12B).

FIG. 13A-13B provide amino acid sequences of wild-type *Eubacterium ventriosum* Cas12a (FIG. 13A) and an example of a variant (FIG. 13B).

FIG. 14A-14C provide amino acid sequences of wild-type *Alicyclobacillus acidoterrestris* Cas12b (FIG. 14A) and examples of variants (FIG. 14B-14C).

FIG. 15A-15C provide amino acid sequences of wild-type *Alicyclobacillus kakegawensis* Cas12b (FIG. 15A) and examples of variants (FIG. 15B-15C).

FIG. 16A-16C provide amino acid sequences of wild-type *Alicyclobacillus macrosporangiidus* Cas12b (FIG. 16A) and examples of variants (FIG. 16B-16C).

FIG. 17A-17C provide amino acid sequences of wild-type *Alicyclobacillus hesperidum* Cas12b (FIG. 17A) and examples of variants (FIG. 17B-17C).

FIG. 18A-18C provide amino acid sequences of wild-type *Sulfobacillus thermotolerans* Cas12b (FIG. 18A) and examples of variants (FIG. 18B-18C).

FIG. 19A-19C provide amino acid sequences of wild-type *Deltaproteobacteria bacterium* GWA2_43_19 Cas X (FIG. 19A) and examples of variants (FIG. 19B-19C).

FIG. 20A-20C provide amino acid sequences of wild-type *Plantomycetes bacterium* (FIG. 20A) and examples of variants (FIG. 20B-20C).

FIGS. 21A and 21B provide examples of crRNAs and a sgRNA (FIG. 21A) and examples of PAM sequences (FIG. 21B).

FIG. 22 depicts structures of examples of type V CRISPR/Cas effector polypeptides and the helix-loop element of examples of type V CRISPR/Cas effector polypeptides.

FIG. 24 provides examples of mutations in the loop of the helix-loop element of Lb Cas12a (Lb Cpf1) that eliminate trans nuclease (cleavage) activity.

DEFINITIONS

Figure 23:
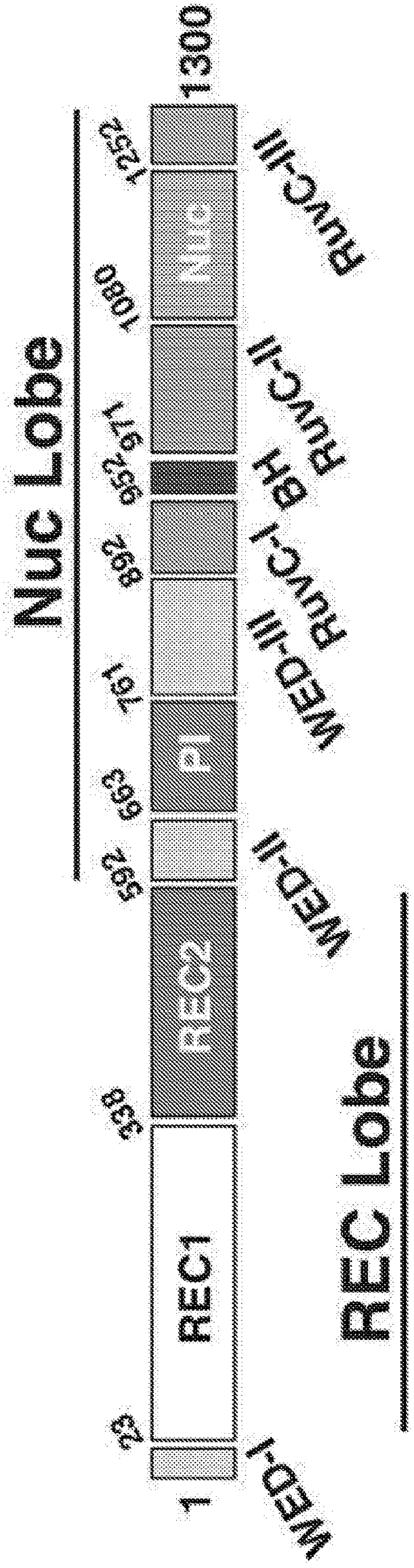
FIG. 23 depicts schematically the domain organization of Cas12a polypeptides.

The terms "polynucleotide" and "nucleic acid," used interchangeably herein, refer to a polymeric form of nucleotides of any length, either ribonucleotides or deoxyribonucleotides. Thus, terms "polynucleotide" and "nucleic acid" encompass single-stranded DNA; double-stranded DNA; multi-stranded DNA; single-stranded RNA; double-stranded RNA; multi-stranded RNA; genomic DNA; cDNA; DNA-RNA hybrids; and a polymer comprising purine and pyrimidine bases or other natural, chemically or biochemically modified, non-natural, or derivatized nucleotide bases.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine/adenosine) (A) pairing with thymidine/thymidine (T), A pairing with uracil/uridine (U), and guanine/guanosine) (G) pairing with cytosine/cytidine (C). In addition, for hybridization between two RNA molecules (e.g., dsRNA), and for hybridization of a DNA molecule with an RNA molecule (e.g., when a DNA target nucleic acid base pairs with a guide RNA, etc.): G can also base pair with U. For example, G/U base-pairing is partially responsible for the degeneracy (i.e., redundancy) of the genetic code in the context of tRNA anti-codon base-pairing with codons in mRNA. Thus, in the context of this disclosure, a G (e.g., of a protein-binding segment (e.g., dsRNA duplex) of a guide RNA molecule; of a target nucleic acid (e.g., target DNA) base pairing with a guide RNA) is considered complementary to both a U and to C. For example, when a G/U base-pair can be made at a given nucleotide position of a protein-binding segment (e.g., dsRNA duplex) of a guide RNA molecule, the position is not considered to be non-complementary, but is instead considered to be complementary.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more).

It is understood that the sequence of a polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure, a 'bulge', and the like). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. The remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Example methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), e.g., using default settings, which uses the algorithm of Smith and Waterman (Adv. Appl. Math., 1981, 2, 482-489).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide, binding to a target nucleic acid, and the like) refers to a non-covalent interaction between macromolecules (e.g., between a protein and a nucleic acid; between a guide RNA and a target nucleic acid; and the like). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_d$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_d$.

By "binding domain" it is meant a protein domain that is able to bind non-covalently to another molecule. A binding domain can bind to, for example, an RNA molecule (an RNA-binding domain) and/or a protein molecule (a protein-binding domain) In the case of a protein having a protein-binding domain, it can in some cases bind to itself (to form homodimers, homotrimers, etc.) and/or it can bind to one or more regions of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various methods and computer programs (e.g., BLAST, T-COFFEE, MUSCLE, MAFFT, Phyre2, etc.), available over the world wide web at sites including ncbi.nlm.nili.gov/BLAST, ebi-.ac.uk/Tools/msa/tcoffee/, ebi.ac.uk/Tools/msa/muscle/, mafft.cbrc.jp/alignment/software/, http://www.sbg.bio.ic.a-c.uk/~phyre2/. See, e.g., Altschul et al. (1990), J. Mol. Bioi. 215:403-10.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide RNA) or a coding sequence (e.g., protein coding) and/or regulate translation of an encoded polypeptide.

As used herein, a "promoter sequence" is a DNA regulatory region capable of binding RNA polymerase and initiating transcription of a downstream (3' direction) coding or non-coding sequence. Eukaryotic promoters will often, but not always, contain "TATA" boxes and "CAT" boxes. Various promoters, including inducible promoters, may be used to drive the various nucleic acids (e.g., vectors) of the present disclosure.

The term "naturally-occurring" or "unmodified" or "wild type" as used herein as applied to a nucleic acid, a polypeptide, a cell, or an organism, refers to a nucleic acid, polypeptide, cell, or organism that is found in nature.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", above). Alternatively, DNA sequences encoding RNA (e.g., guide RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may have a naturally occurring amino acid sequence.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

"Heterologous," as used herein, refers to a nucleotide or polypeptide sequence that is not found in the native nucleic acid or protein, respectively. For example, relative to a variant type V CRISPR/Cas effector polypeptide of the present disclosure, a heterologous polypeptide comprises an amino acid sequence from a protein other than the variant type V CRISPR/Cas effector polypeptide. As another example, a variant type V CRISPR/Cas effector polypeptide of the present disclosure can be fused to an active domain from a non-CRISPR/Cas effector protein (e.g., a histone deacetylase), and the sequence of the active domain could be considered a heterologous polypeptide (it is heterologous to the variant type V CRISPR/Cas effector polypeptide).

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a variant type V CRISPR/Cas effector polypeptide" includes a plurality of such polypeptides and reference to "the guide" includes reference to one or more guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides variant type V CRISPR/Cas effector polypeptides, nucleic acids encoding the variant polypeptides, and systems comprising the variant polypeptides or nucleic acids encoding same. The present disclosure provides methods for modifying a target nucleic acid, using a variant polypeptide of the present disclosure.

Variant Type V Crispr/Cas Effector Polypeptides

The present disclosure provides variant type V CRISPR/Cas effector polypeptides. The present disclosure also provides fusion polypeptides comprising: a) a variant type V CRISPR/Cas effector polypeptide of the present disclosure; and b) a heterologous polypeptide (i.e., one or more heterologous polypeptides, where a heterologous polypeptide is also referred to herein as a "fusion partner").

A wild-type type V CRISPR/Cas protein, e.g., Cas12 proteins such as Cpf1 (Cas12a) and C2c1 (Cas12b), can promiscuously cleave non-targeted single-stranded DNA (ssDNA) once activated by binding of a target DNA (double or single stranded). For example, a wild-type type V CRISPR/Cas effector protein (e.g., a Cas12 protein such as Cas12a, Cas12b, Cas12c, Cas12d, Cas12e, Cas12f, Cas12g, Cas12h, or Cas12i) is activated by a guide RNA, which occurs when the guide RNA hybridizes to a target sequence of a target DNA, the protein becomes a nuclease that promiscuously cleaves ssDNAs (i.e., the nuclease cleaves non-target ssDNAs, i.e., ssDNAs to which the guide sequence of the guide RNA does not hybridize). When a type V CRISPR/Cas effector protein is activated by a guide RNA and exhibits on-target cleavage of the target ssDNA, such on-target cleavage is referred to as "cis" cleavage (Li et al (2018) *Cell Research* 28:491-493).

A variant type V CRISPR/Cas effector polypeptide of the present disclosure, when complexed with a guide RNA, binds a target nucleic acid, where the guide RNA comprises a segment that hybridizes to a complementary segment in the target nucleic acid. A variant type V CRISPR/Cas effector polypeptide of the present disclosure exhibits reduced or no cleavage of a non-target single-stranded DNA. For example, a variant type V CRISPR/Cas effector polypeptide of the present disclosure, when complexed with a guide RNA, binds a target nucleic acid, but exhibits less than 50% (e.g., less than 50%, less than 45%, less than 40%, less than 35%, less than 30%, less than 25%, less than 20%, less than 15%, less than 10%, less than 5%, less than 2%, or less than 1%) of the cleavage of a non-target ssDNA exhibited by a wild-type type V CRISPR/Cas effector polypeptide. Cleavage of a non-target ssDNA is referred to herein as "trans cleavage."

In some cases, a variant type V CRISPR/Cas effector polypeptide of the present disclosure, when complexed with a guide RNA, exhibits less than 50% (e.g., less than 50%, less than 45%, less than 40%, less than 35%, less than 30%, less than 25%, less than 20%, less than 15%, less than 10%, less than 5%, less than 2%, or less than 1%) of the trans cleavage exhibited by a type V CRISPR/Cas effector polypeptide that does not include the one or more mutations in the loop of the helix-loop element of the RuvC domain. In some cases, a variant type V CRISPR/Cas effector polypeptide of the present disclosure, when complexed with a guide RNA, does not exhibit any detectable trans cleavage, as assayed using a method as described in Example 1.

FIG. 22 provides the structures of Cas12a, Cas12b, and a CasX protein. Beneath the structures are amino acid sequences of the loop of the helix-loop element of each protein. FIG. 23 presents a schematic diagram of the domain organization of Cas12a proteins. The amino acid numbering is based on the *Francisella novicida* Cas12a amino acid sequence depicted in FIG. 3A. The helix-loop is within the RuvC domain FIG. 24 shows amino acid changes made to the loop of the helix-loop element in *Lachnospiraceae bacterium* Cas12a (LbCas12a; also referred to as "LbCpf1"; amino acid sequence depicted in FIG. 1A). The wild-type (w t) amino acid sequence SGFKNSRVK (SEQ ID NO: 60)

Figure 25:
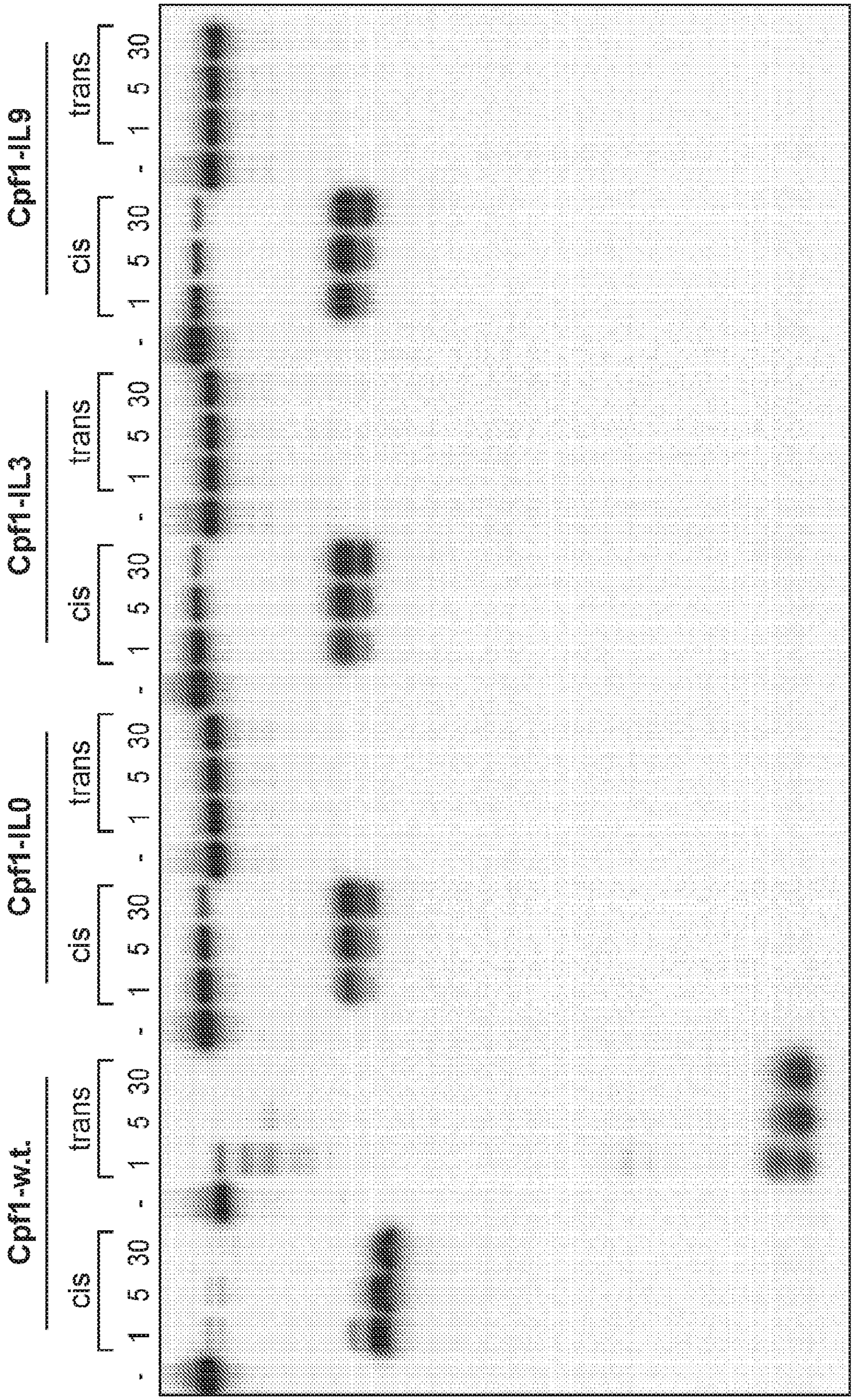
FIG. 25 depicts the effect of mutations in the loop of the helix-loop element of Lb Cas12a (Lb Cpf1) on trans cleavage activity.

(corresponding to amino acids 929-937 of LbCas12a) of the loop of the helix-loop element of *Lachnospiraceae bacterium* Cas12a is shown; below the wild-type amino acid sequence are sequences of the loop of the helix-loop element of 3 variants: IL9, IL3, and ILO. The effect of the changes to the amino acid sequence of the loop in variants IL9 ("Cpf1d-IL9"), IL3 ("Cpf1-IL3"), and ILO ("Cpf1-IL0") is depicted in FIG. 25. As shown in FIG. 25, variant IL9, IL3, and ILO do not exhibit trans cleavage activity (trans DNA nuclease activity), as determined by the assay described in Example 1.

In some cases, a variant type V CRISPR/Cas effector polypeptide of the present disclosure, when complexed with a guide RNA, exhibits less than 50% (e.g., less than 50%, less than 45%, less than 40%, less than 35%, less than 30%, less than 25%, less than 20%, less than 15%, less than 10%, less than 5%, less than 2%, or less than 1%) of the trans cleavage exhibited by a type V CRISPR/Cas effector polypeptide comprising one of the amino acid sequences depicted in FIG. 1A, FIG. 2A, FIG. 3A, FIG. 4A, FIG. 5A, FIG. 6A, FIG. 7A, FIG. 8A, FIG. 9A, FIG. 10A, FIG. 11A, FIG. 12A, FIG. 13A, FIG. 14A, FIG. 15A, FIG. 16A, FIG. 17A, FIG. 18A, FIG. 19A, or FIG. 20A.

In some cases, a variant type V CRISPR/Cas effector polypeptide of the present disclosure, when complexed with a guide RNA, exhibits less than 50% (e.g., less than 50%, less than 45%, less than 40%, less than 35%, less than 30%, less than 25%, less than 20%, less than 15%, less than 10%, less than 5%, less than 2%, or less than 1%) of the trans cleavage exhibited by a type V CRISPR/Cas effector polypeptide comprising the following *Lachnospiraceae bacterium* Cas12a amino acid sequence (where the loop of the helix-loop element is indicated in bold underline):

(SEQ ID NO: 1)

MSKLEKFTNCYSLSKTLRFKAIPVGKTQENIDNKRLLVEDEKRAEDYKGV

KKLLDRYYLSFINDVLHSIKLKNLNNYISLFRKKTRTEKENKELENLEIN

LRKEIAKAFKGNEGYKSLFKKDIIETILPEFLDDKDEIALVNSFNGFTTA

FTGFFDNRENMFSEEAKSTSIAFRCINENLTRYISNMDIFEKVDAIFDKH

EVQEIKEKILNSDYDVEDFFEGEFFNFVLTQEGIDVYNAIIGGFVTESGE

KIKGLNEYINLYNQKTKQKLPKFKPLYKQVLSDRESLSFYGEGYTSDEEV

LEVFRNTLNKNSEIFSSIKKLEKLFKNFDEYSSAGIFVKNGPAISTISKD

IFGEWNVIRDKWNAEYDDIHLKKKAVVTEKYEDDRRKSFKKIGSFSLEQL

QEYADADLSVVEKLKEIIIQKVDEIYKVYGSSEKLFDADFVLEKSLKKND

AVVAIMKDLLDSVKSFENYIKAFFGEGKETNRDESFYGDFVLAYDILLKV

DHIYDAIRNYVTQKPYSKDKFKLYFQNPQFMGGWDKDKETDYRATILRYG

SKYYLAIMDKKYAKCLQKIDKDDVNGNYEKINYKLLPGPNKMLPKVFFSK

KWMAYYNPSEDIQKIYKNGTFKKGDMFNLNDCHKLIDFFKDSISRYPKWS

NAYDFNFSETEKYKDIAGFYREVEEQGYKVSFESASKKEVDKLVEEGKLY

MFQIYNKDFSDKSHGTPNLHTMYFKLLFDENNHGQIRLSGGAELFMRRAS

LKKEELVVHPANSPIANKNPDNPKKTTTLSYDVYKDKRFSEDQYELHIPI

AINKCPKNIFKINTEVRVLLKHDDNPYVIGIDRGERNLLYIVVVDGKGNI

VEQYSLNEIINNFNGIRIKTDYHSLLDKKEKERFEARQNWTSIENIKELK

AGYISQVVHKICELVEKYDAVIALEDLNSGFKNSRVKVEKQVYQKFEKML

-continued

IDKLNYMVDKKSNPCATGGALKGYQITNKFESFKSMSTQNGFIFYIPAWL

TSKIDPSTGFVNLLKTKYTSIADSKKFISSFDRIMYVPEEDLFEFALDYK

NFSRTDADYIKKWKLYSYGNRIRIFRNPKKNNVFDWEEVCLTSAYKELFN

KYGINYQQGDIRALLCEQSDKAFYSSFMALMSLMLQMRNSITGRTDVDFL

ISPVKNSDGIFYDSRNYEAQENAILPKNADANGAYNIARKVLWAIGQFKK

AEDEKLDKVKIAISNKEWLEYAQTSVKH.

In some cases, a variant type V CRISPR/Cas effector polypeptide of the present disclosure, when complexed with a guide RNA, exhibits less than 50% (e.g., less than 50%, less than 45%, less than 40%, less than 35%, less than 30%, less than 25%, less than 20%, less than 15%, less than 10%, less than 5%, less than 2%, or less than 1%) of the trans cleavage exhibited by a type V CRISPR/Cas effector polypeptide comprising the following *Francisella novicida* U112 Cas12a amino acid sequence (where the loop of the helix-loop element is indicated in bold underline):

(SEQ ID NO: 3)

IMSIYQEFVNKYSLSKTLRFELIPQGKTLENIKARGLILDDEKRAKDYKK

AKQIIDKYHQFFIEEILSSVCISEDLLQNYSDVYFKLKKSDDDNLQKDFK

SAKDTIKKQISEYIKDSEKFKNLFNQNLIDAKKGQESDLILWLKQSKDNG

IELFKANSDITDIDEALEIIKSFKGWTTYFKGFHENRKNVYSSNDIPTSI

IYRIVDDNLPKFLENKAKYESLKDKAPEAINYEQIKKDLAEELTFDIDYK

TSEVNQRVFSLDEVFEIANFNNYLNQSGITKFNTIIGGKFVNGENTKRKG

INEYINLYSQQINDKTLKKYKMSVLFKQILSDTESKSFVIDKLEDDSDVV

TTMQSFYEQIAAFKTVEEKSIKETLSLLFDDLKAQKLDLSKIYFKNDKSL

TDLSQQVFDDYSVIGTAVLEYITQQIAPKNLDNPSKKEQELIAKKTEKAK

YLSLETIKLALEEFNKHRDIDKQCRFEEILANFAAIPMIFDEIAQNKDNL

AQISIKYQNQGKKDLLQASAEDDVKAIKDLLDQTNNLLHKLKIFHISQSE

DKANILDKDEHFYLVFEECYFELANIVPLYNKIRNYITQKPYSDEKFKLN

FENSTLANGWDKNKEPDNTAILFIKDDKYYLGVMNKKNNKIFDDKAIKEN

KGEGYKKIVYKLLPGANKMLPKVFFSAKSIKFYNPSEDILRIRNHSTHTK

NGSPQKGYEKFEFNIEDCRKFIDFYKQSISKHPEWKDFGFRFSDTQRYNS

IDEFYREVENQGYKLTFENISESYIDSVVNQGKLYLFQIYNKDFSAYSKG

RPNLHTLYWKALFDERNLQDVVYKLNGEAELFYRKQSIPKKITHPAKEAI

ANKNKDNPKKESVFEYDLIKDKRFTEDKFFFHCPITINFKSSGANKFNDE

INLLLKEKANDVHILSIDRGERHLAYYTLVDGKGNIIKQDTFNIIGNDRM

KTNYHDKLAAIEKDRDSARKDWKKINNIKEMKEGYLSQVVHEIAKLVIEY

NAIVVFEDLNFGFKRGREKVEKQVYQKLEKMLIEKLNYLVFKDNEFDKTG

GVLRAYQLTAPFETFKKMGKQTGIIYYVPAGFTSKICPVTGFVNQLYPKY

ESVSKSQEFFSKFDKICYNLDKGYFEFSFDYKNFGDKAAKGKWTIASFGS

RLINFRNSDKNHNWDTREVYPTKELEKLLKDYSIEYGHGECIKAAICGES

DKKFFAKLTSVLNTILQMRNSKTGTELDYLISPVADVNGNFFDSRQAPKN

MPQDADANGAYHIGLKGLMLLGRIKNNQEGKKLNLVIKNEEYFEFVQNRN

N.

A variant type V CRISPR/Cas effector polypeptide of the present disclosure comprises one or more mutations in the loop of the helix-loop element of the RuvC domain, compared with a wild-type type V CRISPR/Cas effector polypeptide. The one or more mutations can include: one or more amino acid substitutions; deletion of one or more amino acids; insertion of one or more amino acids; or a combination of deletion of one or more amino acids and a substitution of one or more amino acids. In some cases, a variant type V CRISPR/Cas effector polypeptide of the present disclosure comprises a deletion of one or more amino acids in the loop of the helix-loop element of the RuvC domain. In some cases, a variant type V CRISPR/Cas effector polypeptide of the present disclosure comprises a substitution of one or more charged amino acids with an amino acid other than Lys, Arg, His, Asp, or Glu in the loop of the helix-loop element of the RuvC domain. In some cases, a variant type V CRISPR/Cas effector polypeptide of the present disclosure comprises a substitution of one or more charged amino acids with an amino acid having a polar uncharged side chain (e.g., Ser, Thr, Asn, or Gln) in the loop of the helix-loop element of the RuvC domain. In some cases, a variant type V CRISPR/Cas effector polypeptide of the present disclosure comprises a substitution of one or more charged amino acids with an amino acid having a hydrophobic side chain (e.g., Ala, Val, Ile, Leu, Met, Phe, Tyr, or Trp) in the loop of the helix-loop element of the RuvC domain. In some cases, a variant type V CRISPR/Cas effector polypeptide of the present disclosure comprises a substitution of one or more charged amino acids with a Gly or an Ala in the loop of the helix-loop element of the RuvC domain. In some cases, a variant type V CRISPR/Cas effector polypeptide of the present disclosure comprises a substitution of a Lys with an amino acid other than Lys, Arg, His, Asp, or Glu in the loop of the helix-loop element of the RuvC domain. In some cases, a variant type V CRISPR/Cas effector polypeptide of the present disclosure comprises a substitution of an Arg with an amino acid other than Lys, Arg, His, Asp, or Glu in the loop of the helix-loop element of the RuvC domain. In some cases, a variant type V CRISPR/Cas effector polypeptide of the present disclosure comprises a substitution of a Lys and an Arg with amino acids other than Lys, Arg, His, Asp, or Glu in the loop of the helix-loop element of the RuvC domain. In some cases, a variant type V CRISPR/Cas effector polypeptide of the present disclosure comprises a substitution of an Asp with an amino acid other than Lys, Arg, His, Asp, or Glu in the loop of the helix-loop element of the RuvC domain. In some cases, a variant type V CRISPR/Cas effector polypeptide of the present disclosure comprises a substitution of a Glu with an amino acid other than Lys, Arg, His, Asp, or Glu in the loop of the helix-loop element of the RuvC domain. In some cases, a variant type V CRISPR/Cas effector polypeptide of the present disclosure comprises two or more of any of the above disclosed substitutions in the loop of the helix loop element of Cas12a in any order; and exhibits decreased trans cleavage activity as compared with the wild type protein, as measured by methods known in the art (see e.g. Example 1).

For example, the loop of the helix-loop element of a Cas12a polypeptide that exhibits trans cleavage can comprise an amino acid sequence such as SGFKNSRVK (SEQ ID NO: 60), FGFKSKRTG (SEQ ID NO: 62), LSFMKGRKK (SEQ ID NO: 86), FGFKRGRFK (SEQ ID NO: 61), FGFKRGRQK (SEQ ID NO: 73), MGFKRGRFK (SEQ ID NO: 74), MGFKRGRQK (SEQ ID NO: 63), or QGFKRGRFK (SEQ ID NO: 75); and a variant Cas12a polypeptide of the present disclosure can comprise: i) a deletion of the entire loop; or ii) a deletion of 8 amino acids of the loop; or iii) a deletion of 7 amino acids of the loop element; or iv) a deletion of 6 amino acids of the loop; or v) a deletion of 5 amino acids of the loop; or vi) a deletion of 4 amino acids of the loop; or vii) a deletion of 3 amino acids of the loop; or viii) a substitution of one Lys of the loop with an amino acid other than Lys, Arg, or His; or ix) a substitution of both Lys of the loop with an amino acid other than Lys, Arg, or His; or x) a substitution of the Arg of the loop with an amino acid other than Lys, Arg, or His; or xi) an insertion of one or more amino acids into the loop; or xii) a replacement of the loop with 1, 2, 3, 4, 5, 6, 7, 8, or 9 amino acids, where the replacement comprises one or more Gly and/or one or more Ala. In some cases, where a Lys and/or an Arg is substituted with an amino acid other than Lys, Arg, or His, the Lys and/or the Arg is/are substituted with Ala, Val, Ile, Leu, Met, Phe, Tyr, Trp, Gly, Cys, Pro, Ser, Thr, Asn, Gln, Asp, or Glu. In some cases, where a Lys and/or an Arg is substituted with an amino acid other than Lys, Arg, or His, the Lys and/or the Arg is/are substituted with Ala, Val, Ile, Leu, Gly, Ser, or Thr. In some cases, where a Lys and/or an Arg is substituted with an amino acid other than Lys, Arg, or His, the Lys and/or the Arg is/are substituted with Ala or Gly. In some cases, a variant type V CRISPR/Cas effector polypeptide of the present disclosure comprises two or more of any of the above disclosed substitutions in the loop of the helix loop element of Cas12a in any order; and exhibits decreased trans cleavage activity as compared with the wild type protein, as measured by methods known in the art (see e.g. Example 1).

The loop of the helix-loop element of a Cas12a polypeptide can be, e.g., amino acids 929-937, based on the amino acid numbering of LbCas12a, or the corresponding amino acids of another Cas12a polypeptide. The loop of the helix-loop element of a Cas12b polypeptide can be, e.g., amino acids 852-865 of Aa Cas12b, or the corresponding amino acids of another Cas12b polypeptide. The loop of the helix-loop element of a CasX (Cas12e) polypeptide can be, e.g., amino acids 776-788 of Dpb CasX, or the corresponding amino acids of another CasX polypeptide. See, e.g., FIG. 22.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 1B, where the loop having the sequence SGFKNSRVK (SEQ ID NO: 60) as depicted in FIG. 1A is deleted; i.e., the variant type V CRISPR/Cas effector polypeptide does not include the sequence SGFKNSRVK (SEQ ID NO: 60).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 1C, where the loop sequence SGFKNSRVK (SEQ ID NO: 60) present in the variant type V CRISPR/Cas effector polypeptide depicted in FIG. 1A has been mutated to GGAAGGAAP (SEQ ID NO: 76), GGAAGGAAG (SEQ ID NO: 77), or GGAAGGAAA (SEQ ID NO: 78), or some other combination of Gly and Ala.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 1D, where the where the loop sequence SGFKNSRVK (SEQ ID NO: 60) present in the variant type V CRISPR/Cas effector polypeptide depicted in FIG. 1A has been mutated to GAA, GGA, AGG, AAG, or GAP.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 1E, where the loop sequence SGFKNSRVK (SEQ ID NO: 60) present in the variant type V CRISPR/Cas effector polypeptide depicted in FIG. 1A has been mutated to SGFANSRVA (SEQ ID NO: 79).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 1F, where the loop sequence SGFKNSRVK (SEQ ID NO: 60) present in the variant type V CRISPR/Cas effector polypeptide depicted in FIG. 1A has been mutated to SGAKNSAVA (SEQ ID NO: 80).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 2B, where the loop having the sequence FGFKSKRTG (SEQ ID NO: 62) as depicted in FIG. 2A is deleted; i.e., the variant type V CRISPR/Cas effector polypeptide does not include the sequence FGFK-SKRTG (SEQ ID NO: 62).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 2C, where the loop having the sequence FGFKSKRTG (SEQ ID NO: 62) as depicted in FIG. 2A is mutated to GGAAGGAAG (SEQ ID NO: 77), GGAAGGAAP (SEQ ID NO: 76), GGAAGGGAG (SEQ ID NO: 81), or GGAAGGAAA (SEQ ID NO: 78), or some other combination of Gly and Ala.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 2D, where the loop having the sequence FGFKSKRTG (SEQ ID NO: 62) as depicted in FIG. 2A is mutated to GAA, GGA, AGG, AAG, or GAP.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 2E, where the loop having the sequence FGFKSKRTG (SEQ ID NO: 62) as depicted in FIG. 2A is mutated to FGFASARTG (SEQ ID NO: 82).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 2F, where the loop having the sequence FGFKSKRTG (SEQ ID NO: 62) as depicted in FIG. 2A is mutated to FGFASAATG (SEQ ID NO: 83).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 3B, where the loop having the sequence FGFKRGRFK (SEQ ID NO: 61) as depicted in FIG. 3A is deleted; i.e., the variant type V CRISPR/Cas effector polypeptide does not include the sequence FGFKR-GRFK (SEQ ID NO: 61).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 3C, where the loop having the sequence FGFKRGRFK (SEQ ID NO: 61) as depicted in FIG. 3A is mutated to GGAAGGAAG (SEQ ID NO: 77), GGAAGGAAP (SEQ ID NO: 76), GGAAGGGAG (SEQ ID NO: 81), or GGAAGGAAA (SEQ ID NO: 78), or some other combination of Gly and Ala.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 3D, where the loop having the sequence FGFKRGRFK (SEQ ID NO: 61) as depicted in FIG. 3A is mutated to GAA, GGA, AGG, AAG, or GAP.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 3E, where the loop having the sequence FGFKRGRFK (SEQ ID NO: 61) as depicted in FIG. 3A is mutated to FGFARGRFA (SEQ ID NO: 84).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 3F, where the loop having the sequence FGFKRGRFK (SEQ ID NO: 61) as depicted in FIG. 3A is mutated to FGFKAGAFK (SEQ ID NO: 85).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 4B, where the loop having the sequence LSFMKGRKK (SEQ ID NO: 86) as depicted in FIG. 4A is deleted; i.e., the variant type V CRISPR/Cas effector polypeptide does not include the sequence LSFMKGRKK (SEQ ID NO: 86).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 4A, but where the loop having the sequence LSFMKGRKK (SEQ ID NO: 86) is mutated to: GGAAGGAAG (SEQ ID NO: 77), GGAAGGAAP (SEQ ID NO: 76), GGAAGGGAG (SEQ ID NO: 81), GGAAGGAAA (SEQ ID NO: 78), GAA, GGA, AGG, AAG, GAP, LSFMAGRKK (SEQ ID NO: 86), LSFMKGRAA (SEQ ID NO: 87), LSFMAGRAA (SEQ ID NO: 88), or LSFMAGAKK (SEQ ID NO: 39).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 5B, where the loop having the sequence FGFKRGRFK (SEQ ID NO: 61) as depicted in FIG. 5A is deleted; i.e., the variant type V CRISPR/Cas effector polypeptide does not include the sequence FGFKRGRFK (SEQ ID NO: 61).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 5A, but where the loop having the sequence FGFKRGRFK (SEQ ID NO: 61) is mutated to: GGAAGGAAG (SEQ ID NO: 77), GGAAGGAAP (SEQ ID NO: 76), GGAAGGGAG (SEQ ID NO: 81), GGAAGGAAA (SEQ ID NO: 78), GAA, GGA, AGG, AAG, GAP, FGFARGRFA (SEQ ID NO: 84), FGFKAGAFK (SEQ ID NO: 85), or FGFAAGAFA (SEQ ID NO: 90).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 6B, where the loop having the sequence FGFKRGRFK (SEQ ID NO: 61) as depicted in FIG. 6A is deleted; i.e., the variant type V CRISPR/Cas effector polypeptide does not include the sequence FGFKRGRFK (SEQ ID NO: 61).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 6A, but where the loop having the sequence FGFKRGRFK (SEQ ID NO: 61) is mutated to: GGAAGGAAG (SEQ ID NO: 77), GGAAGGAAP (SEQ ID NO: 76), GGAAGGGAG (SEQ ID NO: 81), GGAAGGAAA (SEQ ID NO: 78), GAA, GGA, AGG, AAG, GAP, FGFARGRFA (SEQ ID NO: 84), FGFKAGAFK (SEQ ID NO: 85), FGFARGAFK (SEQ ID NO: 91), or FGFKAGRFA (SEQ ID NO: 92).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 7B, where the loop having the sequence FGFKRGRFK (SEQ ID NO: 61) as depicted in FIG. 7A is deleted; i.e., the variant type V CRISPR/Cas effector polypeptide does not include the sequence FGFKRGRFK (SEQ ID NO: 61).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 7A, but where the loop having the sequence FGFKRGRFK (SEQ ID NO: 61) is mutated to: GGAAGGAAG (SEQ ID NO: 77), GGAAGGAAP (SEQ ID NO: 76), GGAAGGGAG (SEQ ID NO: 81), GGAAGGAAA (SEQ ID NO: 78), GAA, GGA, AGG, AAG, GAP, FGFARGRFA (SEQ ID NO: 84), FGFKAGAFK (SEQ ID NO: 85), FGFARGAFK (SEQ ID NO: 91), or FGFKAGRFA (SEQ ID NO: 92).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 8B, where the loop having the sequence FGFKRGRFK (SEQ ID NO: 61) as depicted in FIG. 8A is deleted; i.e., the variant type V CRISPR/Cas effector polypeptide does not include the sequence FGFKRGRFK (SEQ ID NO: 61).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 8A, but where the loop having the sequence FGFKRGRFK (SEQ ID NO: 61) is mutated to: GGAAGGAAG (SEQ ID NO: 77), GGAAGGAAP (SEQ ID NO: 76), GGAAGGGAG (SEQ ID NO: 81), GGAAGGAAA (SEQ ID NO: 78), GAA, GGA, AGG, AAG, GAP, FGFARGRFA (SEQ ID NO: 84), FGFKAGAFK (SEQ ID NO: 85), FGFARGAFK (SEQ ID NO: 91), or FGFKAGRFA (SEQ ID NO: 92).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 9B, where the loop having the sequence FGFKRGRQK (SEQ ID NO: 73) as depicted in FIG. 9A is deleted; i.e., the variant type V CRISPR/Cas effector polypeptide does not include the sequence FGFKRGRQK (SEQ ID NO: 73).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 9A, but where the loop having the sequence FGFKRGRQK (SEQ ID NO: 73) is mutated to: GGAAGGAAG (SEQ ID NO: 77), GGAAGGAAP (SEQ ID NO: 76), GGAAGGGAG (SEQ ID NO: 81), GGAAGGAAA (SEQ ID NO: 78), GAA, GGA, AGG, AAG, GAP, FGFARGRQA (SEQ ID NO: 93), FGFKAGAQK (SEQ ID NO: 94), FGFARGAQK (SEQ ID NO: 95), or FGFKAGRQA (SEQ ID NO: 96).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 10B, where the loop having the sequence MGFKRGRFK (SEQ ID NO: 74) as depicted in FIG. 10A is deleted; i.e., the variant type V CRISPR/Cas effector polypeptide does not include the sequence MGFKRGRFK (SEQ ID NO: 74).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 10A, but where the loop having the sequence MGFKRGRFK (SEQ ID NO: 74) is mutated to: GGAAGGAAG (SEQ ID NO: 77), GGAAGGAAP (SEQ ID NO: 76), GGAAGGGAG (SEQ ID NO: 81), GGAAGGAAA (SEQ ID NO: 78), GAA, GGA, AGG, AAG, GAP, MGFARGRFA (SEQ ID NO: 97), MGFKAGAFK (SEQ ID NO: 98), MGFAAGRFK (SEQ ID NO: 99), or MGFKRGAFA (SEQ ID NO: 100).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 11B, where the loop having the sequence MGFKRGRQK (SEQ ID NO: 63) as depicted in FIG. 11A is deleted; i.e., the variant type V CRISPR/Cas effector polypeptide does not include the sequence MGFKRGRQK (SEQ ID NO: 63).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 11A, but where the loop having the sequence MGFKRGRQK (SEQ ID NO: 63) is mutated to: GGAAGGAAG (SEQ ID NO: 77), GGAAGGAAP (SEQ ID NO: 76), GGAAGGGAG (SEQ ID NO: 81), GGAAGGAAA (SEQ ID NO: 78), GAA, GGA, AGG, AAG, GAP, MGFARGRQA (SEQ ID NO: 101), MGFKAGAQK (SEQ ID NO: 102), MGFARGAQK (SEQ ID NO: 103), or MGFKAGRQA (SEQ ID NO: 104).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 12B, where the loop having the sequence FGFKRGRFK (SEQ ID NO: 61) as depicted in FIG. 12A is deleted; i.e., the variant type V CRISPR/Cas effector polypeptide does not include the sequence FGFKRGRFK (SEQ ID NO: 61).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 12A, but where the loop having the sequence FGFKRGRFK (SEQ ID NO: 61) is mutated to: GGAAGGAAG (SEQ ID NO: 77), GGAAGGAAP (SEQ ID NO: 76), GGAAGGGAG (SEQ ID NO: 81), GGAAGGAAA (SEQ ID NO: 78), GAA, GGA, AGG, AAG, GAP, FGFARGRFA (SEQ ID NO: 84), FGFKAGAFK (SEQ ID NO: 85), FGFARGAFK (SEQ ID NO: 91), or FGFKAGRFA (SEQ ID NO: 92).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 13B, where the loop having the sequence QGFKRGRFK (SEQ ID NO: 75) as depicted in FIG. 13A is deleted; i.e., the variant type V CRISPR/Cas effector polypeptide does not include the sequence QGFKRGRFK (SEQ ID NO: 75).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 13A, but where the loop having the sequence QGFKRGRFK (SEQ ID NO: 75) is mutated to: GGAAGGAAG (SEQ ID NO: 77), GGAAGGAAP (SEQ ID NO: 76), GGAAGGGAG (SEQ ID NO: 81), GGAAGGAAA (SEQ ID NO: 78), GAA, GGA, AGG, AAG, GAP, QGFARGRFA (SEQ ID NO: 105), QGFKAGAFK (SEQ ID NO: 106), QGFARGAFK (SEQ ID NO: 107), or QGFKAGRFA (SEQ ID NO: 108).

As another example, the loop of the helix-loop element of a Cas12b polypeptide that exhibits trans cleavage can comprise an amino acid sequence such as EYQFNNDRPPSENN (SEQ ID NO: 64), EYRFSNDRPPSENS (SEQ ID NO: 65), RYRFQSDRPPSENS (SEQ ID NO: 66), AYRFSDDRPPSENS (SEQ ID NO: 67), or RYRFRTDRPRSENR (SEQ ID NO: 109); and a variant Cas12b polypeptide of the present disclosure can comprise: i) a deletion of the entire loop; or ii) a deletion of from 1 amino acid to 14 amino acids of the loop (e.g., a deletion of from 1 amino acid (aa) to 5 aa, from 5 aa to 10 aa, or from 10 aa to 14 aa of the loop) (e.g., a deletion of 1 aa, 2 aa, 3 aa, 4 aa, 5 aa, 6 aa, 7 aa, 8 aa, 9 aa, 10 aa, 11 aa, 12 aa, 13 aa, or 14 aa, of the loop); or iii) a substitution of an Asp of the loop with an amino acid other than Arg, His, Lys, Asp, or Glu; or ix) a substitution of an Arg of the loop with an amino acid other than Arg, His, Lys, Asp, or Glu; or x) a substitution of a Glu of the loop with an amino acid other than Arg, His, Lys, Asp, or Glu; or xi) an insertion of one or more amino acids into the loop; or xii) a replacement of the loop with 1, 2, 3, 4, 5, 6, 7, 8, 9, 10, 11, 12, 13, or 14 amino acids, where the replacement comprises one or more Gly and/or one or more Ala. In some cases, where an Asp, and/or an Arg, and/or a Glu is substituted with an amino acid other than Arg, His, Lys, Asp, or Glu, the Asp and/or the Arg and/or the Glu is/are substituted with Ala, Val, Ile, Leu, Met, Phe, Tyr, Trp, Gly, Cys, Pro, Ser, Thr, Asn, or Gln. In some cases, the Asp and/or the Arg and/or the Glu is/are individually substituted with Gly or Ala. In some cases, a variant type V CRISPR/Cas effector polypeptide of the present disclosure comprises two or more of any of the above disclosed substitutions in the loop of the helix loop element of Cas12a in any order; and exhibits decreased trans cleavage activity as compared with the wild type protein, as measured by methods known in the art (see e.g. Example 1).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 14B, where the loop having the sequence EYQFNNDRPPSENN (SEQ ID NO: 64) as depicted in FIG. 14A is deleted; i.e., the variant type V CRISPR/Cas effector polypeptide does not include the sequence EYQFNNDRPPSENN (SEQ ID NO: 64).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 14C, where the loop sequence EYQFNNDRPPSEN (SEQ ID NO: 110) present in the variant type V CRISPR/Cas effector polypeptide depicted in FIG. 14A has been mutated to GAAGAAGAAGAAGG (SEQ ID NO: 111), GGAAGGAAP (SEQ ID NO: 76), GGAAGGAAG (SEQ ID NO: 77), or GGAAGGAAA (SEQ ID NO: 78), or some other combination of Gly and Ala (e.g., a combination of Gly and Ala having a length of from 4 amino acids to 14 amino acids, e.g., from 4 amino acids to 10 amino acids, or from 10 amino acids to 14 amino acids.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 14C, where the where the loop sequence EYQFNNDRPPSEN (SEQ ID NO: 110) present in the variant type V CRISPR/Cas effector polypeptide depicted in FIG. 14A has been mutated to GAA, GGA, AGG, AAG, or GAP.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 15B, where the loop having the sequence AYRFSDDRPPSENS (SEQ ID NO: 67) as depicted in FIG. 15A is deleted; i.e., the variant type V CRISPR/Cas effector polypeptide does not include the sequence AYRFSDDRPPSENS (SEQ ID NO: 67).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 15C, where the loop sequence AYRFSDDRPPSENS (SEQ ID NO: 67) present in the variant type V CRISPR/Cas effector polypeptide depicted in FIG. 15A has been mutated to GAAGAAGAAGAAGG (SEQ ID NO: 111), GGAAGGAAP (SEQ ID NO: 76), GGAAGGAAG (SEQ ID NO: 77), or GGAAGGAAA (SEQ ID NO: 78), or some other combination of Gly and Ala (e.g., a combination of Gly and Ala having a length of from 4 amino acids to 14 amino acids, e.g., from 4 amino acids to 10 amino acids, or from 10 amino acids to 14 amino acids.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 15C, where the where the loop sequence AYRFSDDRPPSENS (SEQ ID NO: 67) present in the variant type V CRISPR/Cas effector polypeptide depicted in FIG. 15A has been mutated to GAA, GGA, AGG, AAG, or GAP.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 16B, where the loop having the sequence EYRFSNDRPPSENS (SEQ ID NO: 65) as depicted in FIG. 16A is deleted; i.e., the variant type V CRISPR/Cas effector polypeptide does not include the sequence EYRFSNDRPPSENS (SEQ ID NO: 65).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 16C, where the loop sequence EYRFSNDRPPSENS (SEQ ID NO: 65) present in the variant type V CRISPR/Cas effector polypeptide depicted in FIG. 16A has been mutated to GAAGAAGAAGAAGG (SEQ ID NO: 111), GGAAGGAAP (SEQ ID NO: 76), GGAAGGAAG (SEQ ID NO: 77), or GGAAGGAAA (SEQ ID NO: 78), or some other combination of Gly and Ala (e.g., a combination of Gly and Ala having a length of from 4 amino acids to 14 amino acids, e.g., from 4 amino acids to 10 amino acids, or from 10 amino acids to 14 amino acids.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 16C, where the where the loop sequence EYRFSNDRPPSENS (SEQ ID NO: 65) present in the variant type V CRISPR/Cas effector polypeptide depicted in FIG. 16A has been mutated to GAA, GGA, AGG, AAG, or GAP.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 17B, where the loop having the sequence RYRFQSDRPPSENS (SEQ ID NO: 66) as depicted in FIG. 17A is deleted; i.e., the variant type V CRISPR/Cas effector polypeptide does not include the sequence RYRFQSDRPPSENS (SEQ ID NO: 66).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 17C, where the loop sequence RYRFQSDRPPSENS (SEQ ID NO: 66) present in the variant type V CRISPR/Cas effector polypeptide depicted in FIG. 17A has been mutated to GAAGAAGAAGAAGG (SEQ ID NO: 111), GGAAGGAAP (SEQ ID NO: 76), GGAAGGAAG (SEQ ID NO: 77), or GGAAGGAAA (SEQ ID NO: 78), or some other combination of Gly and Ala (e.g., a combination of Gly and Ala having a length of from 4 amino acids to 14 amino acids, e.g., from 4 amino acids to 10 amino acids, or from 10 amino acids to 14 amino acids.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 17C, where the where the loop sequence RYRFQSDRPPSENS (SEQ ID NO: 66) present in the variant type V CRISPR/Cas effector polypeptide depicted in FIG. 17A has been mutated to GAA, GGA, AGG, AAG, or GAP.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 18B, where the loop having the sequence RYRFRTDRPRSENR (SEQ ID NO: 109) as depicted in FIG. 18A is deleted; i.e., the variant type V CRISPR/Cas effector polypeptide does not include the sequence RYRFRTDRPRSENR (SEQ ID NO: 109).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 18C, where the loop sequence RYRFRTDRPRSENR (SEQ ID NO: 109) present in the variant type V CRISPR/Cas effector polypeptide depicted in FIG. 18A has been mutated to GAAGAAGAAGAAGG (SEQ ID NO: 111), GGAAGGAAP (SEQ ID NO: 76), GGAAGGAAG (SEQ ID NO: 77), or GGAAGGAAA (SEQ ID NO: 78), or some other combination of Gly and Ala (e.g., a combination of Gly and Ala having a length of from 4 amino acids to 14 amino acids, e.g., from 4 amino acids to 10 amino acids, or from 10 amino acids to 14 amino acids.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 18C, where the where the loop sequence RYRFRTDRPRSENR (SEQ ID NO: 109) present in the variant type V CRISPR/Cas effector polypeptide depicted in FIG. 18A has been mutated to GAA, GGA, AGG, AAG, or GAP.

As another example, the loop of the helix-loop element of a CasX polypeptide that exhibits trans cleavage can comprise an amino acid sequence such as GRQGKRTFMTERQ (SEQ ID NO: 68), or GRQGKRTFMAERQ (SEQ ID NO: 112); and a variant CasX polypeptide of the present disclosure can comprise: i) a deletion of the entire loop; or ii) a deletion of from 1 amino acid to 13 amino acids of the loop (e.g., a deletion of from 1 amino acid (aa) to 4 aa, from 4 aa to 9 aa, or from 9 aa to 13 aa of the loop) (e.g., a deletion of 1 aa, 2 aa, 3 aa, 4 aa, 5 aa, 6 aa, 7 aa, 8 aa, 9 aa, 10 aa, 11 aa, 12 aa, or 13 aa of the loop); or iii) a substitution of an Arg of the loop with an amino acid other than Arg, His, Lys, Asp, or Glu; or ix) a substitution of a Lys of the loop with an amino acid other than Arg, His, Lys, Asp, or Glu; or x) a substitution of a Glu of the loop with an amino acid other than Arg, His, Lys, Asp, or Glu; or xi) an insertion of one or more amino acids into the loop; or xii) a replacement of the loop with 1, 2, 3, 4, 5, 6, 7, 8, 9, 10, 11, 12, 13, or 14 amino acids, where the replacement comprises one or more Gly and/or one or more Ala. In some cases, where an Arg, and/or a Lys, and/or a Glu is substituted with an amino acid other than Arg, His, Lys, Asp, or Glu, the Arg and/or the Lys and/or the Glu is/are substituted with Ala, Val, Ile, Leu, Met, Phe, Tyr, Trp, Gly, Cys, Pro, Ser, Thr, Asn, or Gln. In some cases, the Arg and/or the Lys and/or the Glu is/are individually substituted with Gly or Ala. In some cases, a variant type V CRISPR/Cas effector polypeptide of the present disclosure comprises two or more of any of the above disclosed substitutions in the loop of the helix loop element of Cas12a in any order; and exhibits decreased trans cleavage activity as compared with the wild type protein, as measured by methods known in the art (see e.g. Example 1).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 19B, where the loop having the sequence GRQGKRTFMTERQ (SEQ ID NO: 68) as depicted in FIG. 19A is deleted; i.e., the variant type V CRISPR/Cas effector polypeptide does not include the sequence GRQGKRTFMTERQ (SEQ ID NO: 68).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 19C, where the loop sequence GRQGKRTFMTERQ (SEQ ID NO: 68) present in the variant type V CRISPR/Cas effector polypeptide depicted in FIG. 19A has been mutated to GAAGAAGAAGAAGG (SEQ ID NO: 111), GGAAGGAAP (SEQ ID NO: 76), GGAAGGAAG (SEQ ID NO: 77), or GGAAGGAAA (SEQ ID NO: 78), or some other combination of Gly and Ala (e.g., a combination of Gly and Ala having a length of from 4 amino acids to 14 amino acids, e.g., from 4 amino acids to 10 amino acids, or from 10 amino acids to 14 amino acids.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 19C, where the where the loop sequence GRQGKRTFMTERQ (SEQ ID NO: 68) present in the variant type V CRISPR/Cas effector polypeptide depicted in FIG. 19A has been mutated to GAA, GGA, AGG, AAG, or GAP.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 20B, where the loop having the sequence GRQGKRTFMAERQ (SEQ ID NO: 112) as depicted in FIG. 20A is deleted; i.e., the variant type V CRISPR/Cas effector polypeptide does not include the sequence GRQGKRTFMAERQ (SEQ ID NO: 112).

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 20C, where the loop sequence GRQGKRTFMAERQ (SEQ ID NO: 112) present in the variant type V CRISPR/Cas effector polypeptide depicted in FIG. 20A has been mutated to GAAGAAGAAGAAGG (SEQ ID NO: 111), GGAAGGAAP (SEQ ID NO: 76), GGAAGGAAG (SEQ ID NO: 77), or GGAAGGAAA (SEQ ID NO: 78), or some other combination of Gly and Ala (e.g., a combination of Gly and Ala having a length of from 4 amino acids to 14 amino acids, e.g., from 4 amino acids to 10 amino acids, or from 10 amino acids to 14 amino acids.

In some cases, a variant type V CRISPR/Cas effector polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 20C, where the where the loop sequence GRQGKRTFMAERQ (SEQ ID NO: 112) present in the variant type V CRISPR/Cas effector polypeptide depicted in FIG. 20A has been mutated to GAA, GGA, AGG, AAG, or GAP.

Reference type V CRISPR/Cas Effector Proteins

As noted above, a variant type V CRISPR/Cas effector polypeptide of the present disclosure comprises one or more mutations relative to a reference (e.g., wild-type) type V CRISPR/Cas effector polypeptide, and exhibits reduced trans cleavage, compared to the reference (e.g., a wild-type) type V CRISPR/Cas effector polypeptide. In some cases, a variant type V CRISPR/Cas effector polypeptide of the present disclosure comprises one or more mutations (e.g., one or more of: one or more substitution; one or more deletions; one or more insertions), in the loop of the helix-loop element, relative to a reference (e.g., wild-type) type V CRISPR/Cas effector polypeptide; and exhibits reduced trans cleavage, compared to the reference (e.g., a wild-type) type V CRISPR/Cas effector polypeptide, as assayed by methods known in the art, e.g., a method as described in Example 1.

Type V CRISPR/Cas effector proteins are a subtype of Class 2 CRISPR/Cas effector proteins. For examples of type V CRISPR/Cas systems and their effector proteins (e.g., Cas12 family proteins such as Cas12a), see, e.g., Shmakov et al., Nat Rev Microbiol. 2017 March; 15(3):169-182: "Diversity and evolution of class 2 CRISPR-Cas systems." Examples include, but are not limited to, Cas12 family (Cas12a, Cas12b, Cas12c), C2c4, C2c8, C2c5, C2c10, and C2c9; as well as CasX (Cas12e) and CasY (Cas12d). Also see, e.g., Koonin et al., Curr Opin Microbiol. 2017 June; 37:67-78: "Diversity, classification and evolution of CRISPR-Cas systems."

In some cases, a reference type V CRISPR/Cas effector protein is a Cas12 protein (e.g., Cas12a, Cas12b, Cas12c). In some cases, a reference type V CRISPR/Cas effector protein is a Cas12 protein such as Cas12a, Cas12b, Cas12c, Cas12d, Cas12e, Cas12f, Cas12g, Cas12h, or Cas12i. In some cases, a reference type V CRISPR/Cas effector protein is a Cas12a protein. In some cases, a reference type V CRISPR/Cas effector protein is a Cas12b protein. In some cases, a reference type V CRISPR/Cas effector protein is a Cas12c protein. In some cases, a reference type V CRISPR/Cas effector protein is a Cas12d protein. In some cases, a reference type V CRISPR/Cas effector protein is a CasX (Cas12e) protein.

In some cases, the reference type V CRISPR/Cas effector protein is a naturally-occurring protein (e.g., naturally occurs in prokaryotic cells). In other cases, the reference type V CRISPR/Cas effector protein is not a naturally-occurring polypeptide. Examples of naturally occurring ("wild-type") type V CRISPR/Cas effector proteins include, but are not limited to, those depicted in FIGS. 1A, 2A, 3A, 4A, 5A, 6A, 7A, 8A, 9A, 10A, 11A, 12A, 13A, 14A, 15A, 16A, 17A, 18A, 19A, and 20A. Any type V CRISPR/Cas effector protein can be suitable for modification, to generate a variant type V CRISPR/Cas effector polypeptide. A suitable reference type V CRISPR/Cas effector protein forms a complex with a guide RNA and exhibits ssDNA cleavage activity of non-target ssDNAs (trans cleavage) once it is activated (by hybridization of and associated guide RNA to its target DNA).

In some cases, a reference type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a Cas12 protein (e.g., a Cas12a, Cas12b, Cas12c, Cas12d, Cas12e, Cas12f, Cas12g, Cas12h, or Cas12i, protein). For example, in some cases a reference type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a Cas12a protein depicted in any one of FIGS. 1A, 2A, 3A, 4A, 5A, 6A, 7A, 8A, 9A, 10A, 11A, 12A, and 13A. As another example, in some cases a reference type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a Cas12b protein depicted in any one of FIG. 14A, FIG. 15A, FIG. 16A, FIG. 17A, or FIG. 18A. As another example, in some cases a reference type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasX (Cas12e) protein depicted in FIG. 19A or FIG. 20A.

Fusion Polypeptides

In some cases, a variant type V CRISPR/Cas effector polypeptide of the present disclosure is a fusion protein, e.g., the variant type V CRISPR/Cas effector polypeptide comprises a heterologous polypeptide (i.e., one or more heterologous polypeptides). A heterologous polypeptide is also referred to herein as a "fusion partner."

In some cases, a heterologous polypeptide provides for subcellular localization, e.g., the heterologous polypeptide contains a subcellular localization sequence (e.g., a nuclear localization signal (NLS) for targeting to the nucleus; a sequence to keep the fusion protein out of the nucleus, e.g., a nuclear export sequence (NES); a sequence to keep the fusion protein retained in the cytoplasm; a mitochondrial localization signal for targeting to the mitochondria; a chloroplast localization signal for targeting to a chloroplast, an ER retention signal; and the like. In some cases, the heterologous polypeptide can provide a tag (i.e., the heterologous polypeptide is a detectable label) for ease of tracking and/or purification (e.g., a fluorescent protein, e.g., green fluorescent protein (GFP), yellow fluorescent protein (YFP), red fluorescent protein (RFP), cyan fluorescent protein (CFP), mCherry, tdTomato, and the like; a histidine tag, e.g., a 6×His tag; a hemagglutinin (HA) tag; a FLAG tag; a Myc tag; and the like.

In some cases, a variant type V CRISPR/Cas effector polypeptide of the present disclosure is a fusion protein comprising an NLS as the heterologous polypeptide. In some cases, a fusion protein of the present disclosure comprises: a) a variant type V CRISPR/Cas effector polypeptide of the present disclosure; and b) one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus of the variant type V CRISPR/Cas effector polypeptide. In some cases, one or more NLSs (2 or more, 3 or more, 4 or more, or 5 or more NLSs) are positioned at or near (e.g., within 50 amino acids of) the N-terminus of the variant type V CRISPR/Cas effector polypeptide. In some cases, one or more NLSs (2 or more, 3 or more, 4 or more, or 5 or more NLSs) are positioned at or near (e.g., within 50 amino acids of) the C-terminus of the variant type V CRISPR/Cas effector polypeptide. In some cases, one or more NLSs (3 or more, 4 or more, or 5 or more NLSs) are positioned at or near (e.g., within 50 amino acids of) both the N-terminus and the C-terminus of the variant type V CRISPR/Cas effector polypeptide. In some cases, an NLS is positioned at the N-terminus and an NLS is positioned at the C-terminus of the variant type V CRISPR/Cas effector polypeptide.

Non-limiting examples of NLSs include an NLS sequence derived from: the NLS of the SV40 virus large T-antigen, having the amino acid sequence PKKKRKV (SEQ ID NO: 113); the NLS from nucleoplasmin (e.g., the nucleoplasmin bipartite NLS with the sequence KRPAATKKAGQAKKKK (SEQ ID NO: 114)); the c-myc NLS having the amino acid sequence PAAKRVKLD (SEQ ID NO: 115) or RQRRNELKRSP (SEQ ID NO: 116); the hRNPA1 M9 NLS having the sequence NQSSNFGPMKGGNFGGRSSGPYGGGGQYFAKPRNQGGY (SEQ ID NO: 117); the sequence RMRIZFKNKGKDTAELRRRRVEVSVELRKAKKDEQILKRRNV (SEQ ID NO: 118) of the IBB domain from importin-alpha; the sequences VSRKRPRP (SEQ ID NO: 119) and PPKKARED (SEQ ID NO: 120) of the myoma T protein; the sequence PQPKKKPL (SEQ ID NO: 121) of human p53; the sequence SALIKKKKKMAP (SEQ ID NO: 122) of mouse c-abl IV; the sequences DRLRR (SEQ ID NO: 123) and PKQKKRK (SEQ ID NO: 124) of the influenza virus NS1; the sequence RKLKKKIKKL (SEQ ID NO: 125) of the Hepatitis virus delta antigen; the sequence REKKKFLKRR (SEQ ID NO: 126) of the mouse Mxl protein; the sequence KRKGDEVDGVDEVAKKKSKK (SEQ ID NO: 127) of the human poly(ADP-ribose) polymerase; and the sequence RKCLQAGMNLEARKTKK (SEQ ID NO: 128) of the steroid hormone receptors (human) glucocorticoid. In general, NLS (or multiple NLSs) are of sufficient strength to drive accumulation of the protein in a detectable amount in the nucleus of a eukaryotic cell. Detection of accumulation in the nucleus may be performed by any suitable technique.

In some cases the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a fusion protein of the present disclosure comprises: a) a variant type V CRISPR/Cas effector polypeptide of the present disclosure; and b) a heterologous polypeptide that has enzymatic activity that modifies a target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a fusion protein of the present disclosure comprises: a) a variant type V CRISPR/Cas effector polypeptide of the present disclosure; and b) a heterologous polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used in increase transcription include but are not limited to: transcriptional activators such as VP16, VP64, VP48, VP160, p65 subdomain (e.g., from NFkB), and activation domain of EDLL and/or TAL acitvation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used in decrease transcription include but are not limited to: transcriptional repressors such as the Krüppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

In some cases the fusion partner has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme such as rat APOBEC1; or an adenine deaminase activity such as *E. coli* TadA or ABE7.8, ABE7.9 and ABE7.10), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases, the fusion partner has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragement of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

In some cases, fusion polypeptide of the present disclosure can comprise: a) variant type V CRISPR/Cas effector polypeptide of the present disclosure; and b) an endosomal escape peptide. In some cases, an endosomal escape polypeptide comprises the amino acid sequence GLFXALLXLLXSLWXLLLXA (SEQ ID NO: 129), wherein each X is independently selected from lysine, histidine, and arginine. In some cases, an endosomal escape polypeptide comprises the amino acid sequence GLFHALLHLLHSLWHLLLHA (SEQ ID NO: 130).

Additional suitable heterologous polypeptide include, but are not limited to, a polypeptide that directly and/or indirectly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.). Non-limiting examples of heterologous polypeptides to accomplish increased or decreased transcription include transcription activator and transcription repressor domains. In some such cases, a variant type V CRISPR/Cas effector polypeptide of the present disclosure is targeted by the guide nucleic acid (guide RNA) to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of heterologous polypeptides for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

A fusion protein of the present disclosure can comprise: a) a variant type V CRISPR/Cas effector polypeptide of the present disclosure; and b) a polypeptide capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP S1, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as heterologous polypeptides for a fusion protein of the present disclosure have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP Al binds to exonic splicing silencers (ESSs) through its RRM domains and inhibits exon inclusion through a C-terminal Glycine-rich domain Some splicing factors can regulate alternative use of splice site (ss) by binding to regulatory sequences between the two alternative sites. For example, ASF/SF2 can recognize ESEs and promote the use of intron proximal sites, whereas hnRNP Al can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bch x splicing isoforms is regulated by multiple cω-elements that are located in either the core exon region or the exon extension region (i.e., between the two alternative 5' splice sites). For more examples, see WO2010075303, which is hereby incorporated by reference in its entirety.

Further suitable fusion partners include, but are not limited to proteins (or fragments thereof) that are boundary elements (e.g., CTCF), proteins and fragments thereof that provide periphery recruitment (e.g., Lamin A, Lamin B, etc.), protein docking elements (e.g., FKBP/FRB, Pil1/Aby1, etc.).

In some cases, fusion protein of the present disclosure comprises: a) a variant type V CRISPR/Cas effector polypeptide of the present disclosure; and b) a "Protein Transduction Domain" or PTD (also known as a CPP—cell penetrating peptide). In some cases, a PTD is covalently linked to the amino terminus of a variant type V CRISPR/Cas effector polypeptide of the present disclosure. In some cases, a PTD is covalently linked to the carboxyl terminus of a variant type V CRISPR/Cas effector polypeptide of the present disclosure. In some cases, the PTD is inserted internally in a variant type V CRISPR/Cas effector polypeptide of the present disclosure at a suitable insertion site. In some cases, a subject fusion polypeptide includes one or more PTDs (e.g., two or more, three or more, four or more PTDs). Examples of PTDs include but are not limited to a minimal undecapeptide protein transduction domain (corresponding to residues 47-57 of HIV-1 TAT comprising YGRKKRRQRRR; SEQ ID NO: 131); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO: 132); Transportan GWTLNSAGYLLGKINLKALAALAKKIL (SEQ ID NO: 133); KALAWEAKLAKALAKALAKHLAKALAKALKCEA (SEQ ID NO: 134); and RQIKIWFQNRRMKWKK (SEQ ID NO: 135). Exemplary PTDs include but are not limited to, YGRKKRRQRRR (SEQ ID NO: 131), RKKRRQRRR (SEQ ID NO: 136); an arginine homopolymer of from 3 arginine residues to 50 arginine residues; Exemplary PTD domain amino acid sequences include, but are not limited to, any of the following: YGRKKRRQRRR (SEQ ID NO: 131); RKKRRQRR (SEQ ID NO: 137); YARAAARQARA (SEQ ID NO: 138); THRLPRRRRRR (SEQ ID NO: 139); and GGRRARRRRRR (SEQ ID NO: 140). In some embodiments, the PTD is an activatable CPP (ACPP) (Aguilera et al. (2009) *Integr Biol* (Camb) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Systems

The present disclosure provides a system comprising a variant type V CRISPR/Cas effector polypeptide of the present disclosure. A system of the present disclosure can comprise: a) a variant type V CRISPR/Cas polypeptide of the present disclosure and a type V CRISPR/Cas guide RNA; b) a variant type V CRISPR/Cas polypeptide of the present disclosure, a type V CRISPR/Cas guide RNA, and a donor template nucleic acid; c) a fusion polypeptide of the present disclosure and a type V CRISPR/Cas guide RNA; d) a fusion polypeptide of the present disclosure, a type V CRISPR/Cas guide RNA, and a donor template nucleic acid; e) an mRNA encoding a variant type V CRISPR/Cas polypeptide of the present disclosure; and a type V CRISPR/Cas guide RNA; f) an mRNA encoding a variant type V CRISPR/Cas polypeptide of the present disclosure, a type V CRISPR/Cas guide RNA, and a donor template nucleic acid; g) an mRNA encoding a fusion polypeptide of the present disclosure; and a type V CRISPR/Cas guide RNA; h) an mRNA encoding a fusion polypeptide of the present disclosure, a type V CRISPR/Cas guide RNA, and a donor template nucleic acid; i) a recombinant expression vector comprising a nucleotide sequence encoding a variant type V CRISPR/Cas polypeptide of the present disclosure and a nucleotide sequence encoding a type V CRISPR/Cas guide RNA; j) a recombinant expression vector comprising a nucleotide sequence encoding a variant type V CRISPR/Cas polypeptide of the present disclosure, a nucleotide sequence encoding a type V CRISPR/Cas guide RNA, and a nucleotide sequence encoding a donor template nucleic acid; k) a recombinant expression vector comprising a nucleotide sequence encoding a fusion polypeptide of the present disclosure and a nucleotide sequence encoding a type V CRISPR/Cas guide RNA; 1) a recombinant expression vector comprising a nucleotide sequence encoding a fusion polypeptide of the present disclosure, a nucleotide sequence encoding a type V CRISPR/Cas guide RNA, and a nucleotide sequence encoding a donor template nucleic acid; m) a first recombinant expression vector comprising a nucleotide sequence encoding aa variant type V CRISPR/Cas polypeptide of the present disclosure and a second recombinant expression vector comprising a nucleotide sequence encoding a type V CRISPR/Cas guide RNA; n) a first recombinant expression vector comprising a nucleotide sequence encoding a variant type V CRISPR/Cas polypeptide of the present disclosure, and a second recombinant expression vector comprising a nucleotide sequence encoding a type V CRISPR/Cas guide RNA; and a donor template nucleic acid; o) a first recombinant expression vector comprising a nucleotide sequence encoding a variant type V CRISPR/Cas polypeptide of the present disclosure, and a second recombinant expression vector comprising a nucleotide sequence encoding a type V CRISPR/Cas guide RNA; p) a first recombinant expression vector comprising a nucleotide sequence encoding a fusion polypeptide of the present disclosure, and a second recombinant expression vector comprising a nucleotide sequence encoding a type V CRISPR/Cas guide RNA; and a donor template nucleic acid; q) a recombinant expression vector comprising a nucleotide sequence encoding a variant type V CRISPR/Cas polypeptide of the present disclosure, a nucleotide sequence encoding a first type V CRISPR/Cas guide RNA, and a nucleotide sequence encoding a second type V CRISPR/Cas guide RNA; or r) a recombinant expression vector comprising a nucleotide sequence encoding a fusion polypeptide of the present disclosure, a nucleotide sequence encoding a first type V CRISPR/Cas guide RNA, and a nucleotide sequence encoding a second type V CRISPR/Cas guide RNA; or some variation of one of (a) through (r).

Protospacer Adjacent Motif (PAM)

A type V CRISPR/Cas effector protein binds to target DNA at a target sequence defined by the region of complementarity between the DNA-targeting RNA and the target DNA. As is the case for many CRISPR/Cas endonucleases, site-specific binding (and/or cleavage) of a double stranded target DNA occurs at locations determined by both (i) base-pairing complementarity between the guide RNA and the target DNA; and (ii) a short motif (referred to as the protospacer adjacent motif (PAM)) in the target DNA. A variant type V CRISPR/Cas effector polypeptide of the present disclosure generally recognizes the same PAM as a reference (e.g., wild-type) type V CRISPR/Cas effector polypeptide. Non-limiting examples of PAM sequences are depicted in FIG. 21B.

In some cases, the PAM for a variant type V CRISPR/Cas effector polypeptide of the present disclosure is immediately 5' of the target sequence (e.g., of the non-complementary strand of the target DNA—the complementary strand hybridizes to the guide sequence of the guide RNA while the non-complementary strand does not directly hybridize with the guide RNA and is the reverse complement of the non-complementary strand). In some cases, the PAM sequence is 5'-TTN-3'. In some cases, the PAM sequence is 5'-TTTN-3.'

Guide RNA

A nucleic acid molecule (e.g., a natural crRNA) that binds to a type V CRISPR/Cas effector protein (e.g., a Cas12 protein such as Cas12a, Cas12b, Cas12c, Cas12d, Cas12e, Cas12f, Cas12g, Cas12h, or Cas12i), forming a ribonucleoprotein complex (RNP), and that targets the complex to a specific target sequence within a target DNA is referred to herein as a "guide RNA." It is to be understood that in some cases, a hybrid DNA/RNA can be made such that a guide RNA includes DNA bases in addition to RNA bases—but the term "guide RNA" is still used herein to encompass such hybrid molecules. A subject guide RNA includes a guide sequence (also referred to as a "spacer")(that hybridizes to target sequence of a target DNA) and a constant region (e.g., a region that is adjacent to the guide sequence and binds to the type V CRISPR/Cas effector protein). A "constant region" can also be referred to herein as a "protein-binding segment." In some cases, e.g., for Cas12a, the constant region is 5' of the guide sequence. A variant type V CRISPR/Cas effector polypeptide of the present disclosure will bind guide RNAs in substantially the same manner as a reference (e.g., a wild-type) type V CRISPR/Cas effector polypeptide. Thus, the discussion of guide RNAs, below, pertains to guide RNAs suitable for use with a variant type V CRISPR/Cas effector polypeptide of the present disclosure. A guide RNA that comprises: a) a guide sequence that hybridizes to a target nucleotide sequence of a target nucleic acid; and b) a constant region that binds to a variant type V CRISPR/Cas effector polypeptide is referred to herein as a "type V CRISPR/Cas guide RNA," or a "subject guide RNA."

Guide Sequence

The guide sequence has complementarity with (hybridizes to) a target sequence of the target DNA. In some cases, the guide sequence is 15-28 nucleotides (nt) in length (e.g., 15-26, 15-24, 15-22, 15-20, 15-18, 16-28, 16-26, 16-24, 16-22, 16-20, 16-18, 17-26, 17-24, 17-22, 17-20, 17-18, 18-26, 18-24, or 18-22 nt in length). In some cases, the guide sequence is 18-24 nucleotides (nt) in length. In some cases, the guide sequence is at least 15 nt long (e.g., at least 16, 18, 20, or 22 nt long). In some cases, the guide sequence is at least 17 nt long. In some cases, the guide sequence is at least 18 nt long. In some cases, the guide sequence is at least 20 nt long.

In some cases, the guide sequence has 80% or more (e.g., 85% or more, 90% or more, 95% or more, or 100% complementarity) with the target sequence of the target DNA. In some cases, the guide sequence is 100% complementary to the target sequence of the target DNA. In some cases, the target DNA includes at least 15 nucleotides (nt) of complementarity with the guide sequence of the guide RNA.

Constant Region

Examples of constant regions for guide RNAs that can be used with a type V CRISPR/Cas effector protein (e.g., a Cas12 protein such as Cas12a, Cas12b, Cas12c, Cas12d, Cas12e, Cas12f, Cas12g, Cas12h, or Cas12i) are presented in FIG. 21A.

In some embodiments a "guide RNA" includes two separate molecules (e.g., a tracrRNA and a crRNA) that hybridize to one another—and such a guide RNA can be referred to as a "dual-molecule" or "dual guide" RNA. The constant region of such a guide RNA would include a duplex formed from hybridization of the two separate molecules (e.g., a crRNA hybridized to a tracrRNA). For example, some naturally-occurring type V CRISPR-Cas systems (e.g., Cas12b) include and require a tracrRNA as part of the guide RNA; see, Shmakov et al. (2017) *Nature* 15:169.

In some cases, a "guide RNA" includes two separate molecules (e.g., a crRNA and a tracrRNA) that are covalently linked to one another via a non-nucleic acid linkage (e.g., a non-phosphodiester linkage) (see, e.g., US20180142236, WO2018126176, and He et al., Chembiochem. 2016 Oct. 4; 17(19):1809-1812, "Conjugation and Evaluation of Triazole-Linked Single Guide RNA for CRISPR-Cas9 Gene Editing"). For example, a guide RNA can include: i) a first RNA that comprises a nucleotide sequence that is complementary to a nucleotide sequence in a target nucleic acid (e.g., a target DNA); and ii) a second RNA comprising a nucleotide sequence that interacts with a type V CRISPR/Cas effector polypeptide, where the first RNA and the second RNA are joined via a non-phosphodiester covalent linkage. For example, the non-phosphodiester covalent linkage can comprise a moiety selected from a carbamate, an ether, an ester, an amide, an imine, an amidine, an aminotrizine, a hydrozone, a disulfide, a thioether, a thioester, a phosphorothioate, a phosphorodithioate, a sulfonamide, a sulfonate, a fulfone, a sulfoxide, a urea, a thiourea, a hydrazide, an oxime, a triazole, a photolabile linkage, a C—C bond forming group such as Diels-Alder cyclo-addition pair or ring-closing metathesis pair, and a Michael reaction pair.

In some cases, a "guide RNA" is a single molecule. For example, in some cases, a single-molecule guide RNA includes a crRNA but not a tracrRNA (e.g., some naturally-occurring type V CRISPR-Cas systems (e.g., Cas12a) do not include or require a tracrRNA). In some cases, a single-molecule guide RNA includes a crRNA conjugated to (e.g., via intervening nucleotides) a tracrRNA. For example, some naturally-occurring type V CRISPR-Cas systems include a guide RNA in which the tracrRNA and crRNA are separate molecules hybridized to one another—but those separate molecules can be conjugated (covalently linked) to one another, thus forming a single molecule.

In some embodiments a "guide RNA" is a single molecule. For example, in some cases a single-molecule guide RNA includes a crRNA but not a tracrRNA (e.g., some natural type V CRISPR-Cas systems do not include or require a tracrRNA). In some cases, a single-molecule guide RNA includes a crRNA conjugated to (e.g., via intervening nucleotides) a tracrRNA. For example, some natural type V CRISPR-Cas systems include a guide RNA in which the tracrRNA and crRNA are separate molecules hybridized to one another—but those separate molecules can be conjugated (covalently linked) to one another, thus forming a single molecule In some cases, a subject guide RNA includes a nucleotide sequence having 70% or more identity (e.g., 80% or more, 85% or more, 90% or more, 95% or more, 98% or more, 99% or more, or 100% identity) with any one of the crRNA repeat sequences set forth in FIG. 21A. In some cases, a subject guide RNA includes a nucleotide sequence having 90% or more identity (e.g., 95% or more, 98% or more, 99% or more, or 100% identity) with any one of the crRNA repeat sequences set forth in FIG. 21A. In some cases, a subject guide RNA includes a crRNA nucleotide sequence set forth in FIG. 21A.

In some cases, the guide RNA includes a double stranded RNA duplex (dsRNA duplex). In some cases, a guide RNA includes a dsRNA duplex with a length of from 2 to 12 bp (e.g., from 2 to 10 bp, 2 to 8 bp, 2 to 6 bp, 2 to 5 bp, 2 to 4 bp, 3 to 12 bp, 3 to 10 bp, 3 to 8 bp, 3 to 6 bp, 3 to 5 bp, 3 to 4 bp, 4 to 12 bp, 4 to 10 bp, 4 to 8 bp, 4 to 6 bp, or 4 to 5 bp). In some cases, a guide RNA includes a dsRNA duplex that is 2 or more bp in length (e.g., 3 or more, 4 or more, 5 or more, 6 or more, or 7 or more bp in length). In some cases, a guide RNA includes a dsRNA duplex that is longer than the dsRNA duplex of a corresponding wild type guide RNA. In some cases, a guide RNA includes a dsRNA duplex that is shorter than the dsRNA duplex of a corresponding wild type guide RNA.

In some cases, the constant region of a guide RNA is 15 or more nucleotides (nt) in length (e.g., 18 or more, 20 or more, 21 or more, 22 or more, 23 or more, 24 or more, 25 or more, 26 or more, 27 or more, 28 or more, 29 or more, 30 or more, 31 or more nt, 32 or more, 33 or more, 34 or more, or 35 or more nt in length). In some cases, the constant region of a guide RNA is 18 or more nt in length.

In some cases, the constant region of a guide RNA has a length in a range of from 12 to 100 nt (e.g., from 12 to 90, 12 to 80, 12 to 70, 12 to 60, 12 to 50, 12 to 40, 15 to 100, 15 to 90, 15 to 80, 15 to 70, 15 to 60, 15 to 50, 15 to 40, 20 to 100, 20 to 90, 20 to 80, 20 to 70, 20 to 60, 20 to 50, 20 to 40, 25 to 100, 25 to 90, 25 to 80, 25 to 70, 25 to 60, 25 to 50, 25 to 40, 28 to 100, 28 to 90, 28 to 80, 28 to 70, 28 to 60, 28 to 50, 28 to 40, 29 to 100, 29 to 90, 29 to 80, 29 to 70, 29 to 60, 29 to 50, or 29 to 40 nt). In some cases, the constant region of a guide RNA has a length in a range of from 28 to 100 nt. In some cases, the region of a guide RNA that is 5' of the guide sequence has a length in a range of from 28 to 40 nt.

In some cases, the constant region of a guide RNA is truncated relative to (shorter than) the corresponding region of a corresponding wild type guide RNA. In some cases, the constant region of a guide RNA is extended relative to (longer than) the corresponding region of a corresponding wild type guide RNA. In some cases, a subject guide RNA is 30 or more nucleotides (nt) in length (e.g., 34 or more, 40 or more, 45 or more, 50 or more, 55 or more, 60 or more, 65 or more, 70 or more, or 80 or more nt in length). In some cases, the guide RNA is 35 or more nt in length.

Precursor Guide RNA Array

A Type V CRISPR/Cas effector protein (e.g., a Cas12 protein such as Cas12a, Cas12b, Cas12c, Cas12d, Cas12e) can cleave a precursor guide RNA into a mature guide RNA, e.g., by endoribonucleolytic cleavage of the precursor. A Type V CRISPR/Cas effector protein (e.g., a Cas12 protein such as Cas12a, Cas12b, Cas12c, Cas12d, Cas12e) can cleave a precursor guide RNA array (that includes more than one guide RNA arrayed in tandem) into two or more individual guide RNAs. Similarly, a variant type V CRISPR/Cas effector polypeptide of the present disclosure can cleave a precursor guide RNA into a mature guide RNA. Thus, in some cases, a precursor guide RNA array comprises two or more (e.g., 3 or more, 4 or more, 5 or more, 2, 3, 4, or 5) guide RNAs (e.g., arrayed in tandem as precursor molecules). In other words, in some cases, two or more guide RNAs can be present on an array (a precursor guide RNA array). A Type V CRISPR/Cas effector protein (e.g., a Cas12 protein such as Cas12a, Cas12b, Cas12c, Cas12d, Cas12e) can cleave the precursor guide RNA array into individual guide RNAs. Similarly, a variant type V CRISPR/Cas effector polypeptide of the present disclosure can cleave the precursor guide RNA array into individual guide RNAs.

In some cases, a subject guide RNA array includes 2 or more guide RNAs (e.g., 3 or more, 4 or more, 5 or more, 6 or more, or 7 or more, guide RNAs). The guide RNAs of a given array can target (i.e., can include guide sequences that hybridize to) different target sites of the same target DNA and/or can target different target DNA molecules (e.g., single nucleotide polymorphisms (SNPs), different strains of a particular virus, etc.). In some cases, each guide RNA of a precursor guide RNA array has a different guide sequence. In some cases, two or more guide RNAs of a precursor guide RNA array have the same guide sequence.

In some cases, the precursor guide RNA array comprises two or more guide RNAs that target different target sites within the same target DNA molecule. As such, in some cases as subject composition (e.g., kit) or method includes two or more guide RNAs (in the context of a precursor guide RNA array, or not in the context of a precursor guide RNA array, e.g., the guide RNAs can be mature guide RNAs).

In some cases, the precursor guide RNA array comprises two or more guide RNAs that target different target DNA molecules. As such, in some cases as subject composition (e.g., kit) or method includes two or more guide RNAs (in the context of a precursor guide RNA array, or not in the context of a precursor guide RNA array, e.g., the guide RNAs can be mature guide RNAs).

Nucleic Acid Modifications

In some cases, a guide RNA comprises one or more modifications, e.g., a base modification, a backbone modification, a sugar modification, etc., to provide the nucleic acid with a new or enhanced feature (e.g., improved stability). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Backbones and Modified Internucleoside Linkages

Examples of suitable guide RNA modifications include modified nucleic acid backbones and non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some cases, a guide RNA comprises one or more phosphorothioate and/or heteroatom internucleoside linkages, in particular $—CH_2—NH—O—CH_2—$, $—CH_2—N(CH_3)—O—CH_2—$ (known as a methylene (methylimino) or MMI backbone), $—CH_2—O—N(CH_3)—CH_2—$, $—CH_2—N(CH_3)—N(CH_3)—CH_2—$ and $—O—N(CH_3)—CH_2—CH_2—$ (wherein the native phosphodiester internucleotide linkage is represented as $—O—P(=O)(OH)—O—CH_2—$). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids having morpholino backbone structures as described in, e.g., U.S. Pat. No. 5,034,506. For example, in some cases, a guide RNA comprises a 6-membered morpholino ring in place of a ribose ring. In some cases, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Mimetics

A guide RNA can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general, the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—$CH_2$—), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Modified Sugar Moieties

A guide RNA can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C.sub.1 to $C_{10}$ alkyl or $C_2$ to $C_{10}$ alkenyl and alkynyl. Particularly suitable are $O((CH_2)_nO)_m CH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a $O(CH_2)$ ${}_2ON(CH_3)_2$ group, also known as 2'-DMAOE, as described in examples hereinbelow, and 2'-dimethylaminoethoxy-ethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy $CH_2CH_2CH_2NH_2$), allyl (—$CH_2$—CH═$CH_2$), —O-allyl $CH_2$—CH═$CH_2$) and fluoro (F). 2'-sugar substituent groups may be in the arabino (up) position or ribo (down) position. A suitable 2'-arabino modification is 2'-F Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A guide RNA may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C═C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

Donor Nucleic Acid

In some cases, a system of the present disclosure comprises a donor nucleic acid. By a "donor nucleic acid" or "donor sequence" or "donor polynucleotide" or "donor template" it is meant a nucleic acid sequence to be inserted at the site cleaved by a CRISPR/Cas effector protein (e.g., after dsDNA cleavage, after nicking a target DNA, after dual nicking a target DNA, and the like). The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair (e.g., for gene correction, e.g., to convert a disease-causing base pair or a non disease-causing base pair). In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence is provided to the cell as single-stranded DNA. In some cases, the donor sequence is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance.

Nucleic Acids

The present disclosure provides one or more nucleic acids comprising one or more of: a donor nucleic acid, a nucleotide sequence encoding variant type V CRISPR/Cas effector polypeptide of the present disclosure, a type V CRISPR/Cas guide RNA, and a nucleotide sequence encoding a type V CRISPR/Cas guide RNA. The present disclosure provides a nucleic acid comprising a nucleotide sequence encoding a fusion polypeptide comprising: a) a variant type V CRISPR/Cas effector polypeptide of the present disclosure; and b) a heterologous polypeptide (a fusion partner). The present disclosure provides a recombinant expression vector that comprises a nucleotide sequence encoding a variant type V CRISPR/Cas effector polypeptide of the present disclosure. The present disclosure provides a recombinant expression vector that comprises a nucleotide sequence encoding a fusion polypeptide of the present disclosure. The present disclosure provides a recombinant expression vector that comprises: a) a nucleotide sequence encoding a variant type V CRISPR/Cas effector polypeptide of the present disclosure; and b) a nucleotide sequence encoding a type V CRISPR/Cas guide RNA(s). The present disclosure provides a recombinant expression vector that comprises: a) a nucleotide sequence encoding a fusion polypeptide of the present disclosure; and b) a nucleotide sequence encoding a type V CRISPR/Cas guide RNA(s). In some cases, the nucleotide sequence encoding the variant type V CRISPR/Cas effector polypeptide of the present disclosure and/or the nucleotide sequence encoding the type V CRISPR/Cas guide RNA and/or the nucleotide sequence encoding the fusion polypeptide is operably linked to a promoter that is operable in a cell type of choice (e.g., a prokaryotic cell, a eukaryotic cell, a plant cell, an animal cell, a mammalian cell, a primate cell, a rodent cell, a human cell, etc.). Various nucleic acid and expression vectors are described below in the context of a variant type V CRISPR/Cas effector polypeptide of the present disclosure; these descriptions apply equally to a fusion polypeptide of the present disclosure.

In some cases, a nucleotide sequence encoding a variant type V CRISPR/Cas effector polypeptide of the present disclosure, or a fusion polypeptide of the present disclosure, is codon optimized. This type of optimization can entail a mutation of a variant type V CRISPR/Cas effector polypeptide-encoding nucleotide sequence to mimic the codon preferences of the intended host organism or cell while encoding the same protein. Thus, the codons can be changed, but the encoded protein remains unchanged. For example, if the intended target cell was a human cell, a human codon-optimized variant type V CRISPR/Cas effector polypeptide-encoding nucleotide sequence could be used. As another non-limiting example, if the intended host cell were a mouse cell, then a mouse codon-optimized variant type V CRISPR/Cas effector polypeptide-encoding nucleotide sequence could be generated. As another non-limiting example, if the intended host cell were a plant cell, then a plant codon-optimized variant type V CRISPR/Cas effector polypeptide-encoding nucleotide sequence could be generated. As another non-limiting example, if the intended host cell were an insect cell, then an insect codon-optimized variant type V CRISPR/Cas effector polypeptide-encoding nucleotide sequence could be generated.

The present disclosure provides one or more recombinant expression vectors that include (in separate recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); (ii) a nucleotide sequence that encodes a type V CRISPR/Cas guide RNA that hybridizes to a target sequence of the target locus of the targeted genome (e.g., operably linked to a promoter that is operable in a target cell such as a eukaryotic cell); and (iii) a nucleotide sequence encoding a variant type V CRISPR/Cas effector polypeptide of the present disclosure (e.g., operably linked to a promoter that is operable in a target cell such as a eukaryotic cell). The present disclosure provides one or more recombinant expression vectors that include (in separate recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); and (ii) a nucleotide sequence that encodes a type V CRISPR/Cas guide RNA that hybridizes to a target sequence of the target locus of the targeted genome (e.g., operably linked to a promoter that is operable in a target cell such as a eukaryotic cell). The present disclosure provides one or more recombinant expression vectors that include (in separate recombinant expression vectors in some cases, and in the same recombinant expression vector in some cases): (i) a nucleotide sequence that encodes a type V CRISPR/Cas guide RNA that hybridizes to a target sequence of the target locus of the targeted genome (e.g., operably linked to a promoter that is operable in a target cell such as a eukaryotic cell); and (ii) a nucleotide sequence encoding a variant type V CRISPR/Cas effector polypeptide of the present disclosure (e.g., operably linked to a promoter that is operable in a target cell such as a eukaryotic cell).

Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a type V CRISPR/Cas guide RNA is operably linked to a control element, e.g., a transcriptional control element, such as a promoter. In some embodiments, a nucleotide sequence encoding a variant type V CRISPR/Cas effector polypeptide of the present disclosure or a fusion polypeptide of the present disclosure is operably linked to a control element, e.g., a transcriptional control element, such as a promoter.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., hematopoietic stem cells (e.g., mobilized peripheral blood (mPB) CD34(+) cell, bone marrow (BM) CD34(+) cell, etc.).

Non-limiting examples of eukaryotic promoters (promoters functional in a eukaryotic cell) include EF1α, those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, fluorescent protein, etc.) that can be fused to variant type V CRISPR/Cas effector polypeptide of the present disclosure, thus resulting in a fusion polypeptide.

In some cases, a nucleotide sequence encoding a type V CRISPR/Cas guide RNA and/or a variant type V CRISPR/Cas effector polypeptide of the present disclosure, or a fusion polypeptide of the present disclosure, is operably linked to an inducible promoter. In some cases, a nucleotide sequence encoding a type V CRISPR/Cas guide RNA and/or a variant type V CRISPR/Cas effector polypeptide of the present disclosure is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

In some cases, a nucleotide sequence encoding a type V CRISPR/Cas guide RNA is operably linked to (under the control of) a promoter operable in a eukaryotic cell (e.g., a U6 promoter, an enhanced U6 promoter, an H1 promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (Pol III). Thus, in order to ensure transcription of a guide RNA in a eukaryotic cell it may sometimes be necessary to modify the sequence encoding the guide RNA to eliminate runs of Ts. In some cases, a nucleotide sequence encoding a variant type V CRISPR/Cas effector polypeptide of the present disclosure is operably linked to a promoter operable in a eukaryotic cell (e.g., a CMV promoter, an EF1α promoter, an estrogen receptor-regulated promoter, and the like).

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Methods of introducing a nucleic acid (e.g., a nucleic acid comprising a donor polynucleotide sequence, one or more nucleic acids encoding a variant type V CRISPR/Cas effector polypeptide of the present disclosure (or a fusion polypeptide of the present disclosure) and/or a type V CRISPR/Cas guide RNA, and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing the recombinant expression vector into cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some embodiments, a variant type V CRISPR/Cas effector polypeptide of the present disclosure can be provided as RNA. The RNA can be provided by direct chemical synthesis or may be transcribed in vitro from a DNA (e.g., encoding the variant type V CRISPR/Cas effector polypeptide). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Minis Bio LLC. See also Beumer et al. (2008) PNAS 105(50):19821-19826.

Vectors may be provided directly to a target host cell. In other words, the cells are contacted with vectors comprising the subject nucleic acids (e.g., recombinant expression vectors having the donor template sequence and encoding a type V CRISPR/Cas guide RNA; recombinant expression vectors encoding a variant type V CRISPR/Cas effector polypeptide of the present disclosure (or a fusion polypeptide of the present disclosure); etc.) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

Vectors used for providing the nucleic acids encoding type V CRISPR/Cas guide RNA and/or a variant type V CRISPR/Cas effector polypeptide of the present disclosure (or a fusion polypeptide of the present disclosure) to a target host cell can include suitable promoters for driving the expression, that is, transcriptional activation, of the nucleic acid of interest. In other words, in some cases, the nucleic acid of interest will be operably linked to a promoter. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a nucleic acid encoding a type V CRISPR/Cas guide RNA and/or a variant type V CRISPR/Cas effector polypeptide of the present disclosure to a cell may include nucleic acid sequences that encode for selectable markers in the target cells, so as to identify cells that have taken up the type V CRISPR/Cas guide RNA and/or variant type V CRISPR/Cas effector polypeptide.

A nucleic acid comprising a nucleotide sequence encoding a variant type V CRISPR/Cas effector polypeptide of the present disclosure, or a fusion polypeptide of the present disclosure (a fusion polypeptide comprising: a) a variant type V CRISPR/Cas effector polypeptide of the present disclosure; and b) a heterologous polypeptide), is in some cases an RNA. Thus, a fusion protein of the present disclosure can be introduced into cells as RNA. Methods of introducing RNA into cells are known in the art and may include, for example, direct injection, transfection, or any other method used for the introduction of DNA. A variant type V CRISPR/Cas effector polypeptide of the present disclosure may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally, or alternatively, a variant type V CRISPR/Cas effector polypeptide of the present disclosure may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK (SEQ ID NO: 135). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence can be used. The site at which the fusion is made may be selected in order to optimize the biological activity, secretion or binding characteristics of the polypeptide. The optimal site will be determined by routine experimentation.

A variant type V CRISPR/Cas effector polypeptide of the present disclosure may be produced in vitro or by eukaryotic cells or by prokaryotic cells, and it may be further processed by unfolding, e.g. heat denaturation, dithiothreitol reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also suitable for inclusion in embodiments of the present disclosure are nucleic acids (e.g., encoding a type V CRISPR/Cas guide RNA, encoding a fusion protein of the present disclosure, etc.) and proteins (e.g., a variant type V CRISPR/Cas effector polypeptide of the present disclosure; a fusion protein of the present disclosure) that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable. Analogs of such polypeptides include those containing residues other than naturally occurring L-amino acids, e.g. D-amino acids or non-naturally occurring synthetic amino acids. D-amino acids may be substituted for some or all of the amino acid residues.

A variant type V CRISPR/Cas effector polypeptide of the present disclosure may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus, cysteines can be used to make thioethers, histidines for linking to a metal ion complex, carboxyl groups for forming amides or esters, amino groups for forming amides, and the like.

A variant type V CRISPR/Cas effector polypeptide of the present disclosure may also be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein. Thus, in some cases, a variant type V CRISPR/Cas effector polypeptide of the present disclosure, or a fusion polypeptide of the present disclosure, is at least 80% pure, at least 85% pure, at least 90% pure, at least 95% pure, at least 98% pure, or at least 99% pure (e.g., free of contaminants, non-variant type V CRISPR/Cas proteins or other macromolecules, etc.).

To induce cleavage or any desired modification to a target nucleic acid (e.g., genomic DNA), or any desired modification to a polypeptide associated with target nucleic acid, the type V CRISPR/Cas guide RNA and/or the variant type V CRISPR/Cas effector polypeptide of the present disclosure and/or the donor template sequence, whether they be introduced as nucleic acids or polypeptides, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different type V CRISPR/Cas guide RNAs that are complementary to different sequences within the same or different target nucleic acid), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

To improve the delivery of a DNA vector into a target cell, the DNA can be protected from damage and its entry into the cell facilitated, for example, by using lipoplexes and polyplexes. Thus, in some cases, a nucleic acid of the present disclosure (e.g., a recombinant expression vector of the present disclosure) can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also, as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Dendrimers, a highly branched macromolecule with a spherical shape, may be also be used to genetically modify stem cells. The surface of the dendrimer particle may be functionalized to alter its properties. In particular, it is possible to construct a cationic dendrimer (i.e., one with a positive surface charge). When in the presence of genetic material such as a DNA plasmid, charge complementarity leads to a temporary association of the nucleic acid with the cationic dendrimer. On reaching its destination, the dendrimer-nucleic acid complex can be taken up into a cell by endocytosis.

In some cases, a nucleic acid of the disclosure (e.g., an expression vector) includes an insertion site for a guide sequence of interest. For example, a nucleic acid can include an insertion site for a guide sequence of interest, where the insertion site is immediately adjacent to a nucleotide sequence encoding the portion of a type V CRISPR/Cas guide RNA that does not change when the guide sequence is changed to hybridized to a desired target sequence (e.g., sequences that contribute to the type V CRISRP/Cas polypeptide-binding aspect of the guide RNA, e.g., the sequences that contribute to the dsRNA duplex(es) of the type V CRISPR/Cas guide RNA—this portion of the guide RNA can also be referred to as the 'scaffold' or 'constant region' of the guide RNA). Thus, in some cases, a subject nucleic acid (e.g., an expression vector) includes a nucleotide sequence encoding a type V CRISPR/Cas guide RNA, except that the portion encoding the guide sequence portion of the guide RNA is an insertion sequence (an insertion site). An insertion site is any nucleotide sequence used for the insertion of a desired sequence. "Insertion sites" for use with various technologies are known to those of ordinary skill in the art and any convenient insertion site can be used. An insertion site can be for any method for manipulating nucleic acid sequences. For example, in some cases the insertion site is a multiple cloning site (MCS) (e.g., a site including one or more restriction enzyme recognition sequences), a site for ligation independent cloning, a site for recombination-based cloning (e.g., recombination based on att sites), a nucleotide sequence recognized by a CRISPR/Cas (e.g. Cas9) based technology, and the like.

An insertion site can be any desirable length, and can depend on the type of insertion site (e.g., can depend on whether (and how many) the site includes one or more restriction enzyme recognition sequences, whether the site includes a target site for a CRISPR/Cas protein, etc.). In some cases, an insertion site of a subject nucleic acid is 3 or more nucleotides (nt) in length (e.g., 5 or more, 8 or more, 10 or more, 15 or more, 17 or more, 18 or more, 19 or more, 20 or more or 25 or more, or 30 or more nt in length). In some cases, the length of an insertion site of a subject nucleic acid has a length in a range of from 2 to 50 nucleotides (nt) (e.g., from 2 to 40 nt, from 2 to 30 nt, from 2 to 25 nt, from 2 to 20 nt, from 5 to 50 nt, from 5 to 40 nt, from 5 to 30 nt, from 5 to 25 nt, from 5 to 20 nt, from 10 to 50 nt, from 10 to 40 nt, from 10 to 30 nt, from 10 to 25 nt, from 10 to 20 nt, from 17 to 50 nt, from 17 to 40 nt, from 17 to 30 nt, from 17 to 25 nt). In some cases, the length of an insertion site of a subject nucleic acid has a length in a range of from 5 to 40 nt.

Modified Host Cells

The present disclosure provides a modified cell comprising a variant type V CRISPR/Cas polypeptide of the present disclosure and/or a nucleic acid comprising a nucleotide sequence encoding a variant type V CRISPR/Cas polypeptide of the present disclosure. The description, below, of modified host cells that comprise a variant type V CRISPR/

Cas polypeptide of the present disclosure and/or a nucleic acid comprising a nucleotide sequence encoding a variant type V CRISPR/Cas polypeptide of the present disclosure apply equally to a modified host cell comprising a fusion polypeptide of the present disclosure and/or a nucleic acid comprising a nucleotide sequence encoding a fusion polypeptide of the present disclosure. Thus, for example, the present disclosure provides a modified host cell comprising a fusion polypeptide of the present disclosure and/or a nucleic acid comprising a nucleotide sequence encoding a fusion polypeptide of the present disclosure. The present disclosure provides a modified cell comprising a variant type V CRISPR/Cas polypeptide of the present disclosure, where the modified cell is a cell that does not normally comprise a variant type V CRISPR/Cas polypeptide of the present disclosure. The present disclosure provides a modified cell (e.g., a genetically modified cell) comprising nucleic acid comprising a nucleotide sequence encoding a variant type V CRISPR/Cas polypeptide of the present disclosure. The present disclosure provides a genetically modified cell that is genetically modified with an mRNA comprising a nucleotide sequence encoding a variant type V CRISPR/Cas polypeptide of the present disclosure. The present disclosure provides a genetically modified cell that is genetically modified with a recombinant expression vector comprising a nucleotide sequence encoding a variant type V CRISPR/Cas polypeptide of the present disclosure. The present disclosure provides a genetically modified cell that is genetically modified with a recombinant expression vector comprising: a) a nucleotide sequence encoding a variant type V CRISPR/Cas polypeptide of the present disclosure; and b) a nucleotide sequence encoding a type V CRISP/Cas guide RNA of the present disclosure. The present disclosure provides a genetically modified cell that is genetically modified with a recombinant expression vector comprising: a) a nucleotide sequence encoding a variant type V CRISPR/Cas polypeptide of the present disclosure e; b) a nucleotide sequence encoding a type V CRISPR/Cas guide RNA of the present disclosure; and c) a nucleotide sequence encoding a donor template.

A cell that serves as a recipient for a variant type V CRISPR/Cas polypeptide of the present disclosure and/or a nucleic acid comprising a nucleotide sequence encoding a variant type V CRISPR/Cas polypeptide of the present disclosure and/or a type V CRISPR/Cas guide RNA of the present disclosure, can be any of a variety of cells, including, e.g., in vitro cells; in vivo cells; ex vivo cells; primary cells; cancer cells; animal cells; plant cells; algal cells; fungal cells; etc. A cell that serves as a recipient for variant type V CRISPR/Cas polypeptide of the present disclosure and/or a nucleic acid comprising a nucleotide sequence encoding a variant type V CRISPR/Cas polypeptide of the present disclosure and/or a guide RNA of the present disclosure is referred to as a "host cell" or a "target cell." A host cell or a target cell can be a recipient of a type V CRISPR/Cas system of the present disclosure. A host cell or a target cell can be a recipient of a RNP of the present disclosure. A host cell or a target cell can be a recipient of a single component of a system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, *Cannabis*, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as CD34+ and CD3−. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., *Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera*, or *Lepidoptera.*

A cell is in some cases an insect cell. For example, in some cases, the cell is a cell of a mosquito, a grasshopper, a true bug, a fly, a flea, a bee, a wasp, an ant, a louse, a moth, or a beetle.

Kits

The present disclosure provides a kit comprising a system of the present disclosure, or a component of a system of the present disclosure.

A kit of the present disclosure can comprise: a) a variant type V CRISPR/Cas polypeptide of the present disclosure and a type V CRISPR/Cas guide RNA; b) a variant type V CRISPR/Cas polypeptide of the present disclosure, a type V CRISPR/Cas guide RNA, and a donor template nucleic acid; c) a fusion polypeptide of the present disclosure and a type V CRISPR/Cas guide RNA; d) a fusion polypeptide of the present disclosure, a type V CRISPR/Cas guide RNA, and a donor template nucleic acid; e) an mRNA encoding a variant type V CRISPR/Cas polypeptide of the present disclosure;

and a type V CRISPR/Cas guide RNA; f) an mRNA encoding a variant type V CRISPR/Cas polypeptide of the present disclosure, a type V CRISPR/Cas guide RNA, and a donor template nucleic acid; g) an mRNA encoding a fusion polypeptide of the present disclosure; and a type V CRISPR/Cas guide RNA; h) an mRNA encoding a fusion polypeptide of the present disclosure, a type V CRISPR/Cas guide RNA, and a donor template nucleic acid; i) a recombinant expression vector comprising a nucleotide sequence encoding a variant type V CRISPR/Cas polypeptide of the present disclosure and a nucleotide sequence encoding a type V CRISPR/Cas guide RNA; j) a recombinant expression vector comprising a nucleotide sequence encoding a variant type V CRISPR/Cas polypeptide of the present disclosure, a nucleotide sequence encoding a type V CRISPR/Cas guide RNA, and a nucleotide sequence encoding a donor template nucleic acid; k) a recombinant expression vector comprising a nucleotide sequence encoding a fusion polypeptide of the present disclosure and a nucleotide sequence encoding a type V CRISPR/Cas guide RNA; 1) a recombinant expression vector comprising a nucleotide sequence encoding a fusion polypeptide of the present disclosure, a nucleotide sequence encoding a type V CRISPR/Cas guide RNA, and a nucleotide sequence encoding a donor template nucleic acid; m) a first recombinant expression vector comprising a nucleotide sequence encoding aa variant type V CRISPR/Cas polypeptide of the present disclosure and a second recombinant expression vector comprising a nucleotide sequence encoding a type V CRISPR/Cas guide RNA; n) a first recombinant expression vector comprising a nucleotide sequence encoding a variant type V CRISPR/Cas polypeptide of the present disclosure, and a second recombinant expression vector comprising a nucleotide sequence encoding a type V CRISPR/Cas guide RNA; and a donor template nucleic acid; o) a first recombinant expression vector comprising a nucleotide sequence encoding a variant type V CRISPR/Cas polypeptide of the present disclosure, and a second recombinant expression vector comprising a nucleotide sequence encoding a type V CRISPR/Cas guide RNA; p) a first recombinant expression vector comprising a nucleotide sequence encoding a fusion polypeptide of the present disclosure, and a second recombinant expression vector comprising a nucleotide sequence encoding a type V CRISPR/Cas guide RNA; and a donor template nucleic acid; q) a recombinant expression vector comprising a nucleotide sequence encoding a variant type V CRISPR/Cas polypeptide of the present disclosure, a nucleotide sequence encoding a first type V CRISPR/Cas guide RNA, and a nucleotide sequence encoding a second type V CRISPR/Cas guide RNA; or r) a recombinant expression vector comprising a nucleotide sequence encoding a fusion polypeptide of the present disclosure, a nucleotide sequence encoding a first type V CRISPR/Cas guide RNA, and a nucleotide sequence encoding a second type V CRISPR/Cas guide RNA; or some variation of one of (a) through (r).

A kit of the present disclosure can comprise: a) a component, as described above, of a system of the present disclosure, or can comprise a system of the present disclosure; and b) one or more additional reagents, e.g., i) a buffer; ii) a protease inhibitor; iii) a nuclease inhibitor; iv) a reagent required to develop or visualize a detectable label; v) a positive and/or negative control target DNA; vi) a positive and/or negative control type V CRISPR/Cas guide RNA; and the like. A kit of the present disclosure can comprise: a) a component, as described above, of a system of the present disclosure, or can comprise a system of the present disclosure; and b) a therapeutic agent.

A kit of the present disclosure can comprise a recombinant expression vector comprising: a) an insertion site for inserting a nucleic acid comprising a nucleotide sequence encoding a portion of a type V CRISPR/Cas guide RNA that hybridizes to a target nucleotide sequence in a target nucleic acid; and b) a nucleotide sequence encoding the variant type V CRISPR/Cas effector polypeptide-binding portion of a type V CRISPR/Cas guide RNA. A kit of the present disclosure can comprise a recombinant expression vector comprising: a) an insertion site for inserting a nucleic acid comprising a nucleotide sequence encoding a portion of a type V CRISPR/Cas guide RNA that hybridizes to a target nucleotide sequence in a target nucleic acid; b) a nucleotide sequence encoding the variant type V CRISPR/Cas effector polypeptide-binding portion of a type V CRISPR/Cas guide RNA; and c) a nucleotide sequence encoding a variant type V CRISPR/Cas effector polypeptide of the present disclosure.

Utility

A variant type V CRISPR/Cas effector polypeptide of the present disclosure, or a fusion polypeptide of the present disclosure, finds use in a variety of methods (e.g., in combination with a type V CRISPR/Cas guide RNA and in some cases further in combination with a donor template). For example, a variant type V CRISPR/Cas effector polypeptide of the present disclosure can be used to (i) modify (e.g., cleave, e.g., nick; methylate; base edit; etc.) target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. Thus, the present disclosure provides a method of modifying a target nucleic acid. In some cases, a method of the present disclosure for modifying a target nucleic acid comprises contacting the target nucleic acid with: a) a variant type V CRISPR/Cas effector polypeptide (or fusion polypeptide) of the present disclosure; and b) one or more (e.g., two) type V CRISPR/Cas guide RNAs. In some cases, a method of the present disclosure for modifying a target nucleic acid comprises contacting the target nucleic acid with: a) a variant type V CRISPR/Cas effector polypeptide of the present disclosure; b) a type V CRISPR/Cas guide RNA; and c) a donor nucleic acid (e.g., a donor template). In some cases, the contacting step is carried out in a cell in vitro. In some cases, the contacting step is carried out in a cell in vivo. In some cases, the contacting step is carried out in a cell ex vivo.

Because a method that uses a variant type V CRISPR/Cas effector polypeptide of the present disclosure includes binding of the variant type V CRISPR/Cas effector polypeptide to a particular region in a target nucleic acid (by virtue of being targeted there by an associated type V CRISPR/Cas guide RNA), the methods are generally referred to herein as methods of binding (e.g., a method of binding a target nucleic acid). However, it is to be understood that in some cases, while a method of binding may result in nothing more than binding of the target nucleic acid, in other cases, the method can have different final results (e.g., the method can result in modification of the target nucleic acid, e.g., cleavage/methylation/etc., modulation of transcription from the target nucleic acid; modulation of translation of the target nucleic acid; genome editing; modulation of a protein associated with the target nucleic acid; isolation of the target nucleic acid; etc.).

For examples of suitable methods, see, for example, Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al, Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

For example, the present disclosure provides (but is not limited to) methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like.

As used herein, the terms/phrases "contact a target nucleic acid" and "contacting a target nucleic acid", for example, with a variant type V CRISPR/Cas effector polypeptide of the present disclosure or with a fusion polypeptide of the present disclosure, etc., encompass all methods for contacting the target nucleic acid. For example, a variant type V CRISPR/Cas effector polypeptide of the present disclosure can be provided to a cell as protein, RNA (encoding the variant type V CRISPR/Cas effector polypeptide), or DNA (encoding the variant type V CRISPR/Cas effector polypeptide); while a type V CRISPR/Cas guide RNA can be provided as a guide RNA or as a nucleic acid encoding the guide RNA. As such, when, for example, performing a method in a cell (e.g., inside of a cell in vitro, inside of a cell in vivo, inside of a cell ex vivo), a method that includes contacting the target nucleic acid encompasses the introduction into the cell of any or all of the components in their active/final state (e.g., in the form of a protein(s) for variant type V CRISPR/Cas effector polypeptide; in the form of a protein for a fusion polypeptide; in the form of an RNA in some cases for the guide RNA), and also encompasses the introduction into the cell of one or more nucleic acids encoding one or more of the components (e.g., nucleic acid(s) comprising nucleotide sequence(s) encoding a variant type V CRISPR/Cas effector polypeptide or a fusion polypeptide comprising a variant type V CRISPR/Cas effector polypeptide, nucleic acid(s) comprising nucleotide sequence(s) encoding guide RNA(s), nucleic acid comprising a nucleotide sequence encoding a donor template, and the like). Because the methods can also be performed in vitro outside of a cell, a method that includes contacting a target nucleic acid, (unless otherwise specified) encompasses contacting outside of a cell in vitro, inside of a cell in vitro, inside of a cell in vivo, inside of a cell ex vivo, etc.

In some cases, a method of the present disclosure for modifying a target nucleic acid comprises contacting a target nucleic acid with a variant type V CRISPR/Cas effector polypeptide of the present disclosure, or with a fusion polypeptide of the present disclosure. In some cases, a method of the present disclosure for modifying a target nucleic acid comprises contacting a target nucleic acid with a variant type V CRISPR/Cas effector polypeptide of the present disclosure and a type V CRISPR/Cas guide RNA. In some cases, a method of the present disclosure for modifying a target nucleic acid comprises contacting a target nucleic acid with a variant type V CRISPR/Cas effector polypeptide of the present disclosure, a first type V CRISPR/Cas guide RNA, and a second type V CRISPR/Cas guide RNA In some cases, a method of the present disclosure for modifying a target nucleic acid comprises contacting a target nucleic acid with a variant type V CRISPR/Cas effector polypeptide of the present disclosure and a type V CRISPR/Cas guide RNA and a donor DNA template.

Introducing Components into a Target Cell

A guide RNA (or a nucleic acid comprising a nucleotide sequence encoding the guide RNA) and/or a variant type V CRISPR/Cas effector polypeptide of the present disclosure (or a nucleic acid comprising a nucleotide sequence encoding the variant type V CRISPR/Cas effector polypeptide), and optionally also a donor template nucleic acid, can be introduced into a host cell by any of a variety of well-known methods. As a non-limiting example, a guide RNA and/or a variant type V CRISPR/Cas effector polypeptide of the present disclosure can be combined with a lipid. As a non-limiting example, a guide RNA, a variant type V CRISPR/Cas effector polypeptide of the present disclosure, and a donor template nucleic acid, can be combined with a lipid. As another non-limiting example, a guide RNA and/or variant type V CRISPR/Cas effector polypeptide of the present disclosure can be combined with a particle, or formulated into a particle. As another non-limiting example, a guide RNA, a variant type V CRISPR/Cas effector polypeptide of the present disclosure, and a donor template nucleic acid, can be combined with a particle, or formulated into a particle.

Methods of introducing a nucleic acid and/or protein into a host cell are known in the art, and any convenient method can be used to introduce a subject nucleic acid (e.g., an expression construct/vector) into a target cell (e.g., prokaryotic cell, eukaryotic cell, plant cell, animal cell, mammalian cell, human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al. Adv Drug Deliv Rev. 2012 Sep. 13. pii: 50169-409X(12)00283-9. doi: 10.1016/j.addr.2012.09.023), and the like.

A guide RNA can be introduced, e.g., as a DNA molecule encoding the guide RNA, or can be provided directly as an RNA molecule (or a hybrid molecule when applicable). In some cases, a variant type V CRISPR/Cas effector polypeptide of the present disclosure is provided as a nucleic acid (e.g., an mRNA, a DNA, a plasmid, an expression vector, a viral vector, etc.) that encodes the protein. In some cases, the variant type V CRISPR/Cas effector protein is provided directly as a protein (e.g., without an associated guide RNA or with an associate guide RNA, i.e., as a ribonucleoprotein complex—RNP). Like a guide RNA, a variant type V CRISPR/Cas effector polypeptide of the present disclosure can be introduced into a cell (provided to the cell) by any convenient method; such methods are known to those of ordinary skill in the art. As an illustrative example, a variant type V CRISPR/Cas effector polypeptide of the present disclosure can be injected directly into a cell (e.g., with or without a guide RNA or nucleic acid encoding a guide RNA). As another example, a pre-formed complex of a variant type V CRISPR/Cas effector polypeptide of the present disclosure and a guide RNA (an RNP) can be introduced into a cell (e.g., eukaryotic cell) (e.g., via injection, via nucleofection; via a protein transduction domain (PTD) conjugated to one or more components, e.g., conjugated to the variant type V CRISPR/Cas effector protein, conjugated to a guide RNA; etc.).

In some cases, a nucleic acid (e.g., a guide RNA; a nucleic acid comprising a nucleotide sequence encoding a variant type V CRISPR/Cas effector polypeptide of the present disclosure; a nucleic acid comprising a nucleotide sequence encoding a guide RNA; a donor template nucleic acid; etc.) and/or a polypeptide (e.g., a variant type V CRISPR/Cas effector polypeptide of the present disclosure) is delivered to a cell (e.g., a target host cell) in a particle, or associated with a particle. The terms “particle” and “nanoparticle” can be used interchangeably, as appropriate.

This can be achieved, e.g., using particles or lipid envelopes, e.g., a ribonucleoprotein (RNP) complex can be delivered via a particle, e.g., a delivery particle comprising lipid or lipidoid and hydrophilic polymer, e.g., a cationic lipid and a hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5).

A variant type V CRISPR/Cas effector polypeptide of the present disclosure (or an mRNA or a DNA comprising a nucleotide sequence encoding the protein) and/or a guide RNA (or a nucleic acid such as one or more expression vectors encoding the guide RNA) may be delivered simultaneously using particles or lipid envelopes. For example, a biodegradable core-shell structured nanoparticle with a poly (β-amino ester) (PBAE) core enveloped by a phospholipid bilayer shell can be used. In some cases, particles/nanoparticles based on self assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent publication 20110293703) are also useful in the administration of polynucleotides, and can be used. In one aspect, aminoalcohol lipidoid compounds are combined with an agent to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used, sugar-based particles may be used, for example GalNAc, as described with reference to WO2014118272 (incorporated herein by reference) and Nair, J K et al., 2014, Journal of the American Chemical Society 136 (49), 16958-16961). In some cases, lipid nanoparticles (LNPs) are used. Spherical Nucleic Acid (SNA™) constructs and other nanoparticles (particularly gold nanoparticles) can be used to a target cell. See, e.g., Cutler et al., J. Am. Chem. Soc. 2011 133:9254-9257, Hao et al., Small 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al., Sci. Transl. Med. 5, 209ra152 (2013) and Mirkin, et al., Small, 10:186-192. Semi-solid and soft nanoparticles are also suitable for delivery. An exosome can be used for delivery. Exosomes are endogenous nano-vesicles that transport RNAs and proteins, and which can deliver RNA to the brain and other target organs. Supercharged proteins can be used for delivery to a cell. Supercharged proteins are a class of engineered or naturally occurring proteins with unusually high positive or negative net theoretical charge. Both super-negatively and superpositively charged proteins exhibit the ability to withstand thermally or chemically induced aggregation. Superpositively charged proteins are also able to penetrate mammalian cells. Associating cargo with these proteins, such as plasmid DNA, RNA, or other proteins, can facilitate the functional delivery of these macromolecules into mammalian cells both in vitro and in vivo. Cell Penetrating Peptides (CPPs) can be used for delivery. CPPs typically have an amino acid composition that either contains a high relative abundance of positively charged amino acids such as lysine or arginine or has sequences that contain an alternating pattern of polar/charged amino acids and non-polar, hydrophobic amino acids.

Target Nucleic Acids and Target Cells of Interest

A variant type V CRISPR/Cas effector polypeptide of the present disclosure, or a fusion polypeptide of the present disclosure, when bound to a type V CRISPR/Cas guide RNA, can bind to a target nucleic acid, and in some cases, can bind to and modify a target nucleic acid. A target nucleic acid can be any nucleic acid (e.g., DNA, RNA), can be double stranded or single stranded, can be any type of nucleic acid (e.g., a chromosome (genomic DNA), derived from a chromosome, chromosomal DNA, plasmid, viral, extracellular, intracellular, mitochondrial, chloroplast, linear, circular, etc.) and can be from any organism (e.g., as long as the type V CRISPR/Cas guide RNA comprises a nucleotide sequence that hybridizes to a target sequence in a target nucleic acid, such that the target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro; inside of a cell in vivo; inside of a cell ex vivo; or inside of an organelle (e.g., mitochondrion; nucleus; etc.) within a cell that is in vitro, in vivo, or ex vivo. Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicuña, a sheep, a goat, etc.); a cell of a marine mammal (e.g., a whale, a seal, an elephant seal, a dolphin, a sea lion; etc.) and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), an adult stem cell, a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where “primary cells”, “primary cell lines”, and “primary cultures” are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytopheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA, to cleave or otherwise modify target DNA, to genetically modify a target cell, and the like). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens, C. agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.). In some cases, a variant type V CRISPR/Cas polypeptide of the present disclosure (and/or nucleic acid encoding the protein such as DNA and/or RNA), and/or type V CRISPR/Cas guide RNA (and/or a DNA encoding the guide RNA), and/or donor template, and/or RNP can be introduced into an individual (i.e., the target cell can be in vivo) (e.g., a mammal, a rat, a mouse, a pig, a primate, a non-human primate, a human, etc.). In some case, such an administration can be for the purpose of treating and/or preventing a disease, e.g., by editing the genome of targeted cells.

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Additional examples of target cells are listed above in the section titled “Modified cells.” Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, *Cannabis*, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be an in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some cases, the stem cell is a hematopoietic stem cell (HSC). HSCs are mesoderm-derived cells that can be isolated from bone marrow, blood, cord blood, fetal liver and yolk sac. HSCs are characterized as CD34+ and CD3−. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other cases, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other cases, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., *Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera*, or *Lepidoptera*.

A cell is in some cases an insect cell. For example, in some cases, the cell is a cell of a mosquito, a grasshopper, a true bug, a fly, a flea, a bee, a wasp, an ant, a louse, a moth, or a beetle.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-44 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A variant type V CRISPR/Cas effector polypeptide comprising at least one mutation in the loop of the helix-loop element of the RuvC domain compared to a wild-type type V CRISPR/Cas effector polypeptide, wherein the at least one mutation provides for a reduction of at least 50% in the trans cleavage activity exhibited by the wild-type type V CRISPR/Cas effector polypeptide.

Aspect 2. The variant type V CRISPR/Cas effector polypeptide of aspect 1, wherein the wild-type type V CRISPR/Cas effector polypeptide comprises an amino acid sequence having at least 50% amino acid sequence identity to a Cas12a polypeptide.

Aspect 3. The variant type V CRISPR/Cas effector polypeptide of aspect 1, wherein the wild-type type V CRISPR/Cas effector polypeptide comprises an amino acid sequence having at least 50% amino acid sequence identity to a Cas12b polypeptide.

Aspect 4. The variant type V CRISPR/Cas effector polypeptide of aspect 1, wherein the wild-type type V CRISPR/Cas effector polypeptide comprises an amino acid sequence having at least 50% amino acid sequence identity to a Cas12e polypeptide.

Aspect 5. The variant type V CRISPR/Cas effector polypeptide of any one of aspects 1-4, wherein the at least one mutation provides for a reduction of at least 95% in the trans cleavage activity exhibited by the wild-type type V CRISPR/Cas effector polypeptide.

Aspect 6. The variant type V CRISPR/Cas effector polypeptide of any one of aspects 1-5, wherein the mutation comprises deletion of one or more amino acids of the loop.

Aspect 7. The variant type V CRISPR/Cas effector polypeptide of any one of aspects 1-5, wherein the mutation comprises substitution of one or more Lys and Arg amino acids in the loop with an amino acid other than Lys or Arg.

Aspect 8. The variant type V CRISPR/Cas effector polypeptide of aspect 7, wherein a Lys residue is substituted with an amino acid other than Lys.

Aspect 9. The variant type V CRISPR/Cas effector polypeptide of aspect 7, wherein an Arg residue is substituted with an amino acid other than Arg.

Aspect 10. The variant type V CRISPR/Cas effector polypeptide of any one of aspects 1-5, wherein the mutation comprises substitution of one or more amino acids in the loop with a Gly.

Aspect 11. The variant type V CRISPR/Cas effector polypeptide of any one of aspects 1-5, wherein the mutation comprises substitution of one or more amino acids in the loop with an Ala.

Aspect 12. The variant type V CRISPR/Cas effector polypeptide of any one of aspects 1-11, comprising at least one nuclear localization signal (NLS).

Aspect 13. A nucleic acid comprising a nucleotide sequence encoding the variant type V CRISPR/Cas effector polypeptide of any one of aspects 1-12.

Aspect 14. A recombinant expression vector comprising the nucleic acid of aspect 13.

Aspect 15. The recombinant expression vector of aspect 14, wherein the nucleotide sequence is codon optimized for expression in a host cell.

Aspect 16. The recombinant expression vector of aspect 14 or 15, wherein the nucleotide sequence is operably linked to a promoter.

Aspect 17. The recombinant expression vector of aspect 16, wherein the promoter is a regulatable promoter.

Aspect 18. A composition comprising the variant type V CRISPR/Cas effector polypeptide of any one of aspects 1-12.

Aspect 19. The composition of aspect 18, comprising one or more of: a) a lipid; b) a buffer; c) a nuclease inhibitor; and d) a protease inhibitor.

Aspect 20. A system comprising the variant type V CRISPR/Cas effector polypeptide of any one of aspects 1-12.

Aspect 21. The system of aspect 20, further comprising a type V CRISPR/Cas guide RNA.

Aspect 22. The system of aspect 20, further comprising 2 type V CRISPR/Cas guide RNAs.

Aspect 23. The system of aspect 21 or aspect 22, wherein the guide RNA(s) comprises one or more of a base modification, a sugar modification, and a backbone modification.

Aspect 24. The system of any one of aspects 20-23, further comprising a donor DNA template.

Aspect 25. A fusion polypeptide comprising: a) the variant type V CRISPR/Cas effector polypeptide of any one of aspects 1-12; and b) a heterologous polypeptide.

Aspect 26. The fusion polypeptide of aspect 25, wherein the heterologous polypeptide is a targeting polypeptide that provides for binding to a cell surface moiety on a target cell or target cell type.

Aspect 27. The fusion polypeptide of aspect 25, wherein the heterologous polypeptide exhibits an enzymatic activity that modifies target DNA.

Aspect 28. The fusion polypeptide of aspect 27, wherein the heterologous polypeptide exhibits one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

Aspect 29. The fusion polypeptide of aspect 25, wherein the heterologous polypeptide is an endosomal escape polypeptide.

Aspect 30. A nucleic acid comprising a nucleotide sequence encoding the fusion polypeptide of any one of aspects 25-29.

Aspect 31. A host cell comprising: a) the variant type V CRISPR/Cas effector polypeptide of any one of aspects 1-12; or b) a nucleic acid comprising a nucleotide sequence encoding the variant type V CRISPR/Cas effector polypeptide of any one of aspects 1-12; or c) the fusion polypeptide of any one of aspects 25-29; or d) a nucleic acid comprising a nucleotide sequence encoding the fusion polypeptide of any one of aspects 25-29.

Aspect 32. The host cell of aspect 31, further comprising a CRISPR/Cas guide RNA, or a nucleic acid comprising a nucleotide sequence encoding the CRISPR/Cas guide RNA.

Aspect 33. The host cell of aspect 31 or aspect 32, wherein the host cell is a eukaryotic cell.

Aspect 34. The host cell of aspect 33, wherein the eukaryotic cell is a plant cell, a mammalian cell, an insect cell, an arachnid cell, a fungal cell, a bird cell, a reptile cell, an amphibian cell, an invertebrate cell, a mouse cell, a rat cell, a primate cell, a non-human primate cell, or a human cell.

Aspect 35. The host cell of aspect 31 or aspect 32, wherein the host cell is a prokaryotic cell.

Aspect 36. A method of modifying a target nucleic acid, the method comprising contacting the target nucleic acid with: a) the variant type V CRISPR/Cas effector polypeptide of any one of aspects 1-12 or the fusion polypeptide of any one of aspects 25-29; and b) a CRISPR/Cas guide RNA that comprising a guide sequence that hybridizes to a target sequence of the target nucleic acid, wherein said contacting results in modification of the target nucleic acid by the variant type V CRISPR/Cas effector polypeptide or the fusion polypeptide.

Aspect 37. The method of aspect 36, wherein said modification is cleavage of the target nucleic acid.

Aspect 38. The method of aspect 36 or aspect 37, wherein the target nucleic acid is selected from: double stranded DNA, single stranded DNA, RNA, genomic DNA, and extrachromosomal DNA.

Aspect 39. The method of any one of aspects 36-38, wherein said contacting takes place in vitro outside of a cell.

Aspect 40. The method of any one of aspects 36-38, wherein said contacting takes place inside of a cell in vitro.

Aspect 41. The method of any one of aspects 36-38, wherein said contacting takes place inside of a cell in vivo.

Aspect 42. The method of aspect 40 or aspect 41, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Aspect 43. The method of any one of aspects 36-42, wherein said contacting results in genome editing.

Aspect 44. The method of any one of aspects 40-43, wherein said contacting further comprises: introducing a DNA donor template into the cell.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Effect of Loop Mutations on Cis and Trans Cleavage

Cis- and Trans-DNA Cleavage Assays

Cas12a-mediated DNA cleavage assays were carried out in Cleavage Buffer consisting of 20 mM HEPES (pH 7.5), 150 mM KCl, 10 mM $MgCl_2$, 1% glycerol and 0.5 mM dithiothreitol (DTT), and the 5'-end-labeled DNA substrates used were generated with T4 PNK (NEB) in the presence of gamma $^{32}$P-ATP.

For cis-targeting assays, 30 nM Cas12a was pre-assembled with 36 nM of crRNA for 15 minutes at room temperature. The reaction was initiated by adding 2-4 nM of labeled dsDNA (non-targeting strand labeled) and incubated at 37° C. for indicated time points.

For trans-targeting assays, Cas12a RNP was first formed from 30 nM Cas12a and 36 nM of crRNA by incubation of 15 minutes at room temperature. After addition of 45 nM of activator (target dsDNA pre-annealed from target and non-target 55 nt DNA oligos) to the Cas12a RNP, the mixture was incubated for 30 min at 37 C to form activated Cas12a complex. For cas12a-mediated trans-DNA cleavage assays, the activator-activated Cas12a complex was incubated with a labeled and non-related ssDNA for indicated time points at 37 C.

Reactions from either cis or trans cleavage assays were quenched with loading buffer (final concentration 45% formamide and 15 mM EDTA, with trace amount of xylene cyanol and bromophenol blue) for 3 min at 90° C. The substrates and products were resolved by 12% urea-denaturing polyacrylamide gel electrophoresis (PAGE) gel and quantified with Amersham Typhoon (GE Healthcare).

The data are shown in FIG. 25.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A variant type V CRISPR/Cas effector polypeptide comprising at least one mutation in the loop of the helix-loop element of the RuvC domain compared to a wild-type type V CRISPR/Cas effector polypeptide, wherein the at least one mutation provides for a reduction of at least 50% in the trans cleavage activity exhibited by the wild-type type V CRISPR/Cas effector polypeptide, wherein said trans cleavage is promiscuous cleavage of non-target single stranded DNAs (ssDNAs), and wherein the variant type V CRISPR/Cas effector polypeptide comprises an amino acid sequence having at least 85% amino acid sequence identity to the amino acid sequence set forth in any one of SEQ ID NOs: 2, 4-15, 18-19, 21, 23, 25, 27, 29, 31-32, 34-35, 37-38, 40-41, 43-44, 46-47, 49-50, 52-53, and 141-142.

2. The variant type V CRISPR/Cas effector polypeptide of claim 1, wherein the loop is deleted, or is mutated to: GAA, GGA, AGG, AAG, GAP, P, GGAAGGAAP (SEQ ID NO: 76), GGAAGGAAG (SEQ ID NO: 77), or GGAAGGAAA (SEQ ID NO: 78), SGFANSRVA (SEQ ID NO: 79), GGAAGGGAG (SEQ ID NO: 81), FGFASARTG (SEQ ID NO: 82), FGFASAATG (SEQ ID NO: 83), FGFARGRFA (SEQ ID NO: 84), FGFKAGAFK (SEQ ID NO: 85), LSFMKGRAA (SEQ ID NO: 87), LSFMAGRAA (SEQ ID NO: 88), LSFMAGAKK (SEQ ID NO: 89), FGFAAGAFA (SEQ ID NO: 90), FGFARGAFK (SEQ ID NO: 91), FGFKAGRFA (SEQ ID NO: 92), FGFARGROA (SEQ ID NO: 93), FGFKAGAOK (SEQ ID NO: 94), FGFARGAOK (SEQ ID NO: 95), FGFKAGROA (SEQ ID NO: 96), MGFARGRFA (SEQ ID NO: 97), MGFKAGAFK (SEQ ID NO: 98), MGFAAGRFK (SEQ ID NO: 99), MGFKRGAFA (SEQ ID NO: 100), MGFARGROA (SEQ ID NO: 101), MGFKAGAOK (SEQ ID NO: 102), MGFARGAOK (SEQ ID NO: 103), MGFKAGROA (SEQ ID NO: 104), OGFARGRFA (SEQ ID NO: 105), OGFKAGAFK (SEQ ID NO: 106), QGFARGAFK (SEQ ID NO: 107), QGFKAGRFA (SEQ ID NO: 108), or GAAGAAGAAGAAGG (SEQ ID NO: 111).

3. The variant type V CRISPR/Cas effector polypeptide of claim 1, wherein the loop of the wild-type type V CRISPR/Cas effector polypeptide comprises the amino acid sequence SGFKNSRVK (SEQ ID NO: 60), FGFKSKRTG (SEQ ID NO: 62), LSFMKGRKK (SEQ ID NO: 86), FGFKRGRFK (SEQ ID NO: 61), FGFKRGROK (SEQ ID NO: 73), MGFKRGRFK (SEQ ID NO: 74), MGFKRGRQK (SEQ ID NO: 63), QGFKRGRFK (SEQ ID NO: 75), EYQFNNDRPPSENN (SEQ ID NO: 64), EYRFSNDRPPSENS (SEQ ID NO: 65), RYRFQSDRPPSENS (SEQ ID NO: 66), AYRFSDDRPPSENS (SEQ ID NO: 67), RYRFRTDRPRSENR (SEQ ID NO: 109), GRQGKRTFMTERQ (SEQ ID NO: 68), or GROGKRTFMAERQ (SEQ ID NO: 112).

4. The variant type V CRISPR/Cas effector polypeptide of claim 1, wherein the at least one mutation provides for a reduction of at least 95% in the trans cleavage activity exhibited by the wild-type type V CRISPR/Cas effector polypeptide.

5. The variant type V CRISPR/Cas effector polypeptide of claim 1, wherein the mutation comprises deletion of one or more amino acids of the loop.

6. The variant type V CRISPR/Cas effector polypeptide of claim 1, wherein the mutation comprises substitution of one or more charged amino acids in the loop with one or more uncharged amino acids.

7. The variant type V CRISPR/Cas effector polypeptide of claim 6, wherein a Lys residue is substituted with an uncharged amino acid.

8. The variant type V CRISPR/Cas effector polypeptide of claim 6, wherein an Arg residue is substituted with an uncharged amino acid or an amino acid having a hydrophobic side chain.

9. The variant type V CRISPR/Cas effector polypeptide of claim 1, wherein the mutation comprises substitution of one or more amino acids in the loop with a Gly.

10. The variant type V CRISPR/Cas effector polypeptide of claim 1, wherein the mutation comprises substitution of one or more amino acids in the loop with an Ala.

11. The variant type V CRISPR/Cas effector polypeptide of claim 1, comprising at least one nuclear localization signal (NLS).

12. A nucleic acid comprising a nucleotide sequence encoding the variant type V CRISPR/Cas effector polypeptide of claim 1.

13. A recombinant expression vector comprising the nucleic acid of claim 12.

14. A composition comprising the variant type V CRISPR/Cas effector polypeptide of claim 1.

15. A system comprising the variant type V CRISPR/Cas effector polypeptide of claim 1.

16. A fusion polypeptide comprising:

a) the variant type V CRISPR/Cas effector polypeptide of claim 1; and b) a heterologous polypeptide.

17. A nucleic acid comprising a nucleotide sequence encoding the fusion polypeptide of claim 16.

18. A host cell comprising:

a) the variant type V CRISPR/Cas effector polypeptide of claim 1; or b) a nucleic acid comprising a nucleotide sequence encoding the variant type V CRISPR/Cas effector polypeptide of claim 1; or c) the fusion polypeptide of claim 16; or d) a nucleic acid comprising a nucleotide sequence encoding the fusion polypeptide of claim 16.

19. A method of modifying a target nucleic acid, the method comprising contacting the target nucleic acid with:

a) the variant type V CRISPR/Cas effector polypeptide of claim 1 or the fusion polypeptide of claim 16; and b) a CRISPR/Cas guide RNA that comprising a guide sequence that hybridizes to a target sequence of the target nucleic acid, wherein said contacting results in modification of the target nucleic acid by the variant type V CRISPR/Cas effector polypeptide or the fusion polypeptide.

20. The system of claim 15, further comprising a type V CRISPR/Cas guide RNA.

21. The system of claim 15, further comprising a donor DNA template.

* * * * *